US010697018B2

(12) United States Patent
Valsesia et al.

(10) Patent No.: US 10,697,018 B2
(45) Date of Patent: Jun. 30, 2020

(54) BIOMARKERS FOR PREDICTING WEIGHT LOSS AND WEIGHT MAINTENANCE

(71) Applicant: NESTEC S.A., Vevey (CH)

(72) Inventors: Armand Valsesia, Chavannes-pres-Renens (CH); Jorg Hager, Houtaud (FR)

(73) Assignee: Societe des Produits Nestle S.A., Vevey (CH)

(*) Notice: Subject to any disclaimer, the term of this patent is extended or adjusted under 35 U.S.C. 154(b) by 0 days.

(21) Appl. No.: 15/520,990

(22) PCT Filed: Nov. 9, 2015

(86) PCT No.: PCT/EP2015/076010
§ 371 (c)(1),
(2) Date: Apr. 21, 2017

(87) PCT Pub. No.: WO2016/078944
PCT Pub. Date: May 26, 2016

(65) Prior Publication Data

US 2018/0016636 A1 Jan. 18, 2018

(30) Foreign Application Priority Data

Nov. 21, 2014 (EP) .................................... 14194223

(51) Int. Cl.
*C12Q 1/68* (2018.01)
*C12Q 1/6883* (2018.01)

(52) U.S. Cl.
CPC ...... *C12Q 1/6883* (2013.01); *C12Q 2600/118* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | | |
|---|---|---|---|---|
| 6,582,908 | B2 * | 6/2003 | Fodor .................. | B01J 19/0046 435/288.3 |
| 2007/0196841 | A1 | 8/2007 | Ruano et al. | |
| 2007/0213274 | A1 * | 9/2007 | Salonen .................. | C12Q 1/60 514/44 R |
| 2011/0124121 | A1 | 5/2011 | Dixon et al. | |
| 2014/0087999 | A1 | 3/2014 | Kaplan et al. | |

FOREIGN PATENT DOCUMENTS

| | | | |
|---|---|---|---|
| EP | 2420843 | A1 | 2/2012 |
| WO | 2011070115 | A1 | 6/2011 |
| WO | 2013079388 | A1 | 6/2013 |

OTHER PUBLICATIONS

Langdahl (Journal of Bone and Mineral Research 2000 vol. 15 p. 402) (Year: 2000).*
Wall (Nature Reviews Genetics 2003 vol. 4, pp. 587-597) (Year: 2003).*
Sotos et al. (Statistics Education Research Journal Nov. 8, 2009 p. 33) (Year: 2009).*
Juppner (Bone 1995 vol. 17 No. 2 Supplement 39S-42S) (Year: 1995).*
The World Health Organization, Obesity: Preventing and managing the Global Epidemic, Tech. Rep. Series, Geneva 2000; 894: 1-xii, 1-253.
Ghosh, S., et al., Blood Gene Expression Reveal Pathway Differences Between Diet-Sensitive and Resistant Obese Subjects Prior to Caloric Restriction, Obesity , A Research Journal, 19(2): 457-463, Feb. 2011.
Lijnen, H.R., et al., Caloric restriction improves coagulation and inflammation profile in obese mice, Thrombosis Research, vol. 129, Issue 1, Jan. 2012, pp. 74-79.
Cugno, M, et al. Inflammatory and prothrombotic parameters in normotensive non-diabetic obese women: effect of weight loss obtained by gastric banding. Intern Emerg Med. 2012;7(3):237-42.
Bladbjerg E.M., et al., Long-term effects on haemostatic variables of three ad libitum diets differing in type and amount of fat and carbohydrate: a 6-month randomised study in obese individuals. Br J Nutr. Dec. 2010;104(12):1824-30. Epub Jul. 30, 2010.
Hensrud, D.D., Dietary treatment and long-term weight loss and maintenance in type 2 diabetes, Obes Res. Nov. 2001; 9 Suppl 4:348S-353S.
Sumithran, P., et al., The defence of body weight: a physiological basis for weight regain after weight loss, Clinical Science, 124, 231-241 (2013).
Halder, G., et al., Hippo signaling: growth control and beyond, Development 138, 9-22 (2011).
Sing, A., et al.,, The Atypical Cadherin Fat Directly Regulates Mitochondrial Function and Metabolic State, vol. 158, Issue 6, Sep. 11, 2014, pp. 1293-1308.
Saiki, R.K., et al., Analysis of enzymatically amplified β-globin and HLA-DQα DNA with allele-specific oligonucleotide probes, Nature 324, 163-166 (Nov. 13, 1986).
Wu, Dy, et al., The ligation amplification reaction (LAR)—amplification of specific DNA sequences using sequential rounds of template-dependent ligation, Genomics, 4:560-569, 1989.
Barany, F., Genetic disease detection and DNA amplification using cloned thermostable ligase, Proc. Natl. Acad. Sci., USA, vol. 88 No. 1, 189-193, Jan. 1991.

(Continued)

*Primary Examiner* — Katherine D Salmon
(74) *Attorney, Agent, or Firm* — K&L Gates LLP

(57) ABSTRACT

A method for assessing the predisposition of a subject to weight loss attainable by applying one or more dietary interventions to a subject and/or the predisposition of a subject to maintenance of weight loss following one or more dietary interventions which method comprises determining the nucleotide of the subject at one or more polymorphic positions selected from: (i) position 101 of SEQ ID NO:1 (rs953211) (ii) position 101 of SEQ ID NO:2 (rs1509290) (iii) position 101 of SEQ ID NO:3 (rs1509289) and/or detecting one or more biomarkers genetically linked to said polymorphic positions.

9 Claims, 85 Drawing Sheets

Specification includes a Sequence Listing.

(56) References Cited

OTHER PUBLICATIONS

Erlich, H., ed., Principles and Applications for DNA Amplification, Chapter 7, W. H. Freeman and Co., NY 1992.
Myers, R.M., et al., Meth. Enzymol. 155:501-527, 1986.
Myers, R.M., et al., Genomic Analysis, A Practical Approach, K. Davies Ed IRL Press Ltd., oxford, pp. 95-139, 1988.
Orita, Proc. Nat. Acad. Sci., 85:2766-2770 (1989).
Grompe, M. et al., Improved molecular diagnostics for ornithine transcarbamylase deficiency Am. J. Hum. Genet. 48:212-222, 1991.
Nelson, Nature Genetics, 4:11-18, 1993.
Nollau, Clin. Chem. 43, 1114-1120, 1997.
Laboratory Protocols for Mutuation Detection, Ed. by Univ. of Landegren, Oxford Univ. Press, 1996.
PCR, 2nd Ed., Newton & Graham, Bios Scientific Publishers Limited, 1997.
Agrawal, S., Protocols for Oligonucleotides and Analogues; Synthesis and Properties, Methods in Molecular Biology Series; vol. 20, Ed., Humana Press Inc., 1993.
Sambrook, E.F., 1989, Molecular cloning: A Lab Manual, 2nd Ed., Books 1-3, Cold Spring Harbor Lab press.
Ausubel, F.M., et al., Periodic Supplements, Current Protocols in Molecular Biology, Ch. 9, 13 and 16, Wiley & Sons, NY, NY (1995).
Roe, B, et al., 1996, DNA Isolation and Sequencing: Essential Techniques, John Wiley & Sons.
Polak, J. M., et al., In Situ Hybridization: Principles and Practice, Oxford Univ. Press, Diagnostic Molecular Pathology: Mar. 1992—vol. 1—Issue 1—p. 80, Book Review.
Gait, M.J., et al. Oligonucleotide Synthesis: A Practical Approach, IRL Press, Oxford, England (1984).
Lilley, DMJ, DNA Structure Part A: Synthesis and Physical Analysis of DNA, Methods in Enzymology, Academy Press, vol. 211, pp. 3-619 (1992).
Shevach, E. M., et al. Current Protocols in Immunology, Wiley & Sons, New York, NY 1992.
Larsen, T.M., et al., The Diet, Obesity and Genes (Diogenes) Dietary Study in eight European countries—a comprehensive design for long-term intervention, Journal compilation, 2009 International Association for the Study of Obesity. 11, 76-91.
Aulchenko, Y.S., et al., Genomewide Rapid Association Using Mixed Model and Regression: A Fast and Simple Method for Genomewide Pedigree-Based Quantitative Trait Loci Association Analysis, Genetics 177, 577-585 (2007).
Carlson, C.S., et al., Selecting a Maximally Informative Set of Single-Nucleotide Polymorphisms for Association Analyses Using Linkage Disequilibrium, Am. J. Hum. Genet., Jan. 2004; 74(1): 106-120.
Li, Y., et al., MaCH: Using Sequence and Genotype Data to Estimate Haplotypes and Unobserved Genotypes, Genet Epidemiol, Dec. 2010; 34(8): 816-834.
Fox & Weisberg, An R Companion to Applied Regression, 2nd. Ed., Sage Pub. 2011.
Kuhn, The caret Package, Journal of Statistical Software, vol. 28, 1-26 (2008).
Consortium T1000, The 1000 Genomes Project Consortium, An integrated map of genetic variation from 1,092 human genomes, Nature, Nov. 1, 2012; 491(7422): 56-65.
Purcell, S., Plink: a tool set for whole-genome association and population-based linkage analysis, Am. J. Hum. Genet. 81(3), 559-575 (Sep. 2007).
Davidson, A.C., et al., Bootstrap Methods and Their Application, Cambridge Univ. Press, 1997.
Canty, A., et al., boot: Bootstrap R (S-Plus) Functions. 2013.
McCarthy, M.I., et al., Genome-wide association studies: potential next steps on a genetic journey, Human Mil. Genet., vol. 17, Issue R2, Oct. 15, 2008, Oxford Academic.
Ioannidis, JPA, et al., Meta-analysis in genome-wide association studies, Nat. Review Genetics 10, 318-329 2009.
McCarthy, M. I., et al., Genome-wide association studies for complex traits: consensus, uncertainty and challengesNat. Rev. Genet., 9, 356-369 (2008).
McKenna, A., et al., The Genome Analysis Toolkit: A MapReduce framework for analyzing next-generation DNA sequencing data, Genome Research, 20: 1297-1303, 2010.
Marchini, J, et al, Genotype imputation for genome-wide association studies. Nat Rev Genet. 2010;11:499-511.
Gibbs, The International HapMap Project, international HapMap Consortium, Nature, Dec. 18, 2003;426(6968):789-96.
Ioannidis, JPA, et al., Meta-analysis methods for genome-wide association studies and beyond, Nat. Revi., Genet. 14, 379-389 (2013).
Yang, J., et al., Conditional and joint multiple-SNP analysis of GWAS summary statistics identifies additional variants influencing complex traits, Nature Genetics vol. 44, No. 4, 369-389, S1-3 (Apr. 2012).
DIAbetes Genetics Replication and Meta-analysis (DIAGRAM) Confortium, Genome-wide trans-ancestry meta-analysis provides insight into the genetic architecture of type 2 diabetes susceptibility, Nat. Genet. 46, 234-244 (Mar. 2014).
Moore, J.H., et al., Advances in Genetics, Computational Methods for Genetics of Complex Traits: Advances in Genetics, vol. 72, 101-116 (2010).
Pan, Q., et al., (2013) Epistatis, complexity and multifactor dimentionality reduction, Methods in Molecular Biology, 1019, 465-477 (2013).
Motsinger, A.A., et al., Multifactor dimensionality reduction: An analysis strategy for modelling and detecting gene-gene interactions in human genetics and pharmacogenomics studies, Human Genomics, 2006, 2:318-328.
Larsen, L. H., et al., Analyses of single nucleotide polymorphisms in selected nutrient-sensitive genes in weight-regain prevention: the DIOGENES study, American Journal of Clinical Nutrition, vol. 95, No. 5, May 2012, pp. 1254-1260.
McCaffery, J.M., et al., FTO predicts weight regain in the Look AHEAD clinical trial, Int. J. Obes. (Lond). Dec. 2013;37(12):1545-52.
Goyenechea, E., et al., Weight regain after slimming induced by an energy-restricted diet depends on interleukin-6 and peroxisome-proliferator-activated-receptor-γ2 gene polymorphisms, British Journal of Nutrition,(2006), vol. 96, Issue 5, pp. 965-972.
Hanne H.J., et al., Dietary management and Genetic Predisposition, Current Nutrition Reports, Sep. 2013, vol. 2, Issue 3, pp. 159-166.

* cited by examiner

Figure 3

SEQ ID NO: 1 - rs953211 (chr4 126351049)

ACTCTTCAGTAACTTGCAAGAGCAGACCAACAAATGGGCAGTTGGATCTGACAGCCCAGAGGCAGCAGAAAG
CTTTGGACGGAAGATAAAGTAATAGTAA[A/G]CATTATGCAGCACTTCAAATAGGATGTATCCACTACACGGT
GGGAAACAGTAATACTCCGGAGAACCTCTCCACACAGTTAAAAGGAAGGGTTACATCAC

SEQ ID NO: 2 - rs1509290 (chr4 126306772)

ATACCTTTATTTGAAAACTAAAATCAAAGTATCCCTTGATGTCATAGGATACTTTGAAATTATAGATAATCATA
GTTATATAGTCATAAATTGAGGAAGA[A/G]TGAGAGAGTAGTAGAAAAAAATCATCAAACCGTATTATTTCAT
GGAGATGGTTAGTTGTAGTCAGTATTTATAATTGATGGCTTTTTCCATTACTCTGGA

SEQ ID NO: 3 - rs1509289 (chr4 126308835)

CCTCTAATCTTTGGATTGTTGGAGGGGGAGGAAGAACTTGATATGTATTATTTTGAGTTGCCCCTGACAGATA
GCAGTATGGCATGGTAAGTGAGAATGT[A/G]TAGCTATATAGGGTAGGAAAAGGTATTAATAGATTCAGAGA
AATAAAACTCCCAGTACAAGCCATACAACAGATCAATATACATTAGCTTTTTACTCTTC

Figure 4 (SEQ ID NO: 4)

>ENSG00000196159|FAT4|4|126237554|126414087|FAT atypical cadherin 4 [Source:HGNC Symbol;Acc:23109]|HGNC Symbol|protein_coding GGGAGCCAGGACCATGGACTTAGCACCAGACAGGGCTACTGGCCGCCCGTGGCTCCCGTT
GCACACTCTATCAGTATCTCAGCTCCTTCGAGTGTTTTGGCTACTGTCATTGCTTCCGGG
GCAGGCCTGGGTCCACGGGGCCGAGCCGCGCCAGGTGTTCCAAGTGCTGGAAGAGCAACC
TCCAGGCACTCTGGTAGGCACCATCCAGACGCGCCCCGGCTTCACCTACAGGCTCAGCGA
AAGCCACGCCCTGTTTGCCATAAACAGTAGCACCGGAGCCCTGTACACCACCTCCACCAT
CGACCGCGAGAGCCTGCCCAGCGACGTGATCAACCTGGTGGTCCTTTCCAGCGCGCCCAC
CTACCCCACCGAAGTGCGAGTGCTGGTGCGGGACCTCAATGACAACGCCCCCGTTTTCCC
GGACCCCTCTATCGTGGTCACTTTCAAGGAAGACAGTAGCAGCGGACGCCAAGTCATCTT
AGACACCGCCACCGACTCGGACATCGGCTCAAACGGTGTGGACCACCGCTCCTACCGCAT
CATCCGCGGCAATGAGGCGGGGCGCTTCCGTCTGGACATCACCCTGAACCCGAGCGGCGA
GGGAGCGTTCCTGCATCTGGTGTCCAAGGGCGGACTGGACCGTGAGGTCACTCCGCAGTA
CCAGCTCCTGGTTGAGGTGGAGGACAAGGGTGAGCCTAAGCGGCGGGGCTACCTTCAGGT
AAACGTGACTGTGCAAGACATTAATGACAACCCCCCGGTTTTTGGCAGTTCTCACTACCA
GGCGGGGGTGCCTGAGGACGCGGTTGTGGGTTCCAGCGTCCTCCAGGTGGCGGCGGCGGA
CGCGGACGAGGGCACCAACGCGGACATCCGCTATCGCCTGCAGGACGAGGGGACCCCCTT
CCAAATGGACCCTGAGACGGGACTTATCACGGTGCGGGAGCCCCTGGACTTCGAAGCTCG
GCGCCAATACTCGCTTACGGTGCAGGCGATGGACAGAGGCGTGCCTTCCCTCACTGGGCG
CGCCGAGGCGCTGATTCAGCTGCTGGACGTGAATGACAATGACCCGGTAGTGAAGTTCCG
CTACTTCCCGGCCACCTCGCGCTACGCCTCGGTAGATGAGAATGCTCAAGTGGGCACCGT
GGTGGCTCTGCTCACCGTGACGGACGCAGATTCTCCCGCGGCCAACGGGAACATCTCCGT
GCAAATTCTCGGGGGCAATGAGCAGCGCCACTTTGAAGTGCAAAGCAGCAAAGTGCCGAA
CCTGAGCCTAATCAAGGTGGCCAGCGCCTTGGACCGCGAGCGCATCCCTTCCTACAACCT
CACAGTTTCCGTCTCTGATAACTACGGGGCGCCCCCTGGCGCAGCAGTCCAGGCGCGCTC
TTCTGTGGCAAGCCTGGTGATTTTTGTTAATGACATCAATGACCATCCTCCTGTCTTTTC
ACAGCAAGTGTACAGAGTGAACCTGAGCGAGGAGGCGCCTCCGGGAAGCTATGTGAGTGG
GATATCTGCCACTGATGGCGACTCTGGTCTCAATGCTAATCTGCGTTACAGCATTGTCTC
TGGCAATGGACTGGGATGGTTCCATATCAGTGAACATAGCGGCCTCGTGACCACTGGGTC
CTCTGGGGGCCTGGACCGTGAACTTGCTTCCCAGATTGTTCTGAATATAAGTGCCCGGGA
CCAGGGAGTTCACCCCAAGGTGTCCTATGCCCAGCTTGTAGTAACTCTCCTAGATGTGAA
TGATGAAAAGCCAGTATTTAGCCAGCCAGAAGGGTATGATGTGTCTGTGGTTGAGAATGC
CCCAACAGGGACAGAACTGTTGATGCTCAGGGCAACTGACGGGGACCTGGGTGACAACGG
AACAGTGCGCTTCTCCTTACAAGAGGCAGAGACTGACCGGAGGTCCTTCCGTCTGGATCC
TGTGTCTGGGAGGTTGAGTACTATTTCCTCCTTGGACAGAGAAGAGCAAGCCTTCTACTC
CCTGTTGGTTCTGGCCACAGATCTGGGCTCCCCTCCCCAGTCATCAATGGCTCGCATAAA
TGTGAGTCTTCTGGATATAAATGATAACAGCCCTGTCTTCTACCCGGTCCAATACTTTGC
TCACATTAAGGAGAATGAGCCTGGAGGTAGCTACATCACCACTGTGTCTGCCACTGACCC
AGACTTGGGTACCAATGGTACTGTCAAATATAGCATATCTGCTGGGGACAGGTCTCGGTT
TCAGGTCAATGCTCAGAGTGGGGTTATTTCTACAAGAATGGCCCTAGACAGAGAAGAAAA
AACAGCTTATCAGTTGCAAATAGTAGCTACTGATGGTGGCAATTTACAATCTCCCAACCA
GGCAATAGTAACCATCACTGTATTGGACACTCAAGACAACCCACCTGTATTCAGTCAGGT
TGCCTACAGCTTTGTGGTTTTTGAGAACGTGGCGCTGGGATATCATGTGGGTAGTGTGTC
TGCATCCACCATGGATCTCAATTCCAACATCAGTTATCTCATTACTACTGGGGATCAGAA

FIG 4. (SEQ ID NO. 4) CONT.

AGGTATGTTTGCTATCAACCAGGTCACTGGGCAGCTTACCACAGCAAATGTGATTGATAG
AGAAGAGCAATCCTTTTATCAGCTGAAGGTAGTGGCCAGTGGGGGCACAGTGACTGGAGA
CACTATGGTTAACATAACAGTTAAGGATTTGAATGACAACTCTCCCCATTTCCTTCAGGC
AATAGAGAGTGTAAATGTGGTGGAGAATTGGCAGGCAGGTCACAGCATTTTCCAGGCCAA
AGCTGTGGACCCTGATGAAGGTGTCAATGGCATGGTACTCTATAGTCTGAAGCAAAACCC
CAAGAACCTGTTTGCTATCAATGAAAAGAATGGCACTATTAGTCTGCTTGGGCCCCTGGA
TGTTCATGCTGGCTCCTACCAAATAGAGATCTTGGCATCTGACATGGGTGTCCCACAGCT
CTCCTCTAGTGTCATCTTAACAGTTTATGTCCATGATGTAAATGACAATTCACCAGTGTT
TGACCAACTCTCTTATGAAGTCACCCTTTCTGAGTCAGAACCTGTGAATTCTCGATTCTT
TAAAGTACAAGCTTCTGATAAGGATTCAGGAGCAAATGGTGAAATTGCATACACCATTGC
TGAAGGAAATACAGGGGATGCTTTTGGCATATTCCCAGATGGTCAATTGTATATAAAAAG
TGAACTGGACCGTGAACTTCAAGACAGATATGTTTTAATGGTTGTTGCTTCTGACAGAGC
AGTGGAACCCCTTAGTGCTACTGTGAATGTTACTGTAATTTTAGAAGATGTAAATGATAA
CAGACCTCTTTTTAACAGTACCAATTACACATTTTACTTCGAAGAAGAGCAGAGGGCTGG
GTCGTTTGTGGGCAAAGTAAGTGCTGTAGATAAAGACTTTGGGCCAAATGGAGAAGTAAG
GTATTCTTTTGAAATGGTGCAGCCAGATTTTGAGTTGCATGCCATCAGTGGGGAAATTAC
AAATACTCATCAGTTTGACAGGGAGTCTCTTATGAGGCGGAGAGGGACTGCTGTGTTTAG
CTTTACAGTCATAGCAACAGATCAGGGGATCCCTCAGCCTCTCAAGGATCAGGCCACTGT
ACATGTTTACATGAAGGATATAAATGATAATGCTCCCAAATTTTTAAAAGACTTTTACCA
AGCTACAATATCAGAATCAGCAGCCAATCTGACACAAGTGTTAAGAGTATCTGCCTCAGA
TGTTGATGAAGGTAATAATGGACTTATTCACTATTCTATAATAAAAGGAAATGAAGAAAG
ACAGTTTGCTATAGACAGTACCTCTGGTCAGGTAACACTAATTGGCAAATTAGACTATGA
AGCAACACCTGCCTATTCCCTTGTAATTCAAGCAGTGGATTCAGGGACAATCCCCCTCAA
TTCAACGTGTACTTTAAATATTGATATTTTAGATGAAAATGACAATACCCCTTCTTTCCC
TAAATCAACACTCTTTGTTGATGTTTTGGAAAACATGAGAATTGGTGAACTCGTGTCCTC
TGTTACTGCAACTGATTCCGATTCAGGTGACAATGCTGATTTATATTACAGTATTACTGG
GACTAACAACCACGGAACTTTTAGCATTAGCCCAAACACTGGGAGTATTTTTCTTGCCAA
AAAACTGGACTTTGAAACACAGTCTTTGTATAAATTAAATATAACAGCAAAAGACCAAGG
AAGACCTCCTCGTTCATCTACAATGTCAGTGGTTATTCACGTGAGGGACTTTAATGACAA
TCCTCCTAGCTTTCCTCCTGGAGATATTTTCAAGTCTATTGTTGAGAACATTCCCATCGG
TACATCTGTCATTTCAGTGACTGCACATGACCCTGATGCAGACATTAATGGTCAACTATC
CTACACAATCATTCAACAGATGCCAAGAGGCAACCACTTTACCATAGATGAAGTCAAAGG
GACTATATATACTAATGCTGAAATAGATCGGGAATTTGCTAATCTCTTTGAGTTGACTGT
AAAAGCCAATGATCAAGCTGTGCCAATAGAAACTAGACGGTATGCTTTGAAGAACGTGAC
CATTTTGGTTACAGACCTCAATGACAATGTCCCAATGTTTATATCACAAAACGCCCTTGC
TGCAGACCCATCAGCTGTGATTGGTTCCGTTCTGACAACAATTATGGCTGCTGACCCAGA
TGAAGGTGCTAATGGAGAAATAGAGTATGAGATCATCAATGGGGACACAGACACCTTCAT
TGTTGATCGTTATAGTGGAGACCTGAGAGTGGCTTCAGCGTTGGTGCCTTCACAGTTGAT
CTACAATCTCATAGTTTCAGCAACAGACCTTGGGCCTGAAAGGAGGAAATCGACCACTGA
ATTGACCATCATTCTTCAGGGCCTTGATGGACCTGTTTTTACTCAACCCAAATATATAAC
TATTTTGAAGGAAGGAGAACCCATTGGCACAAACGTGATATCAATAGAAGCAGCTAGCCC
CAGAGGATCTGAGGCCCCAGTGGAGTATTATATTGTTTCAGTTCGTTGTGAAGAAAAAAC
TGTTGGACGCCTCTTTACTATTGGACGACATACTGGTATAATTCAGACCGCAGCCATTCT
GGACCGGGAGCAAGGAGCATGTCTTTACCTGGTGGATGTTTATGCCATAGAAAAATCAAC
TGCTTTTCCCAGAACACAGAGAGCAGAGGTAATGATTTTGTAGTCATTTATTATTTGTTG
ATTTGCTTTTTAGAAAAATCATTCTCTTTATATTTACTCTCTATAATTGTTTACCTTCAT
TGTTTATTGTTAAATTTGTGAACAGGAACACCTAAAAATGTTCTGTCAAAGGCTAACAGA
GAGTTACATAAACTTTAGTTTTAATCTTGGTTGCAACTAAACAACAAACTTTCTTTTCAC
TTTATATTTTACTTTATAGCAATCACATATATAAGGTTAAGGAGAAATCTTTAGCCATTT
CAGAGGGGAAAAAATCCATATATCTAAGCTAAATTGCTGAGGTAATCTAAATACCACTCA
ATAAGGAAGGCTACCAGAAGATGGGCACTTTCAGAATTAAGAAGACCTATTCCAAAATGA
AGAGCTTTGGTAGGAATCAGCATTGTACCATAGCTCTTCAGGAAGAGTGGCCATGGAGGA

FIG 4. (SEQ ID NO. 4) CONT.

TGGGCTGACAGTGTACACCAGGACAGTATTAACTTTCACATCCTCAGCAGTCTTGGCAGT
TTCTTTATAGACAGTGACTAATTTTAATGTGCTGAGCCAAGTTTTGGAAGATTCCTGATT
TCATCTGCCTTAACATTTTAGACACTGTCTTCTGACTTAGGATAATCCTTCCTTTTCCCT
CTTAAATTAAGGCATGCAATGGGCTGTGAATAATCAGAGACTAGGGATTGTTTCTTGACA
ATACTGAGTTCAATGCCATGGGATAGATACACTCTGTTCTGTTTGTTGGTGAGTAAGAAA
TTAGTGTTTCATAGCATAAGCCAAAAGAATTCCAAGCTCAGCCTTCCCTGGAGTGTATTT
TAGGCTACTGCCTCCTTGTATCGTTGATTTGCTTTTTAATTGAACTACTTTCAATGTTAT
TTTGATAATCAACTAGAAATGATATAGCTATACTCCAGAAAACTCTTGTTTGCTGTTTCT
CAGTTCATTCTTTCCCTCCCCAGGCCCCTCAAAGACATTCTAGTGTCAGTCAGCCAAAAA
CACAAACATCAAATGTGGTTTGTGATACTTGGCAGTGACCCAGACACAACATGCAAGTGA
AATTGAGGCTCATGTGCTTGTTTTCTTGCTTCTTTTCTTTTTTGGGGGGAGGAGGTGGGG
ATTTTCTTTATTTTAAATGATAATTTATTATTATTATTATATATTTTTGTATCCTCTGTG
ATTTTTTTTCATAGTAGTTGGTTATGTCTATCTATGGATGGGGAAGAATATTTATGGCTT
AAAGGACCATATTAATTAGAGATATAATTCTAAGGGGAATTCAATTTTATCTTTACCTAC
ATAGCACTGAAAGGATTTCTAAGCCAAATAACCTCTTTTACCTAATTATTTAAAAAATAT
TTTAATATAGGGCTTATATGTTGAGCTATTTGGTGTAGCTCAGGCCATGATTTATATGTA
ATTGAATTTTGATTTGAAGTTATCCATCTTCTAAACCCACAATCCTCTCTCTAACTTTCT
TCTCTGGAATGAATACTTACATGAAAATATTTGATTAGTTTGAAAACCAAAATATTGATT
GAAGGCAGGAAATTAAGTCATTCCAGACTTTAGATGAATTTGTTAAACTGTAAAACAGAT
TATGTTATTAGATGCTGTTGTTTGGTTCAGTGTAGTACATTTTATTAGAATACTATGGAG
AATGAGAATAAATGCTCAGTTTTATCATTAGATTTATTGTGTCTTTTTTATTTACCCATT
AGCTATGCAAAGATTGGCTTAGCATGAAAGTATTAAATAGTGCTGCCTCTGCAATAGGCA
AGAAGATTAAAAATGTTTATAAGTAATTTTGTTATTAATAGGGGATGATTTGTTTATTAC
TTTTTATAAGTCAAGTAACACCAATATGAAAAGTTATCATATATACTATGTTCTATTCAT
TTAAAAATCTGGGGAGAATTCAATGTGATGATTTTTTTAATTAAAAAAAAGTCAGCATAT
CTTCTGTGAACTTAAGTGCTGAAATTGTAAACCCAATTTGAGTTCTCAAGATCCAACCAC
TTTGAAAATGAAAAGCAAATGTGTTTCTCCAAAGAATATTGAAAGCAGTGGTTGTGAGCT
AGAATTTCATATTATTATTGGTTGGATTTTTCAAGTGTATACAATAAAGTGCTGTTTTCC
TTCTGCTCAAACAATTAATTTACTGTGATTCTGCAAAAATAAGTTATACATTTCCTCTTG
TTATCAAAGGCGATTTTTAAATTGTTTGTTTAATTGGACTTTGTCCAGCGCATTTTAAAA
AATTATTCATGTACACTGATAAGAGTCTGGGTTGCTTACTCAGGTTTCTGGCAGAGTCAT
GCTGATCACATTCCATGGGCAGGCAGAGAGTCAGCGGGTAAAAGAGAAACAATTTCATCT
GCATTCTTTTCCTAGCTCTGACATTTGGGGTAAGAGGCTAATGACTATGACTCTGATATT
GTTCATTCCAAAGATGTGTCCAGTTATACACCTTTACTTACGCTACTTGTTATATCCAAA
GATTTGGCATTGGTAGTAATGTCATTGAAAGATTGTGTTTGGGTTTCAGACACAAGATTA
ATTACCTTTTTATTTTGTCTCTTTATGTTCTCAGAAGAGCTTAGATAGTCTTGATTATGT
TAGAATAGGCCATGTAAAGTTTGTGGCATTTTTCTAGGTTCACCAAAAAATAGATATATG
TACTTCAGTAAGCATTTATCCTTTAATGTGTATTACATAGGAACATGCAACTTAGGAACG
TGGTTAGACCTCATGATGGTCAGGGGCTTGTTTTATTGGTCTTTGTTATTTCAGACCGTG
GCATATTACCTGATGTATAGTAGGTGCTCCATACATGTTTGCTGAATAAGATGGTAGAAG
ACCTAAGATCAGAACATATGTCTTTATAACTTGGGAATAAATCACCAGAGAAAAGCTGAG
GAAATGAAGGAAGTTAATAAATCTGATGCTGCTCATTAATTGAACTCAGGTCAGAGCATA
ATAATTATCTCTGCTCTACAAATGAATTGATAACTGTCAGGAAACTCAACAAGGAAGAGG
AATTTACGTGGGTGTTCTGATATGGAGCTTAGTGTTTAAATGGAAGGAAGCAATCTTATA
CATTCAGGTAGTCACCAGGCCATAGTTCCCAAACTTGCTACATTCAGGACCCCTTTATGC
TCTTAAGAATTGTCAAGGACACCCCTGGAGACTTTGTGTAAGCATGTCTTGTCTATTGAT
ATTTACCACTTTTAACAGTACAACTGAGGAAATTAAAAATATTTGTTAATTCATTTTAAA
ACTACATTATATTTTAAATATATAACATGTTTATTTTGTTTTAAAAAAGTTTATTTTTTC
TAACTAAAAATTAAAGAGTGGCATTATCTTACATCTTTACAAATCTCTTTAATATCTAGC
TCAATAGAATACAGCTGGATTCTCAAATCTTCTTGGGCAATATATTGCAATATGTTGTGT
TTTTGGCTAAAATATACAAGCAGAATCCATCCTTACACAGATATTTTGAGTGGGATAATA
GAGAAATAGTTTGCCTACTGCATCAGAAGTCCACAGTGGCAGTTTCTTAAGACTTACTTG

FIG 4. (SEQ ID NO. 4) CONT.

CAGTGTGGAATATGAAACCCTGTCAGCAAACTTTTCATAGTCTGTTACATAAAAATACAT
TTATCTCGCATTCGTAATGATTTTTTTTACCTATTCCTGATTTAGAAATATCAGGCATT
GATCATTTCAAAATTATTGGTGTAACTGATAAGGAATTTATCATAAAAGTCTTTAATATA
TGACTCTCAACCTGTTGGTGATGGTTAGAAGTTTTCCAAATTTGAATTTTTACTCGAAAG
CTCAAATTTCACTATTAGTAACATATATTGTTGTTTTCCTGGAAGTGTCAGGCTTCCTTT
GTTCATGATAAAAAGAAAAGATTATGCATACTCAAATATTTAAAAAGAAACAGTTGCTCT
TTCGAGTAAAAATCGTATTCCACAAATCAAGTGGCTAGTTCAGCTTACAATTCAATTACA
CATATGCATTTCTTTGAGAAAACCACAATACCTAGGTACAGAGTAATGGGTCTTTGTGCA
CATATTGCTTTGTGTCACACAGGATATTGAAAAGACATCAAAGTTGAGTCTAGATTTGAT
AAAATTAATACGTTTTTTGTTTTCTCAAGAAAACTTATTTACCTTTTTAAATGAAATAGT
TTTGTTTGTTTGTTTGTTTTACTGTGAGTATGTGGTGGTGAAGAACACAATTACTGCTAA
AGTACTTTGGATCTACTGCTTTGATTTGTGCTAAAGTACCACCAGTTTTACCCACCATTG
CTTTTGCACCTCTAGCATAAATGCCAACACAGTGAACAAAGGCAGAGGATGGTTTGCATT
ATCATGTAAACAGTGTTGATTTCCCAGGACTCCTTAAACAGGTCTCTGGTTTGCATGGAG
GTCCATGCATACTCCACAGTGAGAGAACCATTGGTGTGGGTAGTGAGATTTTGGCAGTTC
AGTTAACAACCAGGAAAAAAAGAGCCACTCGAAATAATATATTAAAAGTATGTTTGGAAT
ATTAGGTAAATGGACTATGATTCATTAATGATTACAAATGAGTTTTAGCAATCTGATAAT
AAATTAATTTATTTTCACAAGAAACTATTAAGATTTCCAAGAGAAATGATGGAGACATTT
GTGAGGTCAGTTTTGGATACAAACGTTAGAAATGATTTTCTTTCACAGGGTTTTGAATCA
CAGTAGTGCACCTTAGATTAAATGTCTGTATATCTTGTGTATTGAACCTCACAAGCAGAA
TACAGGCAAGAGAGCTGGATATATAATAACTGTTATTATTATAAAATTTATTGAATATTG
CTATGTTTAGACATAATGATAAGTGCATAGTGATAAGTGCATTTTTAGGGATTTTATTTA
ACCCATACAATACTAATATCATTTGCATTTTGTAGCTATGGAAACTGAGTCTCAGATAAG
TTAATAAGTCGCTTAAGTTCATATAGATAGAAAGAAAACCATATCCAGACTTGAGTAACT
TCACAATGCATCCTCATAACTACTCTTCTATCAAGCTGGATCAGTCTGTGGTTTTGGTTA
AGAGAAAAGCTCTTTGCCCTATAGCTATGATGATATATGTATGCTTTTTAATAACTTTGT
TTTCACTCTCTGATTTGTTGCTTAAAAAGCATTTAAGGCCAGGCAAAGTGGCTCACACCT
TAAATGGGAGGCCAAGGCAGACAATTCCTTGAGGCCAGGATTTTGAGACCAGCCTGGGCA
ACATGGTAAAACCCCATCTCTACTAAAAATACAAAAATTTGCCGGGCATGGTGGTGCACG
CCTGTAGTCCCAGCTACTTGGGAGGCTGAGATAGGAGAACCACTCAAACCCTGGGAGCAG
AGGCTGCAGTGAGCTGAGATCATGCCATTGCACTCCAGGCTGGGTGACAGAATTAGACTT
TATCTCAAAAAAAAATTCATAAGTATTTTTATGTATTGTGTAAAATAAAGGGAAACAATT
TTTGCCTACCACAGCTAAGGCCCTCAGCAGATCGGTTACATCCCTAGGCATCATTAGTGG
TGGTAGCAAGGAGCCTAAATTGAATTAGGAAGACTTCCAAGGGTTTCTAGAGCAGGGAAG
AAGATGAGAATTTGAGAGAAGGGAGCTGAAGGCAAATGGAGAGCAAAGGTAGATGAGGGG
CCTCTTCTAACCTACAGCACTATTCACTTTGGAAGCAGTCACTGGAGTTTAAGAAGGTGG
AGAATTATTTTTGAATTTTTAGGTGATAAATCATCTTCTTTGGAATAATGATGGGGTTGG
AGTGGATGGAGTGTGAAGATTATTTTAAATAGGAAAACATTTTACTGCTTCCTATGTGTT
TGAAGTCAAGAGTGTTTCTTTAAAAAACAGCCTGGGATAAATTTTTTGATTTTGTTTCTT
CCCTATTGGTATGTTTTTAAATGTATTGAACAAAATGCTGTGAATTAAAGGGCTTTATAA
ATTTTTAAGATGGGTACAAATGTGTATGACAAACAGGATTATTGATGGCTAATTATGTTC
ATGCTGCATATTTTATATATATCTTCAGGATGCTTGATTTACTCCTGCTGCTAGATTTCT
ATAGACATAACTCATCTTCCAATGAATTTACAATTTATTACTTTTTTATCTTTATTAAAA
CCCTAATGATTTTAATTCTTTTTTGTTTTATTCAATTTTGAGGAATCTGCTCTAGGAATA
GTTTTGAAAAATAGTTATTTACTTAGAATTTTGTGGAATCAATTTTTCATTGCATTGTCT
GCAGCTTGCACTTTGTCATCATTAGAGTGAAAAACTGCCTAAGAACCTCATTAGTTGTGA
GGGACTGTTGCATTAGTGACTGTAGCAAACTGCATAGGCCCTGAGGTGGGTTCTGTATTT
CAAGAATTAATAAATCTAGGCCCAGCGCTTTATAAAACCCATAAAAGTAGGTGGTATTCC
GAATTAGGCACTCGTGAGTGGAAATAGGAAAAGAATAACTGGCAGGTAATGTGGGTCAAG
ATGAATATAAAGTGTCCAATATAGAATATGGTAAATATTTTCTAATAATTTCAAGCTTTA
TGTAGTCTGTGACAAAAGTAGCCATTTTAATAGTATGTTGACTGAGAAGGAGAGTATAGG
GAATGCAGACAGGTGAAAATATTCTATTAAACAAACATTCTGTATAAAATACACACATGT

FIG 4. (SEQ ID NO. 4) CONT.

AATTATATATTAACACGTATGCCCCCATTGTACAAAGACTGTTGGCTTTTCTTTGCTCTT
AATATCCTGAGACAAAATTGGACAATTAAGTCATGAAGAGGAAACAATCTAATTGGCAGA
TAATTTATATGTGGTAATTAAACAGTGATTATAGGACCACAATCTTCTTCAGTTTCCAGA
CGTGTATGCATTTTTAAGAAACGATCAGTGAGTAAAAACCAAAGAATTTTAAGGCTTTGA
AGAAATGTTGAAAGACATTTAGAAACATGCTTTGCTACTGGCAGGTGGGAGCAAGTGGCA
TTTTTGATGATTGTTACAGATTATTTGACATTTCTCTAAGGCTTTTTATCATTCACAGAT
TCTAACATATATAAATCGTTTATGTTATTGTTAGACACTGGTAAACAGTCTTGCCAGGTG
CTGTCTTGCCTTTGCAATGGTTCTGGAGGTAGATACAACATATCATCATTTGACAAATGA
GAATACTGAGGCTCATGGAGGTTGCTTATGGAGTTGGTTTATGGTGGAAGCAGGATTTAA
ACCCAGCAGTCTGCCTCTGAAGTCTGTGCATTTAGTTCCAACACAGCACTAACTAATGCT
ACTTGTAAGAATGATTATTTCTATACATTTGTAGACATAATTCTCACCATGTAAAAAGTT
GTTTTCATATTTCTATACTTGTTCATGTTAATGATGAAAAAATATAAGATAAAATGAAAT
TTTGGTGATGAACCAGTAGTAGGATTACTTTAGGTCCCTATCAATCTTTGTTTAGGTCCC
TATTAACCTTTATAATCTTTATTAACCTATAATCTGTTATTTCTTCATTTTGCTTTCTAA
ATCCCAAGGCAGGAATATATTTCCATTCTTTCAGTTGCTCATTTATTTTCTTCCCTTTGC
AGCAAAACTTTTTGAAAGAGTTGCCTGTACCTGCATTTTTTCTTCTCATGATCTCTTAAA
TCTACTCCCATCAGACTTGGCCCCTGCCACTCCAGTGAAATTGCTCTTACTGAGGCCACT
ATGATGGACACATTGCTAGATCCAATGGCCTTTCTCAATGCTCATTGTAGCTAATCTAAA
GAATATTTGACCTAGTGGATTTTACTTCCATTAAATGCTTTATTCGGTTGGCTTCCGAGT
CATCATATTCTGTGACTTTTTACCCTTTTTTATTTCTTGGACCAATCACTTCTCAGCCTC
GTTCGCAAGCATCTCACCATGTCCTCAAACTCTAAGTGTTGGAACATCCCTAAAGCCAGT
TCTTGCAGTCTTTCTCTTTTTACTCTATACTCATTCCCTTGAGGATCTCAATCTCATAGC
ATTAAATGACATATATACACTGATGACTCCAAAATTTTGCCTCCAGCCCATATGTCTTTT
CTGAACCCTACATTCGTATAACCAATCACTTATTCATTGATTAGCTTCCTAACTGATATT
TTAAATTAACATTTTTAAATCTGAGCTGCTGATATTCTCCCCAATAAAAACATATTCCAT
CTTCACCCATCTTCTTTTCAGTTGATGGCAATTCCAACCTTCTGATTGATCAGGTCAAAA
ATCTTAGCGTTATCTTTGACTCCTAACTTTCTTTCTCACCCTACTTACAACCTTTCAGTT
GATCTTGTTGGCTCTGTCTTCAAAATATTTCATTTCAATATGATCATTTCATGATAATTT
CTCATCATGCTCACTGTTAGTAACTTGGTCTAAGACACCATCATTCTTCCCTTGGATTAT
TGAAGACATCTTCTTGTTGATTTCTGACAGTGTTCCTATTGTTCTCTTCTCTTACTTGGC
TTTACCTACACTGGCTTCTTTCTATTCTCGGAACTTGCTAGGCACACATTAGCCTTCGGG
CTTTTGCCTTGGCTCTTCCTTCTGCATAGAACACCCTTTCTCCAGACATCAGCCTGGACA
ACAACCTCCCATACTTCAAGTATTTTTTTTATCTCACATTGCAAATTAGGCTAAATCTT
CCTTTAATAACTTATTATTGTAACTATCCCCTCATGCTGCCTGATTTCCATTGCCTTGCG
GCATTTCTTCATCTTCCTCTCCCATAAGGCTTACCAGCCTCCTTCACCAATTTCTACTTA
TCTCCTCACATGTTAAATGTTGGAATGCCCCTGGAACTAGTTGTTGAATTTTTTCTCTTT
TTAATCAATTTCACTGAGGAGCTCAACCAATCTCATTCCTTTATATAAAATATGAACACT
ATATATGTATAGGGGTGGGTGTGAGTGATATAATTTATTGATTTATAATGTTGATTATTG
TTTGATCTGTCTTCTTCCCACTGGAATTAATTTCTACGAGGGCAGATATATTGATCTGCT
ATGTTCCTTAACATATCTTAAGAGTCTAGAACATTACTTGGAACAAACATAGTAGACACA
ATATAAGTTTCTGTTGAATGACTAAGTGAATGAATGAATGAACTGGCATCTCAGCCTTTG
TCCTTGTCCCCTTCAGTTTAGTCTAGCAACCAGAGTGAGAGTGATCTTTTAGATCATTTC
ATTTGCCCAAAAACTTCCTATTTCACTTATAGTAAAAGTCAAATTCTTACAATGACCCTG
AAGACCCTAGTTGACTGCTCTTATTAGTTACTGTTTGGACCTCTTTTTTCCTGATTCCCC
TTGCCTGAACTTGTTCAGCAACCATCAGAGCTCCAGGCCCCAGCCTCAGGCGCCCCTCCT
TAGGGTCTTTGTGGCAGCTCTGGCCTGGACTGCTCCCTTCCTCACTTTCCCCACATCATT
TCTGAGAGTCACCTTGCAAAGTCCTTCTTCCCTCCAGTTTTCGTTTTTCTCTTTCCTTCC
TTTTGTTTCTGCTTTTTTCTTATCATCACCCGACATAACACATATGTTACTTGTTTATTC
TGTTTATGGTGTGCCTTCCCTTTAGAATATATGTTTCATGAGGGGAAAGCTTTTCATCTG
TTTCTGCTATATGCACAGCACCTACAGTGTGGCTGGCTCTAGGCAGATGCTCAGTAAATC
ATTGATAAGCTAAGGATTTACTGTTGATAATGCTGCAAATATGCTGCTTAAGCTTCAGGA
GCTCAACCAGTGATGCATGCTGAAGTAGGGGAGTCATTTTTCATCTCTTAAGCCAAGACT

FIG 4. (SEQ ID NO. 4) CONT.

TTAGAGCCTCTTCTGAAATTAGGGAAGTTAACTGATTGGAAAAGACTGGTTTTCCTTCAT
AAAAAGATAGTGGCTACATGACTTGATTGGCTAAGAACGTGTAACCCAAACTTCAGAAAC
ATTTATGGTGTCTGTGAAGGAAAGTGGGACCACTAATGCTATAGATGTTTTGGTAAAGTA
GAACATTTTAGAAAATATATATCACAGTGTATGCTACACCATCTCATGTCTTCTCATCTC
CTTCAACCTTATCTAATTTTGCTTTAGAGAGCAGATCTTAAGTTATTGTTATCGTAAACC
ATGTTGTTCATCAGAAAACAGGTGAATACATAGAAACTTTGAAAACATTACTACTTTTAA
TATTGATAACTTTAATTACTGTCATTCCTTTTTTCTAATTTACCATCCTTGTTCAACATT
TCACATCAATAATATCAGTAAACTTGATTTTAACACGCAGCAAAGAAAATACTGCTGGAC
AATCCCTCTTGCCTTAAGTTTAGTTGAAAGAATGCAGGCTTTTGATTTAAGAGAAGCTTG
ATTCAGATGTTGTCACAGCTACTCTCAGAATCTTATTTTCCTCATTTGTAAAATGGTAAG
GATAGCCTACTTCATAGCTTCTTGTGAGAAAAACAATGGCACTCTATAAAGTTTATTAGT
GCTCTTCCCCTTTTTCCTCAAAATATAGATCTGCACAGGACTATTAACATTTAAGAAAAT
GTCTTTCTATTTTTAAAGTATTTTAGAGTTCCGTTCCATTCTTTTTTTTTTTTTTTTTCC
TTTCTCAATTTCCTCAACAAGCCTGTAAGGAAGTCAAGCATTTTTATGTTCATTTTAAGG
AAAAGACACAAGGAATTTCATTATTTCTGTGTGGTCACAAATCTAGACTAGCACCCAGGT
TTATATGACTTTGGTCAACATGCCTGACATTAAACAATACTGCCCAGTCTGGTGTTAATG
CTATTTTTCATCCACTATTGTATTGTTGTTGACATAATTTAGTAATAGTTATAACCCCTT
AAGTGAAGTTATTTATGAATTGTGAAACTTTTTTAAAGGTTTAGTTGCTCAGGAAACAAA
CAAGTTAGAATATTTGAATATTCAGTGTTTGTTTCATTTTCATTTGATTTAATTTGATTT
GATTTCATTCAGTGTTTTGTTTCATTCAGAGAGAAGCCTTATCTCTGATTTAGATGAGGG
ATATTCATCTCTCAATTTTTAGTGATGGTAGTAAAATATTGACTATTATGGAATTGTGTG
TGTTTGTTTGTGAGCCTATTTAGAAATCGTTTTTTGTCCATGACTTAATGCAGTTTTCTT
AATTGAGGTCGACTTGGCTTCTCCAGTCCAAAAAAGGGAAAACTATCTATCTTTCGAAAC
TACTCTTTAACAAAACATATAAATTCTGGTAACTTTTTAAGTGAAGATTTTCTAACTAAT
GATTAAAACGTTTTCCTGGACAGAAAAGTATTTTCTTACTTCATAAAATATTCAAAATAA
GCAAATACACAAAGAAGATGGGCTTTCTTCTGCTCGGGGTAGTGTTTTATGGTATATACA
TTTTTGTTCTTTGGTTAAAATACTTACTCTTATTTTTATTTATACATTGGCTTCATTCTA
CAATAGATTTGAAGCAGTTTACAAAAGTATATATACAACAAAGAGATACAATATTTAAAT
GAATCTCTAAGTAGTAAAAATAAGTGTTACTAAAAATAATCCTGAAATATATAAGATTAG
CATACAGATATATGTAATTTAGGTAACTCATTGAGTTTATGTTTAGCTTTCTAAAGGCCA
AGTCAAGCAGAGAAGCAAGATCAGATATGTAAGTCATGGTGCTCTTATACTAAACAAACA
CAGGGTAAACAAAGGAAATACAGATTTTCTAAACCCAAGGAACTTAATAGAATTCGTCCC
ACAGATGCTCAAAACAGACCTATTTTAAAGTGATGATTTTCTTAATGGCATCTTCACTAG
TTCAATGACAGATTTTTAACATCATTTTAATGTGACGTCTTTTCGTGTGGATTTGTGGCA
AATTGTAAAAGTGCAGTTCTGGCAAATTATTTATTTATGGATCAAAAGAGATTCCCCATT
GATAAGTGCTTTTGTTTAGCTTTATTTCATGAAGTGGATTAATATTTTATAACCAAAGCA
AGAATATCCCTACTGGGTTTTTTCACATTAGCATATCTGTAGCACATCACAGGAAAAATC
TAACTAGAGAGGTTTTCTGTAAAACTGTAGCTTAATCCTTAAGGAGACTTTATTTTAAGC
TATGCTGCAGTGATTAAAATGCTTAGCACCAATTTCTAGTAATCTGTGTCTTAGATTGTT
TCCATTTTTCAAGAAATAGAAACAATCATCCTGTGAGATAACAAAATTTGCTATTGAAAA
CATCGGTGCTGTTTAAAAATGTCATATATTTTCAAATATTAAAAATATAAAAGAATAACT
ATCACATACACTCTAACTTTTCCTCTGGTGGAGTCACTAATATCCTAAGGCTAGGAAGGT
GAGGAATCAATACCAAGTAAAGGTCAGAGCTCTAGGATGGGAATGGGAGTCTCAGGTTTT
TAATTCTAGGACAGTCATTTGACACCTCATTTTCAAATGATAAACTGAAACAATAGGGTT
TATGTGGCCCACTCATATAACACACTTAGTTGGCAGAGGAGTCCCAGATTAGAATTTCTT
ACTTACTGAGTATAGTCAACCTATACTCAGTGTTGACTCCAGTCCTTAAACTCGGAGTGA
GAAAAGGAGGCTACAGCTTCCTCATGATCTTCACATCTCCATCAGCATCCTCCCAAAGAC
ATCTCCCAAAAACATGGAATTTAAAGTAAAAGAAAGATTTTTTGTTATGCAAATGCGGCT
TCAAGATGAAGCCTTTGGACCCCGATTCTTGCTCTTTCCCACATGCCCCCTCACCTCTTC
CCATGCACCTGTCCCCATCCCATCCATATTGTTGTCCCTAAATCCCATTTGCAAAGATCC
TGGATCCACCAACAGCTATAACCTTTCTTTTTTCATGACACTGCTTCTAAATCCTTTGCA
CAATTCTGAGAAATTGCTTCCTATCAGGTGCTAATGGCATTTAACCTTTTAGGGATCTCC

FIG 4. (SEQ ID NO. 4) CONT.

TGTCTTCAAATTAAAAAATAATAAAATGTATTCAATTCTATTGTCATGTTAATTTCAAAT
TTTTTAACAATTTTGAGATGTTTGACAGTTTCAGGAGATTTGCTTAAAACAAGACATGTA
TTTCATATATTACTTTAATACCAAAACCAATTGTGATTATGTCTATCTAATGGCAAATTT
GAAACATAATTCAGAGTTATTAAATGTTACTTGAATTGATTATATTATATGGTCATAGAA
TTTTCCTCACCAGTAGCTGTATGGCAATCCTTTAATTGCACAAAAGTTAACCCATAGTCT
CTTTTTTTTAAGATAGTACTTTAAAATTTCCACTAAAAACATTAAAATACCAATTCATGT
ATAGTATAGCTATGTGGAACAGAACAGCCTGTGTTGCAACGCCAGCTTAATATTTTATTA
CTTCACATAATAAAATAGGGAACGTATTTATCCACTGAGGTTGTAATTAGTTACAAGTAA
TGAATCTTTAGTGTTCTAATTCCAGAGCCTGGCAGATTTAGAACACCAGTTGACCCTGTC
TTGCTGGAAAATGAAGGAAGTGGGAGTAGAATTTTCTCTGTAGGACAAGACAGCTTTGGA
TGGGAGGGACAATAGAAGCTTGCCAAAAACATGGGTCAAACTGAACACAGATGGCTGTAG
CTGATAGAGGTGTCTATTATTGTGTTTTCTTCTCAGCAGTTTTCTCTTTGTTTGTCAGTA
TTTTTATACTTACATGAAGAAATTTTGTTGCTCAGCAACCAAGAGAAAATATACTAATAG
AATCCATTTTTGTTGGAAAAAAAAATGTTGGTGGTAGATGTTGATGATGGGGTTGAGGTAG
TGTTGTGATTGAGCAGTATTAACGTAGGAGTAGAGGTGATTTTCTCGGAGTGCTGTTTAT
TATAAGTGTCTAAAATTAAATATATCACATTATCCATTTACTGCTTAGCTTGCCTCTGTC
TTACACCTCCAATACTATTTGGGAAAAAAAATGGCCTAAGTAAATGTATTCCATTAGTTAA
TAATATAATTTATAATACACGGAGGAAACATTTGAAGAAATAAAACTATAATTTACATAT
TTTTTATAACTTCAGTGTTTCCTAAAGTCAATTTTTTAAGCTTCATTAAAGGATTTCATG
TGTATTTCATTTTTTTTTTCTGGAGGAGTTCTATTTATTATTCTTGAGTACATCTGTTTT
CTGCATGGTGAAATATTAAAATAAATATATATTTGAAAGTCAGAATAGTTTTGTTCAAAT
ACTGGCTTAACTTTTCATGCTGTGTGACTTTAAGGGAGAAGCCAAACTTCTCTGAACCAC
AGTACCTTTATCTGTTAAAAAAAGAGAATTCCAATCCCTTAATAAGTGTTGTGAGGAAAA
TGTGCAGTACACATAGCACTGCATATTTTCCTAAAAGACTGTTTGATTTACTTTTGTTGA
TGCTACATTCAGTTATTTACTTCTTGTGTGGTCCAGAAGGCAATGATAAAAAAATGTAAA
CAACTCCTGGTCATGTAAATAGCTACTGTTCATACAAAAATTGTGATGACATTTTTAATG
ATACCACATAAAGGGAAATCAAGACCAATCTTACAAATTCTGTTTCTTGGTTTTAAGGAA
ATTATTAAGGAACTGCATTAAAAATAACTCTGTGGTAATTTTCTTCATTGTACTGTATCA
GGTAGAAAAATAATTTTTAAATGAGTGACTAGTGAGCCGCAAGACATAACCAAGAACAGA
AGGGTTATTAGCTAACAAAGGGAAGCAGATGTAATTTTTAAACATTGATTTTGCATTTAT
TTATTTTAAGTAAACTACAGAATTTTTAAATTTTAATATAATGCAAAGGTAGAGTAGCAT
TTTCCAATTTATACACTATGTTTTGATAAGTGTCAGATACTGAAGTTATATTCTAAATAT
AATCCACCCGCCTAGGGAAACGAATAAAAATATAACCTTTGTTAAAAGATAGGGTAAGTG
AATTGTTAATGACTATTCCAGAAGTGAGACTTCAGAACATAGTTTGGCTCTAAAAGACCT
TTCTTTCATTTTAATATTATATTTGAAACACTTAGTAAAGATAAATTTTTAAATGTTCAA
TGTCTGATCATTGTAAGCAATGTCATTTTGTGAGCTCTATTTCTGGAACTAGAAAAATTA
CTTTGAAAACTGTCCATTCTGGTTGTGCTTTTTTGAGTAAGTGGTCTTAGTTGTATTTTA
ATAGAGGAAATGAAACAAGGTACCACTCTTTTAATGTATTTATTCTGATGTTGAGGCGAT
ATGTTAGAACAAATTTAATTATACTATGACTATGAAAACAAAATTAGGCAGAACTAGAGT
GATAGGCGGGAACTCATTGTTGATTTTCAACTTAAATATCATATACTTATTAATATATGC
ATTACAAATATATCATTTAATTATCTCAACAACTCTAGAAGGTAAGTAATGGTATTTCCA
TTTTGTAGATGGAGTATCAAGGATCATGAAATTGTCAGTATATTGTTTTGTGGTAGAGCG
CCATTTGAGTTCATTTGGTTCCAAGGCTTTAGTTCTTTCCAGTACACTTCACTGGTCTTC
AATTGTTATAAATCACAGCCTGCTAATTTCACAGAAAGGAGATTAAAAGCAAAAGCCATA
AATATAAATACGAAGTATTTGAATGCTGATCTATATCATAACTAGATCTTTCTTTTTTGT
TTGGATTATAGTGAATTTTTAAACTAGAAAATATAAGCAAACAGTATTTTTGAAGGATGT
AATAACCACACTCCAAAGTACATCAATGAATCATATTAAATTAACCATTAATTAATCACA
TTAAAAGGAAAAGCATACTTAGGAAACACAGAAAATTTATTTTTTAAGGGTTGAACTTAT
AATTAACTGAATTAAATGAGATGTTAAATTAACTTTGAAAGGCACATTTCGATCACTGAT
ATACCTAAACTTGCCTCCTAATTAAATACTTAAAAATAAATGAATCAACATTTGCTTTTA
ATAATGACCCTGAGAGAAGGAAAATATAGAATATTTAACTACAAGTTAATAACTAATAAT
TAGTGTAGATTTAGTAGTAGAAGAAAAGGTAAGATGGAGCCAATACTGTAACTACATTAT

FIG 4. (SEQ ID NO. 4) CONT.

ATGTTAAAACACTTATGTAAACACAGCCAGATATAATTATATGGAGGTTGCTTTAAGGAT
TACTGTTATTACATATAAAATTTTCCTTACAAGAGTAGGTGAACATAAAAAGACTATTGA
ATTCAAATCTAGGGAACTTGGGAAGAAAAATAAAACTCTTTTAGAGAGTCTATGTAATAC
ATGGGAAGAGTAAGGACTTTTGATTCAAACACACTTGGGTACAATCATGACTTGGGGAAG
CTGTCTTCCCCAAGAGTATCACAGTATCAGTTGCCTCTTTTGTGAAATCTATTTCACAGA
GCAGCTTTGAGAAACAAAACTTAAAAATGCACCCATGATACTCACCCAAAATAAGTATCC
ATTCACTTCTCTCTCATTTTCTTCATTTGCATAGATGCTGGTTTTGTCATTCATCAGACA
AGATTGCCAGGATATAACATTGAGAACTATGTAAATGACACTACATCTTTTCATCCCTGT
TCTTAGATGAAGATAAGTTTGAGAATTTTCTTGGGGTGTTTCAGTAGAGAATTAAACCTC
CTTAGGATTTCTGGTTTTGTTCTGAAATGCAAGATGGACATGGAAGCAGAAGGGACATTA
ACCTGTTTCTCTGCCATTTGCCTGGATGTATATATTTACATTGCTAAGATCTTGGTTCTG
CACACTGTCATTTAGACAATAACTAAGGATTTCCGAATTAGAAGGGATAAGTGTTAACTA
GGACCTTGTTCTTATGTTTTATTGTGGATAATGTGTTGGCCTTTGTACTACCTTCCCATC
CTCAACTATCATTCCAGTATTCAATATGCGAGCTACAGTGTTTCTTACTGGGGATTTAAA
TATGCATAGTTCAGGTCAGATACACATATTTCAAATATGCATGGTTCAAAGGTAAGCAGT
TACCTTTAACAGGATAGCTTCTATTTATAGCTTTTATCCATGCCCTCAAGAGACTAGCAA
TCTAATAGGAAGACAAACATCACATAAACTATTATCAGAAAATCTAAAAGATTGCTGTGA
TGAAAAAGTTTCACCAGCTGATTACGGTAACTGGTTTCTGTAATCTCAACACAATTGAGA
TTATTTATCCTGTCTGAGCTTTTGGTTTTTGCATTTCATAAGGCTTTGTCTGCATATTTT
AAACTATTGGAAATGAATTTTTTTTAATCTATGTGCAGAAAAAATATCAGGCAAATTATA
CCCACCTTTATTCTTCTGTTTTTAAAATACTGAATATGAAATATTACATTCCTATGTAAT
TAAATAGCGTTTGATTTAAAGCATGTGGACCTTGGGCCTCATCCAAGGGATACTCTAGTG
TACCTTGGTCTGAGGCTGCTTATCAGTCCTGATGTGCTTTCCCTTTCCTTCCTGTTTGAA
TACAGGTCCATTCTGTGCTGTTACCATCTCTGTCCTTAAGAGCTTCCTTTGCCCTAAGAT
GCCCCGATGTATGTTTGTATTTGATGACATATTTTTACATCCTGGTCAGGAAATATAATT
ATTCATCTCTCTACAACATTATCAACATTATCTCCTTTTTTTTGAGACGGAGTCTTGCCC
TGTCGCCCAGGCTGGAGTACAGTGGCACGATCTTGGCTCATTACAACCTCTGCCTCCCGG
GTTCAAGCGATTCTCCTGCCTCAGCCTCCCGGGTTCAAGCGATTCTCCTGCCTCAGCCTC
CCGAGTAGCTGGGATTACAGGCTCATGCCACCACGCCTGGCTAATTTTTTTGTATTTTTA
GTAGAGACGGGGTTTCACCGTGTTAGCCAGGATGGTCTCGATCTTCTGACCTCGTGATCC
GCCTGCCTCGGCCTCCCAAAGTGCTGGGATTATAGGAGTGAACCACCGCACCCAGCCTCC
AACATTATTTCTATGGTAATAGTTATTAAACAATAATAGCATCATTATTAATAATTATGG
AACATTAACAGCAACTACCTCTAAAACAACTAAAACTAACATTTATTTAAAACAAATGGC
TATTTATGCTATTTTATTCAAACCTCAAAATAATGCTATGAAATAGTTATCGTTGTTATT
ACCATTTCACTGATGAGAAAACTGAGGCTCAGGGAAGATTAGTTAACTCCCTTTGGATCA
TACAATTAGGAAGACCTAGAGCCAAGATTTCAGCCTAAGCAAAATTCATCCTTAGCAATA
GCACATCCTGACCTGGTCATATATAAGAATTTAATAGTAGTTTCTGATAAAGATATCGGT
TTGGAAAATTTAAAAAAATAATATTTTATTGTACATCTATAATATAATTGTATAGTTAAT
TGTATAATTGTATAATTGTATATGTGTATATGAGATAGACAGTTTAAAAAATATTACTTT
AAGTCCTTTTTGAAATGAATCGTGAATAAAAATAGTTTGAATATAGAAGCAGGATTTTAA
TCAAATGAATATAGAAAATATTCTTTAAAATCACTGACAGAAAATACAAGAATTTCAGAA
AATGAACGTTCAACATATTTTTTCAAGGGCTCTTATTCTTTTCTATTTTGTGGATATTCA
ATATAAGCAAAATTTTAAATTCAAAAAATATTTAATTTTATATGTTGATATATTTTAGTT
TGATTAATTCTCAAAACTTAATGTACATGAGACTCTCTTAGGTGGATATTTATTTAAAAT
GCATATTACTTTTCAGAAGATTTCATGAAAGTTCTTGAAACATATTTTAACAAGTCCCTC
AAGGGATTCTGATGCAAATGTCTCGTAGAGCACATTGTAAGAAACAACTCTTTTTTTTTT
TTTGAGACGGAGCCTCGCTCTGTCGCCCAGGCTGGAGTGCAGTGGCGTGATCTCGGCTAG
CTGCAAGCTCCGCCTCCCGGGTTCACGCCATTCTCCTCCTGCCTCAGTCTCTGGAGAAGC
TGGGACTACAGGCGCCCGCCACCACGCCCGGCTAATTTTTTGTGTTTTTAGTAGAGACGG
GGTTTCACCGTGTTAGCCAGGATGGTCTCGATCTCTTTTTAATAGGTTAGGTCATATATA
AGAATTTAATTACACATTTGCAAATTTAGAAGCTCTTCTCTAAAGTTTTCCAGTTTCACT
AGTTCTTTGAAGTAGTAGTTGTGTAGCAGTTGCGGTGGCAATAGTAGTAGCAGCAGCAGT

FIG 4. (SEQ ID NO. 4) CONT.

```
AGTAGTATTAGCAGTAATAGTAACAGCATAGTAACAGTAGTAGTAGTAGGATAATCAACA
CATGGAACACTAAGGGATAGTTATCTTTTCTAATGTGGTTGCTACTCAAACACATTACAA
GATTTTGGCATTAGTTGACAAGCTATTGCAAGCAATCATTGAGATAATAAACTATAACTT
AAGTAAAAATGTACACTGTCCTGTTTATTAAGTTTGTGTAAATGTGTTATGTGTTGTTAT
GTAGCTTTAGAATACCTTCACTGACTTTTCAGCAATTACCTTTAACAGAATAGTTTTTAT
TTATTTTTACATTTATTATACATTTAGAAAGAAGATGAGAGCAATAGTTTTTTATTAGTA
TAAGGCAAACTTAACTGATTAAACCTTCTTAGGAAAAGCAATAGTTCTGAAAGATATGCA
AGAAAAAAAATGACAAAAGTGAAAGAACTCTAGTGTTTCAAGAACAAGGAATGGCTCTAT
GAGCTATCCCTAGGAAAGCATATTTAAAATGAACTAAAATAAGGATCTTTTGCTTAGCAC
AGAATGTATGAGGTGTTTTTAAAAGAGGTGGCCTGAGGCAGTGGTTATATGGGAATTCAT
ACAAATGTTAGAGATTTGTTAGTTTTTACATTATACTTCTATTAACTGTAGAATTACTAT
TAGTATAGAGACCTCAAGTGTTTCTTATTTCTGAAGTCTTCTTAGTAGTGAAATGATGAG
GGGTATAGTAATGTCCATTTGTAATAAAAATGATTAATGAAAAATAGAATTTTTTATTTT
TTAACTTTTAGGATTCATCATATGCTGAACATCTTTTTAAAGTTCTGACTGTATTGTGCA
ATGTCTTTTAATTCATGTGTGTTCTTCCTTATCTAAAAATCATTTACATTTACAAATAAG
AATATTTTTACCTGCACCAATCAAGATACAATTAGTAGCTATAAATGTAACATTCTATAT
GTAACAGAATAAGAAAACAAGAGAAAAAAATTGTAACTTAGCATAATTGAAACATGTGCC
TAGCCATCTGGAGCACTTCTGCATAATATAAAGACATTTGACATTTTAAATAAAGGATTT
TGAAATAAACAAGAATTCTTTTGTGTCTTCCAAAGACATTGATTTATTGAGACTATGTGT
GGCTTTTCATCATATACAAAAGATTAATGATTCCTAAAAGTCCTTGCATTTCTTCATTT
TATAAAATGTATACACACAGTTAAGAAAAATGAATCCTTGAAGTCCTGTGAAGAAAGGTG
ACAGGAAATAGTTCAAAGTATTTCATTTTAAATAACATCAAATATTATAAAATATAAATT
TTCTCAAAGTAAAAAAATGAGCTTGGCATTATTGAATGTTGGTTGAATGATAAATGCATA
AGTTTATGATTATCCCAATACTATATATGTGATTTTTATCAAACATATTAAAGAGTACTA
TAAAATAATTTTAACTTTTGATCTATAAATTTCTAAAATTTCAGCACGGTGATTGGTGTT
GATAAATTTAAAGCATCAAACAGATCTTGTCTTATCAATAAGAAGTAGTTTAAATAAACA
TTTTTGAAAGTAAAATTTTTATCAAGCTCAAATAATTTCAAAGCATAGTTCAAGAGATTA
GAAAGCTTTTATGGTATAAAATATGAAATTGATACTGGTTTTGTTCAGAATCCCTTCATT
GACTTTTCAGCACTTACCTTTAACAGGATTGTTTTATTTACATATTTTTACATTTATTAT
ACATTTAGAAAGAAGATGAGAGCAATAGCTTTTTATTAGTATATGGCAAACTTAAACTGA
TTAAAGCTTCAGTTAAATTTTGCCTTATACACTCATATTTCCTGTTAAAAATACAATTTA
AATTTAGATATGTTTACATTAAAACACTCAGCACATTATAAACTTAACTATTGACTTAAA
AATTTTGTAGACGTCATCATATATGTTTGAATTTTATTTTTTTATTACAATAACAATATG
GTCAAGAATGAAACACAATTTTATATTACTTTATAGCTAAGAATGTTAAAATGAGATAAA
AATTCAGGTGTAAAATTTTGGTTCATTCTTTTTCACTACTACTTTTATTTCTTAGTTATT
GCATTAAATCAGGATTTTAGAGAAATATTCCATCCAATGTACAGTTCTTTTGAGTAAATA
TTCCAATGCAAATAAATCAATGCAATATCATTTTGAAATTATAAATTGGGTTATAATTAA
CTATATTGGCTAATATTAGTTTTATAAGTGTTTTAATAACTACATAGCAAAAGTTCTGCC
CAATTTTAATGTAATTTAGAAGCTGTGTAAATTTTAAGTAATCATTTACGCTTTTAAAAT
CATATTCATATTCATATATTTTGGTTTCCAAAATAGTGGTTTTTATAAGGCCTCAATTTT
TTTCCCATGTAAATTGAGGTATGCTATTGAGTTCTCTGAATCTGCTCTTGTCCATAAAGA
TAGCTTATTCTCCTTCAGACAGGGCGGATGATATTTCCAGAAGCAAGTCAGTGTATTAAC
CTAGTTACGTTAAACCATATCTCTGCTATTTTAGAAACAATGATGAATTAAGCAGCTTCA
GTTCTTGGGGCAGCATCCAGGGCTAGAACCCATAGCACCAAGTCCATGGGCTCCTCCCAC
TTCACCTCCTGTGCATGTTACCAGCCATTTAATCTGTTTTGGCCCCTAAATCAGTCAGGA
ATTTCCATATGATTTACAACTCCATTTGCTAAGAAGAAAAAAAAAATGAAGAAACTTAAA
TTTCATCTCTTAATATAGTTTTAATAGCACTTAATAATTTTATCTTAGAATTTTGAACAC
ATTTTTAAAACTCTGAGTTCGAGTATTGACTACCTACTATGTGAAGAACTTACTGCTCA
AGAATATACGTTAAAAATACATATTGACCCAGCTCTGAGAGAAAATTTGAGAATCCACAC
TACAGAATAAAAGAAATACAGTAGAAATTGTGGAAGAGGATACAAAGTAAATTAGTTAAG
CATATTATTAGGCAGGTTGATTCGAAAGGGCTTTCTGAAAAAAAGTTTGATCTTAGATTT
ACATGAATTGTTAAATATAAATAAAAAGAGATAAAGCATGAGATATTTCCAAAAGCATAT
```

FIG 4. (SEQ ID NO. 4) CONT.

TTAATCCAGGCCTGTGCAAAAGGAGGGTGAAGAACAGTAATGAATTGGTCTCTGGATCAT
GTTGTGTTCTAATAGATGATTTGATAAAGACTTGGTATGGGATGTGAGTTAGAGGAATTG
AGCAGGAGGAGTGTATTAGGAGAGAGAGCCTTTATTGCTAGGTTAAGTAATTTACATTTT
TGAAGTTGTGGGAACATCTTATAACTCAATTACTAGAATGCAAAAAGTTGCTGATGAATG
TTGAGCAATGCTGTAAGTTTTCCAAAGCATATCCAAGAGAGATTGCATTTGGATTTCGAA
TAAGATTATCTCCTTTATACATCTATTCTTTTAATGTATTCTACTATATTCTACTCTTGA
TTCCCCTTTTCTGTGGTGTATGGATTTCCCAACTACCTTGAAGAATTGAGAAGCAAATTT
ATTAGGTGAATTATTCCAATTTCCTAGTAATTAAACAGCATGAACATAGTTAGTCTAGGA
GGCCTGGTGTTATTTTAATTCACTTTTCCTTGTGAGTTTACTGAAGTGGAGATTATCCAT
TACAGCCAGAGGCTTTAACGACCAGAAAATTCTTCAGCATACCTTAAACACCAATTCCCC
ATGTTGAAATACTTAATCACCACTCTTGCTTCTTTGGGTGCTGAAAAGAAGTTTGATCTT
AGATTACCTGAATTGCTAAATATAAATAAAAAGAGAGAAAACGAGATATTTTCATAACCA
AATAGTATCTGTGATGCCAATGGGCGTTATTCTGCTTTCCTATGTGGAAGATTCCTTCTC
ATCATTCACTGTTTTGGTCAAGAACACCCTGATGAAAAAAATCTTTGGTTGCCTTCCAGG
TAGAGTTAGTCTCTTCTAAGTTCCACCATTTTTATTCACACCATAATTGTAATGCTTACC
CCATTGATAAATTACTTGCATTTCTAACTGTCCCCCCTGCCCCCCACCACCATGACTATG
ATCTCTTTGTGCCTGGTGTATTTCTCACTCATCCCTGGGTCCTCCATGTCTTACAGTGGT
GCCTGGCACATGGCAATAATCAATAAATGCCAAGAGAATGAATACATTGAAATGAATTTG
TGAATGGATGAGTTTTGCTTTCTTTGGTACTGTAGTGATTGTTATTTGCAGATTATTTCT
GTCTTTTACCTAATTTAGAAGGTCCATGTGTAATTTGGTCATGGTTTGAACTGCTAGTAA
AAACAAAGGTCATCCTTTATTTAAATTCCCACAGTAGCTGCTGCTTCCATTTACACATTG
TAGATGGTCAACGATTGTTTAAAATTGGTGAGCAGATGAATATCCAGGTGCTTCCTGGAG
GAAAAGTGAATGGAGCAGATCATCCTCCAACTTAATCACTGCAATGTAATTTTTCATATG
GGAATAGAACAGCGAAAATATTCTCTGCAAACGAAAAATATTGGACAATTAAGGTGCTAA
GATTGCCTTTTTTGTGTTTTTGGTTTGGGGTCTCTGTTTGAAATGACACTAGTGAGCTTC
AGGTTTCTTTCCTTGTTAACTTTTGCTGAAGGCCAAAGAGGAATGATTAAGGACTTCTAA
AGAAGTATTGAAAAAAAAAACACACAAAAAGTGGTGACAAAAATACTTATTATTTTCCTT
TAATTTTTTTCTGCAATTTTGTTGATGTTGTTATTACTACCATTTAAATATAGTTAATAT
TAATGATTACTTTTAGTAGCATTTAAGGATTTTCATCTTTCAAATTACTACTCTGGCATG
TATTATTTATGCACTTTGAATTGCTTTGCATGTTGAAATTTTCTTTTGGCCTCTAATTCA
ATTAGAATGCCCTTAGAGTTTTGAAGGTTGCAGTTTATATAACTTACCTTATTAGCTATA
AATGGAATACAGATTTACCCTTAAAATGATCTAGTTGTCTATATTTTAATCACATATATA
CATGTAGTGCTATAAATGTTAACCAGGTAGATTTTTCCCAGCTGCCTAGCCAAAGAGAAC
GGTATTAGTGTCACAGTTCAGTTGAGCTGTTGTTATCTGTATGAGATCAATCTTTTGGAG
AAGGCAGTGAAGGTTTTCTTATTTAATTTGCTTTCAGCAAGTCCTCCCCCTCTTTTTTTT
TATATATAATTTTAAGTACTGCTCTTAGTGGGTCATTAGACTTTGAGAATTATTCACTTT
GTTAGCCCAAACACTAAAACCTTGTGTCTTTTAACTCTGATTAGTGACACTTTAATAAAG
TCATTTGAAGTTCAGTGGACTGAATTTTCCAACTTTTCTGATGTTTCTATGGTCACGGTA
GAGCAACCTGTATTGAAGCTTGTACACAAACTTTTAAATGCAAATCTTGGAAAGCTGTGT
GTAATTTTGTATATCTGACTTCAACAGGGACTGCAAAATGTGAGGGATTAAAAATAAAAG
CGGTAGCAGTGTTTTCCTTCTTTTTGTTTTTCAAGTTGGGGTACAGTAAGCTTTGGGAAA
TAGAGAAGTTGTCACTTGACTAAACTTGATTCTCTGAGAAAAAAAAACTTGCAGATTAAA
ACTTTTATGGCTATACTTTTTTTTTGACAAACCAATGAGCACAAAACCTCATTTTCTTCC
ACATGATTAGACAATAAGGGTAATGCAAACTATTGAATCATAAATTTCTTAGAGATAGAG
CCTTGAATTTTTTTTTGAAAAAGTAAAGAAAAAGTATATTCAATGGCTATAATTAAATCA
TGCACGGTGAACCCACTTTGGAGGAATTACTTCATTTTGTATTGCATTGCGACTTGAGTG
AACATTTACAACACGTGAGAATGGAAAGGATGAAAAATTATGGTTGTCTTTCGGTTCACA
AGAATTCAAGGAGGCAGGTCATTGAGTTAATTTTCATGGGAAGACTAACTCTGGCCTGCT
CGCATATTCAGAGGCCAAACAACCTGGTATTGACAGCCTCAATTTGGGAGGGGAACATGC
AGCAGCATTGTGCCATGGTTTGTTGAGGAAAAACAAGGGAAGATTTAAAACAAAGCTGTG
AATAGGAACAGTAGCCCTTGTGTCTTGAAGCTGATTGACTTTTCCTTTTTAGACCTTTGT
GAAAGTGTTACCCTCTCCTTTAAATAAGGGCTATACTGTGGTAAGAGAAATATTTAAGAT

FIG 4. (SEQ ID NO. 4) CONT.

ATAATTCAGTGACTCTAGGAATGGGAGCATTTACACTTCTTGAAAGAAATCAGGTGAGAG
CTATTAATTGCAAATGCCATATGAAAGCATCAGCCTGAGCGGTAGGCTCAGTGCTAGGCA
AGGCATATATAAGAATACTAATACTAATAGGCATTTTTTCCAAACCATAGATATATATTA
CCAATCATATGTTATAAATTATATATTATCATAATATATAATATATGGCATATATTATGT
CTATGTATTTCAATCATATAACCTATTTACATATTTTATATACAGAAACATACACATGTA
GATAAAAAGACCAATCAATTAATGGTACTAACAAAAGAAAGAAGATAAGAAAAATCTGTA
TAGTCATATTTACAGATATTTTTAGAAGTAAAAATAAATGTCAACAGTACATCCAGTGGA
AAAATAGTTTTCTAGAACTGCCCTTCTTTTTCCAGTACCTCTTCAGTTTATTGACCTTTG
AAGAGATGGCTGCTAACACTTAACTACCAACATTTGTTTAAAAAAGAAAAATTAGTTTGT
ACTTTTGAATATATATTTGATATATAATTTGAATATTGTATTTAAAATATAAAGCATAAA
TATAAATCATAAATAAAAATTACTAATAAATTACAATTTGTAAGTGTGCTCACTGTGTTA
TATTTCCATTTGGATTTGAATCCACTTATCAGACTACAATAGAAATTACATTTATTTTTA
AAAATTAATACAGATTACATAAAATACTAAGATGATTTCAGTACATACTTACTAAAATTT
TAAGAAGACCCAAGACTTTATAGTAGGACCTCTGAGTTATATGTCTGAAAATTAATTGAC
TTTTGGATTTGAATATATTACTAATTCACTTAGCCAGTTTAATTGGATTTATCAGTTGTT
AAGAGTTAGCAGTTTATCATAATAATCATATTGATGCTTAATACCCTCTGCATCTATTAT
TTGGGATGTCTGGAGTTGAAAAACTCCAGACACAATTTAAATGAACTAGAAAAAATCATA
AGGTTTAGGATCAGAAGGCCCAGAGTTCAAATTTCACATCACTCAGTCCCTGAACTAGCT
CATGATGCTGTAAAAGTTGCACAATATTTCTGAACCTCGATTTCTTTATCCATAAAACAA
TGATGTTAATATTTACATTGTTTAGTTATTGTGTGTCCTAATTAGTTAATGTACCAAAAC
ACCTAACATTGTAGTTTCTATACGAAGCATATTTAAGGAAATAATGTTTATCACATAAAT
TGGAACGTATTCTTTTATATATAAAATGCCCAATTAATATACAACTTTAGAGTTCAGAGA
ACACAACAAAATAGTAGGGTGCCCACATCTGCAATATGAAGAACAATGAAGTTTTTTATG
TAGGGTGTAAACTTCAGAAAGTTGAAGGATCCTTTCTGATCTCATGTGTCCTGCTCATCA
GTGTATCCCCAGCGCTGATCCTGATGCCTGATACCTAGAGAGCAATCAATAATTAATGCT
ATATTGAGGAAGTGAACCAACACCCAGGATTAGAGTGGAGAAAACTAATTTTTCTCCACT
CTAGGTATGACCACTCAAGGTAGTACACTAGAGTAGTTCTTCTTTTTTTAATATGAATAC
ACAAATTAATAATCCTGGAAAATATGTTCAGATTAAGTAAATAGTCAAACTTGGAGCAAT
TATCCAAGACAGCCATATAAGGCTGTCTGCATGGATAATAGCCATAATAATGTTGATAAT
TCTATGTTTAATTGTGATCGAAGCCGACATCTTTTTCCTAAAAGGGTGTGCTGAGTTTAT
TATGAAATTAAATTTAGGATAATTTATATTTTAGTGATCACATCTTAGAGAAAACTGCAG
GCATATTTTATGATGCTAAGGTTGGAGAAATCTAAGAGTTCTCTATAGTTAATTTCCTGA
AAATAGAAGTTAGTTTTCAAAAGTCCAAACAAATCAGGAAGATTAGAAACTAAAATAAAT
TGTCATATAAGAAATAATGAATCTATGCATTGGGGATGTTGCATTTAGTTTTCGTTACCA
CGATTAGGAAAGATTCTGAAAAAGGATTAAATTATCCAGAGGGGTTTAGAAGAGTATACT
AAAAATATGAAAATTAGGACTCTTAAGTCTATGGAAGAAAATATAAAAGGCATTTTTGTT
GAAGTTTATTAAATGATGTAAATTATTACTGAAACTGCATTTGTTTTGAATTTTCCAGTA
TATTAAAACAATGGCTAACAATTATAGTTGAGAGAAATATATTTAGGAAAAGTAATGCAT
TATTCAGCATTCTATTATCTATACTATATTAACACATGTGTTATGGGCTGAAATTACACC
AGTATCACATGAGGGTAAATGGGTTGAAAGTGTAAGTTTAAAAGAGTTTCAAATGAGTTT
GTGAATGGATATCATACCCTTCCACAAATGACAGAGATGGACTATTAAATCAGAGTTGGT
AGTTTTTGCTTTTGTTTACTGTGTTTCTCATTCACCCTAAATGGTCCTATCTATAACAAG
CTTTGGAAAAGCACCATGCACCTGAAATTCTTGCATTCTGATGTTCATACCTAGAGAGAT
TTATGGTGACATAAGCAGCCAAATAGCACAAGTGAAATTTTATATGAAGTATATGACATG
CATGATTCAATATATATGCCCACTTTTAAATATACCAATAGTATATTTGGACTATAATAA
TGAATTCATTTCAAATATTGTCATTTTGCTTGACATTCGTATCATCACATAAGCTAGATT
CCCGTTATATAAAGATGCACAAAGGCTCATTTCAGAAATAAAAACAAATAACTGTTATTA
TTTTTTACAAAGGTGAAGGACAATAAAAATTGACTAAAATCCTGAAAAAACAATTCAGAG
TGCTTCAGTTGGGCCCTAAACTCAATGCGCAATCTTGACACATATATTGAGTTATAATTA
TTTACTACATTATATTTATTTTGTAACTGTCGTCAGTTTTTTATGTATGGATCTATTAAT
TTCAATGAAATTTGGATCCAGTAAATTTCTATACAATGGAGTTTGGTTATTTGGCACTTC
ATAAAAATGTACCTTTCACATAATGAATGAATAATTTATATTATGATTTCTCTTGTGTAG

FIG 4. (SEQ ID NO. 4) CONT.

GACAGTTCTTGCAGGAATACAAAGTAATGGTAAATTTTGATTTAAAGTGCAGCAATTCAT
GCACTTTAGAGCCAGTTGGATGCCAAAGTAACTTGGTTGGTGTTTATTTCTAGTTACAGT
CAGTGTTTTCTTTCTTTCTACCAATGAGATGAGATATTTGAAGGCTTTTTTTCTTCTTAG
GCCATATCAATTCAAAGAAAATGAGAAACCATAGATTTTGGGTTGGCCTTACAATGTGCT
GTCATTTCATCTTTCCAAATATAAAAATCAAAACTTCATCCTACTTCACTTAATCTTTTC
AAAGCTGTGTTCCTTAATGCTGATTTTTTTAAATCAATTTCAATGACTTCGTTTCTTGTA
TACAGCAGAAAGAATCCAGTTTGGTCTTTGTAAGGAGTGAAAGACTAGGAAGGAAGTATG
TGTTGTATAGTCAGTGCTTCAGAGTTGGTAGATTTTGCTTTTGTTTACTGAGTTTCTCAT
TCAGTCCGAATGTTCCTATCTATAACAAGCTTTGGAGAAGCACCTTTGTCCCCAGAGCTG
GCCTCCAGGAAGGCTTGGATCCTTACAAGTTTGGAAAAATGGTTACTGGCGGTCATCCAT
AGGAAAACAGAGCAAGTTTACAAAGTTCCTGCTGATTTCCTTGAAAGTACTCCCTCCTCA
TTCTCTACAGTAAGCCATTGAATGTTACTAGGGATGGACACTAAGCAGAAAGATTTCTGA
GTATCTATTCATCTTCCCCAATCAGACAGTCCTTTAAATTTAAAGAAGAATGCCTGACCC
TTAAGACAGGGAGGTTCATCATATTTCCCATTCTGACAGTTTGGAATGAAAGGACACATA
AATTATTATTATTATTATTGAATTAGAGGTATGGGTATGATGACTGAGGTTTCTCAGCAG
AAGATTTCTGATTCCATGCTTTGCATCATTAGACAGCCAACAGAAGCTGCACTTAGTGGC
CGCGTGATGTGATTGATTGGTTAGATTGGAATAAAACTTTTTTGTTGTTTTTTAAATCCA
ATATTACTTTATTTTTATTTAATTAACTTACATTCAAATGCAATTGATCATATGATTTTC
TAATTTTAGGATTAAAATATATATGAAGATAAGTTTGGTGCCACCAATTTGAAATTAAAT
GTACAGATAAAACAATAGAACAATTACTGATACAGGCCATCACTGATACAGTAACTACTT
TAGAATGCATCATAAATTTCATTTTCATATGGATTTGGTAAATGTGCTTTTAGTTACAGA
ATTGTTAGTCATAAATCAACTAGCAAAACAGAATTTCAAATTTTTGAGAAACCATGAACC
ATGTGATGCATGTTATTTTGTTATCCTCTGCTGTCTCTTAAGAAATTATTTTTTTCTAGT
CACATTATTTGTATCAGCCTGTCTGCAAAACTGAGTCTGTGCATTTCTCTCTGTCTTCAC
AATAAATTCAGTTCCATTGTATGTGCAAGAGTTCTTGTTCATACCATAAGCTTTTTAGCT
GTTTCATGATAGCTTAGTTTTGTTAATATATAGAACCAAACTCCCATATGAAGTGAGGAA
ATAAATGTGTAATGAGTAAGAAGGCAGAATTTTGTTTTGATTTTTCAAAACTTGTTACTG
AAAGTCAGAAATGTTTGTACACATGTTCTCCTGATTATGATCAGTGATTAAACTTTTGTA
TTAAGAACTCTTCCTACCAGAAATACTCATCCTAAGAAAGATGAATTCTTCAGAATTTTC
CCATTTATTACTAAATTCTAGACACTTCCAACTCAGAACAAACTTGGTTTTGAGGAATAC
CAAGTAGGCACAGGATTTAAGGCAGAAATTCAGCTAATTCCAGAACGGTTGATGCTACCT
GTTGAAGCATTTTATAGTGGAATTTCAATAAACAGTAGATATATTATGCCCTTTGATTTA
TTGTAGTATAACTTTTATTTTCCCCAACAAATCCTTTTTTTAAAAAGGGATTTAGGTTGT
TTCAAGTATATACTAATTTAATTGTCATGATTTGTCTAGCTTATAGAATACTACTTATGA
AGACTATTATACATTGAAGTTCTGTGCTTAAATAGAATATAGCTCTAAGTAATTACGTTA
GTGGTAATTAAAATATTCTGGAAACATTTTTTGGTCACCTGGTGCTGTGATTTTCAAACT
AGAGCTGAAAAAAACCTCAAGGGCCAGGGAAAACTTTGTCACTAGTACTTCTCACCCTCT
TCACCATTTCAATCAGTATAGCTCCAAGTGTAACAGCTTTAAATGATTTCTTCCATGTAA
CATTAGTTATTTTTAATATAATAATTTATTGTTCTCAAAAAAATGTTTACACAGAATAGG
TAATCACTAAATGTTTTGTCTGAAAATGCACTAGCATGCAGGCCACCAACATATTTGGGA
AATACATCTCCTGTGCTTGACTGTTCCTCTTTTAAGTAAAAACTTCTTTTTCCATTGTTA
CTTTTTAAGCCTATTGATCAGTGTTTTCTGCACTTCATTTGTGTACATCACAATGAGGAC
ATTTAAAAAATGGGCTTCCCTAATTTCAGAGACAAGTTCTTCAGATTGCTTCCCCATATG
TGCAATACTTTCCTCTCTGAGAGCTGCCAGTCTTCTTTGTAGGGCTAGCACGCATACATT
GCCCTTTTCTGAAATGAAACTAGGGCTTTCTTCTGCTTCTTCAGCATATTGCAGCCTTGG
CTTTAAAAGAAAAAATGCCAGAGTCAACTGTATAAGCCATAAGACTACACTGAATTCTAC
TGGATGCAGTGATGTATTAAAAAAATGATTTATTTCCATATTGCTGTTTCCTCAGCAGAA
TGCCTTGGACATAATAGGACCTTGATGAATGTGTTTTTAATTCCTGGTTAGCCCTCTTCT
GTATGGAAATCTTAAAAATATTATTTCACTCTAATTTGAAGATATTGTCAAATCTTTGTG
AAATTTTAGCAGATTGTAAATTTTAGAAAGATCCAAAGGAAACATTGTTAATACTAATAA
AGATTTTATGTGACCAAAATCGGATCTTATTTTTCAAGAAATACTCAGTTCTATAGAAAG
TTTGGCCTTCAGTCAGAATGACTTCTTCATTCAATCAGTTTTATAATAATTTGAAAATGA

FIG 4. (SEQ ID NO. 4) CONT.

AAACCAGCCAGCATTTACTGATGATAGTTTACAGAAGTTTCACCAAAACATTACTTCATC
ACAAACAAAGAAACTATTCATTGCCTGTTAGGCATCATCTCAACATCTGTCCACTATTGG
CTTGTCCATTTTTATATTGTTTTAGAATATGATATAAATAATTTTTTATTATTTTCTCTT
TAGTTTAAAATTGTACTGTGCCCCAAATTGGTATTGGCTCAGAAATGAGATGAATATGTT
TTAAAGTAAGTCCTTTTCATAATATGTTTAGTATTCTTTGTCAATCTTTTAGTTGGCTTA
GAGCTTGATATTATCTTTAAAAACAGAAATTAATACTTGTCATTAGAGTAAAACAGTGCT
GTAGCAGAGCTCACGGTTACATTGATAAACTATACATACATATATGTATTATATATTTAT
CTTAAGTAGAAACTATCAGTGCTGGTATTGTTGTAAGGGAGATCTGTGGTTTCTATAATA
TGACTTATATGCATACATACTTTATTAAAAGTGAACATTTGTTACATTTTAATCGTTAGA
GTAAAATATTTAGTGACTGAAAAATTCCAAATGAAGACTAAGTAAAATATGTTTTGGTTG
AATTGTGAAGTTTGAGAATTTGCAAAGCCATAATGATAGAATCAACCCAAAGGTCCCAGA
AATTTTCAATAATCTATCATCCTTATTTAAAATTATTATACAATAAAAAATTGTGTTTTA
ATCGCATGAGTAGACAGATGTTTATGCTGTTATTCAGCGAATCTTGCAAAAGTGAGTGTA
ATTCATAGAATAAAACAATGTTGGAAATATGCTTTCTTAAAGGCAATAAAAGTTGAAGTC
TATGTATCAAAGACAAAGGTGGGAAATTGTATTGCATTTTATAATATTTTGGAAAAATTC
TGTAAACTGCTATTACTAAGATTATTTTATAAGATTTTACCCCAGATTTTCATAGGTAAT
AAATGGGCAAATAACTTATCGTTTTCCCTAGTCAGATCGCTGGTGTTAAATTAATATAAA
GTTTTAATATAAGGGATTTTTATTAATAAAGTATTTTGGTAACACTCAACATGTACTTTA
TTTGCTTTTGGATATGTTTTTGATTCAAATATAGAAAAGAATAACTAAGATACTTTGGTG
TTATATATGGATATAGTCAACTTAGAAAATTATACACATTGAATCTTTTTATTGTGCTTA
CTCAAAAATGAATTGGTTTCATTTCTTTGCTGATGGAATATTGAACACGCTCTCACTCTG
ATGTACAGTTATAGTGTATACTAGGTAAGAAAAGAGAGTCCCAGGCCAATTTAAACAATG
ATAGGGTTTGCTTTTCTGAATTCTGAGAAGCTAGTTCAGGGGAAGAAATGAAACCACAGT
GTAGAGGGTCGAATGGTGAAGGTGAAAAATTAGTATCAAGCCTCAGTTCAACAGGAAAAT
GTGTGTGGAAATGGAAGAATGAAGGTAATATTGGTAGATGGGAGAATAGTAAACAAGCCT
TTCAGAGTTTAATGAAAAAAAAAAAAAAAAACTGGTTAGAACAGTTGGGTAAGAAGGAAAA
TAAATCTAAAGTTTAGTTTTTAACTTGATCAGAGTCCTGGATCAAACAGTGGACCTCAAA
GGAACTGTTCAAAGCAGTACTCCTAGTATGGTTTCTGAGACTTTCTGAATTTTAAGATTC
AGAAACGTGGGAGGAAGTCATACTAGCTTAGCTTCAACTGCACATTTATATTATGACAGT
TTTTCCTGTTATCCACATATTTTTTAAATTTAGACATGAATATAGAGAAATTTAGTATAG
CCTCTACTTATTAAAATGTTAGTACTTTACTTTTACCAAATAATTCCCTGCATATCATCA
AAAATTTATATTTTTAGCCAATTTAATTTTAGAGAACCTTCATATGAGGTATTGACACCG
GATAGAAAATTAAAGGAATTTTAAAATATATATTTCTTTCCAAGAAAATGATTTATACAT
TCATGTAATAATTTGTATTACCCTAAAACATATTTACATCTCTAAAGTAAAATTAGTTTC
TAAGGTGGATATGAGAGTTGGCTAGTTATAACAGAAAATTTGGATATCCTCCACATATTT
TAATGTAACAAAAAAACAAATTCTTTTGATCCATCTCATTACAGAATGTGTTCCAGATAT
AATTCCAAATGCATGTAGGTAAATGGAAAGAAAAATTGGATCCTGGAGTTGTACTGATCT
GATGGAAATAATATTACGAACTTGGTTTGAGTGTCAGCTCTTTTTACTAGCTTTGTGCCC
TTGGTCAAGTTACTTGATTTTTGTTAACTTACGCTTTCTTATCTGTGAATGAGGAAACAC
CTATGTTTGGGGTTTTGTAAAGATTAGAGAATGTAATTTATGCATGGTACACATGCCTTT
TATGATACAGGTAAAATATTTCACATCTTCATCTCATTTGTTTCTGGTGATGTAGAGGTG
GTAGGTCAATCTTTTTTTCTTTTTTTTCCTCCAATAATCAGTGGACTCAATTGAATTGGA
GAAGGGGTTGCTTGGTGGAAGAGAAAAAACATATGGCACTGATGATGATGATGATGACAA
AGTTGATTTGCAATTTTTTAACAGATTATCTTTCTATAGGGCCAGAAGCCATATTGTCTC
TTCCTTCCCCAGATATTCTTACATTAGAGGATTTTTTCTATCACAGTTGCACCCCTTGAT
TGACATAGCAATATCCTATAAGTAGCAGCCCTGCTGTTTGGATCATGTTTTTTTTCTGTC
GGCAGTGTATCACAAGTATTTTCCTCAGTGGCCTAAACAGACCCTGAGTGGAAGGCTGGT
AAAAGCAACCTCGTCTGCATGCATCACTTTGAATGATTTCAAAGAGGAAAGAAGCAGCTG
TGACAATGTTCACATGAACCACTCAGAGTGGCCTTATCTTTGTAGTCTAACAATAATAGT
ACACCCTGGCTGCATTCCTCTGCTTGAGAAGAGCAAAGTTGCCTAAGAGCCATCCATACA
TTTGTATTCCTTGACATGTCTTAAAGTTGGATGTATGATAAAGCTAATGACATCTTTACA
TCCCTGAGTAATTTGTCTTGAAAGTAAATGTAGAGAAATGCTCTTTATGGATTTATTGCA

FIG 4. (SEQ ID NO. 4) CONT.

TGTGTGGTCAATATTTATTTTATGCAGATATATGAACTAATATGTAACAGATTGTTATTT
ACAAAAGAAATTTGAAGTTTTATTTATTTGACTAGCTAAAGAAATATAAAAAGAAGTTTT
CTACATATGCAGATCATTATAGAAATAATATTCTTCTCTAAATTTGTAGATATAGGGTGT
TTTGTTTTTTGTTTTTTTTTTTTTTTTGCCATTTATAGGTTACAAGCTATGTTTAGGTAT
TTCAGAGTGCCCCATATATGAGTTATTTTAAAAAGTGACAATATTACAGGTGACAAGACT
AATATAAGTAGAATATAGTTGAGTTACAGAATATGTTGTAATAGTCTTTACAATGCACAT
CCAATGAACATCATATAGACAGATATTAATATCAATATATCTACACATAATTGATATATA
GTATATATTATAATAAATATAAGATATGATAATATAACAGATAATATAATAGAAATCATA
GATATCTGTATATCAATAGATACAGACTATAAGTCAATGGCGGGATACTGCACATTGCAT
TAAATCTCCACTAGTTCTTTGTTGAACATTCATGAATCTAAAAATGTAAAAATTAAGTCC
CCTGAGGGAGTAACTATGTCTTTGCATGCCTTCTATTTTAATATCTCAGTATAGCTCCCC
CAACACTTCCCATTATGTGCTTTTATACAAAGCAACCAGTAATAATGCTGAATGAATAAA
AGTGAACATAGCATATAATGTATTCCATATGTATAAAACAATATTCACATGAATGAAATT
GATCCATCAGTGTGTTCAACTATGAGTCTGTGTTTCTGAGTACCTGTAAACAAAAAGAAG
CGTTGAAACCTTTTAGGGAGTTATGAGAAATAATAGAGTAAAATGATAAATACATTTTTA
CTGAATAAATATACCTGAATGAGTTATTCCAGTTTTTTCATGAATTTAGGCAAATGTACA
GTCTCTCGATTGATAATAAAATTTGTCATTTTCTCAGTTAAATTGATACAGATTCTTGTA
GAGCAAAAAGACCTAAAGATAAGATTTGGGATAGATTTATACCTTAACCCAGGTAATAAA
TAGATTATTCGGGTACTTTAATAGTAACAAAGGAATCAAATGGAATTTTAATTGAAATGA
TTTTACTAATATGGTCATTAGCATTAAGTAAATGAGATACATTTGCCATTTCAGCTGTAT
TTGTTAACATTAGATTTTCATACAAATACAAGAGATGTTATTTTAACTGCTCATTCTTAT
GGATTTTACTGCTTTCACTAAAGAGAAACAAAATATTTTATCTCCTCATTGCAATTTAGG
CTTAGGGAGTAACAACTAAGCATATACATTGTTGAACACTGCTGGCATGTGCTTTGTGAA
TATGTTTGAATCAAGGGCCTTTACAAAGGGCTCAGACCTTCCTCCTAGGGGGTTGTCATT
TACCGTGGATGCTCTCGTTTGTTGTGGTAAACAGCCTCAGAAAACGTCTTGACATTGTCA
ATTCCAACAGATTAATGAAGTAACTGGGCCATACATCCCTTCCCCTTTACATATGAAAGG
AAAAGCTAACTACTTCATAGAGCTGTAAGATTGTTTCCTTTTACCCCTTGGTATTAGTTT
CCTTTGTAGTCAGTTAAGTATGGTTCTTTTAAGTAAGCCAGACCAGAATTCTTTTAAGTA
AGCCAGCTTGGGCGGGGGAACTCCAGTGTGATTATAAGTGAGTATATAGGAAAAAAAGAA
ATGAAATTAACCTTTTTTTCTTTAGAAATCTTGTGTTTAATTTTATGTTCCAGTGTTTTA
AATAACTGAAACCTTATTATGGACAAATTTACCTGTTATGTTAGGAGAAATGAGTTTCAT
TTACCATCTTCATCAGCGATCCCCAACCTTTTTGGCACCAGGGACCGGTTTCATGGAAGA
CAATTTTTCCATGGACCCAGGTGGAGGGATAGTTTCAGGATGATTCAAGTGCATTACATT
TATCGTGCACTTTATTTCTATTATTATTATATTGTAATATCTAATGAAATAGTTATACAA
CTCATCATAATGCAGAATTAGTGGGAGTCCTGAACTCGTTTTCCTGCAACTAGATGTTCC
CATCTGGGTATAAAGGGATACAGTGACAGATCATCACCATTGGATTCTCATAAGGAGCGT
GCAACTTAGATCCCTCACATGCGCACTTCACAATAGGGTTTGTGCTCCTATGAGAATCTA
ATGCTGTGGCTGATCTGACAGGAGGCAGAGCTCAGGTGATAAAGTGAGTGATGGGAAGAT
GGGAAGCGGCTATAAATAGAGATGAAGCTTCACTCCCTTGCTCACTGCTCACCGCTCACC
TCCTGCTGTGTGGCCCAGTTCATATCAGGCCGGTTTCCTATCAGGTAATGGTCTGTGGCC
CAGGGGTTGGGGACCCCTTATCTACATCCACGTTTTCTATGTTTGTGAAGATTTGATGTG
GGGTTATGGGTTTGAGGAGCTAAAAATTATAGTTAGTAGAAGGAAAGACAGCTAGAAGTG
GAAAGTAAAATCACTTACATTGTACTTTTACTAGGACCTATATTGTAGGTATTATAAATC
ATACAAACAAGTTTGTTATACAAAACATGATTACCTTATCATTGTTTTATTAAGTATTTA
ATTGTGCATGAGTAATCATTGCCATTATTGATTTGTCCATATTAAACTTATGATCAGACT
TAGTGGACAAATTTTCAACAAATAATAGAAGCAGCAGCATAAATATCTATATAGAATTAG
CCAGGTTCTAGTCTGGCACATCATCACATAGTAGCACATTTAATGCCCCCAATTATTCTA
TGATATAGATACTACTAGTTTCCCCATTTTCCTAATGAGAAAAGTGAGTCATAGTCAGGT
GGAGATAATTCACCCCACGTCTTAAGGCCAAATGGAAAAAATCTTCTTACTCTGGAATTA
GGTGGTTAAGTATCTTGATTTTAATGGATGTTGTTGTTTTCCTAATAATTGAGTTATTTG
TATTAAAATGCTAAACTGGCAATATATGCCGATGGCCAATTTACCTCCAAATATATTGAG
TTCATACATATTCATTAAGTGGGATATTTTGGAGAATATACTGCTTATATGTTCAAATGC

FIG 4. (SEQ ID NO. 4) CONT.

AAATAATTTAATTCGCTGTGATTTATAATACTGTTACTCAGTAAATGGACTAAAGGCAGG
GTAAGATTTATCAGTCTTAAAAATGTAACTATGAGATCATTATAATCCTATTATCTTCTA
ATTATCCTTTTAAATCAAAAACATACTTTCATGTTGGTATGAGTATCATAACCAAAAGAG
AAGAGAAACTTCAAAGAGAAAACTGAATTAGTGGAGAGTAACTTAATTTCAGAAGAAAAT
CGTACTTTCATATAAATTCATAGTGAAAGGTAACTATGTGATACCAGCATTCAGGGAACA
AATGCCCTTACGTTTTTGCCTGTGTGTTTGTGGGGAGGGAGGTTGTTTCATTTTGTTTTT
ATTTCTTGCCTGTTTAAATTTCTTTTACTCACAGGCTCCAGCCTGGATCTCTGGGAGGGA
GAAGTAGTTCCAAAGATTACAGTGCTTAATCTTAACTCTGAAAACACTACTTATTGACTC
TCCACTGGATTCCACTCGCCCAAATTCCCTAGATGGATTTTCCCTCAGGATGAAACAACC
TAAATTCAAGTGTCCTAAACTGTCTTCCTCTCCCTCCTGCCATTGCCTTTCCTTGTTTCT
CTAGTCTAATCCATCTTATCTTTTGTTCTTTTCTGTTAATCTATTAATCAGGTCTCTGAC
ATTCTAAAAGCTCTCATGCCCCTTCGCAATATTTCCTCCTTTACGCATTGCTAGCACCAG
CACTTCCACTACTCCAGGAATTAACACCTCTTTCTCTCTTTCCTCAATGGCTAAGAGATC
TGGAGTCATCATGTCTGGGTTCATATTCCACTTTCCCAATTTACTGACTTCGTGACCTTA
CCAAGTCAGTTAACTTCATTAAATTTTCATTTCTTCATTTTCAAAACATTTTCATCACGT
TTCCCACACAGGCTTGTAAGGAGGACACAATTATGTCATGAATATAAAGTTCTTAGCGGG
GAGTTTGGCACATAGATCACAGATTAGCCGTTCTTATTATTGCTCCCTCGGTAGAGTCCC
ACTGTGAAGTCATTATTTCTCACATAACTCACTAATTCAGGAACTCTTTAATCAAACCTA
TTATGTCTAAGGACCTGAGTAAACAGTTACTGTTCTCAAGGAACTCACTGTCTAGAAGAA
GAAGAGGCTGACCAGCAAAGCCATAATTACAATAAACCTATGCTATTTGTACTGAACAAT
AATACATATGCACTTAATTGTAGTCATCCCCCTGACTATACTCACAAAACTTAACATGTC
TTTAGGGGAGGAGGATGGATTGCAGATATGCTATTAGAGGCATAGCCATCTTTACTTCAT
TAAAAGTTTAGTTTACTAAAATTTGCAAATGTTTAAAATATGGTCTTGCTTAATTTCACA
AATTCTGGGATAAATATTTAAGGATTTAATATTTATTAAATTTTTTATTTATTTATTATT
TATTTTATTTATTTATTTTATTATTTTTATTTTATTTTATTTATATTTTTATTATTATTT
ATTTTATTTATTTATTATTTATAAATATTTATTAAATATTTATTAAATGAGTGCACTGAT
GTGTATTGTTTCAAATACATTTTATTAAATTTAGTGTCAAATTGCTAGCTACTGTATGGC
TAAATATTACATTTTTCCCCAGTGGGGCAAAGTTCAATTCAATTAGCTGCAATGAATATG
TATTAGATCTCAATTCTCTCCTGTGATAAGTGTTGGAGGGAATTCAGAAATAATAAAAAT
ATATCTCTGTTCTTTGGGATTTCAGTCTATTATTAACTAAGCATCTGGAGCAGTTACACC
TATGAAACAGTTTGGTATGGCATGACAGTGAAAGCAGTAACAAGGTACAAGGGGAATAAA
AAGAATGAGATCCATCAAATTGTTAATCCGGAAGGCACAGGGAGTGAGATGGCATGTGAC
AGTCAATGGTTAGTGATGGGGTAGAGGCCCATATGCTCATGAGAGATTTGAGAAATATAA
AGTCATTGTCTTTGTTTAAAAGGATGGTGTGCAGGTGGTAAATACTGAGAGGTGATCTGA
CAAGTGTTCATTCAAACTCTGCAACCTTGATTGAGACTGTGCTAGATGATATAAAAATAC
ATATGCCCTAACAGGGAGGATAGGCAACCAAACAATTAATTTTAAAATTGTGAATTTACA
AACTGTGGGTTATTATATGCTACAGAAGCCACACAGAGAAAGAGTTATTTGCTCTGTTTC
AGAAAATAGAATAGAGGAGATGTGGGAAGGCAAGATAGTCCTTATAGAAAAGTGGTCGTT
TTATTACCTGCAACCGTTCTGACCCGCTTGTCATTCTATGTCTTCCTACGTCAGTCATGA
GCTCTATTTGTTCTCATGTGCAAATCCCAGCCTCACTAGGATGCACTCCAGTTATCCATT
AAGCACGGAGATTCCCATGAGCAATGGGACAAAATGACTATTGGACTTCTATCTCAACTG
CTTGTGTAGAATGTTGCCTTGTTTATTTTAAGTCCCAGATTCTATTATTTTCCCTACTAA
CCATGGGTAGACTCTGGATCAGACTTCTCATTGAAAGACCTTTGAAATTTGCTTATACTC
AATTGCCATTTCAGTCCCCTCTCTCACTAGATGTTCTTGACTGCTGTACCACTCTTCAGA
TTCATGATGTGCTGATAATACAATGTTTCCTTGCATTGTTATTTTGTTATATTTACCCTT
ATATTATCATGGTTTTTGATTAAAAGCGTATGTGTGTGTTTACACATAAACATTTTTTTT
TCCTTTCTCAACTTTTTAGGGATATGCAGACTATATATTTCTTTTCAAGAGGGCAAGACT
GTAAATAGATTGAGGGCAAGCATCATGTTCTGTCCAGTGTAAGAGAACATTCTGAGAACC
TAGCCGGACATCAGGTATACATTGAAAGATATTAGTTGAAATTATAGGTAGAGCTGTCAT
GATGACATGAGTAGGTAATATTTTGAGAAGTTTGGTGGTATGATATTAGAAGAGAAATGA
TTCTTCTCTTCTGATGCAGGGAAAAAGATTCCCAAAATCTGCAAGCGAAGAATTGGGTAG
AGGAATTATTCAGTTTAGGATCTGGTCTAGAGATATACAGATTTACATTTACTGTTTGGC

FIG 4. (SEQ ID NO. 4) CONT.

CTTTTTTACATGGTTGAATACCATATGAATTTTAAATATTAGTAAAATATCCAAAATTAC
TTTTGATAGAGGAAAATGTATTGCACTATATATTCTTCTTTGAATAGAGAACTTTGTCAA
GTAAGAGAATAAAAAATACAGGATGATTTCTATTAAACATACAGTATTCAAAAGCTATGT
GAGGGAATCCAGCTAGTGTGATTATGTCAAAAGGGAAGATAGCTGGTCTGAAGGTAATGA
GTTATCTCAACTGATTGGTCATGGCCAATTACAGACAGAACTCCTTATTTTACTTCCCCA
CCCCCCGACTACTGCACTTGACTAGTCAAAAAATAAAACAAACACCAAAACCAAACTAAA
GGGAAGACAGTCTTTTCCTAGCTTGGCATTAGTTGGATGGTTTATATAAATGTGAAACTT
TTAGAACTCATTTGAAAAAAAAAATTTAGTAAAGCAAAAAGAAGTTTTTCAAATAGTTAA
AAAATTTAAAAGACTGAAATTATCAAATCATTTTTCACAACAATAAAAATTGTATACAAG
GCAAACTATGTACATATATGTGGGTGTCCTTAGGAATAAATGCATAATTTCAAAGACATG
GAATTTGTAAGTGTTAGTCATGTTCTCACCTGTAATAAAGCAATGTGTTAATGAAATTGG
GTGCTTATATATATTTATATATAATTTCTTAGTTTGAGAGAAGCAAATAGAAGTGAATAT
ATGTAGCCACTTTTTAATATTTGTATTCAGCTATAATTCCTCCTGATTTGCTCCTCGTTT
TAGAGTGATGTACTGGGAATGGAATCCTAAAATTAAACTTATTTTAGATTAAATCATACC
ATGTTAGTTTAATTTTTTTTATTTTTTCAATTCTATATCAATATAGCTTTTTTTTAATTT
ATATATATATTTTTTTGAGAAAGAATCTTGCTGTATTGCCAGCCTGGAGTGCAGTGGTAT
GATCTCGGCTCACTAAAACCTCCGCCTCCTGGGTTCAAGCGATTCCCCTGCCTCAGCCTC
CCAAGTAGCTGGGACAACAGGCGCATGCCACCACTCCTGGCTAATTTTTTGTATTTTAGT
AGAGACGGGGTTTCACTATGTTGGCCAGGATGGGCTCGATCTCCTGACCTCATGATCCGT
CCACCTTGGCCTCTCAAAGTACTGGGATTGCAGGTGTGAGCCACCGTGCCTGGCCTGTAG
CTTATTTTTTAAAACTAGATTTGATTTTGGAATTGCAACGATTATGGATTATTATATTCA
CTACTTATTATCTCATCACTGTTTAGTTTGCAGAAAGGCTTACTTAATATTTCATTTATA
TGTTCCCCTATTGATAGTTCCTGGAAAACTTTTAATGCTGGCCATTAATTTAACATATAT
TTGCTTAGAGTCTACTGTGCATTACAATCATTCTAGATTTCAAGGATGCAAAAGTGAGCA
GAAACAGTTGTCCGTTGTTGATGGACTGATGGAGGTTCTTGAAACTTGCTTATTTTTTGC
TTACTTTTGTGGATGTTCCTATTCCTTCTCTCTCTCTCTCTCTCTTTCTCTCTTCTCTCC
ACCCCATGTGTGCCCTCACTCTAGCTTCCCCTCTTTCATCCTCCCTCTTGCTACAAATTA
AATGTAGTTTTTTTCAAATACCTTTTCTTGGACTTTTTTCTCTCTATAGTGATTCTTGTA
GTAATCTTATAGCATCATCTGTCACATTTATGTTGATCTCTTTTTACTTCTGTCTCTTCT
TCAGCATCACAATCTGTTTATGTGCTGGACCTAGAAATTTAGCCCCCCGTGAATTTCAAC
TTCACCCTGTCTATTAAGAAAGCCAGTTATTAATAACGTATTTTAATAAATTATGATAAG
CATATGATAAGGAGAAAGAATAGGGGACTTTCAGAATATATTAGAAGGGAACCCAAACTA
GACTGTGGATCACCAGAGGAGTCACTAAAGGAGTCTCGGTGGAAGTGATATTTAAACTGC
GATACGAAGGATCGCTTGAATTAACTAGGCCATCTTCAGTGGTCAGGAGTCAGTTTTCTG
AGCAGAAAGAGTAGTATGCATAAATGCCATGAGCTGGAAACGCATACAACTCTGTATAAC
TGAAGGAAGTGAGGTTTTTTCAGCTGGTGCATGGAGTGCTGAAAGGAAACTGAGAAGAGA
CCCTGGAAGGTCAGCTTGGGTGTGAGAGTGAAGAGCACCCAAAGTAAGACTAAAAGTTTG
GTAGTTCTCATACCAAAATGAGAAGCCATCAAGAGTTTTTATCAAATTATTGACTTTATC
TTATTTGTGTTTCATAAAAAGCTTTCTGGCTACATGAAAAGAAAACAGTTAGAGGTTGGG
GGCATTGCGGATTTAGAAATTGAGCATGGAGAACTTGGGGCCCTGGACTAACAGTTGATA
GTAGAGTTGGAGGTACATGCATTGAGTGGAGATGTGTTGAAGATGTGGTCCTGGTATTTC
TTGATGACGAATTGAATGTAGATGTGGAAGATGATGGAAGAACCAAGGAAGATGGCTTAG
TTTCTGCCTTGAGCAACTAAGTGGATGATGAGTTAGGGAATACCGGATGAGGAGTCATAA
CAAGAAGACAATAAATTAGTTCAGGACCTTGTTAAATGTGAGGTCACTCTGAGATACCAG
TGGAAATATCCAGCAGGCAGATGGATATGTGAACTGGAGCACAACAGAGAAGTCTAGATT
AAAATTTGCATTTGGAGTGTAGTATCCATGAAAGTAGCCACGAGCTTGGATATGTTGTCC
AAAAGAATGTGGACTCTCTTCTCATCATTCAAGCTGAAAACCTCAACTTTATTCCTTGAC
TCCTCTTTCTCTTTTTTTCTTGCTTCCTATATGTAAATAAATGGTGAAGTCTTATCAGTT
TTGCTCTCTATTGTCTTTCCTATTCATACCACCATTTCTGTTTCCAATAGTCTAATTAGG
TTCTTGTTATTTCTGACGAGAGAGCTATTATATACTTGAGGATAGCAAGACTGGTTGCCA
GGAGATTCATAGACTATTGCAGTAAGCTGGAGAGTTATGACTGCTGTTTAAACAAGATCA
TTAGCTGTAGGAAAAGAGGAAAGTATATTTAAGAAATAAAGTATATGATAAAGTAATAGA

FIG 4. (SEQ ID NO. 4) CONT.

AAATGAATATTTGACTAAAACTAGTATGGGAAACAGAAACGCCTTGAATATAACTAAATT
AGAATTATCCTCCTTTATAGATTTAACTTTTATTTTAAGTTCAGAGCTAAATGTACAGGT
TCGTTATATAGGTCAGGAGTTCCCAACCCCGGGGCCACTGACCAGTACGGGTCTGTGGTC
TGTTAGGAACCGGGACGCACAGCAGGAGGTGAGCGGCAGGCTAACGAGCATTACCACCTG
AGCTCTGCCTTCTGTCAGATCAGCCCCTGCTTTGGATTCTCGTGGGAGCGTGAACCCTAT
TGTGAAGTGAGCATGTGAGAGATCTAGATTGCGTGCCCTTATGAGACCTGCCCCACCCTG
CTCTGTGGAACAATTGTCTTCCACAAAACTGGTCCCTGGTGCCAAAAAGGTTGGGGACTG
CTGATATAGGTAAACTTCTGTCATGGGGTTTGTTGTACAGATTATTTCATCACCCAGGTA
TTAATTAAGGCTAGTACCCATTAGTTATTTTTCCTGATGCTCTCCCTCCTCCCATCCTCT
GCCCTCTAATAGACCCCAGTATGTGTTGTTCCCTTCTATGTGTTTATATGTTCTCCTCAT
TTAGCTCCCACTTATTAGTAAGAACATGGAATATTTGGTTTTCTGTTCCCAGGTTAGTTG
GGTAAGGAAATGGTCTCCAGCTCCATCCATGTTCCTGCAAAGGACATGATCTTGTTCTTT
TAATGGCTGCGTAGTATTCCATGGTGTGTATGTACTATATATATATTTTTAATCTGGTCT
ACCATTGATGGGTATTTGGGTTGATTCCACGTCTTTGCCATTGTGAATAGTGTTGCAATG
AACATAACATGTGCATCTTTACAATAGAATGATGCATATTCCTTTGGGTATATACCCAGT
AATGGGATTGCTGGGTTGAATGGTATTTCTGTTTTAGGTCTTGGAAGAATTGCCACACTG
TCTTTCACAATGGTTGAACTAATTTACAGTCCCACCTACGGTGTACACATGTTATTTTTT
CTCTGAAAGCTTGCCAGCATCTGTTATTTTTTTGACTTTTTAGTAATAGCCATTCTGCTT
GTATGAGATGGTATCTCATTGTGGTTTTGACTTGCATTTCTCTAATGATCAGTGATATTG
AGCTTTTTGTCATATGCTTGTTGGCCATATGTATGTCTTTTTTTTGAAAAGTGTCTGTTC
ATGTCCTTTGCCCACTTTTTAATGGTATTTGTTATTTTTATGTGTAAATGTGTTTAAGTT
CCTTGTAGATGCTGGATATTAGACCTTTGTCAGATGCATAGTTTGCAAATTTTTTTTGCA
TTCTGTAGGATGTTTGTTCACTCTGTTGATAGTTTCTTTTGCCATACAGAAGCTTTTCTT
TAGTTTAGTTAGAATATAAATAAACCAGAAGTTTCCCTTTTAATTTTAGCATCGCAAATA
TGCATCAAATGTTATCAATTTATTTTACCACATTGCTCCACAAAGTCTCATCCACCAATT
ATAATTCTTCCAGGTAAAATTTACTGGAAGCAATTATTGGTAGAGCTGGAAATAGCATTT
GCCAGACATTTTTCTACACACTGTACATATATTAAATCATTTAATATTTATAAACATTCT
ATGAAACATCACATTTTACAGGTGAGGAAATGAAGAACACAAAGGTTATAGAGGGTATTT
TTCAAGGTCATACAATTTGTAACTGTCAGCAATAGACTTGAACCCAAGTATTCTGGTTCC
AGAATCTACACACTAATCCAGGAAAGTAAAGGACTGCGTATGTTTTAAGCACCTATTAAC
GTGCCAAGAACTGTGGAATATATGAAAAATACATAGGAGTCAATATGTAAATACACATAG
TTTAAATAGCAGGTTGGGGGAAAAAATAACATACTCTGTAACTAGTTTTTTCAACCGTAT
ATCATAGAAAGTTAAGTTATTCAGTTGTTCAAAGTCAGTCAGTTTCCATGAGAGATGGTT
AAAATGAAAAACCTTCCTTATAGGTGAAATTTAGGGTGACCATTGCCATTTTTAATCAGA
TATCCCCAAAATTCACCTTTCCTTGACTAGCATTTAAGAAAGTACTGCAAAATAGTATAT
GCAAACATTGGCTTTGGTAACTTTTGCCAACTAACTTACCATAGTTTTAATCAGGGAAAA
TGGTGAGTTCATGTGTGGAAGTTCTACTCTGACTCAGGTAGGTAGAGATTATGAACAAAA
AGGGAAAAGGCAATTTCCTACCTGATGGTGTGGAACTCTCTAAATCTGCCAGTCCAGTTT
TTTTCCCCCTTCCGTTTAAGGTTTTATAAGACTTTCTAAATAGGCAATTTAGTATTTGTT
ACTAGTTTGGAAATTATTTTTCTGGAGCCATATGAAGTACTAAGTATTTATAGACAAAAA
TGTTGGCAAAGAATATAGAGGTTCTTGAAATGGCCTTTCACTGTGGCAGAAGAACTTGAA
TACATTCAAGTGCAAATCCAGATTTGTAGAGAGTACTGTGGGTTTATGGAAATAAAGCAT
TTGATTGAAAAAGTCATTTTTTCCAGTATGACTTAGTGATTATTAAATAACCATGTTTTT
AATCTGACTCACTGGAGGGAAGCTCCATAGCATTAGTGGTAAACAGTTTATGCAGTTAGA
ATATGAAAAAGACAAAGAAAAGCAAACTAAAAAGACATTTTAGAGTAGAGTGGGAATTGA
GCCAATGTGCCTGACTGGTAAAGTCTTTGGAGGGAAGCCAGGAAGTCTGTGATATTTCTC
TAGTTAGGATATATATATATATGTATGTATATATTATATATATGTATATATATATATATA
TAAAAATCATATTGGATAAAAAATGTTAACCCTTTCTATCAAATTTCAGACTTTCCTGAT
TCTGAAACTCAAAACTGAATGCAAATTAAGATTTTTAAAAAGTATGATTAAAAAAAATAC
CGCATACACACATGACATCTGGCAATGCCTTAGATCTCTCTAAAATGTCAAGATGGGAAA
ATATCCAAAACTTTTTTTTTTTGAGAGAGAGAGAGAGAAAGAGAAAGTTGGCTTCTAGCC
ATAAGCCTGCCGAGGAATTCTTACGAGAATTTCTGGAAACTGTACTTTTTAAGGCAATCA

FIG 4. (SEQ ID NO. 4) CONT.

TGTTCTCCATGCTTTCGTGGCCTCAGATGTTACTTGAAGGAATTTAAAGTTTCATCTATT
TGTGCTTTGTTGCTGTACACCCTTTAGACTTCAGTGGTCAAGTTTCACTTTGGAGAACTG
ACAAAAGAAAAATATTGTGTTTGGCACTACACAATCTTAGAATACTTTAAGAATGAATAT
GCCAAGGGAGAGTCATATTATATAGCTTGAATTGTATTTTTCATGCATGATATGTACATC
ACCTTATGTCACACAAATCTCTATCAGCCTTTTGCTTTTCCATTAAAATAAATACCCATC
AGATACTTGATATAGATATTCTGTGGTTGGAGGGCTTAAGTGAGATGCAGTTTCAGGTAA
ATAACATAAAATCAGCAGACCTCTAATCTGAATTGAATGTGTTAAATCTTATCAACCTAG
AGTTTTAAGGAAGAGGGAACAACTGTCTTCAGTGAGTAATGGCGCGTGCATTAATACCAG
TTACTCAGGAGGCTGAGGCAGGAGAATCACTTTAACCCAGGAGATGGAGGTTGCAGTGAG
CTGAGATTGCCTCATTGCACTCCATCCTGCCTGGGTGATACAGTGAGACTCCATCTCACA
AAACAAGCAAACAAATAAATAAAAAAACAAAAGAAATGGCCAAGAAGAAAAATGCCTAGC
TTTCCTGCAACAATTTGGGAGATTACCATCATCTGTATTAATTCATTCATTCTGTTGTTT
AATGAAAATGGCTAAAGTCTGGCCTTGCCATTGAGGTTTTTAAAAATTCTGGTAAAATAT
GCATAACATATAATTTGCCATTTTAATATTTTTAAGTGTATTATTCTGAGTCATTGAATA
ATTTCAAATTGCTCTGCAACTGTAGCCGTCATCTATCTCCAGAATGTTTTTGTTTCCCAA
ACTGAAACTCTCTACCCATTAAACACTAACTTTCCATTTCCTCCAATCGGCAAGCTCCAG
GCCACCACTGTTCTGCTTTCTGTTCCCATGAAGTTGACTACTTTTGCTAACTGATATAAA
TGGAATCATACATATTTGTTTTTCTGTGTCTGGCTTATTTTACTTAGCATAATGTCCTCC
AGGTAGATCCAAGTTGTAGTAAATGTCAGAATTTCCTTTTTTTTTAAAGACCGAATAGTA
TTCCATTGTATGTATATACTACATTTTGTTTATCAAAAATGGACACTTGGGTTCCTTTCT
CCTTTTTCCATTGGGCGTATTGGGTTTTAATATTACACGTTTGTTATAAAGGCAGATATA
GGGTGATAGAATTCATACTAGATTTGGAAATAATCAAACTAGGCTTTGTTCTGCCACAAC
TAGGTAAAAATGTTACTTCTTTCTGACTTTTTGTAAAATCAGGATGGAAATATATTTCAT
ATCATTGTTATAGCTAATAGCTATTAAGCACTTGTATGTTTCATACTGTGTTAAGGGCTT
TTATATATTTCTCATTGTATTCCGACAGGAACCCTACAAAGTAGAGACAGTTCCAAATTT
CCAGAATGAATGTGAGATTGTGATACATATGACAAACTGCTTATTAAACTGTACAGCACC
TAACAACATGAGGGATTATGCCTAATTCCCTACACAGTGCATGGCATACACAAGGACTCA
TGAGATGCTGTTGAAGAATAAAAGCAGCTCTACTTTACAGCCATAGGAAGCACATACATA
TTCAGCCATTTGAAAACAGTGTGTCTTGATGAAAGAGGATTGCAGTTGGATTAATATGAA
CAGTCACTAAAAAATAAATGAAAACCAAACCTCTAAATCACGTATACAGACAATATTCGC
AATATTGATAATATTCAAATTGTGTAAGGTAAACCTGATTACTCAGCAGAATTAAAGTTT
CACTGGTGATATGGGGTGCAGGCAGTGTCATCTCTCTGACAAAATTTTTCAAATTTTCAA
AATTTTCAAAGTTTGAAAATTTCAAATTGACAAAAATTTTCAAAAAATTTCAAAATTTTA
TAGAAATCATCACAGTTCTCTTTATTAATCAGAGTTTAAATGTTAGGCCAGCCTGGGTGG
CTCACGCCTGTAATCCCAGCACTTTGGGAGGCCAAGGCAGGCGGGTCACCTGAGGTCAGG
AGTTCGAAACCAGCCTGGCCAACGTGGTGAAACCTCGTCTCTACTAAAACTACAAAAAAA
TTAGCCAGGCCTGGTGGTGCATGCCTGTAATCCCAGCTACTTGGGAGACTGAGGCAGGCA
AATCGCTTAAATCTGGGAGGCAGAGGTTGCAGTGAGCTGAGATCGCGCCATTGCACTTCA
GCCTGGGCAATGAGAGCTAAACTCCATCTCAAAAAAAAAAAAAAAAAAAGAAGAAGTTTAA
ATGTCTACTGATAGGCATTATTTTATAGGGTTATTTTATAGGGACTTAAAAATTTCTACA
TATCAAATATCTAACATAAATATTGGATCACATGGATATATATTAATTCTGCAAATAATT
ATACAAATAATATTAAATATACAAATAATTAGTTATACAAATAATATTATACTGTGTATG
CCTTTTTATAGAATTTCTTCCAAAAAGCAACAGTGGATAAGTTGGAGAGAGCCATGAAAT
TCCCCAGGAGAGTGGCTGTGAAGGGTGGCCAGGGATTGAGACATAGGGTATCTTCCTAGA
GTCTATCCATGAGAAACTGACATGATTTCATGCCATCTGCTATAAGTGCTATAAGTAATA
ATATAGAAATAGTTGACCTCACAGTTAATTTATTAAGCAAATAGTGGAGAAGATGCTAGT
AATTTCTAGACCTTGCCTCAGGGGCTGTGAATATAGGAGGGGATAAGATAAAAAGTGGCT
CTTTCATTGGAGTATCAATTGTGGGGAGAGATTGAATATCCTCAATAATATCTTAATTAA
TATATAAATATATATAAGAAATATATAAATTGAATAATTACAGATAGAGTTTTTTGTGAA
TAAAACTGAACAAAGTGATGTAATGGAGAATGATAGCAGTATATGGGGCATATTCTTTAG
ATGGGGTCATTTAGGGAATGTCTTCCTGTGACGGGGGCATCATAAACAACAATTGTTCAA
CTGCTCTATTCCATCAGGGTGGGAATCACATACTCATTGTTGGCTAGCGTGTCTGCAGTG

FIG 4. (SEQ ID NO. 4) CONT.

CCTAGGACAGAACCTGGCACTTGATAGGCATTTACTGAATATTTTTGAATAAAAGAAGA
ACGAAATGGATGACAGTAAATAAGTCTTTTAAAAACGTTGAATCAAGGCTGGGCATAGTG
GCTCATACCTGTAATCCCAACACTTTGGAAGGCAGAGGTGGGAGGGTTGCATGTGCTTAG
GAGTTCAAAACCATCCTGAGCAATGTAGTGAGACCTCGTCTCCACCAAAAAAAAGAAAAA
AGAAAAAAGGAAAATTATCCAGCTGTGGTGGTACACACCTGCAGTTCCAGCTAATCAGGA
GGCTGAGGTGGGAGGATCGCTTGAACCCAGAAGATTCAGAATGCAATGAGTTATGCTTAT
GCCACTGCCCTCCAGCCTGGATGGCATAGAGTGAGACCCTGTTTCAAAAAAAAAAAAAA
AGATGGATCAACAAAAGTGATATCAATAGTAATGACACTAATAACAAAAAAAATAGTGAA
ATCATGACTTGCAAGTATAAATCACTTTAAAAGATTATTTTAATAGAAAACATGTTAATC
TTTAGAACTACCTGAGGTAGTGTGATAGGAACTATTAACTACATTTGATGAATTTGAGGT
ACTTAGAACATATTACTGGTGAATGGGGAAGCTGGCTTAAAAAAAAGGGAGGGTCTTCTC
AGACAGTTCTCTTTTTACATACGTGGCACAATGATTCATGATTTGTTATATTGTGAATGT
TGAATGTGGAATATTTATAGGAATGCAAATCACATTTCCTTTACACAATAGTATTAAACT
GATTTCAAAGTGTTTTGATATATGCTTCTATCCTTACAATGGTCCAGTGAGAAAGAAAAT
ATGATATTCATCATTGTAGACATGGAAATAAAAGTTAAGAAAAGTTGTCTTGATCAATAT
CATATGCAATAGCAAGTGGAAAACCCATGTTTTTAATTTAGAATTTAATACTAACAGTCT
ATGCTCTCATGGATGTTTTATGTAGTTTAATGTTTTTAAAAAACTCTAAGCCCGACAACT
TCGCTGTTTAAAATATTTGAAATAAAAATAGCTTTGCCATTTTTTAAATAAAACATTACC
TTTTATTATAACAAAATTCAGAAAATACACAAAATAACAAAACAGGAATGACCACCAGTT
ATCATTTAATGTGAATCATTGAACTCCTTTCTTTCTATAAAATTACAAAGTTGAAATATG
TTTTAAAATTTGTGTAAAAGTTAGAGGATGATTTGATTTAAATCTATTATTTAAATTTAT
TTTTAGTCAAGTAATAATAATTCAGTGAATTGTTCAAATCAGAATTGCCATGATGCAGGT
TTCACATACATGAAACAAGTTAATATGAGGAATATTCTTTCCTATACTTTCCTTTTTATG
TTGTTTTTATCTTAATTACTCTAACAGAGACAAATTTCATCTAAAGAGGTGATATCTAAA
GGAAATGTAGAGATCAGAATATAGGACAGATTGTTTTAAAAAGTTTGATATTTATTATTA
GGTGCCTAATAAATGCTCCTTCTAGTTTATGAAGCTTTATTTCTAAAACTATAATCTATG
TTTATGTGTGTTTATTGAATATTTGTGTTCCGTTGGTAACAAATGAAATTTAAGTGTACT
ATTAAGTAATGCTAATACTAATATCAGTTCTATTTTGACAAACACTGTGCTGGCCACTAT
TCCATGTGCCTCACACACTTTTATCTCATTTAAATTTCATAAAAACCCTATGACTGAGGT
ACTTTTCTTATCTAGAGATTACTTGATTGAAGAAACAGGGGCACAGGGAGGCAAAACAAT
TTTCCAGGGTCATACAGGTGAACATGAAAAAGCCAAAAGTAACACCCATCAATAGGGCTA
CGGCATTCATGCCTTCCTTTAAAAATTAATTGAGGGCAAGAAACCATTGTTTAATATGTA
ATTTCAAACATCTAGATGAAGAAAATATCTGTATTAGAAAATAATAAGGACTATGTATAT
ATGATTTCAGACGATTTCCTATTTAAATAAATTAGGATAAATGACATATTTGTTATAGGG
TGAAATGTTAGGGAAAATCTCAGTTTTAGTCACAGATCTCTACTAACCTTGAAATCAGAT
ATACCAATTTAACTCTTTGGCTTGGGATTTTTTTATTCAAAGGCATCAGATGAAATGAGC
TCAACAGTCTGCCGGTTCTAAAGTTCTTTGTCACCTTCTGTGTTATCACGTGGTGGTCTG
TGAATCTTACAGAGATTGATGGCTTCAGTCTTCTCCAAATATTTCTCCTACATCCCTCGT
TGTAAAAGGAAACTGAGTGTAAGGAAAGAATGTAAATCCGTAATCACATTTGGATATCTT
TGAAGTTGCAACACTCCAGAAATTTGGTGACAAGCAAATGCCCCTATTTTTAAAATGATG
AAGCATCAGTGTATTAGTGTAAGTTGATAAGCTTGGAGATATTCCATAAGAGATTATTAT
ATTCTTTGGAAAAAACTCAGGAGGAGAGGTGCTATCAATAAGAAGCCATCTTGGCTTCAA
CAGAAATAAATTATTTGAATAGGATTCACGTCCTTATTCTACAGACATTAATTGCAAAAC
GACCCTTACTTATTTTTAAAGAAATTTGAAAAATATAATTCACATGCCACAAAGTTTTCC
CTTTAAAGGGTACAATGTAGTTGTCCCACGTATATTCACAGAGCTGTTCAGATTGTCCCT
TATTGAATCATTTTGCTTATTCAAGAGCATCTAACCCAGTGAAGTATGCAGTGATAGTAT
TGCATCAATATTTGCTGAATTCTCCACTCAATGAATACAAGGTACAGCAAAAGAGACCAG
ATAATTCTAGCTAAACTCAGATGAAATAATTGTAAAATCCAGAATAATTAAGTATTCAGA
TATATTCAGATAAAGATTCCAGAAGGATACAAGTAAATGATAAAAAGAGCACATTTATTT
CTAATATTAGCTGTCATATTAACACATAGAAAAAAATGTAGGCTTGTTAGCATCAAGTAA
GTTGCCAAATATGATATTGCCCCTTATATAACTTGAATAACTTTAGGTGTTACTTAAATT
CATAGGCACATATTGGCATCTTCAGAGCAAGATGAATTAACACTCTGGAGTTTTTATTTT

FIG 4. (SEQ ID NO. 4) CONT.

ATTTATTTAAAAATAGATTATCACTTGAGAAAAGACAGCATCATAACATTTAGTGACAAA
GTGTGAAATTTTCCTACAGGTCTTAGTGATTTAGCAACCACAAAACCAAAGAAAGGAGAG
TTTAATCATTATTTTAGGTTCCCTCATGGTGACTCTAAATTGTAAGTAAGAATAGCAAGA
ACGTTTTCACTGGCAACCTTCTTTATCTTAAAATTTAATGTCATAACACGTTTGGTAAAG
CAGCTAAATTATTTCTAATGTATATGTTTGGCTGAGGCAGTTAATACAAAGTAAAAGGCA
AAAAGTCATGAAGCTTTTATTTTCTATCTTGTTTCACTTGTGCCTCCAATGAGCATTGGC
TTGGAGTGCTTATCGTCATGTCACTGACATTCTTGCCCAGGCCTTGGCAAACTACTTGGA
TACCCTGGTGAGAGAGGTTTCTGGGACTTTGGCCTGGAAATATGCATTTTGAAAATTATA
TCCAGTGATTCTAATTTGTAACTAGTTAGACATCACTGCACTAAGAGTAAACTTTCAGCT
CTCTGGCCTAGTTCAGTAATTTTCTTTATCACAAACACGTCTTTCATAACTTGGTTCCAA
AGGCATTCATGACTTTTGATGTCATCCGTAAATGCATTTTAAGGAATTAATTTCTGCTTT
TAACCAATTACAAGATTTTATTAACAATCTGTTTACTGTTTGACAAGTATTAGTCAGCTT
TTATTTTATGTCATTACTGAGATTTGAAGTCACCTGCACTACGTTTAAACAAAACCTATT
CTTATGATTACAATATATTTACCTGACATTATGCAAAACTGCATTTTTTTTGCATTTGGG
AACACCATTTTATATATGAAGTTGTTGAGGCTTATAAAAGGTCACAAGTAACTGACTAAT
AGCGTCAAGACTAGAACCCATGTAGTGTTGGCATCTGTTTAGGAACCTGTGTCAGATCCC
ACACTTGTAATGGAGAGCTTAATTTCAGAGAACATTAGCCATATCTAGCTATTGCTGTGA
ATTTAAATTGTTTTGAGTGTGCATTTAATTTGCAAATTTGTATTGGTTTGTTATTTGTGT
AAGAATTATACACCTACAAAGATTTTACCAAGTTTATATTTTTACATTTTAAAGTAGTGT
TTTAAAACAAATAAATTAAATTGACACTTGGTGATGCAAGATTTTATTTTTCCTTTTAGA
AAAGGTCTTTACAATATTTAAATTTAAATCAAACAGTTCTCACTGAAATAATTAGGGGTA
AAATGGACCTCTGTTGATGCTATTTGAAAAAACTATTTGAACAATGAGAACACTTGGACA
CAGGGTGGGAAACATCACACACCGGGGCCTGTCGTGACCGGGGCCTGTCGTGGGGTGAGG
GGAGGGGAGAGGAATAGCATTAGGAGAAATACCTAATGTAAATGACGAGTTAATGGGTGC
AGTAAACCAACATGGCATATGTATACATATGTAACAAACCTGCACGTTGTGCACGTGAAC
CCTAGATCTTAAGTATAATTAAAAATAAATAAATAAATAGGCCTGGCGCGGTGGCTCATG
CCTGTAATCCCAGTACTTTGGGAGGCTGAGATAGGCGGATCACCTGAGGTCGGGAGTTCG
AAACCAGACTGACCAACATAGAGAAACCCGGTCTCTACTAAAAATACAAAATTAGTGGGG
CGTGGTGGCGCATGCCTGCAATGGGCTGAGGCAGGAGAATCACTTGAACCCAGGAGGTGG
AGGTTCCGGTGAGCCGAGATCATGCCATTGCACTCCAGCCTGGGCAACAAGAGTGAAACT
CTATCTCAAAAATAAATAAATAAATAACAATAAAATAACAAAATAGAAGAAATTGGTTGG
ATGCCACGATTAAATATAGATTTGTTTTTGCATTTGTAGGCAGTCAGAGCAAAATGGGAG
CATAGTAAATTTTCTCTTATCATAAGGGAAGAAAAATCTGGCTCCTGAGGTGGTTGTTAT
TTTCTTTGTGTTTTTCTTCTTCTAAATTCTAAAAGAAAGTGTCATGTGGGGTTTCATATA
AATGACACAGATGTCATAGACCTTTTTTCAATATTTTTATGGCAATTACAGGCACAAATT
ACCAACGACTATTTGTTATAGAACTTTTTGATCAAAAACTTACTTCATTTTTTCTCTAGA
GGATTTTCAATGAGGAAAAGAAGCCTTTACTATTTACTTTTATATTTCATATGTAGCTAC
AAAGTTGCTTAAATAAAATGAGCATTCTTTATCAAAAAAAAACAAAAAGCTATTCACTGA
AACTTTGGGGATACTCATCTTCATGTACAGTTTCCAACTCTGATTAGACCACAGCTCCTC
CCTATATTTATGATTTGCTTGCTTTATAATCAATATTATTTCTGAAACTAGACCCCAAAC
AAGTCAGTTTTGGTTTTGCTAAGATTTGCTTAAATGTAAACCTTTAGAAAATCTTATGTA
TATTATTTTATGACTCTTAACTGAGTACATACTTGAGTGGTTATTCTGCTGTTACATTTG
TTCTGAAGAATCATGCACATTTTAATAGGCAAGTTATTAATGCAACCAAACCTTTAAGTT
TTGGAGTTTTATAGGTAAAATATGTTTTTCTAGAGGTCTGTTTCTAAAGTTAAAAGCTGT
TCTAATAAATAATAAACAGATTCAAAAACCTTGGCAAACTCTCACAAACCAAAACAAAAT
TAGGACATTTTGATTGATTTTAATATTACTTTATCTAATAAAAAATAAGTTAGATGCTAT
AAAAATATTTTTAAATGTGGAGGTAATTTAGTTCAGTTATCACACAAACATTCTCTCCAA
TATACACTTGAGTGTAAATTATATGTTGTTATTTACTTTAATAACAGTTTGCTCAAGCAG
AAAACCTGAAAAAACTATTGCACGTATGCCCAGGGTTGTATTGCATATTAACACCTGCAA
AATAAGGCACAATTACCTTTCTATTTAGACAATTAAAAACTTCGATAACATAAGCTTAGT
TATTGCCTGATAAAAAATATGCCAATCCTGCTCCAGATTAACAGATGTCTTATTGATTCT
ATGTATGTACCAAGTTAGACATATAAACCAATGGGTTTAGGAATGGTTAGTCTTCTAAAA

FIG 4. (SEQ ID NO. 4) CONT.

TCTAAACTGTTTGTAGCAAAATGTCATTGTAAAAGCCCAATATAAAGAATAGCTTTAAGA
ATTCATTAAAATGTAAGGTACATGAAAGCGGAGTACGTGGTTGGTTTTGTTCATTGCTAT
ATATTTATCACCTATAACAGACACATAGTAACTCCTATAGAAATATTTATTGGATAAGTT
AATGAAGTATAATTATGGAGGCATAGTTATTTTTCAGAAAAGTAACTATACATCACATAT
CAACCATTGTTTATATAAAAATCAGATGTAATTTCATATGATTTGGTGAGCTAAGTATGG
TCAAGAAGCATGTGTTCTTATCACAGATAATCATAAAACTAATTTGAAAATTATAGAAAA
TCTCAAATTATATCCCAAAATGGACAATTATTACTTGTACTATATTTTCTCTTAGTAAGA
TAATATTTGTTTTGTTATAGAATATTTGTTGTCATTCCTACTCATCAATGTTAGTACAAT
TTCTCAAATAGATGTAAGCATAACTTCTAAATTTAACAATCAAAATATGGTCTAATAAAC
TAAGATGAATTCCATACTCAATATTTGTCTTTGTAACCTAGAATATTTTCTCAATTGCTA
CTATGAAAATTAAGAATAAAAAGAAAATTTTAAATGTAGGAAGTGCACTGAACTGAGAAG
ATTATTTTCCTAAAGGGAAATTCCACTGGCTATGGAGTAACTGGGAACTCTGTCCTTTAT
TGTAAAACATTTATGAAAATTGCTTGACTTGCAACTTCATTGGTTGCCTTGGAGAGTTCA
TTCTATAAAAAAAGGTGCATCACGTGAACAAGAAATGTATCTACACAATGCTCAACAGAA
AACCCTTGATTAATTGAAGTATAGTAAATGGTTATTGGTCCATTCCAATTTCCTTTAATT
TGCAGTTGCTTGGAAGCATAAAGCTTTTTAATGTCTTTGTTTTGACAAAGAATTCACTTA
AAAGTGAGAACAAATTTAATTTATTAATATAATTTAAAAACATGTTAAAGCAAATTAAAA
AATTAACATGCGGAACAATCTTTTAAAAAGTTTTTTTTTTTTTAAAGTAGGAAGTACACT
GAACTGAGAAGATTATTTTCCTAAAGGGAAATTCCATTGGCTATTGACTAACTGGGAACT
CTGTCTTTTATTGTAACACATTTATGAAAATTGCTTGACTTGCAACTTCATTGGTTGCCT
TGGAGAGTTTATAAAAAAGTTATTTATTAAGTTAGAACTTTAATAAAAGACTTTTTATTT
TTATTTATTTATTTTTTTGAGATGGAGTCTTGCTCTGTCACCCAGGCTGGAGTACAGTT
GTGCAATCTCGGCTCACTGTAACCTTGGCCTCCTGGCTTCAAGCAATTCTTTTGCCTCAG
ACTACCCAGTAGCTGGGATTACAGGCTCATGCCACCATGTCCAGCTAATTTTTGTATTTT
TAGTGGAGACATGGTTTCACCATGTTGGCCAGGCTGGTATTGAACTCGTGACCTCAGGTA
ATCCACCCACCTCGGCCTCCCAAAGTGCTTGGATTACAGGTATGAGCCACCGCGCTTGGC
CAGACATTGATATTTAACTCTTTCTTAATCAAATTTTGAACTTATTTCATACCTTGTATA
TTCTAAAAAAAAAAACACACACATATATATGTATACATATTTCTAGCTTATATGCCCACG
TGTTTATGGAGTTCACTCTTTTGTTTTGTTTTGAGATGGAGTTTTGCTCTTGTTGCCCAG
GCTGGAGTGCAGTGGCGCGATCTGGGCTCACCGCAACCTCCACCTCCAGAGTTCAAGTGA
TTCTCCTGCCTCAGCCTCCTGAGTAGCTGGGATTACAGGCATATGCCACCACATCCGGCT
AATTTTGTATTTTTAGTAGAGACAGGGTTTCTCCATGTTGGTCAGGATGGTCTCGAACTC
CCAACATCAGGTGATCCACCTGCCTCGGCCTCCCAAAGTGCTGGGATTACAGGCGTGAGC
CACCGCGCCTGGTGTTCACTCTTAGGGAATTTAGGTGAATGCAGATAGTTACCTACTAAA
AAGATATAAATCGAAAGAGATAAACTTTGGCTGTTGGGAAAATGGTTGAATCAATCAAGC
AGCAATATTAACCTGCGAAGGGTAAGTCACTTTTGTCAAAATAAAAAGGCTATGTTGAGG
TTCTTACAGAAAATACTTTTAAAAATAGGGACCTACACAATGTAATGTAGAGGTGTTTTG
GCAGTTTAAGGGAAATGTAATGTAAAAATTTGCATAATGCTTTTACATATGTAATCCATA
CAATATTAAAAACCGTCAATAAAAACATGTTGAAAGTCCTTAATCTCTCTTTAGTATTAG
TTTAACAGTTAACAGAGACTATTAAGATTGTAATTTATTCTCTTATTAAAAATTATTATC
TGATTTACTGAAAAAACAATCACAGGTTTTGAATATCTAAAAACAACCACTAGAGGAAAG
CAATTGATTTCCTGTAACATTTATTAATGTAAGCAGACTGCGAGAATTCTATTAATCTAG
ACAGGAGAACTGTAATGTTTCTGTTGTCTTCTTTATTAAATTTGACAAATTTGAAATGCT
TGCAATTCTGCACTAACAGGATTTCATAAATACTCTTTGCTGACACATTTTAATTTTTGT
GCATTTACTGGATATTCTTAAAATGCAATCATTTATTATATTTCAGGGCAGGAAAACCTA
ATTAGTAGTAAACGATTATATCAAACATTTGCTTTTTTAATAAACTTGGCTTTATATTAC
CTTATTTAGATATCATGAATTCATATTAGTACAGACTTCTGATTACCTATTACAGAAACA
TTCCAATTTCAATAAAACTAACGTTAGTAGTCAAGTAGTTTCTCTAAGCAACTGAAATAA
ATTTGCAAGTGATGGACTATGCATTCTTAGTATTAACTGCAGTCATATAAGGCCATCAGT
AACATGGTATTAAGAGAAAACCAATAAATTTACCCAGTTAGTCAGTCTCTTGGTATGTGA
GTAGAAGAGACAAAAAGAAAAAACTAATAATACAGTTGTCACATATTATTGACCATTTTC
TGCCCTTCTATACTTTTCTAAGCCCATAGGCTGTGGTTATATTGCTATGATCAGTTTGGG

FIG 4. (SEQ ID NO. 4) CONT.

TAGCTACTTGAATTTTTGATCTTTAAATGCAGGTATACCTCTGAGACATTTCAGATTTAG
TTCTAGACAACTGCAATAAAGTGAATATCACAATAAAGCAAGTCATACAGTTTTTTTGGT
GTTTCATTGCATATAAAATTATGTTTATTCTATACTGTAGTCTGTTAAGTGTGCAATAAC
ATTACATTTTTAAAAAACAATGTATATACCTTAATTTAAAAATACTTTATGCTAATACAT
GCTAACAGCTACCTGAGCCTTCAGCAAGTTGTCCTCTTCTTGCTGGTGGAGGATCCTACC
TTAATGTTGATGGCTGCTGACTGATCAGGGTGGTAATTGCTGAAGGTTGTGGTGGCTGTG
GCAATTTTGTGAAATAAGACAACAATGAAGTTTGCGGCTTTGATTGAGTCTGACTGTCAT
GAAAGATTTCTCTGTAGCATTCAATACTGTTTGAGAGCATTTTACACATAGTAGAATGTC
ATTCAAAACTGGAGTCAATCCTCTCAAACCCTGCCACTCTTTTATCAGCTAAGTTGATTT
ATTATTCTAAATATTTTGTTGTCATTTCAACGGTATTTACAGCATCTTCACCAGGAATAG
GTTCCATCTCAAGAAACCACTTTCTTTGCTAATCCATAAGAAGCAAATCTTCATCTGTTC
TAGTTTTATCTTGTGACTGTGGAAATTCAGTCACATCTTTTGGCTCTACTTCTAATTCTA
GTTTTCTTGCTATGTCTACCACATCCGTGGTTACTTTCAGTACTGAAGTTTTGAACCCTT
CAAAGTCATCCTTAAGGGTTGGAAACAATTTCTTCCAAACTCCTGTTGACGTTGGTATTT
TTACCTCCTCCCATGAATCACAAATGTCTTTAATGGCATCTAGAATGGTGAATTCTTTCC
AAGTTTTCAATTACTTTGCCCAGATTCATCAGAGAAATCACTATCTATGGCAGCTATAGC
CTTACAAGATGTATTTCTTCGATCATAAGACTTGAAAGTTTAGATTACTCCTTGATCCAT
TGGCTGCAGAATGGATGCTGTGTTACCAGGAATGTAAACATTAATCTCTTTGCACATCTT
TTTCAGAGCTCTTGGATGACCAGGTAGATTGTCAATGATCAGTAATATTTTGAAAATAAT
CTTTTTTACTGAGCAGTAATTGTCAACAGCGGGCTTAAGATATTCAGCAAATCATGCTGT
AAACATTTGCTGTCATCCAGGGTTTGTTGTTTCATTGGTAGGGAGCAGGTAGAGTAGACA
TAGCATACTTCTGTGGGGCTTCAGGATTTTCAGAATGGTAAAAGATCAGTGGCTTCAGCT
TAAAGTCACCAACTGTACTAGTCCCTGACAAGAAACTCAACCTGTCCTTTGAAGCTTCAA
AGCCAGGCATTGATTTCTCCTCTATAGCTATGAATGTCTCATGTGGCATCTACCAGTAGA
AGGCTGTTCATCTACATTGAAAATCTGTTTTTTAATGAAGCCACCTTTATCAATTATCTT
TGCTAGATCTTCTGGATATCTTCTTGCAGCTTGTACATCAGCATTTGCTGCTTCACCTTG
TGCTTTTATGTTATGGAGATGCCTTCTTCCCTTAAACCTTATGAACCAAGCCCTGCTAGC
TTCCAACTTTTCTTCTGTGGCTTCCTCAGCTCTCTCAGCCTTCAAAGAATTGCAGAATTA
GGGTCTTGCTCTGTATTAGGCTTTGCTTTAAGGGAATGTTGTGGTTAGTTTTCTTCGTGT
CAGCAATAAGGCTGTTTTGTTTTCTTATCTTTTGTGTGTTCTCTGGAGCAGCACTTTTAA
TTTCCTTCAGTATCATTTCCTTTGCATTTACAACTTGGCTAGCTATTTGGCACAAGAGAC
CTAGCTTTTGATTTACCTTGGCTTTCAACTTATCTACTTCACTAAGCTTAATTATTTATA
GCTTTTGATTTAAAATAAGAGATGTGCAGCTACTCCTTTCACATGAACACTTAGAGGCCA
TTGGAGGGTTATTTCAATATTGTGCTTCAGGTCTTGTTTCCATATTGTTGTTCTCAGGAA
TAGGGAGGCCCTAGGAGAAGGTGAGAAATGGAAGAATGGCTGGACAGTAGAGGACTCTGA
ACACACACAATATTTATCCATCCAGTTCACTGTCTTATATGGGTGCAGCTTGTAATTCTC
CCAAGAAAATAGTAACCTCAGTAATCGCTGATCATAGATCACCTTAATAATGAAAAAGTT
TGATGTATTGTAAGAATTACCAAAATGTGACACAGACACAAAGGGAGCACATGCTACTGG
AAAAATAATGCTGATAGAAACTTGCTCAATGCAGGGATGTCACAAACTTCTAATTTGTAA
CAATATGCAAATATCTGTGAAGCATGATAAAGGCAAGTGCAATGAAACATGGTTTTCCAG
TACGTGATATTAAACCATATCATGAAATTCTAGACTCTGAGATTTACAAGGGACTGACAA
CTCAATCAGTTCAGCTTCTCATTTCCACTCTTAAGAGGTACCTCTTTAAATAAAAAAGCC
TATTAAGATCATTAAAATAAATCCATGGAAATCCTTTTTATTAAGCAAAATGTGACAAAA
TTGTTGGAATAACCAGAATGAAAAAGTCTATCATTGTCACTGCCCTATCAGACTGACATA
CTTCATTGAGCATAAGAGGGATACTATAAACTGTACTAATATGACTTTATTTCTTTTTAC
TGCTGAATATGATTCCATTGTATGAATATATCACATTTTGTGTATTCATGCATCAGCTGA
TGGACATTTGGGTTGTTTTCACCTTTTGAATATTATAAATAATGCTGCTCTGAACATTTG
TGTACAAGTTTTTGTGCAAACATGTTTCATTTCTCTATGGTAGAATTCCTATGACTGGAA
TTACAAGTCATGTGATAGCTATATTTAACATATTGAGGAACTGCCAAAGTATTTTCCAAA
GTGGTTGCACCATCTTATATTCTCACCAACAACATATGAGTGTTTTGATTTTTGTATGTA
CTCACCAACACTTGTTATTATCTGTTGTTTTTAATATAGCCATTTTTATGTGTGACATAT
TGTATTTTTAATTTTCATATCTCAAATGACTAATGAATTTAACATCTTTTTATGTGTTGT

FIG 4. (SEQ ID NO. 4) CONT.

TTAACTATTCTTACATTTTCTTTGGAGGATTGTATATTCAAATTCTTTTCCCATTTTAAA
TTGGGTTATTTATTTTTATTATTGAATTGTATTAGTTCTTTATATATTTTGGATATAAGT
CCCTTTCAGATATATGACTTGCAAATGTTTTCTCCCATTCTGTGAGGTTTTCTTTCACTT
AATAATGTCCTTCAAAGCAAAAAAGGTTTAAATTGTGATGAAGTCTAAATTTCCAGTCTT
CTATCACTTGTGCTTTTCCTTTAGACTCTCTGTAATTTTTTACTTAGAGCAACATGTAGT
GTAATTTTGGTTTAGGTGACTGTGCTTCTACTAGACAGTAAATGTGAACACCTGGGTATT
TTGTATCCTAAGCAACAAGCAAAGGGCCTGAGCTCTAGTAAGATATCAATGAATGTTTGT
TGGATTCATTAATGGATTTTTTGATACTCCTTTTCAATAAGTAAATTTAACACTACTCAG
TAACAAAATAATTTTTACTAAGGAATGACAATATTTGATCTTTGAATAATTAATTTTAGA
AACACACACATATATATATATACATATATATATATATATATATATATTTTTTTTTTTTTT
GAGATGGAGTGTTGCTCTTGATGCCCAGGCTGGAGTGCAATGGCATGATCTCCACTCACT
GCAACCTCTGCTTCCCGGGTTCAAGCAATTCTTCTGCCTCAGCCTCCTGAGTAGCTGGAA
CTACAGGCTCCCGCCACCACACCTGGCTAATTTTTTGTATATTTAGTAGAGATGGAGTTT
CACCATGTTGGTCAGGCTGGTCTCAAATTCCTGACCTCAGGTGATCTACCTGCCTCGGCC
TCCCAAAGTGCTGGGATTACAGGCATGAGCCACTGCGCCCTGCCAATTTTAGAAACTTCT
TGGTCATCCTCACACAAAATTCAGATATTGATTCCTTAAATTAAATTTTAGTGTGCATAT
TTAAAAGCATGTTTCAATGATAATATTAAGTAGTTAATTGCCTTATTTTATCTTGGAAAA
AGCAGAATGAGTGATGAAGTGTCATCTGTTTTATTTTTCCAGTTTTTTTCCATAGAACAT
ACCTTTATTTGAAAACTAAAATCAAAGTATCCCTTGATGTCATAGGATACTTTGAAATTA
TAGATAATCATAGTTATATAGTCATAAATTGAGGAAGAGTGAGAGAGTAGTAGAAAAAAA
TCATCAAACCGTATTATTTCATGGAGATGGTTAGTTGTAGTCAGTATTTATAATTGATGG
CTTTTTCCATTACTCTGGAGTCTAATTTCAAATCTTTCATAAGTGTACAGATGTTTTATC
TGATTTTGCACATTATTTTCTTTCTACATTTCCATAGTAGTTCAGACTTCTTAAAAGTCA
ATTTTTAAAAAAAATTCAGCTTTTCGTCCAGCTTTTTGTCATACTCTTATTCCACTAAAA
ATGTTGGTACTTTGGTTTTGACAATGAAAAAATAGAAAACAAATAGCCTTTTATGCTGAAA
CATCTTATTAAAGAAAATTTATTTTGTGATTTATTTCTTTATTTTTCATATTGAAAAATT
TTTCCTTCTGTTAATTAGTTTTAACTCTGATGATCATCAGGGGATAATTCTTAGGACTTT
CATTACTCAATGTAATTGTAATAGTTGGTTCACCTCCTTCTTAATTTGCGTGTGTGTGTA
ACAATAAAATGTACTAGTGCAATGAACAAACTGGTTTTTACATCATTGAATAAATGTACA
TTAAATGCCTTCTGTACCCTAGGCGTTATATTGAAACTGATCTAAATGTTTCACTGTTTG
AAACTTAGAAAAGAAGCAGGCTTTCTGAGTTTTGTTTTGTTTTGTTTTGATTTTTTTGAG
GCGGATTCTCACTCTGTTGCCCAGGCTTGAGTGCAGTGGCACCATCTCGGCTTACTGCAA
CCTCCACCTCTGGGGTTCAAGTGATTCTCCTGCCTCAGCCTCCTGAGTAGCTGGGATTAC
AGGTGCACACCTGGCTAATTTTTGTATTTTTAGTAGAGACAGGGTTTCATCATGTTGGCC
TGGCTGGTCTCAAACTCCTGACCTCAAGTAATCCACCTACCTTGGCCTCCCAAAGTGCTG
GGATTATAGGTGTGAGCCACTGCACCTGGCCCTGAGTTTAGAAAAATAGGATGTCTAAAT
AGAATTAAAGAACAATGCATTTCCAAAAAATTGATTTTGATAAGTTGAATTTCTTTAGAA
CATATACTTTACAATTTATATCACATAAAATTTTATTCATTACTGTTTATTAGTGAGCTA
AAGCTGTTTCATATAAATTAAATTTGTTATTGTTTTGAAGTAAAAATACAACACAAGACT
CTAGAAAGAGACTTTAATTTTATAGTTTAAGATAGCTGTTTAAAAGATATAAGGACATAT
AACTATTATAGACCAGTGGTCCCCAAACTTTTTGGTACCAGGGACCAGTTTGGTGAAAGA
CATTTTTCCACATACTGGGTGGGAGGGTGGTTTTGGGATGAAAGTGTTCCACCTCAGGCC
ATCAGGCATTAGATTCTCATAAAGAGCGTGCAACCTAGATCCTTCGCATGCACCATTCAC
AATAGGGTCCACCCTTCTTTGAGAATCTAATGCCGCAGCTGATCTGACAGGAGGCAGAGC
TCAGGCAGTAACGCTCACTTGCCCGCCCCTCACCTGCTGCTATGGGCCGGGTTCCTAACA
GGCCACAAACCAGTACCGGTCTGTGCCCAGGGGTTGGAGACCCCTGTTATAGACTAATAA
CCAACTGAAATAGAATAGCATAGCTATGAGTCAAAGGTTTGTGTCTTTTGCATCAAAGAA
TAGAAATGTCTGCAAAGGTGAAGACTACTATGCAAATGTGAAATGAGGAAGAGTGATTAT
TTTGACATTGCAGTCATTCCATAAAAGAACTATAGCCAAGTCTCGTGTAGGTTCTAGAAA
ACCACTAAAGATGGCGACCATGTTATCATGGGGGCTGCATTGTTTCTTATTGTACTTGTG
CCATTATTTTGTTCTTGCAATGTTCTTTGTGTTTTTGTTTTGTTTTTGTTTGTTTAAATT
TTCTATTCTTAAAAAAACACAATCTGATGAACTCTCCCCAATCTATGATTCGTTCCTCTT

FIG 4. (SEQ ID NO. 4) CONT.

```
GGATCATGTATTCCCACCACTCCTCTAATCTTTGGATTGTTGGAGGGGGAGGAAGAACTT
GATATGTATTATTTTGAGTTGCCCCTGACAGATAGCAGTATGGCATGGTAAGTGAGAATG
TGTAGCTATATAGGGTAGGAAAAGGTATTAATAGATTCAGAGAAATAAAACTCCCAGTAC
AAGCCATACAACAGATCAATATACATTAGCTTTTTACTCTTCTTTGTGCTGCTCATGTTA
GACCAGTAATTATTTAGAACATGGAAACAAAGTAAAATAACCAGTTAATGAATTCATTGT
TTTGGCTTTTGTATCTGTTAGCTACTGCCAGAATAATGTTGCATAATAAAGAGCCACAAA
AATCTCAAAGGCCTACAAAAATTCACTTTTATCCTCACACATTTCTGGATAACTGCAGTT
GGGCTTCTCTAGGCTAGACTCAACTAGGAAGCTTGGCTTCAGTCTAAAAACCTTCCAGCT
GAGATTCCTCTACTCAGTATCTCTAGTCTTTCTGGTAGTAGTGGGCTAGCAGAAACATAC
TGTTCTAGTGACCATGGCAGAGGTAGAAAAGAATAAGTGTATTTTAAGCCCCTTCTTGTG
CTATTTTTATAGATAGCCCATTGTCCAATCCAAATATTATGAAAGAGCCCAAAAAAGGCA
AGGAGAAAAATCTCACCTTTAGTGGGAGGGACTGCAAAGTTGTTTATGGGGAGGGGTAAC
GGGACCAATAATTCAGTCTACCGTAGTTTGTACCTTTAATAGAAATCAAACCACTTCTTT
ATTTTTCAGTAGTTTGAATAGAAGCCTTCTTTATTTCATAGTATCCAGTACACATTAGGC
AAAAAAAGAGAAGAAAAAATTTAGTGGCATTTTTGTTTGTTTGTTTTATACTAAAATTT
CCCTTTGATATGTGTCTACCACATTCAGATTAACATCTATTGAAAAATATACTACAGGAC
GCATTTGTAGGGTGTTTGTTTTGAAGAATAGTATAAAAATTTCCATAAGTTTCTTATGCA
ACCACACATATTTTAACTTGATGTTTTATTCTGCATTTACTTTTGAGCATCCTTAAGAAT
TTGTTAAAATGCAGAAATTATGCAGTATTGATTTCAGGAAAAATTGAAGTGGTTACACAT
GGTTGCCTTTGCCTTAAAATAAATCCTTATTTGGTTCTAACTTGAACAATATTGAAAGCA
CAACAAAACTAGCTTTTTATTATGTCACCACACATTTAGTGAGTTATGGAAAGCATTTTG
TTTTAAGAATGGAGTTAACTATGTGTTATCCACGCTTCTAGCCATTCTTGTCACTCCTGG
CTACTCTCCAAGCCTGCCTGTTATTCATACATATTTCTTCTTAGTAAGAAATGCATCAAA
ATCCCAGGAACATGTGCTGCTGACTGTTAGAAGAGTTTTAGTGGTGAGAGATTAATGTAA
TTACTTTTGTTTGAGAAATATAATTGGTCACAGTTATATACATGTAGCTTATATGAGAAG
TACATTCAGTTTTAAAACTCATTATGATTAATTTTACTTTCCTTAAAAAATGAAACCAAA
GAGAATCTAAAATGTGTATGCTTCTTTCATTCCTAATATTCCAGAATACTTAGATATTTT
TATGTGAAGTAAATGCCCAGATATCTAAATAGATATAATATTATTTAAATTTAAGGTATA
AACTTTTACATGACAAAATGCTTAATAGCCTATAATCTTAAAAACAGAATTATTCCAATT
CCCATATTGTATGTTACTTCATCAAATATTACCATTATATCATGTTTCTTGTACTAAAGT
GTTTCCTGTGAAATAACGTAATAAAATGGCCTTTAGTATGCATGATAATATTTAAATACG
CATTTTCTAGTAAAATATAATGCTTATTCATTTTTTTCTTCTAGTTCTAAAGAAAAAAAT
GCACCAAATGCATACACTTACTTTATGATAATTTCTGAAACTTAAGTAGAGTTTGGGCCT
GCAACAGACTTGTGTTTTCTAGTAGTTATGTTTCATTCATGCAGGTGGTAGTGGTCCTAT
TAGTTTTCCTTAATAAGTCCCATATAGCTCTGGCCAGTCTTTCATAGAATGAGTTGGTAG
GTCTTTCCTCCAAAGTTTGATTTCTCCCATTTTTTTCACATTGCAATTTCAAACTTTCAG
TAATACCATCAAGATGAGACAGTAAACTATTATTAGAGTTACCACAAGTTTGAACAAAGT
TGATTATACATCGCAAACAAATAAATACTTAAAACCTTGTTCATAGAGATCAGGCCTTGC
ATACCTACATAGTCCAAACATTACATTCCTGACATTTAGAACATTTAAATGCAAACTGTT
CTTTGTTAGGGCTTTCTCATAACTGAAATATGAGTCACTTGCAAACCATAATAGATTTTG
GCTCTGCTACATGATGAAGTGTTCTGGATGTCGTGAAACATTTCACCCAGACTTATGGCA
GTAGAATTCCCAGTGGTCACCCAAAATAGGGAAAAAAATGAAGAACAAACTTAAAGGAAA
TATGCAGACTCTGGCACCATCCTTTCGTGGCAATACAGCTCTTTATTGTTGTTAAGAAAT
GGAAATATTTAGAGCCTAAACCCATAAACTATAGTACAATTAGGCGTTGAATTTTTTTTT
TGTTCCTAATTACGAAATTTAACTCTATACTTGATTCTCATGTTAAGGTCAGGTCATAG
AGTGTTTCTTTACACATCACCCTGATGCGGTCATACTGAGTTGTCTCCCAGCACTGAGCT
TCTCACTGCATTGTGGGCAAACTCATATTCCACACTCTACACTCATCTCAGGCAGGAAAG
GTGGAGTTTTCCTTTTCAGGGCCAAAGGAAGCAACAGCTGAGGCGTGATGGTTGTACTGA
TATTGGTGTGGGTTTCAATTTGGTTAGTTTGCTTTCAATTTCAACTCCTCACTTGAGATT
CCATACAGAAAAGTAAATGGTAGGCTTCCAGCATCTTGTTTCACTCTGGTGAATAAAAAT
TGTTTTGAATGTAAGATTAGAGTTTTTCCTTGCTTAATTTTAGTAGTACCTACACAGCAT
AAACTGAGGCATCATTTAGCAAAATGTTATTGAGTTGACATCATAATGACCTATTAAGGG
```

FIG 4. (SEQ ID NO. 4) CONT.

CAATACACATTTGAATGAGCTCAGTTATTCTTCCAGGTTTACACGTGCCTTTCATGGTGT
TTAGTGTAGCAGCTTTTGAAGCAGAGATGGGCAATGTGTAGGACCTTTTATTCCAGTCTC
CTAAGTGGGAGATATTCTGAACAAAACATATTAAGGATATTTTTTCTGAAGTTTTTGAAA
TTTTAAGTCATGATTCACTTTTCAAAAGAAGACATTTATGTGGCCAACAAACATGAAAAA
AAGCTCAACATCACTGATAATCAGAGAGATGCAAATCAAAACCACATGGAGATACCATCT
CATGCCAGTCAGAATGGCAATTATTAAAAAGTCAGGAAACAATAGATGCTTCTGAGGCTG
TGGAGAAATAAGAACACTTTTACACTGTTGGGGGTAATGTAAGTAAGTTTGACCATTGTA
GAAGACAATGGCAATTCCTCAAGGATCTAGAATCAGAAGTACCATTTGACCCAGCAATCC
CATTACTGGGTATATACCCAAAGGAATATAAATCATTCTGCTATAAAGACATATGCACAT
GTATGTTTACTGCAGCTCTATTTACAATAGCAAAGAAATGGATCCAACCCAAATGCCCAT
CAATGATAGACTAGACAAAGAAAATGTGGTACATATACACCATGGAATACTATGCAGCCA
TAAAAAGGAATGAGATCATGTCCTTTTCAGGGAAATGGATGAAGCTGGAAGCCGTCATCC
TCAGCAAACTAACACAGGAACAGAAAACCATATTCTGCATGCTCTCACTCATAAGTGGAA
GTTGAACAATGAGAACACGTGGACACAGAGAAGGGAACAACACACACCAAGGCTTGTTGG
GGGCAGTGGGAGGCAAGGGGAGGGAAGTTGGAGGTTGGTTCAATCAGTGCAGCAAACCAC
CATGGCACATGTATACCTATGCAACAAACCTACACATTCTGCCCATGTATCCTGTTTTTC
TTTTTTAGAAGAAATGTTTTGTTTTAAAAGAAAAAAATAGTAAGTCATTATTATGAGTAG
TTACTGAATTATCATAAAATATCATTTCATAACATAAAAATTATATATGATAGCATGTTC
CCACACAAAAACTAGGAAATCAATAGGTTTGAATTGCTTTAAAATATCATTGTAATAGTG
GATAACTTTGATTAATACATCTTTATATGCCAGTAGAATGCCTATGTTATTATTACATTT
GCTGAATATGGGACTTTAATAAAAATGTAAAAATGACCTGGATTTGCTTAAAAACAGAAA
TATTTCTAGAGGAGAATTTACATGCTAGACATGGATAAGTTGTCAGAATGAGCAGGACAC
ATTATTGCTCTTGGAATCTCAGAATATAGAAGTCTCTAATTTAAGTAATATAAATGATCT
TCAGTATCCTGAAGATATTTGCAATTACCTATGTTGGTAATATATAAACTTAAATCAGAG
CTACAAAATACTATTATTGAAATAAATATTTCTGACAAAACTGTTACTTGCTTGTATTTA
AAAGCAATCTTGATGGCATTATCTTAATATCTTTAGAGATAACACTTGTGAACTCTAAAC
ATTATTTTTAGTGCAAAGTTTGTCATAATTTATGTGGTTTAAGTGACAATATTACATGAG
ACAATTAATTTTGGAGTGTCAGTTCCACAAATCCAAAAAGTCAATAAAGTAAATAATTAT
TTTTGCCACTAAACAAAACAAAAAATTAAGCACTATTTGCCTTGATGCATCAGGTGTTAC
TATTTTATAGTTTGTACAGTTTCTGTCTATCCTGCCAACTATTTAAATGTAAGCCATTCT
GAAAATGGGTATTTATATGTTGCATCTTTTAAGAAAAAGAAATAGCTTTTTGTATACGTT
TTAATAGTAATCACTTTCACTGATATTTACAGAGAATTTAACTATAGTTTCTTTAGTTGT
AATACATACCTATTGTCTTTCTGCTGAATGTCTGTTTTCCAGTGGCATTGATAAGACGAA
CTCTCACAGATTATTTTATCTTAATATAAATATAAAAGAACCTAAAAATAGGCAAGAAGT
GAATAAAATGTTTTTTAAAGTAGCCCATCAAATATTATTTTCATCAGAAATTATTTTCTT
GTTGACATAAAATGCATATTTTTTATGAAAGATCATTCTCTCTGTGCAAAGATCAGAGAC
ATTGTGTCTTAGGCACATCATTCAGCTTGCTCCACAGCCCTGGCTGTCTCCACTACTCTG
GAAAAATCAGTGCCCTCGAGTAGGAGGCTTAACATTGTTTTTCTTAGATAAATCACTTGA
CATTTCAGTGCCTTAATTTTGACTCTCTGTAAAATAACAGAAATGGAATGGAAATGGACT
TGATGATATTTAACATTCCTACAAAAAGTATTAGTATGTTGACTTGCAAATGAATGGATT
TCTGAACTTTCAGTGTACTACAAATCCTACGGTCTCCCAAAAGAAAACAAAAGATTGTTT
TTCTTCTTTATTTGAGAACCATTTTATGTAGATTGCAGGAAGGTTGTGAATTAAAATATG
TTTAGATTTTTTCATTCCGTTCATTAAGAAACATTTGATTTAAGCTGCAGAGAGGATATG
CATTTAAGAATATGTTTAGAATTGTGGTTGAGGTGGCAACCACCATGCAATTATCAGTTT
ATTAACAGGGGAATGAACTCATAATGGACTTTGCTATTTTAGTCATTTCCTTTAACTTGA
ATATAATCTTCTACTTTCATAATATCAATTTAAATTGGGGAAATAGCATGTTTTATCATT
AGATCCACAAATATATAATGGTTTGATATTAGCGATTGTTAGGTAATGATTGTTCCTTAG
TTATGTAGTTGTATGCTGAAACATTTAAAAAATTAATCCCCATGTATAATAACATTCTTG
ATGTAGAGCAAAATAAAATGATAGACTGCATATTATAAAAAAAAGAGAAAAGCATTATAT
TATTTTATGCACTATTCCCACAGAAATATTTTTTAGTTTTAAAATATCCATTTGACCCTT
CAGCAAGCTGAATACCAGGGATTTTATTCCTTCAGCATAAAGTAATTTGGTAACAATATT
TAAAGGCATATTTCTAACTTAAATTTTACTTTTATAAAATTACCAAAAGACAGATCATTT

FIG 4. (SEQ ID NO. 4) CONT.

GTGAACTAATTGGTTATTAGCTCCTTTAATCTCAGTCATGTGTTTGTCTCTAAATAAAAT
TATTTCATTTACCAGAGTTTTACTGCTCAGGGCTCAGGTGACTCAGTCAAGAAAGTCATT
CTTGTGAAGCTACCTAAATGGTAACAACGGTAGTGGCAGTGGGTGATACCTTAGCTCAAC
CATTAGCTGCAGCTGAAGTGTTTATTGTAAGTCAAGCACAGATCTACCAACTACATTTCT
TCTAATTGTAGCAGATGAAACCACACACATTTTTAAAGGACCAGATATCTAAGCACAAAG
GTCAACATTTGGTAGGCATGCAGAAAACATGGAAGTGCCTTATCTTAACGGGATCATGAA
TCTTCATCTTTAAAGGGCAGTTTTTACAGATTTTCAGAATTGATACCTTAAGTTGTTCTG
AACTTCAATTACAAAAGCTATTGCCAGATTGTGTTTTGTTTTTATTCAAAATGTAGCCAC
TCATGAAGAGAAACTTCTGAGTTTGAAATGTGATTTGTGTTTTTGCAAAATGTTTATTTG
AATGCAATTTTACCTCCAGTCTAAACAAATGTAAAGATAAATGTAAAACACTAAGAGGGG
CAATGCTGGCACTGAAAGCTTAACTATGTAGTAGTATTGGGTTTGTCCTTTAATTTTTAC
AACATATGCTTTTTTAGTTTAGAAATAATATTGTAGACTTTTAAGATCTCAGAATTTTAA
GCTAAACCACTAATAACAACTGTCTTCATTATTTAAAGTGATCTAAATTGTATAGAAATA
AAAGGGTTTTAAGAATTATAAAAATGTAGTTATTGTTTCCTGCTTTTTTCTCTAAACTTC
TAATGTTCAATTCTTGTGTTTTATATAACGTTTTAAAATAAATCACACCAAACCTTAGTC
TAAAGAAGGTATAGTAATGGTTGGTGTCAGATCTGAGAGTGAACCAAGCACATGTTAGGA
TTTAGAATCATCAAGATAAATAGTAACACCAATGGCAACAAGGAAGCAATTTAAAGACAA
ATTTCTGGAATCAAGATGTCAACAGTGTATTTTCCCAGGGATGACTGCTTCTGTTTGTAA
ATATTGCTATTAAAGTACATCACCTATTTTCTACAAGGGATGCTGACTTGTCTTATTTTC
TTTTATATATTTTGGTGACTAATACATACTTGTTATGTGACAGATTCTAAAATATTCAAT
GAATAAATGTTAGATTTAGTGACCACATCACATGTAAATGGGTTCAGAATCTTGCAATTC
TTGGTAGATAAAACCATGGCACTAAGGATCTGGATAAGTGAAGAAATGGCAGGATAACAC
TTATCTATGCTAATGAGTTCAGATCTTCTCTCCTAGATAATTAAAACCGCAGGCTACTGA
GATAACTTTGCCAAACCATGCTGAAAGCTTTTCAGTTATATCTAAGGAACTGTGGAGTAG
AGAAAAGGGAATGGGCAATTAAGGAAAAATATCTAGATTTTCAAGAAATGGAATATGAAG
TTATTCACTTTTCTTTTTTATTCTTTTTTGAGACAGAGTCTCACTCTGTCGCTGAGGCTG
GAGTGCAGTGATGCCATCTTGGCTCACTGCAACCTCTGCATCCTGGGTTCAAGCGATTCT
CCTGTCTCAGCCTCCTGAGTAGCTGGGATTACAGGTGCACGCCACCACGCCCAACTAATT
TTTGTATTTTCAGTAGTGATGGGGTTTTGCCATGTTGGCCAGGCTGGTATTGAACTCAGG
CTTGTCCTGACCTCAGGTGATTCCCCTGCCTAGGCCTCCCAAAGCGTTGGGATTACAGGT
GTGAACCACCGCGCCCGGCCATTATTCACTTTTAGAATGACAAGATGACACTAATTTTGG
GAAAGAGGATAGCCTGATTTATTAAATAAATGACCTATGGAATTCTTACTAAAAATATAA
CTTTGCATATATCAGAATATAATGATGATGAAATGGTCTAGATCTGTATATACAACTGGT
CTATATAGATTCATTCAAAAAGGTGTCGTTTTGAACTCAATAATATTTAACTAAATTTAC
TATCTCTACTAAAGCAAAAAGAAAGACTTTTCCGTATTTGAAATGACCAAAATCTCACAG
AGCATACGGGATCACAGACTTCTAGAGCACTATGTAGTGATCCCCTAGTTTAGTTTTTTA
AAAAATTTTGACAGAGAGAGATTGATTAATAGTTAGTTAGTTCTTATGTAAGTGATCCAG
ATTCCAGATGTGAATGAAATGCACATTTATGAAAATATATTTGTATAGCTGTAGCATATA
TTTTAAAAACATGATTCATTATGTTTTTTTAACACACACGCATGAGACTGTGTAAGTTTT
CTTTACTGACTGATTAGCTCTGTGGCACTAGGTCGTTCCTTACCACTGGACTTTCATTAA
CTCACCTATCCAATGGGAGATAAAGTTCTTAGGTCATAGGGCTCTGCTGAGGTTTTTATA
TGTATATATGTGTGTGTAGGTGTGTATGTATCTACATACACATATAACCTAAAAAAATCA
GGTATGTTTATTAGTTATTTTATTAAAACTATTAAAATATAGAATTGGCTTGCTGAATTC
ATGGACCCACCAGTTACACTGAGACATCTTTTAGGTATACTCAACTTGTTCCTAGTGTGT
GACTCTGTTTCCTGATGTGCCTTTGATGGTCATATTTAATTGGTGTCAATCTAGACCTTC
CTTACGCTCAATTTGATGTTCTTCCCTGCACATACACACTTACATGCACACATTTACACA
CACCCACACATACTTACATAAACACACGTACATTTTTTCACAAAGACATTTACAAAATCA
TACATGCACACGCATGCATGCGAGCACACATGCACACACACACACCCCTAGCATGCACAA
GGGTGGCTTGTTGCTTTCCCAATAAAGTCATAAGATTACAGATGAAAGACAATTTAGAAT
TTTTTAAAATTCTATGAATCTAAAAGTTCAGAGTTGAATTATGATGCATTCAGTTACCTT
TTATTTGTTATTTTTTCTTGTTTTAAGGACTATGCATATATATGCAAAAAATTTACGTGT
ATAAAGTGAAGATATTTAGTAATTTCTGAAGAACATTCATTACATATATGTATGTGTATG

FIG 4. (SEQ ID NO. 4) CONT.

TGTGTGTGTATATATATATATATATATATATATATATATATATATATAAAATATGTATGT
GTGTGTGTATTTCAAAGCTCTTCCCACATGAAAACTCAGTGTACATTCAGTATGTGCCAG
TTGAACCTGTATGTGGGACTGGAATTCTGATTTTTAAAAATACCTTTTCTCAAAGCCTTT
CTCTGGCTCTAAGAAGCTTCCAGATCTGTCCTAACAGCTTGAAAACCAAGATCTTGACTT
TTTATAGAATACTTCACTCTGTGCCAGAAACTGTGTTAAGCATTTTCTTTACCTATATCA
TCAGGATTTAGTCTTCACAAAATACTCTAGGACACATATTATTATACTGATTTTAAAAGG
ATGGACTGAGGCTAAGAGAAATTAAGTGCCCGAGTTCATCTAGCTAATAAGTGTCAGACA
GGAATTTGAAGTCTGGTCTCTCTAATTCTAAAACCCATGATATTTACAACCCTGCAAGGA
AGTTGGAAATGCATCTTCCAGGCTGCAGTTGTAGTTATTGTGGGCATTTCCTTAAAGGAA
ATGGTGTCGAGAATGGTTGTTGCTAGCCAAAATCAGAAGTGTCAGATTTCTAACTGCTGA
GACTTGCCTGTCTTCACCATTCTCTGGACTCATTTGAGCCATTTGTTTTATGATCCACTC
TTCTACTAAAAGGTGGAACTAGAGGTATAACAATTATTTAGTACTTAATTTTATATATTG
TTTTCTATTTTTATAAATTGCTCATTTATTTGTCTAGCTCTTGTATATTTCCCATTCATT
CCTTTTCAGATAATGATGACAGTCCTACTTACTGCCTCTCCCCTTCCCACAGCTTCCATT
CTTCCTGGGAAAGGAGAAATCAGAATTATTTTGCTCTCCCCACTTCCTTCAGATTCATCC
TTATCACTCATCACTGATGGAGTTTTTACAGCATAATTATAAAAGATGACATTTTATCCT
ATGACAAACATGCCCTGGTTATATCCTAACTAAATGGATGGGTGGGTTTTTTAATTAAAT
GGATGACTTAATTTTGTGATCCAGCTGGGAAGATTTCAGTTTTATTAGCAGCTGTCTTTC
CCCTTTTCTTACCAGAACTTGAGCTATTAGCACCTAACTCAAAAGAGAAAATACAGAGTT
TGAAGTTATTATTTTATACTTCACAAATCCTTTCTTCTAAACATTTTTTCTTAGGTGAGG
AAGCAAACAAATAACTCTGGCTAGGATCTTTTAAACAAAGCTGTTAATATTTGCAACCTA
TATCCACATGACATCTGAAAGAAATGATGGCTTAGCTTTAGTCACAAATAGAGAGTGCTG
ATACGAGTGGAAATAGAAAGAAAAGATGTATTTTTCTTCCCATTAAAGGTTGAGCGTGGA
CTTTAAAGGGGGAAATTCTGAGTGATTCTTAAAACAACATGTGAACTTTTTTATTTCCCC
CAGACATTAGTTGCCAATATGTAAACATTTCAGCAAGAAATTTTATACCACCTCCTCTGT
TTGTCAGGCAGCATTTAATGGTTGAATGACAGACAGTGCTGAGCCTTGGCAGTTCCATAG
TGATGTGCAAATCTGGGGATTAAAATGACAGTTAATCAGTGGACCTTTTCTAGTATAAAC
TCCATGGCCACTATTTAAAATCAGTTACTTATCAACAAGGCAGACGATTTTTATTTCGAC
TTTATGTTTTCGTGTAAAGATTTCACAACTTTTCCCTAGGGGTAGTTTCTGTTGTTTGGA
TGTTAGATGCAAAGGTTCCAATTCATTTTGGCAGTCTTGATTGCGTGGATTCCTGGTAGT
CATTTTAATTGGTATCTTGCAGACACGTGGGAGTCATTCACACATTGTTTCCTTTTTCTT
TGTAGGTAGAAATAACACTTCAGGATATCAATGACAATCCACCAGTATTTCCAACGGACA
TGCTGGATCTCACGGTAGAGGAGAACATTGGAGATGGCTCTAAGATTATGCAGCTGACAG
CCATGGATGCTGATGAGGTAGCTCAAGCATGTCTCTGAATTTGTGAAACTTCGTAGTGCA
GTGATTTATCAAATTTCTAGGATATGTTGACTACTTTTATTACCCAATAATTAAGGTTAA
GCATGTGTGCTCCTTTCCAAAGAACATTAATTCTTGAAATGTAACATAAAAATGTTAAAA
AAGAGATTACTATCAAGAGGTAATTTTCCTCTGATCAGCAATCCACAACTCACTTGCTGC
TTGCACTTTAGGTTACTTAGCCAAATTATTTTTTTTCTTTAATAATAAAAATATCTAAAG
AGGTATCTCTATTTTATGCCATTATTATTCCCCTTTGCTATCTTATAGCAGCTAAGGATT
GGTTTTTATTTTATTTGTAATTGTTAAAAGCAAATAATTTAAAACTACAGAATTTTAAGG
TTTAGATTACTATTTTCTATATTTATATATTAAGTTCAGCTATGTAATTATTATGTTTCA
AATGGCATGGAAACAAATACTTTGTGATTTGTATTTTTCTTATGAAAAAAACTCCATAGC
TTATTTTCTCTTTACTGGGTAAGGAGTTTAACTAATGTTCTGGAGTTTAAGGAAGAGAAG
TAACTTTCCAGACACCAGTATCTCCTTACCTCTTTCCCCTTAAGCCAAGCCGAACACAGA
ACAGAGAATTTAATTTTCTTCCTCTCATCTAAACTCAGAAATATCAGAAACTTGATTCCT
GGCATATGAATCAGTGCTTTATAAATGTATTTCTGTAACCTTAAAAATTTAAATAAATAA
ATAATAAAATAATTTTAACTGCCAATACAGAAAGGTAATGACTTAGTCATTTATACATTT
TGCCAAAATCTAACTATTACAAATGAACAAAATAAAGCATACACATTTAGGTAATTGCAA
TTTGCTATTAGAAAAGATACGATGTTTTATGTTTAGTACATTCTACTCAATTTTACAATG
TGAAGTTCACACTTATTTCAAATTTAGCTAGCTTTAAAAGAGTTATCTGACTTAATATTT
CTATTGTTGATAGATATGTGATATCATTAGCCATAATTCAGTAAATATTTCATTTTCTTA
AAGTTTATCATTGATAATATACATTTTGATTTATCAATTCATAAAATTTCATTAACTCTT

FIG 4. (SEQ ID NO. 4) CONT.

ATTTGAAAGTAGCAGCAATAACAAAAAACTCATGTAATTGGCATAGGACAATTGACATCA
AATAATTGAAATTGTAATGACTATTTCATTGGTTATACTCTAAGAATAGAGCAAATAAAA
CTCATTTATTTGAAGTGATTTATTCTAATCACTTTAAAAGAATGAAGTAATAATCATGTT
AATTATAATAGATATTCTAATGGGATGGCTATTTACTCCATGGAATATTATAATTAGAGT
GGGATTATTTAATAGGAATTACAGGAATCACAGGTAGAATTGCATTTGGAAATTTAGTTG
TTTTAATCATCATACTGCTCTCTTAAGAAATGGTTATTTCAGAGATTCCAACACTCACCC
CTTTTAATACTGTTCTCTTGATACTGTTATAATTTTATTTCCTTCCCAATATTTTCTCTT
TAAGAATATTTCATGTAAGTATTAGTATAAATGCAATGCTGCCAGCATTCTTATTTTTCT
CCATCTGACTTCCGTGTGTGTGTTTGTGTATGTGTGCACACACTTGCATTGCCTCCAAGT
TCATCTTTTAAGCTATGTTTACCTTTATGATGAGACTAGAGGAAGCCTAGGAAGGTCCTT
ATACATCTAGGTATTTAGACCAACACTGGTTTTTGTGAATTTTTATTTTATTTCTACTGA
GCTTTGTTTTTTAAGTTTAAAAAAAAATGTAAGTAACCTTGCAGATGTTATCACTTAGAC
ATGCTAGTTAAGAAAAATACAGAATGTAAAGTGATGATAGCTAGGATATATAAGAAGTAC
TTTTGAGATGAGACAGAGTCGGGTATTAGGGCCAGAAAAGTATAAGGCTATAATGTTGGA
ATGAACAAGAGAATTGGAGGGAAGGCTGTTAGCAATTCAAGGGTAGAGAGGGATGCTGAC
AATATGTATGAGGTGTGACTGTGCCTGAAGGCATAAAAATCACCACATTCTTATAACTCG
ATTTGTTTGTGTGCGAGTGTAGAAAGGCAGAGAGGATGGAAGGGAGTAACTAGGTGCACC
TACAACATTAAAGGAAAGGGGGGCATTTCAGGAAAACTACAACCATTGTTTTTAAAGAA
AAAGCTCACAAAGTTGTTTGTCTTCTTAAATGCATTTTTCTCTTAAACAATTTAATAACG
TTTTAATAACTGCTGACTGACTATAACTCTTGACACGAGGAACTCACATGTCTTTGGTTT
CATATTAAGTAGAATGGCTGCCTATGGCATTTAGAATTTTGGGCTGTTTTCTTTTTGTTG
TTGTTTTTAGTTGCTTATAATAAATATTAATGCTTTTAGATAAACCTTTGTTTTATTTTC
TACTTTATTCTCAGCTCCTTACCTCTTAGCCAAATTTTGGGGAAAATATTTTAAAAATTT
TCTCTCTTTTCAAATCCTGGCTCTGTTTTCTTTCTTCATCTAGTTTGAGTAAGACTCGAG
ATTATGTAGGTCATCAGCCAATTGTGTAGATTTTTAAAAATTATTTATATACTTTTCATT
AATTACTTTACCTAACATATAAGTGTTAGTATGCTATAGGAACTCTTGTAGGGCACTGTA
GAACAAAGCCTGGGTAAAGGAATTACAATTTTATAAAACAACATGTACATGTTGAACTTA
ATTTAGATATCATTTGAAATGTGTTGGATCAAGATTTACATGTTTCAGAAGCACATGATT
CCGTTTGTCTCTTGTTCCCTTTTATAAATTATGCTAGTAATGGGCTAGGATACTCAAACT
TTGCTTCGTGGTACCATACATGTTTTTGAAAATACTATTTAAGGTTCTAATATGCATTTG
AAATTTATAGCTATTTACTTTTAGAATTCCTTCTATGTGCTTTTGTCTCTGTGGTTCATC
CGGAGAGCAGAATATTTTTAACCAGCATTATTTCCACTGCAGTGAAGCTGAAACATGATA
TTTGTTTCTTGTTTTGTTGCTGATATGGCATATTTTGAATATTTAGTAAATAGACTTTTC
AAAAGACCTAATTAAATCATTACTCTTGGCCAGATATTTTCAGACATTCACTAATATTAT
GAATTCACCACATCAGCTGATTTTGAATATGAAAAAGATTGTTTTTTATCAACACAGCCT
GATATGTTTACCTCTTTTCAGAAAAATTATTACAACTTTAGGAATATTATTATTTATTAC
AGCCCATTTGTAGACAGGGCATTTCTAAATATCAAACCATTTTTGTAATAGCATTAAATA
GGTTTTTGTTTCTTTTCTTTACCTTAATTTCCAAGTACTTACTATTTTCATGGGTCTGAA
TTGAATGTAGCTACTTCCATACCTCACCCACTTTACTAAAATAATGGAATTCCTAGTGAA
ACAGAACAAATGTACAGAGTGTGGTCAGATGAGAATTCTCACATGCTTATTGAAAGTTTT
TGTTAAACCATAAAATTACAATAAATACGTTAGATATTCAATGTACACCTGAATATACAA
GGTAAATGTGGGTAATGTCTTAGACTCAGCTGTTCCATTATTAAATTTAAATGTGCTTTG
AGGCATTCATTTTACTAAATGTTAAGACTGGCCTGAAGAATGCAGTACAAACTAACACTA
AATATAGCGGGAATATTTTTGCTTTAGACTGTTAGAAATCATCTCCTTATATGTTTGACC
ATGAAGGAAAAAATGTATGTAAGCTATGATGGAAAAGATGTATGGAAACTGTGGATGCTG
TAATCCCCCACTGTGTCAGCTTTACATGCCTATACACTCCAAACTTACCTTCTTCCTAAT
ATTCTCATTGAGAGCTCTGTGTCTTTATATTTTAATAAATACATTCTTTGAGGTTAATTA
CAATAAATGGTATATTTGTTTTAGGTAAGTATATTAAATTAAAGAGTAATTTTTGAAGTC
AACATTTCTAGCACTACTTATACCTAGTGTCAAGGTCAATAATAACATATAATAGGAAAT
CTGATACTGTATTTTCCCATGGATATATGGCAACTCTAGTTATATTTTGATTTAAATTAT
TCATTTGCAGAAGTCTAAGTCATCAAATAAATTTAAGCCATCATGTTTCTCTTATAAGAA
AATAGTAAGAATAAGAATAAAATAACAACTATCATTTTCCTGTGCTTACTATCTGTCAAG

FIG 4. (SEQ ID NO. 4) CONT.

GGTTGTTCTAGGTTTTTAAAATATATGTTCACTAAATTAACCTCCAAAACAATCCTTTTT
GGCAGGTAATATTATCATCCCAGTGTACAGATGAGGAAACATGGGCTTGGAGAGGTTAAG
TATGTGGTCCAATGCCACATGACTAATAAATGGAGCACAAATTCAACCACAAAATATGGC
CCCAGAGCATCATATCTCAATCAGCACAGGGTATATTAAACGCAGTATTTTGATTGTAAT
ATACAGAATTAAGAAATATCTCTCTTCCTTCTTCTTCTGCCGATCCTTGCTTCTCTTCTT
TTTTCCCATTCCTTCACCATCATTCAGTCCTTATATGAGTGTTCCTATCTCTATCTATTC
TAATTTAATTTCTGAACGACTCTTGTGGCTTCAACTGACACCCACATAAAATGACCCTCA
GATATTTATTTTAAACCTCATTCCCAAATCTCTAATTGCCAGATAACCATTTCTATGATG
CTATTCTTTAATCCCTAAATACACCGCAAATAAAATTTCACTTCCTATTTATCCTGCATC
AAAGCAGGTCCTATTCTTGAAATGTCCTCAGTAAGAGTACTCTCTTAATTGCCAGCCAAA
GTAACTTGAAATTTAAAAAGACTTTTTTTTCTTTTTTGCTTTTACTTTGCACATGGGGTT
GTTAAAAAAGTGAGAATATATATGGAAATGTTGAGCAAATGAGAGAGCTATTAGTATTAT
TTCTATTTTCAATAATCTGTCAAATTTTACTAATTTGTCCCATGAATTGATTCAGAGCAA
GACGGCCAGGATTCCAATCCCTTAATTTCTTTTAAAATGGGCATTCTAATAGTACTTACC
TTGCTAGTTTGCCTTTAACAAATTAATTAGTGCCCTGGAATTGATGTGCTCAAGGTGGCG
TTTAGCAGCTAGCAAACACTATGAATATTCTATTTTTCTCTCCGCCATCTCTCTAGTTCA
GAATTTTGAGGGTCACAGCTCAAAGACCTGAGAGTACGTAGGAAATCACCCCCATTTTCA
TTTTCCAGAACAGGGACTTTCATTTTACAGAACTGTTTCAGCAACTTGGGGGAAATGAAG
CCTCAGTCTCTTGGGCCCCAACTGTATTCACAATCTGCCTTCTCTGGCCTCTCCCTACAC
TAGTCCATACTGCAATATCAATATCCTTAAAAGATTGCTTCCAATTAAAACAATATTGGG
GTTCCTTGGCTGTAGAATTGAGGCAAAGTTGTGTTATATTTGAAGTTCTCAAAAAATATA
CCGATACTCTAACATTTTAGCTTGACTTTCTTCTTTTGTTCTATATTAAAATTGTCCACT
CTAACACACTGTTCAACAGTAAGCCAAGTCCATGAATAGTGAATGACTGTAAAATATTGT
ATTCATTTGATACGCTTTTATTTTTATTTTATTGTGATAAGAACATTAATGTGAGATCTG
CCCTTTTAAAAGATTTCTAAATGTACAATACAGTATTGTTAACTATAGGCACGATGTTGT
ACAGTAGATCTAGAAATTATTCCTCTTGCATAAGTGAAGATGTATACCCATGGCTTATAA
GCTCCTGATTTCTCCCTACTGTCTGTCCTGGAAAACCACCATTCTACTCCCTGCTTCTAT
GTGTTTGACCATTTTAGATACTTCATATATATAAATACCTACCAAGCAGCATTTGTCCTT
CTGTGACTATCTAATATAACATCCTTAAGGCTCATCCATGTAGTCACATATGGCAGGATT
TCGTTTTGTTTTTGAGCTGAATAATATTCCTTTGTATGTATATACAGGTTGAGTATTTCT
TATCCGAAATACTTGGGACCAGAAGTGTCTCAAATTCCTTTTTTTTTTTTTTAAATTTTG
GAAGTTGCATTATACATGCTGATTTAGCATCCCTAATCTGAAATGTCAAAATCTGAAATG
TTCCAATAAGCATTTCCTTTGAACATCATATTGGCACTTGGAAATGTTTGGATTTTGGGG
CATTTGGATTTTGGATTAGTTTTGATTAGGGATGCTAAACCTATATCACCTTTTTTTATC
TATTCGTTTGTTAATGGCTATTTAGTTTGTTTCCAAATCATGACCATTGTGAAAAAAGGA
TTGCTGGATCATACGGTGATTCTATTTGTTATTTTTTTGAGGACCTCCATACTGTTTTTC
CACAACAGCTGTATCATTTTGCATTCCCACCAACAGTGTACAAGGGTTCCAATTTCCCCA
CTTCTTCACCAACACTTGTTTTGGTTTATTTGTTATGATAGCCATGCCAACAGGTGTGAG
GTGATTTCTCATTGTGGTTTTGATTTGCATTTCCCTGATGATTAGTGACACTGAGTATTT
TTTATATACTTGTTGGCCTTTTTTTTTTTGAGACAAGAGTCTCGCTCTGTTACCTAGGCT
ACAGTACAGTGGTGCGATCTTGGCTCACTGCAAGCTCTGCCTCCCGAGTTCATGCCATTC
TCCTGCATCAGCCTCCCGAGTAGCTGGGACTCCAGGCTACTGGCTAATGTTTTGAATTTT
TTTTTAGTAGAGACGGGGTTTCACTATGTTGGCCAGGATGGTCTCGATCTCCTGACCTCA
TGATCCGCCCACCTTAGCCTCCCAAAGTGCTGGGATTACAGGTGTGAGCCACCACGCCTG
GCCACTTGTTGGCCATTTTTATGTATTCTTTTAAAGAAACATCTATATAAGACCTTAACC
ATTTTTTTATTGGATTACCAAACTTAATAGCTATTATGTTGTAGGACTTATTTATATATT
TTGAAAATTAACTTTCTATCAGATATACAGTTTGCAAATATTTTCTCACATCCCATAGAT
TGCCTTTTCATTTTCTCGACTGTTTACTGTAGAGAAACTTTAGTTTGATATACTTTCACT
TGTCTGCTTTTGCTTATGTTGCTTGTTTTGGGAGTCATATACATGAAATAATTGCCCAGG
CTGTCTTTTAGCAATTTTCAACTAGGAGTTCTATAGTTTCAGGTCTTAATTTTAAGTCTT
TAATCCATTTTAAATTGATATTTGTGTATAATGTATATTTACATTCTTTTGCATATGGAT
ATCCAGTTTTCCCAACACCCCTTGTTGAAGTGACTATCCTTTCCCCATTATATATCCTTG

FIG 4. (SEQ ID NO. 4) CONT.

GCACCCTTATGGAATATCAATTGACTATCATGCATGGATTTATTTATAGGCGTTCTAGTC
TGTTTGGTTTGTCTGTATGTGTGTCTTTATGCCAGCACAATACTTTATTCATTACTGTAA
CTTTGTAGTATATTTTAAAATCAGGAAGCACAATACCTCTAACTTTGTTTATCTTTCTCA
AGATTGTTTTGGCTATTTAGGCTCCTTTGTGGTTTCGTATGAATTTTGGAATTGCTTTAC
CTATTTGTATAAAAAAATGCTGTTAGGATTTTGATATAAATTGTATTGAATTTGTAAATTG
CATAGATAACATGGACATTTTAACAATATTAAGTCTTCCAATGCATGAACTTGGGATGTC
TTTCCATTTGTTTGTATCTTTGTTGATTTCTTTCAGCAATGTTTTGTAATTTGGGGCATA
CAAAGCTTTTACCGCCTTCGTTAGTTAGTAAGTTTATCTCTCATTACCTGTTTAAGTCTT
ATAATATCATATGAACTTAAAGCCAAAAAGCCTTCCTTTGTCAAATACATGTTCAAAAGA
AAATATAAGGAGCAATGCTTTTCTACTTCCAATAGCTCAGATGCTTGGTCTCTTTTTTTA
GGGTGCAAATGCTCTCGTCACATACACTATCATTAGTGGAGCTGATGATAGTTTTCGCAT
CGACCCAGAATCCGGAGATCTGATAGCAACCAGGCGGTTGGACAGGGAACGCCGCTCCAA
ATATTCACTGCTAGTTCGTGCTGATGATGGTCTTCAGTCCTCGGATATGAGAATTAATAT
CACTGTCAGTGATGTGAATGACCATACACCCAAATTTTCCAGACCCGTGTACTCTTTTGA
CATTCCTGAGGACACAATCCCTGGTAGGTGATGGGTCTCTTATGTGTATTTTGCAAGAAT
CGCTTTTGAACCAAAATTACATACTATGTTTCGGCTGCTCTTAATCAATGATTAGTTTTT
AATCATATACTACTAGTTATAAAAATATATATGCTGGATTGTTGGATCTTTTCATTAACG
ATCTTTGGTAAAATTCTCAAGCAAATGGCTAAATTTTTTAGGATGAATGAGGTTAGCCAT
TTATGTGTCTGAAAGTATTTGTGACATGGGTTATTAATTTTCTGTCAATCACAGTTTTGG
TACTCTTTCTGCTTTAAAAACGTCTAATGTGATTTGGGGGCTATGTATAAAAAGAACAGC
AAAAAAAAAATACATGAAAAACTGTGAATATTGATTCTAACGCTCACTAGCTGTGTGACC
AACGGCAAGTTAATTCATTTCTCTTAGTTTCAATTCTCTATCCTGTAAATGGAAACAGTA
ATTCCTGTTAGAGTTAAGGTAAAGGATAATTTAGAAAGTACATTGAGTTTGCTAACACAG
GGCTTGGGTATTAGCAAATGCCCATTAAGTGTTATAAGAAACTGAATCTTTAATTATAAT
CTTGCTTCTTTGAACATATTATATTGTGATTTTTTTTAGTCTGAGTACTCAATATCCATG
TTTCTGGTGTGTGTGTGTATGCTTCATTCCCATTATTGGAAATTTTTATGTAAAATTAAA
ATTTTATTCTGAATTACATTTGGAATGATTATTCATGATAAGCCATACATTTTAGAAACT
CCATTTGGCAAAGGAATTAAACATCTACAGGAGACTCCTTCTACCTGAAGTTTTTTCTTC
ACTCCTCAAGATATCTTGTGCAAGTCCTTTATGGAAATCCCATCACACTTATTTCTTGAC
TTAGTTATTGCAATGACCACATAAGTTCTAGAGTAGTATCACCAGGGCATAAGTCTATAT
ATTTTTTGGAATCCTCAGTTCCTGACACTAGCAATATGCTACCTTAAATGTTGATTGAAT
TCATCAGTATATTTATGGATAGGTACTGCTAGATGGAAACATAACATCAGATATATTATT
AATTCCTCAGGAAATTTATGCTGAAACCTGAGGTCCACTGGATATCTGATATGTCACATA
CTGTATTCAAATAGGGAAATGGTAATATCAAAATCTGCAGAATGTTATGTTCACTGTATT
TTCATAGCGGTTTTCAGTTAAGATATTTTACTGTACAAATACATTTTTTGGTCTCTTTCT
ATATGTTCTCTTAGTAATACTTCTTACTTCCTTGATTTTATACTATTAATTTATTCTTTT
GATAGGTTCTTTGGTAGCAGCCATTTTAGCCACGGATGATGACTCTGGTGTGAATGGAGA
AATTACATATATTGTGAATGAAGATGATGAAGATGGCATCTTTTTCCTGAATCCTATTAC
TGGGGTCTTTAATTTGACTCGATTATTAGATTATGAAGTACAGCAATATTATATCCTCAC
TGTTCGAGCAGAAGATGGTGGGGGACAATTTACTACCATCAGAGTTTATTTCAATATTCT
AGATGTAAATGATAATCCACCTATTTTCAGCTTGAATTCATACAGCACATCTTTAATGGA
GAATCTACCTGTGGGATCTACTGTTCTTGTGTTTAATGTTACTGATGCAGATGATGGTAT
GTATTTTATTTAATATAATTTTTAAAACATCTATAAACTGTCATCAGATTTATATTACAT
TTATTTATTGTGTTGAGCTGTCACAAAAATGCATTTTGTGAATATAGGTTGGAAGTTGAG
GAATAGAATTATAACTGAACTGTAGAGGATTTTAAAAATTAAGTACTTTATCGGTTAAAT
TCTTATTTATAACAGAAAACATACCTTGTATTGTTTTATAAACTTTATCTTATTTTTCCC
CCTAAATGTAGGGTCGTGTTTCAATTTAGCAATGTAGAAGTCATAAGACCACTTTTTTTT
GTATAATTTTGTTAGATAAATAAAAATATTAGGTTTACATATGTTATTTTAACTTGAAAA
GGATAGAATTTCAAAGCAAAATGAAACCAAAGACTTAAGTAAAAATACTTACGAATGCAA
AAACTAAGTTTCACATTTTTGGCTGACAAATAGCTAATAATTTTTTTTTTTTTTTGAGAC
AGAGTTTCACTCTTGTTGCCCAGGCTGGAGTGCAATGATGCAATCTCAGCTCACTGCAAC
CTCCACCTCCCAGGTTCAAGCAATTCTCCTGCCTCAGCCTCCCGAGTAGCTAGGATTATA

FIG 4. (SEQ ID NO. 4) CONT.

GGCATGCACCACCACGCCTGGCTAATTTTGTATTTTTAGTAGAGACGGGGTTTCTCCATG
TTGGTCAGGCTAATCTCCAACTCCTGACCTCAGATGACCCGCCTGCCTTGGCCTCCCAAA
GTACTGGGATTGCAGGCGTGAGCCACTGCACCCAGCCCAGCTAATAATATTTTAACTAGG
TTTCATTTCAGCTCGAACAGTCTCAGATCTGTTTAATTTATGCTAATGATCAAGTTAAAA
TTTTGCATTAAATTTATACTTTACATGTGTTTGATTTGTATTTATTGCAAAAGCAATTGG
CAAACTTTATTTTAATAGCTGACTCCTTTGGCCTTTCTTCTAACACCTGTTTTGTAAGTA
TACATATCATATAATATAGCATTAGAGAAAACATTGTATGGATTATCAACCTTTAACTGA
ATTGTCTGGAAAATTAGTACGTGTTTTTCCCTTATGTTGGATGCAACTAAATTGTCTCAT
CAATATATAAAACAAGGGACAGTACTTTGAAGAAGAAATAGGTCTCTATTGACAGGCATA
TCTATCTCAATTTAGAATTGCCTTATTCTTATGACTTGGATGATTTGTGAAATCTCAGAA
TACTATTCTATTTTAACATTCTATTCTATACTTACTTTCCTTCTCATAGTGTCTATAAAT
GGCACTTGGAACGATATGAGAAGCAAAAAGGACAGTATTTTATATATGTTTCAATAAGTA
AAATGGGAAATACTTTCTTTAGAATTCATTGAGTAAGAGCATTTTGATGTTTCCTCCTCT
AATTTAAGTGCAGTTAAAATTGGGCACAAAGATATATCTAAAATAGATACAGCTGTAATG
CTAGTACTACTACTATTACTACTACTGTTGCTAGTAACAATACTTTAATGTTAACGATGT
TAATAAGAATCTCAAGAACTGACATCTGCCAAGTGTTTTGCATGTACCCAGTCCTGGCCT
AAGAACATTGCACACTCTATTTCATGTACCTCATCCCAGGTCTGTGGATTGGCTCCAGTT
AGATATCTGTATATAATTGAGGTTAGTCCCTATTTTGGAGATTGGTTTATCTGCTATAAC
TTTTAGTTAGTCTACCTATTCCATAGATAAGAATATTTTCAAAGCTAATCATGTATTCTT
ATTTGTCCTGTGACTGTGCTCAACTTTTCTACAGAGAAGAATTTTCCACCATGTTTCTTT
TTGATTTATTAGTTATGTATTAGAGAGAGCCCATTGTTTCATAGAATTGTATGTTTTCCT
GGAATAAGTTTTATTTACCATCATAACTTAAAATATAGGGAAACTGCGAAGATACCAAAA
AATTAAAAAGAAAAAGAAAAGAATTTTGTTTGTCAAAAACCTGCTGGAATATTCCATGCA
CATGTAAGCACAGAAATACATTGACCATTGTCTCTAAGTAAGTTTTTGTGATATTTTTTC
TTTAATTGCATTGAGTAAAAGTTTCAAGCTATATTTATTCATTGTTTTAGTTTTGAATAC
GTTTATCAGTGTAATTTCCTGCACCTTGACATAAAATATATGACACAATTCCTATTCTTT
CTGAATTTCAAGGACAGTGATAAGGCTATACAAAGGTAAGCTTGTTTGTAAAACTTTCCA
GCTCAGTTACACAAAAGGGTCTCAAGTGTTTCACAGACAATATTAGTCAGACATTTTTTA
AAAATAACAAATTAACAAATAAATCTCAATCACTGATCAGAAGGTTCCAATGAGGTAATA
TTGTCATCTTTTTAGATGAAGGAATTTTATATGAAAATAAATGTCACAATCTGTTATCTG
TCTATGGATTCTGTCAGAGTTTAAAATTTAGCTTACATGATGATTTCATAAACATAAATC
AGATCTTTTACTGTTTTCACAAGAAGGGTAATACCTCTGTTAGCATCAAGACTACTAAGC
ATGCGGTATTACATTGAGGAAATATCGGAGCATCACGGAAATATTCTGGCTTTGATGGTT
ATTTCGTTATCCTATAAATTATTTACACTTTAAATATTGGGAAGTCATATTAAAATGTTT
TGCTAATAATACAATTGGAATTTTTGCTGAATAAATGTAGCTATATAATATTGGTGTACA
ATACAGACCATTGAGTTTCATATATTCCAGTGACCTGATGACCTTGTTGAAACTGCTTTA
TAAAGATGGGTGTTATTCAAAACACTTCTATGTGTTGCAGCTATGTGAAAAGTTGACAAA
TATTAGTTCTTTATAGAAATTAGAAGATAACATTTATAGATTGTGAGTAAATATACATAT
TTTATAGCATGAAACTATACACCTATACTTTTAAAATATATTTTACTATTTATATATATT
TTTATATATTTATAATATATATTTTATGTGCTGTGCTTCTTAGAACAAAATTATTCATGA
GACTGAAATACTATATATAGATATCTACATATCTATATATAGTGTGTGTGTATGTGTGTA
TATATATATATATATGACGAAACCATAAAACCATATGTATGCAATAAAACTGCCAGGAAG
AGTCATGTAACTAAATGACTTGGAGAACATTGAACACAAATGGTTCACAGTGGGCTGTTT
GAAGTTTAAAGATCTGGTGGGCCATTAAAGCCCACTAAATTTAAATTGCAACACTTATGG
CTAAAGCTTAGAATTCAAAACAATGTAAAAATAATAATTTTACAATAATGTGTTTACTGT
CTCATGGTTCAGATATTTGTTGAAAAAATAGAAAAAAATGGTCTGAGCTTAGTATTTTTC
AGTATACTTCAAATATTCCGGGAGAAATTTGAGTTTTGCTATGTCTGCATGTATTTTTTA
GATGTAGTGTATGTGGCCAAAGTCACTTTTTAGACTTGTCAGAAATGAAAAGTTATTTTC
TTTACAGTAAAGTAAATGCAGATGGATTCCATGACCTGTAATTGCAGCAATTAATTTTCA
GTTCCTGAGATGAGAGCTACTTCTTCTATAATATGGCAATATTTTATGTAAAAATAGTTA
TATTTTTTATTTGTTTCATCAACAATAATCTTCAGTTTATTTTTAATGTTGTTACTTAAT
ATATTTGTCATTATGTATTTGAATATAAAAGCAAATTTTTCTTTTGTTATACTTTTAGTT

FIG 4. (SEQ ID NO. 4) CONT.

AGCTTAAAATTTATTACTTCCCTTACCCATTCATCTACCAAACTTTTTGCCTTTATAAAA
GAGGCTGTTCTGCTGTTTACAACAACGCTATAAAATTTTGGGATCGTGTTCTCTTTTTGC
CTCTGCAATTTAGCTGTTTACTCAAGGAAGTAGCATACATGATGGACTAAGGATGATCAG
ATACTTGATTTAATTGCTCCCATTCCTGTTGATTTATGTAGAAATGTTAGGCCATGTAAA
ATGTCAGTATTTTTAATGTATTTTGATCTTAGATATGAAAGATTTTATATGCTTCTCTAG
AATTAAATTTTATATCTTTGCTTGTTGGTATTTATTTTCATTCATGTGTTTTCATAACTG
CATTTCTCAATAATAGTCATGTCCCCAAAAGAATGGGGATTCAATATTTACTGATGAACT
TTTTTGTAGGAAATGCAGAAAATTTTCTTAAAAAGTAATTAAACGTAACTATATATGTAG
ATGTTAATAGAAACACACGTATACACATAATTAAAAATAAATTCTGTGTGTATATATAGA
TACTCAAATATGTATATGTTATAATGTTTGAGTAAATATATATACACACACAATATAATG
TATATACGTATATTTACGTTGTAATGAAAGTCCTAAAAGCTTTATATATATATATGTGAA
GATAGTGGAAATTTTTATCCTCTAAAGCCTGTGGAATTTTAAGACAAGGGGTTGAAATAA
GCTGTTAACCTTGTTCTAGTCAGATTCTACAATTCTGTTTCTTTCCTGCGGGTGAATTGA
CCTCTGACACCTATTAGCTTTATTTATTCATATTTTTCCTGATCTTCAGACTCCTAAGTA
TTCTGAACTTTGTAATCTCTTCCTTGTTCACTTGTGAGTAGTCTTAAATAAACTATAAAG
ATTAAAAGTCACAACTCATAATGAGGGGGAAAAAATAAACTACGCTTTCAACGATTTACT
CAATCATTGTTTATCCTAGAAATTTTTGTTAATAAGTCATTGTCTGAAAGTTATATTCAT
AAATATTTTTCCCATGTTTCAAATTAGGCAAAGGATATTAGAGACAGTAAAGTCACAGAA
TAAGAGTAAGTGTGGCGTTTTTAAAAACATTGAGTTCTACATGGTAGAAAAAAATCTCAT
ACTCAAGTTAAATTTGACTTCTTAAAGAACTTGATGAAGTTCAAAAAAAGGCAAAAGTTA
ACTGAAGTATTGATAGAATAATGAGAAAGAATTTTTTTAAAGAAAAGAGTAAAAGGGTGA
TTAAATTGTTCTAGACGACTTTTGCCAAAAGTGAACATCACTTCTCATAGGTAGAATTCA
GAAACCTGGATAGTTGAAATTAATGTTAGAAATATAGAAGCTAATTGTAGGTAATTCAGG
TTAGTCAGTAGATATTTGCTAGTCCCAGAATATACATCTTTATTAAAGATAGATTACCTG
GATGTACAGTACGTTTTTATCATAATATCCTGTAATTTTTCCAATGTCATTAGGATAAGA
TATAAAAATGCACATCGTTACAGGCCAGAGAAGAAAACATCACTCTGAGGCAGAAACTGA
CTTCTTTCTGTTTTCACTGCTTATTTGTTATTTACCTTTAGTTACTAAAACAGTAAGATG
ATGTATATGCTCCACATCATTTTTGTTATAAGACTCTCTGCAATCATTTTCTGAAGTGAG
GATTTAGAAACAATTTTTAAACTAAAAAATGACACATGATCCTAAGAAAAATCAACAGTA
TCTAAATACAGTTCAATAATAGCATGAGCATTTATATTTGGAAAGTTTTATGTATAATTT
TACTGCTAACAATTTCTTTAAAAATACTTTTTAGAAACTTTAAATATGTTTAATAAAATT
TGAAAGAGAACTATTGTCTCAAAGGTCCATTACTTAGCTAGACACTTAATAGGAATTAAT
AAGTATTTATTGATTTTGACACGAAATATAGAAGTACACTTACAGCATTCATGACTAATG
CCATACATCAGAACATTTTATTACCCTTTCTTGAAAATTGGTGTCAGCCTCCCTAAATTA
CTAAAGTTACAAATGTTTGACTAATAGTATAGCGTGTGGCACTGTTAGTGTTGGACCATC
AGGAATTATGTGATAGAAACAAGGAAATATATAGAAAAATATCTGCTCTCTGGAATATTT
TTCTCCTCTTTACTTTTGTAATTTAACATTTCAACACCCTAGTAAATAGCAAGCAGTATA
TAGATCATTTGTTCACAGGATTTCCTAAAGTGTGTTTGGATGCACGGCATATCAAACATG
CCAAATTACTTGCTAAAAGTTTTGGTATAGCTTGTTCTGCAATCAGCATATGTTTAAGAA
AATTTTTTCTTCCCTTTAATTTCAGGCATCAACTCTCAATTGACTTATAGCATTGCTTCA
GGTGATAGCCTTGGGCAGTTTACTGTTGACAAGAATGGTGTACTCAAAGTCCTAAAAGCT
TTGGATCGGGAAAGTCAGTCCTTCTACAACTTGGTTGTTCAAGTGCATGACCTGCCACAG
ATTCCAGCCTCCAGATTCACAAGCACTGCTCAAGTCTCCATTATTTTGTTGGATGTAAAT
GATAACCCACCGACATTTCTTTCCCCTAAATTGACATACATTCCAGAAAATACACCTATT
GATACTGTTGTTTTCAAAGCTCAAGCAACTGACCCAGATAGTGGCCCAAACAGCTATATT
GAGTACACTCTGCTGAACCCTTTGGGAAACAAGTTCAGTATTGGGACCATTGATGGTGAA
GTGAGGCTCACTGGAGAACTGGACAGAGAAGAAGTTTCTAATTATACTCTAACAGTGGTG
GCTACAGACAAAGGTCAACCATCTCTCTCTTCATCTACAGAGGTTGTAGTTATGGTACTT
GACATCAATGATAACAACCCCATCTTTGCACAAGCTTTGTATAAAGTGGAGATTAATGAA
AACACACTTACTGGAACAGATATAATACAAGTGTTCGCAGCAGATGGAGATGAAGGCACA
AATGGACAGGTTCGCTATGGCATTGTTAATGGTAATACCAATCAGGAATTTCGGATAGAC
TCTGTCACAGGTGCCATCACTGTCGCTAAACCTTTGGATAGAGAAAAGACCCCTACCTAC

FIG 4. (SEQ ID NO. 4) CONT.

CATTTAACTGTTCAGGCAACAGATCGAGGCAGCACACCCAGAACTGATACCTCCACGGTC
AGCATTGTTCTACTGGATATTAATGACTTTGTTCCTGTATTTGAGCTATCTCCATATTCT
GTAAATGTCCCTGAGAATTTAGGGACACTACCCAGAACAATTCTTCAGGTCAGTATATTT
AAATAAAGCAAGTATTGTCTTAATTATAAGACATCTATTTGAAAACCTCCCCTCTTCTAC
AGCGTTTACGCTTCCCCTGTTCTCTCCTCATTCTCATCCATAAATGCTCAATTGCAGATA
CAGCAAATTTTGAAAAGGAAAGGTTTATAAACATCATACCTAAGAACCTCTTAATTTCCT
CATTGATGAAACTTTTGTATTTTACTAGCTTTCTTTTGTGTATACTCATGTTGCACACAT
TTATGTATTTGTGTTTTTGAATTTTGTTCCACAAGGATAATATCTGCACATAGTAAAAAA
CTAAAATGATGGAAATGTTTGAAACTTCGTTATAAATATTGTTCTACTCTTTTCCTTCAT
ATATTTAACTACCTAGGTGAAACTGCTCTTAAAAATTTTTATGAAGCCTTCCAAAAATGC
TGTGCATTAGCTTTACACATATTTTTACACAAATAGACTCGGGTGATATATACTATAGTG
TGCCATTTTTATTTTTTACTTGAAAATCTAAAAATATATCTTTGGAATCTCTTAACATAG
TTTTACCTCATTTTTTTTTAATGGAGGCATTTTATTTCATGAGATGCATTGTTTGTTTTA
CTCACATCTTGGTATGTACTGTTCTACAGGTGGTGGCAAGAGATGATGATCGAGGATCTA
ACAGCAAACTCTCATATGTTCTGTTTGGTGGTAATGAAGACAATGCTTTTACTCTCTCAG
CCAGTGGAGAACTTGGAGTAACACAGAGTCTGGATCGGGAAACAAAAGAGCGCTTTGTCT
TAATGATTACAGCTACAGATTCAGGTAAGTCCATTACACCCTTGTTCATTTGTAGATAAT
TTCTAGGCCAGGCACGGTGGCTCATGCCTGTAACCCCAGCACTTTGGGAGGCCAAGGTGG
ATGGATTACTTGAGGTCGGGAGTTCAAGACCAGCCTGACCAACATGGTGAAACCCCATCA
CTACTAAAAATACAAACATTAGCTGGACATGGTGGTGCGTGCCTGTAATCCCAGCTACTC
AGAAGGCTGAGGCAGGAGAATCGCTTGAAACCAGGAGGCGGAGGTTGCAGTGAGCCGAGA
TCACACCACTGTTCTCCAGCCTGGGCAACAAGAACGAAACTCGTCTCAAAATAAACAAAT
AAATTAAATAATAATAATTTCTTCATAATATGAGTATGAAGTATTTTCTGTTTGCCATTA
AATGAAATATTTGTTCACTTTTACTAATGCTTGAAATTCTGATTGCCTCTATGTTATTGA
TGGCACATCATTCACTTTATGACATTTATATATAAGTGGCAAGGGCTTAAGGACATCGCC
ACCTAAGCCCTATTCCCATAAAACAGAATGAATTGTTGCCCTATAAGCTTATTGAGTACC
TCTGGATGTGACCTTACACTCTACTTCCTGAGCTAGGGGCATTTAAAGTACTTTAGCTTT
GGAAACATGTAGATGGTTCCAACCACTTCTCTTCTGATAGACATGGGTGAGTGAGTCTGT
TAGGAGGAGCTTTCACTAGAAGGTGGCTCAGTATTCAGTGAAGCATTGGTCTAAATGTGC
AGGCTGCTCAAGAACAAAGTCCTGGTTCCAGGGAGCCAAACTATAAGTTCCTGATGCCAT
CAGCCTTGAAAATCAGGGTCAGGGGGAAACCAGGACTTGGAATTATTAGTATAAGTATAA
ATAACAGAAGTCTAACCCTAATTTCTATTAAATAAGAAATATGCAGATCAGATGTGTGAA
GATTCTGCCCAATAGAGTTATGGAGGATTCTAAGTTATGGAGGGTGAGCAATCAGATTAT
CAGTAACATTATGATATGTGGAAGCCTGTCACTCAAAGCTTTAAAAATGATGCTGAAGAC
CATGATGGGAGGCACAAATGAGTTTCAGTGACATTAGTGTCCTAAGTCATGGTGTTTTGG
CAGCTCTAAAAATGAAAGCATTAATTAAACCTTGTTTCAAAGCACAGCTCTCTATGGGCA
CTGTTTTTCGAGTCGCTCTGAAATAGACTGGCATTTCTGAGGCCACTGGTGGATAAATAC
TCAATTAGATGTCTGAAGTTCACTTTTATGAGTGATACAGAAAACAGAAGTTGTGAGGAA
AGTTGAACTGGGTGATCTTGAAATTAATTCCCTTGGATACTCTTGATATGAATAACCACT
TTTTTCAGGAGAATGTGAGTTTTAGACATCCGGTTTTAGAATCTACAGTTTAATCTTATT
TTCCAAGAATGAGATCTTTGACAGAGGACTTAAATTACATATTCACTGTTTTCATTCAAA
AGTCAAACTTGTAGATGACATGAGAAATTTCGGAAAAATATGGCAGCTATTAGATCCCAG
ATGCAATGTTTTTCTCAAATCTGTAGTGTTCTAAGGGCCTGGAAAATATCAAAGTGTTTC
AAAAAAATTTTGAGAGTTTAATTCTTTATCTCACAAATCACCTTTCCTTTGCATTTTTTT
TGAACTATTACCTTAGCCCAGAGATAGGTCAACTTCATCAGTATGGCACAGATTGCAGTG
GCAGTTTTTAATCATGCAAACCACTAAATGTTTCAATGTGGGAGGGAGAAAACATTACCA
TTTAAACTCTCATCATATTTTTATTTACTGACTGCATGGTTACAGAGTAGCACATTTGGA
AACTCTAACTACTCCTGTCTACTGCTCCAGTAAGCTACAACCACAGTATCATATGTATGC
AGTGCTAAAAGTTACATTACTAAATTACAAAACCGGAAGAGGGTATAATAATTATATCTC
ATTTTTCCTGTAGATAATTAAATTGCTAAACAGACTACAATTCCATTACTGATGATATGT
TGCTTAGCTATAACAGAAAGTATGGATATTCGGCCTTCATTATGCATTACTTATAGTTAT
TTCTTCTGGAAATATTTACTGTACCAAGTAGAAACTCATAGGAGGCTAACACATCCACCT

FIG 4. (SEQ ID NO. 4) CONT.

GGTATAGTAATGCAGGTACTACTACATGGTTTAAAGGAGAATTTGCTCAAAAGCAGTTAT
GTCCTTCATATGGGTTAGGCATTCTACTCCTAAGTAGCCTTTCTTACAAGAGTTTGCCTT
ACCATTTTCTCATATGTGCAATAAATAAAATAATGTTTTAAATGGAGCAAGTAGCAGGAA
ATTATCAGGGAAACTAGAAGAGTATACTTTAAAAAATGAATTCAGATAATTAATTTAGAA
ATGGAAGTATATCATGTAGTTAAATACATAGACTTTATAGTTAAACCCCAGTTCACATCC
TACCTCTGACATTCCCAGCTATATGACCTTCAACAACTTTACTATTCCTTCATGTTTGTA
TCTATGATTGGAAATACTAATATCTATATGAAAGTTTATTGATCAAATAGATAAAAAGGA
ATACTTATTCTAGCTATTAATGTCAGTCAGCATGTTTACTAGACATTTCAAGCTTAGTAA
GGCCAAAGTAACACTTTTGACTTCTATTCACCTCCCTACCTTAAATGAATTGCTTCATAG
ATCATTTCACAATTGCTGAAGGCAAACCTTGTTATTATTCTTCATTCCTCTTCCTCTGTA
CACCATATCCAACAAATTCATTAACAAGGAGACTCAGCTTCAAAAATGTCCAAAAGTGTC
CTGAATTTATCCACTTTTCTTTACCTCCAAAACGACCTCCTTAGTCTAAGCTGGGGTAGT
ATGATAGCTTGCTAACTGCCTATCTTTTCTCCTGCATGGTGCATTATTCAACAGGCAACC
CAAGAACATTTAAAACTATAAATTAGATAATCATACCCTATCTCTTGCATAGACAGCATG
CAGTGATTTCTAAGAATAAAATTTAAATGTCTTACCATTGACTACATGGGATTCAATAAC
TTGGTCTCTGTCCATTTATCTGAACCCCTCCACCACCACCAGCTGCCACCTTTATTTTGA
GCCAGAGTCGTGCACTGGCCCCAGCTCACCCTTTGTCTCCTGTCAGTTCTGCATTTAGTA
TCATCACATTATTAGATTGTAATTGGCCAACATGGAAGTATTTACACCCTGGAAATCAGT
AAGTGCTTTGAATGTAGTTGGCCTGTTTCTTGAAAGCAGTTGCTAAACATTTACTGAATA
CTGCCAATGCCAACCAATCAATCAGGCTTCCTTAAAAATGCCAACCTTTCTGCCATGTTG
GCCTTTTGCACTTGTAGTTCTCTCTGCCTGGAATTTTCTATTCTACAGCGAGCTGTTTGG
TTTGGTTTGGTGAGGGAGAAGGGCATCCATGTCATGGTCATTTTGTCATTATTTTAGATA
AAATGTCAACTTCTCAGAGAGGACTTGTCTGACCAGTAATGTTATGTTTGCCCTTTCCCT
TTTCCCAGTGTCACTCTATCAACTTCCTCTTTATGATTTCTTAACACAAATTCCTATCTA
AAATTGTGTTCTTCTACATAAAATATATGAGTATATAGAGTTTGTTTACCTTATCCTTCT
CTATCAGATTTCCAGAGAAAGTAAACTTCCTAAGTCTTATTCAAAATGGGATTCTCAGAA
ACACTTAGAAAAGGACCTGCAACATAATAGGTGCTTAATAAATATTTGTTGAATGAGTAA
GTTATATATGTTGAATAATGATAGTTGTCATTTGAAAGACAACCTATTATTTTAATATGC
AACTGTTATTTATATTTATTTAACATACTTATATTTAGTTTATTGTTATATATTCATTGT
TTGCAGATTTTTTTAAAGAAACTTCCAAAAGAAAAAAGTGCAAATCATTTTTAATTCATG
GCTGAAATTCCAGAAGTTTTTGCTACATTGGCTGTGGTCATTCAAAGTGACCTCTCTTTT
GAAAAGCAGCACAAGTGTTTAAAGCTTTGTGGTGTTTAGTGTGATGTGACAAATTGCAGT
CACATGTAAGGACCCAGTGAAGCATTTTATGGCTTTAATTCAGTTTCAAGTGCTTAAAAT
ACTGCTTGAGCTATATTCTCATGACTTTCCCCTGAACCTTCTGGCTCTGATTCAATTCTG
TTATCTATTAGACGTTTCTAGACAGGTCGTATTGCTACTCTGTGCTTTACTATCCACCTT
TTCTTACTCTGGTTCATAAGATTTAATTCAAAACCTGCATGAGCAGAAACTACATGCTTC
TGAATAGTTTTTGTTTGTTTGTTTGTTTTGGAGAGGGAGTCTCACTCTGTTGTGCAGGCT
GGTGTGTAGTGGCATGATCTTGGCTCACTGCAACCTTCGCCTCCCGGGTTCAAACAATTC
TCCTGCCTCAGCCTCCCAAGTAACTGGGACTACAGGCACATGCCTGGCTAATTTTTTTTT
ATTTTAGTAGAGACAGGGTTTCACCATGTTGCCAGGCTGGTCTCGAACCCCTGAGCACAG
ACAATCCATCTGCCTTGGCCTCCCAAAGTGCTAGGCGTGAGCCACTGCGCCTGGCCTGAA
TAGTTTCACCATTCGACAATTCTTTTATACCTGGTTTTCCCAAAGCAAACAATTGTGAAT
CTTCCATATCTCCCACATATCTAAGCACTTTCTAAGCACACGTGGCAATTGGTTTCACAT
AGCTTAAATATAAGGGCCCATCATTTCACACCAACTTAATATGAAAAATTTGCTTGTTTT
AAATTTTATTATGGAAATTTTGGTGTTCACATAAATTATTCCAACAGATATATACTTACG
CAAGTAATTTGTCCAGACCTTTTAGAATTTTTTTAACTCAAGATGAGATTATACCCTCAA
AAATAAATTTAAATGCTGTGAGGCATTAATATCTGCCACTACTCTTTCAGGGAACTGAAT
TAATGTGCGAGAAAGCAGTAAAACAAACTGGTATGACACTTTGGGGATGCTACAGTTATA
CTCAGAGGAGTTTTTAAAGAAAGCTACATATGAAAAAATTCTAAGTTAGAGAAATCTGAC
ATTAAGTGATGGTTTTTTTTTGGCCAGGAGGTTTCTTGGAGATGAGCCAGTCCACTTCCT
TTATTTTCCAGATAAGAAAATTGAAGGCTGGGATAGATAAGCAGTGTGCTAGAACTTGCA
GACCCAGGTAGTAGCAAAGTCAGGTATAATATTTAGAATTTCTGCCTTTCAACTAAATTC

FIG 4. (SEQ ID NO. 4) CONT.

TTGCTCATCCATATCATATTTATTAAATTTTTTTAAGGAAATCAGGATATTCCTTAAAAT
ATATTGCTGACTCTCTCCATGAAATAAATTTATAAATATGCAATTTAAAAAATATTTTCT
TTTTTACTTTATTCATTTCACTTTAATAAATGAAACATTCAACTGCTATTTTTCTTTCCC
CAAATAAATAAATGTTTGAAAACATTTTTAAATGAAGCCAAATTAAGTGGAATCAGTAAT
TTCAATATTGGTATTTTGAAAATAAGCTTAAATTTAGACATTGTTTAAATTTAATTGTTA
AATAAAGAAGATATAAAGAATTTGTTAGGCTTTATGCCTAGAAGATGATAATATTGGTAA
TTATCACTGCCAATTATCATTTTGCATTAATTAAAATCAAACTATGGTGCTAATTTAATG
CACTTTATAAATAAGTTCTGATTACAGTTAGTGATATGGTTTGCCTGTGTGTCCACCAAA
TCGCATCTTGAATTGTGGTTCCCATAATCCCCATGTGTCATGGGAGGGACCTGGTGGAAA
GTTATTGAATCATGGGGGCAGTTACCTCCATGCTGTTCTCCTGATAGTGAGTGAGTTCTT
ATGAGATCTAATGGTTTTATAAGGGGATTTTCCCCCTTTGCTCAGCACTTCTCTCTCCTG
CCACCATGTGAAGAAAGACGTGATTGCTTCCCCCTCCGCTGTGATTGTAAGTTTCTTGAG
GCCTTCCCAGCCATGCCAAACTGTGGGTCAATTAAACCTCTTTCCTTTATAAATTACCCA
GTCTTGGGTATGTCTTTATTAGCTGCATGACAGCAGACTAATACAGGTTACTGATATCAG
AGAGAGTAGGGCACTGCTGTAAAAATACCAAAGTGACTTTGGAACTGGGTAACTGGCAGA
GACTGGAACAGTTTGGAGGGTTCAGAATAAGAGAGAAAAATGTTGGAAAGTTTGGAACTT
CCTACAGACTTTTTGAATGGCTTTGACCAAAATGCTGAGGTGTTATGGAAAATGAAGTCC
AGGCTGAGGTGGTCACAGATGGAGATGAGGAACTTCTTGGAAACTGGAGCAAAGGTCACT
CTTGCTATGCAAAGAGACTGGCAACATTTTGCCCCTGCCCTAGAGATCTGTGGAACTTTG
AACTGGAGAGAGATGATTTAAGGTATCTGGCAGAGGAAATTTCTAAATGACAAAGGATTT
AAGATGAAGCAGAGCATAAAAGTTTGGAAAATTTGCAGCCTGAGATTGCAATATAAAAGA
AAAACCCATTTTCTGGGGAGAAATTCAAGCCCACTGCAGAAATTTGCATGAGTAACCAAG
AGCTGAATGATAATCACCAAGACAGTGGGAAAAATGTCTCCAAGGCATGTCAGAGACCTT
CTCGACAGCCTCTCCCATCACAGGCCTGGAAGTCCAGGAGGAAAAAATGGTTTCCTTGGG
TGGGCCCAGGGCACCCCTGCTGTGTAAAACCTAGGGATGTGGTGCCCCACATCATAGTCA
CTCTAGCCATGGCTAAAAGGGGCCAAGGTTCAGCTCAGGCTGTTGCTTCAGAGGGTACAA
ACCCTAAGCCTTGGAAGTTTCCACATGGTGTTGAGCCTGCAGGTGCACAGAGGTCAAGAA
GTAAGGTTTGGGAACCTCCGCCTGAATTTCAGAGGATGAAAATAAGCTTAAATTTATACA
TTGTTTAAATTTAATTGTTAAATAAAGAAGATATATGCCTGCTGGGGCATTGCCTCATGG
AGCTGTGAGAAGAAGGCCAGCATCCTCCAGACCCTAGAATGGTAGCTCCACTGACAACTT
GCAGCTATGCACCTGGCAAAGCTGCAGGCACTCACCACCAGCCTGTGAAGGCAGCTGGGA
GTGGGACTGTACCCTGCAAAGCCACAGGGGCAGAGCTGCCCAAGACCATGGGAGCCCATG
TCTTGCATCAGCATGCCCTGGATGTGAGACATGGAGTCAAAGGAGATCAATTTGGAGCTT
TAAGCTTTAACTGCCCCTCTGCATTTTGGACTTTCAGGGGCCTGTAGCCCCTTCATTTTG
GCCAATTTCTCCCATTTGGAATGGGTGTATTTACCTAATGCCTGTACCGTATTATATCTA
TGAAGTAACTGCTTTGCTTTTGATTTTACAGGCTCATAGGTGGAAGGAATGTACCTTTTC
TCAGATAAGACTTTGGACTTGGACTTTTGAGTTAATGCTGAAATAAGTTAAGACTTTGGG
AGACTGTTGGGAAGGCATGATTGTGTTTTGAAATGTGAGGACATGAGATTTGAGAGGGGC
CAGGGACAGAATGATATGATTTGGCTGTGTGCCCAGCCAAATCTCATCGTGAATTGTAGT
TCCCTTAATCCCCATGTGTCCTGAGAGGGACCTAGTGGGTGGTAATTAAATCATGGGGGC
AGTTACCTCCATGCTGTTCTCCTAATAGTGAGTGAGTTCTCAGGAGATGTGATGGTTCTA
TAAGGGCTTCACCCCACTTCACTCTGCACATCTCATTTTTCTCTCTCCTGCTGCCTTGTG
AATAAGGACATGTTTGCTTCTGATTCTGCCACGATTATAAGTTTCCTGAGGCCTCCCCAG
CTCTGGGTTAATTGTGAGTCAATTAAACCTCTTTCCTTTATAAATTGCCCAGTCCCAGGT
ATGGCCTTATAGCAGTGTGAGAAGGGATTAACACAGTCAGTGAGACTATTATACTTCTAT
GGGCTTATTGATATTTAACAAGTCTCTTAATATTGCTTTTTCACAAAATGTTTATAGAGC
ACTCTACTCCAGATATTCTTCTAGGTGCTGAAGATAGGCTGGTGAAGAGGTCTCTGTCTT
TATACAGCTTAAATTACAATCACAAAAATAGACAGTAAAAAATAAACAATATAGTATATA
GATTGGGAGTGTTATGAAACATGATGCGGTTAAATTAACTGGCGAGAGAGTGTTAAGTAC
TTACGTATTTTACCCATTTTGAAAGTTGAATCTTTGGACTTGATGGTAGAATCGGAAGGA
TAGGAAGCTGCAAAAAGGCACGAATCAGGCATGAGTCCTAGAATATTTGGATGAACAATT
TGGAGATGGGGAGAAAAAAGATTTTAGGGCAAATTACCAAGACTTAGTTTTTGGACATAT

FIG 4. (SEQ ID NO. 4) CONT.

TACGTTTGAAATATTATAACTAATTGAGATGTCACGTAGAAAGTTAAATATAAAAGTTTA
GTTCTCAGGGAAGACATTCAAGTAGAGATACATCTTAGAAAGTCATAAACATTAGATGAT
ATTCATTATATGCACACTTAGTGCTTGTAAGTTCCAGAATATGTATTATATTATCTCATT
TAATCTCACAATAGCCCTGAAAGTTAGGGACTAGTATCTCAATTTTATTGATTTATAAAA
CAACCAACAAAAATTTGTGTTATAAAAACTAAACAACTTGTACTGCCCATTCAGCTGTTT
GTCAGTGACTACAGGATTTGAGGCCAACCCACTTAACAGGTGATGATTTCTTAACAATTA
TTTACCAATTCCCAAATGTCAGCCTGTCTACCATATTCTGTTTTATATAGACTATGTTTA
TACGAATTTCTTCCCTTTGGATTAAATTTTATTTTTATATTAAAGAGAACATTGGTTTAG
GAAGCAAAAAATCTTGTGGTTCTCTCTAAGTAAAATAGCTGGTAAAGTCATAATATTCAT
GAATTAGAAATCACAGCATTATTCCCCTCAATAAATAAAAAATATGTATCCAAGGGTTTT
ATTAAGTATAAAGTACAAAGCGAATCTTAGATATTATACTATGAACGTACAATACATATG
ATATGCTCATACCTGCATAGACAATGCAGTTAGTTGGGCTGTATGTTTGCATTGAATTTG
GGGGTAGGAGATTAATCTGCGCACAAATTAAATATGTTATCCTTTATCCTTTATAGATAA
TTCTCAGTCTGTTGTACTAAAGGGATATAGAGATTCTGTCTCTAGATTTGGCACAAAAGT
TTAGTTATAAAGTATTTGTGTGTCAGCATAAATAGTAGGTCTTCAGGGAACAGTTCAGTT
ATTAGCATTTCTAATTAAGGGCATTTATCATCCAACTGAAAGGGAATATATTTCATTCTT
ATGCAGGGATTGAAAATTGCTTTTTAATGGAGGGAAACATGCTGTTTTTGCAAAGTTAAT
GCTAAAAGCTAAAAGGAGTGATCATCATGCTTTATTTTATTGGTGAGCACCTGGTAACAT
TTTGAATTGTTGTCTGTCACATTATTTAGTTGAAGCTGGTCATTGCATTATAAATGGCTC
TGTAATCAAAAGAGAGGTCAGAATTGTGTAATATGACATTTTACATCCGAAGATAATTGT
TTTTAAATATTCCAGAAAGATCACATTTTGTCAATATTATTTGTGGGAATGTATGATAGA
AAAGTTTGCCTTGTCTGTTATGATCAACATTTTTAATAATGAAAATTGCTTGAAAACTTT
TAAGGCCCCAATAATTCTATAAATCAAATCATGCTAGAGTTGCCTTCAATTACCAGACAT
GAAATGCATTTGACTTAATTTTATTTTTGAGTCTCGGGCAGCTTTTGTTATTTCCATTGG
CATATTTGTCATAGATGGGAATCTTGTTTCCAAAGTTGATAACTGGTTATTGTTTTAATT
CCTCTTATTTGTAGCAGACTTTCTATGAAGTTTGTTAGTGATCTAAATATTATTCTAAAT
CATTTATTTAAATAGCATTCTTTTAAATCAGCTACTCTTTAGTCAGAAAAAAATATTTCT
ACATAGAATTTTATTTGTGTTTTCTTAAGATAAAACTCCAGAAACATTTAATTTCCAAAA
TTCCATTGAATAAGAGCTAAAGTTGCCATCAGGTTCCATAGAATTGAAATTTGATAAAAC
AGTTTCAATCTATTATCCATTTACTCCATGTGAGCTACAAATCTGAGTATACAAAGTAAA
TTAAACTTTGAAATGGCAATAAACTATGATTAATATTTATGATAAAATTTATAGAAACTG
AATGATAAAGATTATATAAAATCAAAACCAACATGATTTCATTATGAGGATTTCATTATT
TTCAAAAAAGTTTTCTAATTCTATCTTTTTGAAACAAACCTTTTTTAAAGCTTATTTTGA
TAAGTATTCTTAAATATATAATTTGATATTTTCACTCAGGAGGCAGGCAGAGGTAGGTTG
AGTTTAAAATTAGGTGGTAGCCTCTAGTGTTTCAGAGTTTCAATAACTGTGTTGAAATTT
TTGGGTTTCTTTAATGTCCTCCAAATAGTAATTCCTCATATGTGCTTTTTGCAGGCATAA
AATATTTGGTTATTATTATTTTTTATTTTATAATTTTTAAAAATTATGATAAGATGTACT
TATCATTACATTTCTCATTTTAACGATTTTTTAAGTGTATGGTTTAGTGATTAAGTATAT
TCACTTTGTTGTGCAATTTTTCAGTGGCATTGTCATAACTTTACTAAAGTAATTATTTTA
GTTTTACTTCATGCCTTTATTTAGTATGTAATTTATCTTAAGGAAATATAGTGTTTTTGA
TAGATTCCTATGCAAAAATAATGAAAAAAATATTAAGTGTGTATATATCTAATTTATATA
AGCATATATGTAGAACTAATTAGCAGCAATACATTATTTTATAAAACAGAATTTTTAAAA
TACAGAAGTGTTGTTAATATTTAAATTGTTACATACCTTTTGTTTTATGTATTTTTTGTA
TTCAAATTTTAATCTAACCACATAATCTTCAATGCTAATATAGGATGACTGAATTTCAAT
ACATTTTTTAGTGGATGGCTTACTTACTGTGAGAAAAATGAGTTTACTTCATGGGGAAAA
AAAGAAGCTAATACTTTATTACAACAAACACACCGCTAGTCAGGGGACCCATTTACCAAA
TATTTGATGTCAAGAAAGAAAATGGCTTTGTTGCAAAGCAACAGAATTAAGTTAAGCAGA
ATTCTATTTCTGCTGAATAGCCTTTTATGTTTCAGAGAAGTATTTTTGATTTATAGTTGC
TATTATAAAAAATATAATCTTCCTGACATTTGAACTTCAATCGTTTAAACTCATTCATTA
CACTTATTATCTGTGTATATTCTGATAGAGCAGTGACCTGAAACTTTTTTCTTTTTTCAA
ATCTTATTTTAAGTTTTAGGCCAGGTGCGGTGGCTCACACCTGTAATCTCAGCACTTTTG
GAGGCTGAGGCAGGAGATCACTTGAGGTCAGGAGTTCGAGACTAGCCTGACCGACAAGGT

Figure 4:
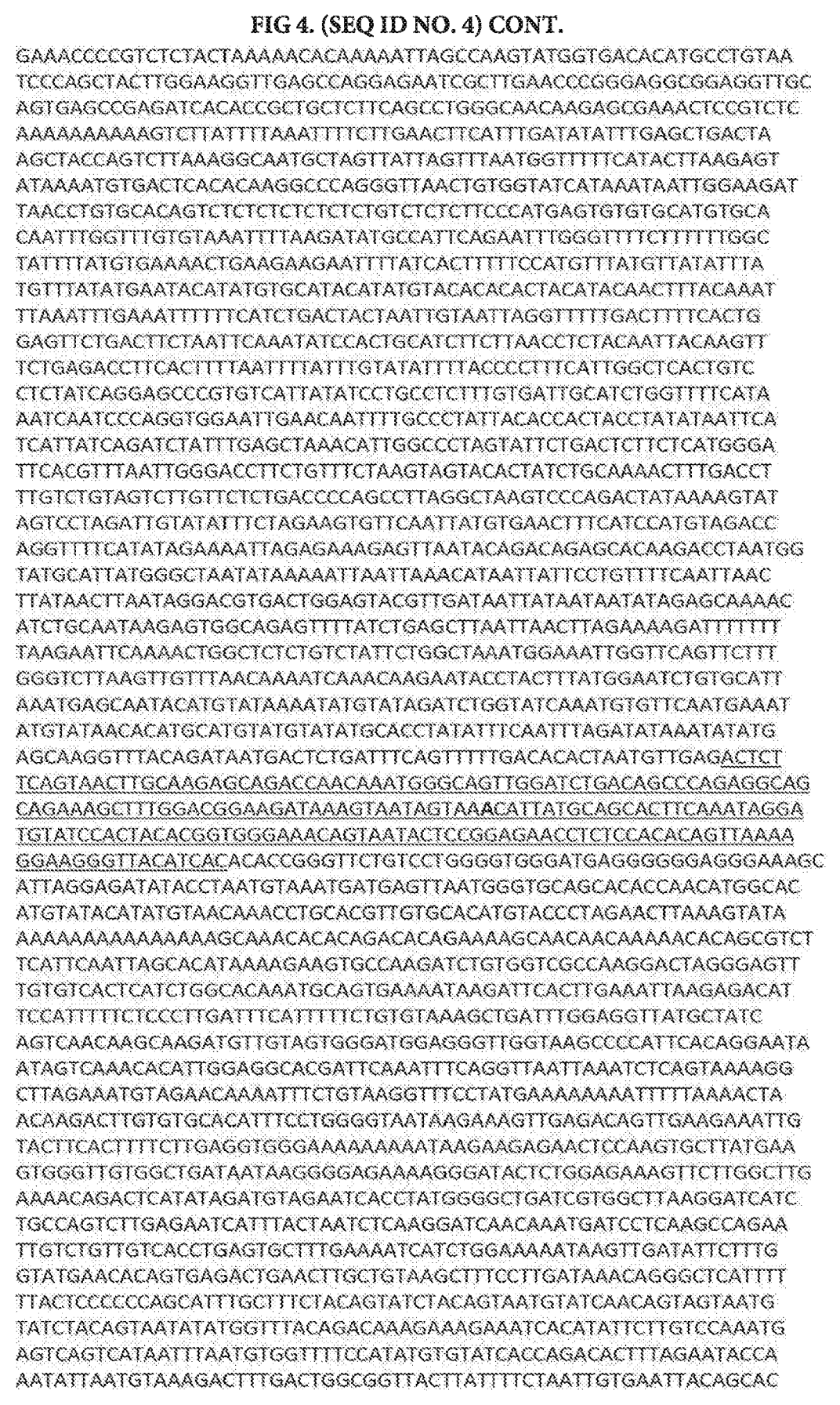

FIG 4. (SEQ ID NO. 4) CONT.

GAAACCCCGTCTCTACTAAAAACACAAAAATTAGCCAAGTATGGTGACACATGCCTGTAA
TCCCAGCTACTTGGAAGGTTGAGCCAGGAGAATCGCTTGAACCCGGGAGGCGGAGGTTGC
AGTGAGCCGAGATCACACCGCTGCTCTTCAGCCTGGGCAACAAGAGCGAAACTCCGTCTC
AAAAAAAAAAGTCTTATTTTAAATTTTCTTGAACTTCATTTGATATATTTGAGCTGACTA
AGCTACCAGTCTTAAAGGCAATGCTAGTTATTAGTTTAATGGTTTTTCATACTTAAGAGT
ATAAAATGTGACTCACACAAGGCCCAGGGTTAACTGTGGTATCATAAATAATTGGAAGAT
TAACCTGTGCACAGTCTCTCTCTCTCTCTGTCTCTCTTCCCATGAGTGTGTGCATGTGCA
CAATTTGGTTTGTGTAAATTTTAAGATATGCCATTCAGAATTTGGGTTTTCTTTTTTGGC
TATTTTATGTGAAAACTGAAGAAGAATTTTATCACTTTTTCCATGTTTATGTTATATTTA
TGTTTATATGAATACATATGTGCATACATATGTACACACACTACATACAACTTTACAAAT
TTAAATTTGAAATTTTTTCATCTGACTACTAATTGTAATTAGGTTTTTGACTTTTCACTG
GAGTTCTGACTTCTAATTCAAATATCCACTGCATCTTCTTAACCTCTACAATTACAAGTT
TCTGAGACCTTCACTTTTAATTTTATTTGTATATTTTACCCCTTTCATTGGCTCACTGTC
CTCTATCAGGAGCCCGTGTCATTATATCCTGCCTCTTTGTGATTGCATCTGGTTTTCATA
AATCAATCCCAGGTGGAATTGAACAATTTTGCCCTATTACACCACTACCTATATAATTCA
TCATTATCAGATCTATTTGAGCTAAACATTGGCCCTAGTATTCTGACTCTTCTCATGGGA
TTCACGTTTAATTGGGACCTTCTGTTTCTAAGTAGTACACTATCTGCAAAACTTTGACCT
TTGTCTGTAGTCTTGTTCTCTGACCCCAGCCTTAGGCTAAGTCCCAGACTATAAAAGTAT
AGTCCTAGATTGTATATTTCTAGAAGTGTTCAATTATGTGAACTTTCATCCATGTAGACC
AGGTTTTCATATAGAAAATTAGAGAAAGAGTTAATACAGACAGAGCACAAGACCTAATGG
TATGCATTATGGGCTAATATAAAAATTAATTAAACATAATTATTCCTGTTTTCAATTAAC
TTATAACTTAATAGGACGTGACTGGAGTACGTTGATAATTATAATAATATAGAGCAAAAC
ATCTGCAATAAGAGTGGCAGAGTTTTATCTGAGCTTAATTAACTTAGAAAAGATTTTTTT
TAAGAATTCAAAACTGGCTCTCTGTCTATTCTGGCTAAATGGAAATTGGTTCAGTTCTTT
GGGTCTTAAGTTGTTTAACAAAATCAAACAAGAATACCTACTTTATGGAATCTGTGCATT
AAATGAGCAATACATGTATAAAATATGTATAGATCTGGTATCAAATGTGTTCAATGAAAT
ATGTATAACACATGCATGTATGTATATGCACCTATATTTCAATTTAGATATAAATATATG
AGCAAGGTTTACAGATAATGACTCTGATTTCAGTTTTTGACACACTAATGTTGAGACTCT
TCAGTAACTTGCAAGAGCAGACCAACAAATGGGCAGTTGGATCTGACAGCCCAGAGGCAG
CAGAAAGCTTTGGACGGAAGATAAAGTAATAGTAAACATTATGCAGCACTTCAAATAGGA
TGTATCCACTACACGGTGGGAAACAGTAATACTCCGGAGAACCTCTCCACACAGTTAAAA
GGAAGGGTTACATCACACACCGGGTTCTGTCCTGGGGTGGGATGAGGGGGGAGGGAAAGC
ATTAGGAGATATACCTAATGTAAATGATGAGTTAATGGGTGCAGCACACCAACATGGCAC
ATGTATACATATGTAACAAACCTGCACGTTGTGCACATGTACCCTAGAACTTAAAGTATA
AAAAAAAAAAAAAAAGCAAACACACAGACACAGAAAAGCAACAACAAAAACACAGCGTCT
TCATTCAATTAGCACATAAAAGAAGTGCCAAGATCTGTGGTCGCCAAGGACTAGGGAGTT
TGTGTCACTCATCTGGCACAAATGCAGTGAAAATAAGATTCACTTGAAATTAAGAGACAT
TCCATTTTTCTCCCTTGATTTCATTTTTCTGTGTAAAGCTGATTTGGAGGTTATGCTATC
AGTCAACAAGCAAGATGTTGTAGTGGGATGGAGGGTTGGTAAGCCCCATTCACAGGAATA
ATAGTCAAACACATTGGAGGCACGATTCAAATTTCAGGTTAATTAAATCTCAGTAAAAGG
CTTAGAAATGTAGAACAAAATTTCTGTAAGGTTTCCTATGAAAAAAAATTTTTAAAACTA
ACAAGACTTGTGTGCACATTTCCTGGGGTAATAAGAAAGTTGAGACAGTTGAAGAAATTG
TACTTCACTTTTCTTGAGGTGGGAAAAAAAAATAAGAAGAGAACTCCAAGTGCTTATGAA
GTGGGTTGTGGCTGATAATAAGGGGAGAAAAGGGATACTCTGGAGAAAGTTCTTGGCTTG
AAAACAGACTCATATAGATGTAGAATCACCTATGGGGCTGATCGTGGCTTAAGGATCATC
TGCCAGTCTTGAGAATCATTTACTAATCTCAAGGATCAACAAATGATCCTCAAGCCAGAA
TTGTCTGTTGTCACCTGAGTGCTTTGAAAATCATCTGGAAAAATAAGTTGATATTCTTTG
GTATGAACACAGTGAGACTGAACTTGCTGTAAGCTTTCCTTGATAAACAGGGCTCATTTT
TTACTCCCCCCAGCATTTGCTTTCTACAGTATCTACAGTAATGTATCAACAGTAGTAATG
TATCTACAGTAATATATGGTTTACAGACAAAGAAAGAAATCACATATTCTTGTCCAAATG
AGTCAGTCATAATTTAATGTGGTTTTCCATATGTGTATCACCAGACACTTTAGAATACCA
AATATTAATGTAAAGACTTTGACTGGCGGTTACTTATTTTCTAATTGTGAATTACAGCAC

FIG 4. (SEQ ID NO. 4) CONT.

AATGTGTATATCAGAAATATTCAGATCTTTCTTGAAATCTCACTGTAAGTCTTAAAATAC
CACATTTAAAAATGTCCAATTTACTATGTCTTCCATAAAGCTGTGAATTTTTAGAGAGCT
AAATGTCTCATGTATTTTTACCACAAGTGAATCATTGAGATGAATTATTATTCAAAATAT
TTTCCTGAATAATATGAGACTGAATTGAAAGGTTTGGGGAGGGGGCAGAATCCTGAGAGC
TGTAATACAGAAAACTATATAATAAAAAATGACTTTTTATAGTCAATTTCTGTGAGTTTT
TTGGTCTCTAAAACAAGTACAAGAAGAACAATGGGTAACATAGAATATAATTTATGTGCT
AGGTAGTGTCCTAAGCACATTACATTTTTCTCAATACCCCTTTGGGGTAGAGTCTATTAT
AATTCTCATTTTATGGATGAAGATTGATTTTTAGTGAGTAGAGTGAAATATCAGTAAAAG
AGATTAAAGAACCCTGCATCTCCTCCCATCCTTTGCCTCTCTGGAACCTTGATTAATGTA
TCCCCTCTTTCAGTTTCTCTCTCTCTTCCATGACACCTCCTTTTGCTCACACAAATGCAC
ACATATTCCCTAGGTAATTTTTTTTTTATGCAACTGGTGGGAATTCTACTAACATTATTC
AGAGCATTAACTTCCATTTCATAAAATTGTATATAGTGAAACACACATTCAAGAAATTTA
AGCCAAACATTGGTACTCAACAATACACTCCAAACTGTTTATTTTAGCCTTAATATATTG
CTTGTGAGAAATTTAAAATCTATGCCAAGATTATTGTGCTCAAATGTCCCACAAACTTAA
GCTGGCCAGTAGTGAAGGTCCCTCCCTGTTGGGCCTCTTCACCTCCTGCCTGGTGCTCTT
CTAGGCTCAGCGACAGAGCTGCTTGTCCAGACCCCCAAAGCAGCGCAGGAAGCAGCACTG
TTCCCCCTACTGGCAGTACCTTCCAGCTTCTTGTCAGTGGTAAAGACTCCAGGGCTGCTT
TACATGGGTCACATCTCAGTGACATTCCTCACTAGGTCTGTGGCCTTGAAAAAGCTACTT
AAACTTTCTAAACTTGAGCTTACTCATATACCAAATGGAGATGACAGCAGTGCTGATTTA
TGGGGATTAGATAAGACAGTTTATGTAAACTTCTTAAACCAGTGCATGCATATCTAAGGA
CTAAACAAATATTTACTGTTATTGATATTTCTTTCAATATGTTGCATGGAATTTTGACAG
TCTTATTTGATGTGTTTCTTATCGTATCCTACATTCATATCTATTTTGTGTGTGTGAAAT
ATTTGTTGCATAATTTTACCATTGCTTACAGTAAGCAAGTACTAAAAAGGCATTTACATT
TTTTTTTAGTTTATAGTTCATTATGCATATTACCAATAGATTGAGGGCTATTTTTCCCTT
TAGTGTAAAATCAAACACTAATAGGTAAGATTTCTGAAGTCATAAACTTTATGTTAAATT
TTTAGATATTTCTTAGACGTCAAAATTTTTTGACTTTGTATGTTAATTTAAATGAAACAC
TTAATATAAAATATCTTATGATATATATATATATATGGCAACAATGATCAGTGTGCAGTC
TAAATTTAATTGCATCATTTTCTGGGAGGTATCATGCTTCTTTATTGTGCTCTGCTCAAC
TGGGTATACACATTCTTTCATCTAACCTAGAATTCACAAAAATAACAGATCTCCAAAACC
ATTTCATTCCATAATTTCCCCATCTGTTGATTTTGGTTCCTATACACACATCTGAGCATA
AAAGCTCATTGGTACTAGGCCACGAGTAATTACAATCTAAGAACATAGAAGAATGATTGA
ATAGTGGTAAAGGAAATACCAGCAAATCACTTGACTATTAGAAAATAATATGGTAAGGTT
GTGAATCTCAATACCATTCTGTGATAATGAGGGCACTCCATAAACATTTTACAAATAAAT
GAATGAGTGGCTTTATTTACAGAATATTGAATGGTAAAGTTAAGTAGAATTTAAATGTCA
TATTAAGGGAAATAACTTTATTGAAGGTAAAGTAGTATCTTAAGCAGAAAAGGAGAGTAT
CTGGGGTTTTATTTTATTTTACATAAATGCAGTTAAATGGATCTTCATTGTTTCTATTTA
GAAGAGTTTGAGTTTGAAAAACGGTTTTGAAAACACAACCAACAGCAGATAATTTGTCTT
TCAGTTATGGGGACAGCCCACAGAATTCCAACACATATGGCATCTAGCCTTCACCACAAA
ATTAGTCTAGTACAGATAGTGTGGCCCAAGTGTTTGGCAAATGTTGGGTTTTCACCATAT
ATTGATAGCAGCTGGAACAGGAAATAAAAATGAATCATTTCACGTTACATTGAATTTTAA
GTAGAAGCAGCACACATGATTCTGAGTTAGCTCATCATTATGAAGTTATTCTAGCACGTA
GAAGATAACACTTTTGAGATATAACTTGAAGCTATTTTTTGTTTCCCACAGACAGTATGG
GAAAGGGATTTAAATACCTCAGAGACTCTGGAATTTGTGATAGTAACAATGATAGTCACA
GCTGAGAGTCCAGTTTTTAACATTGCCTTGTTAGTTGGCCAGCTCTTCCATGCCTGTGGG
TATTCTTCAAATCTGGTTTTGTGCTATTTTAATGTAATTTCAGAGAAATTACCGGCAGTG
CCTCTTTTGTGGCATTCAAATGATATTGTTGTGTTCTACATTGTTGAATCAGCACCTTTA
AAATAGAATAAGAGCATGACATATACTTTTCGTGCAGAGTTACTAGGAAAGAGTTGAAAT
TCTAGTTCACAAATGAAAACATTTGTCTTGTAACAAAATTAAAAATCACTCAATCACTTA
TGTGTTCAGAAATTTTACTTTGATGTTTCCTAAATTCTCTTTAGTAATTCTGTCTACAGC
TAATTTTTGTTAAATTTGTTATTTTTTGTTTATAAACATTGAGACTTGATTTTCTTTTCT
TTTTAGGATCCCCTGCCTTGACTGGAACTGGAACAATCAACGTCATAGTAGATGATGTCA
ATGACAATGTCCCCACATTTGCCAGTAAAGCGTATTTCACAACAATTCCTGAGGATGCAC

FIG 4. (SEQ ID NO. 4) CONT.

CAACTGGAACAGATGTTTTATTGGTAAATGCCTCAGATGCTGATGCTTCAAAGAATGCAG
TTATAAGGTCAGTACATTTTCCTTTGTAAAGTTTGTCTGTTTTCTCATTAAACATTAGTT
TTTGAACTACATGAATATAATGTTTAATTTAAATGAACGTCATATTAACACATATCCTCT
TCTTGTTATCCATTGCTGATAGCCAACAATTCATTAAATGAAGATTCAAACAGTAAACAT
TTTACTTATTACTCTAAGATTTTATTTAATTTTTATTTTATTTATATTTTTATCATATCT
CATGGTTTTGTGGTTTGGGACTACACTGGGTGCTTCTGTCTCATGAGGTTGACTGGTGGC
ACTTCACAGTATTTACATGGTGACTGAATGATCTGGAGGGGCCAAGATGACTTTGCATGC
CTGCTGCCTTGGCAGGGTTGGTTGGAAGGTTCAGGATCATCTTGGCCCCCTCTGTCCTCA
AGTAGTCTCAGAACTTCCTGATGTGGTTCTTTAGCAAAGTAGTTGGACTTTTTAGTTGGT
GGTTCTCAACTCCAAGAGCCACAAGTGAAAGCTCCCAGAACTCTCAAAGGTCAGACTCAG
ATGTGCCATAGCAGCACTTCTATAATACTCTGTTGGTCAAAGCAGTGGTGACCAGCTCAG
ATTCACTGTGAGGAGAAACATGCATCACTCGTTGATTGGAGAAATGTCAAAGAATTTTGA
CCATTTTTATTCCACTACTAGCTCTAATAAGAATATTTGTGTATTCTTCATTTAGTAAAT
GTATTTTACTTTGCTTAAATCCTCTTAAAATTGAGAACACAAATATGATAACTTGTTCAG
AGAGGATGTGAAAGAAATTTGAGTTGCAACATTTTATCAACCTAGATTGTCCCCTTCTTC
CATATCTATTCTAAACTACAAGAAATGAAGATTTCCAAAGGTTCTAGAGAAAAACTCACA
CACATAAATATTTTATACCCCTCCTCCACTTTCTATAGGCTGGTATTAGGTAAATTAGAG
TTGGTTAGATGGCTATGAAAGTAATGGAGCAGAAGATAAAATTTGAGACATTAAGAATTA
TCAGCTATGGGTACCAGATATACGGATATGGTAATGAGCTGATTCATGTCTTATTTTGTT
GTTTGTTACCAATTTTCTTTTAACAAAATCATTTTGGAAAACTGGTTTTCACCACACAAA
TTTTAAGAAACACATTCAGACCACAATACTTGGTCTCTCTAAGAAATGACCTTTAAGCTG
AAAGGACTGAGCTATGGAATGGAATTAATCTCGTTGTTTTATCTAAGAAGGTCAGCATGT
CTGGACCAGAGTGAGAAAGGAGTCAGAGAGGTAGGCAGGGGCTAAATCATGCAGGCCATA
TACAGGCCATATATGTCACGATACAGAATTGGGGTTTTCCAATTTACCTTTAGGTGAGAA
ACTACTGGGGAGTTTTAAACAGAAGAGACACATAAACTGGTCTACATTTGGATAGAATCT
GATGAGAGAGGATTTACGGAGAGAAACCAGTGCACCATTTAGGCACTAATTAATATAGTT
ATCCAAGTAGAGTAACTTTGTACTTACGTGGAGAAATGAAAATTGAGTAAATAGATTTGG
GGCATACCTTTGAAATTGGATGTGAGACAGGAAGGGGAACATCACACACCGGGGCCTGTC
ATGGGGTCGGGGGAGGGGGGGAGGGATAGCATTAGGAGATATACCTAATGTAAATGATGA
GTTAATGGGTGCAGCACACCAACATGGCACATGTATACATATGTAACAAACCTGCACATT
GTGCACATGTACCCTAGAACTTAAAGTATAATAATAAAAAAAAAACAAAGAAATTGGACG
TGAGATCAAATGAAAGAGAGAAATCAGAATCATCTAAGTTTTCCACTCAAACACCTAGGC
AGATCATGATATGATATCATTTACTGAAATGGGTAGCATTGAAGGAGGAACAGTTTTGTG
AGAAGTCAGAAGTATTCTATTTGAATACAGTTTCAAATGACTGTTACTCATTCATTTAGA
GATACCAGTTAGGAAGCTGGAGATATGAGTGTGGAGCTTAGGGTTGGGGTTAGGGCTGGA
TATACACATTTGAGAGTCATCAGTGTTTAGAGGACATTTAAAACCAATAAACTGAATGAG
AACACGTTTGCGGAGTGTATTAGTCTGTTCTCATGCTGCTAATAAAGACATACCTGAGAC
TGGGTAATTTATAAAGAAAAAGAAGTTTAATGGGCATATAGTTCCACATTGGCTGGGGAG
GCCTCAAAATCATGGCCGAAGGTGAGGAAGAGCAAAATCACGTCTTACATGGTAGCAGGC
AAGAGAGCTTGTACAGGGGAACTCCCATTTATAAAACCATCAGTTCTTGTGAGACTTATT
CACTACCACAAGAACAGTATGCTCGAAGCTGCCCCCATGATTCAATTATCTCCACCTGAC
CCTGCCCTTGACACATGGGGATTATTTTTATTTATTTATCTATGTATTTTTTTTGAGATG
GAGTCTTGCTTTGTCACCCAGGCTGGAGTGCAGTGGCACAATCTCAGCTCACTGCAGCCT
CTGCTTCCCAGGTTCCAGTGATTCTCCTGCCTCAGCCTCCTGGGTAGCTGGGATTACAGG
TGCACGCCACCACACTCGGCTAATTTTTGTATTTTTAGTTGAGATGGGGTTTCACCATGT
TGGCCACACTGGTCTCCAACTCCTGATCTCAGGTGATCTGCCCACTTCCGCCTTCCAAAG
TGCTGGGATTACAGGCATGAGCCACCATGCCTGGCCGACACATGGGGATTATTACAATTC
AGGGTGAGATTTGAGTGAGGACACAGCCAAACCATATCAGAGAGAGTATAGCAGGATAAG
GAAAGAGGCACTAGAACCAGTCACTGGGAATTCTCCAACACTTTAAAGGTAGGTTTAGGA
GGAAAGGTCTCCAAGGAGACTAGGAGTTAAGGTAGGAGTTAAGAAGGTCTGAAGTTAAGG
AGGCCTGGCTAGAGACAACAGAGGAAATGCAGGACAGAATGAATTATTTGCATGCATTGC
AAAAGGATGGAAAGCTATATACAAATTTCTTTCAGTGAGCTACATACAGATTTCTTTCAG

FIG 4. (SEQ ID NO. 4) CONT.

TGGACCAAGACTTATTCCAAGAGAAGAGTTGAGTTCTCAGAGTCCTGTAAAGTCAAATCA
TAGAGGACTGAGAAATTTCTGTCCAGGGTCATAACCCGTTTGAGTCATTGTACTTAGCAC
CAACCAGAGAGAGGCAGGTACAACTGAACTTCTTCCAGGTTATGAGCTTCAAAAGGCCAC
TAAATACCCTTTCTTTTACTTGTCTTATACCAAAGCATAGAAATAATAAAAATCATATCA
TAAGATTCAATCCAAAGTCTTTAGCTTAACATTAAGAGTAGAACCTTGGGAATTAAGTTG
TGTGGAATTGAATCCTGACTCTACTATTACTATTGCATTAGTATGGGCAAATTAACATTT
CTGGACCCGGTTTTCAGTGGATTAAGCAGAGTAATAATGAAACTAACTTTAAAGAGAGTA
AGTAAAATAATTTAAGTGAGCTGGTTAGAATAGCACCAGGAACAAAAAACAATGCTCAAT
AAATGTCAACCCATATTGTTCTAATCATGCAAAGCACCTAGCCCTCTACCTGTCTATCAT
TTGTTAGTGCTAAATAAGTTTCTGATAATGATTTTGGAAGAGATGCCCTATCTATTGTAA
TGTTATAATCTAATAATTCTTTATCTGCCATGCAGATGCTGTTTCTTAGACAGTATATAG
AATATTACCAATCAGATATAGGGAAATTCTCTTGTATGAGATGTATAAATTCCTGAATAT
GAAGTTGAATGTTTACAAACTTGATCCTGTCTTCCATTGAGTCATTCATTTATTTCTATA
ATAAAGTAAATGCTGTGATGACCTGCTGTTTTTTTCTAGTGCATGTTAAAGATTCATTGC
AAAATGCTATCCTATGCTTGTGAATTATGCTTGTAAATTTGGTCTAGAAAAATTGTATTC
ATACTCTCAAACTGTTTTACAAAGCTGTACTGGTAGGTCTGATGGGATTGTTTTGCTTTG
GTAGTATGTATTTTGGTTATTTGATTGGTTGATTAAATTTTCTTCTTTTAACATGAGAAT
TAACATTATACTTTTACATACATTGAAATCCAAAAACCCCATCAGTGAAAATCTTAAAAT
GACTCTACAGACTATCATATATTCAGTTAAAATGAAAATTGAAGCTATTTTTGTCTTGTG
AATAAAAAACATTCAATTCACTTGCAAATTAACAGGGCAAACAATTATTGCAGCTTAAAT
AGAAAATATTTTCACAGACAAAGTAAATAGTTATTATAACCTCAACTTTATTTACTCTGG
TTTGATAAAATCTTAATGGAATATAATGTATTTTATGGTTGGTGTTAATAACTCCTTGCT
ATTCATGGTATCCTGAAGAAAATCTATTCTTTCTTCAGATTAAAAGAGCTATTGGTTTAA
TTATTTATCTCCCATTTAAATTTTACATGGTTCGGTTATTTACTGAACTACTGTTGGGAT
CTCCAGGAGCATAAACTTTTATGTGTCTTATAAGTTAATTTTTTTCCAATGATCTAGCAT
GATTTTGCATATAGCATCCAGCCAACAATGTTTCTTTTTTACTTCTACCTATTTGATCAA
ACTTTGTATTTCTACAAATGGTGTACTTACTTTATGTTATACATTTTACTTCACCTTTAG
TATTTTCCCTTATAGAAAATCAGACTGTATTAATTCTTAGTCTTTCTCTATCCAGATTAT
GTCTTTGCCTTCCACATATCTATTCCAGAGCTTAGCTTTTACAGATATGTATCCCCTTTT
CTCCCAACTGGACCAAATCTCTATTCAAGCCCCACTTCTAATTCTTCTGTATCACAACCC
TGGAGACAGCCACAAACTCCACTGACAAAGTCAACATTCTAAGGAAGATTTCTTTTCTTT
TTTTTTTTTTTTGAGATGGAGTCTCGCTCTGTCACCCAGGCTGGCGTGCTGCGTCGTGAT
CTCAGCTCACTGCAACCTCCGCCTTCCAGGTTCACGCCATTCTCCTGTCTCAGCCTCCTG
AGTAGCTGGGACTACAGGCACCCACCACCATGCCCGGCTAATTTTTTTTTTTTTGTATTT
TTAGTAGAGATGGGGTTTCACCGTGTTAGCCAGGATGGTCTCGATCTTCTGATCTCGTGA
TCTGCCTGCCTTGGCCTCCCAAAGTGCTGGGATTACAGGCGTGAGCCACCGCGCCCCGGC
CAGGAAAATTTCTTAATATGTGCTATTAATCTCTTCCCATTCAATTTCCTCCAACTCTTT
AATTCAAAAGTTACTCATTTTTCTTGTGTTTCTTCAAGTTCTCTCTCTTCCTTGAACCAT
GTAGATATCTATATAAATGCTCATTTACATAAGTTAGCGTATCTACAGAAATGCTCAGAA
TTTCTGTTGAATTCTGGTTCTTTTATTTGCCTCCCATGGCCTAGGAAAGTCATTTTAGTG
CCTCAAAGGCTTAGTTTCTGCATCAATAAAAATGAACATAAAAATTTATACTTTACAGTT
TGTGAGACAAACATTTACTAACCACCTACTATGTATCAAACAGTATGTATGGAATCAGTT
AATATCCATAAATGTCTCTGGCATAATTATTAGGACATAGAAGTCACTAAATTAATTCAA
GGTTTCTTTTTTCTTTTTATTCTTCTCATATCATCTTTTTTACTCCTAATATATTCTTTC
TTTTACAATATCTGGTACATAACAGTGGTTGTCACTTAAATAAATGCATTGAATGAACGA
TTTTAATATTCTCTGGAATGGCTGCTTTTACTCATTCTATTTTTACTACAACATTCTTGA
AAGCTTCACAACCTGTTTTCTCTGACCATTTATTCCTGAAAATCTTTAGTCTGATTTTTT
TTTTCCTTCATTGCTTTACTAAAAAAAGGCCCTGTCAGAAGACTACTGAAATTTTTCAAG
TCCAGTGACTTTTCTAAGTCCTTATTCTCCTTTACTTTTTGCAATGTTCACACTACAGGC
CAGGCCATCTTTTCTTTTTGGCATTTTTTCCTGCTCAATGTCTATATAAATATTATTTCT
TATCATCCTGCATCTCTGATCACACACAGTTTGTTTTCTGTTTCTCTTTTCTCTCTCTGG
AAAGTAATTTGAATACTTCTCACTGCATTATTTTCTCAGTACTTGTGTGTGTGTGTGTGT

FIG 4. (SEQ ID NO. 4) CONT.

GTGTGTGTGTGTGAGAGAGAGAGAGAGAGAGAGAGAGAGAGAGAGAGAATTTATTCCATTGC
TGCAAGCATCAATTCTGTGAACAAAACCTCCAAATCTGTACTATCAACTCTGATTCCACT
CCAAAATTTTGCACCCATATTTATAACTCGCTGATAGACATATTACACTGGAGGTTCTGT
TGGCATCATAAACACAGTGTACCTAAAATTCTTTGCTTTTCCTGTTTCTCATTTTGGTTT
TCTGCTTTGTTTTAATAATATTGTCTTGGTTTGTTTTTTACCACACCTTGCAGCTAAGGG
TCATCCCCTCTCTTATACTCAATCAGTGGACAAATTCTCATGTTTCTTCTTTTCTAATGC
ATCTGGCACCCATTCTTTTCAGTGCATCCCTTCTGCCAAGATCCTAGTTCAGTTCATAAT
TACATCATGCCTGTACTATTATAATAAGAATTAACTCACTTCCACGCCTCTAGTTTCTAA
TCCTTCCAATCTATGTAGTACACTGTCCTGTAAAATTATGAAGCCCTGACTATGCACCAA
AAATTTATTAAACTCTCAGGAGTTTGGAACTCTAGGGCCCATAAGAAGTGCAATTTAATA
GAAGAGATAATTTTGTAATTTCTTAAGTGTAGTACCGTATAACAAGTATAGTTTAAGCAC
AGAATAGGTGGAAAGAATAGTATGGCCAATGATCCTTCAATGATACTAAGTAGAAGTAGT
TTATGGAGAAATAAAGGAATGAAAGATATTCTAGGCAAAGACAGTATCAGGTACTAAGGC
AAAGAGCTATGCAAAAAAACATGGCATTAGAGAAAGAAAGTATTTCCATATGGTTGGTGTG
GGTTAGGAATGGACTTTGTATACCATATAAAAAATTCAAAATTTCTTTCTGCATCTAAGG
AGAGAAACAATGGAAATGTTTTAAGCAGCAAGCACAAAAACATGCCTAGTTATATTTCAT
AATTATTTCTTTCCCAGCATTATAGGAAATAATTTGTACAAAGCAAAGCTGGAGTCAGTG
AATTAAAGGGCAATGGCAGAAGTATGCATCAACATGAGCATCTCTTGGCTCTGCTTTAAC
AATTATACTTCCTTCCTCAAAATCTTTCAATTCCAGTTTGCCTATGGTATAACCCCCAGT
CTTCAAATTCTAGTCACCCCATAAATGGCCCCAGCTAATTCTGCAAAACTCTGCAACATA
TGGCCAAAAGTTCAGTATTACTGGATCATTTTCTGCTCATGGGACAAGGATCTGTGCTTT
CCCAAGCCTTATAGGTTTGCTCAATTTATTCTATATCTTTGACCAGGGCTTGGCAAACTA
CTACCTGCAGGCCAAATTGGGCCTAGTGCCTGTTTTTGTAAATAAAGTGTTATTGGAACA
CAGCCATGCCCATTCATGTACCTATTGTCTTTGGCTGCTCTTGCCATATGATGGTAAGCT
GAGTATTGCAACAGAGAATATATGACCTGTAAAACTGAATATCTTTACAATCTGGCCCAT
TATATAAAAGGTTTGCTGACCACTAGCCTAGACCTTCTTTTGTTTCTGCCTTTTTGAACA
CTATTGAAAGATGGGTAGCCCCTTTACAACTTATGTTAAATTTACCTTTCTCTGAGGAAG
CTTTATTTTAATCATTCCAGTCAAGAGTGTTCTGTCTTCTGAATACCTACAGTGACACCT
CTTTACTGTTTCATAGCACTTTACTGTTTTGTAATTACCTTTTTTTTATATCTTTCTGTC
ATAAAGGACATAAACTTGAAACCAGGATTTTTTTTAACCTACTTAACCGTGTCTCTGTTT
TGAATTTTTAGTCCCTTTATCCATTTAACTATCTAAATATAGGTTGAGCATCCCTAATCT
GAAAGTCCAAAATCTAAAATGCACCAAAATCCTAAACTTTTTGAGCATGAACATGATGCC
ACAGGTGGAAAATTCCACACCTGATACCTTTGCTTTCTGATGTTTCAATGTTCACAAACC
TTGTTTCAAGCAATTATCAAAAATATTAGATAAAATTATCTTCTGGCTATGTATATGAGG
TATATGAAACATAAATGAATTTTGTGTTCAGACTTGAGACCCATCCCCTAGATCTCTCAT
TATGTATATGCAAATATTCTATCCAGAGAAATCCAAACACCCCTGGTTCCAAGAATTTTG
GATAATGGATACTCAACCTATGTATAGATAGATATGGATAGATTGTATGTAATAGACTAT
TACGTTATACATATATATTATATAGGTCCTATTATGTTGGTAAACTTAGACTTTTAAAGG
CTCACCATTTATCAATTACAATGCCAAGTGCTCTTTATACAAAATATTTTTAATAGTCAA
AACTACCAAATAAAAAGTAAAATATGACCTCCACTTTACAGATAAAGAAAGAAGGCTTAA
AAATGTTAAGAAATTTTTGTGAATTTAAGTGCTATTCATGGGGTTTAAATTTATGTCCAA
GTGAACTATGTTCTAAAGTCCAGTCTCTTAACTAAATGATCATATTCTCCCAGCAGACAG
TATAATGCCTATAACCCTAGTAGATCTCAGGAAGAGGCAAAGAAGTTTTACAAAATCAAA
TGGGGATATTTTAACTTTACAAAAGCAATAGTTGATTTAGGGTTCAGATCACAGTGGTCT
CTGTTTATGCAAATAATTTGAAATAGTAATGTATTCTCAAATTAGAAAATAATTTAACGT
GTTTATTGATTTTCATTGAACTAAATGTGAACAAATTCTATATTGACACAACTTGAGCAA
GAGTCCATGTTGGCCTTCGCAATTGGTACATTTTCCGTCTTCACTACATTCCCTCAGTTG
AGTTTTACCTTCCTTCTACTGTGGAATAATGGGAAAAGTGCATGGTGAAGTCATAAAGAC
AGAAATTCAAACTCTAGATCTGCTATTTATAGATTGTATGTTTCTTTGTGCAACTACTTT
AGTCTCTGTTAGATTCAGATTCATTATCCCTAAACAGTCAAAACTAAAACTAAACTATAA
GGATAGTTTTGGGATTTAAATAAGAGCATATATAAATTGCCCAGTAGTGTGCTTGACATG
CACTAAGAAATCAATAAGCTCCTGGAAATATTTAAGTAACAGCATAAATGTTTAACTGTT

FIG 4. (SEQ ID NO. 4) CONT.

AAGAAGATACCACAAGACACAATCTAATAAAGTTTTTAACTTTACAAAAATTAATGCAGG
CCAGAGAAGCAAGAGAGGTCATCAGGAGGGATGAGAATAGAACCAAGCCTCAAGTAAGAG
ATGTGGCAAAAATCTAGACATATTATCTTAACTGTCGATCTACGTACAGAGCTTATTGTG
TTTCTTCTATTTTTAAAATTAGAAGTATAAATTTTCATCCAACTGGTGTTATAGAACATC
TCATATTTAAAATATACTTTTATATGCTTTAGAATCTAGTGAAGTCTAGAAAAAATTAAT
TAGATATTAATGACTATTTGCTCATTCATTTTAAAAAATACTAAATATATTACCTACTTT
AAAATAGACAGTCATACGGGCAATAGCATGTGCAATAGCATAAAATTAAAAAATCAGAAT
TTATACCATAGGTTTCTTTGTCTGTTTTGTGCTGCTATAGCTACAGACTGGGTAATTTAT
AAAGAATAGAAGTGTATTTGGCTCACAGTTCTGGAGGCTGGGAAGTCTAAGGGCATGGGG
CCTGCTTTTGGTGAGTGCTTCCTGTGTGTTATTTCATGGCAGAAGGGCAGAAGGCATCAC
ATGGTGAGCAATCATGTGAGACAGAGAGAGGGAATCAGGCTGAACTCATTCTTTTATCAG
AAGCTCACTCCCTCAATAACTAACTCCCACTTCCGTGATAATGGCATTAATCCACTCATA
ATGATGGAACCCTGATGGTCTAATTCACCTCTTAAAGGCCCTACTTCTCAACATTGTTAC
AACACTGTTACAATGACTAATTTCAAGGAACATTTAAATGATAGCAAGTCTTTTTGAATG
GATCATTTAGTGAAACTGGACTAAAGGCCACACCATTTGCCTATCAACACATTACGCTTA
ATAATACACCATGGTCTTGGCATATACAAAACATCCAGATGAAAATTTATGTTTTTTATC
AATCTCATTTTATTTTTATTTGTGAATATTTATAGGAATAAATATTTGATTGAACCTTGA
TCCTTGCCATTATAAAACTAAAAAAGTTTATGGCAGCATGGCTTACTTTATTTTCCTATT
AAATTATTTGATTATTTCTACATCCACTGACAGCAACAAGGTTCCAAAAATAAAATTACA
CAATTCTCAAATCCAGTTTTCTACACTTTGTAAAACGTTAAGGTATTTTGATTATTTTGT
GAGTCCTGAATTTTCAAGTTTTAAGAATTCATGTATAAAACTTGATATTTATATTTTGAT
AAAGAGAATATATATTATCTACTGTAAAGGGCAATAATTATACCTAATAGTCACTTCTGG
CCCAATAACTATAGTTAATGCTATTTTCACACATGCCTGATTCTGTCGTGTGATTTGCCA
AGCATATTAAAAATCTGAGTGACACAAAGTATTTTATCAATACTGAAGCCATTTCTCAAC
CAAACCACTTCTCTATTCTTTCCCTGTTTTGCTATCATTTTATAAGACTTCTAATAGTTT
TAAATATAAGGTCCTCAACAGTTGATTATTTCACTAAAGTAGGATAAAAAATGCTGAAAT
ATTTGTTTTAAGCTGTGAGCATAATAGGAGAATGAACATACTACTGGCTGCAATATAGTT
TTTTCCCCTGCAGTTTATATTAGATATATGCTGTTGCTATGTTTATATAGACACAAAGCA
AACTGTAGAAACATGCAGCCAACTCCAACAAGGGTATCTATTTGTTGGTATAAAAGAAGA
AAACTTTTAAAGATATCTATTTCCATGCTATCTTTCAACTTTAAAAATTACGGACCATAG
CCAATTTCTGAACCTTCAAGCTTAGCTACTTCTTTCCTGGCTGATCTTTGGGACCTCACC
TTATACACAAAATCAGGAATATATGCAGACAACTGTACTCTTCAGAAAGAAGAGAGAAGC
TTTTCTCAGTGGAAACTCTTGCCCGTTAACCTATCTGGTTAGCATCAAAACATCCATGAA
GATGTCATACCTCTCCTGACAAGAAAGCAACAAAACCATATGAGGAATGACAAAGACAGA
ATTAATCACTAGAAAGGTCTTTGTATAAATAATCAGTCCTTGAGTTGTTCTGAGAAGCAG
ATACATGTCAAATACAGGTTTTGTCTTAAAAGAATACAATTTTCAACTGATCTTCTCTGG
TTTATTATGGTATACAGCAGAAAAATAATTTTTAGTTTCATTTAAAAGATATTCATTTGT
AATCCTGGCTACTAACCACAATATTAGAGCAAGTCCCCTGATTTATGCTTTTAGGCTCAT
TTATTTAAAGCCTTAGGGGTTTGTTTGGTGGCCTTGCACAACTTAAGAGTCCTAAAAACC
TTGTGAAGACTTCCTTGACATCACTGGACATCTCACGATAAAGACTGTCAATGTGATGTT
CACAGAAAATTTGAAATATTTATTAGCTAGACTAGTTGTATTCTTTCCAACATTGTTGTA
TGATCTTTCTTGTAACGTTTTCTTGCATTTCTACCTCAGTTTTTTAATTATAGTAAATAG
AAGTTACGATATTAAAACTATATGACATATCCCTATTTCTGCTTTCTGCTTTAGTTATAG
GATCATCGGTGGAAACTCTCAGTTCACGATCAACCCATCGACAGGACAAATCATCACCAG
CGCATTGTTAGATAGGGAAACAAAAGATAATTATACTTTGGTAGTGGTCTGCAGTGATGC
GGGATCCCCAGAGCCTCTTTCCAGTTCCACCAGTGTGCTTGTCACTGTGACTGATGTCAA
TGACAATCCACCAAGATTTCAGCATCACCCATATGTCACTCACATCCCATCTCCTACTCT
TCCAGGTAATCAACCAAATTCTGAGGCCACATGGATATAAACAAACTATGTATCAGACAT
TTCTATAAAAATATTTATGATATTTTACATACATATTTCTGATATAGCCTAATTTTGCAA
ATCCTCTAAAATTCAGGTTGTTTTGTCTGATGGAAATGAAAAAATGCTTGAAACTTGAAA
ATTAACCCTTTCTTGCTAGACTAATTGTGTATAATGTTTTATAATTGTTATGTATTATTA
TTTCTTAATATTACTTGAATATTATAAATAATTAACATATATATTACATCATCGTTAATG

FIG 4. (SEQ ID NO. 4) CONT.

ATGTTTATGGCCTGAGGTATAACTTTGTGTAAGTTTGCTAAGAGGAGGGGCATTGTCTCT
ATTTTGCATGCCATATGCCACTACCTGAAACATGATATGGGAGATAATAGGCATTCAACT
ATGTTTGTCAGTGGAAAATGAATATTTGACTTCAATTTTTCATAGATATGTTTTCAAAAA
GTTTAATAAATGGATAATTCTTGTTAATATTTATTTTATTCCAGGTTTTACAAATGAAAA
CTGTTCTGTTAGCAAGTTTATGGATCCATTTATGAATCATTTTCATATTGACAATATGCA
TTTATCCTTCTGTATCTCTTTAAATTTAGTTTGACATTTGCTAAGAAAGGCATACTCTAA
GAACTGCACAAATCTGCCATTTTAATTTTTAAAATGAGTTTTCAAAGAGGAAAATATAGA
AATATAGCTCATTATTGATTTAATCTTCCTTGCTCGGAAATATTTTTAATTATTAGAAGA
AAAACTTAACAGATAGAGTTAACAGATCCTCCTTTCAGTGATCTTTGATCTTCTATTAAT
CTGAGAATGATACCAATCTAAAATATAGGATTCATAAATTTATGTGCCAACTTTCTATCA
AAGGAAATGTCAGTATCAAAATGATAAATACCTGCTAAAGGTCTTCAGATGAAATGATGT
TGGCAGGCATGGTTCTAATTACATCCAATGTGTGGTGGTGCAAGATAAAATTTCCTATGT
AAAATGAGGTATGCTTAAGCATCTTTTCCTCATTGGACTTATAACCACTGGCCTTTTTAA
AATTAAAGATATTTTACTTTTGTTACCGTTTCTTCTGTAGGGGTGAGAGTGCAGGTTTGG
GAATGGTTTCTGAATGAGTAGATTGAAAATATGTCCTTATGGCAGCTTTTCTGCATATTT
TTACGACAATCTGTTTCATTGGCACTCAGTCTAAGCACTAACTTTTGGAGTCCAAGTTGA
GTCCATTATCCCTCAATTCTTATTTCTTACTACTTTACAATTATTTTAATTGGCTTATGT
ATATATCTGTGTATGTATATACACACACATATAAACATACACATATGCACTTTTTTTTCC
ATCTGATAATAGTTCACGTATAAAGGAATTTTGTCATAAAACAGTGGGGACAAGGAATAA
ATGGTAATGAACATGATTTTTGTTGACAAGATTACATATAAAGTGATTGGAAGATATTTT
AAGACACACTAGAGCAACGGTATCATTGCATTGGGTAGAGGCATAGCACTTTGCAGAGCT
CGCATATTATGTTTCTTGGAATGTTGTTTTATGTGCAGATTTTTCTCCTAGAAACTATGA
TTTTTGAACGATTAGCAAGTTCTTTTCCCTAGGCTTCTCTCAAAGGCATACTGAAAAGTA
TTAAATCCAACAGACTGTATAAATTTTAGTTAGAAAATGGCAGGTTAGTCTCTGAAGACA
ATCATAGAGCAGATTTGACTTGTGAACCTCGGAGAAAATATAGGAGATACTGTTCTCCCT
AGTAATCATGAGAAAATAAGGTCACATCAAGCAGCAATAGAGTGTCTTATATGCACTTAT
CTGCTACCAAATATTTTATTTAAATTCCACGTGAGTATAACTGCACACTTTCTCTTTTAT
AGGTTCCTTTGTCTTTGCGGTTACAGTCACAGATGCTGATATTGGACCAAATTCTGAACT
GCATTATTCTCTTTCGGGTAGAAATTCTGAAAAAATTTCACATTGACCCACTGAGGGGAGC
CATTATGGCCGCCGGACCACTAAACGGAGCTTCAGAAGTGACATTTTCTGTGCATGTAAA
AGATGGTGGCTCATTTCCAAAGACAGATTCTACAACAGTGACTGTTAGATTCGTGAATAA
GGCCGATTTCCCTAAAGTGAGAGCCAAAGAACAAACGTTCATGTTTCCTGAAAACCAACC
AGTCAGCTCTCTTGTCACCACCATCACAGGATCCTCTTTAAGAGGAGAACCTATGTCATA
TTATATCGCAAGTGGGAATCTTGGCAATACTTTCCAGATTGATCAGTTAACAGGGCAGGT
GTCTATTAGTCAACCTCTGGATTTTGAAAAGATACAAAAATATGTTGTATGGATAGAGGC
CAGAGACGGTGGTTTCCCTCCTTTCTCCTCTTACGAGAAACTTGATATAACAGTATTAGA
TGTCAATGATAATGCCCCAATTTTTAAGGAAGACCCATTTATATCTGAAATATTGGAAAA
CCTTTCCCCTCGAAAAATACTTACTGTTTCGGCAATGGACAAGGACAGTGGACCCAATGG
ACAGTTAGATTATGAAATTGTTAATGGCAACATGGAAAATAGTTTCAGTATCAATCATGC
TACTGGTGAAATTAGAAGCGTTAGACCTTTGGACAGGGAAAAAGTATCTCATTATGTCCT
AACCATAAAATCATCAGACAAAGGGTCCCCGTCTCAGAGTACTTCAGTAAAAGTCATGAT
TAACATTTTAGATGAAAATGATAATGCCCCTAGGTTTTCTCAGATATTTAGTGCCCATGT
TCCTGAAAATTCCCCCTTAGGATACACAGTTACCCGTGTCACAACTTCTGATGAAGACAT
TGGGATCAATGCAATTAGTAGATATTCTATAATGGATGCAAGTCTTCCATTTACAATTAA
TCCCAGCACAGGGGATATTGTCATAAGCAGACCTTTAAATAGGGAAGATACAGACCGTTA
CAGAATTCGAGTTTCCGCACATGATTCTGGGTGGACTGTAAGTACAGATGTCACAATATT
TGTGACAGACATCAATGACAATGCTCCAAGATTTAGCAGAACTTCCTATTATTTAGATTG
CCCTGAACTTACTGAGATTGGCTCCAAAGTAACTCAGGTATTTGCAACAGATCCTGATGA
GGGATCAAATGGACAAGTGTTTTATTTCATAAAATCCCAATCAGAATATTTCAGGATTAA
TGCCACCACTGGAGAGATTTTCAATAAACAGATCTTAAAATACCAAAATGTCACTGGCTT
CAGTAATGTGAATATCAACAGGCATAGTTTTATAGTGACATCTTCAGATCGAGGTAAACC
TTCCTTAATTAGTGAGACAACAGTTACCATCAATATAGTGGACAGTAATGACAATGCACC

FIG 4. (SEQ ID NO. 4) CONT.

TCAATTTCTTAAAAGTAAATATTTCACTCCAGTCACCAAAAATGTTAAGGTTGGTACGAA
GTTAATCAGAGTTACAGCAATAGATGACAAAGATTTTGGACTGAATTCAGAAGTGGAGTA
TTTCATTTCTAATGATAACCATTTAGGAAAATTTAAGTTGGACAATGATACGGGGTGGAT
TTCAGTAGCATCCTCCCTGATTTCTGACTTGAACCAAAACTTTTTTATCACAGTCACTGC
AAAGGATAAGGGAAACCCTCCACTTTCTTCCCAAGCAACTGTTCACATAACTGTCACTGA
GGAAAACTACCATACACCTGAATTCTCTCAAAGCCACATGAGTGCAACCATCCCTGAGAG
CCATAGCATTGGGTCCATTGTCAGAACTGTTTCTGCAAGAGATAGAGATGCAGCGATGAA
TGGCTTGATTAAGTACAGCATTTCTTCAGGAAATGAAGAAGGCATTTTTGCAATCAATTC
TTCTACAGGTATATTAACACTAGCCAAAGCTCTTGATTATGAGCTATGCCAGAAACACGA
AATGACGATTAGTGCTATAGATGGAGGATGGGTTGCAAGAACTGGTTACTGCAGTGTGAC
CGTAAATGTGATTGATGTGAATGATAATTCTCCAGTATTCCTCTCTGATGACTATTTCCC
TACTGTTTTGGAAAATGCCCCAAGTGGAACAACAGTTATCCACCTAAATGCAACAGATGC
TGACTCTGGAACAAATGCTGTGATTGCGTATACTGTACAGTCATCTGACAGTGACCTCTT
TGTCATTGACCCTAACACAGGAGTCATAACCACTCAAGGCTTCTTGGATTTTGAAACCAA
GCAGAGCTACCATCTTACTGTGAAAGCCTTCAATGTCCCCGATGAGGAAAGGTGTAGCTT
TGCCACTGTTAATATACAATTAAAAGGGACAAATGAATATGTGCCCCGTTTTGTTTCCAA
ACTTTACTATTTTGAAATCTCAGAAGCAGCTCCTAAAGGTACTATTGTTGGAGAAGTGTT
TGCTAGCGACCGTGATTTGGGCACTGATGGGGAGGTACACTATTTGATTTTTGGTAATAG
TCGAAAGAAGGGTTTCCAGATCAATAAGAAGACTGGACAGATTTATGTTTCTGGAATTCT
TGATCGAGAAAAAGAAGAAAGGGTGTCTTTGAAGGTATTGGCCAAGAACTTTGGCAGCAT
TAGAGGTGCAGATATAGATGAGGTCACTGTAAATGTCACCGTGCTTGATGCAAATGACCC
ACCCATTTTTACTCTAAACATCTACAGTGTGCAGATCAGTGAAGGGGTCCCAATAGGAAC
TCATGTGACCTTTGTCAGTGCCTTTGACTCAGACTCCATCCCCAGCTGGAGCAGGTTTTC
TTACTTCATCGGATCAGGGAATGAAAATGGTGCCTTTTCTATTAATCCGCAGACAGGACA
GATCACCGTTACTGCAGAATTAGATCGAGAAACCCTTCCCATCTATAATCTCTCAGTTTT
GGCTGTTGATTCAGGGACCCCCTCAGCTACAGGTAGTGCCTCTTTATTAGTCACCCTGGA
AGATATAAATGATAACGGGCCCATGCTGACTGTCAGTGAAGGAGAAGTCATGGAAAACAA
ACGGCCAGGCACTTTGGTGATGACCCTTCAGTCCACTGACCCTGATCTCCCTCCAAATCA
AGGTCCCTTTACTTATTACTTGCTGAGCACAGGTCCTGCCACCAGTTATTTCAGTCTGAG
CACTGCTGGAGTTCTGAGCACAACCAGAGAGATTGACAGAGAGCAGATTGCAGACTTCTA
TCTGTCTGTGGTTACCAAGGATTCTGGTGTTCCTCAAATGTCTTCCACAGGAACTGTGCA
TATCACAGTTATAGACCAAAATGACAATCCTTCACAGTCTCGGACGGTGGAGATATTTGT
TAATTATTATGGTAACTTGTTTCCCGGTGGGATTTTAGGCTCTGTGAAGCCACAGGATCC
AGATGTGTTAGACAGCTTCCACTGCTCCCTTACTTCAGGAGTTACCAGCCTCTTCAGTAT
TCCAGGGGGTACTTGTGATCTGAATTCCCAGCCAAGGTCCACAGATGGCACGTTTGATCT
GACTGTCCTTAGCAATGATGGAGTTCACAGCACAGTCACGAGCAACATCCGAGTTTTCTT
TGCTGGATTTTCCAATGCCACAGTGGATAACAGCATCTTACTTCGTCTCGGCGTACCAAC
AGTAAAGGACTTCTTGACCAACCACTATCTTCATTTTTTACGCATTGCCAGCTCACAGCT
GACAGGCTTAGGGACTGCTGTGCAACTGTACAGTGCATATGAAGAGAACAATAGAACGTT
TCTTTTGGCAGCTGTGAAGCGAAATCATAATCAGTATGTGAATCCCAGTGGCGTAGCCAC
CTTCTTTGAAAGCATCAAAGAGATCCTTCTCCGGCAGAGTGGAGTAAAGGTGGAATCTGT
GGATCATGACTCCTGTGTGCATGGCCCATGTCAGAATGGAGGGAGCTGTCTACGAAGATT
GGCTGTGAGCTCCGTATTAAAAAGCCGTGAGAGTCTTCCAGTCATCATCGTGGCAAATGA
ACCTCTGCAGCCTTTCTTATGCAAGTGTCTGCCAGGATATGCGGGTAGCTGGTGTGAAAT
AGATATAGATGAATGTCTTCCATCACCTTGCCACAGTGGTGGAACCTGTCACAATTTAGT
GGGAGGATTTTCATGCAGCTGCCCAGATGGCTTCACTGGTAGGGCGTGTGAGAGAGATAT
CAATGAGTGCCTGCAGAGTCCTTGCAAGAATGGTGCCATCTGCCAGAATTTTCCAGGAAG
CTTCAACTGTGTTTGCAAAACTGGATACACAGGTATGACAACGTTTGTACTTTTCTCACT
AAGACTTTAGCCATGTCAAGTATATTGAAACGAAATAATTTTATCATTTTCCAATGATTT
TCATATAAATGAGCATAATAGTAACAAATGTTTTTAAACATTTACTGTTGGTCAAATACT
GTTCTAAGCACTTTTTATGTATTTGTTTTGTTTACTTCTTACAAGAAAACTTATGAGGTA
GGAATATTTTCCAGTTTCTATAGGCAAGGAAGTTGAAGTAGAGAGTAAGTAATTAGGTTT

FIG 4. (SEQ ID NO. 4) CONT.

```
TCTCAGGTGATTCAGTTACTTTGCTGTAATGTCACTATTCAAGTCTACACAGTTAAATCC
AGAACTTAAGTGCTTAATCTCGTAGCGTCTCTTACAAGAGCAAAAAAGAGAATAATATCT
ACTTAAAAGAGTATTCTAGATATTAAAGGATAAAATATATACAAAACATAAGATTTGGAC
CATTTTGTGTGTTAAATAATTGTTAACAATGATTGTTGTTGATTCTTTATCATCATCGTT
TTTGTGACCTTTTAAAATCATAGTCGTCATTATTATCGAAATGTGATCCACATCGTGAGA
AGAGCGAGAATCATGTTTTCAGATTTAGATTAAAATGATGTGTTATTGGGCCAGGCAAGG
TGGCTCATGCCTGTAATCCCAGCACTTTGGAAGGCCAAGGCGGGCAGATCACGAGGCTGA
GAGATCGAGACCATCCTGGCCAACATGTGAAAACCCATCTCTACTAAAAATGCAAAAATT
AACTGGGCGCGGTGTTGTGCGCCTGTAGTCCCAGCTACTCGGGAGGCTGAGGCAGAAGAA
TCACTTAAATTCGGGAGGCAGAGGTTGCAGTGAGCCGAGATCGCGTCACTGCACTCCAGC
CTGGCAACAGAGCAAGACTCTGTCTTAAAAAAAAAAAAAAATGGTGTGTTATTCCTAAT
GGTTGGGTAGAAAGCACAATAGGCTTATTTCTCAAGAAAGCTAGAACACAACTGAGCCAC
AGCTTATCTTGACAGACTAGAAAGCAGCATTAAACATAGCAGTAAAAATTTTGAACTAGT
CTTTGGCACCCTAGTGGGATATGATGTCCATATATACATAGATCTCTACCTATTTCTACT
CCATGTCTATATCATTATTATCTATCAACCTATCTATTAGTTAATCAGTGGTTGATGTTC
CTTCAAATGTGAATAAATGTTATGCTATTGATAAGTTCGAGGAGAGCAAAATTCTATCTT
ATAACTTGCACATTATACATTTGTAAAGCATGCATATTACATTGAGTTACTCTGCAGTAT
TTATAAACATAATTTACAGTACTAGTAGTATAGGTAGAATCAAGATAGATTGCTTTAACT
TTTGTAGATGTATTACAGAATAATATTTTAAGCAAATGCATTTCTATGTTATATTTTCAA
AAGTGTCCATTATGTGTATACTGATGGTTTTATATTTGGAGAATTGAATCACTTGAGGAA
AATATAGAGCAAGTTTGAAAATGTTGAAACAGAACATGCAGTCTTTGCCTTCTAATGAAA
TAACTTTGAAATGTAAATGAAGAAAAAGTGGCAGAAAACATGTGTAATAGAAAAAGTGAT
AGATTTCACAGAATCTGATTTAGCTATAGCTTTTGGGAAGTCACCTAACCTTAGCTGATT
CTTCATTTCTCTGTCCACAAAATGGGAATAATCATAAGTACTTTCAGGGTTTTTGTAATG
AGTAAATATAATGTTTGTAAAACACCTAGTACAGGCCAGGTGCAGTGGCTCACGCCTGTA
ATCCCAGGACTTTGGGAGGCTGAGGCAGGTGGATCACCTGAGGTCAGGAGTTCAAGACCA
GCCTGTCCAACATGGTGAAACCCATCTCTACTAAAAATACAAAAATTAGCTGGGCGTGGT
GGCAGGTGCCTGTAATCTCAGCTACTCAGGAGACTGAGGCAGAGGAATTGCTGGAACCCG
GGAGATGGAGGTTGCAGTGAGCTGAGGTCGCGCCATTGCACTCCAGCCCAGGCCGACAAC
AGTAAGACTCCATTTCAAAACAAACAAACAAAACCCACGTGGTACACTGTGCAGTATTCA
GTAATTGCAGTCTAATTAGTAGTAGTAATAATGGTATTAGTATAGTGGTAGTAATAGAGG
AGTACCACAGAATTTTTAAAAAGACATGAAACCTGTGTAGCGGAAGTTAACTGTGAGTCT
TATGAGAGTTATTTATATGCTAAGATCATGAATAATAGAGCTATATACATGCTGAGGTCA
GGATTTCTAGAACACTTCCCTCACTCTTTCTTACCCATCCCCAAAATTACTTTATCGGCT
GGGAATTCAACAATAAGAGTTTTTATATTCTACATTAGTCTAATGCATTTATTCACACTT
AGGTTTAGATTGAGTTTACATTTAGTCCTAGAATGAAGAAAGTGCAAATGTATTAGGTAT
GGATAAGAAACATGGAAAGTACTACTGGTGTGAACAAAGGCACCATTTGCTGATTTTAGC
ATAAATGATGAGTAAGTTACTTCTGTCTGGCTTGTTTATTTCTTTGTTTCATTTCATTTA
AATATACATTGCATACTTTTCTAAACGTGATAGTTGAAACTCTTAAAAATGCCTTTCCTT
ACATCATAAAATATTAATAACATTTATCAAGCAGTTATGTAAAGCACTTTTTAAATCTCC
TTGCATTATAGACATTATTACATTTAGTTCTTACAACTCTGTAAGATGGATATTATGATT
ATTGTTCCAATTTTGAAGACCAAAAAATTAAGTCTTCGAGTCATTAAAAGAGATTAGACA
ACTTGCCTCCAGCCATGGCACAGAAAGTGTTCTAACTAGTTTTTTTACTAGAAACTTGGCT
CTGGTGCCTCTGCTATTTATATACATGTCGCACTCATCACACTTTGATTTGCACTTGCTA
TGGAGTGTTATGGTGAGTTCTATGGTGATATTATTTAAGAATGTTTTGTCCATCATTCTA
TTAATACTTAATCCTCACAGAAAGCCTATAAGACAGTGTATTGTCTGAGACTGATCAGAA
ATCGGAACTACTCTCAGACTTTGAGGCAGGAAAGTATTTGCTACAAGGAAACAGCTTACA
AAATCTTCAAACTGGCTAAGAATACAGGTCAGGAACATTCACCAATGGGCGCAGCAATAA
AGACATGGCAGGCATTGCAAGACACCGCTGCTGATCCTCTTGCCCACCTGCAGTGCTGCA
CCAAGTGATCTGAGGAGAATGGTTCCTGCTTTGCTTTTACCATTCAGATATCATCACAGT
CTTTTTTGCTGGCAGAATATAAACTTGAACCCCGCTGGAAGGGAGTCTGGAAAAGGTAGT
TTTCAGACTTCCAGCCCTTGCAATATGGAAAGGTAGGAACGATGCTGAATGTCAGCAGAT
```

FIG 4. (SEQ ID NO. 4) CONT.

GATATGTGGCTCAGGAAGATGTTATTATTCTTCCTGTTTTACACTGTAGGAAATTGAGCC
TACAGTCTGGTGACTCCAGGGCCAGAGCTGCCAAAGTCTATATCATAAACTCTTTCTAGG
GAAGGTTGTTTGAAGTTATACATTAACGTTACATACTTCTCCTCAGAGTTCACTTCAGTC
TTCATTTGCATAGTAGGAGATAATCCAACTGATCAGGAATGATATAAACAAACATAAAAT
TGAATGATTAAGATGAATCTTACATTTTTTAAATCAAGTTTCAAATTCTGTATGAAAAAA
ACCATCCAGTAAAACTGGCAGATAATTAATGTCTGACAGTTTTATTTCCTTTTTGTATTT
TGTAGGAAACAATATGAAAAAAGCATAGTGAGTGGCAAATGTTAATCCATACTTTAAATT
AGAAATGTATTGCTTAAATTTCTATAGTTTGTTAATTTTTTTTGTAGAGGTAATCTCTGA
AGGATCATTCTGAGTTATTCTTTTTACCTAGTCTCTGCCAGATAGCCTGGCTCAGGAAGA
CAGAGCTAATATACCAAAACATCTTAACATCTAACCTAGTCAGAGCTAATAAACCATAAG
ACAAAATTTACACATAACTGTATGTGTGCCTCATAGAATGATTTTTTAAAAAATTACTCA
TAATAGCTAGATTTTACTTCAGTTAACATGAATTAAATTGTAGTGCCTTAGTAAAGCTTC
ACTTCTTCAAGGTCTGTATATAATTTTTGGCCATCAGAATTATTTTAAATTACTGTATTT
TTCATACTCTACTTTTGTGGGCTTCCACCTGCATTTTATCAATAGGTTTCAAAGTCTGTG
AAATTACAAATTGGAGCTGCACAATTTTCTGAACTTTCTGCTTAAAATAATCCTCAGCCA
CTACCCATACCCAGTTTCTCTCATACACACACACACACACACACACACACACACACACCA
CTGAGTATTTTATGTGGATTTAGAAATTGTGTTAAGGATTAGAAGAGTAAGTGGCTTATG
AGTTGATGCAAACTAAGAGACTTTATCCCCAGAATCCCCTAGGGTGTGATTAAATGTTAG
CTGAATGGAGATTTTATGTAGAGAACAACTTATAAGGACGCAAGTATGAAAATGATAATC
ATGGAACAAAAAATAGGAAGGGATATAGTTATTATCATACTGTCACAAGTTTATTTCTGA
AATATTCTTAAAGTTTATTTTCAAGTCTGTAACCATGCACATAAGTATAAAACAACTATA
TTTTTTAATGAATGAGTGATTTAGAGGGAATGAATTTGTATAACATGTATTTCTTATCTC
TTTTCCTTAGTTACTGGAAAAAGAACCAAAAGAAAATTGAAAAAAAGTAACATATTCAGT
TATAATCACTTCATATGTTTCATTATTAAGAAAATTTTCTTATAATTTTTATATTAATAT
CACCATATGAAGCTTTGATTAACTGTAACATAAATTATTAGAAAAGATGGATAAAGTTTA
TTATAGTATAGGCCATGTGAAAAATTAATTTCTAAATTTTCACAAAATGTAATGACACCA
AAAATTAACATCAGTTGTCAGTATGCCTCAGTGAATAAAAACTATTATTCCTGCCACATA
AGTCTAGGGGTTCCTAGAGGAAAACTTTAGCCTAATAACGACACATGTAGTATTTATTTT
CATATACAAATGAAAATGTCTTGCACTTAATAGAACACTAATTAGAAAGTACAGTAATAG
TAACCACATCAACATTTGTCTACTGCTGCCAGGTTTTCGCTGTTTGCATCACATTCCTGG
CATTAAATCCTTCATGGGAATGGATGGTGTTATAAAATGCAGCATTTTGATAGAGCTTAT
TTATAAATCTGGCTATCTTATAACATAATTAGTTCATAGTCTCTTTAACCTTTTCCATTC
ACTTTCACACATCTGGATGCATTTCAGGTGTAGTATTTGGAATAATGCCGGGGGTTTATT
ACCTTATGGAGAAGTTTTCCTATGTTCTCAATTAAGTCCCGATATTTCAGGAAAGATGAG
GTTTGTTCATTCATCACTTTTATGTCATTTGACAGTATAAACAGTAAAATTTTTTCAGAC
ATACCAACTTATATACAGAATATGCATAGTAATTTTACTGAGAAACTTGCCAGATATTTG
CTTTCATAAAGATGGAAAGAGTTACTAAGAGTGATTCTTTTAAAATTACTACGGTCATGT
ATTGGTGTTGTTGATGATCATGTGACCGGAAAACCATATAATATAAAAGAAATTTAGTAA
ATATATATGAAATTAAATTTTGTTTGAGATAAAGAAGAGTGGCTCATGTAAGAGACAATA
AAGAGTGCAATTATTTTTATTTAATTTGATTCCTGAAAGCAGAATTAGGCAGTTTACATT
AGGTAATACATTAACTTATAAAAGCATTAATAACGTATGTTTCTAAGAAGTAGCTTAAAT
GCTTATTTCTGTAGAAAATAAGCATATATTTATAAGCTTATGAACATTATGTGTGTAATC
ATATGTAATCATTTGTAGTCTCATTGAGGTTGTGTTTGTGCTTGTTTTACAAGACAAAGG
TAAAAACTTTTTTTGGTTGTTGCTTTTGTTACTGGCAGCCCTTATTAAAACATGGTATTT
TTGCTTTTGTTTCAATGCAAAAAAGCCATAAGGCTATTGAACAGGATACTTAGACTATCT
TCATAGCTCCTTAACAATAATGGGAAACATTTGCATACTGTGCAAAAGACAGCTACTTTT
TGCTAAAATAATTTGGAAAATATATAAGATAAATGCCTAGAATGAATAGCATATATTTAT
TATAGAATTTCTTTATTAATAACATAATCAATTTAGACCTAAAATGGATTTTTAGAGTTG
CACATATTCTCCCATCTCCTCTGTGTAGAAATACAGGAGATTTAAAAATAATATTTATGG
TAGTCTAATATGTATATATAATCTAAGATCTTAAATTGAAGGCTACATGTATCATAGGGT
ATCAAAAATTATCGTATCTTCATGGAGTGGTCCAATTTAGCAGTTGAGAATAAATTTAGC
TCTATTTCACATAATCCAACATTAAAATGTGCTTGGACAAGTGAAACTTGAATATACATT

FIG 4. (SEQ ID NO. 4) CONT.

CTTGTTGAAAAGACCATAGGTGATTACAATAGATTCAGTTTATGTTCAACACGTCATCAC
ATCTTCTGCCCCCAAACATGAAAATAGACACAAAATTTCTCCTGTAAGTTTAGGAAAGTC
TGCGGATACCATGGATTCCTATTATGCATTTATTTTCACCTTAAGCTATTCCCACTTTCC
ATGTGCTAAGAATTTACACTTCTTCAAGCACATCTCCTTCTAGTTATGATAAATAGTGTA
TGGCAACACAATTAATTGATGGATGTCAAAGCAATGAGATCAATTTATTCTTCTAAACAG
CTGCTATGGCAGTAAACATATCTTAATGGAAGGAGGCCTCTTGAGTTCAAGAGGAATAAA
TGCCTGTCTTTGTGCAAGTCCTATCAGCATACTTCCAAGCCTGAAGGCGTTTGGCAAGTA
TTGTTAATTGACTTGTAGCATTAATTAAGTTAATGATCCAAGATTTTGTTTCACAGTGCT
TCAACACATCAGATTATTGTACCAAGAGCATGTTAGAGTAATTCAAACTACTGCATTCTC
TGATACTCATTATGCTATTAACACTACAATTTAAGTAGATAGACTTGCACAAAACAATTC
AGAATTTTGTTAATTTCTAATTGGGTAAAAAAGCATAAACTTTCCAAACCTGAGAAATAT
GCATTTAGAAGCTTTCTTTTGATTCTAAGTAAAATTATGGAATCCTTTTCTCACACAAAA
GACACAGGTGTTTTAAATAATAATTTAAATTTAAATCTGTTTTCCTACTATGTCTTTGAA
TTCAAGTATCTGCTATGGCAACCTCTGAGTTCATGAATTGTAAAAAATTTTTACTCTTTA
AATGGAGAACTCAATTTTTAAATAGTAAATAATTTACATACTCTACCACCAACAGATAAG
ACTATTTTTTCCAAACTCAACAACAAATTCCTTTATTTAACCCCAAACAAAGCCATTTTA
TCTATTTTTTTAACTTATATTTTAGGTTCTGGGTACATGTGAAGGTTTGGTACATAGGTA
AACTCATGTCACAGGGTTCGTTATACAGATTATTTCATCAACTAGGAATTAAGCCCAATA
CCAAATAGTGATCTTTCCTGCTCCCCTCCCTCCTCCCACCCTCCACCCTCCAGTAGACCC
CAGTGTCTGTTGTTTCCTTCTCTGTGTCCATGTGTTCTCATCATTTAGCTCCCACTTATA
AGTGAGAACAGGTGGTATTTGGTTTTCTGTTCCTATGTTAGTTTGCTGAGGATAATAGCC
TCCAGCTCCATCCATGTTCCCACAAAAGACATAATCTTGTTCTTTTTTATGACTGCATAG
TATTCCATGATGTGTATGTACCACATTTTCTTTATCCAATCTGTCATTTATCAGCATTTA
GGTTAATTCCATGTCTTTGCTATTGTGAATAGTGCTGCATTGCACATTCATTTGTATGTG
TCTGTATGGTAAAATGATTTATATTCCTCTGGGTATATACCCAGTAATGGGATTGTTGGG
TCAAACAGTAGTTCTGCTTTTAGCTCTTGAGGAATAGCCATTATTAATTATTTGTAATTA
TCCACTAAGACAAAGTAAAAAGGAACAACCTTATTTTTAAACTGAAATACTGAATGCAAG
GTTGAATTTGTTTTTTCTTAACAATTTCTATTTCTATTTGTGTATACTTGAAGAATCAGA
TTCTATTGAGAATTTAAGTTTTATAGGAAATTCGTTCTCAAAATTAGTATTTTATTGGTT
TGTAACATCTTCTGCCACTTTGTAATCACTGTATGTTTTAATAAATGAATAAGTCTTATT
TGTGTTAGGATATATTTCCACTCCTCACTCTGGAGTAACTGCAATAGCCTGTATTTTATA
TTTAAATTAAACTCAGATGTCTATGTTAAAATATTTTATACAGGGTTAAATAAGAATTGA
TTCATATAATTATACACAAAAAGAACAACACGTAAATTTCATTTGTTGCTATTTAACTCA
AGATTTATAAAGGTAGTATTTGTAAATGAAATTCAAAAAACATATAGTAGCTTTATAGGA
ACAATGACTTGGGATTTATACTCATATATTTTTGTCAGAGAGCACATATGTCCAATTATT
TGAGTAAGTATACATAGCAGTACCCTCTACATTTGTTACTTCTTATTTGTTCCTCATTTC
CAGTCGTTAAGAAGTGAAGGTGGCAATTTTGTAACCCACTAACATGTTTTCATGATAACA
AGGCTATATTGAACACACTTATAAATACATATATAAGTCTATGTATTTTATACATGTTAC
TTTTAACACAACTCTAAAATAATTTTTTGGATAAAGAAAGGAATGAAAGAAAGTAAAACT
GTACCTAGTCAAAAAGCACAAGTGAAAATTATGTGTGCTTTTACAGTGAAAACCAAATGG
AAAGAGTAGAATATTACTTTATTGATGACAACTAATCAAAAATATGGCCAGTAGACCTTA
TGTATTTGCAACTGGGAAATACTGTGCTGTAAGAAAAAAAAATCTACATCACTAAAATGG
CCTTCACATAATCAGTTGAAAAACAAAACAGGAAAGAGTTCTGTGAAACCGCAACTCTCT
GGTGAGAAATCAAGCACTATTTGAAGTTTTCCTGCCTATTTCTCCAATGTAGTACACTGC
TACAATACTTAAAACCTGATTTCTGTGCCCATAAATTTGTAACTTGTTTATTTTCATGCC
CTTGCCTTAACAATACAAAGGTATTCTGAAATTGTTAGCTCAATGTTTTGCCTTATAAGG
AGGTTCCCAATTTATTTATAAGGGAAAAAATGTTGTGTTTATGATTCTGTGATGTACAGA
AATGGGCTTAGTTAGCATCATGAGATCTGACTCACACTTATAATTTCAGACCAGAATAAG
TGTGGCTCCGTAATCAAGCCACAAAAACAGAACCAATTTAAACAAAATTTTGACTGTGTT
TTAAGCAAAGTTAGTATGATGAAATGAAGTATCTATGCTCAGCAGTAGGTCTCGTTGTGC
ATATAGAATGCATATCATTTCCTGAGCTATCTAATAAATGCATTAGTGAAATTGGGCTGG
GAAGTAGAAAGTAACTTCCAGAAACAAATGATGTAGTATTTACAATCCTACTCTCAATGA

FIG 4. (SEQ ID NO. 4) CONT.

AAAGAAATTAACTAAGAATTCTGTAACATCTCACTGCATTATGAAATTTGAAAATTAGAT
CCTAACGAATGTATCAAATGATTGCAATACTTTAAAGTTATAGAACAGTGGTATTAGAAC
ATGTTTAAGTTTAGGTAAAAATAAGTAACAACAACAAAAACAAGTGGGACTTATACTCCA
AGTTTTATACACCACGTGATCAACTACCATAGTTTTGTGAAACCTGGATATGGGAGCAGA
AGCCCTAAATTGGTCTGTGTCATAGTTTTACAGTTTCACAGACAATATATTAGCCTCCAA
GAGGCTTTTATTCTTCACTTTTGAAATGTAAATATTTCCTTTGTATGGATTAATACTCCC
TACTGAAATGGAAACACAGTCTGAAGACACTTGTTTGCTTTCTTCACTGCCATATCCCCC
TCCATTATCATGTCTGGCCCATAATAAGCACTCACTCAATATTAGTTGATTCAATTTAAC
AAGATCATGTATGAGAAAAGTCTTTATAAACTGAAAAATATGCTGTTTAGGTATTATCGC
TTCAGACAAAAGACAAAGTATACATAATCTGTAGTCAAGAATAAATTTTCATAAGCATTT
GAAAATATGATGTGTTTTCTTATTTCTTATTCTGCTTTACAACAGATATGTGTAATTCAA
GTGATATTTCTTAGTAGTAGAAAGAGTGTAGTTTGATAAATAAGATAAGTTATTATCTTT
GAAATACCTAAGTCAAGAAAATCTCTGCAGTGAAAAGAATACTGTAAGTTTCAACTTTCT
ATCTATAAAATATAAAAGATGAAGGGACATTGACACAGAAAATAAATTCAGTGAAAGCAT
TTAAATATGTTTATCATGTCATTTCTCTGCAAACAGTATTTTCTTCCAAGATGATTATGT
AAATTATTTCCTAAGTATTATAATGCACATTTTACAATAGGACAACTAAACAAGATTTTA
AATTCTAAGATATTATTCTAATTTCCTTATGTCAAGTAAAACGTTTTTATATTTCTTTTC
TCCGTGATATGCCTTAGGAAAGATTTTTACGTATGGTAATGGTGTAACGGTGTTAATATA
TTTATGTATGAGATTTAAAAAAAACTGAATTTGATATATTTTAGGGAAAATGTGTGAATC
TTCAGTCAATTACTGTGAATGCAACCCCTGCTTTAATGGTGGTTCCTGCCAAAGTGGTGT
GGATTCTTATTATTGTCATTGTCCATTTGGTGAGTAAAACTTATTTGTTGATATAAAATA
TAAGTTTATTTTTGCACACAGTTTAGCAATTTTGTTTTATTATGAGTATGAAAGACCAAA
AAATTATTGTTTTACATGGAAGGTTTTATTAAAATAAAATCTTAAATGTTTAACATTTGT
AAAAGTTATGGAAATCCCATTGAATACATTGCATTGGTCATTACTAGAAAAAGAGTCAAC
TCAAGATAATTGAATTAATATTGTTTCCATAGGATATTTCCCCCCAAAGATTTATGGATA
TCTTCTTTTCAGCTGAGAAGTTATGAAATAAAAAAATTCTGTAAGCACTCTTTCACGTCA
CTCTCTATTTCAAATCTTTAAGAGTAGTCAAAGTAAGGTTTTTTGTTTGTTTCACTTTTG
TGAATTTTGCTTTATTTTTTATTTTTGTTTTTTACATTAGTTTTTAATTTTGTTTTTTAT
GTTAATTCAGCCACTTTTATTAGAAGGACTTAGTAACTATACCTGACGTTTTCATAATAG
GCTTTTTGTAGCTGATACTACCTGACTAATAAAATTTCAGACTAATCTGTCTTTTGGATA
AGAAAAATTGTTAAAAAGAACTTTTTTGTATACATACATATTTATTCACCCTAGTGGAAT
GAACTAAAAGATTCCTTCCAGGTCTTATCCAGCTGTTACCCATTACTGTGCCAGCCAAAA
ACCATGAGATTCAGAGGAAGCATTTGTATTAGCTTGGCTTGTTTCATAAGTTTGTGATTA
TTCCATTCTTTTTAAAGGCTGCTTTACACCACAGCATAGAATCCATCTCCAAATGACTCT
GTCTCTTTTCTTTTTTTTTTTGTCCCCTTTGTATATCTATTTATTTATTTTTTTATTATA
CTTTAAGTTCTAGGGTAATGTGCACAACGTGCAGGTTTGTTACATATGTATACATGTGCC
ATGTTGGTTTGCTGCACCCATCAACTCGTCATTTACATTAGGTATTTCTCCTAATGCTAT
CCCTCCCCCCTTCCCCACCCCATGACAGGTCACGGTGTGTGAAGATCCCCTTCCTGTGTC
CAAGTGTTCTCATTGTTCAATTCCCACCTATGAGTGAGAACATGCGGTGTTTGGTTTTTT
GTCCTTGCGATAGTTTGCTGAGAATGATGGTTTCCAGCTTCATCTATGTCTCTTTTCTTA
AGCAAGAAAGAGCAAGGATATTTTTCTAGTCTTCCTTTGGGCATATAACTGTGCTATATG
GACCTGAACAGTAAAGCTCAATCTATAGTAGATAATAGAATTTAAAAGACATACGCAGTT
CCTAATAACCTGTATAATTTACTAGGTATTTTTAATTTCCAAACAACTTCATGACTATCT
GTTTTTATTAAGCACATCCATAGAATGATAAAGACAAACAAAATAGAAAAATATCTAATT
TTGAGGAATGTATTTTACCAATGGTTTTGAGGCCCAGAAATTGGCTGATTTGCCCAAAGT
CAAAAAATGAAGTTGAGGCAAAACTACCCCAAGACGATGTAGCAACTAGAACACAATTTT
TTATTTTCAGTCCAGTATGACATTCACAGAACCCCTTTTTATACAATTTCTTTGAAATTC
TAACAATGCCTGTGAAGTAATGAAAGGTATATCAAGGTCAAAATAACCACAACTTGAGAT
GTCCAAAAACTTTTTCTTTCTTTCAATGGTGTCTCATCATTTTAAGTGGTGCTGCTTTCT
ACAGATAACCACAGTCAAATTTCATGGTTTAACTTAACATTTTGAGATAAAAGATAAGGG
GATTAGAGTGTAAACTAGAAATGATTTTCAAGTGACTGAACAGAGATGTTCATATTTTTA
GGGATCCCTTTGCAAATTTTAAGGATTTAAGTTTTGAGGATTTTGAGTTGCAAATTTGGG

FIG 4. (SEQ ID NO. 4) CONT.

GATTTAAGAAAATTGATACACAATAAAAACAAGTTGCTGCTGCAGTGTAGTGGTACAACT
GTCGTTGCCTATTAAGTGGAACTACTTGAGGGGCCAAATGTACCTTCTTGTCACTCTGTA
GACATCGCCAGGGGAAGAGGAATAGCACAATGTAAATTAAAATAGACACAAATCACACAT
AGCCGGCAGTGCAAATTTCTCCCCCTATTCCTTCCAGGGGCAAAGACAAAAAACATTATC
TAAACTTAGATATTGTCAGTTGACAACATAAGCACTTACAAAAGAAAACAAAAATCACTG
AAACACTGCTATGTAATTTGAAACTAAAGAGATAGAAGCAGAAACAAAAATGATTTTTGT
TCTCAAATGGAATGTGGATGAAAGGTACAAATAACCATGTCAGATGGCATGCCTCAAATA
AATAGCCAGAGGTAGGTAGTTACACTTGCATCCTTTAAAACAAAACTTTATCATTTTGAA
GTTAGAAAAAAGTTTTTTGCACTGTTTAGCTTCTCATCAATAAAAGATTGGCTATTTGGA
TTTCAAAAAAATTTTTTCGATACTTAGATTTTTTAATTTAAATTACATCTTAGGAAAAACA
TAGTGCTTCAGACATTATAAAGGCGACATGTATAATTATAACTTCTTAGAATTAAGATGC
GACCTTTCTGTGAAAACAGTACCAAAACCTTTTAAGAATAAATATTTTAAATTCCATAAA
GAAATATTTTCATGTTTGAAAATACAGTATCAATTTGAATTAAAATGTAAGTATCTATAT
ACTTTCTCCATATATTTACACTCAAATATTCAGCACATTGTTATAGATTTATTGAAGTTT
ATTCAGAAGAGACCTAAGTGAACACATAATACAAATTTTTTCAGTAGTATTTTTATTTCA
TTTATATGCTTTATTTTTCCTTTTACTTTAACTTCACTTACTCTTTCTGCATAGATAGCA
TATTTATATACAAATTATTAATACATACAAATTATAAATATTAAATATAGATGCCACAGA
AATGTATAAAATACAAATACAAATTCTACAGGATAGATATAAGTATATAATGTATAAGAT
TATACTATGTATAAAATATTATCTCTATATATCATATATATGACATAACATATATATCAA
TAAATATCATTTCTATAATTCCTTTGCCTTTTCTTCAACTTTGGTTAAAGATTAAAAATT
AAAAATTATGTATAATTTCTTTTTTTTTTTTTTTGAGACGGAGTCTCGCTCTGTCGCCCA
GGCTGGAGTGCAGTGGCATGTTCTAGGCTCACTGCAAGCTCAGCCTCCCAGGTTCACGCC
ATTCTCCTGCCTCAGCCTCCCGAGTAGCTGTGACTGCAGGTGCCTGCCACCATGCCCGGC
TAATTTTTTTTTGTATTTTTAGTAGAAACGGGGTTTCACCGTGTTAGCCAGGATGGTCTT
GATCTCCTGACCTCGTGATCCGCCCACCTCGGCCTCCCAAAGTGCTGGGATTACAGGCGT
GAGCCACCATGCCTGGCCAAAATGATGTTTAATTTCTACTCATTTATAATAAATATTATT
TCAGTCTGGACAGAAAAGGAAAAGATAAATAACACAAACTTTTATAGCAACTTCTAGGCT
GTTTTAATTTTAAAAATGTTCTGATATAACATGTGGTAGTCAAAATAGCTAGACAATCAG
TAGATCTGGCCTCAAATTTTGGCTGTTTCTCTTGGTTCTGTGACCTTAGGCAAGTTTTAA
ATACTCTATAAAATAATGGCATTGGTTCCTTCTAGCTGAACAATTCTCTCACTCTAAATT
TTATGCATTTATGGGACATATAAAGCCAAAATTAAGAAATGAAACTTTTGCAAGTTAATA
AGAATCATGAGGTATTGGCATGGGTTAATTTTCCAATCATTTGCCACAGTCTACTAATAT
TTGTGGGAAAAGAATTTTGGCATAACATTGTAACATCAATAAAACTCATTTTTCAAGTTT
GAAAAAGAACCAGCACAAACAAATGGGAATGCTGACTTTCAGAAAAACAGACAGCTATTT
TAAAGTAGCCTGCTATAAATCATACCCACAGAGGGTATAAAACAAGAAAGAGATAAAAAC
TTAAAAGACAGTTATTTCCTTTCCTAAACCAATGATTCCACTTGTCAGATTTTGTGGCCC
TTGAAAATAACATGAATATAGGTACTGATTTTAAAAAAATCAAAACAAATGCATTTGCCA
TCTTCAATTGAGTTGAAATAGTTTTTAAGAACTATATATTATGAAGGAAGTATGTTGGCT
GAAAATTGTAGCATAATACAACTTTTAAAAGATCAACAAATTTGGGCCGCTTGCGGTAGC
TCATGCCTGTAATCCCAACACTTTGGGAGGCTGAGGCAGGCGGATCACCTGAGGTCAGGA
GTTCAAGACCAGCCTGACCAACAAGGTGAAATCTCGTCTCTATTAAAAATACAAAATTAG
CCAGGCATGGTTCCCGGCACCTATAATCCCAGCTTCTCGGGAAGCTGAGACAAGAGAATC
GCTTGAACCCAGTAGGCAGAGGTTGCAGTGAGCAGGCACTCTAGTCTAGGCAACAAGAGC
AAAACTCTGTCCCAAAATAAAAAAAATAAAAAAAAAATCAATGAATTTTGAAACGTTTCT
GGGAAAGAAATCTCTTCAGACATACTCCATTCCACTAAGCCTTTCATTTTGAGAAACAAA
ACATACTTAGATATGTTCCCTAATTAGACAATGAAAAATAATTACATCAGTTAATCATTT
CTGCCATGTTTTAAAGATCATTCATTCATAAAGATCATTAACTATTTTAATTTTAGTTTA
GATGAAATTTTTTGGAAAGTAAAAAAAGTTGTTAAAAGATATCTCATTTTATAATTCAAA
AATATTTTAATCAAAATATATAATAAAATTTTCATGAAATTTTATGCCAGTTTGTCAATT
TTCCCTCCAACAGGTGTCTTTGGAAAACACTGCGAGTTGAACAGTTATGGATTTGAGGAG
TTATCATACATGGAATTTCCAAGCTTGGACCCCAATAACAACTATATTTATGTCAAATTT
GCCACGATTAAAAGTCATGCCTTATTGCTTTACAACTATGACAACCAGACAGGCGACCGG

FIG 4. (SEQ ID NO. 4) CONT.

GCTGAGTTTTTGGCCCTTGAAATTGCCGAAGAAAGACTAAGATTCTCTTATAATTTAGGC
AGTGGTACATATAAGCTCACCACCATGAAGAAGGTGTCAGATGGACATTTTCACACTGTG
ATTGCCAGGAGAGCAGGAATGGTAAGATATTTCATTTTATTGTTGTTGTATATCCAACTG
GATCTTCAAATAAAGTATGAATTGGGGTGCAAATCATGTTAAATTAGGTTTATTCATTAA
ATGAACACTTTAGTTATGAAAAACTTAGACATAATATTTTTCTTTTGCTCATGACAACTC
TGTTCAAAAACAATAAAAAGGAGAACAATTGAGAATATAGCCTAGTGCGTGAAATAATTT
CATTGATATTTTTTGTATGTTTTTAAGGCCATGTCAGGACTATACTTAAAATAACTACCT
TTCTTTCCTAAGTATTTCTGCCTTGACTAAGTATTTCTGCCTTGACTGAAGAAACAATTT
AGGAACAGAGGAGACTTTTCTACAAAATCTACATAAAATAACTTAATCAAAAACACTTTA
TTGTTAAAAAATGGTAACAATAGTCTTAGCTAGTCATAGTCTTTTTGCTGGTGGAGGGTC
TTGCCTTGATATTGGTGGCTCCTGACTGAGCCAGGTAGTAGTGGCTGAAGATTCGTGGTG
GGGGCTATGGAAATGTCTTAAAATAAAACAACAGGAAACGTTGTCACATTGATTAACTCC
TTTTTCATGAAAGATTTCTCTGTAGCATTTGAGGCTATTTGATTGATACCATTTTACCCA
CAGATGAAATTGTTTCAAACTTGAAGTCAAGCCTCTCTCAAACCTTGATGCTAATTTATT
AATTAAGCCTATGGAATATTCTAAATCCTCTGTTGTCATTTCAACAATGTTCACAGCATC
TTCACCTGGAGTAAGTTGTATCTTAATAAACCGCTTCCTTTGTTTATCCCTAAGAAGCAG
CTTCTCATCCTTTCATGTTTGTTTTGCAAGATTGTAGCAGCTCAATCACATCTTCGGGCT
TCACTTCAAATTCTAGTTCTCCCACTGTGTCTACCACATTGGCAATTACTTCCTCCATTG
AAGTCTGGAAGCCCTCAAGCTCATCCATGAGAGTCAAAAATCAACTTCCTCCGAACTCCT
TTTAATATTTGATATTTTGACCTCCTTCCATTAATCATGAATGTTCTTCATGGCATCTAG
AATGGTGACTCCTTTCCAGAAGGTTTTTAATTTACTTTGCCCAGACCTATCAGAGGAATC
ATCATCTGTGGCAGCTATAGCCTTATGAAATGTATTTTTTAAATAATAGGACTTGAAAGT
CCAAGTGACTCTTTGATCCATAGGCTGTAGTCTGGATGCTGTGTTAGCAAGCATGAAAAC
AACACTAATCTCCTTATACATCATTGTCAGAGCTTTTGGGTGACCAGGTGCATTGTCAGT
GAGCAGTAATATTTTGAAAGGAATCTTTTTTTCCGAGTAGTAGATCTTAACAGTAGGCTA
AAAAATATTCAATAAACCATGCTGTAAACAGATGCACTGTCATCCAGGCATTTCTGTTTA
CTGATAGAGCACAGATGCAGTAGATTTAGCATAATTCTTAAAGACCCTAGGATTTTTAAT
ATGGAAAAGGAGCACTGGTTTCAATTTCAAGACACCAGCTATATTCACCCCTGATGAGAG
AGTCAGCCTATCCTTTGAAGCTTTTAACCCAGGCATTCACTTCTTTTCTCTAGCTATGAA
AATCCTAGATGACATCTTCTAATAAAAGGCTGTTTTTTTACATTGAAAGTCTGTTCTTTA
GTGTAACCACCTTCATCAATGACCTTAGCTAGATCTTCTGGATAACTTGCTGCAGCTTCT
ATATCACCATTCACTGCTTTGCTTTGTCCTACTACCTTACAGAGATGACTTCTTTCCTTA
AACCTCATGAGCCAACCTCTGCTACATTCCAACTTTTCTTCTGTACTTTCCTCACCTCTC
TCAGCCTTCATGCAATGGAAGAGAGTTAGTGCCTTTTTCTAGATTAGATGTTGGCTTAAG
GGAATGTTGTAACAGGTTTGATCTTCTATCCAGACTGCTAAAACTTTCTCCATATCAGCA
ATAAGGCTGTCTTGCTTTCTTATCATTTGTATATTCACTGGAGTAGCACCTTTAATTTCC
TTCAAGAACTTTTACTTTGCATTTACAGCTCGGCTAACTATTTGGCACAAGAAGCCTATT
TGGCCTATCTTGACTTTCGAAATGCCTTCGTCACTAAGCTTATTCATTTTTACATTTTCA
TATAAAGTGAGAGAAATGCAACTCTTCCTTTCACTTGAGCACTTAGAGGCCATTGTAGGG
TTATTCGTTGGCATAATTTCAGTAGTGTTTTATCTCAAGGTACAAGGAAGCCTGAGGATA
GGTAGAGAGACCAGAGACAGATAATTGCTGGAACAGCCAGAACATAAATAACATTTATCA
ATTAAGCTTGCCATCGTATATGGCACGGTTCATGTTGCCACAAAATAATTATAATAGTAA
CATCCAAGGACACTTCACTCATCACAGATCACCATACCACATAAAATAATAATGAAATAT
TTGAAATATTGTGAGAATTATTCAAATGTGACTCACAGTCACAAAGTAAGCACATGCTGT
TGGAAAAATGGTGCTGATAGACTTGCTGGATGCAGGATTACCAGAAACCTTCAATTGGTA
AAAAATAAAATATCTGCAAAGTGCAATAAAGTGAAGAGCAATAAAATGAGGCATGCATGT
ATTTATAGATTATATTGATTTTATTATGTGGCTTTCATGTTACAAGAATGACATATCTAT
TTAGGACTTGTGTTTATTAAATAAATACTTTTCTTTATAAAGGAAAATGCATCACATCTT
TTCTTTATTAATGTTTGAAAATATTTGACATAGTATAATAGAATGGAATGGCTTATTTAT
TTTTTATTCTTTATTTATCTTCACAACTATCTCTCCATATTTCCCCCATCTCTAACAGCT
ATCAAGGATTTTTAATAAGAAAATGCTAACAAATCTGTCTTAAAGTATTTTTGCACTTTA
ACTTTGAGCCTTTAAAAGTGTAGTTACTGGTGGCCAGGCGGGGTGGCTCACGCCTGTAAT

FIG 4. (SEQ ID NO. 4) CONT.

CCCAGCACTTTGGGAGGCCGAGGCGGGCGGATCACGAGGTCAGGAGATCGAGACCATCCT
GGCTAACACAGTGAAACCCTGTCTCTACTAAAAATACAAAAAAAAAAAAAAAAAAAAAAA
AAAAAAAAAATTAGCCCGGCATAGCGGTGTGCGCCTGTAGTCCCAGCTGCTGGGGATAGGC
AGGAGAATGGCGTGAACCTGGGAGGCGGAGCTTGCAGTGAGCCGAGATCTCGCCACTGCA
CGCCAGCCTGGGTGACAGAGCAAGACTCTGTCTCAAAAAAAAAAAAAAAAAAGGGTAGTTA
CTGGTAAGATTTATAATTCACCCTAGATAAAGGAATTGTGTAAAATGTTAAATTGTCTGT
TAAAAAGAAAGCCTAGCCAAAACAACAAAATAAGTGCCCTTAAATCATTTTAAATGAAAA
AACTTGGTATGTAAATGATTATAATTGTATTTCTGACTTCATGGCAATCTTTAAAATATA
TGACAACTTATATAGTCCTTAGACTGATCATATGAATCATACATTTGTGTGACTATAGAG
AAATTTTTGCCACTAAATGTATGGAATATGTTATATTGCTGAATGCATATCAGCAATATT
CAGAAGTAATATTTAAAATGTTTTTAACCAAGCTTTTGCTAGTTTTTTTCCCTATGACAC
GTAGTTAATTTTAAAGGCTAAAATTTATGCAATCTATAATTACCAATTTCATAAGGGCAT
AAGACAGAAACTACCTTATAATATTAATTATTTTTGACCAGTACACATAACAGACAATCT
ATTATGAAAGAACAAAATTTGTCATTTGATCTCAGGAATATTTTATAAATCCATGTTTAT
TTTGAATTGGCATCAGATACAATGACATTTCTCTCCTCCACTCTAATTTACTACAACATT
AAAGGAAATTTAAGCAAGTTTTAAAATACAGAACTATTTTTAATTATGAGGGGGAAAAAG
AATAATGATTAGCTTTAAATATAACCAATTGATTGTGTCAACATGGTCAAGGGTAGCTGC
TCAGACATGTCATTCACGGATATCGCCACATCCATCAAACTGCATTCAGGGTCCTACCAG
GTTATTAAATGTATGTTACTTGAAATATTGGTGAGAAAACAACAGAAGTATTGTATGGTT
TTTATCAATCATTTTAGTTATAGATGGTTTTCCATTTCCTTTTGAACTTAGTGTTAATAT
TTTCCAGCTGGAACATTTTTCTAATATATTTAATTTATATAGTGTTTACTTAATAAAATT
ACCCCCAACATTCCAAAAAATGTTGTCAAGACATAATGTTATATTTTATATTTTAATTCTA
ATATGCCCACATTTCCATATTATTGTAAAGGTTAATATTAATCATAATTAAAATTTTATT
TCTGTGAATTAGGTGCTTAAACAGGTGTTGGTCACCCTGAATTATCACCAACACAACCCA
CATATAACCTTTTGAAGTAAAATAATGGAATATTTTACTTGATCTTGGTCTCAATGAAGT
TTACATTATGAGTAGTGCCTAAAAAATCCACCTGACTTTAATGAACATTAGTAGAGGTATA
ACAAACAAATCTTGGATAAAATATATTTTCTGATTAGTATAGGTTACTGCACTGATTTTT
GCTTGAGATTTTAAAAATCCAGCATTCTCTGGAAGAATATAGATTTAATCAATTCTAGTA
TTCCTGATGATTGATGTAACCAGAAATATTGGGCCTTAAAGAATTAGAAAAACATTTAGA
GATTGATATATATAGATTGGGCTCACATTAGCCATAATAATATCCTAAAACTGATGAGTA
ATAGTAGACATCACCTCACCCCCATTCTCCACACATATGTAAGATAACCATATTTCTGAT
ATGTTGTCAAGTATACTATAATGTAAAATAAACGATTTTACCTGATGACCTCCAAGGTCT
CTTTAAACTTCATGAGCATTTGATTCTATCAGACAAGGACATGGGATCAAGAGGTGAGTG
GAGAAGGATGCAGTTTCATTTGTATTATTGTGACCATAGTCATCAATTTTTAATAATACC
AAATGTGAAAAAAAACTCTGTCATTATTACTTGAGTCATAGGAAAAAATGTCTTCCTGTTTC
AGAAAACATCCAAAATAAGGCCCCTACTGGATTCTGAATTTGTCATTTTCTACATTTCAA
AATAATTTTGGTTGGAAACTGGCAAAATCATTAACCTCTAAGCTTTAAGTCATTGCATAG
TTGGGATAAAACATTTTAATTTATGGTGGTAAAGCTATAAAAATTCAACAGTAAAAGAGA
ATTTAACTCTGAAGATTAAATTGCATAAGCTTACTATTAAAATAAAACATCTCCTCCATT
ATTCTTTCTTTGAGTTGTATCAGCAAGCTTTTAGATGTATACGAAATATTAACAATGACT
AAAATATAATTATGTTATCCAAGGTTATTTTTCTAATTGAGGCATTTATAAATATCCATG
TGGTACTTTCTAGTTTATGATACTTTTAGGGATCTCTACAAGGATACTTGCATAATATAT
GTGGAGAGATGTGTTCAATCAAGTAGTCACCTAAGCAGCAGAAGTTGAATTATAAAAACC
TAATACTGCTTTTGAGATTGGATGTCACCGCATTTTACAGATAACTGAAAATAATCATAA
CTATCAAAAGAGTAAACTAAATGGGGCATGAATGACTTGCCAGAGAATTGGAAGTATAAA
TTTTTCCTACAAATGTTAGTATTTATTATAATTTACTTGAAAAAAATGGCAAAAAAAATT
CCATGTGGCTCACAAGAGTTTACTGTATAGAGCTTATAATAATTAACTTAGAAACATTTA
AGAATATGTTAGCCAGTAATATTTGATAAACAATTAATAAATGGATTATACATTCACCTC
AGTCTTTGTTTTTAAAATGTGAGATACTTCAGATAAATTTTTACAAGTCTCCCATTTAAA
TATATGTTTTATGGATACTGCCTAAAAATCATAAGCAATATTGATAAAAGTAGGATATTA
AGGAAATTAATCATTTTCATTCCTAATGAAAGTGGCCTGATTTTTTAATACAGAAAATTT
GATATCCAAAACTTTGCATTTAAGTTTGGCATGTTATTAGTCAACTTGCTTAACTTCCTG

FIG 4. (SEQ ID NO. 4) CONT.

CACTGTTTTCTACATTTGCTTTGCTCTTATTAAACTGAAATGATAAGCATCCTGATAAAT
GAATAGTTGCATTGTATTTATATTTCTCTGCTACATATGTAACAAATTTGGATTAACCCT
GTCTGTGGCATTCGTAAATTTAGAATAACGCTTTATTGTCTGCATTGGGAGAAACCTTTC
AACCTCTTGTCCATTTGGATAATGAATTATTGCTATTCCTGTGATATACTGGCACTACAC
TCCATCCTTCTTACAATTTCAGCAAGTAAAGTGTGCAAAGTTTGTCATTTGTCAAATTTT
AATGAAGTTTGGGGAACAAAGGAGGTGTATCACAATAGCATTGGAGATTACACAATAATA
TAGATATACAACTTTGGTCTTAGACTGCACTGCAGCCATCCTCACTTGCTGGTACTCATT
ATACAGGACTCTGACTTGTATGGTTATCATGTTCTGAGGCCTTTTAACCATAAATTTATG
ACTTTGTTTATCAATCAAAAGGAGTATTCATATGTTCTACTAAACAGAAGGCTTTTGTCT
CAAGGGAATACGCATCCCTTAGAATGCAAAAATACTACTTAGTCATTATTTAAATACTAT
TGGGGATTTTTTACTGTAAAGTGATCTACAGTAATACATCCTGATTATACAGAAATATGC
TGTAATGTTATTTATAAATAATTATTCTTAACAAAAATGAGAGGAGCACTTACTTGATTT
AACAAATTTCAAATTTTAATCCAAATATTTAAATTTTCATAGATTGCTATATAGTATTTA
TATTGTATTTTCCTAATCTTTTTGTAAATGTGGCTGAAATCATATTAGAATAAGACTTTT
GAAAATCAAAAATTAAGTGTCTTTTGTTAACATAGCTTGACAGTACAATAAACACGTTTC
TTAAGATTGTAATCTACAGGAAGATGTTTCAGACCTATTGTGTATTATTCTAAAAAAGAT
TAACGGCATTTTTATCTTTTTTCACCTATAAAACAGGGGAGCAGGAGAGGATTTTTAAAG
GTACCCTTTTACCTCTCATAGGTATAGATAGTCATAATTTTAGTTTGAGATATCAAAGAA
ACATGTGCCCATGATTCAATATTATAATTATGTGATTTATACATTAAATCAAGATGTTAT
CATAGTTTCTAAGTCATGTTCACATAGAAGCAAGTCATGGGTAGTGTTGGCTGGAAAGGC
TAATAGGGACGGTAGAACTCAAAGTTGAATGTTTCTTTCTCTTGCTTCGTAGGCAGCCTC
CTTAACTGTGGACTCCTGTTCTGAGAACCAAGAGCCAGGATATTGTACTGTCAGTAATGT
GGCAGTTTCAGATGACTGGTAAGGAATAGGATTAGTTTAATTTTTATTATTACTTAAAAT
TTTTTAAAATAAACTTTATACCTAAAAATAATTATAGGATGCTAAGTAGTACATAAAGCT
TAAGATATTTTATTTCCCTCTCCAAATTTTCATAATATAAAATAGTCAATAATTACTGTG
CAAAATGTGTTAAAATGTGTGAAATGAAGTGGTAGAAATAAGGATAAAATTGGAGAAAAG
GAAATTAAATATAGCCAGTAGTCTTTGGAAAGATTCATGAAATAATTGCATATGACCTTC
ATTCTGAAAAACATGTAGGATAAAGACCTCAGTTCTTTCAAATGCGTTTCTAAAAGTTTA
CGTGAAAATTATTAACAGATATTTTTCCATAGCACTTAAAGCTGAGCACAGCAGTAATCT
ACCAGAAAATAAGTGATTTTAATAGGAAAAATGATAAACAGAGAAAAATAAGTAGTCACG
CATCATGATGCATCATTCATTGCCTCAATCAACTTATTGGCATCCCTTGCATTGATCAAC
TTACTGATATTCTTTATCATCTCTTCAGGGAAGGAGCAGTGTAATCTAACGTAAATATTA
GAGTTGTCACTAATTCTACAGCATTTTATTTTCCCTCTGAGAGTATGCTCCTTCTTGTTG
ACTCAGTATTGTGATAATATACATCTAACTTGACTAATTGAAAACATAATTTCCATAAAT
ATTATTATTTTTCATAATTCGGAAGTCTAACAACTCTGTGTGTGTATTGGACACTCTTCT
ACATATTTTCCATTGAAATTTATCACACTATAATAAATGTCAAAAAAAAGCTATATTCAC
TCTTTTTCGAACTAAACATTATACTAAAAATGTAATCTTTTGACACTAATATTTATATCT
TCCATTATTTATTTAGGACTCTTGATGTTCAGCCAAATAGAGTTACAGTTGGAGGTATCA
GATCTCTAGAACCAATCCTTCAGAGAAGAGGACACGTGGAAAGCCATGATTTTGTTGGGT
GTATAATGGAGTTTGCAGTCAATGGAAGGCCTCTGGAACCCAGCCAAGCTTTGGCAGCAC
AAGGCATCCTAGATCAGTATGGCGATTTTATTTCTTACTGTTTTAAAGAAAAAAAATGCA
AAAAAGTATGCTTCAGTGAGCATCAAAAGATGAAATTATTATGCTCAAATCTCTAAAAAT
ACCAAATGATTTACATTGTTTTGAATTTTAAATACTATACCTTTGAAATTTTGGCATAAA
GTATGATATTTAATTAGAAAATTAATATGTTTCTAGATTCTTATACATATATATATATAT
ATATATGCATGTGGGCATGTATATGTTTTATCCTCTTACAGAGAGTTGTGAAGATTAAAT
TAGTTAAGTTGGTAAATTATATAAAAAAGGGTTCCAGCACAGAGAGATATGTAGATGTTA
GCCATCATGGACACATAGAACTTTATTTCACATTAAATAGTTTTACTTATAGACATACAT
ATTCCTAAAAACTTGATACAGCTTTAAAAACAGGCAATAACTTGATTAATTATGAACTGT
AAGGCTTTTTTATTTGATTATTAATTAGGTTTCTAGCAATAACTTAGGGATGTTAGAAAT
TACATATTTTATTTTAAAATTCCTTTTGTTCATTATCGAAGTTTGAAAAATTCTGAAAAA
ATACAAGGAAGAAAACAAAATTAACCTATAATCTAACCACCCAGAGACAACTACTCTTAG
GTTATTGTCATGTTTTGACTGCTTAGTATCCCAAGATGTGAATGTGCTATATTTTAACTG

FIG 4. (SEQ ID NO. 4) CONT.

TTGCTATACACTTTAGTTATTTCCAATTTTATTAATATACCAATTACCCTGTGATGAACA
CATTTTCACAAAAATCTTTGCTCACATTATTTTTGGATGAGATTACCAGAAATAAAACT
ATTAAAGGCAAAGCTAGGAATACTTTCTAATGTTTGTAACTTAAGTATTTTAATAACATT
TTCTATTTGCCTTTCTTTTCCTACATGTTGTTACTGTTTTGTTACAAAGTCACACTAGTT
CGTTATTATTATTAATCAAACAGTACAGAAAAACAAAGGATTGGGATTGCCACCATTGTT
AATACTTCGGTGTGCATCCTTTTATATCTCCGTGTTCACACAAGTACTTTTTTAAATATC
AATTTTTTTTTCATTTAGAGATATTTTGTGAACATCTTTTTAGGTCAAAACCTACTGAA
ACAAAACTTTTAGACTTACCTTTAACTCCTCTGTTTCTGTTAGACCTTATGTCCAGAATG
ATGTTTCTGTTTGTTTGTTTGTTTGCTTTTTGAGACAGAGTCTTGTTCTGTCGCCCAGGC
TGGAGTGCAATGGCGGGATCTCGGCCCCCTGCAACCTCCACCTCCTGGGTTCAAGCAATT
ATCTGCCTCAGCCTCCGGAGTAGCTGGGATTACAGGTGCCTGCCACCACGCACAGCTAAT
TTTTGTATTTTTAGTAGAGACGGGGTTTCACCATGTTGACCAGGCTGGTCTTGAACTCCT
GACCTCATGATCCACCACCTCAGCCTCCCAAAGTGCTGGGATTATAGAGGAGAGCCACTG
CACCCAGCCTAGAATGGTTTTTAAAACATAAGTCAGTTAACTTTTCACTTCTTGGCTCAA
AGTGCTTCAATAGCTTCCCATCTCACCCAGCTTCAAAGCCAAAATCCTGACCCTGAATGA
AAACATTTTTATGATCTGCCATCTCCCTTCACTTCCTGAACATATCTAACTATTCTTCTT
CTTGTGCCCTGAGCTCCAACCATGTTGGGCCTCGGTGTTTCTCAAACATGGCAGTACGCT
TTCACTTCAAGGCTTTCTCACTGGCTGTTTCCTCTAGCTGAAAAGATATTCTACCAGATA
TACTTCATTCCCTTATTTTATTTAGGTCTTAACAAAGATTAAGATTAATTCACTGCCTAA
TCTAAAGATTCAGCAAACCCGCAAACTCACTATACCCTTTCTCACCTTGATTTTCTCTAT
AGCTATTTTTTTCTTTATTTTCTGCCTCTTCCACAAGAAAAAATAAGTACTTCCTCAGTA
CACGGTTATTTTTTCATTACTTTACTTCCATGCTTAGAACAGTGCTTAGCATATGGTAGG
CATTCAATAAACATTAGTTGCATGAGTATCCTGATAGACATGTGTCAAAAAATATGTGGT
CCCTGGATCATATGTATTAACCAAAGTGTTTATTTGACCAAGGTATTTTATTCAAGTAAG
AATTAATTTAAAGAAGAAATTGTCACAGCTTTCTCATTATTATATAAGACATAATTTTTT
TTGAATCTTCTTTAGTGTGAGGCAGACTATGTTTTCTAGGAAAACTTCTGGTTTGATTAG
TTTCTCCAAATGTAGTTGTAACTTGAGCTTCAAATAATGGAGTGCTTGAAATTAAACAAG
CTAATAAAAGTGTATATTGAGTTTTAGCAAACTTCTCCTCATCTTTTATGTGCGTTATTG
TTCTCATTATGATTTATTTTAGATGCCCTAGGCTGGAAGGCGCTTGTACTCGCAGCCCAT
GCCAACATGGTGGCACATGTATGGATTACTGGTCATGGCAGCAGTGTCATTGCAAAGAGG
GACTCACTGGGAAATACTGTGAAAAATGTATGTAAGGTCTTCCGTCTTCCCCTGGAAATT
TTAATAACTATGAAAAGTAAAATATATGCACCCAAGTATGTAATCAAATTAAAAATTATG
CTTTCATTCTAAATATTAAAATATTAAATGGACAATAATTGGTAAAATACAGTGACATTT
TAAAAATTATTTTTGTAACCTGAAGAAGAATGATATCCTTTTAAAAAATCGTTTACTAAC
TAAATCTCTAGCTTCCACTTTAAAGGTATTTTATTCACTTATTTTTGTTTGTTTTATTTC
TTAGAATTCTAGGCAATCTAAAAGATCAAAGGTTATAGTTAGGCTTTTTTTCATATTATC
TGCCTTTGGGGGATATTTTTCTGGTGAATTTTTGTGCATAAAAAGGTATACACACTAAAT
CACTCAACACTGAGATCAAAACATCATACAGAGCCATCATAATATGTTAAAATTAATGTT
GATACTTTCATTTTAATGTACAAGTAGTAGAATTAATTTTGAATATTACTTTTTAAAATC
CTTTCATCATTGTCTTCTAAGCCTAATGTTATTATTTAGACATTAATGATGTTCATATCA
TCATTAGAAAATGGTGCTCTCTAATTTCGAGCTGCACATCTCACTAACTAACCCTAATGG
TTCCTCTTTTGTAAAAATTCTTCATTTTCAAACAAGTGGTTACTACTTAACTCCATTGCA
GGTATCTGACTACATTTAAGGAGTCATTTGATTAAATTATATTATGAAAACAAATAGAAA
TGCATAATAAAATTGAGGATATAATATAATCTAAAAGGTCTTAGCAGAAAGTGTAATTGT
GTGTAATAATATTAGATATAATGAAAACATAGAAAATATATACTGTCATGTGATTTTCAA
TGTAATAAATATTTATTAAGGAGCCTAATTATATCTGAAATATGAGTCATTGGCTAGATA
AATACCAGAGACACTTTTTCTTAAATCATGATATAACTCACATACTATAAAATGTATTCT
TTTAAAGTGTATCTTTCAGGGCTGAAATCCATTTGAGCTCATTTTCTTAATATTCTTTCT
TTAGCTATATTATTTGTTTCTATAACTTAAGCTTCAATATTTCTGGAATGTGGATTTTTT
TCAGATTACAATAAACTATAATATACATACTGATTATACATGATGATAAATTATATGTGA
TGATTACTGAAAATAAAGTTAGTTACCGATGTAAATACTTGATTGAACACTTCTTTGTCC
TAATTTATAGCATACTAGAGACTAAAGATTACAAATCATTTTAACCATGCAAACGTATAT

FIG 4. (SEQ ID NO. 4) CONT.

TTTGGAAACACAGTGAAAATGATTACAAACAAATTTTTCAAGTACATATTACCAACAAGT
GCCTGTCTTTAGATATTCATAATTTACGTAATGTGGCAAATAGTTTAGTAAAATATTTCC
CAAATGGTTAATGACTGTCATAGAGTATTTTAAGTTCATGGTTCTGAAATGCATTTAAAC
ATGTGAAATCAACTTATATAATGATTCATAAATGGAAATTATTTTTTAAGAGTAGAGTTG
GGGGACATTAATTCCCAAAACGACATTTTCATTGTCCTTTTTATATTTTTGTCACTATAG
AAAACACTCCAAGAAATGCCAAATGAATGCATTCATTTTCCCTTTTTTCCTTTGACTTCC
AGCTGTTACTCCTGACACTGCCTTATCATTAGAAGGCAAAGGGCGCTTGGACTACCACAT
GAGTCAGAATGAGAAGCGGGAATATTTGTTAAGGCAAAGCTTACGAGGTGCCATGTTGGA
GCCTTTTGGTGTGAACAGTCTGGAAGTAAAATTTAGGACCAGAAGCGAGAATGGCGTTTT
AATCCATATCCAAGAAAGCAGCAATTACACTACTGTGAAGGTGAGATAAAAGCTAATGGT
GACTTCATTTGATTAGACCGCCTGCCGTGTAGTGGTTTAAATCACTTCCCCCATAATTTC
TGTCCTTTTCTTTACAACCCATTAGAGTTCCGACTAATGCTGGGCACTATTCCAATGTCA
TCTATCTTAACTATTCCCCAGGCATTGGCCAGAGTAACAAAGATCTGAATGGTTTGGTTT
CTACACACTTTTGTGTTGCTTTAGAGTAGAGAACCCTGCCAGGTAGGCCAGCACACAAAG
AATTAGTTGCAATCTATTTTTCTGGTAAGAATTTATATCACTTCTTTTCTTACTTTTAGA
CAAAGCAAACCAAAAAATATAATGTTTGTTTGAAATACAAAAAATATTTTTCTCCAACAATT
ATTTCAAATATTGATATGTATATGTCAATTGACAGGATTAGAATAAGGAAAAACATTTTG
AAATAAGCAAAAACATTTTGAAATTATATGATTTCTGGAGCATATATTCAATTCTCTATA
TAAACTCTGTGGAGTAAAGTATATTTGGAATTCATTATAATTTTACTTAACCTTTCCAAA
TAATTTTTAAATAATCTTAAAAATTATGCTTCATGAGAACAATGGATTTATCATTAGGCT
TTTACATAATTTGTTTTTTCTTATCTGTAAATAAGATACTAGACTTATATACAGATGAAT
AATTTCATTAGATATCCATTTTTGCATCGGCCCTTAGCTTTCTGAAGTTTTAAACCTATG
TTCTGCTTTCTTTCCCACAAATAAGTCATCTCCTAGACCAACAGTTTCTTTAGTTTAGTT
ATATTTACTGCCTTCCATTAATATTACTTTGTATCATTCTACTGATAATTTTTTATATAA
ATTTTAGTAAATTCTTAAGATAACAAATCCAGATTTCCTGAATTATTTTCATCTATTAGT
CAATATTTAATAACTACTCCAGGGATAGTTCACAGAGAAAAAGAGCAATTTGTTCAGAAA
AATTATTTGGTTTAATTCACATATAATACTAAAAATAAAAATAGATGTTCACTTCTAAAC
TTCAGCCTCTTTCATCCTCAAAATTTTTCTCTGTGCAAGCCAACCATGATTATGTTGCAT
ATAAATATATTTAATAAGTAGTACAAAAACCAATATTTCTTACCTTCTCAAATGATAATT
CCTCTAGTCCAGTCATTTCCAACTAGGATAGATTTTACCCCCATGGGACATTTGGCAATA
TCTGGAGACATTTTCAATTGTCACGGTTAGGAGTTGGGAGAGTACTTCTGGCGTCTAGCG
GTAGAGGTCAAGAATGCTGCTAAACAGTAGCACTTCACAACAAAGAGTTATCTGGCCCCA
AATATCATTAGTGCCAAATGGCAGACACTCTACCCTTTTCCCTTACAAGAGAACATCTTC
AGGTTTTAACTTTACCTCTATTGAAGCAAAGGACCCAGTTCCAGAGTTAATAAAACAACT
GTAAAAGAGAACACATAAGCCATTGTATTACATTATTATCTGGTACTTATAATTTTCATT
GAAAATGGTATTAGAAGTAAACAAAGTAAAGAAGCAAAAAAAGAAATAGATCCTCATCTT
CTATAAGAAACATATTTTATATGGTTTGAGAGGCTTTGACATTGAGGTCTGTGTGTTATC
TGTTAAGTTGCTTCCAAGTCTTCGTGCCATTTAAATGACATATGAAATATTTCTGTACTA
ACGTACACTTAAAGCCAAGGAATTCAGTCAAAATACAATGTGGTTGAAAAAAATCAGAGA
CACATTTTTTTCTTCACTAAGGAAAAAGCTGAATGTCAGGATCCATTTTTGTCACCATAA
ATTCTTCTACTTCCAACAGGACAGCGCATACAACTCCAGATTTTGTTAGCTTGGTAGCAA
TAACTTAATTTTTTTCCTGAAAGGAAAGTAAGTGCAAATTAATAAAAAAATGAATAATAC
AGACCAAAATGCATAGTTTTATATGAAAATTTTGAAAAGAAGCTTTTCAAAGGGGCTTGG
CAGGTAAAGAGAATAGGTAAGAAAAAAATAACAACAGTGAATTAAGAATAACTAAGTAAAC
CAAAAGAAAGTGGCTGTTGTAAGCAGGCAAATTATTTGGATGATAGGAGTATCAAGTGCT
TATACAGACTAGGAAGCTAGTTAGGATGGACTTTTACTTATCAATTAGCTTATTGGTCAC
CAAGACCCCAGGGTTCCGTTTTTTTTTTTTTTTTTTTTGGCTCCTTTTCTGATCCTTTCT
TTAACTCTTTCTTATGGTTTGCATTCTCTCTCTCTCATTCTCTTTTCTATCATTCTTTCT
CTCTCTCTCTACAGACACACATACACACACACACACACACACACACACACACACACACGC
AGACAGAAGATGAGGACATTTTGTGAAAAATGAGGAAGGGTGTTGGGTAAATGGGATTCC
ATGTGGCTAGAAGAGAGAGAGGGTGTCAGTGTCAGGTGTGGGCAGCAATAGTGATGAGAG
GAGAGAGAAGAATATGTAGAATCAATTGGGTCTATTCAGAAAAAGAAAAAAATTAAGAAAA

FIG 4. (SEQ ID NO. 4) CONT.

GAAAGTTTCAGAGAGAAAGGCAAAAGGAAAGCATAATTGTGTAAAACTTTGTAGGCCAAT
ATTTAACTCATTTCACAAATCTCTCTTCATTCATGGCATGCCCTATAGCTCCATATTTGA
TGTTCTGTAATAATAGTAATGTGATGGACTTTATTTCTACTCTAAATCAGTTCTTTTGTG
TTTGTCTGGTTTTTTTAAGTGGGCAACATAGGTGATACAGAATAATTGGAATAAGGAATT
CAAAGCTCTATAGATTCAAATTAAATAAATGAACAAATAAATGCAGTCATGAGTTGCATA
ATGACAGGAATGCATTTCGATAAATGCATTGTTAGGTGATTTCATTCTTGTGCAAACATC
ATAGAGTGAACTTGCTCAAACCTAGATGGTACAACCTACTATACACCTAGGCTATATGGA
ATAGTCTATTGCTCCTGTGCTATAAACCTGTATGGCATGTTTACTGTACTAAATACTGTA
GGCAATTGTGACACAGTGGAAAGTATTTGTGTATATAATCATATCCAAAAATAAAAAAGG
TACAGTAAAAAGGCTGCATTGAAGATTTTTGGGGGGATGGGGGACAGCCTGGGCAACAGG
GTCTTGCTCTGTTGCCCAGGCTGGAGTGCAGTGGCATGATCTCGGCTCACTGCAGCCTCT
GCCTCCTGGGCTCAATGTATCCTCCCACCTCAGCCTCCCAAGTAGATGGGACTACAGGTG
TGCGTAACCATGCCGGGCTAACTTTTGTATTTTTTTGTAGGGATGAGGTTTCACATGTTG
CCTAAATTGCACTTACTGTGACTGAAGCTTGTAGGACTGAAAGTTGCTCTGAGTCAGAGA
GTCATTAAGCAAGTGGTGGGTCAATGTGAAGGCCTAAGACATTATTATACACTTCTGCAG
ACTTTATAAACACTGTATGCTTAGGTTACATTAAATTTATCAAAAATATTTTTCTTCAAT
AATAAATTAACTTTAGCTTACTGTAACTCTTTTAGTTTATAAACTTAAAATTTTTAACTT
TTTTCTCTTTTGTAATAACAATTAAAACACAAATACATTGTACAGCTGTACAAAAATATT
TTCTTTCCTTATACCCTTATTCCATAAGCTTTTTTTCTATTTTAAAAGTTTTTTATTTCA
TTTTATTTTTACTTTTAAACTTTTGCATTAGTAACTAAGAAACAAAAAAACACATTAGCC
TCAGCCTACACAGGGTCAGTATCATCAAATCCCTGTCTTCCACCTCCACATCTTGTCCCA
GTGGAAGGTCTTCAGGGACAATAACACAGATGGAACTGTCATCTCCTATGATAACAATGC
CTTCTTCTGGAATCCCACCTAAAGGACCTGGATGAGGCTGGTTTACAGCTATTTTTTATA
TCATTAGAAGCAGTACCCTCTAAAATAATGATTAAAAAAACGGTGTAGTAAATGCATAAA
CCACTAATATAGTCATTTATTATCAAATTGCATGTGATATACTTTTATACAACTGGCAGC
TCAGTAGGCTTGCTTACACCTGTATCCCCGCAATGAGTAATTCGTTGTGCTATGACATTA
CAATGGCTACTAGGTCACTAGGCAATAATAATTTTTCAGCTCCTATGGTTCATCATTGAC
TGTTTATTAATAAATAAAACCAAGCAAAAATTAGCATGATGTTTTAAAAGTGAAGAATTA
TATAAGTGTTAAGTACAGTACTGCCAGGGAGAAGGAAAACATTAAGAATGTTATAATGGG
AACTTATATTCTTATCCACCCCAATTTGTGGTATATTCCAAGTGCTCTTTCATCAAAAAT
TTATTGAATAAAAGGATGACATGATGAAATCAATTAGGAGGAAAGAGCTGGGAGAAGGCT
TTTCCTTTTTTTTTTTTTCAAAAAGGACTCCAGCTATAACCAAAGAAAGTTGCTGTTTTT
ACTGTGTGTCATGAGATGTTGCCCATTTGATGAAATGTTATTGTCATTTAGCTAGAATTT
TCTGTTTTTTTTTTTTAGTTTGGTACTGAAATATATTATTATCTGGAAAAATTGGCTTTA
ATAAAATATTGCTATATGAATAACATATGTAAATGTGTTAGACATCTTTTCGGTAAAGTA
CAAATGAACTGATTTTTAGTTTTACCAGATGTGTTTGTTACATGTAGAAATAGCATTTGA
TCTGAGTGACAAAATAAACTGATCCATCTTTTCATTCCCGTTATTTGAGGAACAGTGCCA
CTGCATCCCCCTGCCAACACACCAGCTCTGTCTGGCAGTGGTAACAGGATTATGCTCCCT
GAACCAAATGTTCATCTTGCCTCATAAATTATCTCATTTTCTAAAATGGTCTACTCAGGA
TACTGGAAACTCGGTAGCTGGAAACTGGAGTGGGAGCACCCTGTTACCCAATGTTCTCCT
GGACAAAATAAAATAAACCAAATATCCTTTAGATAAATTGTAAAAGACAGCCAAAGTGAA
GGCTTGCCCAGACACCTCATTAAGAATTCACTCTTTGTTCATCATAGTTTTTGATCTCAA
TAAATGATATAAACAATAGGCATCATTTTTTCCTAAAATTTGTGTGTAAAAGATGAGAGG
TAAAACAATTATTTTCATCTTTATTTTTAAACTATGCTTCCCTTTTAGCTGAGCATTCTT
TTTCTTTTTGCAAGTGGTTTTCACAATTTTTTAGTACTATGGGCCTTTTACTAAACGAAC
CAGCATAACACACTCCAATGGCAGGTTGTCATTGGAATACAAATAATTTAAAAAGGTATA
ATTTAATTATCTTAAATGGACATTCGCCCCTTTATTATTTCAATTGTGTTCTGGAAAATA
ATTCATCAAGTTTTGAGAAATTAGGTATACATATAAGAATACGTTGAAAACCATTGAAAC
TTAAATGTAAAAGTACATGTTGCCTAAAATTAGAGACAAAGTGTGTAAGTATATTCTAAT
ACAACCAGATTCTTCAGCTATTCTATCTGCTGTGGACTGGTCAAAAATTTAAGTTTAGTT
TTGTTAATGATTTTTATTTAAGCATACCATATTTTAATTGCATACTATTTTTAATATGTT
TTACAGATTAAGAATGGCAAAGTATATTTTACATCCGATGCAGGAATTGCTGGGAAAGTG

FIG 4. (SEQ ID NO. 4) CONT.

GAGAGAAATATTCCTGAAGTATATGTTGCAGACGGCCACTGGCACACTTTTCTAATTGGG
AAAAATGGAACAGCAACAGTATTGTCTGTTGACAGAATATATAACAGAGATATTATCCAC
CCTACTCAGGACTTCGGTGGCCTTGATGTGCTTACTATATCACTTGGAGGAATTCCACCC
AATCAAGCACATCGAGATGCCCAAACAGGTAAATGCCTTTATTAAGTAGAGTCACAAGGG
AAGTAAAATTGTTCTTCAAAAAGTAATTGCTTTTTCTTGTGGCAAGACTACACATTTAAC
ATGAATCTCATATACAGAACAATTTCATTCAATAAAATTTATGTTTAAAAAAGTAGTTTG
ATGTCTGATAATATCAATTATAAATATCCTAAGAATGTCATAACTATCTTCAGAAAGTTT
GTAATAAACTATTAGCCACCACTTTCTCGAGAGCTTGCATCTTTCTTACCAAGGTTGTAA
TTCAGTCCATAGTGTTTTGATGCTTTGCTTGTCCACCAAGCATTTCATATACATTTGTTC
ATTTATTTATTCATTCACAGCCACTCTCTTCATAGACCATTAATGGAGACAAACATTAAT
CAAATTCTTACACAAGTAACTGCATTATTCTAATGTGTGATAAATAATACAAATGAAGAA
TGTAGAATTCTAAAATATAGTGAAAAAAGAGAAAGGAAGGGGAATTTTGCTGTGGAATTG
ACATGTATACATAAATCTGAATGATGAGGAGGATGAAAGTGTACGAAAGGTTAATTTATG
TTGATAGGAATTTTTTTAAAGAAATCGTTTAAGCCAAAGTTATAGAAGACAACACATTGG
AGGCTAACATCATAGGCAAATGATGAAGTTGGAGAATGAAGCAACTTCCTGACCATGTTG
CAGTTTTGGTCTTATTTACAGAGCAATGGGAAGTAATTGAAAACTTTAATCACAGTAGGA
TCAAGTTAGATATGCAGTAATATTACAGATCATTCAGGCTACAGCATGGAGAATGAATTG
GAGGAGGACACGAGTGGATCTACAGAAATGAGTTGGGATCTGGGCAAGATGTCTTCTGAG
CTCCTACTAGTGTGGTGGCTGAGGAGTTAGAAAGAAATGGATAGGCAAGAAATATTCTGG
GAACTAAAATCAACCAAACTGTTAGTGATTATGGTAAAATTCAAGGAGGTTTCTACTTCT
CAACTCAAAGAAGGGTAGGTCAGCAAGAGAGGAAACTGCAGAACCCTCCAAAAGCAGCAT
ATGTCTGAGAAATATTAGATTTGGTTTGGGACATTTTGGATTTGAAGCATCTTTGAGAAA
ATCCTTTGGATGGATGGGCTGGAAATCAGAAATAGACTTTAGCTGGAAATATATATTTAA
GAGTGGTCAGTGTCAAGCAGGTAACTGAAGTACTGGACATGGATGTGATCACCTAACATG
AGGGCGTAGAGTGAAAAGAAAGCCTGGGACGTCATCTTGATTAACCGTAAGAGTTAATGG
TTATGTAGAGGAGAATAAGTCGGAAAAGAAGACTAAGTAATAGGAAGAAAATCAGGAGTA
TAGGAACAAAAAGAAAAGATGTCACAAAAGCTCATGGAAAAAATATATCAAGAATGAGAA
TGTCACTATGGTAGAATGATGCATTAAATAAGAGGAAAAAAATGCATGTGAGACTAATAG
ATTTAAGGCATAAAAGTTAAAGTCCAGGTCATAAGTCCTTTTTATATGGTTATTATAGAA
TGTTGTGAGAAAACAAACCAATGGAAATTACGCTTTTTGTAGTGTCAAAATAGATTGTTG
GGCCCTGAGATAGGAATATCAGCACTGTTAACACACTCAAGTGTAATGAAGTGTTTCTTA
ACTTTGCATTTTATCTTTATCATTCCCCTAAGGAGACACTTAATATAGTCTAAACTTTGC
CATCCCCAAGTCATAAAATGTTAACACCAGAGGTATGTTTTTATCTGCCTTTTAGAGGCC
CACAAACCATTGTAATAGCTAAGATTTTTTTGTTTTGCTCCCCAAGAACCTATGTTCCAC
ACCTTTGGTGTATTATCACCTTCAATGGGAATGCATGATTTAGTAGTTGAAGCCATTGGC
CTATTTCATGTTCTTTACAAATTTAAAAAATATATATTTTATTTGTATGTATGCAATTTT
TGGTATATGGGATGTAAAAAGGAAGGAAATTGATAAATAAATGAGTAAGAAAAAGAAAAT
TCAGCCTGCCCAAGTCATTCATAAATCTTCAGAATGAGTGGGATTCAAGCAATCTGACCC
ATGTTTGGTCATGGTAATCTTAACGCACCTTGCTAAGTTATAAGATGCACAGCTTAATTA
TCTTTCAGCTGGATGATGGTTCTGAGACTGAGGTTTCTGTATTCATGTATTCATATGAGG
TGATTGTGGAGCTTCTCTTTACAAGAACCCAGCAGTGTAGTATAAGCTCTTTTTTTTTTT
TTTTTTTTTTGTAAAAAGCCTTACTCCTTCTTCTTCTCCCAGCAGGTTTTGATGGCTGCA
TTGCTTCTATGTGGTATGGTGGAGAAAGTCTTCCTTTCAGCGGGAAGCATAGCTTGGCCT
CCATCTCAAAAACAGATCCCTCAGTGAAGATTGGCTGCCGTGGCCCGAACATTTGTGCCA
GCAACCCCTGCTGGGGTGATTTGCTGTGCATTAATCAGTGGTATGCCTACAGGTGTGTCC
CTCCTGGGGACTGTGCCTCCCACCCGTGCCAGAATGGTGGCAGCTGTGAGCCAGGCCTGC
ACTCCGGCTTCACCTGTAGCTGCCCAGACTCGCACACGGGAAGGACCTGTGAGATGGTGG
TGGCCTGTCTTGGCGTCCTCTGTCCTCAGGGGAAGGTGTGCAAAGCTGGAAGTCCTGCGG
GGCATGTCTGTGTTCTGAGTCAGGGCCCTGAAGAGATCTCTCTGCCTTTGTGGGCTGTGC
CTGCCATCGTGGGCAGCTGCGCAACCGTCTTGGCCCTCCTGGTCCTTAGCCTGATCCTGT
GTAACCAGTGCAGGGGGAAGAAGGCCAAAAATCCCAAAGAGGAGAAGAAACCGAAGGAGA
AGAAGAAAAAGGGAAGTGAGAACGTTGCTTTTGATGACCCTGACAATATCCCTCCCTATG

FIG 4. (SEQ ID NO. 4) CONT.

GGGATGACATGACTGTGAGGAAGCAGCCTGAAGGGAACCCAAAACCAGATATCATTGAAA
GGGAAAACCCCTACCTTATCTATGATGAAACTGATATTCCTCACAACTCAGAAACCATCC
CCAGCGCCCCTTTGGCATCTCCAGAGCAGGAGATAGAGCACTATGACATTGACAACGCCA
GCAGCATCGCCCCTTCGGATGCAGACATCATTCAACACTACAAGCAGTTCCGCAGCCACA
CACCAAAATTTTCAATCCAGAGGCACAGTCCCCTAGGCTTTGCAAGGCAATCCCCCATGC
CCTTAGGAGCAAGCAGTTTGACTTACCAGCCTTCATATGGTCAAGGTTTGAGAACCAGCT
CCCTAAGCCACTCAGCATGCCCAACTCCCAACCCTCTGTCTCGACACAGTCCAGCCCCTT
TCTCCAAATCTTCTACGTTCTATAGAAACAGCCCAGCAAGGGAATTGCATCTTCCTATAA
GGGATGGTAATACTTTGGAAATGCATGGTGACACCTGCCAACCTGGCATTTTCAACTATG
CCACAAGGCTGGGAAGGAGAAGCAAGAGTCCTCAGGCCATGGCATCACATGGTTCTAGAC
CAGGGAGTCGCCTAAAGCAGCCGATTGGGCAGATTCCACTGGAATCTTCTCCTCCAGTCG
GACTTTCTATTGAAGAAGTGGAGAGGCTCAACACACCTCGCCCTAGAAACCCAAGTATCT
GCAGTGCAGACCATGGGAGGTCTTCTTCAGAGGAGGACTGCAGAAGGCCACTGTCTAGAA
CAAGGAATCCAGCGGATGGCATTCCAGCTCCAGAATCCTCTTCTGATAGTGACTCCCATG
AATCTTTCACTTGCTCAGAAATGGAATATGACAGGGAGAAGCCAATGGTATATACTTCCA
GAATGCCCAAATTATCTCAAGTCAATGAATCTGATGCAGATGATGAAGATAATTATGGAG
CCAGACTGAAGCCTCGAAGGTACCACGGTCGCAGGGCCGAGGGAGGACCTGTGGGCACCC
AGGCAGCAGCACCAGGCACTGCTGACAACACACTGCCCATGAAGCTAGGGCAGCAAGCAG
GGACTTTCAACTGGGACAACCTTTTGAACTGGGGCCCTGGCTTTGGCCATTATGTAGATG
TTTTTAAAGATTTGGCATCTCTTCCAGAAAAAGCAGCAGCAAATGAAGAAGGCAAAGCTG
GGACAACTAAACCAGTCCCCAAAGATGGGGAAGCAGAACAGTATGTGTGAAGTTTATGTA
CTGGCACTATAAAATATAAAAACAAGAAATAATACTCAAACCATTGTAAAGTTGCTGACT
AGGTTGGGTCACATTTGAAAAACAGGCCAGTATGGACTAGTGGTGGAGGGAAAACTTTAA
AAATAATAACCACAATGCTGCTGAAACAGACTCACAACAACTCTTAATTTAAACATGTGT
GGTTGAATTTATTTCCCTGCATGCATTGTGTTTTGTAACTAGTTATGTGGCATGCAGCAT
TTGGAAAATTTTTCTTATTTACCAGTGTTTGATTTGTGATTTTTAAAAATTGATACCTTT
ACCATTGCAGAAAAGAACTTGTGCTTTCCCAGTGGCGTATGTGTATTGTTTCAACTGTAT
TATTATAATTATATTTTGCATTGCAAGATTCTTGATGTTAAACCAATCCTTGTAAAGTGT
AAAAAGGAACCCTCCTATCGTGGAATGAAAGATTAAGTATATTAACACTTTTCAGAATGA
TAGTTTCTGTATTTGATGTTGCTCAGAAATGTCTCAGTATTTGAGTAAGTTTTACATGAC
AGTGGGTACTGAAATTAAGTCATTTTGTTCAGCACTTTAACGCTTTCTTATAGAATTGTC
TTAAAACTTCTGGATCCTTGAGCAAATGATTATAGTCTCCTGACTTTCATGAGGCTTCCA
TTAGGAACAGAATGATTGCATGTTGTCCCCAGAACACTGCCACCTTGCTATGCGAATGAT
GTTCTCAGCAGCACTTCTAAGAAACACTCTTAAAAGTTATTTATTGAAAATTTTTCGTAT
GCTTTTAATATTTTAAAGAATTGACCTAAGGAAAGCTTATGATTGGACTTATTTTCCAAC
CAGATAACATTTACTCTAAGTACCCAGTTTTTATAATTTATATGAAATCAGATTTCAACA
CTTACTTTGTCATTTTGTAGATCATTTTTTTAAAATACTGTGTAAAAACTTTTTTTACAC
CTAAGCTGTGTTTTTGATACTGATATTTTCCTATGCTGAATAGTTTTCTTACTTTCAGGG
AAGGTAAGAAAATACTTTTTTTATATTTGTTACTTATGTAACATTCATATTTTTCTCATT
TTGATATTTGTAACATACTGTATGCTTTCTACTTGTAAATGTCAACAATAGAATTAAAAT
ATTTATTTAAAATA

Figure 5A (SEQ ID NO: 5)

>ENSG00000196159|ENSP00000377862|ENST00000394329|FAT4

GGGAGCCAGGACCATGGACTTAGCACCAGACAGGGCTACTGGCCGCCCGTGGCTCCCGTT
GCACACTCTATCAGTATCTCAGCTCCTTCGAGTGTTTTGGCTACTGTCATTGCTTCCGGG
GCAGGCCTGGGTCCACGGGGCCGAGCCGCGCCAGGTGTTCCAAGTGCTGGAAGAGCAACC
TCCAGGCACTCTGGTAGGCACCATCCAGACGCGCCCCGGCTTCACCTACAGGCTCAGCGA
AAGCCACGCCCCTGTTTGCCATAAACAGTAGCACCGGAGCCCTGTACACCACCTCCACCAT
CGACCGCGAGAGCCTGCCCAGCGACGTGATCAACCTGGTGGTCCTTTCCAGCGCGCCCAC
CTACCCCACCGAAGTGCGAGTGCTGGTGCGGGACCTCAATGACAACGCCCCCGTTTTCCC
GGACCCCTCTATCGTGGTCACTTTCAAGGAAGACAGTAGCAGCGGACGCCAAGTCATCTT
AGACACCGCCACCGACTCGGACATCGGCTCAAACGGTGTGGACCACCGCTCCTACCGCAT
CATCCGCGGCAATGAGGCGGGGCGCTTCCGTCTGGACATCACCCTGAACCCGAGCGGCGA
GGGAGCGTTCCTGCATCTGGTGTCCAAGGGCGGACTGGACCGTGAGGTCACTCCGCAGTA
CCAGCTCCTGGTTGAGGTGGAGGACAAGGGTGAGCCTAAGCGGCGGGGCTACCTTCAGGT
AAACGTGACTGTGCAAGACATTAATGACAACCCCCCGGTTTTTGGCAGTTCTCACTACCA
GGCGGGGGTGCCTGAGGACGCGGTTGTGGGTTCCAGCGTCCTCCAGGTGGCGGCGGCGGA
CGCGGACGAGGGCACCAACGCGGACATCCGCTATCGCCTGCAGGACGAGGGGACCCCCTT
CCAAATGGACCCTGAGACGGGACTTATCACGGTGCGGGAGCCCCTGGACTTCGAAGCTCG
GCGCCAATACTCGCTTACGGTGCAGGCGATGGACAGAGGCGTGCCTTCCCTCACTGGGCG
CGCCGAGGCGCTGATTCAGCTGCTGGACGTGAATGACAATGACCCGGTAGTGAAGTTCCG
CTACTTCCCGGCCACCTCGCGCTACGCCTCGGTAGATGAGAATGCTCAAGTGGGCACCGT
GGTGGCTCTGCTCACCGTGACGGACGCAGATTCTCCCGCGGCCAACGGGAACATCTCCGT
GCAAATTCTCGGGGGCAATGAGCAGCGCCACTTTGAAGTGCAAAGCAGCAAAGTGCCGAA
CCTGAGCCTAATCAAGGTGGCCAGCGCCTTGGACCGCGAGCGCATCCCTTCCTACAACCT
CACAGTTTCCGTCTCTGATAACTACGGGGCGCCCCCTGGCGCAGCAGTCCAGGCGCGCTC
TTCTGTGGCAAGCCTGGTGATTTTTGTTAATGACATCAATGACCATCCTCCTGTCTTTTC
ACAGCAAGTGTACAGAGTGAACCTGAGCGAGGAGGCGCCTCCGGGAAGCTATGTGAGTGG
GATATCTGCCACTGATGGCGACTCTGGTCTCAATGCTAATCTGCGTTACAGCATTGTCTC
TGGCAATGGACTGGGATGGTTCCATATCAGTGAACATAGCGGCCTCGTGACCACTGGGTC
CTCTGGGGGCCTGGACCGTGAACTTGCTTCCCAGATTGTTCTGAATATAAGTGCCCGGGA
CCAGGGAGTTCACCCCAAGGTGTCCTATGCCCAGCTTGTAGTAACTCTCCTAGATGTGAA
TGATGAAAAGCCAGTATTTAGCCAGCCAGAAGGGTATGATGTGTCTGTGGTTGAGAATGC
CCCAACAGGGACAGAACTGTTGATGCTCAGGGCAACTGACGGGGACCTGGGTGACAACGG
AACAGTGCGCTTCTCCTTACAAGAGGCAGAGACTGACCGGAGGTCCTTCCGTCTGGATCC
TGTGTCTGGGAGGTTGAGTACTATTTCCTCCTTGGACAGAGAAGAGCAAGCCTTCTACTC
CCTGTTGGTTCTGGCCACAGATCTGGGCTCCCCTCCCCAGTCATCAATGGCTCGCATAAA
TGTGAGTCTTCTGGATATAAATGATAACAGCCCTGTCTTCTACCCGGTCCAATACTTTGC
TCACATTAAGGAGAATGAGCCTGGAGGTAGCTACATCACCACTGTGTCTGCCACTGACCC
AGACTTGGGTACCAATGGTACTGTCAAATATAGCATATCTGCTGGGGACAGGTCTCGGTT
TCAGGTCAATGCTCAGAGTGGGGTTATTTCTACAAGAATGGCCCTAGACAGAGAAGAAAA
AACAGCTTATCAGTTGCAAATAGTAGCTACTGATGGTGGCAATTTACAATCTCCCAACCA
GGCAATAGTAACCATCACTGTATTGGACACTCAAGACAACCCACCTGTATTCAGTCAGGT
TGCCTACAGCTTTGTGGTTTTTGAGAACGTGGCGCTGGGATATCATGTGGGTAGTGTGTC
TGCATCCACCATGGATCTCAATTCCAACATCAGTTATCTCATTACTACTGGGGATCAGAA
AGGTATGTTTGCTATCAACCAGGTCACTGGGCAGCTTACCACAGCAAATGTGATTGATAG
AGAAGAGCAATCCTTTTATCAGCTGAAGGTAGTGGCCAGTGGGGGCACAGTGACTGGAGA
CACTATGGTTAACATAACAGTTAAGGATTTGAATGACAACTCTCCCCATTTCCTTCAGGC
AATAGAGAGTGTAAATGTGGTGGAGAATTGGCAGGCAGGTCACAGCATTTTCCAGGCCAA
AGCTGTGGACCCTGATGAAGGTGTCAATGGCATGGTACTCTATAGTCTGAAGCAAAACCC
CAAGAACCTGTTTGCTATCAATGAAAAGAATGGCACTATTAGTCTGCTTGGGCCCCTGGA
TGTTCATGCTGGCTCCTACCAAATAGAGATCTTGGCATCTGACATGGGTGTCCCACAGCT
CTCCTCTAGTGTCATCTTAACAGTTTATGTCCATGATGTAAATGACAATTCACCAGTGTT
TGACCAACTCTCTTATGAAGTCACCCTTTCTGAGTCAGAACCTGTGAATTCTCGATTCTT
TAAAGTACAAGCTTCTGATAAGGATTCAGGAGCAAATGGTGAAATTGCATACACCATTGC
TGAAGGAAATACAGGGGATGCTTTTGGCATATTCCCAGATGGTCAATTGTATATAAAAAG
TGAACTGGACCGTGAACTTCAAGACAGATATGTTTTAATGGTTGTTGCTTCTGACAGAGC
AGTGGAACCCCTTAGTGCTACTGTGAATGTTACTGTAATTTTAGAAGATGTAAATGATAA
CAGACCTCTTTTTAACAGTACCAATTACACATTTTACTTCGAAGAAGAGCAGAGGGCTGG
GTCGTTTGTGGGCAAAGTAAGTGCTGTAGATAAAGACTTTGGGCCAAATGGAGAAGTAAG
GTATTCTTTTGAAATGGTGCAGCCAGATTTTGAGTTGCATGCCATCAGTGGGGAAATTAC
AAATACTCATCAGTTTGACAGGGAGTCTCTTATGAGGCGGAGAGGGACTGCTGTGTTTAG
CTTTACAGTCATAGCAACAGATCAGGGGATCCCTCAGCCTCTCAAGGATCAGGCCACTGT

FIG 5A. (SEQ ID NO. 5) CONT.

ACATGTTTACATGAAGGATATAAATGATAATGCTCCCAAATTTTTAAAAGACTTTTACCA
AGCTACAATATCAGAATCAGCAGCCAATCTGACACAAGTGTTAAGAGTATCTGCCTCAGA
TGTTGATGAAGGTAATAATGGACTTATTCACTATTCTATAATAAAAGGAAATGAAGAAAG
ACAGTTTGCTATAGACAGTACCTCTGGTCAGGTAACACTAATTGGCAAATTAGACTATGA
AGCAACACCTGCCTATTCCCTTGTAATTCAAGCAGTGGATTCAGGGACAATCCCCCTCAA
TTCAACGTGTACTTTAAATATTGATATTTTAGATGAAAATGACAATACCCCTTCTTTCCC
TAAATCAACACTCTTTGTTGATGTTTTGGAAAACATGAGAATTGGTGAACTCGTGTCCTC
TGTTACTGCAACTGATTCCGATTCAGGTGACAATGCTGATTTATATTACAGTATTACTGG
GACTAACAACCACGGAACTTTTAGCATTAGCCCAAACACTGGGAGTATTTTTCTTGCCAA
AAAACTGGACTTTGAAACACAGTCTTTGTATAAATTAAATATAACAGCAAAAGACCAAGG
AAGACCTCCTCGTTCATCTACAATGTCAGTGGTTATTCACGTGAGGGACTTTAATGACAA
TCCTCCTAGCTTTCCTCCTGGAGATATTTTCAAGTCTATTGTTGAGAACATTCCCATCGG
TACATCTGTCATTTCAGTGACTGCACATGACCCTGATGCAGACATTAATGGTCAACTATC
CTACACAATCATTCAACAGATGCCAAGAGGCAACCACTTTACCATAGATGAAGTCAAAGG
GACTATATATACTAATGCTGAAATAGATCGGGAATTTGCTAATCTCTTTGAGTTGACTGT
AAAAGCCAATGATCAAGCTGTGCCAATAGAAACTAGACGGTATGCTTTGAAGAACGTGAC
CATTTTGGTTACAGACCTCAATGACAATGTCCCAATGTTTATATCACAAAACGCCCTTGC
TGCAGACCCATCAGCTGTGATTGGTTCCGTTCTGACAACAATTATGGCTGCTGACCCAGA
TGAAGGTGCTAATGGAGAAATAGAGTATGAGATCATCAATGGGGACACAGACACCTTCAT
TGTTGATCGTTATAGTGGAGACCTGAGAGTGGCTTCAGCGTTGGTGCCTTCACAGTTGAT
CTACAATCTCATAGTTTCAGCAACAGACCTTGGGCCTGAAAGGAGGAAATCGACCACTGA
ATTGACCATCATTCTTCAGGGCCTTGATGGACCTGTTTTTACTCAACCCAAATATATAAC
TATTTTGAAGGAAGGAGAACCCATTGGCACAAACGTGATATCAATAGAAGCAGCTAGCCC
CAGAGGATCTGAGGCCCCAGTGGAGTATTATATTGTTTCAGTTCGTTGTGAAGAAAAAAC
TGTTGGACGCCTCTTTACTATTGGACGACATACTGGTATAATTCAGACCGCAGCCATTCT
GGACCGGGAGCAAGGAGCATGTCTTTACCTGGTGGATGTTTATGCCATAGAAAAATCAAC
TGCTTTTCCCAGAACACAGAGAGCAGAGGTAGAAATAACACTTCAGGATATCAATGACAA
TCCACCAGTATTTCCAACGGACATGCTGGATCTCACGGTAGAGGAGAACATTGGAGATGG
CTCTAAGATTATGCAGCTGACAGCCATGGATGCTGATGAGGGTGCAAATGCTCTCGTCAC
ATACACTATCATTAGTGGAGCTGATGATAGTTTTCGCATCGACCCAGAATCCGGAGATCT
GATAGCAACCAGGCGGTTGGACAGGGAACGCCGCTCCAAATATTCACTGCTAGTTCGTGC
TGATGATGGTCTTCAGTCCTCGGATATGAGAATTAATATCACTGTCAGTGATGTGAATGA
CCATACACCCAAATTTTCCAGACCCGTGTACTCTTTTGACATTCCTGAGGACACAATCCC
TGGTTCTTTGGTAGCAGCCATTTTAGCCACGGATGATGACTCTGGTGTGAATGGAGAAAT
TACATATATTGTGAATGAAGATGATGAAGATGGCATCTTTTTCCTGAATCCTATTACTGG
GGTCTTTAATTTGACTCGATTATTAGATTATGAAGTACAGCAATATTATATCCTCACTGT
TCGAGCAGAAGATGGTGGGGGACAATTTACTACCATCAGAGTTTATTTCAATATTCTAGA
TGTAAATGATAATCCACCTATTTTCAGCTTGAATTCATACAGCACATCTTTAATGGAGAA
TCTACCTGTGGGATCTACTGTTCTTGTGTTTAATGTTACTGATGCAGATGATGGCATCAA
CTCTCAATTGACTTATAGCATTGCTTCAGGTGATAGCCTTGGGCAGTTTACTGTTGACAA
GAATGGTGTACTCAAAGTCCTAAAAGCTTTGGATCGGGAAAGTCAGTCCTTCTACAACTT
GGTTGTTCAAGTGCATGACCTGCCACAGATTCCAGCCTCCAGATTCACAAGCACTGCTCA
AGTCTCCATTATTTTGTTGGATGTAAATGATAACCCACCGACATTTCTTTCCCCTAAATT
GACATACATTCCAGAAAATACACCTATTGATACTGTTGTTTTCAAAGCTCAAGCAACTGA
CCCAGATAGTGGCCCAAACAGCTATATTGAGTACACTCTGCTGAACCCTTTGGGAAACAA
GTTCAGTATTGGGACCATTGATGGTGAAGTGAGGCTCACTGGAGAACTGGACAGAGAAGA
AGTTTCTAATTATACTCTAACAGTGGTGGCTACAGACAAAGGTCAACCATCTCTCTCTTC
ATCTACAGAGGTTGTAGTTATGGTACTTGACATCAATGATAACAACCCCATCTTTGCACA
AGCTTTGTATAAAGTGGAGATTAATGAAAACACACTTACTGGAACAGATATAATACAAGT
GTTCGCAGCAGATGGAGATGAAGGCACAAATGGACAGGTTCGCTATGGCATTGTTAATGG
TAATACCAATCAGGAATTTCGGATAGACTCTGTCACAGGTGCCATCACTGTCGCTAAACC
TTTGGATAGAGAAAAGACCCCTACCTACCATTTAACTGTTCAGGCAACAGATCGAGGCAG
CACACCCAGAACTGATACCTCCACGGTCAGCATTGTTCTACTGGATATTAATGACTTTGT
TCCTGTATTTGAGCTATCTCCATATTCTGTAAATGTCCCTGAGAATTTAGGGACACTACC
CAGAACAATTCTTCAGGTGGTGGCAAGAGATGATGATCGAGGATCTAACAGCAAACTCTC
ATATGTTCTGTTTGGTGGTAATGAAGACAATGCTTTTACTCTCTCAGCCAGTGGAGAACT
TGGAGTAACACAGAGTCTGGATCGGGAAACAAAAGAGCGCTTTGTCTTAATGATTACAGC
TACAGATTCAGGATCCCCTGCCTTGACTGGAACTGGAACAATCAACGTCATAGTAGATGA
TGTCAATGACAATGTCCCCACATTTGCCAGTAAAGCGTATTTCACAACAATTCCTGAGGA
TGCACCAACTGGAACAGATGTTTTATTGGTAAATGCCTCAGATGCTGATGCTTCAAAGAA
TGCAGTTATAAGGATCATCGGTGGAAACTCTCAGTTCACGATCAACCCATCGACAGGACA
AATCATCACCAGCGCATTGTTAGATAGGGAAACAAAAGATAATTATACTTTGGTAGTGGT
CTGCAGTGATGCGGGATCCCCAGAGCCTCTTTCCAGTTCCACCAGTGTGCTTGTCACTGT
GACTGATGTCAATGACAATCCACCAAGATTTCAGCATCACCCATATGTCACTCACATCCC
ATCTCCTACTCTTCCAGGTTCCTTTGTCTTTGCGGTTACAGTCACAGATGCTGATATTGG
ACCAAATTCTGAACTGCATTATTCTCTTTCGGGTAGAAATTCTGAAAAATTTCACATTGA
CCCACTGAGGGGAGCCATTATGGCCGCCGGACCACTAAACGGAGCTTCAGAAGTGACATT
TTCTGTGCATGTAAAAGATGGTGGCTCATTTCCAAAGACAGATTCTACAACAGTGACTGT

FIG 5A. (SEQ ID NO. 5) CONT.

TAGATTCGTGAATAAGGCCGATTTCCCTAAAGTGAGAGCCAAAGAACAAACGTTCATGTT
TCCTGAAAACCAACCAGTCAGCTCTCTTGTCACCACCATCACAGGATCCTCTTTAAGAGG
AGAACCTATGTCATATTATATCGCAAGTGGGAATCTTGGCAATACTTTCCAGATTGATCA
GTTAACAGGGCAGGTGTCTATTAGTCAACCTCTGGATTTTGAAAAGATACAAAAATATGT
TGTATGGATAGAGGCCAGAGACGGTGGTTTCCCTCCTTTCTCCTCTTACGAGAAACTTGA
TATAACAGTATTAGATGTCAATGATAATGCCCCAATTTTTAAGGAAGACCCATTTATATC
TGAAATATTGGAAAACCTTTCCCCTCGAAAAATACTTACTGTTTCGGCAATGGACAAGGA
CAGTGGACCCAATGGACAGTTAGATTATGAAATTGTTAATGGCAACATGGAAAATAGTTT
CAGTATCAATCATGCTACTGGTGAAATTAGAAGCGTTAGACCTTTGGACAGGGAAAAAGT
ATCTCATTATGTCCTAACCATAAAATCATCAGACAAAGGGTCCCCGTCTCAGAGTACTTC
AGTAAAAGTCATGATTAACATTTTAGATGAAAATGATAATGCCCCTAGGTTTTCTCAGAT
ATTTAGTGCCCATGTTCCTGAAAATTCCCCCTTAGGATACACAGTTACCCGTGTCACAAC
TTCTGATGAAGACATTGGGATCAATGCAATTAGTAGATATTCTATAATGGATGCAAGTCT
TCCATTTACAATTAATCCCAGCACAGGGGATATTGTCATAAGCAGACCTTTAAATAGGGA
AGATACAGACCGTTACAGAATTCGAGTTTCCGCACATGATTCTGGGTGGACTGTAAGTAC
AGATGTCACAATATTTGTGACAGACATCAATGACAATGCTCCAAGATTTAGCAGAACTTC
CTATTATTTAGATTGCCCTGAACTTACTGAGATTGGCTCCAAAGTAACTCAGGTATTTGC
AACAGATCCTGATGAGGGATCAAATGGACAAGTGTTTTATTTCATAAAATCCCAATCAGA
ATATTTCAGGATTAATGCCACCACTGGAGAGATTTTCAATAAACAGATCTTAAAATACCA
AAATGTCACTGGCTTCAGTAATGTGAATATCAACAGGCATAGTTTTATAGTGACATCTTC
AGATCGAGGTAAACCTTCCTTAATTAGTGAGACAACAGTTACCATCAATATAGTGGACAG
TAATGACAATGCACCTCAATTTCTTAAAAGTAAATATTTCACTCCAGTCACCAAAAATGT
TAAGGTTGGTACGAAGTTAATCAGAGTTACAGCAATAGATGACAAAGATTTTGGACTGAA
TTCAGAAGTGGAGTATTTCATTTCTAATGATAACCATTTAGGAAAATTTAAGTTGGACAA
TGATACGGGGTGGATTTCAGTAGCATCCTCCCTGATTTCTGACTTGAACCAAAACTTTTT
TATCACAGTCACTGCAAAGGATAAGGGAAACCCTCCACTTTCTTCCCAAGCAACTGTTCA
CATAACTGTCACTGAGGAAAACTACCATACACCTGAATTCTCTCAAAGCCACATGAGTGC
AACCATCCCTGAGAGCCATAGCATTGGGTCCATTGTCAGAACTGTTTCTGCAAGAGATAG
AGATGCAGCGATGAATGGCTTGATTAAGTACAGCATTTCTTCAGGAAATGAAGAAGGCAT
TTTTGCAATCAATTCTTCTACAGGTATATTAACACTAGCCAAAGCTCTTGATTATGAGCT
ATGCCAGAAACACGAAATGACGATTAGTGCTATAGATGGAGGATGGGTTGCAAGAACTGG
TTACTGCAGTGTGACCGTAAATGTGATTGATGTGAATGATAATTCTCCAGTATTCCTCTC
TGATGACTATTTCCCTACTGTTTTGGAAAATGCCCCAAGTGGAACAACAGTTATCCACCT
AAATGCAACAGATGCTGACTCTGGAACAAATGCTGTGATTGCGTATACTGTACAGTCATC
TGACAGTGACCTCTTTGTCATTGACCCTAACACAGGAGTCATAACCACTCAAGGCTTCTT
GGATTTTGAAACCAAGCAGAGCTACCATCTTACTGTGAAAGCCTTCAATGTCCCCGATGA
GGAAAGGTGTAGCTTTGCCACTGTTAATATACAATTAAAAGGGACAAATGAATATGTGCC
CCGTTTTGTTTCCAAACTTTACTATTTTGAAATCTCAGAAGCAGCTCCTAAAGGTACTAT
TGTTGGAGAAGTGTTTGCTAGCGACCGTGATTTGGGCACTGATGGGGAGGTACACTATTT
GATTTTTGGTAATAGTCGAAAGAAGGGTTTCCAGATCAATAAGAAGACTGGACAGATTTA
TGTTTCTGGAATTCTTGATCGAGAAAAAGAAGAAAGGGTGTCTTTGAAGGTATTGGCCAA
GAACTTTGGCAGCATTAGAGGTGCAGATATAGATGAGGTCACTGTAAATGTCACCGTGCT
TGATGCAAATGACCCACCCATTTTTACTCTAAACATCTACAGTGTGCAGATCAGTGAAGG
GGTCCCAATAGGAACTCATGTGACCTTTGTCAGTGCCTTTGACTCAGACTCCATCCCCAG
CTGGAGCAGGTTTTCTTACTTCATCGGATCAGGGAATGAAAATGGTGCCTTTTCTATTAA
TCCGCAGACAGGACAGATCACCGTTACTGCAGAATTAGATCGAGAAACCCTTCCCATCTA
TAATCTCTCAGTTTTGGCTGTTGATTCAGGGACCCCCTCAGCTACAGGTAGTGCCTCTTT
ATTAGTCACCCTGGAAGATATAAATGATAACGGGCCCATGCTGACTGTCAGTGAAGGAGA
AGTCATGGAAAACAAACGGCCAGGCACTTTGGTGATGACCCTTCAGTCCACTGACCCTGA
TCTCCCTCCAAATCAAGGTCCCTTTACTTATTACTTGCTGAGCACAGGTCCTGCCACCAG
TTATTTCAGTCTGAGCACTGCTGGAGTTCTGAGCACAACCAGAGAGATTGACAGAGAGCA
GATTGCAGACTTCTATCTGTCTGTGGTTACCAAGGATTCTGGTGTTCCTCAAATGTCTTC
CACAGGAACTGTGCATATCACAGTTATAGACCAAAATGACAATCCTTCACAGTCTCGGAC
GGTGGAGATATTTGTTAATTATTATGGTAACTTGTTTCCCGGTGGGATTTTAGGCTCTGT
GAAGCCACAGGATCCAGATGTGTTAGACAGCTTCCACTGCTCCCTTACTTCAGGAGTTAC
CAGCCTCTTCAGTATTCCAGGGGGTACTTGTGATCTGAATTCCCAGCCAAGGTCCACAGA
TGGCACGTTTGATCTGACTGTCCTTAGCAATGATGGAGTTCACAGCACAGTCACGAGCAA
CATCCGAGTTTTCTTTGCTGGATTTTCCAATGCCACAGTGGATAACAGCATCTTACTTCG
TCTCGGCGTACCAACAGTAAAGGACTTCTTGACCAACCACTATCTTCATTTTTTACGCAT
TGCCAGCTCACAGCTGACAGGCTTAGGGACTGCTGTGCAACTGTACAGTGCATATGAAGA
GAACAATAGAACGTTTCTTTTGGCAGCTGTGAAGCGAAATCATAATCAGTATGTGAATCC
CAGTGGCGTAGCCACCTTCTTTGAAAGCATCAAAGAGATCCTTCTCCGGCAGAGTGGAGT
AAAGGTGGAATCTGTGGATCATGACTCCTGTGTGCATGGCCCATGTCAGAATGGAGGGAG
CTGTCTACGAAGATTGGCTGTGAGCTCCGTATTAAAAAGCCGTGAGAGTCTTCCAGTCAT
CATCGTGGCAAATGAACCTCTGCAGCCTTTCTTATGCAAGTGTCTGCCAGGATATGCGGG
TAGCTGGTGTGAAATAGATATAGATGAATGTCTTCCATCACCTTGCCACAGTGGTGGAAC
CTGTCACAATTTAGTGGGAGGATTTTCATGCAGCTGCCCAGATGGCTTCACTGGTAGGGC
GTGTGAGAGAGATATCAATGAGTGCCTGCAGAGTCCTTGCAAGAATGGTGCCATCTGCCA

FIG 5A. (SEQ ID NO. 5) CONT.

GAATTTTCCAGGAAGCTTCAACTGTGTTTGCAAAACTGGATACACAGGGAAAATGTGTGA
ATCTTCAGTCAATTACTGTGAATGCAACCCCTGCTTTAATGGTGGTTCCTGCCAAAGTGG
TGTGGATTCTTATTATTGTCATTGTCCATTTGGTGTCTTTGGAAAACACTGCGAGTTGAA
CAGTTATGGATTTGAGGAGTTATCATACATGGAATTTCCAAGCTTGGACCCCAATAACAA
CTATATTTATGTCAAATTTGCCACGATTAAAAGTCATGCCTTATTGCTTTACAACTATGA
CAACCAGACAGGCGACCGGGCTGAGTTTTTGGCCCTTGAAATTGCCGAAGAAAGACTAAG
ATTCTCTTATAATTTAGGCAGTGGTACATATAAGCTCACCACCATGAAGAAGGTGTCAGA
TGGACATTTTCACACTGTGATTGCCAGGAGAGCAGGAATGGCAGCCTCCTTAACTGTGGA
CTCCTGTTCTGAGAACCAAGAGCCAGGATATTGTACTGTCAGTAATGTGGCAGTTTCAGA
TGACTGGACTCTTGATGTTCAGCCAAATAGAGTTACAGTTGGAGGTATCAGATCTCTAGA
ACCAATCCTTCAGAGAAGAGGACACGTGGAAAGCCATGATTTTGTTGGGTGTATAATGGA
GTTTGCAGTCAATGGAAGGCCTCTGGAACCCAGCCAAGCTTTGGCAGCACAAGGCATCCT
AGATCAATGCCCTAGGCTGGAAGGCGCTTGTACTCGCAGCCCATGCCAACATGGTGGCAC
ATGTATGGATTACTGGTCATGGCAGCAGTGTCATTGCAAAGAGGGACTCACTGGGAAATA
CTGTGAAAAATCTGTTACTCCTGACACTGCCTTATCATTAGAAGGCAAAGGGCGCTTGGA
CTACCACATGAGTCAGAATGAGAAGCGGGAATATTTGTTAAGGCAAAGCTTACGAGGTGC
CATGTTGGAGCCTTTTGGTGTGAACAGTCTGGAAGTAAAATTTAGGACCAGAAGCGAGAA
TGGCGTTTTAATCCATATCCAAGAAAGCAGCAATTACACTACTGTGAAGATTAAGAATGG
CAAAGTATATTTTACATCCGATGCAGGAATTGCTGGGAAAGTGGAGAGAAATATTCCTGA
AGTATATGTTGCAGACGGCCACTGGCACACTTTTCTAATTGGGAAAAATGGAACAGCAAC
AGTATTGTCTGTTGACAGAATATATAACAGAGATATTATCCACCCTACTCAGGACTTCGG
TGGCCTTGATGTGCTTACTATATCACTTGGAGGAATTCCACCCAATCAAGCACATCGAGA
TGCCCAAACAGCAGGTTTTGATGGCTGCATTGCTTCTATGTGGTATGGTGGAGAAAGTCT
TCCTTTCAGCGGGAAGCATAGCTTGGCCTCCATCTCAAAAACAGATCCCTCAGTGAAGAT
TGGCTGCCGTGGCCCGAACATTTGTGCCAGCAACCCCTGCTGGGGTGATTTGCTGTGCAT
TAATCAGTGGTATGCCTACAGGTGTGTCCCTCCTGGGGACTGTGCCTCCCACCCGTGCCA
GAATGGTGGCAGCTGTGAGCCAGGCCTGCACTCCGGCTTCACCTGTAGCTGCCCAGACTC
GCACACGGGAAGGACCTGTGAGATGGTGGTGGCCTGTCTTGGCGTCCTCTGTCCTCAGGG
GAAGGTGTGCAAAGCTGGAAGTCCTGCGGGGCATGTCTGTGTTCTGAGTCAGGGCCCTGA
AGAGATCTCTCTGCCTTTGTGGGCTGTGCCTGCCATCGTGGGCAGCTGCGCAACCGTCTT
GGCCCTCCTGGTCCTTAGCCTGATCCTGTGTAACCAGTGCAGGGGGAAGAAGGCCAAAAA
TCCCAAAGAGGAGAAGAAACCGAAGGAGAAGAAGAAAAAGGGAAGTGAGAACGTTGCTTT
TGATGACCCTGACAATATCCCTCCCTATGGGGATGACATGACTGTGAGGAAGCAGCCTGA
AGGGAACCCAAAACCAGATATCATTGAAAGGGAAAACCCCTACCTTATCTATGATGAAAC
TGATATTCCTCACAACTCAGAAACCATCCCCAGCGCCCCTTTGGCATCTCCAGAGCAGGA
GATAGAGCACTATGACATTGACAACGCCAGCAGCATCGCCCCTTCGGATGCAGACATCAT
TCAACACTACAAGCAGTTCCGCAGCCACACACCAAAATTTTCAATCCAGAGGCACAGTCC
CCTAGGCTTTGCAAGGCAATCCCCCATGCCCTTAGGAGCAAGCAGTTTGACTTACCAGCC
TTCATATGGTCAAGGTTTGAGAACCAGCTCCCTAAGCCACTCAGCATGCCCAACTCCCAA
CCCTCTGTCTCGACACAGTCCAGCCCCTTTCTCCAAATCTTCTACGTTCTATAGAAACAG
CCCAGCAAGGGAATTGCATCTTCCTATAAGGGATGGTAATACTTTGGAAATGCATGGTGA
CACCTGCCAACCTGGCATTTTCAACTATGCCACAAGGCTGGGAAGGAGAAGCAAGAGTCC
TCAGGCCATGGCATCACATGGTTCTAGACCAGGGAGTCGCCTAAAGCAGCCGATTGGGCA
GATTCCACTGGAATCTTCTCCTCCAGTCGGACTTTCTATTGAAGAAGTGGAGAGGCTCAA
CACACCTCGCCCTAGAAACCCAAGTATCTGCAGTGCAGACCATGGGAGGTCTTCTTCAGA
GGAGGACTGCAGAAGGCCACTGTCTAGAACAAGGAATCCAGCGGATGGCATTCCAGCTCC
AGAATCCTCTTCTGATAGTGACTCCCATGAATCTTTCACTTGCTCAGAAATGGAATATGA
CAGGGAGAAGCCAATGGTATATACTTCCAGAATGCCCAAATTATCTCAAGTCAATGAATC
TGATGCAGATGATGAAGATAATTATGGAGCCAGACTGAAGCCTCGAAGGTACCACGGTCG
CAGGGCCGAGGGAGGACCTGTGGGCACCCAGGCAGCAGCACCAGGCACTGCTGACAACAC
ACTGCCCATGAAGCTAGGGCAGCAAGCAGGGACTTTCAACTGGGACAACCTTTTGAACTG
GGGCCCTGGCTTTGGCCATTATGTAGATGTTTTTAAAGATTTGGCATCTCTTCCAGAAAA
AGCAGCAGCAAATGAAGAAGGCAAAGCTGGGACAACTAAACCAGTCCCCAAAGATGGGGA
AGCAGAACAGTATGTGTGAAGTTTATGTACTGGCACTATAAAATATAAAAACAAGAAATA
ATACTCAAACCATTGTAAAGTTGCTGACTAGGTTGGGTCACATTTGAAAAACAGGCCAGT
ATGGACTAGTGGTGGAGGGAAAACTTTAAAAATAATAACCACAATGCTGCTGAAACAGAC
TCACAACAACTCTTAATTTAAACATGTGTGGTTGAATTTATTTCCCTGCATGCATTGTGT
TTTGTAACTAGTTATGTGGCATGCAGCATTTGGAAAATTTTTCTTATTTACCAGTGTTTG
ATTTGTGATTTTTAAAAATTGATACCTTTACCATTGCAGAAAAGAACTTGTGCTTTCCCA
GTGGCGTATGTGTATTGTTTCAACTGTATTATTATAATTATATTTTGCATTGCAAGATTC
TTGATGTTAAACCAATCCTTGTAAAGTGTAAAAAGGAACCCTCCTATCGTGGAATGAAAG
ATTAAGTATATTAACACTTTTCAGAATGATAGTTTCTGTATTTGATGTTGCTCAGAAATG
TCTCAGTATTTGAGTAAGTTTTACATGACAGTGGGTACTGAAATTAAGTCATTTTGTTCA
GCACTTTAACGCTTTCTTATAGAATTGTCTTAAAACTTCTGGATCCTTGAGCAAATGATT
ATAGTCTCCTGACTTTCATGAGGCTTCCATTAGGAACAGAATGATTGCATGTTGTCCCCA
GAACACTGCCACCTTGCTATGCGAATGATGTTCTCAGCAGCACTTCTAAGAAACACTCTT
AAAAGTTATTTATTGAAAATTTTTCGTATGCTTTTAATATTTTAAAGAATTGACCTAAGG
AAAGCTTATGATTGGACTTATTTTCCAACCAGATAACATTTACTCTAAGTACCCAGTTTT

FIG 5A. (SEQ ID NO. 5) CONT.

TATAATTTATATGAAATCAGATTTCAACACTTACTTTGTCATTTTGTAGATCATTTTTTT
AAAATACTGTGTAAAAACTTTTTTTACACCTAAGCTGTGTTTTTGATACTGATATTTTCC
TATGCTGAATAGTTTTCTTACTTTCAGGGAAGGTAAGAAAATACTTTTTTTATATTTGTT
ACTTATGTAACATTCATATTTTTCTCATTTTGATATTTGTAACATACTGTATGCTTTCTA
CTTGTAAATGTCAACAATAGAATTAAAATATTTATTTAAAATA

Figure 5B (SEQ ID NO: 6)

>ENSG00000196159|ENSP00000335169|ENST00000335110|FAT4

ATGGTAACAACGGTAGTGGCAGTGGGTGATACCTTAGCTCAACCATTAGCTGCAGCTGAA
GTGTTTATTGTAGAAATAACACTTCAGGATATCAATGACAATCCACCAGTATTTCCAACG
GACATGCTGGATCTCACGGTAGAGGAGAACATTGGAGATGGCTCTAAGATTATGCAGCTG
ACAGCCATGGATGCTGATGAGGGTGCAAATGCTCTCGTCACATACACTATCATTAGTGGA
GCTGATGATAGTTTTCGCATCGACCCAGAATCCGGAGATCTGATAGCAACCAGGCGGTTG
GACAGGGAACGCCGCTCCAAATATTCACTGCTAGTTCGTGCTGATGATGGTCTTCAGTCC
TCGGATATGAGAATTAATATCACTGTCAGTGATGTGAATGACCATACACCCAAATTTTCC
AGACCCGTGTACTCTTTTGACATTCCTGAGGACACAATCCCTGGTTCTTTGGTAGCAGCC
ATTTTAGCCACGGATGATGACTCTGGTGTGAATGGAGAAATTACATATATTGTGAATGAA
GATGATGAAGATGGCATCTTTTTCCTGAATCCTATTACTGGGGTCTTTAATTTGACTCGA
TTATTAGATTATGAAGTACAGCAATATTATATCCTCACTGTTCGAGCAGAAGATGGTGGG
GGACAATTTACTACCATCAGAGTTTATTTCAATATTCTAGATGTAAATGATAATCCACCT
ATTTTCAGCTTGAATTCATACAGCACATCTTTAATGGAGAATCTACCTGTGGGATCTACT
GTTCTTGTGTTTAATGTTACTGATGCAGATGATGGCATCAACTCTCAATTGACTTATAGC
ATTGCTTCAGGTGATAGCCTTGGGCAGTTTACTGTTGACAAGAATGGTGTACTCAAAGTC
CTAAAAGCTTTGGATCGGGAAAGTCAGTCCTTCTACAACTTGGTTGTTCAAGTGCATGAC
CTGCCACAGATTCCAGCCTCCAGATTCACAAGCACTGCTCAAGTCTCCATTATTTTGTTG
GATGTAAATGATAACCCACCGACATTTCTTTCCCCTAAATTGACATACATTCCAGAAAAT
ACACCTATTGATACTGTTGTTTTCAAAGCTCAAGCAACTGACCCAGATAGTGGCCCAAAC
AGCTATATTGAGTACACTCTGCTGAACCCTTTGGGAAACAAGTTCAGTATTGGGACCATT
GATGGTGAAGTGAGGCTCACTGGAGAACTGGACAGAGAAGAAGTTTCTAATTATACTCTA
ACAGTGGTGGCTACAGACAAAGGTCAACCATCTCTCTCTTCATCTACAGAGGTTGTAGTT
ATGGTACTTGACATCAATGATAACAACCCCATCTTTGCACAAGCTTTGTATAAAGTGGAG
ATTAATGAAAACACACTTACTGGAACAGATATAATACAAGTGTTCGCAGCAGATGGAGAT
GAAGGCACAAATGGACAGGTTCGCTATGGCATTGTTAATGGTAATACCAATCAGGAATTT
CGGATAGACTCTGTCACAGGTGCCATCACTGTCGCTAAACCTTTGGATAGAGAAAAGACC
CCTACCTACCATTTAACTGTTCAGGCAACAGATCGAGGCAGCACACCCAGAACTGATACC
TCCACGGTCAGCATTGTTCTACTGGATATTAATGACTTTGTTCCTGTATTTGAGCTATCT
CCATATTCTGTAAATGTCCCTGAGAATTTAGGGACACTACCCAGAACAATTCTTCAGGTG
GTGGCAAGAGATGATGATCGAGGATCTAACAGCAAACTCTCATATGTTCTGTTTGGTGGT
AATGAAGACAATGCTTTTACTCTCTCAGCCAGTGGAGAACTTGGAGTAACACAGAGTCTG
GATCGGGAAACAAAAGAGCGCTTTGTCTTAATGATTACAGCTACAGATTCAGGATCCCCT
GCCTTGACTGGAACTGGAACAATCAACGTCATAGTAGATGATGTCAATGACAATGTCCCC
ACATTTGCCAGTAAAGCGTATTTCACAACAATTCCTGAGGATGCACCAACTGGAACAGAT
GTTTTATTGGTAAATGCCTCAGATGCTGATGCTTCAAAGAATGCAGTTATAAGGATCATC
GGTGGAAACTCTCAGTTCACGATCAACCCATCGACAGGACAAATCATCACCAGCGCATTG
TTAGATAGGGAAACAAAAGATAATTATACTTTGGTAGTGGTCTGCAGTGATGCGGGATCC
CCAGAGCCTCTTTCCAGTTCCACCAGTGTGCTTGTCACTGTGACTGATGTCAATGACAAT
CCACCAAGATTTCAGCATCACCCATATGTCACTCACATCCCATCTCCTACTCTTCCAGGT
TCCTTTGTCTTTGCGGTTACAGTCACAGATGCTGATATTGGACCAAATTCTGAACTGCAT
TATTCTCTTTCGGGTAGAAATTCTGAAAAATTTCACATTGACCCACTGAGGGGAGCCATT
ATGGCCGCCGGACCACTAAACGGAGCTTCAGAAGTGACATTTTCTGTGCATGTAAAAGAT
GGTGGCTCATTTCCAAAGACAGATTCTACAACAGTGACTGTTAGATTCGTGAATAAGGCC
GATTTCCCTAAAGTGAGAGCCAAAGAACAAACGTTCATGTTTCCTGAAAACCAACCAGTC
AGCTCTCTTGTCACCACCATCACAGGATCCTCTTTAAGAGGAGAACCTATGTCATATTAT
ATCGCAAGTGGGAATCTTGGCAATACTTTCCAGATTGATCAGTTAACAGGGCAGGTGTCT
ATTAGTCAACCTCTGGATTTTGAAAAGATACAAAAATATGTTGTATGGATAGAGGCCAGA
GACGGTGGTTTCCCTCCTTTCTCCTCTTACGAGAAACTTGATATAACAGTATTAGATGTC
AATGATAATGCCCCAATTTTTAAGGAAGACCCATTTATATCTGAAATATTGGAAAACCTT
TCCCCTCGAAAAATACTTACTGTTTCGGCAATGGACAAGGACAGTGGACCCAATGGACAG
TTAGATTATGAAATTGTTAATGGCAACATGGAAAATAGTTTCAGTATCAATCATGCTACT
GGTGAAATTAGAAGCGTTAGACCTTTGGACAGGGAAAAAGTATCTCATTATGTCCTAACC
ATAAAATCATCAGACAAAGGGTCCCCGTCTCAGAGTACTTCAGTAAAAGTCATGATTAAC
ATTTTAGATGAAAATGATAATGCCCCTAGGTTTTCTCAGATATTTAGTGCCCATGTTCCT
GAAAATTCCCCCTTAGGATACACAGTTACCCGTGTCACAACTTCTGATGAAGACATTGGG

FIG 5B. (SEQ ID NO. 6) CONT.

ATCAATGCAATTAGTAGATATTCTATAATGGATGCAAGTCTTCCATTTACAATTAATCCC
AGCACAGGGGATATTGTCATAAGCAGACCTTTAAATAGGGAAGATACAGACCGTTACAGA
ATTCGAGTTTCCGCACATGATTCTGGGTGGACTGTAAGTACAGATGTCACAATATTTGTG
ACAGACATCAATGACAATGCTCCAAGATTTAGCAGAACTTCCTATTATTTAGATTGCCCT
GAACTTACTGAGATTGGCTCCAAAGTAACTCAGGTATTTGCAACAGATCCTGATGAGGGA
TCAAATGGACAAGTGTTTTATTTCATAAAATCCCAATCAGAATATTTCAGGATTAATGCC
ACCACTGGAGAGATTTTCAATAAACAGATCTTAAAATACCAAAATGTCACTGGCTTCAGT
AATGTGAATATCAACAGGCATAGTTTTATAGTGACATCTTCAGATCGAGGTAAACCTTCC
TTAATTAGTGAGACAACAGTTACCATCAATATAGTGGACAGTAATGACAATGCACCTCAA
TTTCTTAAAAGTAAATATTTCACTCCAGTCACCAAAAATGTTAAGGTTGGTACGAAGTTA
ATCAGAGTTACAGCAATAGATGACAAAGATTTTGGACTGAATTCAGAAGTGGAGTATTTC
ATTTCTAATGATAACCATTTAGGAAAATTTAAGTTGGACAATGATACGGGGTGGATTTCA
GTAGCATCCTCCCTGATTTCTGACTTGAACCAAAACTTTTTTATCACAGTCACTGCAAAG
GATAAGGGAAACCCTCCACTTTCTTCCCAAGCAACTGTTCACATAACTGTCACTGAGGAA
AACTACCATACACCTGAATTCTCTCAAAGCCACATGAGTGCAACCATCCCTGAGAGCCAT
AGCATTGGGTCCATTGTCAGAACTGTTTCTGCAAGAGATAGAGATGCAGCGATGAATGGC
TTGATTAAGTACAGCATTTCTTCAGGAAATGAAGAAGGCATTTTTGCAATCAATTCTTCT
ACAGGTATATTAACACTAGCCAAAGCTCTTGATTATGAGCTATGCCAGAAACACGAAATG
ACGATTAGTGCTATAGATGGAGGATGGGTTGCAAGAACTGGTTACTGCAGTGTGACCGTA
AATGTGATTGATGTGAATGATAATTCTCCAGTATTCCTCTCTGATGACTATTTCCCTACT
GTTTTGGAAAATGCCCCAAGTGGAACAACAGTTATCCACCTAAATGCAACAGATGCTGAC
TCTGGAACAAATGCTGTGATTGCGTATACTGTACAGTCATCTGACAGTGACCTCTTTGTC
ATTGACCCTAACACAGGAGTCATAACCACTCAAGGCTTCTTGGATTTTGAAACCAAGCAG
AGCTACCATCTTACTGTGAAAGCCTTCAATGTCCCCGATGAGGAAAGGTGTAGCTTTGCC
ACTGTTAATATACAATTAAAAGGGACAAATGAATATGTGCCCCGTTTTGTTTCCAAACTT
TACTATTTTGAAATCTCAGAAGCAGCTCCTAAAGGTACTATTGTTGGAGAAGTGTTTGCT
AGCGACCGTGATTTGGGCACTGATGGGGAGGTACACTATTTGATTTTTGGTAATAGTCGA
AAGAAGGGTTTCCAGATCAATAAGAAGACTGGACAGATTTATGTTTCTGGAATTCTTGAT
CGAGAAAAAGAAGAAAGGGTGTCTTTGAAGGTATTGGCCAAGAACTTTGGCAGCATTAGA
GGTGCAGATATAGATGAGGTCACTGTAAATGTCACCGTGCTTGATGCAAATGACCCACCC
ATTTTTACTCTAAACATCTACAGTGTGCAGATCAGTGAAGGGGTCCCAATAGGAACTCAT
GTGACCTTTGTCAGTGCCTTTGACTCAGACTCCATCCCCAGCTGGAGCAGGTTTTCTTAC
TTCATCGGATCAGGGAATGAAAATGGTGCCTTTTCTATTAATCCGCAGACAGGACAGATC
ACCGTTACTGCAGAATTAGATCGAGAAACCCTTCCCATCTATAATCTCTCAGTTTTGGCT
GTTGATTCAGGGACCCCCTCAGCTACAGGTAGTGCCTCTTTATTAGTCACCCTGGAAGAT
ATAAATGATAACGGGCCCATGCTGACTGTCAGTGAAGGAGAAGTCATGGAAAACAAACGG
CCAGGCACTTTGGTGATGACCCTTCAGTCCACTGACCCTGATCTCCCTCCAAATCAAGGT
CCCTTTACTTATTACTTGCTGAGCACAGGTCCTGCCACCAGTTATTTCAGTCTGAGCACT
GCTGGAGTTCTGAGCACAACCAGAGAGATTGACAGAGAGCAGATTGCAGACTTCTATCTG
TCTGTGGTTACCAAGGATTCTGGTGTTCCTCAAATGTCTTCCACAGGAACTGTGCATATC
ACAGTTATAGACCAAAATGACAATCCTTCACAGTCTCGGACGGTGGAGATATTTGTTAAT
TATTATGGTAACTTGTTTCCCGGTGGGATTTTAGGCTCTGTGAAGCCACAGGATCCAGAT
GTGTTAGACAGCTTCCACTGCTCCCTTACTTCAGGAGTTACCAGCCTCTTCAGTATTCCA
GGGGGTACTTGTGATCTGAATTCCCAGCCAAGGTCCACAGATGGCACGTTTGATCTGACT
GTCCTTAGCAATGATGGAGTTCACAGCACAGTCACGAGCAACATCCGAGTTTTCTTTGCT
GGATTTTCCAATGCCACAGTGGATAACAGCATCTTACTTCGTCTCGGCGTACCAACAGTA
AAGGACTTCTTGACCAACCACTATCTTCATTTTTTACGCATTGCCAGCTCACAGCTGACA
GGCTTAGGGACTGCTGTGCAACTGTACAGTGCATATGAAGAGAACAATAGAACGTTTCTT
TTGGCAGCTGTGAAGCGAAATCATAATCAGTATGTGAATCCCAGTGGCGTAGCCACCTTC
TTTGAAAGCATCAAAGAGATCCTTCTCCGGCAGAGTGGAGTAAAGGTGGAATCTGTGGAT
CATGACTCCTGTGTGCATGGCCCATGTCAGAATGGAGGGAGCTGTCTACGAAGATTGGCT
GTGAGCTCCGTATTAAAAAGCCGTGAGAGTCTTCCAGTCATCATCGTGGCAAATGAACCT
CTGCAGCCTTTCTTATGCAAGTGTCTGCCAGGATATGCGGGTAGCTGGTGTGAAATAGAT
ATAGATGAATGTCTTCCATCACCTTGCCACAGTGGTGGAACCTGTCACAATTTAGTGGGA
GGATTTTCATGCAGCTGCCCAGATGGCTTCACTGGTAGGGCGTGTGAGAGAGATATCAAT
GAGTGCCTGCAGAGTCCTTGCAAGAATGGTGCCATCTGCCAGAATTTTCCAGGAAGCTTC
AACTGTGTTTGCAAAACTGGATACACAGGTGTCTTTGGAAAACACTGCGAGTTGAACAGT
TATGGATTTGAGGAGTTATCATACATGGAATTTCCAAGCTTGGACCCCAATAACAACTAT
ATTTATGTCAAATTTGCCACGATTAAAAGTCATGCCTTATTGCTTTACAACTATGACAAC
CAGACAGGCGACCGGGCTGAGTTTTTGGCCCTTGAAATTGCCGAAGAAAGACTAAGATTC
TCTTATAATTTAGGCAGTGGTACATATAAGCTCACCACCATGAAGAAGGTGTCAGATGGA
CATTTTCACACTGTGATTGCCAGGAGAGCAGGAATGGCAGCCTCCTTAACTGTGGACTCC
TGTTCTGAGAACCAAGAGCCAGGATATTGTACTGTCAGTAATGTGGCAGTTTCAGATGAC
TGGACTCTTGATGTTCAGCCAAATAGAGTTACAGTTGGAGGTATCAGATCTCTAGAACCA
ATCCTTCAGAGAAGAGGACACGTGGAAAGCCATGATTTTGTTGGGTGTATAATGGAGTTT
GCAGTCAATGGAAGGCCTCTGGAACCCAGCCAAGCTTTGGCAGCACAAGGCATCCTAGAT
CAGTATGGCGATTTTATTTCTTACTGTTTTAAAGAAAAAAAATGCAAAAAAGTATGCTTC
ACTGTTACTCCTGACACTGCCTTATCATTAGAAGGCAAAGGGCGCTTGGACTACCACATG

FIG 5B. (SEQ ID NO. 6) CONT.

AGTCAGAATGAGAAGCGGGAATATTTGTTAAGGCAAAGCTTACGAGGTGCCATGTTGGAG
CCTTTTGGTGTGAACAGTCTGGAAGTAAAATTTAGGACCAGAAGCGAGAATGGCGTTTTA
ATCCATATCCAAGAAAGCAGCAATTACACTACTGTGAAGATTAAGAATGGCAAAGTATAT
TTTACATCCGATGCAGGAATTGCTGGGAAAGTGGAGAGAAATATTCCTGAAGTATATGTT
GCAGACGGCCACTGGCACACTTTTCTAATTGGGAAAAATGGAACAGCAACAGTATTGTCT
GTTGACAGAATATATAACAGAGATATTATCCACCCTACTCAGGACTTCGGTGGCCTTGAT
GTGCTTACTATATCACTTGGAGGAATTCCACCCAATCAAGCACATCGAGATGCCCAAACA
GCAGGTTTTGATGGCTGCATTGCTTCTATGTGGTATGGTGGAGAAAGTCTTCCTTTCAGC
GGGAAGCATAGCTTGGCCTCCATCTCAAAAACAGATCCCTCAGTGAAGATTGGCTGCCGT
GGCCCGAACATTTGTGCCAGCAACCCCTGCTGGGGTGATTTGCTGTGCATTAATCAGTGG
TATGCCTACAGGTGTGTCCCTCCTGGGGACTGTGCCTCCCACCCGTGCCAGAATGGTGGC
AGCTGTGAGCCAGGCCTGCACTCCGGCTTCACCTGTAGCTGCCCAGACTCGCACACGGGA
AGGACCTGTGAGATGGTGGTGGCCTGTCTTGGCGTCCTCTGTCCTCAGGGGAAGGTGTGC
AAAGCTGGAAGTCCTGCGGGGCATGTCTGTGTTCTGAGTCAGGGCCCTGAAGAGATCTCT
CTGCCTTTGTGGGCTGTGCCTGCCATCGTGGGCAGCTGCGCAACCGTCTTGGCCCTCCTG
GTCCTTAGCCTGATCCTGTGTAACCAGTGCAGGGGGAAGAAGGCCAAAAATCCCAAAGAG
GAGAAGAAACCGAAGGAGAAGAAGAAAAAGGGAAGTGAGAACGTTGCTTTTGATGACCCT
GACAATATCCCTCCCTATGGGGATGACATGACTGTGAGGAAGCAGCCTGAAGGGAACCCA
AAACCAGATATCATTGAAAGGGAAAACCCCTACCTTATCTATGATGAAACTGATATTCCT
CACAACTCAGAAACCATCCCCAGCGCCCCTTTGGCATCTCCAGAGCAGGAGATAGAGCAC
TATGACATTGACAACGCCAGCAGCATCGCCCCTTCGGATGCAGACATCATTCAACACTAC
AAGCAGTTCCGCAGCCACACACCAAAATTTTCAATCCAGAGGCACAGTCCCCTAGGCTTT
GCAAGGCAATCCCCCATGCCCTTAGGAGCAAGCAGTTTGACTTACCAGCCTTCATATGGT
CAAGGTTTGAGAACCAGCTCCCTAAGCCACTCAGCATGCCCAACTCCCAACCCTCTGTCT
CGACACAGTCCAGCCCCTTTCTCCAAATCTTCTACGTTCTATAGAAACAGCCCAGCAAGG
GAATTGCATCTTCCTATAAGGGATGGTAATACTTTGGAAATGCATGGTGACACCTGCCAA
CCTGGCATTTTCAACTATGCCACAAGGCTGGGAAGGAGAAGCAAGAGTCCTCAGGCCATG
GCATCACATGGTTCTAGACCAGGGAGTCGCCTAAAGCAGCCGATTGGGCAGATTCCACTG
GAATCTTCTCCTCCAGTCGGACTTTCTATTGAAGAAGTGGAGAGGCTCAACACACCTCGC
CCTAGAAACCCAAGTATCTGCAGTGCAGACCATGGGAGGTCTTCTTCAGAGGAGGACTGC
AGAAGGCCACTGTCTAGAACAAGGAATCCAGCGGATGGCATTCCAGCTCCAGAATCCTCT
TCTGATAGTGACTCCCATGAATCTTTCACTTGCTCAGAAATGGAATATGACAGGGAGAAG
CCAATGGTATATACTTCCAGAATGCCCAAATTATCTCAAGTCAATGAATCTGATGCAGAT
GATGAAGATAATTATGGAGCCAGACTGAAGCCTCGAAGGTACCACGGTCGCAGGGCCGAG
GGAGGACCTGTGGGCACCCAGGCAGCAGCACCAGGCACTGCTGACAACACACTGCCCATG
AAGCTAGGGCAGCAAGCAGGGACTTTCAACTGGGACAACCTTTTGAACTGGGGCCCTGGC
TTTGGCCATTATGTAGATGTTTTTAAAGATTTGGCATCTCTTCCAGAAAAAGCAGCAGCA
AATGAAGAAGGCAAAGCTGGGACAACTAAACCAGTCCCCAAAGATGGGGAAGCAGAACAG
TATGTGTGA

Figure 5C (SEQ ID NO:7)

>ENSG00000196159||ENST00000509444|FAT4

GTGATGTTCACAGAAAATTTGAAATATTTATTAGCTAGACTAGTTGTATTCTTTCCAACA
TTGTTGTATGATCTTTCTTGTAACGTTTTCTTGCATTTCTACCTCAGTTTTTTAATTATA
GTAAATAGAAGTTACGATATTAAAACTATATGACATATCCCTATTTCTGCTTTCTGCTTT
AGTTATAGGATCATCGGTGGAAACTCTCAGTTCACGATCAACCCATCGACAGGACAAATC
ATCACCAGCGCATTGTTAGATAGGGAAACAAAAGATAATTATACTTTGGTAGTGGTCTGC
AGTGATGCGGGATCCCCAGAGCCTCTTTCCAGTTCCACCAGTGTGCTTGTCACTGTGACT
GATGTCAATGACAATCCACCAAGATTTCAGCATCACCCATATGTCACTCACATCCCATCT
CCTACTCTTCCAGGTTCCTTTGTCTTTGCGGTTACAGTCACAGATGCTGATATTGGACCA
AATTCTGAACTGCATTATTCTCTTTCGGGTAGAAATTCTGAAAAATTTCACATTGACCCA
CTGAGGGGAGC

Figure 6A (SEQ ID NO: 8)

>ENSG00000196159|ENSP00000377862|ENST00000394329|FAT4

MDLAPDRATGRPWLPLHTLSVSQLLRVFWLLSLLPGQAWVHGAEPRQVFQVLEEQPPGTL
VGTIQTRPGFTYRLSESHALFAINSSTGALYTTSTIDRESLPSDVINLVVLSSAPTYPTE
VRVLVRDLNDNAPVFPDPSIVVTFKEDSSSGRQVILDTATDSDIGSNGVDHRSYRIIRGN
EAGRFRLDITLNPSGEGAFLHLVSKGGLDREVTPQYQLLVEVEDKGEPKRRGYLQVNVTV
QDINDNPPVFGSSHYQAGVPEDAVVGSSVLQVAAADADEGTNADIRYRLQDEGTPFQMDP
ETGLITVREPLDFEARRQYSLTVQAMDRGVPSLTGRAEALIQLLDVNDNDPVVKFRYFPA
TSRYASVDENAQVGTVVALLTVTDADSPAANGNISVQILGGNEQRHFEVQSSKVPNLSLI
KVASALDRERIPSYNLTVSVSDNYGAPPGAAVQARSSVASLVIFVNDINDHPPVFSQQVY
RVNLSEEAPPGSYVSGISATDGDSGLNANLRYSIVSGNGLGWFHISEHSGLVTTGSSGGL
DRELASQIVLNISARDQGVHPKVSYAQLVVTLLDVNDEKPVFSQPEGYDVSVVENAPTGT
ELLMLRATDGDLGDNGTVRFSLQEAETDRRSFRLDPVSGRLSTISSLDREEQAFYSLLVL
ATDLGSPPQSSMARINVSLLDINDNSPVFYPVQYFAHIKENEPGGSYITTVSATDPDLGT
NGTVKYSISAGDRSRFQVNAQSGVISTRMALDREEKTAYQLQIVATDGGNLQSPNQAIVT
ITVLDTQDNPPVFSQVAYSFVVFENVALGYHVGSVSASTMDLNSNISYLITTGDQKGMFA
INQVTGQLTTANVIDREEQSFYQLKVVASGGTVTGDTMVNITVKDLNDNSPHFLQAIESV
NVVENWQAGHSIFQAKAVDPDEGVNGMVLYSLKQNPKNLFAINEKNGTISLLGPLDVHAG
SYQIEILASDMGVPQLSSSVILTVYVHDVNDNSPVFDQLSYEVTLSESEPVNSRFFKVQA
SDKDSGANGEIAYTIAEGNTGDAFGIFPDGQLYIKSELDRELQDRYVLMVVASDRAVEPL
SATVNVTVILEDVNDNRPLFNSTNYTFYFEEEQRAGSFVGKVSAVDKDFGPNGEVRYSFE
MVQPDFELHAISGEITNTHQFDRESLMRRRGTAVFSFTVIATDQGIPQPLKDQATVHVYM
KDINDNAPKFLKDFYQATISESAANLTQVLRVSASDVDEGNNGLIHYSIIKGNEERQFAI
DSTSGQVTLIGKLDYEATPAYSLVIQAVDSGTIPLNSTCTLNIDILDENDNTPSFPKSTL
FVDVLENMRIGELVSSVTATDSDSGDNADLYYSITGTNNHGTFSISPNTGSIFLAKKLDF
ETQSLYKLNITAKDQGRPPRSSTMSVVIHVRDFNDNPPSFPPGDIFKSIVENIPIGTSVI
SVTAHDPDADINGQLSYTIIQQMPRGNHFTIDEVKGTIYTNAEIDREFANLFELTVKAND
QAVPIETRRYALKNVTILVTDLNDNVPMFISQNALAADPSAVIGSVLTTIMAADPDEGAN
GEIEYEIINGDTDTFIVDRYSGDLRVASALVPSQLIYNLIVSATDLGPERRKSTTELTII
LQGLDGPVFTQPKYITILKEGEPIGTNVISIEAASPRGSEAPVEYYIVSVRCEEKTVGRL
FTIGRHTGIIQTAAILDREQGACLYLVDVYAIEKSTAFPRTQRAEVEITLQDINDNPPVF
PTDMLDLTVEENIGDGSKIMQLTAMDADEGANALVTYTIISGADDSFRIDPESGDLIATR
RLDRERRSKYSLLVRADDGLQSSDMRINITVSDVNDHTPKFSRPVYSFDIPEDTIPGSLV
AAILATDDDSGVNGEITYIVNEDDEDGIFFLNPITGVFNLTRLLDYEVQQYYILTVRAED
GGGQFTTIRVYFNILDVNDNPPIFSLNSYSTSLMENLPVGSTVLVFNVTDADDGINSQLT
YSIASGDSLGQFTVDKNGVLKVLKALDRESQSFYNLVVQVHDLPQIPASRFTSTAQVSII
LLDVNDNPPTFLSPKLTYIPENTPIDTVVFKAQATDPDSGPNSYIEYTLLNPLGNKFSIG
TIDGEVRLTGELDREEVSNYTLTVVATDKGQPSLSSSTEVVVMVLDINDNNPIFAQALYK
VEINENTLTGTDIIQVFAADGDEGTNGQVRYGIVNGNTNQEFRIDSVTGAITVAKPLDRE
KTPTYHLTVQATDRGSTPRTDTSTVSIVLLDINDFVPVFELSPYSVNVPENLGTLPRTIL
QVVARDDDRGSNSKLSYVLFGGNEDNAFTLSASGELGVTQSLDRETKERFVLMITATDSG
SPALTGTGTINVIVDDVNDNVPTFASKAYFTTIPEDAPTGTDVLLVNASDADASKNAVIR
IIGGNSQFTINPSTGQIITSALLDRETKDNYTLVVVCSDAGSPEPLSSSTSVLVTVTDVN
DNPPRFQHHPYVTHIPSPTLPGSFVFAVTVTDADIGPNSELHYSLSGRNSEKFHIDPLRG
AIMAAGPLNGASEVTFSVHVKDGGSFPKTDSTTVTVRFVNKADFPKVRAKEQTFMFPENQ
PVSSLVTTITGSSLRGEPMSYYIASGNLGNTFQIDQLTGQVSISQPLDFEKIQKYVVWIE
ARDGGFPPFSSYEKLDITVLDVNDNAPIFKEDPFISEILENLSPRKILTVSAMDKDSGPN
GQLDYEIVNGNMENSFSINHATGEIRSVRPLDREKVSHYVLTIKSSDKGSPSQSTSVKVM
INILDENDNAPRFSQIFSAHVPENSPLGYTVTRVTTSDEDIGINAISRYSIMDASLPFTI
NPSTGDIVISRPLNREDTDRYRIRVSAHDSGWTVSTDVTIFVTDINDNAPRFSRTSYYLD
CPELTEIGSKVTQVFATDPDEGSNGQVFYFIKSQSEYFRINATTGEIFNKQILKYQNVTG
FSNVNINRHSFIVTSSDRGKPSLISETTVTINIVDSNDNAPQFLKSKYFTPVTKNVKVGT
KLIRVTAIDDKDFGLNSEVEYFISNDNHLGKFKLDNDTGWISVASSLISDLNQNFFITVT
AKDKGNPPLSSQATVHITVTEENYHTPEFSQSHMSATIPESHSIGSIVRTVSARDRDAAM
NGLIKYSISSGNEEGIFAINSSTGILTLAKALDYELCQKHEMTISAIDGGWVARTGYCSV
TVNVIDVNDNSPVFLSDDYFPTVLENAPSGTTVIHLNATDADSGTNAVIAYTVQSSDSDL
FVIDPNTGVITTQGFLDFETKQSYHLTVKAFNVPDEERCSFATVNIQLKGTNEYVPRFVS
KLYYFEISEAAPKGTIVGEVFASDRDLGTDGEVHYLIFGNSRKKGFQINKKTGQIYVSGI
LDREKEERVSLKVLAKNFGSIRGADIDEVTVNVTVLDANDPPIFTLNIYSVQISEGVPIG
THVTFVSAFDSDSIPSWSRFSYFIGSGNENGAFSINPQTGQITVTAELDRETLPIYNLSV
LAVDSGTPSATGSASLLVTLEDINDNGPMLTVSEGEVMENKRPGTLVMTLQSTDPDLPPN

FIG 6A. (SEQ ID NO. 8) CONT.

QGPFTYYLLSTGPATSYFSLSTAGVLSTTREIDREQIADFYLSVVTKDSGVPQMSSTGTV
HITVIDQNDNPSQSRTVEIFVNYYGNLFPGGILGSVKPQDPDVLDSFHCSLTSGVTSLFS
IPGGTCDLNSQPRSTDGTFDLTVLSNDGVHSTVTSNIRVFFAGFSNATVDNSILLRLGVP
TVKDFLTNHYLHFLRIASSQLTGLGTAVQLYSAYEENNRTFLLAAVKRNHNQYVNPSGVA
TFFESIKEILLRQSGVKVESVDHDSCVHGPCQNGGSCLRRLAVSSVLKSRESLPVIIVAN
EPLQPFLCKCLPGYAGSWCEIDIDECLPSPCHSGGTCHNLVGGFSCSCPDGFTGRACERD
INECLQSPCKNGAICQNFPGSFNCVCKTGYTGKMCESSVNYCECNPCFNGGSCQSGVDSY
YCHCPFGVFGKHCELNSYGFEELSYMEFPSLDPNNNYIYVKFATIKSHALLLYNYDNQTG
DRAEFLALEIAEERLRFSYNLGSGTYKLTTMKKVSDGHFHTVIARRAGMAASLTVDSCSE
NQEPGYCTVSNVAVSDDWTLDVQPNRVTVGGIRSLEPILQRRGHVESHDFVGCIMEFAVN
GRPLEPSQALAAQGILDQCPRLEGACTRSPCQHGGTCMDYWSWQQCHCKEGLTGKYCEKS
VTPDTALSLEGKGRLDYHMSQNEKREYLLRQSLRGAMLEPFGVNSLEVKFRTRSENGVLI
HIQESSNYTTVKIKNGKVYFTSDAGIAGKVERNIPEVYVADGHWHTFLIGKNGTATVLSV
DRIYNRDIIHPTQDFGGLDVLTISLGGIPPNQAHRDAQTAGFDGCIASMWYGGESLPFSG
KHSLASISKTDPSVKIGCRGPNICASNPCWGDLLCINQWYAYRCVPPGDCASHPCQNGGS
CEPGLHSGFTCSCPDSHTGRTCEMVVACLGVLCPQGKVCKAGSPAGHVCVLSQGPEEISL
PLWAVPAIVGSCATVLALLVLSLILCNQCRGKKAKNPKEEKKPKEKKKKGSENVAFDDPD
NIPPYGDDMTVRKQPEGNPKPDIIERENPYLIYDETDIPHNSETIPSAPLASPEQEIEHY
DIDNASSIAPSDADIIQHYKQFRSHTPKFSIQRHSPLGFARQSPMPLGASSLTYQPSYGQ
GLRTSSLSHSACPTPNPLSRHSPAPFSKSSTFYRNSPARELHLPIRDGNTLEMHGDTCQP
GIFNYATRLGRRSKSPQAMASHGSRPGSRLKQPIGQIPLESSPPVGLSIEEVERLNTPRP
RNPSICSADHGRSSSEEDCRRPLSRTRNPADGIPAPESSSDSDSHESFTCSEMEYDREKP
MVYTSRMPKLSQVNESDADDEDNYGARLKPRRYHGRRAEGGPVGTQAAAPGTADNTLPMK
LGQQAGTFNWDNLLNWGPGFGHYVDVFKDLASLPEKAAANEEGKAGTTKPVPKDGEAEQY
V*

Figure 6B (SEQ ID NO: 9)

>ENSG00000196159|ENSP00000335169|ENST00000335110|FAT4

MVTTVVAVGDTLAQPLAAAEVFIVEITLQDINDNPPVFPTDMLDLTVEENIGDGSKIMQL
TAMDADEGANALVTYTIISGADDSFRIDPESGDLIATRRLDRERRSKYSLLVRADDGLQS
SDMRINITVSDVNDHTPKFSRPVYSFDIPEDTIPGSLVAAILATDDDSGVNGEITYIVNE
DDEDGIFFLNPITGVFNLTRLLDYEVQQYYILTVRAEDGGGQFTTIRVYFNILDVNDNPP
IFSLNSYSTSLMENLPVGSTVLVFNVTDADDGINSQLTYSIASGDSLGQFTVDKNGVLKV
LKALDRESQSFYNLVVQVHDLPQIPASRFTSTAQVSIILLDVNDNPPTFLSPKLTYIPEN
TPIDTVVFKAQATDPDSGPNSYIEYTLLNPLGNKFSIGTIDGEVRLTGELDREEVSNYTL
TVVATDKGQPSLSSSTEVVVMVLDINDNNPIFAQALYKVEINENTLTGTDIIQVFAADGD
EGTNGQVRYGIVNGNTNQEFRIDSVTGAITVAKPLDREKTPTYHLTVQATDRGSTPRTDT
STVSIVLLDINDFVPVFELSPYSVNVPENLGTLPRTILQVVARDDDRGSNSKLSYVLFGG
NEDNAFTLSASGELGVTQSLDRETKERFVLMITATDSGSPALTGTGTINVIVDDVNDNVP
TFASKAYFTTIPEDAPTGTDVLLVNASDADASKNAVIRIIGGNSQFTINPSTGQIITSAL
LDRETKDNYTLVVVCSDAGSPEPLSSSTSVLVTVTDVNDNPPRFQHHPYVTHIPSPTLPG
SFVFAVTVTDADIGPNSELHYSLSGRNSEKFHIDPLRGAIMAAGPLNGASEVTFSVHVKD
GGSFPKTDSTTVTVRFVNKADFPKVRAKEQTFMFPENQPVSSLVTTITGSSLRGEPMSYY
IASGNLGNTFQIDQLTGQVSISQPLDFEKIQKYVVWIEARDGGFPPFSSYEKLDITVLDV
NDNAPIFKEDPFISEILENLSPRKILTVSAMDKDSGPNGQLDYEIVNGNMENSFSINHAT
GEIRSVRPLDREKVSHYVLTIKSSDKGSPSQSTSVKVMINILDENDNAPRFSQIFSAHVP
ENSPLGYTVTRVTTSDEDIGINAISRYSIMDASLPFTINPSTGDIVISRPLNREDTDRYR
IRVSAHDSGWTVSTDVTIFVTDINDNAPRFSRTSYYLDCPELTEIGSKVTQVFATDPDEG
SNGQVFYFIKSQSEYFRINATTGEIFNKQILKYQNVTGFSNVNINRHSFIVTSSDRGKPS
LISETTVTINIVDSNDNAPQFLKSKYFTPVTKNVKVGTKLIRVTAIDDKDFGLNSEVEYF
ISNDNHLGKFKLDNDTGWISVASSLISDLNQNFFITVTAKDKGNPPLSSQATVHITVTEE
NYHTPEFSQSHMSATIPESHSIGSIVRTVSARDRDAAMNGLIKYSISSGNEEGIFAINSS
TGILTLAKALDYELCQKHEMTISAIDGGWVARTGYCSVTVNVIDVNDNSPVFLSDDYFPT
VLENAPSGTTVIHLNATDADSGTNAVIAYTVQSSDSDLFVIDPNTGVITTQGFLDFETKQ
SYHLTVKAFNVPDEERCSFATVNIQLKGTNEYVPRFVSKLYYFEISEAAPKGTIVGEVFA
SDRDLGTDGEVHYLIFGNSRKKGFQINKKTGQIYVSGILDREKEERVSLKVLAKNFGSIR
GADIDEVTVNVTVLDANDPPIFTLNIYSVQISEGVPIGTHVTFVSAFDSDSIPSWSRFSY
FIGSGNENGAFSINPQTGQITVTAELDRETLPIYNLSVLAVDSGTPSATGSASLLVTLED
INDNGPMLTVSEGEVMENKRPGTLVMTLQSTDPDLPPNQGPFTYYLLSTGPATSYFSLST
AGVLSTTREIDREQIADFYLSVVTKDSGVPQMSSTGTVHITVIDQNDNPSQSRTVEIFVN
YYGNLFPGGILGSVKPQDPDVLDSFHCSLTSGVTSLFSIPGGTCDLNSQPRSTDGTFDLT
VLSNDGVHSTVTSNIRVFFAGFSNATVDNSILLRLGVPTVKDFLTNHYLHFLRIASSQLT
GLGTAVQLYSAYEENNRTFLLAAVKRNHNQYVNPSGVATFFESIKEILLRQSGVKVESVD
HDSCVHGPCQNGGSCLRRLAVSSVLKSRESLPVIIVANEPLQPFLCKCLPGYAGSWCEID

FIG 6B. (SEQ ID NO. 9) CONT.

IDECLPSPCHSGGTCHNLVGGFSCSCPDGFTGRACERDINECLQSPCKNGAICQNFPGSF
NCVCKTGYTGVFGKHCELNSYGFEELSYMEFPSLDPNNNYIYVKFATIKSHALLLYNYDN
QTGDRAEFLALEIAEERLRFSYNLGSGTYKLTTMKKVSDGHFHTVIARRAGMAASLTVDS
CSENQEPGYCTVSNVAVSDDWTLDVQPNRVTVGGIRSLEPILQRRGHVESHDFVGCIMEF
AVNGRPLEPSQALAAQGILDQYGDFISYCFKEKKCKKVCFTVTPDTALSLEGKGRLDYHM
SQNEKREYLLRQSLRGAMLEPFGVNSLEVKFRTRSENGVLIHIQESSNYTTVKIKNGKVY
FTSDAGIAGKVERNIPEVYVADGHWHTFLIGKNGTATVLSVDRIYNRDIIHPTQDFGGLD
VLTISLGGIPPNQAHRDAQTAGFDGCIASMWYGGESLPFSGKHSLASISKTDPSVKIGCR
GPNICASNPCWGDLLCINQWYAYRCVPPGDCASHPCQNGGSCEPGLHSGFTCSCPDSHTG
RTCEMVVACLGVLCPQGKVCKAGSPAGHVCVLSQGPEEISLPLWAVPAIVGSCATVLALL
VLSLILCNQCRGKKAKNPKEEKKPKEKKKKGSENVAFDDPDNIPPYGDDMTVRKQPEGNP
KPDIIERENPYLIYDETDIPHNSETIPSAPLASPEQEIEHYDIDNASSIAPSDADIIQHY
KQFRSHTPKFSIQRHSPLGFARQSPMPLGASSLTYQPSYGQGLRTSSLSHSACPTPNPLS
RHSPAPFSKSSTFYRNSPARELHLPIRDGNTLEMHGDTCQPGIFNYATRLGRRSKSPQAM
ASHGSRPGSRLKQPIGQIPLESSPPVGLSIEEVERLNTPRPRNPSICSADHGRSSSEEDC
RRPLSRTRNPADGIPAPESSSDSDSHESFTCSEMEYDREKPMVYTSRMPKLSQVNESDAD
DEDNYGARLKPRRYHGRRAEGGPVGTQAAAPGTADNTLPMKLGQQAGTFNWDNLLNWGPG
FGHYVDVFKDLASLPEKAAANEEGKAGTTKPVPKDGEAEQYV*

Figure 7

Proxy SNPs (chromosome position/strand/rsidsequence)

chr4 126347460 + rs6842220

ATATTCCAGAAAGATCACATTTTGTCAATATTATTTGTGGGAATGTATGATAGAAAAGTTTGCCTTGTCTGTTAT
GATCAACATTTTTAATAATGAAAAT[C/T]GCTTGAAAACTTTTAAGGCCCCAATAATTCTATAAATCAAATCATG
CTAGAGTTGCCTTCAATTACCAGACATGAAATGCATTTGACTTAATTTTATTTT (SEQ ID NO:10)

chr4 126359002 + rs7656978

ACATTAAGAGTAGAACCTTGGGAATTAAGTTGTGTGGAATTGAATCCTGACTCTACTATTACTATTGCATTAGT
ATGGGCAAATTAACATTTCTGGACCC[A/G]GTTTTCAGTGGATTAAGCAGAGTAATAATGAAACTAACTTTAAA
GAGAGTAAGTAAAATAATTTAAGTGAGCTGGTTAGAATAGCACCAGGAACAAAAAA (SEQ ID NO:11)

chr4 126352482 + rs13141820

GAATTACAGCACAATGTGTATATCAGAAATATTCAGATCTTTCTTGAAATCTCACTGTAAGTCTTAAAATACCA
CATTTAAAAATGTCCAATTTACTATG[C/T]CTTCCATAAAGCTGTGAATTTTTAGAGAGCTAAATGTCTCATGTA
TTTTTACCACAAGTGAATCATTGAGATGAATTATTATTCAAAATATTTTCCTGAA (SEQ ID NO:12)

chr4 126353466 + rs10021618

GCAGTACCTTCCAGCTTCTTGTCAGTGGTAAAGACTCCAGGGCTGCTTTACATGGGTCACATCTCAGTGACATT
CCTCACTAGGTCTGTGGCCTTGAAAA[A/G]GCTACTTAAACTTTCTAAACTTGAGCTTACTCATATACCAAATG
GAGATGACAGCAGTGCTGATTTATGGGGATTAGATAAGACAGTTTATGTAAACTTC (SEQ ID NO:13)

chr4 126343279 + rs11931967

ATAAATGAAACATTCAACTGCTATTTTTCTTTCCCCAAATAAATAAATGTTTGAAAACATTTTTAAATGAAGCCA
AATTAAGTGGAATCAGTAATTTCAA[A/T]ATTGGTATTTTGAAAATAAGCTTAAATTTAGACATTGTTTAAATTT
AATTGTTAAATAAAGAAGATATAAAGAATTTGTTAGGCTTTATGCCTAGAAGAT (SEQ ID NO:14)

chr4 126349342 + rs28694074

FIG. 7 CONT.

CAGGAGTTCGAGACTAGCCTGACCGACAAGGTGAAACCCCGTCTCTACTAAAAACACAAAAATTAGCCAAGTA
TGGTGACACATGCCTGTAATCCCAGCT[A/G]CTTGGAAGGTTGAGCCAGGAGAATCGCTTGAACCCGGGAGG
CGGAGGTTGCAGTGAGCCGAGATCACACCGCTGCTCTTCAGCCTGGGCAACAAGAGCGA    (SEQ ID NO:15)

chr4    126357469    +    rs35589914

GGACGTGAGATCAAATGAAAGAGAGAAATCAGAATCATCTAAGTTTTCCACTCAAACACCTAGGCAGATCATG
ATATGATATCATTTACTGAAATGGGTA[A/G]CATTGAAGGAGGAACAGTTTTGTGAGAAGTCAGAAGTATTCT
ATTTGAATACAGTTTCAAATGACTGTTACTCATTCATTTAGAGATACCAGTTAGGAAG    (SEQ ID NO:16)

chr4    126359365    +    rs17803313

GCAGATGCTGTTTCTTAGACAGTATATAGAATATTACCAATCAGATATAGGGAAATTCTCTTGTATGAGATGTA
TAAATTCCTGAATATGAAGTTGAATG[C/T]TTACAAACTTGATCCTGTCTTCCATTGAGTCATTCATTTATTTCTA
TAATAAAGTAAATGCTGTGATGACCTGCTGTTTTTTTCTAGTGCATGTTAAAGA    (SEQ ID NO:17)

chr4    126353280    +    rs7677254

AGAAATTTAAAATCTATGCCAAGATTATTGTGCTCAAATGTCCCACAAACTTAAGCTGGCCAGTAGTGAAGGT
CCCTCCCTGTTGGGCCTCTTCACCTCC[C/T]GCCTGGTGCTCTTCTAGGCTCAGCGACAGAGCTGCTTGTCCAG
ACCCCCAAAGCAGCGCAGGAAGCAGCACTGTTCCCCCTACTGGCAGTACCTTCCAGC    (SEQ ID NO:18)

chr4    126345585    +    rs28453293

ATGGTTCTATAAGGGCTTCACCCCACTTCACTCTGCACATCTCATTTTTCTCTCTCCTGCTGCCTTGTGAATAAG
GACATGTTTGCTTCTGATTCTGCCA[C/T]GATTATAAGTTTCCTGAGGCCTCCCCAGCTCTGGGTTAATTGTGAG
TCAATTAAACCTCTTTCCTTTATAAATTGCCCAGTCCCAGGTATGGCCTTATAG    (SEQ ID NO:19)

chr4    126359456    +    rs1395241

AGTTGAATGTTTACAAACTTGATCCTGTCTTCCATTGAGTCATTCATTTATTTCTATAATAAAGTAAATGCTGTG
ATGACCTGCTGTTTTTTTCTAGTGC[A/G]TGTTAAAGATTCATTGCAAAATGCTATCCTATGCTTGTGAATTATG
CTTGTAAATTTGGTCTAGAAAAATTGTATTCATACTCTCAAACTGTTTTACAAA    (SEQ ID NO:20)

chr4    126361331    +    rs9307564

TATTCTTCTCATATCATCTTTTTTACTCCTAATATATTCTTTCTTTTACAATATCTGGTACATAACAGTGGTTGTCA
CTTAAATAAATGCATTGAATGAA[C/T]GATTTTAATATTCTCTGGAATGGCTGCTTTTACTCATTCTATTTTTACT
ACAACATTCTTGAAAGCTTCACAACCTGTTTTCTCTGACCATTTATTCCTG    (SEQ ID NO:21)

FIG. 7 CONT.

chr4 126361095 + rs9307563

TTTATTTGCCTCCCATGGCCTAGGAAAGTCATTTTAGTGCCTCAAAGGCTTAGTTTCTGCATCAATAAAAATGA
ACATAAAAATTTATACTTTACAGTTT[A/G]TGAGACAAACATTTACTAACCACCTACTATGTATCAAACAGTATG
TATGGAATCAGTTAATATCCATAAATGTCTCTGGCATAATTATTAGGACATAGAA (SEQ ID NO:22)

chr4 126319493 + rs7697927

GATACGAGTGGAAATAGAAAGAAAAGATGTATTTTTCTTCCCATTAAAGGTTGAGCGTGGACTTTAAAGGGG
GAAATTCTGAGTGATTCTTAAAACAACA[G/T]GTGAACTTTTTTATTTCCCCCAGACATTAGTTGCCAATATGTA
AACATTTCAGCAAGAAATTTTATACCACCTCCTCTGTTTGTCAGGCAGCATTTAATG (SEQ ID NO:23)

chr4 126333397 + rs4623022

TGAGCTTAGTATTTTTCAGTATACTTCAAATATTCCGGGAGAAATTTGAGTTTTGCTATGTCTGCATGTATTTTT
TAGATGTAGTGTATGTGGCCAAAGT[C/T]ACTTTTTAGACTTGTCAGAAATGAAAAGTTATTTTCTTTACAGTA
AAGTAAATGCAGATGGATTCCATGACCTGTAATTGCAGCAATTAATTTTCAGTTC (SEQ ID NO:24)

chr4 126343978 + rs2136345

AGTAGGGCACTGCTGTAAAAATACCAAAGTGACTTTGGAACTGGGTAACTGGCAGAGACTGGAACAGTTTGG
AGGGTTCAGAATAAGAGAGAAAAATGTT[C/G]GAAAGTTTGGAACTTCCTACAGACTTTTTGAATGGCTTTGA
CCAAAATGCTGAGGTGTTATGGAAAATGAAGTCCAGGCTGAGGTGGTCACAGATGGAGA (SEQ ID NO:25)

chr4 126348639 + rs11098812

ATATAGTGTTTTTGATAGATTCCTATGCAAAAATAATGAAAAAAATATTAAGTGTGTATATATCTAATTTATATA
AGCATATATGTAGAACTAATTAGCA[A/G]CAATACATTATTTTATAAAACAGAATTTTTAAAATACAGAAGTGT
TGTTAATATTTAAATTGTTACATACCTTTTGTTTTATGTATTTTTTGTATTCAAA (SEQ ID NO:26)

chr4 126354307 + rs1395233

ACTAGGCCACGAGTAATTACAATCTAAGAACATAGAAGAATGATTGAATAGTGGTAAAGGAAATACCAGCAA
ATCACTTGACTATTAGAAAATAATATGG[G/T]AAGGTTGTGAATCTCAATACCATTCTGTGATAATGAGGGCAC
TCCATAAACATTTTACAAATAAATGAATGAGTGGCTTTATTTACAGAATATTGAATGG (SEQ ID NO:27)

chr4 126362855 + rs17803397

FIG. 7 CONT.

AGCAAAGCTGGAGTCAGTGAATTAAAGGGCAATGGCAGAAGTATGCATCAACATGAGCATCTCTTGGCTCTG
CTTTAACAATTATACTTCCTTCCTCAAA[A/G]TCTTTCAATTCCAGTTTGCCTATGGTATAACCCCCAGTCTTCAA
ATTCTAGTCACCCCATAAATGGCCCCAGCTAATTCTGCAAAACTCTGCAACATATG (SEQ ID NO:28)

chr4 126368878 + rs13108706

AAAGATATTTTACTTTTGTTACCGTTTCTTCTGTAGGGGTGAGAGTGCAGGTTTGGGAATGGTTTCTGAATGAG
TAGATTGAAAATATGTCCTTATGGCA[A/G]CTTTTCTGCATATTTTTACGACAATCTGTTTCATTGGCACTCAGT
CTAAGCACTAACTTTTGGAGTCCAAGTTGAGTCCATTATCCCTCAATTCTTATTT (SEQ ID NO:29)

chr4 126307341 + rs13146586

GTTCACCTCCTTCTTAATTTGCGTGTGTGTGTAACAATAAAATGTACTAGTGCAATGAACAAACTGGTTTTTACA
TCATTGAATAAATGTACATTAAATG[C/T]CTTCTGTACCCTAGGCGTTATATTGAAACTGATCTAAATGTTTCAC
TGTTTGAAACTTAGAAAAGAAGCAGGCTTTCTGAGTTTTGTTTTGTTTTGTTTT (SEQ ID NO:30)

chr4 126302984 + rs7669346

TGACTGTCATGAAAGATTTCTCTGTAGCATTCAATACTGTTTGAGAGCATTTTACACATAGTAGAATGTCATTC
AAAACTGGAGTCAATCCTCTCAAACC[C/T]TGCCACTCTTTTATCAGCTAAGTTGATTTATTATTCTAAATATTTT
GTTGTCATTTCAACGGTATTTACAGCATCTTCACCAGGAATAGGTTCCATCTCA (SEQ ID NO:31)

chr4 126325798 + rs62322574

ATTTGATACGCTTTTATTTTTATTTTATTGTGATAAGAACATTAATGTGAGATCTGCCCTTTTAAAAGATTTCTAA
ATGTACAATACAGTATTGTTAACT[A/C]TAGGCACGATGTTGTACAGTAGATCTAGAAATTATTCCTCTTGCAT
AAGTGAAGATGTATACCCATGGCTTATAAGCTCCTGATTTCTCCCTACTGTCTG (SEQ ID NO:32)

chr4 126316472 + rs1986721

TATCTAAGGAACTGTGGAGTAGAGAAAAGGGAATGGGCAATTAAGGAAAAATATCTAGATTTTCAAGAAATG
GAATATGAAGTTATTCACTTTTCTTTTT[A/C/T]ATTCTTTTTTGAGACAGAGTCTCACTCTGTCGCTGAGGCTGG
AGTGCAGTGATGCCATCTTGGCTCACTGCAACCTCTGCATCCTGGGTTCAAGCGATTC (SEQ ID NO:33)

chr4 126310531 + rs4349616

TTAAAAACAGAATTATTCCAATTCCCATATTGTATGTTACTTCATCAAATATTACCATTATATCATGTTTCTTGTA
CTAAAGTGTTTCCTGTGAAATAAC[A/G]TAATAAAATGGCCTTTAGTATGCATGATAATATTTAAATACGCATT
TTCTAGTAAAATATAATGCTTATTCATTTTTTTCTTCTAGTTCTAAAGAAAAAA (SEQ ID NO:34)

FIG. 7 CONT.

chr4 126308245 + rs885272

AACCTAGATCCTTCGCATGCACCATTCACAATAGGGTCCACCCTTCTTTGAGAATCTAATGCCGCAGCTGATCT
GACAGGAGGCAGAGCTCAGGCAGTAA[C/T]GCTCACTTGCCCGCCCCTCACCTGCTGCTATGGGCCGGGTTCC
TAACAGGCCACAAACCAGTACCGGTCTGTGCCCAGGGGTTGGAGACCCCTGTTATAG (SEQ ID NO:35)

chr4 126312920 + rs1509292

AAAGAAAAAAATAGTAAGTCATTATTATGAGTAGTTACTGAATTATCATAAAATATCATTTCATAACATAAAAA
TTATATATGATAGCATGTTCCCACAC[A/C]AAAACTAGGAAATCAATAGGTTTGAATTGCTTTAAAATATCATT
GTAATAGTGGATAACTTTGATTAATACATCTTTATATGCCAGTAGAATGCCTATGT (SEQ ID NO:36)

chr4 126313149 + rs1912044

TTAATAAAAATGTAAAAATGACCTGGATTTGCTTAAAAACAGAAATATTTCTAGAGGAGAATTTACATGCTAG
ACATGGATAAGTTGTCAGAATGAGCAG[A/G]ACACATTATTGCTCTTGGAATCTCAGAATATAGAAGTCTCTA
ATTTAAGTAATATAAATGATCTTCAGTATCCTGAAGATATTTGCAATTACCTATGTTG (SEQ ID NO:37)

chr4 126300866 + rs6855908

CACCATGTCCAGCTAATTTTTGTATTTTTAGTGGAGACATGGTTTCACCATGTTGGCCAGGCTGGTATTGAACT
CGTGACCTCAGGTAATCCACCCACCT[C/T]GGCCTCCCAAAGTGCTTGGATTACAGGTATGAGCCACCGCGCTT
GGCCAGACATTGATATTTAACTCTTTCTTAATCAAATTTTGAACTTATTTCATACC (SEQ ID NO:38)

chr4 126297735 + rs34874968

AGGAGAAATACCTAATGTAAATGACGAGTTAATGGGTGCAGTAAACCAACATGGCATATGTATACATATGTAA
CAAACCTGCACGTTGTGCACGTGAACC[C/G]TAGATCTTAAGTATAATTAAAAATAAATAAATAAATAGGCCT
GGCGCGGTGGCTCATGCCTGTAATCCCAGTACTTTGGGAGGCTGAGATAGGCGGATCA (SEQ ID NO:39)

chr4 126295062 + rs1396694

TCAATAGGGCTACGGCATTCATGCCTTCCTTTAAAAATTAATTGAGGGCAAGAAACCATTGTTTAATATGTAAT
TTCAAACATCTAGATGAAGAAAATAT[A/C]TGTATTAGAAAATAATAAGGACTATGTATATATGATTTCAGACG
ATTTCCTATTTAAATAAATTAGGATAAATGACATATTTGTTATAGGGTGAAATGTT (SEQ ID NO:40)

chr4 126270636 + rs7697665

FIG. 7 CONT.

AGAGTTTCAAATGAGTTTGTGAATGGATATCATACCCTTCCACAAATGACAGAGATGGACTATTAAATCAGAG
TTGGTAGTTTTTGCTTTTGTTTACTGT[A/G]TTTCTCATTCACCCTAAATGGTCCTATCTATAACAAGCTTTGGAA
AAGCACCATGCACCTGAAATTCTTGCATTCTGATGTTCATACCTAGAGAGATTTA (SEQ ID NO:41)

chr4 126272004 + rs9307560

GCTGATTTCCTTGAAAGTACTCCCTCCTCATTCTCTACAGTAAGCCATTGAATGTTACTAGGGATGGACACTAA
GCAGAAAGATTTCTGAGTATCTATTC[A/G]TCTTCCCCAATCAGACAGTCCTTTAAATTTAAAGAAGAATGCCT
GACCCTTAAGACAGGGAGGTTCATCATATTTCCCATTCTGACAGTTTGGAATGAAA (SEQ ID NO:42)

chr4 126270451 + rs10032352

CATTTGTTTTGAATTTTCCAGTATATTAAAACAATGGCTAACAATTATAGTTGAGAGAAATATATTTAGGAAAA
GTAATGCATTATTCAGCATTCTATTA[A/T]CTATACTATATTAACACATGTGTTATGGGCTGAAATTACACCAGT
ATCACATGAGGGTAAATGGGTTGAAAGTGTAAGTTTAAAAGAGTTTCAAATGAGT (SEQ ID NO:43)

chr4 126338088 + rs6534478

CTACTCAGAAGGCTGAGGCAGGAGAATCGCTTGAAACCAGGAGGCGGAGGTTGCAGTGAGCCGAGATCACA
CCACTGTTCTCCAGCCTGGGCAACAAGAA[C/T]GAAACTCGTCTCAAAATAAACAAATAAATTAAATAATAATA
ATTTCTTCATAATATGAGTATGAAGTATTTTCTGTTTGCCATTAAATGAAATATTTGTT (SEQ ID NO:44)

chr4 126282761 + rs1396685

AGAGGTGATCTGACAAGTGTTCATTCAAACTCTGCAACCTTGATTGAGACTGTGCTAGATGATATAAAAATAC
ATATGCCCTAACAGGGAGGATAGGCAA[A/C]CAAACAATTAATTTTAAAATTGTGAATTTACAAACTGTGGGT
TATTATATGCTACAGAAGCCACACAGAGAAAGAGTTATTTGCTCTGTTTCAGAAAATA (SEQ ID NO:45)

chr4 126281130 + rs17193280

TCCAGCCTGGATCTCTGGGAGGGAGAAGTAGTTCCAAAGATTACAGTGCTTAATCTTAACTCTGAAAACACTA
CTTATTGACTCTCCACTGGATTCCACT[C/T]GCCCAAATTCCCTAGATGGATTTTCCCTCAGGATGAAACAACCT
AAATTCAAGTGTCCTAAACTGTCTTCCTCTCCCTCCTGCCATTGCCTTTCCTTGTT (SEQ ID NO:46)

chr4 126281923 + rs2663251
TACTGAACAATAATACATATGCACTTAATTGTAGTCATCCCCCTGACTATACTCACAAAACTTAACATG
TCTTTAGGGGAGGAGGATGGATTGCAGATAT[A/G]CTATTAGAGGCATAGCCATCTTTACTTCATTAAAAGTTT
AGTTTACTAAAATTTGCAAATGTTTAAAATATGGTCTTGCTTAATTTCACAAATTCTGGGA (SEQ ID NO:47)

FIG. 7 CONT.

chr4 126280485 + rs62321342

TAGTCAGGTGGAGATAATTCACCCCACGTCTTAAGGCCAAATGGAAAAAATCTTCTTACTCTGGAATTAGGTG
GTTAAGTATCTTGATTTTAATGGATGT[C/T]GTTGTTTTCCTAATAATTGAGTTATTTGTATTAAAATGCTAAACT
GGCAATATATGCCGATGGCCAATTTACCTCCAAATATATTGAGTTCATACATATT (SEQ ID NO:48)

chr4 126278969 + rs62321341

ACACTGCTGGCATGTGCTTTGTGAATATGTTTGAATCAAGGGCCTTTACAAAGGGCTCAGACCTTCCTCCTAGG
GGGTTGTCATTTACCGTGGATGCTCT[C/T]GTTTGTTGTGGTAAACAGCCTCAGAAAACGTCTTGACATTGTCA
ATTCCAACAGATTAATGAAGTAACTGGGCCATACATCCCTTCCCCTTTACATATGA (SEQ ID NO:49)

chr4 126279303 + rs2663295

GGGCGGGGGAACTCCAGTGTGATTATAAGTGAGTATATAGGAAAAAAAGAAATGAAATTAACCTTTTTTTCTT
TAGAAATCTTGTGTTTAATTTTATGTT[C/T]CAGTGTTTTAAATAACTGAAACCTTATTATGGACAAATTTACCTG
TTATGTTAGGAGAAATGAGTTTCATTTACCATCTTCATCAGCGATCCCCAACCTT (SEQ ID NO:50)

chr4 126280623 + rs2710556

GCTAAACTGGCAATATATGCCGATGGCCAATTTACCTCCAAATATATTGAGTTCATACATATTCATTAAGTGGG
ATATTTTGGAGAATATACTGCTTATA[C/T]GTTCAAATGCAAATAATTTAATTCGCTGTGATTTATAATACTGTT
ACTCAGTAAATGGACTAAAGGCAGGGTAAGATTTATCAGTCTTAAAAATGTAACT (SEQ ID NO:51)

chr4 126280021 + rs2710559

TGGGGACCCCTTATCTACATCCACGTTTTCTATGTTTGTGAAGATTTGATGTGGGGTTATGGGTTTGAGGAGCT
AAAAATTATAGTTAGTAGAAGGAAAG[A/G]CAGCTAGAAGTGGAAAGTAAAATCACTTACATTGTACTTTTAC
TAGGACCTATATTGTAGGTATTATAAATCATACAAACAAGTTTGTTATACAAAACAT (SEQ ID NO:52)

chr4 126280006 + rs2710560

CTGTGGCCCAGGGGGTTGGGGACCCCTTATCTACATCCACGTTTTCTATGTTTGTGAAGATTTGATGTGGGGTTA
TGGGTTTGAGGAGCTAAAAATTATAG[C/T]TAGTAGAAGGAAAGACAGCTAGAAGTGGAAAGTAAAATCACT
TACATTGTACTTTTACTAGGACCTATATTGTAGGTATTATAAATCATACAAACAAGTT (SEQ ID NO:53)

chr4 126277240 + rs2940782

FIG. 7 CONT.

GTTTTTTTTCTGTCGGCAGTGTATCACAAGTATTTTCCTCAGTGGCCTAAACAGACCCTGAGTGGAAGGCTGGT
AAAAGCAACCTCGTCTGCATGCATCA[C/T]TTTGAATGATTTCAAAGAGGAAAGAAGCAGCTGTGACAATGTT
CACATGAACCACTCAGAGTGGCCTTATCTTTGTAGTCTAACAATAATAGTACACCCT (SEQ ID NO:54)

chr4 126275098 + rs2036725

GTGAAGTTTGAGAATTTGCAAAGCCATAATGATAGAATCAACCCAAAGGTCCCAGAAATTTTCAATAATCTAT
CATCCTTATTTAAAATTATTATACAAT[A/T]AAAAATTGTGTTTTAATCGCATGAGTAGACAGATGTTTATGCTG
TTATTCAGCGAATCTTGCAAAAGTGAGTGTAATTCATAGAATAAAACAATGTTGGA (SEQ ID NO:55)

chr4 126408586 + rs17009825

AATATGTTTTACAGATTAAGAATGGCAAAGTATATTTTACATCCGATGCAGGAATTGCTGGGAAAGTGGAGAG
AAATATTCCTGAAGTATATGTTGCAGA[C/T]GGCCACTGGCACACTTTTCTAATTGGGAAAAATGGAACAGCA
ACAGTATTGTCTGTTGACAGAATATATAACAGAGATATTATCCACCCTACTCAGGACT (SEQ ID NO:56)

chr4 126280338 + rs2710558

ATAGAAGCAGCAGCATAAATATCTATATAGAATTAGCCAGGTTCTAGTCTGGCACATCATCACATAGTAGCAC
ATTTAATGCCCCCAATTATTCTATGAT[A/G]TAGATACTACTAGTTTCCCCATTTTCCTAATGAGAAAAGTGAGT
CATAGTCAGGTGGAGATAATTCACCCCACGTCTTAAGGCCAAATGGAAAAAATCTT (SEQ ID NO:57)

chr4 126297549 + rs10011289

ATTTAAATTTAAATCAAACAGTTCTCACTGAAATAATTAGGGGTAAAATGGACCTCTGTTGATGCTATTTGAAA
AAACTATTTGAACAATGAGAACACTT[A/G]GACACAGGGTGGGAAACATCACACACCGGGGCCTGTCGTGAC
CGGGGCCTGTCGTGGGGTGAGGGGAGGGGAGAGGAATAGCATTAGGAGAAATACCTAA (SEQ ID NO:58)

chr4 126423687 + rs1395227

ATTTCAAAGCTTATTATTTTTCCATTACTACCTAACACTTGTGTATCTCTTCTTCAGCTTTCAAAGAGTTTTCAGG
TGAGTTATCTAATTTGAACATTAC[A/G]TTACATCTGTGAGGTTGATTACAGAAAAGTAATTAACACATTTTAG
AGAAAGGAAAACATAAATGAAAAGAGACTTACTCAAAGTCACAAAGTAACGGTG (SEQ ID NO:59)

chr4 126422859 + rs9995724

AAATAACTCATACAATTCACTTTAAGCTGTTTCTTTGATATGCAATTCTTAGCCATTACTCTTTGAGCCTGTCGTA
CTACTGTCATTATTATCATTATTT[G/T]TGACCCTGCCTTTTGCATTCCGCATCATTACACATTCTTTAGTTCAAA
GTGGAGAACTAATGTCTTCCTGCTTCAAGCGAGGCTGTCTTGTCAGCTCTTT (SEQ ID NO:60)

FIG. 7 CONT.

chr4 126314379 + rs13146027

AACAAAAGATTGTTTTTCTTCTTTATTTGAGAACCATTTTATGTAGATTGCAGGAAGGTTGTGAATTAAAATAT
GTTTAGATTTTTTCATTCCGTTCATT[A/G]AGAAACATTTGATTTAAGCTGCAGAGAGGATATGCATTTAAGAA
TATGTTTAGAATTGTGGTTGAGGTGGCAACCACCATGCAATTATCAGTTTATTAAC (SEQ ID NO:61)

chr4 126318288 + rs13136889

TGCCAGTTGAACCTGTATGTGGGACTGGAATTCTGATTTTTAAAAATACCTTTTCTCAAAGCCTTTCTCTGGCTC
TAAGAAGCTTCCAGATCTGTCCTAA[C/T]AGCTTGAAAACCAAGATCTTGACTTTTTATAGAATACTTCACTCTG
TGCCAGAAACTGTGTTAAGCATTTTCTTTACCTATATCATCAGGATTTAGTCTT (SEQ ID NO:62)

chr4 126292769 + rs2663256

TCTGCTATAAGTGCTATAAGTAATAATATAGAAATAGTTGACCTCACAGTTAATTTATTAAGCAAATAGTGGAG
AAGATGCTAGTAATTTCTAGACCTTG[C/T]CTCAGGGGCTGTGAATATAGGAGGGGATAAGATAAAAAGTGG
CTCTTTCATTGGAGTATCAATTGTGGGGAGAGATTGAATATCCTCAATAATATCTTAA (SEQ ID NO:63)

chr4 126270773 + rs7676058

GCTTTGGAAAAGCACCATGCACCTGAAATTCTTGCATTCTGATGTTCATACCTAGAGAGATTTATGGTGACATA
AGCAGCCAAATAGCACAAGTGAAATT[G/T]TATATGAAGTATATGACATGCATGATTCAATATATATGCCCACT
TTTAAATATACCAATAGTATATTTGGACTATAATAATGAATTCATTTCAAATATTG (SEQ ID NO:64)

chr4 126286443 + rs2663252

AATAAATTAGTTCAGGACCTTGTTAAATGTGAGGTCACTCTGAGATACCAGTGGAAATATCCAGCAGGCAGAT
GGATATGTGAACTGGAGCACAACAGAG[A/T]AGTCTAGATTAAAATTTGCATTTGGAGTGTAGTATCCATGAA
AGTAGCCACGAGCTTGGATATGTTGTCCAAAAGAATGTGGACTCTCTTCTCATCATTC (SEQ ID NO:65)

chr4 126286314 + rs9307561

TTGATGACGAATTGAATGTAGATGTGGAAGATGATGGAAGAACCAAGGAAGATGGCTTAGTTTCTGCCTTGA
GCAACTAAGTGGATGATGAGTTAGGGAA[C/T]ACCGGATGAGGAGTCATAACAAGAAGACAATAAATTAGTT
CAGGACCTTGTTAAATGTGAGGTCACTCTGAGATACCAGTGGAAATATCCAGCAGGCAGA (SEQ ID NO:66)

chr4 126287648 + rs2952841

FIG. 7 CONT.

CTCCAGCTCCATCCATGTTCCTGCAAAGGACATGATCTTGTTCTTTTAATGGCTGCGTAGTATTCCATGGTGTGT
ATGTACTATATATATATTTTTAATC[C/T]GGTCTACCATTGATGGGTATTTGGGTTGATTCCACGTCTTTGCCATT
GTGAATAGTGTTGCAATGAACATAACATGTGCATCTTTACAATAGAATGATGC (SEQ ID NO:67)

chr4 126296175 + rs2710582

ACACATAGAAAAAAATGTAGGCTTGTTAGCATCAAGTAAGTTGCCAAATATGATATTGCCCCTTATATAACTTG
AATAACTTTAGGTGTTACTTAAATTC[A/G]TAGGCACATATTGGCATCTTCAGAGCAAGATGAATTAACACTCT
GGAGTTTTTATTTTATTTATTTAAAAATAGATTATCACTTGAGAAAAGACAGCATC (SEQ ID NO:68)

chr4 126369279 + rs6846428

ATTGGAAGATATTTTAAGACACACTAGAGCAACGGTATCATTGCATTGGGTAGAGGCATAGCACTTTGCAGAG
CTCGCATATTATGTTTCTTGGAATGTT[G/T]TTTTATGTGCAGATTTTTCTCCTAGAAACTATGATTTTTGAACGA
TTAGCAAGTTCTTTTCCCTAGGCTTCTCTCAAAGGCATACTGAAAAGTATTAAAT (SEQ ID NO:69)

chr4 126351995 + rs17009641

GGAGAAAGTTCTTGGCTTGAAAACAGACTCATATAGATGTAGAATCACCTATGGGGCTGATCGTGGCTTAAG
GATCATCTGCCAGTCTTGAGAATCATTT[A/G]CTAATCTCAAGGATCAACAAATGATCCTCAAGCCAGAATTGT
CTGTTGTCACCTGAGTGCTTTGAAAATCATCTGGAAAAATAAGTTGATATTCTTTGGT (SEQ ID NO:70)

chr4 126368263 + rs13129279

GTTTTCAAAAAGTTTAATAAATGGATAATTCTTGTTAATATTTATTTTATTCCAGGTTTTACAAATGAAAACTGT
TCTGTTAGCAAGTTTATGGATCCAT[A/T]TATGAATCATTTTCATATTGACAATATGCATTTATCCTTCTGTATCT
CTTTAAATTTAGTTTGACATTTGCTAAGAAAGGCATACTCTAAGAACTGCACA (SEQ ID NO:71)

chr4 126294586 + rs62321346

TTTTTATGTTGTTTTTATCTTAATTACTCTAACAGAGACAAATTTCATCTAAAGAGGTGATATCTAAAGGAAATG
TAGAGATCAGAATATAGGACAGATT[G/T]TTTTAAAAAGTTTGATATTTATTATTAGGTGCCTAATAAATGCTC
CTTCTAGTTTATGAAGCTTTATTTCTAAAACTATAATCTATGTTTATGTGTGTTT (SEQ ID NO:72)

chr4 126291032 + rs6854625

TCCTCCAATCGGCAAGCTCCAGGCCACCACTGTTCTGCTTTCTGTTCCCATGAAGTTGACTACTTTTGCTAACTG
ATATAAATGGAATCATACATATTTG[C/T]TTTTCTGTGTCTGGCTTATTTTACTTAGCATAATGTCCTCCAGGTA
GATCCAAGTTGTAGTAAATGTCAGAATTTCCTTTTTTTTTAAAGACCGAATAGT (SEQ ID NO:73)

FIG. 7 CONT.

chr4 126293819 + rs62321345

GAACATATTACTGGTGAATGGGGAAGCTGGCTTAAAAAAAAGGGAGGGTCTTCTCAGACAGTTCTCTTTTTAC
ATACGTGGCACAATGATTCATGATTTG[C/T]TATATTGTGAATGTTGAATGTGGAATATTTATAGGAATGCAAA
TCACATTTCCTTTACACAATAGTATTAAACTGATTTCAAAGTGTTTTGATATATGCT (SEQ ID NO:74)

chr4 126284351 + rs6817722

AATTATCAAATCATTTTTCACAACAATAAAAATTGTATACAAGGCAAACTATGTACATATATGTGGGTGTCCTT
AGGAATAAATGCATAATTTCAAAGAC[A/G]TGGAATTTGTAAGTGTTAGTCATGTTCTCACCTGTAATAAAGCA
ATGTGTTAATGAAATTGGGTGCTTATATATATTTATATATAATTTCTTAGTTTGAG (SEQ ID NO:75)

chr4 126275717 + rs79129861

TCTTTGCTGATGGAATATTGAACACGCTCTCACTCTGATGTACAGTTATAGTGTATACTAGGTAAGAAAAGAG
AGTCCCAGGCCAATTTAAACAATGATA[A/G]GGTTTGCTTTTCTGAATTCTGAGAAGCTAGTTCAGGGGAAGA
AATGAAACCACAGTGTAGAGGGTCGAATGGTGAAGGTGAAAAATTAGTATCAAGCCTC (SEQ ID NO:76)

chr4 126277903 + rs79626418

GTGACAAGACTAATATAAGTAGAATATAGTTGAGTTACAGAATATGTTGTAATAGTCTTTACAATGCACATCCA
ATGAACATCATATAGACAGATATTAA[C/T]ATCAATATATCTACACATAATTGATATATAGTATATATTATAATA
AATATAAGATATGATAATATAACAGATAATATAATAGAAATCATAGATATCTGTA (SEQ ID NO:77)

chr4 126278572 + rs78188548

CAGTCTCTCGATTGATAATAAAATTTGTCATTTTCTCAGTTAAATTGATACAGATTCTTGTAGAGCAAAAAGAC
CTAAAGATAAGATTTGGGATAGATTT[A/T]TACCTTAACCCAGGTAATAAATAGATTATTCGGGTACTTTAATA
GTAACAAAGGAATCAAATGGAATTTTAATTGAAATGATTTTACTAATATGGTCATT (SEQ ID NO:78)

chr4 126280842 + rs74646069

TATTATCTTCTAATTATCCTTTTAAATCAAAAACATACTTTCATGTTGGTATGAGTATCATAACCAAAAGAGAAG
AGAAACTTCAAAGAGAAAACTGAAT[C/T]AGTGGAGAGTAACTTAATTTCAGAAGAAAATCGTACTTTCATAT
AAATTCATAGTGAAAGGTAACTATGTGATACCAGCATTCAGGGAACAAATGCCCTT (SEQ ID NO:79)

chr4 126302971 + rs79145530

FIG. 7 CONT.

CTTTGATTGAGTCTGACTGTCATGAAAGATTTCTCTGTAGCATTCAATACTGTTTGAGAGCATTTTACACATAGT
AGAATGTCATTCAAAACTGGAGTCA[A/G]TCCTCTCAAACCCTGCCACTCTTTTATCAGCTAAGTTGATTTATTA
TTCTAAATATTTTGTTGTCATTTCAACGGTATTTACAGCATCTTCACCAGGAAT (SEQ ID NO:80)

chr4 126308282 + rs78474635

CCACCCTTCTTTGAGAATCTAATGCCGCAGCTGATCTGACAGGAGGCAGAGCTCAGGCAGTAACGCTCACTTG
CCCGCCCCTCACCTGCTGCTATGGGCC[A/G]GGTTCCTAACAGGCCACAAACCAGTACCGGTCTGTGCCCAGG
GGTTGGAGACCCCTGTTATAGACTAATAACCAACTGAAATAGAATAGCATAGCTATGA (SEQ ID NO:81)

chr4 126310980 + rs79031396

CATCAAGATGAGACAGTAAACTATTATTAGAGTTACCACAAGTTTGAACAAAGTTGATTATACATCGCAAACA
AATAAATACTTAAAACCTTGTTCATAG[A/G]GATCAGGCCTTGCATACCTACATAGTCCAAACATTACATTCCTG
ACATTTAGAACATTTAAATGCAAACTGTTCTTTGTTAGGGCTTTCTCATAACTGAA (SEQ ID NO:82)

chr4 126322550 + rs74733937

GTTGTTGTTTTTAGTTGCTTATAATAAATATTAATGCTTTTAGATAAACCTTTGTTTTATTTTCTACTTTATTCTCA
GCTCCTTACCTCTTAGCCAAATT[A/T]TGGGGAAAATATTTTAAAAATTTTCTCTCTTTTCAAATCCTGGCTCTGT
TTTCTTTCTTCATCTAGTTTGAGTAAGACTCGAGATTATGTAGGTCATCAG (SEQ ID NO:83)

chr4 126337327 + rs74829391

TTTTTGAATTTTGTTCCACAAGGATAATATCTGCACATAGTAAAAAACTAAAATGATGGAAATGTTTGAAACTT
CGTTATAAATATTGTTCTACTCTTTT[C/G]CTTCATATATTTAACTACCTAGGTGAAACTGCTCTTAAAAATTTTT
ATGAAGCCTTCCAAAAATGCTGTGCATTAGCTTTACACATATTTTTACACAAAT (SEQ ID NO:84)

chr4 126340181 + rs74340824

CAAGTAGCAGGAAATTATCAGGGAAACTAGAAGAGTATACTTTAAAAAATGAATTCAGATAATTAATTTAGAA
ATGGAAGTATATCATGTAGTTAAATAC[A/G]TAGACTTTATAGTTAAACCCCAGTTCACATCCTACCTCTGACAT
TCCCAGCTATATGACCTTCAACAACTTTACTATTCCTTCATGTTTGTATCTATGAT (SEQ ID NO:85)

chr4 126343877 + rs74856924

TGGGTCAATTAAACCTCTTTCCTTTATAAATTACCCAGTCTTGGGTATGTCTTTATTAGCTGCATGACAGCAGAC
TAATACAGGTTACTGATATCAGAGA[A/G]AGTAGGGCACTGCTGTAAAAATACCAAAGTGACTTTGGAACTGG
GTAACTGGCAGAGACTGGAACAGTTTGGAGGGTTCAGAATAAGAGAGAAAAATGTT (SEQ ID NO:86)

FIG. 7 CONT.

chr4 126357601 + rs77217742

AGAAGTATTCTATTTGAATACAGTTTCAAATGACTGTTACTCATTCATTTAGAGATACCAGTTAGGAAGCTGGA
GATATGAGTGTGGAGCTTAGGGTTGG[A/G]GTTAGGGCTGGATATACACATTTGAGAGTCATCAGTGTTTAG
AGGACATTTAAAACCAATAAACTGAATGAGAACACGTTTGCGGAGTGTATTAGTCTGT (SEQ ID NO:87)

chr4 126359840 + rs74501747

TTAAAATGAAAATTGAAGCTATTTTTGTCTTGTGAATAAAAAACATTCAATTCACTTGCAAATTAACAGGGCAA
ACAATTATTGCAGCTTAAATAGAAAA[C/T]ATTTTCACAGACAAAGTAAATAGTTATTATAACCTCAACTTTATT
TACTCTGGTTTGATAAAATCTTAATGGAATATAATGTATTTTATGGTTGGTGTTA (SEQ ID NO:88)

chr4 126364496 + rs79033360

GTTTATGCAAATAATTTGAAATAGTAATGTATTCTCAAATTAGAAAATAATTTAACGTGTTTATTGATTTTCATT
GAACTAAATGTGAACAAATTCTATA[C/T]TGACACAACTTGAGCAAGAGTCCATGTTGGCCTTCGCAATTGGTA
CATTTTCCGTCTTCACTACATTCCCTCAGTTGAGTTTTACCTTCCTTCTACTGTG (SEQ ID NO:89)

chr4 126369230 + rs76891791

ATAAATGGTAATGAACATGATTTTTGTTGACAAGATTACATATAAAGTGATTGGAAGATATTTTAAGACACACT
AGAGCAACGGTATCATTGCATTGGGT[A/G]GAGGCATAGCACTTTGCAGAGCTCGCATATTATGTTTCTTGGA
ATGTTGTTTTATGTGCAGATTTTTCTCCTAGAAACTATGATTTTTGAACGATTAGCA (SEQ ID NO:90)

chr4 126369554 + rs115240175

TGTGAACCTCGGAGAAAATATAGGAGATACTGTTCTCCCTAGTAATCATGAGAAAATAAGGTCACATCAAGCA
GCAATAGAGTGTCTTATATGCACTTAT[C/T]TGCTACCAAATATTTTATTTAAATTCCACGTGAGTATAACTGCA
CACTTTCTCTTTTATAGGTTCCTTTGTCTTTGCGGTTACAGTCACAGATGCTGATA (SEQ ID NO:91)

chr4 126381199 + rs115962084

TAAAAAAGCATAAACTTTCCAAACCTGAGAAATATGCATTTAGAAGCTTTCTTTTGATTCTAAGTAAAATTATG
GAATCCTTTTCTCACACAAAAGACAC[A/C]GGTGTTTTAAATAATAATTTAAATTTAAATCTGTTTTCCTACTAT
GTCTTTGAATTCAAGTATCTGCTATGGCAACCTCTGAGTTCATGAATTGTAAAAA (SEQ ID NO:92)

chr4 126381679 + rs141880214

FIG. 7 CONT.

CTCCCTCCTCCCACCCTCCACCCTCCAGTAGACCCCAGTGTCTGTTGTTTCCTTCTCTGTGTCCATGTGTTCTCAT
CATTTAGCTCCCACTTATAAGTGA[A/G]AACAGGTGGTATTTGGTTTTCTGTTCCTATGTTAGTTTGCTGAGGAT
AATAGCCTCCAGCTCCATCCATGTTCCCACAAAAGACATAATCTTGTTCTTTT (SEQ ID NO:93)

chr4 126399393 + rs114235331

GAGATTACCAGAAATAAAACTATTAAAGGCAAAGCTAGGAATACTTTCTAATGTTTGTAACTTAAGTATTTTAA
TAACATTTTCTATTTGCCTTTCTTTT[C/T]CTACATGTTGTTACTGTTTTGTTACAAAGTCACACTAGTTCGTTATT
ATTATTAATCAAACAGTACAGAAAAACAAAGGATTGGGATTGCCACCATTGTT (SEQ ID NO:94)

chr4 126402260 + rs114783000

ATACTGATTATACATGATGATAAATTATATGTGATGATTACTGAAAATAAAGTTAGTTACCGATGTAAATACTT
GATTGAACACTTCTTTGTCCTAATTT[A/G]TAGCATACTAGAGACTAAAGATTACAAATCATTTTAACCATGCAA
ACGTATATTTTGGAAACACAGTGAAAATGATTACAAACAAATTTTTCAAGTACAT (SEQ ID NO:95)

chr4 126410669 + rs115415133

TGCTCCCCAAGAACCTATGTTCCACACCTTTGGTGTATTATCACCTTCAATGGGAATGCATGATTTAGTAGTTG
AAGCCATTGGCCTATTTCATGTTCTT[C/T]ACAAATTTAAAAAATATATATTTTATTTGTATGTATGCAATTTTTG
GTATATGGGATGTAAAAAGGAAGGAAATTGATAAATAAATGAGTAAGAAAAAGA (SEQ ID NO:96)

chr4 126415682 + rs115572680

ATTATGACCTGAGAATTTTAATCCATCCCCTGTCAAGTTTTATTGGATTTCCTGGAATACAGTTACTCTACTCTG
TAGAGGGCAGAGCAACTCCATCTTG[G/T]ATGCTCATCTTCCATGTCTACTTCTGATTAACCCCAGTTCTGGGA
ATGCCTCTAATATTTCCAGTATATCTATAGTTCCTTATGTAAGAGCTTGTACTAA (SEQ ID NO:97)

chr4 126419863 + rs78127669

TAAGTTAGCCTGTAAGTCTTGCTATTGCATCCACTTTTTAAATTTGTTCAACACCAGAGCTACTGTGTGCCAAGC
ACCATATTTAGATAAGTGAGAGATG[A/G]CTCTTGCCTTCAAGAGGTTTGCAGTTTTTGGTGACTAGACTTTCC
CTTTTCCAAAGTAGTTTAAGATTTGCATAGCTCTGTTTGCAGAGAATTATTTAAA (SEQ ID NO:98)

chr4 126420770 + rs148385122

CTCTATAATATTAATTTCATATTACATCTTAAGACTTTCATTTAAGCAAATTACATAACTCCTAAAAGGTGCTGC
ATTGAGGCCAGGCACGGTGGCTCAT[A/G]CCTGTAATCCCAGCACTTTGGGAGGCCGAGACAGGTGGATCAC
CTGAGGTCAGGAGTTTCAGACCAGCCTGGCTAACATGGTGAAACCCCATTTGTACTA (SEQ ID NO:99)

FIG. 7 CONT.

chr4 126423297 + rs79771845

CAATAAATTTGTTACCTTTATATTCAGAAACCTAATTGAATCGGAGTAGACGAGGACTAAAAGCATAAGGAAT
AATAATCACTAATCTTCACTATTTTTC[C/T]TTGTTTGTGTTGCAAATATTGTGTGTTGGCTGGTGTTAGGCATG
GTGAAATATATGAAAATGATATTAATATAAAACAATGTCCAAGTCCTAGAGGCAAC (SEQ ID NO:100)

chr4 126343915 + rs115504303

TCTTGGGTATGTCTTTATTAGCTGCATGACAGCAGACTAATACAGGTTACTGATATCAGAGAGAGTAGGGCAC
TGCTGTAAAAATACCAAAGTGACTTTG[A/G]AACTGGGTAACTGGCAGAGACTGGAACAGTTTGGAGGGTTC
AGAATAAGAGAGAAAAATGTTGGAAAGTTTGGAACTTCCTACAGACTTTTTGAATGGCT (SEQ ID NO:101)

SEQUENCE LISTING

<160> NUMBER OF SEQ ID NOS: 101

<210> SEQ ID NO 1
<211> LENGTH: 201
<212> TYPE: DNA
<213> ORGANISM: Homo sapiens

<400> SEQUENCE: 1
actcttcagt aacttgcaag agcagaccaa caaatgggca gttggatctg acagcccaga 60
ggcagcagaa agctttggac ggaagataaa gtaatagtaa rcattatgca gcacttcaaa 120
taggatgtat ccactacacg gtgggaaaca gtaatactcc ggagaacctc tccacacagt 180
taaaaggaag ggttacatca c 201

<210> SEQ ID NO 2
<211> LENGTH: 201
<212> TYPE: DNA
<213> ORGANISM: Homo sapiens

<400> SEQUENCE: 2
atacctttat ttgaaaacta aaatcaaagt atcccttgat gtcataggat actttgaaat 60
tatagataat catagttata tagtcataaa ttgaggaaga rtgagagagt agtagaaaaa 120
aatcatcaaa ccgtattatt tcatggagat ggttagttgt agtcagtatt tataattgat 180
ggctttttcc attactctgg a 201

<210> SEQ ID NO 3
<211> LENGTH: 201
<212> TYPE: DNA
<213> ORGANISM: Homo sapiens

<400> SEQUENCE: 3
cctctaatct ttggattgtt ggagggggag gaagaacttg atatgtatta ttttgagttg 60
cccctgacag atagcagtat ggcatggtaa gtgagaatgt rtagctatat agggtaggaa 120
aaggtattaa tagattcaga gaaataaaac tcccagtaca agccatacaa cagatcaata 180
tacattagct ttttactctt c 201

<210> SEQ ID NO 4
<211> LENGTH: 176534
<212> TYPE: DNA
<213> ORGANISM: Homo sapiens

<400> SEQUENCE: 4
gggagccagg accatggact tagcaccaga cagggctact ggccgcccgt ggctcccgtt 60
gcacactcta tcagtatctc agctccttcg agtgttttgg ctactgtcat tgcttccggg 120
gcaggcctgg gtccacgggg ccgagccgcg ccaggtgttc caagtgctgg aagagcaacc 180
tccaggcact ctggtaggca ccatccagac gcgccccggc ttcacctaca ggctcagcga 240
aagccacgcc ctgtttgcca taaacagtag caccggagcc ctgtacacca cctccaccat 300
cgaccgcgag agcctgccca gcgacgtgat caacctggtg gtcctttcca gcgcgcccac 360
ctaccccacc gaagtgcgag tgctggtgcg ggacctcaat gacaacgccc ccgttttccc 420
ggacccctct atcgtggtca ctttcaagga agacagtagc agcggacgcc aagtcatctt 480
agacaccgcc accgactcgg acatcggctc aaacggtgtg gaccaccgct cctaccgcat 540
catccgcggc aatgaggcgg ggcgcttccg tctggacatc accctgaacc cgagcggcga 600
gggagcgttc ctgcatctgg tgtccaaggg cggactggac cgtgaggtca ctccgcagta 660
ccagctcctg gttgaggtgg aggacaaggg tgagcctaag cggcggggct accttcaggt 720
aaacgtgact gtgcaagaca ttaatgacaa ccccccggtt tttggcagtt ctcactacca 780
ggcgggggtg cctgaggacg cggttgtggg ttccagcgtc ctccaggtgg cggcggcgga 840
cgcggacgag ggcaccaacg cggacatccg ctatcgcctg caggacgagg ggaccccctt 900
ccaaatggac cctgagacgg gacttatcac ggtgcgggag cccctggact tcgaagctcg 960
gcgccaatac tcgcttacgg tgcaggcgat ggacagaggc gtgccttccc tcactgggcg 1020
cgccgaggcg ctgattcagc tgctggacgt gaatgacaat gacccggtag tgaagttccg 1080
ctacttcccg gccacctcgc gctacgcctc ggtagatgag aatgctcaag tgggcaccgt 1140

-continued

```
ggtggctctg ctcaccgtga cggacgcaga ttctcccgcg gccaacggga acatctccgt   1200
gcaaattctc gggggcaatg agcagcgcca ctttgaagtg caaagcagca aagtgccgaa   1260
cctgagccta atcaaggtgg ccagcgcctt ggaccgcgag cgcatccctt cctacaacct   1320
cacagtttcc gtctctgata actacggggc gccccctggc gcagcagtcc aggcgcgctc   1380
ttctgtggca agcctggtga tttttgttaa tgacatcaat gaccatcctc ctgtcttttc   1440
acagcaagtg tacagagtga acctgagcga ggaggcgcct ccgggaagct atgtgagtgg   1500
gatatctgcc actgatggcg actctggtct caatgctaat ctgcgttaca gcattgtctc   1560
tggcaatgga ctgggatggt tccatatcag tgaacatagc ggcctcgtga ccactgggtc   1620
ctctgggggc ctggaccgtg aacttgcttc ccagattgtt ctgaatataa gtgcccggga   1680
ccagggagtt caccccaagg tgtcctatgc ccagcttgta gtaactctcc tagatgtgaa   1740
tgatgaaaag ccagtattta gccagccaga agggtatgat gtgtctgtgg ttgagaatgc   1800
cccaacaggg acagaactgt tgatgctcag ggcaactgac ggggacctgg gtgacaacgg   1860
aacagtgcgc ttctccttac aagaggcaga gactgaccgg aggtccttcc gtctggatcc   1920
tgtgtctggg aggttgagta ctatttcctc cttggacaga gaagagcaag ccttctactc   1980
cctgttggtt ctggccacag atctgggctc ccctccccag tcatcaatgg ctcgcataaa   2040
tgtgagtctt ctggatataa atgataacag ccctgtcttc tacccggtcc aatactttgc   2100
tcacattaag gagaatgagc ctggaggtag ctacatcacc actgtgtctg ccactgaccc   2160
agacttgggt accaatggta ctgtcaaata tagcatatct gctggggaca ggtctcggtt   2220
tcaggtcaat gctcagagtg gggttatttc tacaagaatg gccctagaca gagaagaaaa   2280
aacagcttat cagttgcaaa tagtagctac tgatggtggc aatttacaat ctcccaacca   2340
ggcaatagta accatcactg tattggacac tcaagacaac ccacctgtat tcagtcaggt   2400
tgcctacagc tttgtggttt ttgagaacgt ggcgctggga tatcatgtgg gtagtgtgtc   2460
tgcatccacc atggatctca attccaacat cagttatctc attactactg ggatcagaa   2520
aggtatgttt gctatcaacc aggtcactgg gcagcttacc acagcaaatg tgattgatag   2580
agaagagcaa tccttttatc agctgaaggt agtggccagt gggggcacag tgactggaga   2640
cactatggtt aacataacag ttaaggattt gaatgacaac tctccccatt tccttcaggc   2700
aatagagagt gtaaatgtgg tggagaattg gcaggcaggt cacagcattt tccaggccaa   2760
agctgtggac cctgatgaag gtgtcaatgg catggtactc tatagtctga agcaaaaccc   2820
caagaacctg tttgctatca atgaaaagaa tggcactatt agtctgcttg ggcccctgga   2880
tgttcatgct ggctcctacc aaatagagat cttggcatct gacatgggtg tcccacagct   2940
ctcctctagt gtcatcttaa cagtttatgt ccatgatgta aatgacaatt caccagtgtt   3000
tgaccaactc tcttatgaag tcaccctttc tgagtcagaa cctgtgaatt ctcgattctt   3060
taaagtacaa gcttctgata aggattcagg agcaaatggt gaaattgcat acaccattgc   3120
tgaaggaaat acaggggatg cttttggcat attcccagat ggtcaattgt atataaaaag   3180
tgaactggac cgtgaacttc aagacagata tgttttaatg gttgttgctt ctgacagagc   3240
agtggaaccc cttagtgcta ctgtgaatgt tactgtaatt ttagaagatg taaatgataa   3300
cagacctctt tttaacagta ccaattacac attttacttc gaagaagagc agagggctgg   3360
gtcgtttgtg ggcaaagtaa gtgctgtaga taaagacttt gggccaaatg gagaagtaag   3420
gtattctttt gaaatggtgc agccagattt tgagttgcat gccatcagtg gggaaattac   3480
aaatactcat cagtttgaca gggagtctct tatgaggcgg agagggactg ctgtgtttag   3540
```

-continued

```
ctttacagtc atagcaacag atcaggggat ccctcagcct ctcaaggatc aggccactgt   3600
acatgtttac atgaaggata taaatgataa tgctcccaaa tttttaaaag acttttacca   3660
agctacaata tcagaatcag cagccaatct gacacaagtg ttaagagtat ctgcctcaga   3720
tgttgatgaa ggtaataatg gacttattca ctattctata ataaaaggaa atgaagaaag   3780
acagtttgct atagacagta cctctggtca ggtaacacta attggcaaat tagactatga   3840
agcaacacct gcctattccc ttgtaattca agcagtggat tcagggacaa tccccctcaa   3900
ttcaacgtgt actttaaata ttgatatttt agatgaaaat gacaataccc cttctttccc   3960
taaatcaaca ctctttgttg atgttttgga aaacatgaga attggtgaac tcgtgtcctc   4020
tgttactgca actgattccg attcaggtga caatgctgat ttatattaca gtattactgg   4080
gactaacaac cacggaactt ttagcattag cccaaacact gggagtattt ttcttgccaa   4140
aaaactggac tttgaaacac agtctttgta taaattaaat ataacagcaa aagaccaagg   4200
aagacctcct cgttcatcta caatgtcagt ggttattcac gtgagggact ttaatgacaa   4260
tcctcctagc tttcctcctg gagatatttt caagtctatt gttgagaaca ttcccatcgg   4320
tacatctgtc atttcagtga ctgcacatga ccctgatgca gacattaatg gtcaactatc   4380
ctacacaatc attcaacaga tgccaagagg caaccacttt accatagatg aagtcaaagg   4440
gactatatat actaatgctg aaatagatcg ggaatttgct aatctctttg agttgactgt   4500
aaaagccaat gatcaagctg tgccaataga aactagacgg tatgctttga agaacgtgac   4560
cattttggtt acagacctca atgacaatgt cccaatgttt atatcacaaa acgcccttgc   4620
tgcagaccca tcagctgtga ttggttccgt tctgacaaca attatggctg ctgacccaga   4680
tgaaggtgct aatggagaaa tagagtatga gatcatcaat ggggacacag acaccttcat   4740
tgttgatcgt tatagtggag acctgagagt ggcttcagcg ttggtgcctt cacagttgat   4800
ctacaatctc atagtttcag caacagacct tgggcctgaa aggaggaaat cgaccactga   4860
attgaccatc attcttcagg gccttgatgg acctgttttt actcaaccca aatatataac   4920
tattttgaag gaaggagaac ccattggcac aaacgtgata tcaatagaag cagctagccc   4980
cagaggatct gaggccccag tggagtatta tattgtttca gttcgttgtg aagaaaaaac   5040
tgttggacgc ctctttacta ttggacgaca tactggtata attcagaccg cagccattct   5100
ggaccgggag caaggagcat gtctttacct ggtggatgtt tatgccatag aaaaatcaac   5160
tgcttttccc agaacacaga gagcagaggt aatgattttg tagtcattta ttatttgttg   5220
atttgctttt tagaaaaatc attctcttta tatttactct ctataattgt ttaccttcat   5280
tgtttattgt taaatttgtg aacaggaaca cctaaaaatg ttctgtcaaa ggctaacaga   5340
gagttacata aactttagtt ttaatcttgg ttgcaactaa acaacaaact ttcttttcac   5400
tttatatttt actttatagc aatcacatat ataaggttaa ggagaaatct ttagccattt   5460
cagaggggaa aaaatccata tatctaagct aaattgctga ggtaatctaa ataccactca   5520
ataaggaagg ctaccagaag atgggcactt tcagaattaa gaagacctat tccaaaatga   5580
agagctttgg taggaatcag cattgtacca tagctcttca ggaagagtgg ccatggagga   5640
tgggctgaca gtgtacacca ggacagtatt aactttcaca tcctcagcag tcttggcagt   5700
ttctttatag acagtgacta attttaatgt gctgagccaa gttttggaag attcctgatt   5760
tcatctgcct taacatttta gacactgtct tctgacttag gataatcctt ccttttccct   5820
cttaaattaa ggcatgcaat gggctgtgaa taatcagaga ctagggattg tttcttgaca   5880
```

-continued

```
atactgagtt caatgccatg ggatagatac actctgttct gtttgttggt gagtaagaaa   5940
ttagtgtttc atagcataag ccaaaagaat tccaagctca gccttccctg gagtgtattt   6000
taggctactg cctccttgta tcgttgattt gctttttaat tgaactactt tcaatgttat   6060
tttgataatc aactagaaat gatatagcta tactccagaa aactcttgtt tgctgtttct   6120
cagttcattc tttccctccc caggcccctc aaagacattc tagtgtcagt cagccaaaaa   6180
cacaaacatc aaatgtggtt tgtgatactt ggcagtgacc cagacacaac atgcaagtga   6240
aattgaggct catgtgcttg ttttcttgct tcttttcttt tttgggggga ggaggtgggg   6300
attttcttta ttttaaatga taatttatta ttattattat atatttttgt atcctctgtg   6360
atttttttc atagtagttg gttatgtcta tctatggatg gggaagaata tttatggctt   6420
aaaggaccat attaattaga gatataattc taaggggaat tcaattttat ctttacctac   6480
atagcactga aaggatttct aagccaaata acctctttta cctaattatt taaaaaatat   6540
tttaatatag ggcttatatg ttgagctatt tggtgtagct caggccatga tttatatgta   6600
attgaatttt gatttgaagt tatccatctt ctaaacccac aatcctctct ctaactttct   6660
tctctggaat gaatacttac atgaaaatat ttgattagtt tgaaaaccaa aatattgatt   6720
gaaggcagga aattaagtca ttccagactt tagatgaatt tgttaaactg taaaacagat   6780
tatgttatta gatgctgttg tttggttcag tgtagtacat tttattagaa tactatggag   6840
aatgagaata aatgctcagt tttatcatta gatttattgt gtctttttta tttacccatt   6900
agctatgcaa agattggctt agcatgaaag tattaaatag tgctgcctct gcaataggca   6960
agaagattaa aaatgtttat aagtaatttt gttattaata ggggatgatt tgtttattac   7020
tttttataag tcaagtaaca ccaatatgaa aagttatcat atatactatg ttctattcat   7080
ttaaaaatct ggggagaatt caatgtgatg atttttttaa ttaaaaaaaa gtcagcatat   7140
cttctgtgaa cttaagtgct gaaattgtaa acccaattg agttctcaag atccaaccac   7200
tttgaaaatg aaaagcaaat gtgtttctcc aaagaatatt gaaagcagtg gttgtgagct   7260
agaatttcat attattattg gttggatttt tcaagtgtat acaataaagt gctgttttcc   7320
ttctgctcaa acaattaatt tactgtgatt ctgcaaaaat aagttataca tttcctcttg   7380
ttatcaaagg cgatttttaa attgtttgtt taattggact ttgtccagcg cattttaaaa   7440
aattattcat gtacactgat aagagtctgg gttgcttact caggtttctg gcagagtcat   7500
gctgatcaca ttccatgggc aggcagagag tcagcgggta aaagagaaac aatttcatct   7560
gcattctttt cctagctctg acatttgggg taagaggcta atgactatga ctctgatatt   7620
gttcattcca aagatgtgtc cagttataca cctttactta cgctacttgt tatatccaaa   7680
gatttggcat tggtagtaat gtcattgaaa gattgtgttt gggtttcaga cacaagatta   7740
attacctttt tattttgtct ctttatgttc tcagaagagc ttagatagtc ttgattatgt   7800
tagaataggc catgtaaagt ttgtggcatt tttctaggtt caccaaaaaa tagatatatg   7860
tacttcagta agcatttatc ctttaatgtg tattacatag gaacatgcaa cttaggaacg   7920
tggttagacc tcatgatggt caggggcttg ttttattggt ctttgttatt tcagaccgtg   7980
gcatattacc tgatgtatag taggtgctcc atacatgttt gctgaataag atggtagaag   8040
acctaagatc agaacatatg tctttataac ttgggaataa atcaccagag aaaagctgag   8100
gaaatgaagg aagttaataa atctgatgct gctcattaat tgaactcagg tcagagcata   8160
ataattatct ctgctctaca aatgaattga taactgtcag gaaactcaac aaggaagagg   8220
aatttacgtg ggtgttctga tatggagctt agtgtttaaa tggaaggaag caatcttata   8280
```

```
cattcaggta gtcaccaggc catagttccc aaacttgcta cattcaggac ccctttatgc   8340
tcttaagaat tgtcaaggac acccctggag actttgtgta agcatgtctt gtctattgat   8400
atttaccact tttaacagta caactgagga aattaaaaat atttgttaat tcattttaaa   8460
actacattat attttaaata tataacatgt ttattttgtt ttaaaaaagt ttatttttc    8520
taactaaaaa ttaaagagtg gcattatctt acatctttac aaatctcttt aatatctagc   8580
tcaatagaat acagctggat tctcaaatct tcttgggcaa tatattgcaa tatgttgtgt   8640
ttttggctaa aatatacaag cagaatccat ccttacacag atattttgag tgggataata   8700
gagaaatagt ttgcctactg catcagaagt ccacagtggc agtttcttaa gacttacttg   8760
cagtgtggaa tatgaaaccc tgtcagcaaa cttttcatag tctgttacat aaaaatacat   8820
ttatctcgca ttcgtaatga ttttttttta cctattcctg atttagaaat atcaggcatt   8880
gatcatttca aaattattgg tgtaactgat aaggaattta tcataaaagt ctttaatata   8940
tgactctcaa cctgttggtg atggttagaa gttttccaaa tttgaatttt tactcgaaag   9000
ctcaaatttc actattagta acatatattg ttgttttcct ggaagtgtca ggcttccttt   9060
gttcatgata aaaagaaaag attatgcata ctcaaatatt taaaaagaaa cagttgctct   9120
ttcgagtaaa aatcgtattc cacaaatcaa gtggctagtt cagcttacaa ttcaattaca   9180
catatgcatt tctttgagaa aaccacaata cctaggtaca gagtaatggg tctttgtgca   9240
catattgctt tgtgtcacac aggatattga aaagacatca aagttgagtc tagatttgat   9300
aaaattaata cgtttttgt tttctcaaga aaacttattt acctttttaa atgaaatagt    9360
tttgtttgtt tgtttgtttt actgtgagta tgtggtggtg aagaacacaa ttactgctaa   9420
agtactttgg atctactgct ttgatttgtg ctaaagtacc accagtttta cccaccattg   9480
cttttgcacc tctagcataa atgccaacac agtgaacaaa ggcagaggat ggtttgcatt   9540
atcatgtaaa cagtgttgat ttcccaggac tccttaaaca ggtctctggt ttgcatggag   9600
gtccatgcat actccacagt gagagaacca ttggtgtggg tagtgagatt ttggcagttc   9660
agttaacaac caggaaaaaa agagccactc gaaataatat attaaaagta tgtttggaat   9720
attaggtaaa tggactatga ttcattaatg attacaaatg agttttagca atctgataat   9780
aaattaattt attttcacaa gaaactatta agatttccaa gagaaatgat ggagacattt   9840
gtgaggtcag ttttggatac aaacgttaga aatgattttc tttcacaggg ttttgaatca   9900
cagtagtgca ccttagatta aatgtctgta tatcttgtgt attgaacctc acaagcagaa   9960
tacaggcaag agagctggat atataataac tgttattatt ataaaattta ttgaatattg  10020
ctatgtttag acataatgat aagtgcatag tgataagtgc atttttaggg attttattta  10080
acccatacaa tactaatatc atttgcattt tgtagctatg gaaactgagt ctcagataag  10140
ttaataagtc gcttaagttc atatagatag aaagaaaacc atatccagac ttgagtaact  10200
tcacaatgca tcctcataac tactcttcta tcaagctgga tcagtctgtg gttttggtta  10260
agagaaaagc tctttgccct atagctatga tgatatatgt atgcttttta ataactttgt  10320
tttcactctc tgatttgttg cttaaaaagc atttaaggcc aggcaaagtg gctcacacct  10380
taaatgggag gccaaggcag acaattcctt gaggccagga ttttgagacc agcctgggca  10440
acatggtaaa accccatctc tactaaaaat acaaaaattt gccgggcatg gtggtgcacg  10500
cctgtagtcc cagctacttg ggaggctgag ataggagaac cactcaaacc ctgggagcag  10560
aggctgcagt gagctgagat catgccattg cactccaggc tgggtgacag aattagactt  10620
```

-continued

```
tatctcaaaa aaaaattcat aagtattttt atgtattgtg taaaataaag ggaaacaatt  10680
tttgcctacc acagctaagg ccctcagcag atcggttaca tccctaggca tcattagtgg  10740
tggtagcaag gagcctaaat tgaattagga agacttccaa gggtttctag agcagggaag  10800
aagatgagaa tttgagagaa gggagctgaa ggcaaatgga gagcaaaggt agatgagggg  10860
cctcttctaa cctacagcac tattcacttt ggaagcagtc actggagttt aagaaggtgg  10920
agaattattt ttgaattttt aggtgataaa tcatcttctt tggaataatg atggggttgg  10980
agtggatgga gtgtgaagat tattttaaat aggaaaacat tttactgctt cctatgtgtt  11040
tgaagtcaag agtgtttctt taaaaaacag cctgggataa atttttgat tttgtttctt  11100
ccctattggt atgtttttaa atgtattgaa caaaatgctg tgaattaaag ggctttataa  11160
atttttaaga tgggtacaaa tgtgtatgac aaacaggatt attgatggct aattatgttc  11220
atgctgcata ttttatatat atcttcagga tgcttgattt actcctgctg ctagatttct  11280
atagacataa ctcatcttcc aatgaattta caatttatta ctttttatc tttattaaaa  11340
ccctaatgat tttaattctt ttttgtttta ttcaattttg aggaatctgc tctaggaata  11400
gttttgaaaa atagttattt acttagaatt ttgtggaatc aatttttcat tgcattgtct  11460
gcagcttgca ctttgtcatc attagagtga aaaactgcct aagaacctca ttagttgtga  11520
gggactgttg cattagtgac tgtagcaaac tgcataggcc ctgaggtggg ttctgtattt  11580
caagaattaa taaatctagg cccagcgctt tataaaaccc ataaaagtag gtggtattcc  11640
gaattaggca ctcgtgagtg gaaataggaa aagaataact ggcaggtaat gtgggtcaag  11700
atgaatataa agtgtccaat atagaatatg gtaaatattt tctaataatt tcaagcttta  11760
tgtagtctgt gacaaaagta gccattttaa tagtatgttg actgagaagg agagtatagg  11820
gaatgcagac aggtgaaaat attctattaa acaaacattc tgtataaaat acacacatgt  11880
aattatatat taacacgtat gcccccattg tacaaagact gttggctttt ctttgctctt  11940
aatatcctga gacaaaattg gacaattaag tcatgaagag gaaacaatct aattggcaga  12000
taatttatat gtggtaatta aacagtgatt ataggaccac aatcttcttc agtttccaga  12060
cgtgtatgca tttttaagaa acgatcagtg agtaaaaacc aaagaatttt aaggctttga  12120
agaaatgttg aaagacattt agaaacatgc tttgctactg gcaggtggga gcaagtggca  12180
tttttgatga ttgttacaga ttatttgaca tttctctaag gctttttatc attcacagat  12240
tctaacatat ataaatcgtt tatgttattg ttagacactg gtaaacagtc ttgccaggtg  12300
ctgtcttgcc tttgcaatgg ttctggaggt agatacaaca tatcatcatt tgacaaatga  12360
gaatactgag gctcatggag gttgcttatg gagttggttt atggtggaag caggatttaa  12420
acccagcagt ctgcctctga agtctgtgca tttagttcca acacagcact aactaatgct  12480
acttgtaaga atgattattt ctatacattt gtagacataa ttctcaccat gtaaaaagtt  12540
gttttcatat ttctatactt gttcatgtta atgatgaaaa aatataagat aaaatgaaat  12600
tttggtgatg aaccagtagt aggattactt taggtcccta tcaatctttg tttaggtccc  12660
tattaacctt tataatcttt attaacctat aatctgttat ttcttcattt tgctttctaa  12720
atcccaaggc aggaatatat ttccattctt tcagttgctc atttattttc ttccctttgc  12780
agcaaaactt tttgaaagag ttgcctgtac ctgcattttt tcttctcatg atctcttaaa  12840
tctactccca tcagacttgg cccctgccac tccagtgaaa ttgctcttac tgaggccact  12900
atgatggaca cattgctaga tccaatggcc tttctcaatg ctcattgtag ctaatctaaa  12960
gaatatttga cctagtggat tttacttcca ttaaatgctt tattcggttg gcttccgagt  13020
```

catcatattc tgtgactttt taccctttt tatttcttgg accaatcact tctcagcctc 13080
gttcgcaagc atctcaccat gtcctcaaac tctaagtgtt ggaacatccc taaagccagt 13140
tcttgcagtc tttctctttt tactctatac tcattccctt gaggatctca atctcatagc 13200
attaaatgac atatatacac tgatgactcc aaaattttgc ctccagccca tatgtctttt 13260
ctgaacccta cattcgtata accaatcact tattcattga ttagcttcct aactgatatt 13320
ttaaattaac atttttaaat ctgagctgct gatattctcc ccaataaaaa catattccat 13380
cttcacccat cttcttttca gttgatggca attccaacct tctgattgat caggtcaaaa 13440
atcttagcgt tatctttgac tcctaacttt ctttctcacc ctacttacaa cctttcagtt 13500
gatcttgttg gctctgtctt caaaatattt catttcaata tgatcatttc atgataattt 13560
ctcatcatgc tcactgttag taacttggtc taagacacca tcattcttcc cttggattat 13620
tgaagacatc ttcttgttga tttctgacag tgttcctatt gttctcttct cttacttggc 13680
tttacctaca ctggcttctt tctattctcg gaacttgcta ggcacacatt agccttcggg 13740
cttttgcctt ggctcttcct tctgcataga acaccctttc tccagacatc agcctggaca 13800
acaacctccc atacttcaag tatttttttt tatctcacat tgcaaattag gctaaatctt 13860
cctttaataa cttattattg taactatccc ctcatgctgc ctgatttcca ttgccttgcg 13920
gcatttcttc atcttcctct cccataaggc ttaccagcct ccttcaccaa tttctactta 13980
tctcctcaca tgttaaatgt tggaatgccc ctggaactag ttgttgaatt ttttctcttt 14040
ttaatcaatt tcactgagga gctcaaccaa tctcattcct ttatataaaa tatgaacact 14100
atatatgtat aggggtgggt gtgagtgata taatttattg atttataatg ttgattattg 14160
tttgatctgt cttcttccca ctggaattaa tttctacgag ggcagatata ttgatctgct 14220
atgttcctta acatatctta agagtctaga acattacttg gaacaaacat agtagacaca 14280
atataagttt ctgttgaatg actaagtgaa tgaatgaatg aactggcatc tcagcctttg 14340
tccttgtccc cttcagttta gtctagcaac cagagtgaga gtgatctttt agatcatttc 14400
atttgcccaa aaacttccta tttcacttat agtaaaagtc aaattcttac aatgaccctg 14460
aagaccctag ttgactgctc ttattagtta ctgtttggac ctctttttc ctgattcccc 14520 ttgcctgaac ttgttcagca accatcagag ctccaggccc cagcctcagg cgcccctcct 14580
tagggtcttt gtggcagctc tggcctggac tgctcccttc ctcactttcc ccacatcatt 14640
tctgagagtc accttgcaaa gtccttcttc cctccagttt tcgtttttct ctttccttcc 14700
ttttgtttct gctttttct tatcatcacc cgacataaca catatgttac ttgtttattc 14760
tgtttatggt gtgccttccc tttagaatat atgtttcatg aggggaaagc ttttcatctg 14820
tttctgctat atgcacagca cctacagtgt ggctggctct aggcagatgc tcagtaaatc 14880
attgataagc taaggattta ctgttgataa tgctgcaaat atgctgctta agcttcagga 14940
gctcaaccag tgatgcatgc tgaagtaggg gagtcatttt tcatctctta agccaagact 15000
ttagagcctc ttctgaaatt agggaagtta actgattgga aaagactggt tttccttcat 15060
aaaaagatag tggctacatg acttgattgg ctaagaacgt gtaacccaaa cttcagaaac 15120
atttatggtg tctgtgaagg aaagtgggac cactaatgct atagatgttt tggtaaagta 15180
gaacatttta gaaaatatat atcacagtgt atgctacacc atctcatgtc ttctcatctc 15240
cttcaacctt atctaatttt gctttagaga gcagatctta agttattgtt atcgtaaacc 15300
atgttgttca tcagaaaaca ggtgaataca tagaaacttt gaaaacatta ctacttttaa 15360

-continued

```
tattgataac tttaattact gtcattcctt ttttctaatt taccatcctt gttcaacatt  15420
tcacatcaat aatatcagta aacttgattt taacacgcag caaagaaaat actgctggac  15480
aatccctctt gccttaagtt tagttgaaag aatgcaggct tttgatttaa gagaagcttg  15540
attcagatgt tgtcacagct actctcagaa tcttattttc ctcatttgta aaatggtaag  15600
gatagcctac ttcatagctt cttgtgagaa aaacaatggc actctataaa gtttattagt  15660
gctcttcccc tttttcctca aaatatagat ctgcacagga ctattaacat ttaagaaaat  15720
gtctttctat ttttaaagta ttttagagtt ccgttccatt cttttttttt ttttttttcc  15780
tttctcaatt tcctcaacaa gcctgtaagg aagtcaagca tttttatgtt cattttaagg  15840
aaaagacaca aggaatttca ttatttctgt gtggtcacaa atctagacta gcacccaggt  15900
ttatatgact ttggtcaaca tgcctgacat taaacaatac tgcccagtct ggtgttaatg  15960
ctatttttca tccactattg tattgttgtt gacataattt agtaatagtt ataacccctt  16020
aagtgaagtt atttatgaat tgtgaaactt ttttaaaggt ttagttgctc aggaaacaaa  16080
caagttagaa tatttgaata ttcagtgttt gtttcatttt catttgattt aatttgattt  16140
gatttcattc agtgttttgt ttcattcaga gagaagcctt atctctgatt tagatgaggg  16200
atattcatct ctcaattttt agtgatggta gtaaaatatt gactattatg gaattgtgtg  16260
tgtttgtttg tgagcctatt tagaaatcgt tttttgtcca tgacttaatg cagttttctt  16320
aattgaggtc gacttggctt ctccagtcca aaaaagggaa aactatctat ctttcgaaac  16380
tactctttaa caaaacatat aaattctggt aactttttaa gtgaagattt tctaactaat  16440
gattaaaacg ttttcctgga cagaaaagta ttttcttact tcataaaata ttcaaaataa  16500
gcaaatacac aaagaagatg ggctttcttc tgctcggggt agtgttttat ggtatataca  16560
tttttgttct ttggttaaaa tacttactct tatttttatt tatacattgg cttcattcta  16620
caatagattt gaagcagttt acaaaagtat atatacaaca aagagataca atatttaaat  16680
gaatctctaa gtagtaaaaa taagtgttac taaaaaataat cctgaaatat ataagattag  16740
catacagata tatgtaattt aggtaactca ttgagtttat gtttagcttt ctaaaggcca  16800
agtcaagcag agaagcaaga tcagatatgt aagtcatggt gctcttatac taaacaaaca  16860
cagggtaaac aaaggaaata cagattttct aaacccaagg aacttaatag aattcgtccc  16920
acagatgctc aaaacagacc tattttaaag tgatgatttt cttaatggca tcttcactag  16980
ttcaatgaca gatttttaac atcattttaa tgtgacgtct tttcgtgtgg atttgtggca  17040
aattgtaaaa gtgcagttct ggcaaattat ttatttatgg atcaaaagag attccccatt  17100
gataagtgct tttgtttagc tttatttcat gaagtggatt aatattttat aaccaaagca  17160
agaatatccc tactgggttt tttcacatta gcatatctgt agcacatcac aggaaaaatc  17220
taactagaga ggttttctgt aaaactgtag cttaatcctt aaggagactt tattttaagc  17280
tatgctgcag tgattaaaat gcttagcacc aatttctagt aatctgtgtc ttagattgtt  17340
tccatttttc aagaaataga aacaatcatc ctgtgagata acaaaatttg ctattgaaaa  17400
catcggtgct gtttaaaaat gtcatatatt ttcaaatatt aaaaatataa aagaataact  17460
atcacataca ctctaacttt tcctctggtg gagtcactaa tatcctaagg ctaggaaggt  17520
gaggaatcaa taccaagtaa aggtcagagc tctaggatgg gaatgggagt ctcaggtttt  17580
taattctagg acagtcattt gacacctcat tttcaaatga taaactgaaa caatagggtt  17640
tatgtggccc actcatataa cacacttagt tggcagagga gtcccagatt agaatttctt  17700
acttactgag tatagtcaac ctatactcag tgttgactcc agtccttaaa ctcggagtga  17760
```

-continued

```
gaaaaggagg ctacagcttc ctcatgatct tcacatctcc atcagcatcc tcccaaagac  17820
atctcccaaa aacatggaat ttaaagtaaa agaaagattt tttgttatgc aaatgcggct  17880
tcaagatgaa gcctttggac cccgattctt gctctttccc acatgccccc tcacctcttc  17940
ccatgcacct gtccccatcc catccatatt gttgtcccta aatcccattt gcaaagatcc  18000
tggatccacc aacagctata acctttcttt tttcatgaca ctgcttctaa atcctttgca  18060
caattctgag aaattgcttc ctatcaggtg ctaatggcat ttaacctttt agggatctcc  18120
tgtcttcaaa ttaaaaaata ataaaatgta ttcaattcta ttgtcatgtt aatttcaaat  18180
tttttaacaa ttttgagatg tttgacagtt tcaggagatt tgcttaaaac aagacatgta  18240
tttcatatat tactttaata ccaaaaccaa ttgtgattat gtctatctaa tggcaaattt  18300
gaaacataat tcagagttat taaatgttac ttgaattgat tatattatat ggtcatagaa  18360
ttttcctcac cagtagctgt atggcaatcc tttaattgca caaaagttaa cccatagtct  18420
cttttttta agatagtact ttaaaatttc cactaaaaac attaaaatac caattcatgt  18480
atagtatagc tatgtggaac agaacagcct gtgttgcaac gccagcttaa tatttatta  18540
cttcacataa taaaataggg aacgtattta tccactgagg ttgtaattag ttacaagtaa  18600
tgaatcttta gtgttctaat tccagagcct ggcagattta gaacaccagt tgaccctgtc  18660
ttgctggaaa atgaaggaag tgggagtaga attttctctg taggacaaga cagctttgga  18720
tgggagggac aatagaagct tgccaaaaac atgggtcaaa ctgaacacag atggctgtag  18780
ctgatagagg tgtctattat tgtgttttct tctcagcagt tttctctttg tttgtcagta  18840
tttttatact tacatgaaga aattttgttg ctcagcaacc aagagaaaat atactaatag  18900
aatccatttt tgttggaaaa aaaatgttgg tggtagatgt tgatgatggg gttgaggtag  18960
tgttgtgatt gagcagtatt aacgtaggag tagaggtgat tttctcggag tgctgtttat  19020
tataagtgtc taaaattaaa tatatcacat tatccattta ctgcttagct tgcctctgtc  19080
ttacacctcc aatactattt gggaaaaaaa tggcctaagt aaatgtattc cattagttaa  19140
taatataatt tataatacac ggaggaaaca tttgaagaaa taaaactata atttacatat  19200
tttttataac ttcagtgttt cctaaagtca attttttaag cttcattaaa ggatttcatg  19260
tgtatttcat tttttttttc tggaggagtt ctatttatta ttcttgagta catctgtttt  19320
ctgcatggtg aaatattaaa ataaatatat atttgaaagt cagaatagtt ttgttcaaat  19380
actggcttaa cttttcatgc tgtgtgactt taagggagaa gccaaacttc tctgaaccac  19440
agtaccttta tctgttaaaa aaagagaatt ccaatccctt aataagtgtt gtgaggaaaa  19500
tgtgcagtac acatagcact gcatattttc ctaaaagact gtttgattta cttttgttga  19560
tgctacattc agttatttac ttcttgtgtg gtccagaagg caatgataaa aaaatgtaaa  19620
caactcctgg tcatgtaaat agctactgtt catacaaaaa ttgtgatgac atttttaatg  19680
ataccacata aagggaaatc aagaccaatc ttacaaattc tgtttcttgg ttttaaggaa  19740
attattaagg aactgcatta aaaataactc tgtggtaatt ttcttcattg tactgtatca  19800
ggtagaaaaa taatttttaa atgagtgact agtgagccgc aagacataac caagaacaga  19860
agggttatta gctaacaaag ggaagcagat gtaattttta aacattgatt ttgcatttat  19920
ttattttaag taaactacag aatttttaaa ttttaatata atgcaaaggt agagtagcat  19980
tttccaattt atacactatg ttttgataag tgtcagatac tgaagttata ttctaaatat  20040
aatccacccg cctagggaaa cgaataaaaa tataaccttt gttaaaagat agggtaagtg  20100
```

-continued

```
aattgttaat gactattcca gaagtgagac ttcagaacat agtttggctc taaaagacct  20160
ttctttcatt ttaatattat atttgaaaca cttagtaaag ataaattttt aaatgttcaa  20220
tgtctgatca ttgtaagcaa tgtcattttg tgagctctat ttctggaact agaaaaatta  20280
ctttgaaaac tgtccattct ggttgtgctt ttttgagtaa gtggtcttag ttgtatttta  20340
atagaggaaa tgaaacaagg taccactctt ttaatgtatt tattctgatg ttgaggcgat  20400
atgttagaac aaatttaatt atactatgac tatgaaaaca aaattaggca gaactagagt  20460
gataggcggg aactcattgt tgattttcaa cttaaatatc atatacttat taatatatgc  20520
attacaaata tatcatttaa ttatctcaac aactctagaa ggtaagtaat ggtatttcca  20580
ttttgtagat ggagtatcaa ggatcatgaa attgtcagta tattgttttg tggtagagcg  20640
ccatttgagt tcatttggtt ccaaggcttt agttctttcc agtacacttc actggtcttc  20700
aattgttata aatcacagcc tgctaatttc acagaaagga gattaaaagc aaaagccata  20760
aatataaata cgaagtattt gaatgctgat ctatatcata actagatctt tctttttgt  20820
ttggattata gtgaattttt aaactagaaa atataagcaa acagtatttt tgaaggatgt  20880
aataaccaca ctccaaagta catcaatgaa tcatattaaa ttaaccatta attaatcaca  20940
ttaaaaggaa aagcatactt aggaaacaca gaaaatttat tttttaaggg ttgaacttat  21000
aattaactga attaaatgag atgttaaatt aactttgaaa ggcacatttc gatcactgat  21060
atacctaaac ttgcctccta attaaatact taaaaataaa tgaatcaaca tttgctttta  21120
ataatgaccc tgagagaagg aaaatataga atatttaact acaagttaat aactaataat  21180
tagtgtagat ttagtagtag aagaaaaggt aagatggagc caatactgta actacattat  21240
atgttaaaac acttatgtaa acacagccag atataattat atggaggttg ctttaaggat  21300
tactgttatt acatataaaa ttttccttac aagagtaggt gaacataaaa agactattga  21360
attcaaatct agggaacttg ggaagaaaaa taaaactctt ttagagagtc tatgtaatac  21420
atgggaagag taaggacttt tgattcaaac acacttgggt acaatcatga cttggggaag  21480
ctgtcttccc caagagtatc acagtatcag ttgcctcttt tgtgaaatct atttcacaga  21540
gcagctttga gaaacaaaac ttaaaaatgc acccatgata ctcacccaaa ataagtatcc  21600
attcacttct ctctcatttt cttcatttgc atagatgctg gttttgtcat tcatcagaca  21660
agattgccag gatataacat tgagaactat gtaaatgaca ctacatcttt tcatccctgt  21720
tcttagatga agataagttt gagaattttc ttggggtgtt tcagtagaga attaaacctc  21780
cttaggattt ctggttttgt tctgaaatgc aagatggaca tggaagcaga agggacatta  21840
acctgtttct ctgccatttg cctggatgta tatatttaca ttgctaagat cttggttctg  21900
cacactgtca tttagacaat aactaaggat ttccgaatta gaagggataa gtgttaacta  21960
ggaccttgtt cttatgtttt attgtggata atgtgttggc ctttgtacta ccttcccatc  22020
ctcaactatc attccagtat tcaatatgcg agctacagtg tttcttactg ggatttaaa  22080
tatgcatagt tcaggtcaga tacacatatt tcaaatatgc atggttcaaa ggtaagcagt  22140
tacctttaac aggatagctt ctatttatag cttttatcca tgccctcaag agactagcaa  22200
tctaatagga agacaaacat cacataaact attatcagaa aatctaaaag attgctgtga  22260
tgaaaaagtt tcaccagctg attacggtaa ctggtttctg taatctcaac acaattgaga  22320
ttatttatcc tgtctgagct tttggttttt gcatttcata aggctttgtc tgcatatttt  22380
aaactattgg aaatgaattt tttttaatct atgtgcagaa aaaatatcag gcaaattata  22440
cccaccttta ttcttctgtt tttaaaatac tgaatatgaa atattacatt cctatgtaat  22500
```

taaatagcgt ttgatttaaa gcatgtggac cttgggcctc atccaaggga tactctagtg 22560
taccttggtc tgaggctgct tatcagtcct gatgtgcttt ccctttcctt cctgtttgaa 22620
tacaggtcca ttctgtgctg ttaccatctc tgtccttaag agcttccttt gccctaagat 22680
gccccgatgt atgtttgtat ttgatgacat atttttacat cctggtcagg aaatataatt 22740
attcatctct ctacaacatt atcaacatta tctccttttt tttgagacgg agtcttgccc 22800
tgtcgcccag gctggagtac agtggcacga tcttggctca ttacaacctc tgcctcccgg 22860
gttcaagcga ttctcctgcc tcagcctccc gggttcaagc gattctcctg cctcagcctc 22920
ccgagtagct gggattacag gctcatgcca ccacgcctgg ctaatttttt tgtattttta 22980
gtagagacgg ggtttcaccg tgttagccag gatggtctcg atcttctgac ctcgtgatcc 23040
gcctgcctcg gcctcccaaa gtgctgggat tataggagtg aaccaccgca cccagcctcc 23100
aacattattt ctatggtaat agttattaaa caataatagc atcattatta ataattatgg 23160
aacattaaca gcaactacct ctaaaacaac taaaactaac atttatttaa aacaaatggc 23220
tatttatgct attttattca aacctcaaaa taatgctatg aaatagttat cgttgttatt 23280
accatttcac tgatgagaaa actgaggctc agggaagatt agttaactcc ctttggatca 23340
tacaattagg aagacctaga gccaagattt cagcctaagc aaaattcatc cttagcaata 23400
gcacatcctg acctggtcat atataagaat ttaatagtag tttctgataa agatatcggt 23460
ttggaaaatt taaaaaaata atattttatt gtacatctat aatataattg tatagttaat 23520
tgtataattg tataattgta tatgtgtata tgagatagac agtttaaaaa atattacttt 23580
aagtcctttt tgaaatgaat cgtgaataaa aatagtttga atatagaagc aggattttaa 23640
tcaaatgaat atagaaaata ttctttaaaa tcactgacag aaaatacaag aatttcagaa 23700
aatgaacgtt caacatattt tttcaagggc tcttattctt ttctattttg tggatattca 23760
atataagcaa aattttaaat tcaaaaaata tttaatttta tatgttgata tattttagtt 23820
tgattaattc tcaaaactta atgtacatga gactctctta ggtggatatt tatttaaaat 23880
gcatattact tttcagaaga tttcatgaaa gttcttgaaa catattttaa caagtccctc 23940
aagggattct gatgcaaatg tctcgtagag cacattgtaa gaaacaactc tttttttttt 24000
tttgagacgg agcctcgctc tgtcgcccag gctggagtgc agtggcgtga tctcggctag 24060
ctgcaagctc cgcctcccgg gttcacgcca ttctcctcct gcctcagtct ctggagaagc 24120
tgggactaca ggcgcccgcc accacgcccg gctaattttt tgtgttttta gtagagacgg 24180
ggtttcaccg tgttagccag gatggtctcg atctcttttt aataggttag gtcatatata 24240
agaatttaat tacacatttg caaatttaga agctcttctc taaagttttc cagtttcact 24300
agttctttga agtagtagtt gtgtagcagt tgcggtggca atagtagtag cagcagcagt 24360
agtagtatta gcagtaatag taacagcata gtaacagtag tagtagtagg ataatcaaca 24420
catggaacac taagggatag ttatcttttc taatgtggtt gctactcaaa cacattacaa 24480
gattttggca ttagttgaca agctattgca agcaatcatt gagataataa actataactt 24540
aagtaaaaat gtacactgtc ctgtttatta agtttgtgta aatgtgttat gtgttgttat 24600
gtagctttag aataccttca ctgacttttc agcaattacc tttaacagaa tagtttttat 24660
ttatttttac atttattata catttagaaa gaagatgaga gcaatagttt tttattagta 24720
taaggcaaac ttaactgatt aaaccttctt aggaaaagca atagttctga aagatatgca 24780
agaaaaaaaa tgacaaaagt gaaagaactc tagtgtttca agaacaagga atggctctat 24840

```
gagctatccc taggaaagca tatttaaaat gaactaaaat aaggatcttt tgcttagcac  24900
agaatgtatg aggtgttttt aaaagaggtg gcctgaggca gtggttatat gggaattcat  24960
acaaatgtta gagatttgtt agtttttaca ttatacttct attaactgta gaattactat  25020
tagtatagag acctcaagtg tttcttattt ctgaagtctt cttagtagtg aaatgatgag  25080
gggtatagta atgtccattt gtaataaaaa tgattaatga aaaatagaat tttttatttt  25140
ttaactttta ggattcatca tatgctgaac atctttttaa agttctgact gtattgtgca  25200
atgtctttta attcatgtgt gttcttcctt atctaaaaat catttacatt tacaaataag  25260
aatattttta cctgcaccaa tcaagataca attagtagct ataaatgtaa cattctatat  25320
gtaacagaat aagaaaacaa gagaaaaaaa ttgtaactta gcataattga aacatgtgcc  25380
tagccatctg gagcacttct gcataatata aagacatttg acattttaaa taaaggattt  25440
tgaaataaac aagaattctt ttgtgtcttc caaagacatt gatttattga gactatgtgt  25500
ggcttttcat catatacaaa agattaatga tttcctaaaa gtccttgcat ttcttcattt  25560
tataaaatgt atacacacag ttaagaaaaa tgaatccttg aagtcctgtg aagaaaggtg  25620
acaggaaata gttcaaagta tttcatttta aataacatca aatattataa aatataaatt  25680
ttctcaaagt aaaaaaatga gcttggcatt attgaatgtt ggttgaatga taaatgcata  25740
agtttatgat tatcccaata ctatatatgt gatttttatc aaacatatta aagagtacta  25800
taaaataatt ttaacttttg atctataaat ttctaaaatt tcagcacggt gattggtgtt  25860
gataaattta aagcatcaaa cagatcttgt cttatcaata agaagtagtt taaataaaca  25920
tttttgaaag taaaattttt atcaagctca aataatttca aagcatagtt caagagatta  25980
gaaagctttt atggtataaa atatgaaatt gatactggtt ttgttcagaa tcccttcatt  26040
gacttttcag cacttacctt taacaggatt gttttattta catattttta catttattat  26100
acatttagaa agaagatgag agcaatagct ttttattagt atatggcaaa cttaaactga  26160
ttaaagcttc agttaaattt tgccttatac actcatattt cctgttaaaa atacaattta  26220
aatttagata tgtttacatt aaaacactca gcacattata aacttaacta ttgacttaaa  26280
aattttgtag acgtcatcat atatgtttga attttatttt tttattacaa taacaatatg  26340
gtcaagaatg aaacacaatt ttatattact ttatagctaa gaatgttaaa atgagataaa  26400
aattcaggtg taaaattttg gttcattctt tttcactact acttttattt cttagttatt  26460
gcattaaatc aggattttag agaaatattc catccaatgt acagttcttt tgagtaaata  26520
ttccaatgca aataaatcaa tgcaatatca ttttgaaatt ataaattggg ttataattaa  26580
ctatattggc taatattagt tttataagtg ttttaataac tacatagcaa aagttctgcc  26640
caattttaat gtaatttaga agctgtgtaa attttaagta atcatttacg cttttaaaat  26700
catattcata ttcatatatt ttggtttcca aaatagtggt ttttataagg cctcaatttt  26760
tttcccatgt aaattgaggt atgctattga gttctctgaa tctgctcttg tccataaaga  26820
tagcttattc tccttcagac agggcggatg atatttccag aagcaagtca gtgtattaac  26880
ctagttacgt taaaccatat ctctgctatt ttagaaacaa tgatgaatta agcagcttca  26940
gttcttgggg cagcatccag ggctagaacc catagcacca agtccatggg ctcctcccac  27000
ttcacctcct gtgcatgtta ccagccattt aatctgtttt ggcccctaaa tcagtcagga  27060
atttccatat gatttacaac tccatttgct aagaagaaaa aaaaaatgaa gaaacttaaa  27120
tttcatctct taatatagtt ttaatagcac ttaataattt tatcttagaa ttttgaacac  27180
atttttaaaa ctctgagttc gagtattgac tacctactat gtgaagaact ttactgctca  27240
```

agaatatacg ttaaaaatac atattgaccc agctctgaga gaaaatttga gaatccacac 27300
tacagaataa aagaaataca gtagaaattg tggaagagga tacaaagtaa attagttaag 27360
catattatta ggcaggttga ttcgaaaggg ctttctgaaa aaaagtttga tcttagattt 27420
acatgaattg ttaaatataa ataaaaagag ataaagcatg agatatttcc aaaagcatat 27480
ttaatccagg cctgtgcaaa aggagggtga agaacagtaa tgaattggtc tctggatcat 27540
gttgtgttct aatagatgat ttgataaaga cttggtatgg gatgtgagtt agaggaattg 27600
agcaggagga gtgtattagg agagagagcc tttattgcta ggttaagtaa tttacatttt 27660
tgaagttgtg ggaacatctt ataactcaat tactagaatg caaaaagttg ctgatgaatg 27720
ttgagcaatg ctgtaagttt tccaaagcat atccaagaga gattgcattt ggatttcgaa 27780
taagattatc tcctttatac atctattctt ttaatgtatt ctactatatt ctactcttga 27840 ttccccttt ctgtggtgta tggatttccc aactaccttg aagaattgag aagcaaattt 27900
attaggtgaa ttattccaat ttcctagtaa ttaaacagca tgaacatagt tagtctagga 27960
ggcctggtgt tattttaatt cacttttcct tgtgagttta ctgaagtgga gattatccat 28020
tacagccaga ggctttaacg accagaaaat tcttcagcat accttaaaca ccaattcccc 28080
atgttgaaat acttaatcac cactcttgct tctttgggtg ctgaaaagaa gtttgatctt 28140
agattacctg aattgctaaa tataaataaa aagagagaaa acgagatatt ttcataacca 28200
aatagtatct gtgatgccaa tgggcgttat tctgctttcc tatgtggaag attccttctc 28260
atcattcact gttttggtca agaacaccct gatgaaaaaa atctttggtt gccttccagg 28320
tagagttagt ctcttctaag ttccaccatt tttattcaca ccataattgt aatgcttacc 28380
ccattgataa attacttgca tttctaactg tccccccctgc cccccaccac catgactatg 28440
atctctttgt gcctggtgta tttctcactc atccctgggt cctccatgtc ttacagtggt 28500
gcctggcaca tggcaataat caataaatgc caagagaatg aatacattga aatgaatttg 28560
tgaatggatg agttttgctt tctttggtac tgtagtgatt gttatttgca gattatttct 28620
gtcttttacc taatttagaa ggtccatgtg taatttggtc atggtttgaa ctgctagtaa 28680
aaacaaaggt catcctttat ttaaattccc acagtagctg ctgcttccat ttacacattg 28740
tagatggtca acgattgttt aaaattggtg agcagatgaa tatccaggtg cttcctggag 28800
gaaaagtgaa tggagcagat catcctccaa cttaatcact gcaatgtaat ttttcatatg 28860
ggaatagaac agcgaaaata ttctctgcaa acgaaaaata ttggacaatt aaggtgctaa 28920
gattgccttt tttgtgtttt tggtttgggg tctctgtttg aaatgacact agtgagcttc 28980
aggtttcttt ccttgttaac ttttgctgaa ggccaaagag gaatgattaa ggacttctaa 29040
agaagtattg aaaaaaaaaa cacacaaaaa gtggtgacaa aaatacttat tattttcctt 29100
taattttttt ctgcaatttt gttgatgttg ttattactac catttaaata tagttaatat 29160
taatgattac ttttagtagc atttaaggat tttcatcttt caaattacta ctctggcatg 29220
tattatttat gcactttgaa ttgctttgca tgttgaaatt ttcttttggc ctctaattca 29280
attagaatgc ccttagagtt ttgaaggttg cagtttatat aacttacctt attagctata 29340
aatggaatac agatttaccc ttaaaatgat ctagttgtct atattttaat cacatatata 29400
catgtagtgc tataaatgtt aaccaggtag atttttccca gctgcctagc caaagagaac 29460
ggtattagtg tcacagttca gttgagctgt tgttatctgt atgagatcaa tcttttggag 29520
aaggcagtga aggttttctt atttaatttg ctttcagcaa gtcctccccc tcttttttt 29580

-continued

```
tatatataat tttaagtact gctcttagtg ggtcattaga ctttgagaat tattcacttt  29640
gttagcccaa acactaaaac cttgtgtctt ttaactctga ttagtgacac tttaataaag  29700
tcatttgaag ttcagtggac tgaattttcc aacttttctg atgtttctat ggtcacggta  29760
gagcaacctg tattgaagct tgtacacaaa cttttaaatg caaatcttgg aaagctgtgt  29820
gtaattttgt atatctgact tcaacaggga ctgcaaaatg tgagggatta aaaataaaag  29880
cggtagcagt gttttccttc tttttgtttt tcaagttggg gtacagtaag ctttgggaaa  29940
tagagaagtt gtcacttgac taaacttgat tctctgagaa aaaaaaactt gcagattaaa  30000
acttttatgg ctatactttt tttttgacaa accaatgagc acaaaacctc attttcttcc  30060
acatgattag acaataaggg taatgcaaac tattgaatca taaatttctt agagatagag  30120
ccttgaattt ttttttgaaa aagtaaagaa aaagtatatt caatggctat aattaaatca  30180
tgcacggtga acccactttg gaggaattac ttcattttgt attgcattgc gacttgagtg  30240
aacatttaca acacgtgaga atggaaagga tgaaaaatta tggttgtctt tcggttcaca  30300
agaattcaag gaggcaggtc attgagttaa ttttcatggg aagactaact ctggcctgct  30360
cgcatattca gaggccaaac aacctggtat tgacagcctc aatttgggag gggaacatgc  30420
agcagcattg tgccatggtt tgttgaggaa aaacaaggga agatttaaaa caaagctgtg  30480
aataggaaca gtagcccttg tgtcttgaag ctgattgact tttccttttt agacctttgt  30540
gaaagtgtta ccctctcctt taaataaggg ctatactgtg gtaagagaaa tatttaagat  30600
ataattcagt gactctagga atgggagcat ttacacttct tgaaagaaat caggtgagag  30660
ctattaattg caaatgccat atgaaagcat cagcctgagc ggtaggctca gtgctaggca  30720
aggcatatat aagaatacta atactaatag gcattttttc caaaccatag atatatatta  30780
ccaatcatat gttataaatt atatattatc ataatatata atatatggca tatattatgt  30840
ctatgtattt caatcatata acctatttac atattttata tacagaaaca tacacatgta  30900
gataaaaaga ccaatcaatt aatggtacta acaaaagaaa gaagataaga aaaatctgta  30960
tagtcatatt tacagatatt tttagaagta aaaataaatg tcaacagtac atccagtgga  31020
aaaatagttt tctagaactg cccttctttt tccagtacct cttcagttta ttgacctttg  31080
aagagatggc tgctaacact taactaccaa catttgttta aaaaagaaaa attagtttgt  31140
acttttgaat atatatttga tatataattt gaatattgta tttaaaatat aaagcataaa  31200
tataaatcat aaataaaaat tactaataaa ttacaatttg taagtgtgct cactgtgtta  31260
tatttccatt tggatttgaa tccacttatc agactacaat agaaattaca tttattttta  31320
aaaattaata cagattacat aaaatactaa gatgatttca gtacatactt actaaaattt  31380
taagaagacc caagacttta tagtaggacc tctgagttat atgtctgaaa attaattgac  31440
ttttggattt gaatatatta ctaattcact tagccagttt aattggattt atcagttgtt  31500
aagagttagc agtttatcat aataatcata ttgatgctta ataccctctg catctattat  31560
ttgggatgtc tggagttgaa aaactccaga cacaatttaa atgaactaga aaaaatcata  31620
aggtttagga tcagaaggcc cagagttcaa atttcacatc actcagtccc tgaactagct  31680
catgatgctg taaaagttgc acaatatttc tgaacctcga tttctttatc cataaaacaa  31740
tgatgttaat atttacattg tttagttatt gtgtgtccta attagttaat gtaccaaaac  31800
acctaacatt gtagtttcta tacgaagcat atttaaggaa ataatgttta tcacataaat  31860
tggaacgtat tcttttatat ataaaatgcc caattaatat acaactttag agttcagaga  31920
acacaacaaa atagtagggt gcccacatct gcaatatgaa gaacaatgaa gtttttttatg  31980
```

-continued tagggtgtaa acttcagaaa gttgaaggat cctttctgat ctcatgtgtc ctgctcatca 32040
gtgtatcccc agcgctgatc ctgatgcctg atacctagag agcaatcaat aattaatgct 32100
atattgagga agtgaaccaa cacccaggat tagagtggag aaaactaatt tttctccact 32160
ctaggtatga ccactcaagg tagtacacta gagtagttct tcttttttta atatgaatac 32220
acaaattaat aatcctggaa aatatgttca gattaagtaa atagtcaaac ttggagcaat 32280
tatccaagac agccatataa ggctgtctgc atggataata gccataataa tgttgataat 32340
tctatgttta attgtgatcg aagccgacat ctttttccta aaagggtgtg ctgagtttat 32400
tatgaaatta aatttaggat aatttatatt ttagtgatca catcttagag aaaactgcag 32460
gcatatttta tgatgctaag gttggagaaa tctaagagtt ctctatagtt aatttcctga 32520
aaatagaagt tagttttcaa aagtccaaac aaatcaggaa gattagaaac taaaataaat 32580
tgtcatataa gaaataatga atctatgcat tggggatgtt gcatttagtt ttcgttacca 32640
cgattaggaa agattctgaa aaaggattaa attatccaga ggggtttaga agagtatact 32700
aaaaatatga aaattaggac tcttaagtct atggaagaaa atataaaagg catttttgtt 32760
gaagtttatt aaatgatgta aattattact gaaactgcat ttgttttgaa ttttccagta 32820
tattaaaaca atggctaaca attatagttg agagaaatat atttaggaaa agtaatgcat 32880
tattcagcat tctattatct atactatatt aacacatgtg ttatgggctg aaattacacc 32940
agtatcacat gagggtaaat gggttgaaag tgtaagttta aaagagtttc aaatgagttt 33000
gtgaatggat atcataccct tccacaaatg acagagatgg actattaaat cagagttggt 33060
agtttttgct tttgtttact gtgtttctca ttcaccctaa atggtcctat ctataacaag 33120
ctttggaaaa gcaccatgca cctgaaattc ttgcattctg atgttcatac ctagagagat 33180
ttatggtgac ataagcagcc aaatagcaca agtgaaattt tatatgaagt atatgacatg 33240
catgattcaa tatatatgcc cacttttaaa tataccaata gtatatttgg actataataa 33300
tgaattcatt tcaaatattg tcattttgct tgacattcgt atcatcacat aagctagatt 33360
cccgttatat aaagatgcac aaaggctcat ttcagaaata aaaacaaata actgttatta 33420
ttttttacaa aggtgaagga caataaaaat tgactaaaat cctgaaaaaa caattcagag 33480
tgcttcagtt gggccctaaa ctcaatgcgc aatcttgaca catatattga gttataatta 33540
tttactacat tatatttatt ttgtaactgt cgtcagtttt ttatgtatgg atctattaat 33600
ttcaatgaaa tttggatcca gtaaatttct atacaatgga gtttggttat ttggcacttc 33660
ataaaaatgt acctttcaca taatgaatga ataatttata ttatgatttc tcttgtgtag 33720
gacagttctt gcaggaatac aaagtaatgg taaattttga tttaaagtgc agcaattcat 33780
gcactttaga gccagttgga tgccaaagta acttggttgg tgtttatttc tagttacagt 33840
cagtgttttc tttctttcta ccaatgagat gagatatttg aaggcttttt ttcttcttag 33900
gccatatcaa ttcaaagaaa atgagaaacc atagattttg ggttggcctt acaatgtgct 33960
gtcatttcat ctttccaaat ataaaaatca aaacttcatc ctacttcact taatcttttc 34020
aaagctgtgt tccttaatgc tgattttttt aaatcaattt caatgacttc gtttcttgta 34080
tacagcagaa agaatccagt ttggtctttg taaggagtga aagactagga aggaagtatg 34140
tgttgtatag tcagtgcttc agagttggta gattttgctt ttgtttactg agtttctcat 34200
tcagtccgaa tgttcctatc tataacaagc tttggagaag cacctttgtc cccagagctg 34260
gcctccagga aggcttggat ccttacaagt ttggaaaaat ggttactggc ggtcatccat 34320

-continued aggaaaacag agcaagttta caaagttcct gctgatttcc ttgaaagtac tccctcctca 34380
ttctctacag taagccattg aatgttacta gggatggaca ctaagcagaa agatttctga 34440
gtatctattc atcttcccca atcagacagt cctttaaatt taaagaagaa tgcctgaccc 34500
ttaagacagg gaggttcatc atatttccca ttctgacagt ttggaatgaa aggacacata 34560
aattattatt attattattg aattagaggt atgggtatga tgactgaggt ttctcagcag 34620
aagatttctg attccatgct ttgcatcatt agacagccaa cagaagctgc acttagtggc 34680
cgcgtgatgt gattgattgg ttagattgga ataaaacttt tttgttgttt tttaaatcca 34740
atattacttt atttttattt aattaactta cattcaaatg caattgatca tatgattttc 34800
taattttagg attaaaatat atatgaagat aagtttggtg ccaccaattt gaaattaaat 34860
gtacagataa aacaatagaa caattactga tacaggccat cactgataca gtaactactt 34920
tagaatgcat cataaatttc attttcatat ggatttggta aatgtgcttt tagttacaga 34980
attgttagtc ataaatcaac tagcaaaaca gaatttcaaa tttttgagaa accatgaacc 35040
atgtgatgca tgttattttg ttatcctctg ctgtctctta agaaattatt tttttctagt 35100
cacattattt gtatcagcct gtctgcaaaa ctgagtctgt gcatttctct ctgtcttcac 35160
aataaattca gttccattgt atgtgcaaga gttcttgttc ataccataag ctttttagct 35220
gtttcatgat agcttagttt tgttaatata tagaaccaaa ctcccatatg aagtgaggaa 35280
ataaatgtgt aatgagtaag aaggcagaat tttgttttga tttttcaaaa cttgttactg 35340
aaagtcagaa atgtttgtac acatgttctc ctgattatga tcagtgatta aacttttgta 35400
ttaagaactc ttcctaccag aaatactcat cctaagaaag atgaattctt cagaattttc 35460
ccatttatta ctaaattcta gacacttcca actcagaaca aacttggttt tgaggaatac 35520
caagtaggca caggatttaa ggcagaaatt cagctaattc cagaacggtt gatgctacct 35580
gttgaagcat tttatagtgg aatttcaata aacagtagat atattatgcc ctttgattta 35640
ttgtagtata acttttattt tccccaacaa atcctttttt taaaaaggga tttaggttgt 35700
ttcaagtata tactaattta attgtcatga tttgtctagc ttatagaata ctacttatga 35760
agactattat acattgaagt tctgtgctta aatagaatat agctctaagt aattacgtta 35820
gtggtaatta aaatattctg gaaacatttt ttggtcacct ggtgctgtga ttttcaaact 35880
agagctgaaa aaaacctcaa gggccaggga aaactttgtc actagtactt ctcaccctct 35940
tcaccatttc aatcagtata gctccaagtg taacagcttt aaatgatttc ttccatgtaa 36000
cattagttat ttttaatata ataatttatt gttctcaaaa aaatgtttac acagaatagg 36060
taatcactaa atgttttgtc tgaaaatgca ctagcatgca ggccaccaac atatttggga 36120
aatacatctc ctgtgcttga ctgttcctct tttaagtaaa aacttctttt tccattgtta 36180
ctttttaagc ctattgatca gtgttttctg cacttcattt gtgtacatca caatgaggac 36240
atttaaaaaa tgggcttccc taatttcaga gacaagttct tcagattgct tccccatatg 36300
tgcaatactt tcctctctga gagctgccag tcttctttgt agggctagca cgcatacatt 36360
gcccttttct gaaatgaaac tagggctttc ttctgcttct tcagcatatt gcagccttgg 36420
ctttaaaaga aaaaatgcca gagtcaactg tataagccat aagactacac tgaattctac 36480
tggatgcagt gatgtattaa aaaaatgatt tatttccata ttgctgtttc ctcagcagaa 36540
tgccttggac ataataggac cttgatgaat gtgtttttaa ttcctggtta gccctcttct 36600
gtatggaaat cttaaaaata ttatttcact ctaatttgaa gatattgtca aatctttgtg 36660
aaattttagc agattgtaaa ttttagaaag atccaaagga aacattgtta atactaataa 36720
agattttatg tgaccaaaat cggatcttat ttttcaagaa atactcagtt ctatagaaag 36780
tttggccttc agtcagaatg acttcttcat tcaatcagtt ttataataat ttgaaaatga 36840
aaaccagcca gcatttactg atgatagttt acagaagttt caccaaaaca ttacttcatc 36900
acaaacaaag aaactattca ttgcctgtta ggcatcatct caacatctgt ccactattgg 36960
cttgtccatt tttatattgt tttagaatat gatataaata attttttatt attttctctt 37020
tagtttaaaa ttgtactgtg ccccaaattg gtattggctc agaaatgaga tgaatatgtt 37080
ttaaagtaag tccttttcat aatatgttta gtattctttg tcaatctttt agttggctta 37140
gagcttgata ttatctttaa aaacagaaat taatacttgt cattagagta aaacagtgct 37200
gtagcagagc tcacggttac attgataaac tatacataca tatatgtatt atatatttat 37260
cttaagtaga aactatcagt gctggtattg ttgtaaggga gatctgtggt ttctataata 37320
tgacttatat gcatacatac tttattaaaa gtgaacattt gttacatttt aatcgttaga 37380
gtaaaatatt tagtgactga aaaattccaa atgaagacta agtaaaatat gttttggttg 37440
aattgtgaag tttgagaatt tgcaaagcca taatgataga atcaacccaa aggtcccaga 37500
aattttcaat aatctatcat ccttatttaa aattattata caataaaaaa ttgtgtttta 37560
atcgcatgag tagacagatg tttatgctgt tattcagcga atcttgcaaa agtgagtgta 37620
attcatagaa taaaacaatg ttggaaatat gctttcttaa aggcaataaa agttgaagtc 37680
tatgtatcaa agacaaaggt gggaaattgt attgcatttt ataatatttt ggaaaaattc 37740
tgtaaactgc tattactaag attattttat aagattttac cccagatttt cataggtaat 37800
aaatgggcaa ataacttatc gttttcccta gtcagatcgc tggtgttaaa ttaatataaa 37860
gttttaatat aagggatttt tattaataaa gtattttggt aacactcaac atgtacttta 37920
tttgcttttg gatatgtttt tgattcaaat atagaaaaga ataactaaga tactttggtg 37980
ttatatatgg atatagtcaa cttagaaaat tatacacatt gaatcttttt attgtgctta 38040
ctcaaaaatg aattggtttc atttctttgc tgatggaata ttgaacacgc tctcactctg 38100
atgtacagtt atagtgtata ctaggtaaga aaagagagtc ccaggccaat ttaaacaatg 38160
atagggtttg cttttctgaa ttctgagaag ctagttcagg ggaagaaatg aaaccacagt 38220
gtagagggtc gaatggtgaa ggtgaaaaat tagtatcaag cctcagttca acaggaaaat 38280
gtgtgtggaa atggaagaat gaaggtaata ttggtagatg ggagaatagt aaacaagcct 38340
ttcagagttt aatgaaaaaa aaaaaaaaaa ctggttagaa cagttgggta agaaggaaaa 38400
taaatctaaa gtttagtttt taacttgatc agagtcctgg atcaaacagt ggacctcaaa 38460
ggaactgttc aaagcagtac tcctagtatg gtttctgaga ctttctgaat tttaagattc 38520
agaaacgtgg gaggaagtca tactagctta gcttcaactg cacatttata ttatgacagt 38580
ttttcctgtt atccacatat tttttaaatt tagacatgaa tatagagaaa tttagtatag 38640
cctctactta ttaaaatgtt agtactttac ttttaccaaa taattccctg catatcatca 38700
aaaatttata tttttagcca atttaatttt agagaacctt catatgaggt attgacaccg 38760
gatagaaaat taaaggaatt ttaaaatata tatttctttc caagaaaatg atttatacat 38820
tcatgtaata atttgtatta ccctaaaaca tatttacatc tctaaagtaa aattagtttc 38880
taaggtggat atgagagttg gctagttata acagaaaatt tggatatcct ccacatattt 38940
taatgtaaca aaaaaacaaa ttcttttgat ccatctcatt acagaatgtg ttccagatat 39000
aattccaaat gcatgtaggt aaatggaaag aaaaattgga tcctggagtt gtactgatct 39060
gatggaaata atattacgaa cttggtttga gtgtcagctc tttttactag ctttgtgccc 39120
ttggtcaagt tacttgattt ttgttaactt acgctttctt atctgtgaat gaggaaacac 39180
ctatgtttgg ggttttgtaa agattagaga atgtaattta tgcatggtac acatgccttt 39240
tatgatacag gtaaaatatt tcacatcttc atctcatttg tttctggtga tgtagaggtg 39300
gtaggtcaat ctttttttct ttttttttcct ccaataatca gtggactcaa ttgaattgga 39360
gaaggggttg cttggtggaa gagaaaaaac atatggcact gatgatgatg atgatgacaa 39420
agttgatttg caatttttta acagattatc tttctatagg gccagaagcc atattgtctc 39480
ttccttcccc agatattctt acattagagg atttttttcta tcacagttgc accccttgat 39540
tgacatagca atatcctata agtagcagcc ctgctgtttg gatcatgttt tttttctgtc 39600
ggcagtgtat cacaagtatt ttcctcagtg gcctaaacag accctgagtg gaaggctggt 39660
aaaagcaacc tcgtctgcat gcatcacttt gaatgatttc aaagaggaaa gaagcagctg 39720
tgacaatgtt cacatgaacc actcagagtg gccttatctt tgtagtctaa caataatagt 39780
acaccctggc tgcattcctc tgcttgagaa gagcaaagtt gcctaagagc catccataca 39840
tttgtattcc ttgacatgtc ttaaagttgg atgtatgata aagctaatga catctttaca 39900
tccctgagta atttgtcttg aaagtaaatg tagagaaatg ctctttatgg atttattgca 39960
tgtgtggtca atatttattt tatgcagata tatgaactaa tatgtaacag attgttattt 40020
acaaaagaaa tttgaagttt tatttatttg actagctaaa gaaatataaa aagaagtttt 40080
ctacatatgc agatcattat agaaataata ttcttctcta aatttgtaga tatagggtgt 40140
tttgtttttt gttttttttt ttttttgcc atttataggt tacaagctat gtttaggtat 40200
ttcagagtgc cccatatatg agttatttta aaaagtgaca atattacagg tgacaagact 40260
aatataagta gaatatagtt gagttacaga atatgttgta atagtcttta caatgcacat 40320
ccaatgaaca tcatatagac agatattaat atcaatatat ctacacataa ttgatatata 40380
gtatatatta taataaatat aagatatgat aatataacag ataatataat agaaatcata 40440
gatatctgta tatcaataga tacagactat aagtcaatgg cgggatactg cacattgcat 40500
taaatctcca ctagttcttt gttgaacatt catgaatcta aaaatgtaaa aattaagtcc 40560
cctgagggag taactatgtc tttgcatgcc ttctatttta atatctcagt atagctcccc 40620
caacacttcc cattatgtgc ttttatacaa agcaaccagt aataatgctg aatgaataaa 40680
agtgaacata gcatataatg tattccatat gtataaaaca atattcacat gaatgaaatt 40740
gatccatcag tgtgttcaac tatgagtctg tgtttctgag tacctgtaaa caaaaagaag 40800
cgttgaaacc ttttagggag ttatgagaaa taatagagta aaatgataaa tacattttta 40860
ctgaataaat atacctgaat gagttattcc agttttttca tgaatttagg caaatgtaca 40920
gtctctcgat tgataataaa atttgtcatt ttctcagtta aattgataca gattcttgta 40980
gagcaaaaag acctaaagat aagatttggg atagatttat accttaaccc aggtaataaa 41040
tagattattc gggtacttta atagtaacaa aggaatcaaa tggaatttta attgaaatga 41100
ttttactaat atggtcatta gcattaagta aatgagatac atttgccatt tcagctgtat 41160
ttgttaacat tagattttca tacaaataca agagatgtta ttttaactgc tcattcttat 41220
ggattttact gctttcacta aagagaaaca aaatatttta tctcctcatt gcaatttagg 41280
cttagggagt aacaactaag catatacatt gttgaacact gctggcatgt gctttgtgaa 41340
tatgtttgaa tcaagggcct ttacaaaggg ctcagacctt cctcctaggg ggttgtcatt 41400
taccgtggat gctctcgttt gttgtggtaa acagcctcag aaaacgtctt gacattgtca 41460
attccaacag attaatgaag taactgggcc atacatccct tccccctttac atatgaaagg 41520
aaaagctaac tacttcatag agctgtaaga ttgtttcctt ttacccccttg gtattagttt 41580
cctttgtagt cagttaagta tggttctttt aagtaagcca gaccagaatt cttttaagta 41640
agccagcttg ggcgggggaa ctccagtgtg attataagtg agtatatagg aaaaaaagaa 41700
atgaaattaa cctttttttc tttagaaatc ttgtgtttaa ttttatgttc cagtgtttta 41760
aataactgaa accttattat ggacaaattt acctgttatg ttaggagaaa tgagtttcat 41820
ttaccatctt catcagcgat ccccaacctt tttggcacca gggaccggtt tcatggaaga 41880
caatttttcc atggacccag gtggagggat agtttcagga tgattcaagt gcattacatt 41940
tatcgtgcac tttatttcta ttattattat attgtaatat ctaatgaaat agttatacaa 42000
ctcatcataa tgcagaatta gtgggagtcc tgaactcgtt ttcctgcaac tagatgttcc 42060
catctgggta taaagggata cagtgacaga tcatcaccat tggattctca taaggagcgt 42120
gcaacttaga tccctcacat gcgcacttca caatagggtt tgtgctccta tgagaatcta 42180
atgctgtggc tgatctgaca ggaggcagag ctcaggtgat aaagtgagtg atgggaagat 42240
gggaagcggc tataaataga gatgaagctt cactcccttg ctcactgctc accgctcacc 42300
tcctgctgtg tggcccagtt catatcaggc cggtttccta tcaggtaatg gtctgtggcc 42360
caggggttgg ggaccccttta tctacatcca cgttttctat gtttgtgaag atttgatgtg 42420
gggttatggg tttgaggagc taaaaattat agttagtaga aggaaagaca gctagaagtg 42480
gaaagtaaaa tcacttacat tgtactttta ctaggaccta tattgtaggt attataaatc 42540
atacaaacaa gtttgttata caaaacatga ttaccttatc attgttttat taagtattta 42600
attgtgcatg agtaatcatt gccattattg atttgtccat attaaactta tgatcagact 42660
tagtggacaa attttcaaca aataatagaa gcagcagcat aaatatctat atagaattag 42720
ccaggttcta gtctggcaca tcatcacata gtagcacatt taatgccccc aattattcta 42780
tgatatagat actactagtt tccccatttt cctaatgaga aaagtgagtc atagtcaggt 42840
ggagataatt caccccacgt cttaaggcca aatggaaaaa atcttcttac tctggaatta 42900
ggtggttaag tatcttgatt ttaatggatg ttgttgtttt cctaataatt gagttatttg 42960
tattaaaatg ctaaactggc aatatatgcc gatggccaat ttacctccaa atatattgag 43020
ttcatacata ttcattaagt gggatatttt ggagaatata ctgcttatat gttcaaatgc 43080
aaataattta attcgctgtg atttataata ctgttactca gtaaatggac taaaggcagg 43140
gtaagattta tcagtcttaa aaatgtaact atgagatcat tataatccta ttatcttcta 43200
attatccttt taaatcaaaa acatactttc atgttggtat gagtatcata accaaaagag 43260
aagagaaact tcaaagagaa aactgaatta gtggagagta acttaatttc agaagaaaat 43320
cgtactttca tataaattca tagtgaaagg taactatgtg ataccagcat tcagggaaca 43380
aatgccctta cgtttttgcc tgtgtgtttg tggggaggga ggttgtttca ttttgttttt 43440
atttcttgcc tgtttaaatt tcttttactc acaggctcca gcctggatct ctgggaggga 43500
gaagtagttc caaagattac agtgcttaat cttaactctg aaaacactac ttattgactc 43560
tccactggat tccactcgcc caaattccct agatggattt tccctcagga tgaaacaacc 43620
taaattcaag tgtcctaaac tgtcttcctc tccctcctgc cattgccttt ccttgtttct 43680
ctagtctaat ccatcttatc ttttgttctt ttctgttaat ctattaatca ggtctctgac 43740
attctaaaag ctctcatgcc ccttcgcaat atttcctcct ttacgcattg ctagcaccag 43800

-continued

```
cacttccact actccaggaa ttaacacctc tttctctctt tcctcaatgg ctaagagatc  43860
tggagtcatc atgtctgggt tcatattcca ctttcccaat ttactgactt cgtgacctta  43920
ccaagtcagt taacttcatt aaattttcat ttcttcattt tcaaaacatt ttcatcacgt  43980
ttcccacaca ggcttgtaag gaggacacaa ttatgtcatg aatataaagt tcttagcggg  44040
gagtttggca catagatcac agattagccg ttcttattat tgctccctcg gtagagtccc  44100
actgtgaagt cattatttct cacataactc actaattcag gaactcttta atcaaaccta  44160
ttatgtctaa ggacctgagt aaacagttac tgttctcaag gaactcactg tctagaagaa  44220
gaagaggctg accagcaaag ccataattac aataaaccta tgctatttgt actgaacaat  44280
aatacatatg cacttaattg tagtcatccc cctgactata ctcacaaaac ttaacatgtc  44340
tttaggggag gaggatggat tgcagatatg ctattagagg catagccatc tttacttcat  44400
taaaagttta gtttactaaa atttgcaaat gtttaaaata tggtcttgct taatttcaca  44460
aattctggga taaatattta aggatttaat atttattaaa tttttattt atttattatt  44520
tattttattt atttatttta ttatttttat tttattttat ttatattttt attattattt  44580
attttattta tttattattt ataaatattt attaaatatt tattaaatga gtgcactgat  44640
gtgtattgtt tcaaatacat tttattaaat ttagtgtcaa attgctagct actgtatggc  44700
taaatattac atttttcccc agtggggcaa agttcaattc aattagctgc aatgaatatg  44760
tattagatct caattctctc ctgtgataag tgttggaggg aattcagaaa taataaaaat  44820
atatctctgt tctttgggat ttcagtctat tattaactaa gcatctggag cagttacacc  44880
tatgaaacag tttggtatgg catgacagtg aaagcagtaa caaggtacaa ggggaataaa  44940
aagaatgaga tccatcaaat tgttaatccg gaaggcacag ggagtgagat ggcatgtgac  45000
agtcaatggt tagtgatggg gtagaggccc atatgctcat gagagatttg agaaatataa  45060
agtcattgtc tttgtttaaa aggatggtgt gcaggtggta aatactgaga ggtgatctga  45120
caagtgttca ttcaaactct gcaaccttga ttgagactgt gctagatgat ataaaaatac  45180
atatgcccta acagggagga taggcaacca aacaattaat tttaaaattg tgaatttaca  45240
aactgtgggt tattatatgc tacagaagcc acacagagaa agagttattt gctctgtttc  45300
agaaaataga atagaggaga tgtgggaagg caagatagtc cttatagaaa agtggtcgtt  45360
ttattacctg caaccgttct gacccgcttg tcattctatg tcttcctacg tcagtcatga  45420
gctctatttg ttctcatgtg caaatcccag cctcactagg atgcactcca gttatccatt  45480
aagcacggag attcccatga gcaatgggac aaaatgacta ttggacttct atctcaactg  45540
cttgtgtaga atgttgcctt gtttatttta agtcccagat tctattattt tccctactaa  45600
ccatgggtag actctggatc agacttctca ttgaaagacc tttgaaattt gcttatactc  45660
aattgccatt tcagtcccct ctctcactag atgttcttga ctgctgtacc actcttcaga  45720
ttcatgatgt gctgataata caatgtttcc ttgcattgtt attttgttat atttaccctt  45780
atattatcat ggtttttgat taaaagcgta tgtgtgtgtt tacacataaa catttttttt  45840
tcctttctca actttttagg gatatgcaga ctatatattt cttttcaaga gggcaagact  45900
gtaaatagat tgagggcaag catcatgttc tgtccagtgt aagagaacat tctgagaacc  45960
tagccggaca tcaggtatac attgaaagat attagttgaa attataggta gagctgtcat  46020
gatgacatga gtaggtaata ttttgagaag tttggtggta tgatattaga agagaaatga  46080
ttcttctctt ctgatgcagg gaaaaagatt cccaaaatct gcaagcgaag aattgggtag  46140
aggaattatt cagtttagga tctggtctag agatatacag atttacattt actgtttggc  46200
```

-continued

```
cttttttaca tggttgaata ccatatgaat tttaaatatt agtaaaatat ccaaaattac  46260
ttttgataga ggaaaatgta ttgcactata tattcttctt tgaatagaga actttgtcaa  46320
gtaagagaat aaaaaataca ggatgatttc tattaaacat acagtattca aaagctatgt  46380
gagggaatcc agctagtgtg attatgtcaa aagggaagat agctggtctg aaggtaatga  46440
gttatctcaa ctgattggtc atggccaatt acagacagaa ctccttattt tacttcccca  46500
ccccccgact actgcacttg actagtcaaa aaataaaaca aacaccaaaa ccaaactaaa  46560
gggaagacag tcttttccta gcttggcatt agttggatgg tttatataaa tgtgaaactt  46620
ttagaactca tttgaaaaaa aaaatttagt aaagcaaaaa gaagtttttc aaatagttaa  46680
aaaatttaaa agactgaaat tatcaaatca tttttcacaa caataaaaat tgtatacaag  46740
gcaaactatg tacatatatg tgggtgtcct taggaataaa tgcataattt caaagacatg  46800
gaatttgtaa gtgttagtca tgttctcacc tgtaataaag caatgtgtta atgaaattgg  46860
gtgcttatat atatttatat ataatttctt agtttgagag aagcaaatag aagtgaatat  46920
atgtagccac tttttaatat ttgtattcag ctataattcc tcctgatttg ctcctcgttt  46980
tagagtgatg tactgggaat ggaatcctaa aattaaactt attttagatt aaatcatacc  47040
atgttagttt aatttttttt attttttcaa ttctatatca atatagcttt tttttaattt  47100
atatatatat ttttttgaga aagaatcttg ctgtattgcc agcctggagt gcagtggtat  47160
gatctcggct cactaaaacc tccgcctcct gggttcaagc gattcccctg cctcagcctc  47220
ccaagtagct gggacaacag gcgcatgcca ccactcctgg ctaatttttt gtattttagt  47280
agagacgggg tttcactatg ttggccagga tgggctcgat ctcctgacct catgatccgt  47340
ccaccttggc ctctcaaagt actgggattg caggtgtgag ccaccgtgcc tggcctgtag  47400
cttatttttt aaaactagat ttgattttgg aattgcaacg attatggatt attatattca  47460
ctacttatta tctcatcact gtttagtttg cagaaaggct tacttaatat ttcatttata  47520
tgttccccta ttgatagttc ctggaaaact tttaatgctg gccattaatt taacatatat  47580
ttgcttagag tctactgtgc attacaatca ttctagattt caaggatgca aaagtgagca  47640
gaaacagttg tccgttgttg atggactgat ggaggttctt gaaacttgct tatttttttgc  47700
ttacttttgt ggatgttcct attccttctc tctctctctc tctctttctc tcttctctcc  47760
accccatgtg tgccctcact ctagcttccc ctctttcatc ctccctcttg ctacaaatta  47820
aatgtagttt ttttcaaata ccttttcttg gactttttttc tctctatagt gattcttgta  47880
gtaatcttat agcatcatct gtcacattta tgttgatctc tttttacttc tgtctcttct  47940
tcagcatcac aatctgttta tgtgctggac ctagaaattt agccccccgt gaatttcaac  48000
ttcaccctgt ctattaagaa agccagttat taataacgta ttttaataaa ttatgataag  48060
catatgataa ggagaaagaa taggggactt tcagaatata ttagaaggga acccaaacta  48120
gactgtggat caccagagga gtcactaaag gagtctcggt ggaagtgata tttaaactgc  48180
gatacgaagg atcgcttgaa ttaactaggc catcttcagt ggtcaggagt cagttttctg  48240
agcagaaaga gtagtatgca taaatgccat gagctggaaa cgcatacaac tctgtataac  48300
tgaaggaagt gaggtttttt cagctggtgc atggagtgct gaaaggaaac tgagaagaga  48360
ccctggaagg tcagcttggg tgtgagagtg aagagcaccc aaagtaagac taaaagtttg  48420
gtagttctca taccaaaatg agaagccatc aagagttttt atcaaattat tgactttatc  48480
ttatttgtgt ttcataaaaa gctttctggc tacatgaaaa gaaaacagtt agaggttggg  48540
```

```
ggcattgcgg atttagaaat tgagcatgga gaacttgggg ccctggacta acagttgata  48600
gtagagttgg aggtacatgc attgagtgga gatgtgttga agatgtggtc ctggtatttc  48660
ttgatgacga attgaatgta gatgtggaag atgatggaag aaccaaggaa gatggcttag  48720
tttctgcctt gagcaactaa gtggatgatg agttagggaa taccggatga ggagtcataa  48780
caagaagaca ataaattagt tcaggacctt gttaaatgtg aggtcactct gagataccag  48840
tggaaatatc cagcaggcag atggatatgt gaactggagc acaacagaga agtctagatt  48900
aaaatttgca tttggagtgt agtatccatg aaagtagcca cgagcttgga tatgttgtcc  48960
aaaagaatgt ggactctctt ctcatcattc aagctgaaaa cctcaacttt attccttgac  49020
tcctctttct cttttttct tgcttcctat atgtaaataa atggtgaagt cttatcagtt  49080
ttgctctcta ttgtctttcc tattcatacc accatttctg tttccaatag tctaattagg  49140
ttcttgttat ttctgacgag agagctatta tatacttgag gatagcaaga ctggttgcca  49200
ggagattcat agactattgc agtaagctgg agagttatga ctgctgttta aacaagatca  49260
ttagctgtag gaaaagagga aagtatattt aagaaataaa gtatatgata aagtaataga  49320
aaatgaatat ttgactaaaa ctagtatggg aaacagaaac gccttgaata taactaaatt  49380
agaattatcc tcctttatag atttaacttt tattttaagt tcagagctaa atgtacaggt  49440
tcgttatata ggtcaggagt tcccaacccc ggggccactg accagtacgg gtctgtggtc  49500
tgttaggaac cgggacgcac agcaggaggt gagcggcagg ctaacgagca ttaccacctg  49560
agctctgcct tctgtcagat cagcccctgc tttggattct cgtgggagcg tgaaccctat  49620
tgtgaagtga gcatgtgaga gatctagatt gcgtgccctt atgagacctg ccccaccctg  49680
ctctgtggaa caattgtctt ccacaaaact ggtccctggt gccaaaaagg ttggggactg  49740
ctgatatagg taaacttctg tcatggggtt tgttgtacag attatttcat cacccaggta  49800
ttaattaagg ctagtaccca ttagttattt ttcctgatgc tctccctcct cccatcctct  49860
gccctctaat agaccccagt atgtgttgtt cccttctatg tgtttatatg ttctcctcat  49920
ttagctccca cttattagta agaacatgga atatttggtt ttctgttccc aggttagttg  49980
ggtaaggaaa tggtctccag ctccatccat gttcctgcaa aggacatgat cttgttcttt  50040
taatggctgc gtagtattcc atggtgtgta tgtactatat atatattttt aatctggtct  50100
accattgatg ggtatttggg ttgattccac gtctttgcca ttgtgaatag tgttgcaatg  50160
aacataacat gtgcatcttt acaatagaat gatgcatatt cctttgggta tatacccagt  50220
aatgggattg ctgggttgaa tggtatttct gttttaggtc ttggaagaat tgccacactg  50280
tctttcacaa tggttgaact aatttacagt cccacctacg gtgtacacat gttatttttt  50340
ctctgaaagc ttgccagcat ctgttatttt tttgactttt tagtaatagc cattctgctt  50400
gtatgagatg gtatctcatt gtggttttga cttgcatttc tctaatgatc agtgatattg  50460
agctttttgt catatgcttg ttggccatat gtatgtcttt tttttgaaaa gtgtctgttc  50520
atgtcctttg cccactttt aatggtattt gttattttta tgtgtaaatg tgtttaagtt  50580
ccttgtagat gctggatatt agacctttgt cagatgcata gtttgcaaat tttttttgca  50640
ttctgtagga tgtttgttca ctctgttgat agtttctttt gccatacaga agcttttctt  50700
tagtttagtt agaatataaa taaaccagaa gtttcccttt taattttagc atcgcaaata  50760
tgcatcaaat gttatcaatt tattttacca cattgctcca caaagtctca tccaccaatt  50820
ataattcttc caggtaaaat ttactggaag caattattgg tagagctgga aatagcattt  50880
gccagacatt tttctacaca ctgtacatat attaaatcat ttaatattta taaacattct  50940
```

atgaaacatc acattttaca ggtgaggaaa tgaagaacac aaaggttata gagggtattt 51000
ttcaaggtca tacaatttgt aactgtcagc aatagacttg aacccaagta ttctggttcc 51060
agaatctaca cactaatcca ggaaagtaaa ggactgcgta tgttttaagc acctattaac 51120
gtgccaagaa ctgtggaata tatgaaaaat acataggagt caatatgtaa atacacatag 51180
tttaaatagc aggttggggg aaaaaataac atactctgta actagttttt tcaaccgtat 51240
atcatagaaa gttaagttat tcagttgttc aaagtcagtc agtttccatg agagatggtt 51300
aaaatgaaaa accttcctta taggtgaaat ttagggtgac cattgccatt tttaatcaga 51360
tatccccaaa attcaccttt ccttgactag catttaagaa agtactgcaa aatagtatat 51420
gcaaacattg gctttggtaa cttttgccaa ctaacttacc atagttttaa tcagggaaaa 51480
tggtgagttc atgtgtggaa gttctactct gactcaggta ggtagagatt atgaacaaaa 51540
agggaaaagg caatttccta cctgatggtg tggaactctc taaatctgcc agtccagttt 51600
ttttccccct tccgtttaag gttttataag actttctaaa taggcaattt agtatttgtt 51660
actagtttgg aaattatttt tctggagcca tatgaagtac taagtattta tagacaaaaa 51720
tgttggcaaa gaatatagag gttcttgaaa tggcctttca ctgtggcaga agaacttgaa 51780
tacattcaag tgcaaatcca gatttgtaga gagtactgtg ggtttatgga aataaagcat 51840
ttgattgaaa aagtcatttt ttccagtatg acttagtgat tattaaataa ccatgttttt 51900
aatctgactc actggaggga agctccatag cattagtggt aaacagttta tgcagttaga 51960
atatgaaaaa gacaaagaaa agcaaactaa aaagacattt tagagtagag tgggaattga 52020
gccaatgtgc ctgactggta aagtctttgg agggaagcca ggaagtctgt gatatttctc 52080
tagttaggat atatatatat atgtatgtat atattatata tatgtatata tatatatata 52140
taaaaatcat attggataaa aaatgttaac cctttctatc aaatttcaga ctttcctgat 52200
tctgaaactc aaaactgaat gcaaattaag atttttaaaa agtatgatta aaaaaaatac 52260
cgcatacaca catgacatct ggcaatgcct tagatctctc taaaatgtca agatgggaaa 52320
atatccaaaa cttttttttt ttgagagaga gagagagaaa gagaaagttg gcttctagcc 52380
ataagcctgc cgaggaattc ttacgagaat ttctggaaac tgtacttttt aaggcaatca 52440
tgttctccat gctttcgtgg cctcagatgt tacttgaagg aatttaaagt ttcatctatt 52500
tgtgctttgt tgctgtacac cctttagact tcagtggtca agtttcactt tggagaactg 52560
acaaaagaaa aatattgtgt ttggcactac acaatcttag aatactttaa gaatgaatat 52620
gccaagggag agtcatatta tatagcttga attgtatttt tcatgcatga tatgtacatc 52680
accttatgtc acacaaatct ctatcagcct tttgcttttc cattaaaata aatacccatc 52740
agatacttga tatagatatt ctgtggttgg agggcttaag tgagatgcag tttcaggtaa 52800
ataacataaa atcagcagac ctctaatctg aattgaatgt gttaaatctt atcaacctag 52860
agttttaagg aagagggaac aactgtcttc agtgagtaat ggcgcgtgca ttaataccag 52920
ttactcagga ggctgaggca ggagaatcac tttaacccag gagatggagg ttgcagtgag 52980
ctgagattgc ctcattgcac tccatcctgc ctgggtgata cagtgagact ccatctcaca 53040
aaacaagcaa acaaataaat aaaaaaacaa aagaaatggc caagaagaaa aatgcctagc 53100
tttcctgcaa caatttggga gattaccatc atctgtatta attcattcat tctgttgttt 53160
aatgaaaatg gctaaagtct ggccttgcca ttgaggtttt taaaaattct ggtaaaatat 53220
gcataacata taatttgcca ttttaatatt tttaagtgta ttattctgag tcattgaata 53280

-continued

```
atttcaaatt gctctgcaac tgtagccgtc atctatctcc agaatgtttt tgtttcccaa  53340
actgaaactc tctacccatt aaacactaac tttccatttc ctccaatcgg caagctccag  53400
gccaccactg ttctgctttc tgttcccatg aagttgacta cttttgctaa ctgatataaa  53460
tggaatcata catatttgtt tttctgtgtc tggcttattt tacttagcat aatgtcctcc  53520
aggtagatcc aagttgtagt aaatgtcaga atttcctttt tttttaaaga ccgaatagta  53580
ttccattgta tgtatatact acattttgtt tatcaaaaat ggacacttgg gttcctttct  53640
ccttttttcca ttgggcgtat tgggttttaa tattacacgt ttgttataaa ggcagatata  53700
gggtgataga attcatacta gatttggaaa taatcaaact aggctttgtt ctgccacaac  53760
taggtaaaaa tgttacttct ttctgacttt ttgtaaaatc aggatggaaa tatatttcat  53820
atcattgtta tagctaatag ctattaagca cttgtatgtt tcatactgtg ttaagggctt  53880
ttatatattt ctcattgtat tccgacagga accctacaaa gtagagacag ttccaaattt  53940
ccagaatgaa tgtgagattg tgatacatat gacaaactgc ttattaaact gtacagcacc  54000
taacaacatg agggattatg cctaattccc tacacagtgc atggcataca caaggactca  54060
tgagatgctg ttgaagaata aaagcagctc tactttacag ccataggaag cacatacata  54120
ttcagccatt tgaaaacagt gtgtcttgat gaaagaggat tgcagttgga ttaatatgaa  54180
cagtcactaa aaaataaatg aaaaccaaac ctctaaatca cgtatacaga caatattcgc  54240
aatattgata atattcaaat tgtgtaaggt aaacctgatt actcagcaga attaaagttt  54300
cactggtgat atggggtgca ggcagtgtca tctctctgac aaaatttttc aaattttcaa  54360
aattttcaaa gtttgaaaat ttcaaattga caaaaatttt caaaaaattt caaaatttta  54420
tagaaatcat cacagttctc tttattaatc agagtttaaa tgttaggcca gcctgggtgg  54480
ctcacgcctg taatcccagc actttgggag gccaaggcag gcgggtcacc tgaggtcagg  54540
agttcgaaac cagcctggcc aacgtggtga aacctcgtct ctactaaaac tacaaaaaaa  54600
ttagccaggc ctggtggtgc atgcctgtaa tcccagctac ttgggagact gaggcaggca  54660
aatcgcttaa atctgggagg cagaggttgc agtgagctga gatcgcgcca ttgcacttca  54720
gcctgggcaa tgagagctaa actccatctc aaaaaaaaaa aaaaaaaaga agaagtttaa  54780
atgtctactg ataggcatta ttttataggg ttattttata gggacttaaa aatttctaca  54840
tatcaaatat ctaacataaa tattggatca catggatata tattaattct gcaaataatt  54900
atacaaataa tattaaatat acaaataatt agttatacaa ataatattat actgtgtatg  54960
ccttttttata gaatttcttc caaaaagcaa cagtggataa gttggagaga gccatgaaat  55020
tccccaggag agtggctgtg aagggtggcc agggattgag acatagggta tcttcctaga  55080
gtctatccat gagaaactga catgatttca tgccatctgc tataagtgct ataagtaata  55140
atatagaaat agttgacctc acagttaatt tattaagcaa atagtggaga agatgctagt  55200
aatttctaga ccttgcctca ggggctgtga atataggagg ggataagata aaaagtggct  55260
ctttcattgg agtatcaatt gtggggagag attgaatatc ctcaataata tcttaattaa  55320
tatataaata tatataagaa atatataaat tgaataatta cagatagagt tttttgtgaa  55380
taaaactgaa caaagtgatg taatggagaa tgatagcagt atatggggca tattctttag  55440
atggggtcat ttagggaatg tcttcctgtg acgggggcat cataaacaac aattgttcaa  55500
ctgctctatt ccatcagggt gggaatcaca tactcattgt tggctagcgt gtctgcagtg  55560
cctaggacag aacctggcac ttgataggca tttactgaat attttttgaa taaaagaaga  55620
acgaaatgga tgacagtaaa taagtctttt aaaaacgttg aatcaaggct gggcatagtg  55680
```

-continued

```
gctcatacct gtaatcccaa cactttggaa ggcagaggtg ggagggttgc atgtgcttag  55740
gagttcaaaa ccatcctgag caatgtagtg agacctcgtc tccaccaaaa aaaagaaaaa  55800
agaaaaaagg aaaattatcc agctgtggtg gtacacacct gcagttccag ctaatcagga  55860
ggctgaggtg ggaggatcgc ttgaacccag aagattcaga atgcaatgag ttatgcttat  55920
gccactgccc tccagcctgg atggcataga gtgagaccct gtttcaaaaa aaaaaaaaaa  55980
agatggatca acaaaagtga tatcaatagt aatgacacta ataacaaaaa aaatagtgaa  56040
atcatgactt gcaagtataa atcactttaa aagattattt taatagaaaa catgttaatc  56100
tttagaacta cctgaggtag tgtgatagga actattaact acatttgatg aatttgaggt  56160
acttagaaca tattactggt gaatggggaa gctggcttaa aaaaaaggga gggtcttctc  56220
agacagttct ctttttacat acgtggcaca atgattcatg atttgttata ttgtgaatgt  56280
tgaatgtgga atatttatag gaatgcaaat cacatttcct ttacacaata gtattaaact  56340
gatttcaaag tgttttgata tatgcttcta tccttacaat ggtccagtga gaaagaaaat  56400
atgatattca tcattgtaga catggaaata aaagttaaga aaagttgtct tgatcaatat  56460
catatgcaat agcaagtgga aaacccatgt ttttaattta gaatttaata ctaacagtct  56520
atgctctcat ggatgtttta tgtagtttaa tgtttttaaa aaactctaag cccgacaact  56580
tcgctgttta aaatatttga aataaaaata gctttgccat tttttaaata aaacattacc  56640
ttttattata acaaaattca gaaaatacac aaaataacaa aacaggaatg accaccagtt  56700
atcatttaat gtgaatcatt gaactccttt ctttctataa aattacaaag ttgaaatatg  56760
ttttaaaatt tgtgtaaaag ttagaggatg atttgattta aatctattat ttaaatttat  56820
ttttagtcaa gtaataataa ttcagtgaat tgttcaaatc agaattgcca tgatgcaggt  56880
ttcacataca tgaaacaagt taatatgagg aatattcttt cctatacttt cctttttatg  56940
ttgtttttat cttaattact ctaacagaga caaatttcat ctaaagaggt gatatctaaa  57000
ggaaatgtag agatcagaat ataggacaga ttgttttaaa aagtttgata tttattatta  57060
ggtgcctaat aaatgctcct tctagtttat gaagctttat ttctaaaact ataatctatg  57120
tttatgtgtg tttattgaat atttgtgttc cgttggtaac aaatgaaatt taagtgtact  57180
attaagtaat gctaatacta atatcagttc tattttgaca aacactgtgc tggccactat  57240
tccatgtgcc tcacacactt ttatctcatt taaatttcat aaaaacccta tgactgaggt  57300
acttttctta tctagagatt acttgattga agaaacaggg gcacagggag gcaaaacaat  57360
tttccagggt catacaggtg aacatgaaaa agccaaaagt aacacccatc aatagggcta  57420
cggcattcat gccttccttt aaaaattaat tgagggcaag aaaccattgt ttaatatgta  57480
atttcaaaca tctagatgaa gaaaatatct gtattagaaa ataataagga ctatgtatat  57540
atgatttcag acgatttcct atttaaataa attaggataa atgacatatt tgttataggg  57600
tgaaatgtta gggaaaatct cagttttagt cacagatctc tactaacctt gaaatcagat  57660
ataccaattt aactctttgg cttgggattt ttttattcaa aggcatcaga tgaaatgagc  57720
tcaacagtct gccggttcta aagttctttg tcaccttctg tgttatcacg tggtggtctg  57780
tgaatcttac agagattgat ggcttcagtc ttctccaaat atttctccta catccctcgt  57840
tgtaaaagga aactgagtgt aaggaaagaa tgtaaatccg taatcacatt tggatatctt  57900
tgaagttgca acactccaga aatttggtga caagcaaatg cccctatttt taaaatgatg  57960
aagcatcagt gtattagtgt aagttgataa gcttggagat attccataag agattattat  58020
```

-continued

```
attctttgga aaaaactcag gaggagaggt gctatcaata agaagccatc ttggcttcaa  58080
cagaaataaa ttatttgaat aggattcacg tccttattct acagacatta attgcaaaac  58140
gacccttact tatttttaaa gaaatttgaa aaatataatt cacatgccac aaagttttcc  58200
ctttaaaggg tacaatgtag ttgtcccacg tatattcaca gagctgttca gattgtccct  58260
tattgaatca ttttgcttat tcaagagcat ctaacccagt gaagtatgca gtgatagtat  58320
tgcatcaata tttgctgaat tctccactca atgaatacaa ggtacagcaa aagagaccag  58380
ataattctag ctaaactcag atgaaataat tgtaaaatcc agaataatta agtattcaga  58440
tatattcaga taaagattcc agaaggatac aagtaaatga taaaaagagc acatttattt  58500
ctaatattag ctgtcatatt aacacataga aaaaaatgta ggcttgttag catcaagtaa  58560
gttgccaaat atgatattgc cccttatata acttgaataa ctttaggtgt tacttaaatt  58620
cataggcaca tattggcatc ttcagagcaa gatgaattaa cactctggag tttttatttt  58680
atttatttaa aaatagatta tcacttgaga aaagacagca tcataacatt tagtgacaaa  58740
gtgtgaaatt ttcctacagg tcttagtgat ttagcaacca caaaaccaaa gaaaggagag  58800
tttaatcatt attttaggtt ccctcatggt gactctaaat tgtaagtaag aatagcaaga  58860
acgttttcac tggcaacctt ctttatctta aaatttaatg tcataacacg tttggtaaag  58920
cagctaaatt atttctaatg tatatgtttg gctgaggcag ttaatacaaa gtaaaaggca  58980
aaaagtcatg aagcttttat tttctatctt gtttcacttg tgcctccaat gagcattggc  59040
ttggagtgct tatcgtcatg tcactgacat tcttgcccag gccttggcaa actacttgga  59100
taccctggtg agagaggttt ctgggacttt ggcctggaaa tatgcatttt gaaaattata  59160
tccagtgatt ctaatttgta actagttaga catcactgca ctaagagtaa actttcagct  59220
ctctggccta gttcagtaat tttctttatc acaaacacgt ctttcataac ttggttccaa  59280
aggcattcat gacttttgat gtcatccgta aatgcatttt aaggaattaa tttctgcttt  59340
taaccaatta caagatttta ttaacaatct gtttactgtt tgacaagtat tagtcagctt  59400
ttattttatg tcattactga gatttgaagt cacctgcact acgtttaaac aaaacctatt  59460
cttatgatta caatatattt acctgacatt atgcaaaact gcattttttt tgcatttggg  59520
aacaccattt tatatatgaa gttgttgagg cttataaaag gtcacaagta actgactaat  59580
agcgtcaaga ctagaaccca tgtagtgttg gcatctgttt aggaacctgt gtcagatccc  59640
acacttgtaa tggagagctt aatttcagag aacattagcc atatctagct attgctgtga  59700
atttaaattg ttttgagtgt gcatttaatt tgcaaatttg tattggtttg ttatttgtgt  59760
aagaattata cacctacaaa gattttacca agtttatatt tttacatttt aaagtagtgt  59820
tttaaaacaa ataaattaaa ttgacacttg gtgatgcaag attttatttt tccttttaga  59880
aaaggtcttt acaatattta aatttaaatc aaacagttct cactgaaata attaggggta  59940
aaatggacct ctgttgatgc tatttgaaaa aactatttga acaatgagaa cacttggaca  60000
cagggtggga aacatcacac accggggcct gtcgtgaccg gggcctgtcg tggggtgagg  60060
ggaggggaga ggaatagcat taggagaaat acctaatgta aatgacgagt taatgggtgc  60120
agtaaaccaa catggcatat gtatacatat gtaacaaacc tgcacgttgt gcacgtgaac  60180
cctagatctt aagtataatt aaaaataaat aaataaatag gcctggcgcg gtggctcatg  60240
cctgtaatcc cagtactttg ggaggctgag ataggcggat cacctgaggt cgggagttcg  60300
aaaccagact gaccaacata gagaaacccg gtctctacta aaaatacaaa attagtgggg  60360
cgtggtggcg catgcctgca atgggctgag gcaggagaat cacttgaacc caggaggtgg  60420
```

aggttccggt gagccgagat catgccattg cactccagcc tgggcaacaa gagtgaaact 60480
ctatctcaaa aataaataaa taaataacaa taaaataaca aaatagaaga aattggttgg 60540
atgccacgat taaatataga tttgtttttg catttgtagg cagtcagagc aaaatgggag 60600
catagtaaat tttctcttat cataagggaa gaaaaatctg gctcctgagg tggttgttat 60660
tttctttgtg tttttcttct tctaaattct aaaagaaagt gtcatgtggg gtttcatata 60720
aatgacacag atgtcataga cctttttttca atatttttat ggcaattaca ggcacaaatt 60780
accaacgact atttgttata gaactttttg atcaaaaact tacttcattt tttctctaga 60840
ggattttcaa tgaggaaaag aagcctttac tatttacttt tatatttcat atgtagctac 60900
aaagttgctt aaataaaatg agcattcttt atcaaaaaaa aacaaaaagc tattcactga 60960
aactttgggg atactcatct tcatgtacag tttccaactc tgattagacc acagctcctc 61020
cctatattta tgatttgctt gctttataat caatattatt tctgaaacta gaccccaaac 61080
aagtcagttt tggttttgct aagatttgct taaatgtaaa cctttagaaa atcttatgta 61140
tattatttta tgactcttaa ctgagtacat acttgagtgg ttattctgct gttacatttg 61200
ttctgaagaa tcatgcacat tttaataggc aagttattaa tgcaaccaaa cctttaagtt 61260
ttggagtttt ataggtaaaa tatgtttttc tagaggtctg tttctaaagt taaaagctgt 61320
tctaataaat aataaacaga ttcaaaaacc ttggcaaact ctcacaaacc aaaacaaaat 61380
taggacattt tgattgattt taatattact ttatctaata aaaaataagt tagatgctat 61440
aaaaatattt ttaaatgtgg aggtaattta gttcagttat cacacaaaca ttctctccaa 61500
tatacacttg agtgtaaatt atatgttgtt atttacttta ataacagttt gctcaagcag 61560
aaaacctgaa aaaactattg cacgtatgcc cagggttgta ttgcatatta acacctgcaa 61620
aataaggcac aattaccttt ctatttagac aattaaaaac ttcgataaca taagcttagt 61680
tattgcctga taaaaaatat gccaatcctg ctccagatta acagatgtct tattgattct 61740
atgtatgtac caagttagac atataaacca atgggtttag gaatggttag tcttctaaaa 61800
tctaaactgt ttgtagcaaa atgtcattgt aaaagcccaa tataaagaat agctttaaga 61860
attcattaaa atgtaaggta catgaaagcg gagtacgtgg ttggttttgt tcattgctat 61920
atatttatca cctataacag acacatagta actcctatag aaatatttat tggataagtt 61980
aatgaagtat aattatggag gcatagttat ttttcagaaa agtaactata catcacatat 62040
caaccattgt ttatataaaa atcagatgta atttcatatg atttggtgag ctaagtatgg 62100
tcaagaagca tgtgttctta tcacagataa tcataaaact aatttgaaaa ttatagaaaa 62160
tctcaaatta tatcccaaaa tggacaatta ttacttgtac tatattttct cttagtaaga 62220
taatatttgt tttgttatag aatatttgtt gtcattccta ctcatcaatg ttagtacaat 62280
ttctcaaata gatgtaagca taacttctaa atttaacaat caaaatatgg tctaataaac 62340
taagatgaat tccatactca atatttgtct ttgtaaccta gaatattttc tcaattgcta 62400
ctatgaaaat taagaataaa aagaaaattt taaatgtagg aagtgcactg aactgagaag 62460
attattttcc taaagggaaa ttccactggc tatggagtaa ctgggaactc tgtcctttat 62520
tgtaaaacat ttatgaaaat tgcttgactt gcaacttcat tggttgcctt ggagagttca 62580
ttctataaaa aaaggtgcat cacgtgaaca agaaatgtat ctacacaatg ctcaacagaa 62640
aacccttgat taattgaagt atagtaaatg gttattggtc cattccaatt tcctttaatt 62700
tgcagttgct tggaagcata aagcttttta atgtctttgt tttgacaaag aattcactta 62760

-continued

```
aaagtgagaa caaatttaat ttattaatat aatttaaaaa catgttaaag caaattaaaa  62820
aattaacatg cggaacaatc ttttaaaaag ttttttttt tttaaagtag gaagtacact  62880
gaactgagaa gattattttc ctaaagggaa attccattgg ctattgacta actgggaact  62940
ctgtctttta ttgtaacaca tttatgaaaa ttgcttgact tgcaacttca ttggttgcct  63000
tggagagttt ataaaaaagt tatttattaa gttagaactt taataaaaga ctttttattt  63060
ttatttattt attttttttg agatggagtc ttgctctgtc acccaggctg gagtacagtt  63120
gtgcaatctc ggctcactgt aaccttggcc tcctggcttc aagcaattct tttgcctcag  63180
actacccagt agctgggatt acaggctcat gccaccatgt ccagctaatt tttgtatttt  63240
tagtggagac atggtttcac catgttggcc aggctggtat tgaactcgtg acctcaggta  63300
atccacccac ctcggcctcc caaagtgctt ggattacagg tatgagccac cgcgcttggc  63360
cagacattga tatttaactc tttcttaatc aaattttgaa cttatttcat accttgtata  63420
ttctaaaaaa aaaaacacac acatatatat gtatacatat ttctagctta tatgcccacg  63480
tgtttatgga gttcactctt ttgttttgtt ttgagatgga gttttgctct tgttgcccag  63540
gctggagtgc agtggcgcga tctgggctca ccgcaacctc cacctccaga gttcaagtga  63600
ttctcctgcc tcagcctcct gagtagctgg gattacaggc atatgccacc acatccggct  63660
aattttgtat ttttagtaga gacagggttt ctccatgttg gtcaggatgg tctcgaactc  63720
ccaacatcag gtgatccacc tgcctcggcc tcccaaagtg ctgggattac aggcgtgagc  63780
caccgcgcct ggtgttcact cttagggaat ttaggtgaat gcagatagtt acctactaaa  63840
aagatataaa tcgaaagaga taaactttgg ctgttgggaa aatggttgaa tcaatcaagc  63900
agcaatatta acctgcgaag ggtaagtcac ttttgtcaaa ataaaaaggc tatgttgagg  63960
ttcttacaga aaatactttt aaaaataggg acctacacaa tgtaatgtag aggtgttttg  64020
gcagtttaag ggaaatgtaa tgtaaaaatt tgcataatgc ttttacatat gtaatccata  64080
caatattaaa aaccgtcaat aaaaacatgt tgaaagtcct taatctctct ttagtattag  64140
tttaacagtt aacagagact attaagattg taatttattc tcttattaaa aattattatc  64200
tgatttactg aaaaaacaat cacaggtttt gaatatctaa aaacaaccac tagaggaaag  64260
caattgattt cctgtaacat ttattaatgt aagcagactg cgagaattct attaatctag  64320
acaggagaac tgtaatgttt ctgttgtctt ctttattaaa tttgacaaat ttgaaatgct  64380
tgcaattctg cactaacagg atttcataaa tactctttgc tgacacattt taatttttgt  64440
gcatttactg gatattctta aaatgcaatc atttattata tttcagggca ggaaaaccta  64500
attagtagta aacgattata tcaaacattt gctttttttaa taaacttggc tttatattac  64560
cttatttaga tatcatgaat tcatattagt acagacttct gattacctat tacagaaaca  64620
ttccaatttc aataaaacta acgttagtag tcaagtagtt tctctaagca actgaaataa  64680
atttgcaagt gatggactat gcattcttag tattaactgc agtcatataa ggccatcagt  64740
aacatggtat taagagaaaa ccaataaatt tacccagtta gtcagtctct tggtatgtga  64800
gtagaagaga caaaaagaaa aaactaataa tacagttgtc acatattatt gaccattttc  64860
tgcccttcta tacttttcta agcccatagg ctgtggttat attgctatga tcagtttggg  64920
tagctacttg aatttttgat ctttaaatgc aggtatacct ctgagacatt tcagatttag  64980
ttctagacaa ctgcaataaa gtgaatatca caataaagca agtcatacag tttttttggt  65040
gtttcattgc atataaaatt atgtttattc tatactgtag tctgttaagt gtgcaataac  65100
attacatttt taaaaaacaa tgtatatacc ttaatttaaa aatactttat gctaatacat  65160
```

```
gctaacagct acctgagcct tcagcaagtt gtcctcttct tgctggtgga ggatcctacc    65220

ttaatgttga tggctgctga ctgatcaggg tggtaattgc tgaaggttgt ggtggctgtg    65280

gcaattttgt gaaataagac aacaatgaag tttgcggctt tgattgagtc tgactgtcat    65340

gaaagatttc tctgtagcat tcaatactgt ttgagagcat tttacacata gtagaatgtc    65400

attcaaaact ggagtcaatc ctctcaaacc ctgccactct tttatcagct aagttgattt    65460

attattctaa atattttgtt gtcatttcaa cggtatttac agcatcttca ccaggaatag    65520

gttccatctc aagaaaccac tttctttgct aatccataag aagcaaatct tcatctgttc    65580

tagttttatc ttgtgactgt ggaaattcag tcacatcttt tggctctact tctaattcta    65640

gttttcttgc tatgtctacc acatccgtgg ttactttcag tactgaagtt ttgaaccctt    65700

caaagtcatc cttaagggtt ggaaacaatt tcttccaaac tcctgttgac gttggtattt    65760

ttacctcctc ccatgaatca caaatgtctt taatggcatc tagaatggtg aattctttcc    65820

aagttttcaa ttactttgcc cagattcatc agagaaatca ctatctatgg cagctatagc    65880

cttacaagat gtatttcttc gatcataaga cttgaaagtt tagattactc cttgatccat    65940

tggctgcaga atggatgctg tgttaccagg aatgtaaaca ttaatctctt tgcacatctt    66000

tttcagagct cttggatgac caggtagatt gtcaatgatc agtaatattt tgaaaataat    66060

cttttttact gagcagtaat tgtcaacagc gggcttaaga tattcagcaa atcatgctgt    66120

aaacatttgc tgtcatccag ggtttgttgt tcattggta gggagcaggt agagtagaca    66180

tagcatactt ctgtggggct tcaggatttt cagaatggta aaagatcagt ggcttcagct    66240

taaagtcacc aactgtacta gtccctgaca agaaactcaa cctgtccttt gaagcttcaa    66300

agccaggcat tgatttctcc tctatagcta tgaatgtctc atgtggcatc taccagtaga    66360

aggctgttca tctacattga aaatctgttt tttaatgaag ccacctttat caattatctt    66420

tgctagatct tctggatatc ttcttgcagc ttgtacatca gcatttgctg cttcaccttg    66480

tgcttttatg ttatggagat gccttcttcc cttaaacctt atgaaccaag ccctgctagc    66540

ttccaacttt tcttctgtgg cttcctcagc tctctcagcc ttcaaagaat tgcagaatta    66600

gggtcttgct ctgtattagg ctttgcttta agggaatgtt gtggttagtt ttcttcgtgt    66660

cagcaataag gctgttttgt tttcttatct tttgtgtgtt ctctggagca gcacttttaa    66720

tttccttcag tatcatttcc tttgcattta caacttggct agctatttgg cacaagagac    66780

ctagcttttg atttaccttg gctttcaact tatctacttc actaagctta attatttata    66840

gcttttgatt taaaataaga gatgtgcagc tactcctttc acatgaacac ttagaggcca    66900

ttggagggtt atttcaatat tgtgcttcag gtcttgtttc catattgttg ttctcaggaa    66960

tagggaggcc ctaggagaag gtgagaaatg gaagaatggc tggacagtag aggactctga    67020

acacacacaa tatttatcca tccagttcac tgtcttatat gggtgcagct tgtaattctc    67080

ccaagaaaat agtaacctca gtaatcgctg atcatagatc accttaataa tgaaaaagtt    67140

tgatgtattg taagaattac caaaatgtga cacagacaca aagggagcac atgctactgg    67200

aaaaataatg ctgatagaaa cttgctcaat gcagggatgt cacaaacttc taatttgtaa    67260

caatatgcaa atatctgtga agcatgataa aggcaagtgc aatgaaacat ggttttccag    67320

tacgtgatat taaaccatat catgaaattc tagactctga gatttacaag ggactgacaa    67380

ctcaatcagt tcagcttctc atttccactc ttaagaggta cctctttaaa taaaaaagcc    67440

tattaagatc attaaaataa atccatggaa atccttttta ttaagcaaaa tgtgacaaaa    67500
```

```
ttgttggaat aaccagaatg aaaaagtcta tcattgtcac tgccctatca gactgacata  67560
cttcattgag cataagaggg atactataaa ctgtactaat atgactttat ttctttttac  67620
tgctgaatat gattccattg tatgaatata tcacattttg tgtattcatg catcagctga  67680
tggacatttg ggttgttttc accttttgaa tattataaat aatgctgctc tgaacatttg  67740
tgtacaagtt tttgtgcaaa catgtttcat ttctctatgg tagaattcct atgactggaa  67800
ttacaagtca tgtgatagct atatttaaca tattgaggaa ctgccaaagt attttccaaa  67860
gtggttgcac catcttatat tctcaccaac aacatatgag tgttttgatt tttgtatgta  67920
ctcaccaaca cttgttatta tctgttgttt ttaatatagc catttttatg tgtgacatat  67980
tgtattttta attttcatat ctcaaatgac taatgaattt aacatctttt tatgtgttgt  68040
ttaactattc ttacattttc tttggaggat tgtatattca aattcttttc ccattttaaa  68100
ttgggttatt tatttttatt attgaattgt attagttctt tatatatttt ggatataagt  68160
ccctttcaga tatatgactt gcaaatgttt tctcccattc tgtgaggttt tctttcactt  68220
aataatgtcc ttcaaagcaa aaaaggttta aattgtgatg aagtctaaat ttccagtctt  68280
ctatcacttg tgcttttcct ttagactctc tgtaattttt tacttagagc aacatgtagt  68340
gtaattttgg tttaggtgac tgtgcttcta ctagacagta aatgtgaaca cctgggtatt  68400
ttgtatccta agcaacaagc aaagggcctg agctctagta agatatcaat gaatgtttgt  68460
tggattcatt aatggatttt ttgatactcc ttttcaataa gtaaatttaa cactactcag  68520
taacaaaata atttttacta aggaatgaca atatttgatc tttgaataat taattttaga  68580
aacacacaca tatatatata tacatatata tatatatata tatatatttt tttttttttt  68640
gagatggagt gttgctcttg atgcccaggc tggagtgcaa tggcatgatc tccactcact  68700
gcaacctctg cttcccgggt tcaagcaatt cttctgcctc agcctcctga gtagctggaa  68760
ctacaggctc ccgccaccac acctggctaa tttttttgtat atttagtaga gatggagttt  68820
caccatgttg gtcaggctgg tctcaaattc ctgacctcag gtgatctacc tgcctcggcc  68880
tcccaaagtg ctgggattac aggcatgagc cactgcgccc tgccaatttt agaaacttct  68940
tggtcatcct cacacaaaat tcagatattg attccttaaa ttaaatttta gtgtgcatat  69000
ttaaaagcat gtttcaatga taatattaag tagttaattg ccttatttta tcttggaaaa  69060
agcagaatga gtgatgaagt gtcatctgtt ttatttttcc agttttttttc catagaacat  69120
acctttattt gaaaactaaa atcaaagtat ccccttgatgt cataggatac tttgaaatta  69180
tagataatca tagttatata gtcataaatt gaggaagagt gagagagtag tagaaaaaaa  69240
tcatcaaacc gtattatttc atggagatgg ttagttgtag tcagtattta taattgatgg  69300
ctttttccat tactctggag tctaatttca aatctttcat aagtgtacag atgttttatc  69360
tgattttgca cattattttc tttctacatt tccatagtag ttcagacttc ttaaaagtca  69420
atttttaaaa aaaattcagc ttttcgtcca gctttttgtc atactcttat tccactaaaa  69480
atgttggtac tttggttttg acaatgaaaa atagaaaaca aatagccttt tatgctgaaa  69540
catcttatta aagaaaattt attttgtgat ttatttcttt atttttcata ttgaaaaatt  69600
tttccttctg ttaattagtt ttaactctga tgatcatcag gggataattc ttaggacttt  69660
cattactcaa tgtaattgta atagttggtt cacctccttc ttaatttgcg tgtgtgtgta  69720
acaataaaat gtactagtgc aatgaacaaa ctggttttta catcattgaa taaatgtaca  69780
ttaaatgcct tctgtaccct aggcgttata ttgaaactga tctaaatgtt tcactgtttg  69840
aaacttagaa aagaagcagg ctttctgagt tttgttttgt tttgttttga tttttttgag  69900
```

```
gcggattctc actctgttgc ccaggcttga gtgcagtggc accatctcgg cttactgcaa  69960
cctccacctc tggggttcaa gtgattctcc tgcctcagcc tcctgagtag ctgggattac  70020
aggtgcacac ctggctaatt tttgtatttt tagtagagac agggtttcat catgttggcc  70080
tggctggtct caaactcctg acctcaagta atccacctac cttggcctcc caaagtgctg  70140
ggattatagg tgtgagccac tgcacctggc cctgagttta gaaaaatagg atgtctaaat  70200
agaattaaag aacaatgcat ttccaaaaaa ttgattttga taagttgaat ttctttagaa  70260
catatacttt acaatttata tcacataaaa ttttattcat tactgtttat tagtgagcta  70320
aagctgtttc atataaatta aatttgttat tgttttgaag taaaaataca acacaagact  70380
ctagaaagag actttaattt tatagtttaa gatagctgtt taaaagatat aaggacatat  70440
aactattata gaccagtggt ccccaaactt tttggtacca gggaccagtt tggtgaaaga  70500
catttttcca catactgggt gggagggtgg ttttgggatg aaagtgttcc acctcaggcc  70560
atcaggcatt agattctcat aaagagcgtg caacctagat ccttcgcatg caccattcac  70620
aatagggtcc acccttcttt gagaatctaa tgccgcagct gatctgacag gaggcagagc  70680
tcaggcagta acgctcactt gcccgcccct cacctgctgc tatgggccgg gttcctaaca  70740
ggccacaaac cagtaccggt ctgtgcccag gggttggaga cccctgttat agactaataa  70800
ccaactgaaa tagaatagca tagctatgag tcaaaggttt gtgtcttttg catcaaagaa  70860
tagaaatgtc tgcaaaggtg aagactacta tgcaaatgtg aaatgaggaa gagtgattat  70920
tttgacattg cagtcattcc ataaaagaac tatagccaag tctcgtgtag gttctagaaa  70980
accactaaag atggcgacca tgttatcatg ggggctgcat tgtttcttat tgtacttgtg  71040
ccattatttt gttcttgcaa tgttctttgt gtttttgttt tgtttttgtt tgtttaaatt  71100
ttctattctt aaaaaaacac aatctgatga actctcccca atctatgatt cgttcctctt  71160
ggatcatgta ttcccaccac tcctctaatc tttggattgt tggaggggga ggaagaactt  71220
gatatgtatt attttgagtt gcccctgaca gatagcagta tggcatggta agtgagaatg  71280
tgtagctata tagggtagga aaaggtatta atagattcag agaaataaaa ctcccagtac  71340
aagccataca acagatcaat atacattagc tttttactct tctttgtgct gctcatgtta  71400
gaccagtaat tatttagaac atggaaacaa agtaaaataa ccagttaatg aattcattgt  71460
tttggctttt gtatctgtta gctactgcca gaataatgtt gcataataaa gagccacaaa  71520
aatctcaaag gcctacaaaa attcactttt atcctcacac atttctggat aactgcagtt  71580
gggcttctct aggctagact caactaggaa gcttggcttc agtctaaaaa ccttccagct  71640
gagattcctc tactcagtat ctctagtctt tctggtagta gtgggctagc agaaacatac  71700
tgttctagtg accatggcag aggtagaaaa gaataagtgt attttaagcc ccttcttgtg  71760
ctatttttat agatagccca ttgtccaatc caaatattat gaaagagccc aaaaaaggca  71820
aggagaaaaa tctcaccttt agtgggaggg actgcaaagt tgtttatggg gaggggtaac  71880
gggaccaata attcagtcta ccgtagtttg tacctttaat agaaatcaaa ccacttcttt  71940
atttttcagt agtttgaata gaagccttct ttatttcata gtatccagta cacattaggc  72000
aaaaaaagag aagaaaaaat ttagtggcat tttttgtttg tttgttttat actaaaattt  72060
ccctttgata tgtgtctacc acattcagat taacatctat tgaaaaatat actacaggac  72120
gcatttgtag ggtgtttgtt ttgaagaata gtataaaaat ttccataagt ttcttatgca  72180
accacacata ttttaacttg atgttttatt ctgcatttac ttttgagcat ccttaagaat  72240
```

-continued

```
ttgttaaaat gcagaaatta tgcagtattg atttcaggaa aaattgaagt ggttacacat  72300
ggttgccttt gccttaaaat aaatccttat ttggttctaa cttgaacaat attgaaagca  72360
caacaaaact agctttttat tatgtcacca cacatttagt gagttatgga aagcattttg  72420
ttttaagaat ggagttaact atgtgttatc cacgcttcta gccattcttg tcactcctgg  72480
ctactctcca agcctgcctg ttattcatac atatttcttc ttagtaagaa atgcatcaaa  72540
atcccaggaa catgtgctgc tgactgttag aagagtttta gtggtgagag attaatgtaa  72600
ttacttttgt ttgagaaata taattggtca cagttatata catgtagctt atatgagaag  72660
tacattcagt tttaaaactc attatgatta attttacttt ccttaaaaaa tgaaaccaaa  72720
gagaatctaa aatgtgtatg cttctttcat tcctaatatt ccagaatact tagatatttt  72780
tatgtgaagt aaatgcccag atatctaaat agatataata ttatttaaat ttaaggtata  72840
aacttttaca tgacaaaatg cttaatagcc tataatctta aaaacagaat tattccaatt  72900
cccatattgt atgttacttc atcaaatatt accattatat catgtttctt gtactaaagt  72960
gtttcctgtg aaataacgta ataaaatggc ctttagtatg catgataata tttaaatacg  73020
cattttctag taaaatataa tgcttattca tttttttctt ctagttctaa agaaaaaaat  73080
gcaccaaatg catacactta ctttatgata atttctgaaa cttaagtaga gtttgggcct  73140
gcaacagact tgtgttttct agtagttatg tttcattcat gcaggtggta gtggtcctat  73200
tagttttcct taataagtcc catatagctc tggccagtct ttcatagaat gagttggtag  73260
gtctttcctc caaagtttga tttctcccat ttttttcaca ttgcaatttc aaactttcag  73320
taataccatc aagatgagac agtaaactat tattagagtt accacaagtt tgaacaaagt  73380
tgattataca tcgcaaacaa ataaatactt aaaaccttgt tcatagagat caggccttgc  73440
atacctacat agtccaaaca ttacattcct gacatttaga acatttaaat gcaaactgtt  73500
ctttgttagg gctttctcat aactgaaata tgagtcactt gcaaaccata atagattttg  73560
gctctgctac atgatgaagt gttctggatg tcgtgaaaca tttcacccag acttatggca  73620
gtagaattcc cagtggtcac ccaaaatagg gaaaaaaatg aagaacaaac ttaaaggaaa  73680
tatgcagact ctggcaccat cctttcgtgg caatacagct ctttattgtt gttaagaaat  73740
ggaaatattt agagcctaaa cccataaact atagtacaat taggcgttga attttttttt  73800
tgttcctaat tacgaaattt aactctatac ttgattctca tgtttaaggt caggtcatag  73860
agtgtttctt tacacatcac cctgatgcgg tcatactgag ttgtctccca gcactgagct  73920
tctcactgca ttgtgggcaa actcatattc cacactctac actcatctca ggcaggaaag  73980
gtggagtttt ccttttcagg gccaaaggaa gcaacagctg aggcgtgatg gttgtactga  74040
tattggtgtg ggtttcaatt tggttagttt gctttcaatt tcaactcctc acttgagatt  74100
ccatacagaa aagtaaatgg taggcttcca gcatcttgtt tcactctggt gaataaaaat  74160
tgttttgaat gtaagattag agtttttcct tgcttaattt tagtagtacc tacacagcat  74220
aaactgaggc atcatttagc aaaatgttat tgagttgaca tcataatgac ctattaaggg  74280
caatacacat ttgaatgagc tcagttattc ttccaggttt acacgtgcct ttcatggtgt  74340
ttagtgtagc agcttttgaa gcagagatgg gcaatgtgta ggacctttta ttccagtctc  74400
ctaagtggga gatattctga acaaaacata ttaaggatat tttttctgaa gtttttgaaa  74460
ttttaagtca tgattcactt ttcaaaagaa gacatttatg tggccaacaa acatgaaaaa  74520
aagctcaaca tcactgataa tcagagagat gcaaatcaaa accacatgga gataccatct  74580
catgccagtc agaatggcaa ttattaaaaa gtcaggaaac aatagatgct tctgaggctg  74640
```

-continued tggagaaata agaacacttt tacactgttg gggtaatgt aagtaagttt gaccattgta 74700
gaagacaatg gcaattcctc aaggatctag aatcagaagt accatttgac ccagcaatcc 74760
cattactggg tatataccca aaggaatata aatcattctg ctataaagac atatgcacat 74820
gtatgtttac tgcagctcta tttacaatag caaagaaatg gatccaaccc aaatgcccat 74880
caatgataga ctagacaaag aaaatgtggt acatatacac catggaatac tatgcagcca 74940
taaaaaggaa tgagatcatg tccttttcag ggaaatggat gaagctggaa gccgtcatcc 75000
tcagcaaact aacacaggaa cagaaaacca tattctgcat gctctcactc ataagtggaa 75060
gttgaacaat gagaacacgt ggacacagag aagggaacaa cacacaccaa ggcttgttgg 75120
gggcagtggg aggcaagggg agggaagttg gaggttggtt caatcagtgc agcaaaccac 75180
catggcacat gtatacctat gcaacaaacc tacacattct gcccatgtat cctgtttttc 75240
ttttttagaa gaaatgtttt gttttaaaag aaaaaaatag taagtcatta ttatgagtag 75300
ttactgaatt atcataaaat atcatttcat aacataaaaa ttatatatga tagcatgttc 75360
ccacacaaaa actaggaaat caataggttt gaattgcttt aaaatatcat tgtaatagtg 75420
gataactttg attaatacat ctttatatgc cagtagaatg cctatgttat tattacattt 75480
gctgaatatg ggactttaat aaaaatgtaa aaatgacctg gatttgctta aaaacagaaa 75540
tatttctaga ggagaattta catgctagac atggataagt tgtcagaatg agcaggacac 75600
attattgctc ttggaatctc agaatataga agtctctaat ttaagtaata taaatgatct 75660
tcagtatcct gaagatattt gcaattacct atgttggtaa tatataaact taaatcagag 75720
ctacaaaata ctattattga aataaatatt tctgacaaaa ctgttacttg cttgtattta 75780
aaagcaatct tgatggcatt atcttaatat ctttagagat aacacttgtg aactctaaac 75840
attattttta gtgcaaagtt tgtcataatt tatgtggttt aagtgacaat attacatgag 75900
acaattaatt ttggagtgtc agttccacaa atccaaaaag tcaataaagt aaataattat 75960
ttttgccact aaacaaaaca aaaaattaag cactatttgc cttgatgcat caggtgttac 76020
tattttatag tttgtacagt ttctgtctat cctgccaact atttaaatgt aagccattct 76080
gaaaatgggt atttatatgt tgcatctttt aagaaaaaga aatagctttt tgtatacgtt 76140
ttaatagtaa tcactttcac tgatatttac agagaattta actatagttt ctttagttgt 76200
aatacatacc tattgtcttt ctgctgaatg tctgttttcc agtggcattg ataagacgaa 76260
ctctcacaga ttattttatc ttaatataaa tataaaagaa cctaaaaata ggcaagaagt 76320
gaataaaatg ttttttaaag tagcccatca aatattattt tcatcagaaa ttattttctt 76380
gttgacataa aatgcatatt ttttatgaaa gatcattctc tctgtgcaaa gatcagagac 76440
attgtgtctt aggcacatca ttcagcttgc tccacagccc tggctgtctc cactactctg 76500
gaaaaatcag tgccctcgag taggaggctt aacattgttt ttcttagata aatcacttga 76560
catttcagtg ccttaatttt gactctctgt aaaataacag aaatggaatg gaaatggact 76620
tgatgatatt taacattcct acaaaaagta ttagtatgtt gacttgcaaa tgaatggatt 76680
tctgaacttt cagtgtacta caaatcctac ggtctcccaa aagaaaacaa aagattgttt 76740
ttcttcttta tttgagaacc attttatgta gattgcagga aggttgtgaa ttaaaatatg 76800
tttagatttt ttcattccgt tcattaagaa acatttgatt taagctgcag agaggatatg 76860
catttaagaa tatgtttaga attgtggttg aggtggcaac caccatgcaa ttatcagttt 76920
attaacaggg gaatgaactc ataatggact ttgctatttt agtcatttcc tttaacttga 76980

-continued

```
atataatctt ctactttcat aatatcaatt taaattgggg aaatagcatg ttttatcatt  77040
agatccacaa atatataatg gtttgatatt agcgattgtt aggtaatgat tgttccttag  77100
ttatgtagtt gtatgctgaa acatttaaaa aattaatccc catgtataat aacattcttg  77160
atgtagagca aaataaaatg atagactgca tattataaaa aaaagagaaa agcattatat  77220
tattttatgc actattccca cagaaatatt ttttagtttt aaaatatcca tttgaccctt  77280
cagcaagctg aataccaggg attttattcc ttcagcataa agtaatttgg taacaatatt  77340
taaaggcata tttctaactt aaattttact tttataaaat taccaaaaga cagatcattt  77400
gtgaactaat tggttattag ctcctttaat ctcagtcatg tgtttgtctc taaataaaat  77460
tatttcattt accagagttt tactgctcag ggctcaggtg actcagtcaa gaaagtcatt  77520
cttgtgaagc tacctaaatg gtaacaacgg tagtggcagt gggtgatacc ttagctcaac  77580
cattagctgc agctgaagtg tttattgtaa gtcaagcaca gatctaccaa ctacatttct  77640
tctaattgta gcagatgaaa ccacacacat ttttaaagga ccagatatct aagcacaaag  77700
gtcaacattt ggtaggcatg cagaaaacat ggaagtgcct tatcttaacg ggatcatgaa  77760
tcttcatctt taaagggcag tttttacaga ttttcagaat tgatacctta agttgttctg  77820
aacttcaatt acaaaagcta ttgccagatt gtgttttgtt tttattcaaa atgtagccac  77880
tcatgaagag aaacttctga gtttgaaatg tgatttgtgt ttttgcaaaa tgtttatttg  77940
aatgcaattt tacctccagt ctaaacaaat gtaaagataa atgtaaaaca ctaagagggg  78000
caatgctggc actgaaagct taactatgta gtagtattgg gtttgtcctt taatttttac  78060
aacatatgct tttttagttt agaaataata ttgtagactt ttaagatctc agaattttaa  78120
gctaaaccac taataacaac tgtcttcatt atttaaagtg atctaaattg tatagaaata  78180
aaagggtttt aagaattata aaaatgtagt tattgtttcc tgcttttttc tctaaacttc  78240
taatgttcaa ttcttgtgtt ttatataacg ttttaaaata aatcacacca aaccttagtc  78300
taaagaaggt atagtaatgg ttggtgtcag atctgagagt gaaccaagca catgttagga  78360
tttagaatca tcaagataaa tagtaacacc aatggcaaca aggaagcaat ttaaagacaa  78420
atttctggaa tcaagatgtc aacagtgtat tttcccaggg atgactgctt ctgtttgtaa  78480
atattgctat taaagtacat cacctatttt ctacaaggga tgctgacttg tcttattttc  78540
ttttatatat tttggtgact aatacatact tgttatgtga cagattctaa aatattcaat  78600
gaataaatgt tagatttagt gaccacatca catgtaaatg ggttcagaat cttgcaattc  78660
ttggtagata aaaccatggc actaaggatc tggataagtg aagaaatggc aggataacac  78720
ttatctatgc taatgagttc agatcttctc tcctagataa ttaaaaccgc aggctactga  78780
gataactttg ccaaaccatg ctgaaagctt ttcagttata tctaaggaac tgtggagtag  78840
agaaaaggga atgggcaatt aaggaaaaat atctagattt tcaagaaatg gaatatgaag  78900
ttattcactt ttctttttta ttcttttttg agacagagtc tcactctgtc gctgaggctg  78960
gagtgcagtg atgccatctt ggctcactgc aacctctgca tcctgggttc aagcgattct  79020
cctgtctcag cctcctgagt agctgggatt acaggtgcac gccaccacgc ccaactaatt  79080
tttgtatttt cagtagtgat ggggttttgc catgttggcc aggctggtat tgaactcagg  79140
cttgtcctga cctcaggtga ttcccctgcc taggcctccc aaagcgttgg gattacaggt  79200
gtgaaccacc gcgcccggcc attattcact tttagaatga caagatgaca ctaattttgg  79260
gaaagaggat agcctgattt attaaataaa tgacctatgg aattcttact aaaaatataa  79320
ctttgcatat atcagaatat aatgatgatg aaatggtcta gatctgtata tacaactggt  79380
```

ctatatagat tcattcaaaa aggtgtcgtt ttgaactcaa taatatttaa ctaaatttac 79440
tatctctact aaagcaaaaa gaaagacttt tccgtatttg aaatgaccaa aatctcacag 79500
agcatacggg atcacagact tctagagcac tatgtagtga tcccctagtt tagtttttta 79560
aaaaattttg acagagagag attgattaat agttagttag ttcttatgta agtgatccag 79620
attccagatg tgaatgaaat gcacatttat gaaaatatat ttgtatagct gtagcatata 79680
ttttaaaaac atgattcatt atgttttttt aacacacacg catgagactg tgtaagtttt 79740
ctttactgac tgattagctc tgtggcacta ggtcgttcct taccactgga ctttcattaa 79800
ctcacctatc caatgggaga taaagttctt aggtcatagg gctctgctga ggtttttata 79860
tgtatatatg tgtgtgtagg tgtgtatgta tctacataca catataacct aaaaaaatca 79920
ggtatgttta ttagttattt tattaaaact attaaaatat agaattggct tgctgaattc 79980
atggacccac cagttacact gagacatctt ttaggtatac tcaacttgtt cctagtgtgt 80040
gactctgttt cctgatgtgc ctttgatggt catatttaat tggtgtcaat ctagaccttc 80100
cttacgctca atttgatgtt cttccctgca catacacact tacatgcaca catttacaca 80160
cacccacaca tacttacata aacacacgta catttttca caaagacatt tacaaaatca 80220
tacatgcaca cgcatgcatg cgagcacaca tgcacacaca cacaccccta gcatgcacaa 80280
gggtggcttg ttgctttccc aataaagtca taagattaca gatgaaagac aatttagaat 80340
tttttaaaat tctatgaatc taaaagttca gagttgaatt atgatgcatt cagttacctt 80400
ttatttgtta ttttttcttg ttttaaggac tatgcatata tatgcaaaaa atttacgtgt 80460
ataaagtgaa gatatttagt aatttctgaa gaacattcat tacatatatg tatgtgtatg 80520
tgtgtgtgta tatatatata tatatatata tatatatata tatatataaa atatgtatgt 80580
gtgtgtgtat ttcaaagctc ttcccacatg aaaactcagt gtacattcag tatgtgccag 80640
ttgaacctgt atgtgggact ggaattctga tttttaaaaa taccttttct caaagccttt 80700
ctctggctct aagaagcttc cagatctgtc ctaacagctt gaaaaccaag atcttgactt 80760
tttatagaat acttcactct gtgccagaaa ctgtgttaag cattttcttt acctatatca 80820
tcaggattta gtcttcacaa aatactctag gacacatatt attatactga ttttaaaagg 80880
atggactgag gctaagagaa attaagtgcc cgagttcatc tagctaataa gtgtcagaca 80940
ggaatttgaa gtctggtctc tctaattcta aaacccatga tatttacaac cctgcaagga 81000
agttggaaat gcatcttcca ggctgcagtt gtagttattg tgggcatttc cttaaaggaa 81060
atggtgtcga gaatggttgt tgctagccaa aatcagaagt gtcagatttc taactgctga 81120
gacttgcctg tcttcaccat tctctggact catttgagcc atttgtttta tgatccactc 81180
ttctactaaa aggtggaact agaggtataa caattattta gtacttaatt ttatatattg 81240
ttttctattt ttataaattg ctcatttatt tgtctagctc ttgtatattt cccattcatt 81300
ccttttcaga taatgatgac agtcctactt actgcctctc cccttcccac agcttccatt 81360
cttcctggga aaggagaaat cagaattatt ttgctctccc cacttccttc agattcatcc 81420
ttatcactca tcactgatgg agtttttaca gcataattat aaaagatgac attttatcct 81480
atgacaaaca tgccctggtt atatcctaac taaatggatg ggtgggtttt ttaattaaat 81540
ggatgactta attttgtgat ccagctggga agatttcagt tttattagca gctgtctttc 81600
cccttttctt accagaactt gagctattag cacctaactc aaaagagaaa atacagagtt 81660
tgaagttatt attttatact tcacaaatcc tttcttctaa acatttttc ttaggtgagg 81720

-continued

```
aagcaaacaa ataactctgg ctaggatctt ttaaacaaag ctgttaatat ttgcaaccta  81780
tatccacatg acatctgaaa gaaatgatgg cttagcttta gtcacaaata gagagtgctg  81840
atacgagtgg aaatagaaag aaaagatgta tttttcttcc cattaaaggt tgagcgtgga  81900
ctttaaaggg ggaaattctg agtgattctt aaaacaacat gtgaactttt ttatttcccc  81960
cagacattag ttgccaatat gtaaacattt cagcaagaaa ttttatacca cctcctctgt  82020
ttgtcaggca gcatttaatg gttgaatgac agacagtgct gagccttggc agttccatag  82080
tgatgtgcaa atctggggat taaaatgaca gttaatcagt ggaccttttc tagtataaac  82140
tccatggcca ctatttaaaa tcagttactt atcaacaagg cagacgattt ttatttcgac  82200
tttatgtttt cgtgtaaaga tttcacaact tttccctagg ggtagtttct gttgtttgga  82260
tgttagatgc aaaggttcca attcattttg gcagtcttga ttgcgtggat tcctggtagt  82320
cattttaatt ggtatcttgc agacacgtgg gagtcattca cacattgttt ccttttttctt  82380
tgtaggtaga aataacactt caggatatca atgacaatcc accagtattt ccaacggaca  82440
tgctggatct cacggtagag gagaacattg gagatggctc taagattatg cagctgacag  82500
ccatggatgc tgatgaggta gctcaagcat gtctctgaat ttgtgaaact tcgtagtgca  82560
gtgatttatc aaatttctag gatatgttga ctacttttat tacccaataa ttaaggttaa  82620
gcatgtgtgc tcctttccaa agaacattaa ttcttgaaat gtaacataaa aatgttaaaa  82680
aagagattac tatcaagagg taattttcct ctgatcagca atccacaact cacttgctgc  82740
ttgcacttta ggttacttag ccaaattatt ttttttcttt aataataaaa atatctaaag  82800
aggtatctct attttatgcc attattattc ccctttgcta tcttatagca gctaaggatt  82860
ggtttttatt ttatttgtaa ttgttaaaag caaataattt aaaactacag aattttaagg  82920
tttagattac tattttctat atttatatat taagttcagc tatgtaatta ttatgtttca  82980
aatggcatgg aaacaaatac tttgtgattt gtatttttct tatgaaaaaa actccatagc  83040
ttattttctc tttactgggt aaggagttta actaatgttc tggagtttaa ggaagagaag  83100
taactttcca gacaccagta tctccttacc tctttcccct taagccaagc cgaacacaga  83160
acagagaatt taattttctt cctctcatct aaactcagaa atatcagaaa cttgattcct  83220
ggcatatgaa tcagtgcttt ataaatgtat ttctgtaacc ttaaaaattt aaataaataa  83280
ataataaaat aattttaact gccaatacag aaaggtaatg acttagtcat tttatacatt  83340
tgccaaaatc taactattac aaatgaacaa aataaagcat acacatttag gtaattgcaa  83400
tttgctatta gaaaagatac gatgttttat gtttagtaca ttctactcaa ttttacaatg  83460
tgaagttcac acttatttca aatttagcta gctttaaaag agttatctga cttaatattt  83520
ctattgttga tagatatgtg atatcattag ccataattca gtaaatattt cattttctta  83580
aagtttatca ttgataatat acattttgat ttatcaattc ataaaatttc attaactctt  83640
atttgaaagt agcagcaata acaaaaaact catgtaattg gcataggaca attgacatca  83700
aataattgaa attgtaatga ctatttcatt ggttatactc taagaataga gcaaataaaa  83760
ctcatttatt tgaagtgatt tattctaatc actttaaaag aatgaagtaa taatcatgtt  83820
aattataata gatattctaa tgggatggct atttactcca tggaatatta taattagagt  83880
gggattattt aataggaatt acaggaatca caggtagaat tgcatttgga aatttagttg  83940
ttttaatcat catactgctc tcttaagaaa tggttatttc agagattcca acactcaccc  84000
cttttaatac tgttctcttg atactgttat aattttattt ccttcccaat attttctctt  84060
taagaatatt tcatgtaagt attagtataa atgcaatgct gccagcattc ttatttttct  84120
```

ccatctgact tccgtgtgtg tgtttgtgta tgtgtgcaca cacttgcatt gcctccaagt 84180
tcatctttta agctatgttt acctttatga tgagactaga ggaagcctag gaaggtcctt 84240
atacatctag gtatttagac caacactggt ttttgtgaat ttttatttta tttctactga 84300
gctttgtttt ttaagtttaa aaaaaaatgt aagtaacctt gcagatgtta tcacttagac 84360
atgctagtta agaaaaatac agaatgtaaa gtgatgatag ctaggatata taagaagtac 84420
ttttgagatg agacagagtc gggtattagg gccagaaaag tataaggcta taatgttgga 84480
atgaacaaga gaattggagg gaaggctgtt agcaattcaa gggtagagag ggatgctgac 84540
aatatgtatg aggtgtgact gtgcctgaag gcataaaaat caccacattc ttataactcg 84600
atttgtttgt gtgcgagtgt agaaaggcag agaggatgga agggagtaac taggtgcacc 84660
tacaacatta aaggaaaggg gggcatttca ggaaaactac aaccattgtt ttttaaagaa 84720
aaagctcaca aagttgtttg tcttcttaaa tgcatttttc tcttaaacaa tttaataacg 84780
ttttaataac tgctgactga ctataactct tgacacgagg aactcacatg tctttggttt 84840
catattaagt agaatggctg cctatggcat ttagaatttt gggctgtttt ctttttgttg 84900
ttgtttttag ttgcttataa taaatattaa tgcttttaga taaacctttg ttttattttc 84960
tactttattc tcagctcctt acctcttagc caaattttgg ggaaaatatt ttaaaaattt 85020
tctctctttt caaatcctgg ctctgttttc tttcttcatc tagtttgagt aagactcgag 85080
attatgtagg tcatcagcca attgtgtaga tttttaaaaa ttatttatat acttttcatt 85140
aattacttta cctaacatat aagtgttagt atgctatagg aactcttgta gggcactgta 85200
gaacaaagcc tgggtaaagg aattacaatt ttataaaaca acatgtacat gttgaactta 85260
atttagatat catttgaaat gtgttggatc aagatttaca tgtttcagaa gcacatgatt 85320
ccgtttgtct cttgttccct tttataaatt atgctagtaa tgggctagga tactcaaact 85380
ttgcttcgtg gtaccataca tgtttttgaa aatactattt aaggttctaa tatgcatttg 85440
aaatttatag ctatttactt ttagaattcc ttctatgtgc ttttgtctct gtggttcatc 85500
cggagagcag aatattttta accagcatta tttccactgc agtgaagctg aaacatgata 85560
tttgtttctt gttttgttgc tgatatggca tattttgaat atttagtaaa tagacttttc 85620
aaaagaccta attaaatcat tactcttggc cagatatttt cagacattca ctaatattat 85680
gaattcacca catcagctga ttttgaatat gaaaaagatt gtttttttatc aacacagcct 85740
gatatgttta cctcttttca gaaaaattat tacaacttta ggaatattat tatttattac 85800
agcccatttg tagacagggc atttctaaat atcaaaccat ttttgtaata gcattaaata 85860
ggtttttgtt tcttttcttt accttaattt ccaagtactt actattttca tgggtctgaa 85920
ttgaatgtag ctacttccat acctcaccca ctttactaaa ataatggaat tcctagtgaa 85980
acagaacaaa tgtacagagt gtggtcagat gagaattctc acatgcttat tgaaagtttt 86040
tgttaaacca taaaattaca ataaatacgt tagatattca atgtacacct gaatatacaa 86100
ggtaaatgtg ggtaatgtct tagactcagc tgttccatta ttaaatttaa atgtgctttg 86160
aggcattcat tttactaaat gttaagactg gcctgaagaa tgcagtacaa actaacacta 86220
aatatagcgg gaatattttt gctttagact gttagaaatc atctccttat atgtttgacc 86280
atgaaggaaa aaatgtatgt aagctatgat ggaaaagatg tatggaaact gtggatgctg 86340
taatccccca ctgtgtcagc tttacatgcc tatacactcc aaacttacct tcttcctaat 86400
attctcattg agagctctgt gtctttatat tttaataaat acattctttg aggttaatta 86460

```
caataaatgg tatatttgtt ttaggtaagt atattaaatt aaagagtaat ttttgaagtc  86520
aacatttcta gcactactta tacctagtgt caaggtcaat aataacatat aataggaaat  86580
ctgatactgt attttcccat ggatatatgg caactctagt tatattttga tttaaattat  86640
tcatttgcag aagtctaagt catcaaataa atttaagcca tcatgtttct cttataagaa  86700
aatagtaaga ataagaataa aataacaact atcattttcc tgtgcttact atctgtcaag  86760
ggttgttcta ggtttttaaa atatatgttc actaaattaa cctccaaaac aatccttttt  86820
ggcaggtaat attatcatcc cagtgtacag atgaggaaac atgggcttgg agaggttaag  86880
tatgtggtcc aatgccacat gactaataaa tggagcacaa attcaaccac aaaatatggc  86940
cccagagcat catatctcaa tcagcacagg gtatattaaa cgcagtattt tgattgtaat  87000
atacagaatt aagaaatatc tctcttcctt cttcttctgc cgatccttgc ttctcttctt  87060
ttttcccatt ccttcaccat cattcagtcc ttatatgagt gttcctatct ctatctattc  87120
taatttaatt tctgaacgac tcttgtggct tcaactgaca cccacataaa atgaccctca  87180
gatatttatt ttaaacctca ttcccaaatc tctaattgcc agataaccat ttctatgatg  87240
ctattcttta atccctaaat acaccgcaaa taaaatttca cttcctattt atcctgcatc  87300
aaagcaggtc ctattcttga aatgtcctca gtaagagtac tctcttaatt gccagccaaa  87360
gtaacttgaa atttaaaaag actttttttt cttttttgct tttactttgc acatggggtt  87420
gttaaaaaag tgagaatata tatggaaatg ttgagcaaat gagagagcta ttagtattat  87480
ttctattttc aataatctgt caaattttac taatttgtcc catgaattga ttcagagcaa  87540
gacggccagg attccaatcc cttaatttct tttaaaatgg gcattctaat agtacttacc  87600
ttgctagttt gcctttaaca aattaattag tgccctggaa ttgatgtgct caaggtggcg  87660
tttagcagct agcaaacact atgaatattc tatttttctc tccgccatct ctctagttca  87720
gaattttgag ggtcacagct caaagacctg agagtacgta ggaaatcacc cccattttca  87780
ttttccagaa cagggacttt cattttacag aactgtttca gcaacttggg ggaaatgaag  87840
cctcagtctc ttgggcccca actgtattca caatctgcct tctctggcct ctccctacac  87900
tagtccatac tgcaatatca atatccttaa aagattgctt ccaattaaaa caatattggg  87960
gttccttggc tgtagaattg aggcaaagtt gtgttatatt tgaagttctc aaaaaatata  88020
ccgatactct aacattttag cttgactttc ttcttttgtt ctatattaaa attgtccact  88080
ctaacacact gttcaacagt aagccaagtc catgaatagt gaatgactgt aaaatattgt  88140
attcatttga tacgctttta tttttatttt attgtgataa gaacattaat gtgagatctg  88200
ccccttttaaa agatttctaa atgtacaata cagtattgtt aactataggc acgatgttgt  88260
acagtagatc tagaaattat tcctcttgca taagtgaaga tgtataccca tggcttataa  88320
gctcctgatt tctccctact gtctgtcctg gaaaaccacc attctactcc ctgcttctat  88380
gtgtttgacc attttagata cttcatatat ataaatacct accaagcagc atttgtcctt  88440
ctgtgactat ctaatataac atccttaagg ctcatccatg tagtcacata tggcaggatt  88500
tcgttttgtt tttgagctga ataatattcc tttgtatgta tatacaggtt gagtatttct  88560
tatccgaaat acttgggacc agaagtgtct caaattcctt tttttttttt ttaaattttg  88620
gaagttgcat tatacatgct gatttagcat ccctaatctg aaatgtcaaa atctgaaatg  88680
ttccaataag catttccttt gaacatcata ttggcacttg gaaatgtttg gattttgggg  88740
catttggatt ttggattagt tttgattagg gatgctaaac ctatatcacc tttttttatc  88800
tattcgtttg ttaatggcta tttagtttgt ttccaaatca tgaccattgt gaaaaaagga  88860
```

-continued

```
ttgctggatc atacggtgat tctatttgtt attttttga ggacctccat actgtttttc  88920
cacaacagct gtatcatttt gcattcccac caacagtgta caagggttcc aatttcccca  88980
cttcttcacc aacacttgtt ttggtttatt tgttatgata gccatgccaa caggtgtgag  89040
gtgatttctc attgtggttt tgatttgcat ttccctgatg attagtgaca ctgagtattt  89100
tttatatact tgttggcctt ttttttttg agacaagagt ctcgctctgt tacctaggct  89160
acagtacagt ggtgcgatct tggctcactg caagctctgc ctcccgagtt catgccattc  89220
tcctgcatca gcctcccgag tagctgggac tccaggctac tggctaatgt tttgaatttt  89280
tttttagtag agacggggtt tcactatgtt ggccaggatg gtctcgatct cctgacctca  89340
tgatccgccc accttagcct cccaaagtgc tgggattaca ggtgtgagcc accacgcctg  89400
gccacttgtt ggccattttt atgtattctt ttaaagaaac atctatataa gaccttaacc  89460
attttttat tggattacca aacttaatag ctattatgtt gtaggactta tttatatatt  89520
ttgaaaatta actttctatc agatatacag tttgcaaata ttttctcaca tcccatagat  89580
tgccttttca ttttctcgac tgtttactgt agagaaactt tagtttgata tactttcact  89640
tgtctgcttt tgcttatgtt gcttgttttg ggagtcatat acatgaaata attgcccagg  89700
ctgtctttta gcaattttca actaggagtt ctatagtttc aggtcttaat tttaagtctt  89760
taatccattt taaattgata tttgtgtata atgtatattt acattctttt gcatatggat  89820
atccagtttt cccaacaccc cttgttgaag tgactatcct ttccccatta tatatccttg  89880
gcacccttat ggaatatcaa ttgactatca tgcatggatt tatttatagg cgttctagtc  89940
tgtttggttt gtctgtatgt gtgtctttat gccagcacaa tactttattc attactgtaa  90000
ctttgtagta tattttaaaa tcaggaagca caatacctct aactttgttt atctttctca  90060
agattgtttt ggctatttag gctcctttgt ggtttcgtat gaattttgga attgctttac  90120
ctatttgtat aaaaaatgct gttaggattt tgatataaat tgtattgaat ttgtaaattg  90180
catagataac atggacattt taacaatatt aagtcttcca atgcatgaac ttgggatgtc  90240
tttccatttg tttgtatctt tgttgatttc tttcagcaat gttttgtaat ttggggcata  90300
caaagctttt accgccttcg ttagttagta agtttatctc tcattacctg tttaagtctt  90360
ataatatcat atgaacttaa agccaaaaag ccttcctttg tcaaatacat gttcaaaaga  90420
aaatataagg agcaatgctt ttctacttcc aatagctcag atgcttggtc tcttttttta  90480
gggtgcaaat gctctcgtca catacactat cattagtgga gctgatgata gttttcgcat  90540
cgacccagaa tccggagatc tgatagcaac caggcggttg gacagggaac gccgctccaa  90600
atattcactg ctagttcgtg ctgatgatgg tcttcagtcc tcggatatga gaattaatat  90660
cactgtcagt gatgtgaatg accatacacc caaattttcc agacccgtgt actcttttga  90720
cattcctgag gacacaatcc ctggtaggtg atgggtctct tatgtgtatt ttgcaagaat  90780
cgcttttgaa ccaaaattac atactatgtt tcggctgctc ttaatcaatg attagttttt  90840
aatcatatac tactagttat aaaaatatat atgctggatt gttggatctt ttcattaacg  90900
atctttggta aaattctcaa gcaaatggct aaattttttta ggatgaatga ggttagccat  90960
ttatgtgtct gaaagtattt gtgacatggg ttattaattt tctgtcaatc acagttttgg  91020
tactctttct gctttaaaaa cgtctaatgt gatttggggg ctatgtataa aaagaacagc  91080
aaaaaaaaaa tacatgaaaa actgtgaata ttgattctaa cgctcactag ctgtgtgacc  91140
aacggcaagt taattcattt ctcttagttt caattctcta tcctgtaaat ggaaacagta  91200
```

```
attcctgtta gagttaaggt aaaggataat ttagaaagta cattgagttt gctaacacag  91260
ggcttgggta ttagcaaatg cccattaagt gttataagaa actgaatctt taattataat  91320
cttgcttctt tgaacatatt atattgtgat tttttttagt ctgagtactc aatatccatg  91380
tttctggtgt gtgtgtgtat gcttcattcc cattattgga aatttttatg taaaattaaa  91440
attttattct gaattacatt tggaatgatt attcatgata agccatacat tttagaaact  91500
ccatttggca aaggaattaa acatctacag gagactcctt ctacctgaag tttttttcttc  91560
actcctcaag atatcttgtg caagtccttt atggaaatcc catcacactt atttcttgac  91620
ttagttattg caatgaccac ataagttcta gagtagtatc accagggcat aagtctatat  91680
attttttgga atcctcagtt cctgacacta gcaatatgct accttaaatg ttgattgaat  91740
tcatcagtat atttatggat aggtactgct agatggaaac ataacatcag atatattatt  91800
aattcctcag gaaatttatg ctgaaacctg aggtccactg gatatctgat atgtcacata  91860
ctgtattcaa atagggaaat ggtaatatca aaatctgcag aatgttatgt tcactgtatt  91920
ttcatagcgg ttttcagtta agatatttta ctgtacaaat acattttttg gtctctttct  91980
atatgttctc ttagtaatac ttcttacttc cttgatttta tactattaat ttattctttt  92040
gataggttct ttggtagcag ccatttttagc cacggatgat gactctggtg tgaatggaga  92100
aattacatat attgtgaatg aagatgatga agatggcatc tttttcctga atcctattac  92160
tggggtcttt aatttgactc gattattaga ttatgaagta cagcaatatt atatcctcac  92220
tgttcgagca gaagatggtg ggggacaatt tactaccatc agagtttatt tcaatattct  92280
agatgtaaat gataatccac ctattttcag cttgaattca tacagcacat ctttaatgga  92340
gaatctacct gtgggatcta ctgttcttgt gtttaatgtt actgatgcag atgatggtat  92400
gtattttatt taatataatt tttaaaacat ctataaactg tcatcagatt tatattacat  92460
ttatttattg tgttgagctg tcacaaaaat gcattttgtg aatataggtt ggaagttgag  92520
gaatagaatt ataactgaac tgtagaggat tttaaaaatt aagtacttta tcggttaaat  92580
tcttatttat aacagaaaac ataccttgta ttgttttata aactttatct tatttttccc  92640
cctaaatgta gggtcgtgtt tcaatttagc aatgtagaag tcataagacc acttttttttt  92700
gtataatttt gttagataaa taaaaatatt aggtttacat atgttatttt aacttgaaaa  92760
ggatagaatt tcaaagcaaa atgaaaccaa agacttaagt aaaaatactt acgaatgcaa  92820
aaactaagtt tcacattttt ggctgacaaa tagctaataa tttttttttt tttttgagac  92880
agagtttcac tcttgttgcc caggctggag tgcaatgatg caatctcagc tcactgcaac  92940
ctccacctcc caggttcaag caattctcct gcctcagcct cccgagtagc taggattata  93000
ggcatgcacc accacgcctg gctaattttg tatttttagt agagacgggg tttctccatg  93060
ttggtcaggc taatctccaa ctcctgacct cagatgaccc gcctgccttg gcctcccaaa  93120
gtactgggat tgcaggcgtg agccactgca cccagcccag ctaataatat tttaactagg  93180
tttcatttca gctcgaacag tctcagatct gtttaattta tgctaatgat caagttaaaa  93240
ttttgcatta aatttatact ttacatgtgt ttgatttgta tttattgcaa aagcaattgg  93300
caaactttat tttaatagct gactcctttg gcctttcttc taacacctgt tttgtaagta  93360
tacatatcat ataatatagc attagagaaa acattgtatg gattatcaac ctttaactga  93420
attgtctgga aaattagtac gtgtttttcc cttatgttgg atgcaactaa attgtctcat  93480
caatatataa aacaagggac agtactttga agaagaaata ggtctctatt gacaggcata  93540
tctatctcaa tttagaattg ccttattctt atgacttgga tgatttgtga aatctcagaa  93600
```

```
tactattcta ttttaacatt ctattctata cttactttcc ttctcatagt gtctataaat  93660
ggcacttgga acgatatgag aagcaaaaag gacagtattt tatatatgtt tcaataagta  93720
aaatgggaaa tactttcttt agaattcatt gagtaagagc attttgatgt ttcctcctct  93780
aatttaagtg cagttaaaat tgggcacaaa gatatatcta aaatagatac agctgtaatg  93840
ctagtactac tactattact actactgttg ctagtaacaa tactttaatg ttaacgatgt  93900
taataagaat ctcaagaact gacatctgcc aagtgttttg catgtaccca gtcctggcct  93960
aagaacattg cacactctat ttcatgtacc tcatcccagg tctgtggatt ggctccagtt  94020
agatatctgt atataattga ggttagtccc tattttggag attggtttat ctgctataac  94080
ttttagttag tctacctatt ccatagataa gaatattttc aaagctaatc atgtattctt  94140
atttgtcctg tgactgtgct caacttttct acagagaaga attttccacc atgtttcttt  94200
ttgatttatt agttatgtat tagagagagc ccattgtttc atagaattgt atgttttcct  94260
ggaataagtt ttatttacca tcataactta aaatataggg aaactgcgaa gataccaaaa  94320
aattaaaaag aaaaagaaaa gaattttgtt tgtcaaaaac ctgctggaat attccatgca  94380
catgtaagca cagaaataca ttgaccattg tctctaagta agtttttgtg atattttttc  94440
tttaattgca ttgagtaaaa gtttcaagct atatttattc attgttttag ttttgaatac  94500
gtttatcagt gtaatttcct gcaccttgac ataaaatata tgacacaatt cctattcttt  94560
ctgaatttca aggacagtga taaggctata caaaggtaag cttgtttgta aaactttcca  94620
gctcagttac acaaaagggt ctcaagtgtt tcacagacaa tattagtcag acattttta  94680
aaaataacaa attaacaaat aaatctcaat cactgatcag aaggttccaa tgaggtaata  94740
ttgtcatctt tttagatgaa ggaattttat atgaaaataa atgtcacaat ctgttatctg  94800
tctatggatt ctgtcagagt ttaaaattta gcttacatga tgatttcata aacataaatc  94860
agatctttta ctgttttcac aagaagggta atacctctgt tagcatcaag actactaagc  94920
atgcggtatt acattgagga aatatcggag catcacggaa atattctggc tttgatggtt  94980
atttcgttat cctataaatt atttacactt taaatattgg gaagtcatat taaaatgttt  95040
tgctaataat acaattggaa tttttgctga ataaatgtag ctatataata ttggtgtaca  95100
atacagacca ttgagtttca tatattccag tgacctgatg accttgttga aactgcttta  95160
taaagatggg tgttattcaa aacacttcta tgtgttgcag ctatgtgaaa agttgacaaa  95220
tattagttct ttatagaaat tagaagataa catttataga ttgtgagtaa atatacatat  95280
tttatagcat gaaactatac acctatactt ttaaaatata ttttactatt tatatatatt  95340
tttatatatt tataatatat attttatgtg ctgtgcttct tagaacaaaa ttattcatga  95400
gactgaaata ctatatatag atatctacat atctatatat agtgtgtgtg tatgtgtgta  95460
tatatatata tatatgacga aaccataaaa ccatatgtat gcaataaaac tgccaggaag  95520
agtcatgtaa ctaaatgact tggagaacat tgaacacaaa tggttcacag tgggctgttt  95580
gaagtttaaa gatctggtgg gccattaaag cccactaaat ttaaattgca acacttatgg  95640
ctaaagctta gaattcaaaa caatgtaaaa ataataattt tacaataatg tgtttactgt  95700
ctcatggttc agatatttgt tgaaaaaata gaaaaaaatg gtctgagctt agtatttttc  95760
agtatacttc aaatattccg ggagaaattt gagttttgct atgtctgcat gtattttta  95820
gatgtagtgt atgtggccaa agtcactttt tagacttgtc agaaatgaaa agttattttc  95880
tttacagtaa agtaaatgca gatggattcc atgacctgta attgcagcaa ttaattttca  95940
```

-continued gttcctgaga tgagagctac ttcttctata atatggcaat attttatgta aaaatagtta 96000
tattttttat ttgtttcatc aacaataatc ttcagtttat ttttaatgtt gttacttaat 96060
atatttgtca ttatgtattt gaatataaaa gcaaattttt cttttgttat acttttagtt 96120
agcttaaaat ttattacttc ccttacccat tcatctacca aactttttgc ctttataaaa 96180
gaggctgttc tgctgtttac aacaacgcta taaaattttg ggatcgtgtt ctctttttgc 96240
ctctgcaatt tagctgttta ctcaaggaag tagcatacat gatggactaa ggatgatcag 96300
atacttgatt taattgctcc cattcctgtt gatttatgta gaaatgttag gccatgtaaa 96360
atgtcagtat ttttaatgta ttttgatctt agatatgaaa gattttatat gcttctctag 96420
aattaaattt tatatctttg cttgttggta tttattttca ttcatgtgtt ttcataactg 96480
catttctcaa taatagtcat gtccccaaaa gaatggggat tcaatattta ctgatgaact 96540
tttttgtagg aaatgcagaa aattttctta aaaagtaatt aaacgtaact atatatgtag 96600
atgttaatag aaacacacgt atacacataa ttaaaaataa attctgtgtg tatatataga 96660
tactcaaata tgtatatgtt ataatgtttg agtaaatata tatacacaca caatataatg 96720
tatatacgta tatttacgtt gtaatgaaag tcctaaaagc tttatatata tatatgtgaa 96780
gatagtggaa atttttatcc tctaaagcct gtggaatttt aagacaaggg gttgaaataa 96840
gctgttaacc ttgttctagt cagattctac aattctgttt ctttcctgcg ggtgaattga 96900
cctctgacac ctattagctt tatttattca tatttttcct gatcttcaga ctcctaagta 96960
ttctgaactt tgtaatctct tccttgttca cttgtgagta gtcttaaata aactataaag 97020
attaaaagtc acaactcata atgaggggga aaaaataaac tacgctttca acgatttact 97080
caatcattgt ttatcctaga aatttttgtt aataagtcat tgtctgaaag ttatattcat 97140
aaatattttt cccatgtttc aaattaggca aaggatatta gagacagtaa agtcacagaa 97200
taagagtaag tgtggcgttt ttaaaaacat tgagttctac atggtagaaa aaaatctcat 97260
actcaagtta aatttgactt cttaaagaac ttgatgaagt tcaaaaaaag gcaaaagtta 97320
actgaagtat tgatagaata atgagaaaga attttttaa agaaaagagt aaaagggtga 97380
ttaaattgtt ctagacgact tttgccaaaa gtgaacatca cttctcatag gtagaattca 97440
gaaacctgga tagttgaaat taatgttaga aatatagaag ctaattgtag gtaattcagg 97500
ttagtcagta gatatttgct agtcccagaa tatacatctt tattaaagat agattacctg 97560
gatgtacagt acgtttttat cataatatcc tgtaattttt ccaatgtcat taggataaga 97620
tataaaaatg cacatcgtta caggccagag aagaaaacat cactctgagg cagaaactga 97680
cttctttctg ttttcactgc ttatttgtta tttaccttta gttactaaaa cagtaagatg 97740
atgtatatgc tccacatcat ttttgttata agactctctg caatcatttt ctgaagtgag 97800
gatttagaaa caatttttaa actaaaaaat gacacatgat cctaagaaaa atcaacagta 97860
tctaaataca gttcaataat agcatgagca tttatatttg gaaagtttta tgtataattt 97920
tactgctaac aatttcttta aaaatacttt ttagaaactt taaatatgtt taataaaatt 97980
tgaaagagaa ctattgtctc aaaggtccat tacttagcta gacacttaat aggaattaat 98040
aagtatttat tgattttgac acgaaatata gaagtacact tacagcattc atgactaatg 98100
ccatacatca gaacatttta ttaccctttc ttgaaaattg gtgtcagcct ccctaaatta 98160
ctaaagttac aaatgtttga ctaatagtat agcgtgtggc actgttagtg ttggaccatc 98220
aggaattatg tgatagaaac aaggaaatat atagaaaaat atctgctctc tggaatattt 98280
ttctcctctt tacttttgta atttaacatt tcaacaccct agtaaatagc aagcagtata 98340

-continued

```
tagatcattt gttcacagga tttcctaaag tgtgtttgga tgcacggcat atcaaacatg  98400
ccaaattact tgctaaaagt tttggtatag cttgttctgc aatcagcata tgtttaagaa  98460
aatttttct tccctttaat ttcaggcatc aactctcaat tgacttatag cattgcttca  98520
ggtgatagcc ttgggcagtt tactgttgac aagaatggtg tactcaaagt cctaaaagct  98580
ttggatcggg aaagtcagtc cttctacaac ttggttgttc aagtgcatga cctgccacag  98640
attccagcct ccagattcac aagcactgct caagtctcca ttattttgtt ggatgtaaat  98700
gataacccac cgacatttct ttcccctaaa ttgacataca ttccagaaaa tacacctatt  98760
gatactgttg ttttcaaagc tcaagcaact gacccagata gtggcccaaa cagctatatt  98820
gagtacactc tgctgaaccc tttgggaaac aagttcagta ttgggaccat tgatggtgaa  98880
gtgaggctca ctggagaact ggacagagaa gaagtttcta attatactct aacagtggtg  98940
gctacagaca aaggtcaacc atctctctct tcatctacag aggttgtagt tatggtactt  99000
gacatcaatg ataacaaccc catctttgca caagctttgt ataaagtgga gattaatgaa  99060
aacacactta ctggaacaga tataatacaa gtgttcgcag cagatggaga tgaaggcaca  99120
aatggacagg ttcgctatgg cattgttaat ggtaatacca atcaggaatt tcggatagac  99180
tctgtcacag gtgccatcac tgtcgctaaa cctttggata gagaaaagac ccctacctac  99240
catttaactg ttcaggcaac agatcgaggc agcacaccca gaactgatac ctccacggtc  99300
agcattgttc tactggatat taatgacttt gttcctgtat ttgagctatc tccatattct  99360
gtaaatgtcc ctgagaattt agggacacta cccagaacaa ttcttcaggt cagtatattt  99420
aaataaagca agtattgtct taattataag acatctattt gaaaacctcc cctcttctac  99480
agcgtttacg cttcccctgt tctctcctca ttctcatcca taaatgctca attgcagata  99540
cagcaaattt tgaaaaggaa aggtttataa acatcatacc taagaacctc ttaatttcct  99600
cattgatgaa acttttgtat tttactagct ttcttttgtg tatactcatg ttgcacacat  99660
ttatgtattt gtgtttttga attttgttcc acaaggataa tatctgcaca tagtaaaaaa  99720
ctaaaatgat ggaaatgttt gaaacttcgt tataaatatt gttctactct tttccttcat  99780
atatttaact acctaggtga aactgctctt aaaaattttt atgaagcctt ccaaaaaatgc  99840
tgtgcattag ctttacacat atttttacac aaatagactc gggtgatata tactatagtg  99900
tgccattttt attttttact tgaaaatcta aaaatatatc tttggaatct cttaacatag  99960
ttttacctca ttttttttta atggaggcat tttatttcat gagatgcatt gtttgtttta 100020
ctcacatctt ggtatgtact gttctacagg tggtggcaag agatgatgat cgaggatcta 100080
acagcaaact ctcatatgtt ctgtttggtg gtaatgaaga caatgctttt actctctcag 100140
ccagtggaga acttggagta acacagagtc tggatcggga aacaaaagag cgctttgtct 100200
taatgattac agctacagat tcaggtaagt ccattacacc cttgttcatt tgtagataat 100260
ttctaggcca ggcacggtgg ctcatgcctg taaccccagc actttgggag gccaaggtgg 100320
atggattact tgaggtcggg agttcaagac cagcctgacc aacatggtga aaccccatca 100380
ctactaaaaa tacaaacatt agctggacat ggtggtgcgt gcctgtaatc ccagctactc 100440
agaaggctga ggcaggagaa tcgcttgaaa ccaggaggcg gaggttgcag tgagccgaga 100500
tcacaccact gttctccagc ctgggcaaca agaacgaaac tcgtctcaaa ataaacaaat 100560
aaattaaata ataataattt cttcataata tgagtatgaa gtattttctg tttgccatta 100620
aatgaaatat ttgttcactt ttactaatgc ttgaaattct gattgcctct atgttattga 100680
```

-continued tggcacatca ttcactttat gacatttata tataagtggc aagggcttaa ggacatcgcc 100740
acctaagccc tattcccata aaacagaatg aattgttgcc ctataagctt attgagtacc 100800
tctggatgtg accttacact ctacttcctg agctaggggc atttaaagta ctttagcttt 100860
ggaaacatgt agatggttcc aaccacttct cttctgatag acatgggtga gtgagtctgt 100920
taggaggagc tttcactaga aggtggctca gtattcagtg aagcattggt ctaaatgtgc 100980
aggctgctca agaacaaagt cctggttcca gggagccaaa ctataagttc ctgatgccat 101040
cagccttgaa aatcagggtc agggggaaac caggacttgg aattattagt ataagtataa 101100
ataacagaag tctaacccta atttctatta aataagaaat atgcagatca gatgtgtgaa 101160
gattctgccc aatagagtta tggaggattc taagttatgg agggtgagca atcagattat 101220
cagtaacatt atgatatgtg gaagcctgtc actcaaagct ttaaaaatga tgctgaagac 101280
catgatggga ggcacaaatg agtttcagtg acattagtgt cctaagtcat ggtgttttgg 101340
cagctctaaa aatgaaagca ttaattaaac cttgtttcaa agcacagctc tctatgggca 101400
ctgtttttcg agtcgctctg aaatagactg gcatttctga ggccactggt ggataaatac 101460
tcaattagat gtctgaagtt cacttttatg agtgatacag aaaacagaag ttgtgaggaa 101520
agttgaactg ggtgatcttg aaattaattc ccttggatac tcttgatatg aataaccact 101580
tttttcagga gaatgtgagt tttagacatc cggttttaga atctacagtt taatcttatt 101640
ttccaagaat gagatctttg acagaggact taaattacat attcactgtt ttcattcaaa 101700
agtcaaactt gtagatgaca tgagaaattt cggaaaaata tggcagctat tagatcccag 101760
atgcaatgtt tttctcaaat ctgtagtgtt ctaagggcct ggaaaatatc aaagtgtttc 101820
aaaaaaattt tgagagttta attctttatc tcacaaatca cctttccttt gcattttttt 101880
tgaactatta ccttagccca gagataggtc aacttcatca gtatggcaca gattgcagtg 101940
gcagttttta atcatgcaaa ccactaaatg tttcaatgtg ggagggagaa aacattacca 102000
tttaaactct catcatattt ttatttactg actgcatggt tacagagtag cacatttgga 102060
aactctaact actcctgtct actgctccag taagctacaa ccacagtatc atatgtatgc 102120
agtgctaaaa gttacattac taaattacaa aaccggaaga gggtataata attatatctc 102180
atttttcctg tagataatta aattgctaaa cagactacaa ttccattact gatgatatgt 102240
tgcttagcta taacagaaag tatggatatt cggccttcat tatgcattac ttatagttat 102300
ttcttctgga aatatttact gtaccaagta gaaactcata ggaggctaac acatccacct 102360
ggtatagtaa tgcaggtact actacatggt ttaaaggaga atttgctcaa aagcagttat 102420
gtccttcata tgggttaggc attctactcc taagtagcct ttcttacaag agtttgcctt 102480
accattttct catatgtgca ataaataaaa taatgtttta aatggagcaa gtagcaggaa 102540
attatcaggg aaactagaag agtatacttt aaaaaatgaa ttcagataat taatttagaa 102600
atggaagtat atcatgtagt taaatacata gactttatag ttaaacccca gttcacatcc 102660
tacctctgac attcccagct atatgacctt caacaacttt actattcctt catgtttgta 102720
tctatgattg gaaatactaa tatctatatg aaagtttatt gatcaaatag ataaaaagga 102780
atacttattc tagctattaa tgtcagtcag catgtttact agacatttca agcttagtaa 102840
ggccaaagta acacttttga cttctattca cctccctacc ttaaatgaat tgcttcatag 102900
atcatttcac aattgctgaa ggcaaacctt gttattattc ttcattcctc ttcctctgta 102960
caccatatcc aacaaattca ttaacaagga gactcagctt caaaaatgtc caaaagtgtc 103020
ctgaatttat ccacttttct ttacctccaa aacgacctcc ttagtctaag ctggggtagt 103080
atgatagctt gctaactgcc tatcttttct cctgcatggt gcattattca acaggcaacc 103140
caagaacatt taaaactata aattagataa tcataccta tctcttgcat agacagcatg 103200
cagtgatttc taagaataaa atttaaatgt cttaccattg actacatggg attcaataac 103260
ttggtctctg tccatttatc tgaacccctc caccaccacc agctgccacc tttattttga 103320
gccagagtcg tgcactggcc ccagctcacc ctttgtctcc tgtcagttct gcatttagta 103380
tcatcacatt attagattgt aattggccaa catggaagta tttacaccct ggaaatcagt 103440
aagtgctttg aatgtagttg gcctgtttct tgaaagcagt tgctaaacat ttactgaata 103500
ctgccaatgc caaccaatca atcaggcttc cttaaaaatg ccaacctttc tgccatgttg 103560
gcctttgca cttgtagttc tctctgcctg gaattttcta ttctacagcg agctgtttgg 103620
tttggtttgg tgagggagaa gggcatccat gtcatggtca ttttgtcatt attttagata 103680
aaatgtcaac ttctcagaga ggacttgtct gaccagtaat gttatgtttg ccctttccct 103740
tttcccagtg tcactctatc aacttcctct ttatgatttc ttaacacaaa ttcctatcta 103800
aaattgtgtt cttctacata aaatatatga gtatatagag tttgtttacc ttatccttct 103860
ctatcagatt tccagagaaa gtaaacttcc taagtcttat tcaaaatggg attctcagaa 103920
acacttagaa aaggacctgc aacataatag gtgcttaata aatatttgtt gaatgagtaa 103980
gttatatatg ttgaataatg atagttgtca tttgaaagac aacctattat tttaatatgc 104040
aactgttatt tatatttatt taacatactt atatttagtt tattgttata tattcattgt 104100
ttgcagattt ttttaaagaa acttccaaaa gaaaaaagtg caaatcattt ttaattcatg 104160
gctgaaattc cagaagtttt tgctacattg gctgtggtca ttcaaagtga cctctctttt 104220
gaaaagcagc acaagtgttt aaagctttgt ggtgtttagt gtgatgtgac aaattgcagt 104280
cacatgtaag gacccagtga agcattttat ggctttaatt cagtttcaag tgcttaaaat 104340
actgcttgag ctatattctc atgactttcc cctgaacctt ctggctctga ttcaattctg 104400
ttatctatta gacgtttcta gacaggtcgt attgctactc tgtgctttac tatccacctt 104460
ttcttactct ggttcataag atttaattca aaacctgcat gagcagaaac tacatgcttc 104520
tgaatagttt ttgtttgttt gtttgttttg gagagggagt ctcactctgt tgtgcaggct 104580
ggtgtgtagt ggcatgatct tggctcactg caaccttcgc ctcccgggtt caaacaattc 104640
tcctgcctca gcctcccaag taactgggac tacaggcaca tgcctggcta attttttttt 104700
attttagtag agacagggtt tcaccatgtt gccaggctgg tctcgaaccc ctgagcacag 104760
acaatccatc tgccttggcc tcccaaagtg ctaggcgtga gccactgcgc ctggcctgaa 104820
tagtttcacc attcgacaat tcttttatac ctggttttcc caaagcaaac aattgtgaat 104880
cttccatatc tcccacatat ctaagcactt tctaagcaca cgtggcaatt ggtttcacat 104940
agcttaaata taagggccca tcatttcaca ccaacttaat atgaaaaatt tgcttgtttt 105000
aaattttatt atggaaattt tggtgttcac ataaattatt ccaacagata tatacttacg 105060
caagtaattt gtccagacct tttagaattt ttttaactca agatgagatt ataccctcaa 105120
aaataaattt aaatgctgtg aggcattaat atctgccact actctttcag ggaactgaat 105180
taatgtgcga gaaagcagta aaacaaactg gtatgacact ttggggatgc tacagttata 105240
ctcagaggag tttttaaaga aagctacata tgaaaaaatt ctaagttaga gaaatctgac 105300
attaagtgat ggtttttttt tggccaggag gtttcttgga gatgagccag tccacttcct 105360
ttattttcca gataagaaaa ttgaaggctg ggatagataa gcagtgtgct agaacttgca 105420

-continued gacccaggta gtagcaaagt caggtataat atttagaatt tctgcctttc aactaaattc 105480
ttgctcatcc atatcatatt tattaaattt ttttaaggaa atcaggatat tccttaaaat 105540
atattgctga ctctctccat gaaataaatt tataaatatg caatttaaaa aatattttct 105600
tttttacttt attcatttca ctttaataaa tgaaacattc aactgctatt tttctttccc 105660
caaataaata aatgtttgaa aacattttta aatgaagcca aattaagtgg aatcagtaat 105720
ttcaatattg gtattttgaa aataagctta aatttagaca ttgtttaaat ttaattgtta 105780
aataaagaag atataaagaa tttgttaggc tttatgccta gaagatgata atattggtaa 105840
ttatcactgc caattatcat tttgcattaa ttaaaatcaa actatggtgc taatttaatg 105900
cactttataa ataagttctg attacagtta gtgatatggt ttgcctgtgt gtccaccaaa 105960
tcgcatcttg aattgtggtt cccataatcc ccatgtgtca tgggagggac ctggtggaaa 106020
gttattgaat catgggggca gttacctcca tgctgttctc ctgatagtga gtgagttctt 106080
atgagatcta atggttttat aaggggattt tcccctttg ctcagcactt ctctctcctg 106140
ccaccatgtg aagaaagacg tgattgcttc cccctccgct gtgattgtaa gtttcttgag 106200
gccttcccag ccatgccaaa ctgtgggtca attaaacctc tttcctttat aaattaccca 106260
gtcttgggta tgtctttatt agctgcatga cagcagacta atacaggtta ctgatatcag 106320
agagagtagg gcactgctgt aaaaatacca aagtgacttt ggaactgggt aactggcaga 106380
gactggaaca gtttggaggg ttcagaataa gagagaaaaa tgttggaaag tttggaactt 106440
cctacagact ttttgaatgg ctttgaccaa aatgctgagg tgttatggaa aatgaagtcc 106500
aggctgaggt ggtcacagat ggagatgagg aacttcttgg aaactggagc aaaggtcact 106560
cttgctatgc aaagagactg gcaacatttt gcccctgccc tagagatctg tggaactttg 106620
aactggagag agatgattta aggtatctgg cagaggaaat ttctaaatga caaaggattt 106680
aagatgaagc agagcataaa agtttggaaa atttgcagcc tgagattgca atataaaaga 106740
aaaacccatt ttctggggag aaattcaagc ccactgcaga aatttgcatg agtaaccaag 106800
agctgaatga taatcaccaa gacagtggga aaaatgtctc caaggcatgt cagagacctt 106860
ctcgacagcc tctcccatca caggcctgga agtccaggag gaaaaaatgg tttccttggg 106920
tgggcccagg gcacccctgc tgtgtaaaac ctagggatgt ggtgccccac atcatagtca 106980
ctctagccat ggctaaaagg ggccaaggtt cagctcaggc tgttgcttca gagggtacaa 107040
accctaagcc ttggaagttt ccacatggtg ttgagcctgc aggtgcacag aggtcaagaa 107100
gtaaggtttg ggaacctccg cctgaatttc agaggatgaa aataagctta aatttataca 107160
ttgtttaaat ttaattgtta aataaagaag atatatgcct gctggggcat tgcctcatgg 107220
agctgtgaga agaaggccag catcctccag accctagaat ggtagctcca ctgacaactt 107280
gcagctatgc acctggcaaa gctgcaggca ctcaccacca gcctgtgaag gcagctggga 107340
gtgggactgt accctgcaaa gccacagggg cagagctgcc caagaccatg ggagcccatg 107400
tcttgcatca gcatgccctg gatgtgagac atggagtcaa aggagatcaa tttggagctt 107460
taagctttaa ctgcccctct gcattttgga ctttcagggg cctgtagccc cttcattttg 107520
gccaatttct cccatttgga atgggtgtat ttacctaatg cctgtaccgt attatatcta 107580
tgaagtaact gctttgcttt tgattttaca ggctcatagg tggaaggaat gtaccttttc 107640
tcagataaga ctttggactt ggacttttga gttaatgctg aaataagtta agactttggg 107700
agactgttgg gaaggcatga ttgtgttttg aaatgtgagg acatgagatt tgagaggggc 107760
cagggacaga atgatatgat ttggctgtgt gcccagccaa atctcatcgt gaattgtagt 107820
tcccttaatc cccatgtgtc ctgagaggga cctagtgggt ggtaattaaa tcatgggggc 107880
agttacctcc atgctgttct cctaatagtg agtgagttct caggagatgt gatggttcta 107940
taagggcttc accccacttc actctgcaca tctcattttt ctctctcctg ctgccttgtg 108000
aataaggaca tgtttgcttc tgattctgcc acgattataa gtttcctgag gcctccccag 108060
ctctgggtta attgtgagtc aattaaacct ctttccttta taaattgccc agtcccaggt 108120
atggccttat agcagtgtga gaagggatta acacagtcag tgagactatt atacttctat 108180
gggcttattg atatttaaca agtctcttaa tattgctttt tcacaaaatg tttatagagc 108240
actctactcc agatattctt ctaggtgctg aagataggct ggtgaagagg tctctgtctt 108300
tatacagctt aaattacaat cacaaaaata gacagtaaaa aataaacaat atagtatata 108360
gattgggagt gttatgaaac atgatgcggt taaattaact ggcgagagag tgttaagtac 108420
ttacgtattt tacccatttt gaaagttgaa tctttggact tgatggtaga atcggaagga 108480
taggaagctg caaaaaggca cgaatcaggc atgagtccta gaatatttgg atgaacaatt 108540
tggagatggg gagaaaaaag attttagggc aaattaccaa gacttagttt ttggacatat 108600
tacgtttgaa atattataac taattgagat gtcacgtaga aagttaaata taaaagttta 108660
gttctcaggg aagacattca agtagagata catcttagaa agtcataaac attagatgat 108720
attcattata tgcacactta gtgcttgtaa gttccagaat atgtattata ttatctcatt 108780
taatctcaca atagccctga aagttaggga ctagtatctc aattttattg atttataaaa 108840
caaccaacaa aaatttgtgt tataaaaact aaacaacttg tactgcccat tcagctgttt 108900
gtcagtgact acaggatttg aggccaaccc acttaacagg tgatgatttc ttaacaatta 108960
tttaccaatt cccaaatgtc agcctgtcta ccatattctg ttttatatag actatgttta 109020
tacgaatttc ttccctttgg attaaatttt atttttatat taaagagaac attggtttag 109080
gaagcaaaaa atcttgtggt tctctctaag taaaatagct ggtaaagtca taatattcat 109140
gaattagaaa tcacagcatt attcccctca ataaataaaa aatatgtatc caagggtttt 109200
attaagtata aagtacaaag cgaatcttag atattatact atgaacgtac aatacatatg 109260
atatgctcat acctgcatag acaatgcagt tagttgggct gtatgtttgc attgaatttg 109320
ggggtaggag attaatctgc gcacaaatta aatatgttat cctttatcct ttatagataa 109380
ttctcagtct gttgtactaa agggatatag agattctgtc tctagatttg gcacaaaagt 109440
ttagttataa agtatttgtg tgtcagcata aatagtaggt cttcagggaa cagttcagtt 109500
attagcattt ctaattaagg gcatttatca tccaactgaa agggaatata tttcattctt 109560
atgcagggat tgaaaattgc tttttaatgg agggaaacat gctgtttttg caaagttaat 109620
gctaaaagct aaaaggagtg atcatcatgc tttattttat tggtgagcac ctggtaacat 109680
tttgaattgt tgtctgtcac attatttagt tgaagctggt cattgcatta taaatggctc 109740
tgtaatcaaa agagaggtca gaattgtgta atatgacatt ttacatccga agataattgt 109800
ttttaaatat tccagaaaga tcacattttg tcaatattat ttgtgggaat gtatgataga 109860
aaagtttgcc ttgtctgtta tgatcaacat ttttaataat gaaaattgct tgaaaacttt 109920
taaggcccca ataattctat aaatcaaatc atgctagagt tgccttcaat taccagacat 109980
gaaatgcatt tgacttaatt ttatttttga gtctcgggca gcttttgtta tttccattgg 110040
catatttgtc atagatggga atcttgtttc caaagttgat aactggttat tgttttaatt 110100
cctcttattt gtagcagact ttctatgaag tttgttagtg atctaaatat tattctaaat 110160
catttattta aatagcattc ttttaaatca gctactcttt agtcagaaaa aaatatttct 110220
acatagaatt ttatttgtgt tttcttaaga taaaactcca gaaacattta atttccaaaa 110280
ttccattgaa taagagctaa agttgccatc aggttccata gaattgaaat ttgataaaac 110340
agtttcaatc tattatccat ttactccatg tgagctacaa atctgagtat acaaagtaaa 110400
ttaaactttg aaatggcaat aaactatgat taatatttat gataaaattt atagaaactg 110460
aatgataaag attatataaa atcaaaacca acatgatttc attatgagga tttcattatt 110520
ttcaaaaaag ttttctaatt ctatcttttt gaaacaaacc ttttttaaag cttattttga 110580
taagtattct taaatatata atttgatatt ttcactcagg aggcaggcag aggtaggttg 110640
agtttaaaat taggtggtag cctctagtgt ttcagagttt caataactgt gttgaaattt 110700
ttgggtttct ttaatgtcct ccaaatagta attcctcata tgtgcttttt gcaggcataa 110760
aatatttggt tattattatt ttttatttta taatttttaa aaattatgat aagatgtact 110820
tatcattaca tttctcattt taacgatttt ttaagtgtat ggtttagtga ttaagtatat 110880
tcactttgtt gtgcaatttt tcagtggcat tgtcataact ttactaaagt aattatttta 110940
gttttacttc atgcctttat ttagtatgta atttatctta aggaaatata gtgtttttga 111000
tagattccta tgcaaaaata atgaaaaaaa tattaagtgt gtatatatct aatttatata 111060
agcatatatg tagaactaat tagcagcaat acattatttt ataaaacaga atttttaaaa 111120
tacagaagtg ttgttaatat ttaaattgtt acataccttt tgttttatgt attttttgta 111180
ttcaaatttt aatctaacca cataatcttc aatgctaata taggatgact gaatttcaat 111240
acatttttta gtggatggct tacttactgt gagaaaaatg agtttacttc atggggaaaa 111300
aaagaagcta atactttatt acaacaaaca caccgctagt caggggaccc atttaccaaa 111360
tatttgatgt caagaaagaa aatggctttg ttgcaaagca acagaattaa gttaagcaga 111420
attctatttc tgctgaatag ccttttatgt ttcagagaag tatttttgat ttatagttgc 111480
tattataaaa aatataatct tcctgacatt tgaacttcaa tcgtttaaac tcattcatta 111540
cacttattat ctgtgtatat tctgatagag cagtgacctg aaactttttt ctttttttcaa 111600
atcttatttt aagttttagg ccaggtgcgg tggctcacac ctgtaatctc agcacttttg 111660
gaggctgagg caggagatca cttgaggtca ggagttcgag actagcctga ccgacaaggt 111720
gaaaccccgt ctctactaaa aacacaaaaa ttagccaagt atggtgacac atgcctgtaa 111780
tcccagctac ttggaaggtt gagccaggag aatcgcttga acccgggagg cggaggttgc 111840
agtgagccga gatcacaccg ctgctcttca gcctgggcaa caagagcgaa actccgtctc 111900
aaaaaaaaaa gtcttatttt aaattttctt gaacttcatt tgatatattt gagctgacta 111960
agctaccagt cttaaaggca atgctagtta ttagtttaat ggtttttcat acttaagagt 112020
ataaaatgtg actcacacaa ggcccagggt taactgtggt atcataaata attggaagat 112080
taacctgtgc acagtctctc tctctctctg tctctcttcc catgagtgtg tgcatgtgca 112140
caatttggtt tgtgtaaatt ttaagatatg ccattcagaa tttgggtttt cttttttggc 112200
tattttatgt gaaaactgaa gaagaatttt atcacttttt ccatgtttat gttatattta 112260
tgtttatatg aatacatatg tgcatacata tgtacacaca ctacatacaa ctttacaaat 112320
ttaaatttga aattttttca tctgactact aattgtaatt aggtttttga cttttcactg 112380
gagttctgac ttctaattca aatatccact gcatcttctt aacctctaca attacaagtt 112440
tctgagacct tcacttttaa ttttatttgt atattttacc cctttcattg gctcactgtc 112500
ctctatcagg agcccgtgtc attatatcct gcctctttgt gattgcatct ggttttcata 112560
aatcaatccc aggtggaatt gaacaatttt gccctattac accactacct atataattca 112620
tcattatcag atctatttga gctaaacatt ggccctagta ttctgactct tctcatggga 112680
ttcacgttta attgggacct tctgtttcta agtagtacac tatctgcaaa actttgacct 112740
ttgtctgtag tcttgttctc tgaccccagc cttaggctaa gtcccagact ataaaagtat 112800
agtcctagat tgtatatttc tagaagtgtt caattatgtg aactttcatc catgtagacc 112860
aggttttcat atagaaaatt agagaaagag ttaatacaga cagagcacaa gacctaatgg 112920
tatgcattat gggctaatat aaaaattaat taaacataat tattcctgtt ttcaattaac 112980
ttataactta ataggacgtg actggagtac gttgataatt ataataatat agagcaaaac 113040
atctgcaata agagtggcag agttttatct gagcttaatt aacttagaaa agattttttt 113100
taagaattca aaactggctc tctgtctatt ctggctaaat ggaaattggt tcagttcttt 113160
gggtcttaag ttgtttaaca aaatcaaaca agaataccta ctttatggaa tctgtgcatt 113220
aaatgagcaa tacatgtata aaatatgtat agatctggta tcaaatgtgt tcaatgaaat 113280
atgtataaca catgcatgta tgtatatgca cctatatttc aatttagata taaatatatg 113340
agcaaggttt acagataatg actctgattt cagtttttga cacactaatg ttgagactct 113400
tcagtaactt gcaagagcag accaacaaat gggcagttgg atctgacagc ccagaggcag 113460
cagaaagctt tggacggaag ataaagtaat agtaaacatt atgcagcact tcaaatagga 113520
tgtatccact acacggtggg aaacagtaat actccggaga acctctccac acagttaaaa 113580
ggaagggtta catcacacac cgggttctgt cctggggtgg gatgaggggg gagggaaagc 113640
attaggagat atacctaatg taaatgatga gttaatgggt gcagcacacc aacatggcac 113700
atgtatacat atgtaacaaa cctgcacgtt gtgcacatgt accctagaac ttaaagtata 113760
aaaaaaaaaa aaaaagcaaa cacacagaca cagaaaagca acaacaaaaa cacagcgtct 113820
tcattcaatt agcacataaa agaagtgcca agatctgtgg tcgccaagga ctagggagtt 113880
tgtgtcactc atctggcaca aatgcagtga aaataagatt cacttgaaat taagagacat 113940
tccatttttc tcccttgatt tcatttttct gtgtaaagct gatttggagg ttatgctatc 114000
agtcaacaag caagatgttg tagtgggatg gagggttggt aagccccatt cacaggaata 114060
atagtcaaac acattggagg cacgattcaa atttcaggtt aattaaatct cagtaaaagg 114120
cttagaaatg tagaacaaaa tttctgtaag gtttcctatg aaaaaaaatt tttaaaacta 114180
acaagacttg tgtgcacatt tcctggggta ataagaaagt tgagacagtt gaagaaattg 114240
tacttcactt ttcttgaggt gggaaaaaaa aataagaaga gaactccaag tgcttatgaa 114300
gtgggttgtg gctgataata aggggagaaa agggatactc tggagaaagt tcttggcttg 114360
aaaacagact catatagatg tagaatcacc tatggggctg atcgtggctt aaggatcatc 114420
tgccagtctt gagaatcatt tactaatctc aaggatcaac aaatgatcct caagccagaa 114480
ttgtctgttg tcacctgagt gctttgaaaa tcatctggaa aaataagttg atattctttg 114540
gtatgaacac agtgagactg aacttgctgt aagctttcct tgataaacag ggctcatttt 114600
ttactccccc cagcatttgc tttctacagt atctacagta atgtatcaac agtagtaatg 114660
tatctacagt aatatatggt ttacagacaa agaaagaaat cacatattct tgtccaaatg 114720
agtcagtcat aatttaatgt ggttttccat atgtgtatca ccagacactt tagaatacca 114780
aatattaatg taaagacttt gactggcggt tacttatttt ctaattgtga attacagcac 114840
aatgtgtata tcagaaatat tcagatcttt cttgaaatct cactgtaagt cttaaaatac 114900

-continued cacatttaaa aatgtccaat ttactatgtc ttccataaag ctgtgaattt ttagagagct 114960
aaatgtctca tgtattttta ccacaagtga atcattgaga tgaattatta ttcaaaatat 115020
tttcctgaat aatatgagac tgaattgaaa ggtttgggga gggggcagaa tcctgagagc 115080
tgtaatacag aaaactatat aataaaaaat gactttttat agtcaatttc tgtgagtttt 115140
ttggtctcta aaacaagtac aagaagaaca atgggtaaca tagaatataa tttatgtgct 115200
aggtagtgtc ctaagcacat tacatttttc tcaatacccc tttggggtag agtctattat 115260
aattctcatt ttatggatga agattgattt ttagtgagta gagtgaaata tcagtaaaag 115320
agattaaaga accctgcatc tcctcccatc ctttgcctct ctggaacctt gattaatgta 115380
tcccctcttt cagtttctct ctctcttcca tgacacctcc ttttgctcac acaaatgcac 115440
acatattccc taggtaattt tttttttatg caactggtgg gaattctact aacattattc 115500
agagcattaa cttccatttc ataaaattgt atatagtgaa acacacattc aagaaattta 115560
agccaaacat tggtactcaa caatacactc caaactgttt attttagcct taatatattg 115620
cttgtgagaa atttaaaatc tatgccaaga ttattgtgct caaatgtccc acaaacttaa 115680
gctggccagt agtgaaggtc cctccctgtt gggcctcttc acctcctgcc tggtgctctt 115740
ctaggctcag cgacagagct gcttgtccag acccccaaag cagcgcagga agcagcactg 115800
ttccccctac tggcagtacc ttccagcttc ttgtcagtgg taaagactcc agggctgctt 115860
tacatgggtc acatctcagt gacattcctc actaggtctg tggccttgaa aaagctactt 115920
aaactttcta aacttgagct tactcatata ccaaatggag atgacagcag tgctgattta 115980
tggggattag ataagacagt ttatgtaaac ttcttaaacc agtgcatgca tatctaagga 116040
ctaaacaaat atttactgtt attgatattt ctttcaatat gttgcatgga attttgacag 116100
tcttatttga tgtgtttctt atcgtatcct acattcatat ctattttgtg tgtgtgaaat 116160
atttgttgca taattttacc attgcttaca gtaagcaagt actaaaaagg catttacatt 116220
tttttttagt ttatagttca ttatgcatat taccaataga ttgagggcta tttttccctt 116280
tagtgtaaaa tcaaacacta ataggtaaga tttctgaagt cataaacttt atgttaaatt 116340
tttagatatt tcttagacgt caaaattttt tgactttgta tgttaattta aatgaaacac 116400
ttaatataaa atatcttatg atatatatat atatatggca acaatgatca gtgtgcagtc 116460
taaatttaat tgcatcattt tctgggaggt atcatgcttc tttattgtgc tctgctcaac 116520
tgggtataca cattctttca tctaacctag aattcacaaa aataacagat ctccaaaacc 116580
atttcattcc ataatttccc catctgttga ttttggttcc tatacacaca tctgagcata 116640
aaagctcatt ggtactaggc cacgagtaat tacaatctaa gaacatagaa gaatgattga 116700
atagtggtaa aggaaatacc agcaaatcac ttgactatta gaaaataata tggtaaggtt 116760
gtgaatctca ataccattct gtgataatga gggcactcca taaacatttt acaaataaat 116820
gaatgagtgg ctttatttac agaatattga atggtaaagt taagtagaat ttaaatgtca 116880
tattaaggga aataacttta ttgaaggtaa agtagtatct taagcagaaa aggagagtat 116940
ctggggtttt attttatttt acataaatgc agttaaatgg atcttcattg tttctattta 117000
gaagagtttg agtttgaaaa acggttttga aaacacaacc aacagcagat aatttgtctt 117060
tcagttatgg ggacagccca cagaattcca acacatatgg catctagcct tcaccacaaa 117120
attagtctag tacagatagt gtggcccaag tgtttggcaa atgttgggtt ttcaccatat 117180
attgatagca gctggaacag gaaataaaaa tgaatcattt cacgttacat tgaattttaa 117240
gtagaagcag cacacatgat tctgagttag ctcatcatta tgaagttatt ctagcacgta 117300

-continued gaagataaca cttttgagat ataacttgaa gctatttttt gtttcccaca gacagtatgg 117360
gaaagggatt taaatacctc agagactctg gaatttgtga tagtaacaat gatagtcaca 117420
gctgagagtc cagtttttaa cattgccttg ttagttggcc agctcttcca tgcctgtggg 117480
tattcttcaa atctggtttt gtgctatttt aatgtaattt cagagaaatt accggcagtg 117540
cctcttttgt ggcattcaaa tgatattgtt gtgttctaca ttgttgaatc agcaccttta 117600
aaatagaata agagcatgac atatactttt cgtgcagagt tactaggaaa gagttgaaat 117660
tctagttcac aaatgaaaac atttgtcttg taacaaaatt aaaaatcact caatcactta 117720
tgtgttcaga aattttactt tgatgtttcc taaattctct ttagtaattc tgtctacagc 117780
taatttttgt taaatttgtt attttttgtt tataaacatt gagacttgat tttcttttct 117840
ttttaggatc ccctgccttg actggaactg gaacaatcaa cgtcatagta gatgatgtca 117900
atgacaatgt ccccacattt gccagtaaag cgtatttcac aacaattcct gaggatgcac 117960
caactggaac agatgtttta ttggtaaatg cctcagatgc tgatgcttca aagaatgcag 118020
ttataaggtc agtacatttt cctttgtaaa gtttgtctgt tttctcatta aacattagtt 118080
tttgaactac atgaatataa tgtttaattt aaatgaacgt catattaaca catatcctct 118140
tcttgttatc cattgctgat agccaacaat tcattaaatg aagattcaaa cagtaaacat 118200
tttacttatt actctaagat tttatttaat ttttatttta tttatatttt tatcatatct 118260
catggttttg tggtttggga ctacactggg tgcttctgtc tcatgaggtt gactggtggc 118320
acttcacagt atttacatgg tgactgaatg atctggaggg gccaagatga ctttgcatgc 118380
ctgctgcctt ggcagggttg gttggaaggt tcaggatcat cttggccccc tctgtcctca 118440
agtagtctca gaacttcctg atgtggttct ttagcaaagt agttggactt tttagttggt 118500
ggttctcaac tccaagagcc acaagtgaaa gctcccagaa ctctcaaagg tcagactcag 118560
atgtgccata gcagcacttc tataatactc tgttggtcaa agcagtggtg accagctcag 118620
attcactgtg aggagaaaca tgcatcactc gttgattgga gaaatgtcaa agaattttga 118680
ccatttttat tccactacta gctctaataa gaatatttgt gtattcttca tttagtaaat 118740
gtattttact ttgcttaaat cctcttaaaa ttgagaacac aaatatgata acttgttcag 118800
agaggatgtg aaagaaattt gagttgcaac attttatcaa cctagattgt ccccttcttc 118860
catatctatt ctaaactaca agaaatgaag atttccaaag gttctagaga aaaactcaca 118920
cacataaata ttttataccc ctcctccact ttctataggc tggtattagg taaattagag 118980
ttggttagat ggctatgaaa gtaatggagc agaagataaa atttgagaca ttaagaatta 119040
tcagctatgg gtaccagata tacggatatg gtaatgagct gattcatgtc ttattttgtt 119100
gtttgttacc aattttcttt taacaaaatc attttggaaa actggttttc accacacaaa 119160
ttttaagaaa cacattcaga ccacaatact tggtctctct aagaaatgac ctttaagctg 119220
aaaggactga gctatggaat ggaattaatc tcgttgtttt atctaagaag gtcagcatgt 119280
ctggaccaga gtgagaaagg agtcagagag gtaggcaggg gctaaatcat gcaggccata 119340
tacaggccat atatgtcacg atacagaatt ggggttttcc aatttacctt taggtgagaa 119400
actactgggg agttttaaac agaagagaca cataaactgg tctacatttg gatagaatct 119460
gatgagagag gatttacgga gagaaaccag tgcaccattt aggcactaat taatatagtt 119520
atccaagtag agtaactttg tacttacgtg gagaaatgaa aattgagtaa atagatttgg 119580
ggcatacctt tgaaattgga tgtgagacag gaaggggaac atcacacacc ggggcctgtc 119640

-continued

```
atggggtcgg gggagggggg gagggatagc attaggagat atacctaatg taaatgatga 119700
gttaatgggt gcagcacacc aacatggcac atgtatacat atgtaacaaa cctgcacatt 119760
gtgcacatgt accctagaac ttaaagtata ataataaaaa aaaaacaaag aaattggacg 119820
tgagatcaaa tgaaagagag aaatcagaat catctaagtt ttccactcaa acacctaggc 119880
agatcatgat atgatatcat ttactgaaat gggtagcatt gaaggaggaa cagttttgtg 119940
agaagtcaga agtattctat ttgaatacag tttcaaatga ctgttactca ttcatttaga 120000
gataccagtt aggaagctgg agatatgagt gtggagctta gggttggggt tagggctgga 120060
tatacacatt tgagagtcat cagtgtttag aggacattta aaaccaataa actgaatgag 120120
aacacgtttg cggagtgtat tagtctgttc tcatgctgct aataaagaca tacctgagac 120180
tgggtaattt ataaagaaaa agaagtttaa tgggcatata gttccacatt ggctggggag 120240
gcctcaaaat catggccgaa ggtgaggaag agcaaaatca cgtcttacat ggtagcaggc 120300
aagagagctt gtacagggga actcccattt ataaaaccat cagttcttgt gagacttatt 120360
cactaccaca agaacagtat gctcgaagct gcccccatga ttcaattatc tccacctgac 120420
cctgcccttg acacatgggg attattttta tttatttatc tatgtatttt ttttgagatg 120480
gagtcttgct ttgtcaccca ggctggagtg cagtggcaca atctcagctc actgcagcct 120540
ctgcttccca ggttccagtg attctcctgc ctcagcctcc tgggtagctg ggattacagg 120600
tgcacgccac cacactcggc taatttttgt atttttagtt gagatggggt ttcaccatgt 120660
tggccacact ggtctccaac tcctgatctc aggtgatctg cccacttccg ccttccaaag 120720
tgctgggatt acaggcatga gccaccatgc ctggccgaca catggggatt attacaattc 120780
agggtgagat ttgagtgagg acacagccaa accatatcag agagagtata gcaggataag 120840
gaaagaggca ctagaaccag tcactgggaa ttctccaaca ctttaaaggt aggtttagga 120900
ggaaaggtct ccaaggagac taggagttaa ggtaggagtt aagaaggtct gaagttaagg 120960
aggcctggct agagacaaca gaggaaatgc aggacagaat gaattatttg catgcattgc 121020
aaaaggatgg aaagctatat acaaatttct ttcagtgagc tacatacaga tttctttcag 121080
tggaccaaga cttattccaa gagaagagtt gagttctcag agtcctgtaa agtcaaatca 121140
tagaggactg agaaatttct gtccagggtc ataacccgtt tgagtcattg tacttagcac 121200
caaccagaga gaggcaggta caactgaact tcttccaggt tatgagcttc aaaaggccac 121260
taaataccct ttcttttact tgtcttatac caaagcatag aaataataaa aatcatatca 121320
taagattcaa tccaaagtct ttagcttaac attaagagta gaaccttggg aattaagttg 121380
tgtggaattg aatcctgact ctactattac tattgcatta gtatgggcaa attaacattt 121440
ctggacccgg ttttcagtgg attaagcaga gtaataatga aactaacttt aaagagagta 121500
agtaaaataa tttaagtgag ctggttagaa tagcaccagg aacaaaaaac aatgctcaat 121560
aaatgtcaac ccatattgtt ctaatcatgc aaagcaccta gccctctacc tgtctatcat 121620
ttgttagtgc taaataagtt tctgataatg attttggaag agatgcccta tctattgtaa 121680
tgttataatc taataattct ttatctgcca tgcagatgct gtttcttaga cagtatatag 121740
aatattacca atcagatata gggaaattct cttgtatgag atgtataaat tcctgaatat 121800
gaagttgaat gtttacaaac ttgatcctgt cttccattga gtcattcatt tatttctata 121860
ataaagtaaa tgctgtgatg acctgctgtt tttttctagt gcatgttaaa gattcattgc 121920
aaaatgctat cctatgcttg tgaattatgc ttgtaaattt ggtctagaaa aattgtattc 121980
atactctcaa actgttttac aaagctgtac tggtaggtct gatgggattg ttttgctttg 122040
```

gtagtatgta ttttggttat ttgattggtt gattaaattt tcttctttta acatgagaat 122100
taacattata cttttacata cattgaaatc caaaaacccc atcagtgaaa atcttaaaat 122160
gactctacag actatcatat attcagttaa aatgaaaatt gaagctattt ttgtcttgtg 122220
aataaaaaac attcaattca cttgcaaatt aacagggcaa acaattattg cagcttaaat 122280
agaaaatatt ttcacagaca aagtaaatag ttattataac ctcaacttta tttactctgg 122340
tttgataaaa tcttaatgga atataatgta ttttatggtt ggtgttaata actccttgct 122400
attcatggta tcctgaagaa aatctattct ttcttcagat taaaagagct attggtttaa 122460
ttatttatct cccatttaaa ttttacatgg ttcggttatt tactgaacta ctgttgggat 122520
ctccaggagc ataaactttt atgtgtctta taagttaatt tttttccaat gatctagcat 122580
gattttgcat atagcatcca gccaacaatg tttctttttt acttctacct atttgatcaa 122640
actttgtatt tctacaaatg gtgtacttac tttatgttat acattttact tcacctttag 122700
tattttccct tatagaaaat cagactgtat taattcttag tctttctcta tccagattat 122760
gtctttgcct tccacatatc tattccagag cttagctttt acagatatgt atccccttttt 122820
ctcccaactg gaccaaatct ctattcaagc cccacttcta attcttctgt atcacaaccc 122880
tggagacagc cacaaactcc actgacaaag tcaacattct aaggaagatt tcttttcttt 122940
tttttttttt ttgagatgga gtctcgctct gtcacccagg ctggcgtgct gcgtcgtgat 123000
ctcagctcac tgcaacctcc gccttccagg ttcacgccat tctcctgtct cagcctcctg 123060
agtagctggg actacaggca cccaccacca tgcccggcta attttttttt ttttgtattt 123120
ttagtagaga tggggtttca ccgtgttagc caggatggtc tcgatcttct gatctcgtga 123180
tctgcctgcc ttggcctccc aaagtgctgg gattacaggc gtgagccacc gcgccccggc 123240
caggaaaatt tcttaatatg tgctattaat ctcttcccat tcaatttcct ccaactcttt 123300
aattcaaaag ttactcattt ttcttgtgtt tcttcaagtt ctctctcttc cttgaaccat 123360
gtagatatct atataaatgc tcatttacat aagttagcgt atctacagaa atgctcagaa 123420
tttctgttga attctggttc ttttatttgc ctcccatggc ctaggaaagt cattttagtg 123480
cctcaaaggc ttagtttctg catcaataaa aatgaacata aaaatttata ctttacagtt 123540
tgtgagacaa acatttacta accacctact atgtatcaaa cagtatgtat ggaatcagtt 123600
aatatccata aatgtctctg gcataattat taggacatag aagtcactaa attaattcaa 123660
ggtttctttt ttctttttat tcttctcata tcatcttttt tactcctaat atattctttc 123720
ttttacaata tctggtacat aacagtggtt gtcacttaaa taaatgcatt gaatgaacga 123780
ttttaatatt ctctggaatg gctgctttta ctcattctat ttttactaca acattcttga 123840
aagcttcaca acctgttttc tctgaccatt tattcctgaa aatctttagt ctgatttttt 123900
ttttccttca ttgctttact aaaaaaaggc cctgtcagaa gactactgaa atttttcaag 123960
tccagtgact tttctaagtc cttattctcc tttacttttt gcaatgttca cactacaggc 124020
caggccatct tttctttttg gcattttttc ctgctcaatg tctatataaa tattatttct 124080
tatcatcctg catctctgat cacacacagt ttgttttctg tttctctttt ctctctctgg 124140
aaagtaattt gaatacttct cactgcatta ttttctcagt acttgtgtgt gtgtgtgtgt 124200
gtgtgtgtgt gtgagagaga gagagagaga gagagagaga gagagaattt attccattgc 124260
tgcaagcatc aattctgtga acaaaacctc caaatctgta ctatcaactc tgattccact 124320
ccaaaatttt gcacccatat ttataactcg ctgatagaca tattacactg gaggttctgt 124380
tggcatcata aacacagtgt acctaaaatt ctttgctttt cctgtttctc attttggttt 124440
tctgctttgt tttaataata ttgtcttggt ttgtttttta ccacaccttg cagctaaggg 124500
tcatcccctc tcttatactc aatcagtgga caaattctca tgtttcttct tttctaatgc 124560
atctggcacc cattcttttc agtgcatccc ttctgccaag atcctagttc agttcataat 124620
tacatcatgc ctgtactatt ataataagaa ttaactcact tccacgcctc tagtttctaa 124680
tccttccaat ctatgtagta cactgtcctg taaaattatg aagccctgac tatgcaccaa 124740
aaatttatta aactctcagg agtttggaac tctagggccc ataagaagtg caatttaata 124800
gaagagataa ttttgtaatt tcttaagtgt agtaccgtat aacaagtata gtttaagcac 124860
agaataggtg gaaagaatag tatggccaat gatccttcaa tgatactaag tagaagtagt 124920
ttatggagaa ataaaggaat gaaagatatt ctaggcaaag acagtatcag gtactaaggc 124980
aaagagctat gcaaaaaaca tggcattaga gaaagaaagt atttccatat ggttggtgtg 125040
ggttaggaat ggactttgta taccatataa aaaattcaaa atttctttct gcatctaagg 125100
agagaaacaa tggaaatgtt ttaagcagca agcacaaaaa catgcctagt tatatttcat 125160
aattatttct ttcccagcat tataggaaat aatttgtaca aagcaaagct ggagtcagtg 125220
aattaaaggg caatggcaga agtatgcatc aacatgagca tctcttggct ctgctttaac 125280
aattatactt ccttcctcaa aatctttcaa ttccagtttg cctatggtat aaccccccagt 125340
cttcaaattc tagtcacccc ataaatggcc ccagctaatt ctgcaaaact ctgcaacata 125400
tggccaaaag ttcagtatta ctggatcatt ttctgctcat gggacaagga tctgtgcttt 125460
cccaagcctt ataggtttgc tcaatttatt ctatatcttt gaccagggct tggcaaacta 125520
ctacctgcag gccaaattgg gcctagtgcc tgtttttgta aataaagtgt tattggaaca 125580
cagccatgcc cattcatgta cctattgtct ttggctgctc ttgccatatg atggtaagct 125640
gagtattgca acagagaata tatgacctgt aaaactgaat atctttacaa tctggcccat 125700
tatataaaag gtttgctgac cactagccta gaccttcttt tgtttctgcc tttttgaaca 125760
ctattgaaag atgggtagcc cctttacaac ttatgttaaa tttacctttc tctgaggaag 125820
ctttatttta atcattccag tcaagagtgt tctgtcttct gaatacctac agtgacacct 125880
ctttactgtt tcatagcact ttactgtttt gtaattacct ttttttttata tctttctgtc 125940
ataaaggaca taaacttgaa accaggattt tttttaacct acttaaccgt gtctctgttt 126000
tgaattttta gtccctttat ccatttaact atctaaatat aggttgagca tccctaatct 126060
gaaagtccaa aatctaaaat gcaccaaaat cctaaacttt ttgagcatga acatgatgcc 126120
acaggtggaa aattccacac ctgatacctt tgctttctga tgtttcaatg ttcacaaacc 126180
ttgtttcaag caattatcaa aaatattaga taaaattatc ttctggctat gtatatgagg 126240
tatatgaaac ataaatgaat tttgtgttca gacttgagac ccatccccta gatctctcat 126300
tatgtatatg caaatattct atccagagaa atccaaacac ccctggttcc aagaattttg 126360
gataatggat actcaaccta tgtatagata gatatggata gattgtatgt aatagactat 126420
tacgttatac atatatatta tataggtcct attatgttgg taaacttaga cttttaaagg 126480
ctcaccattt atcaattaca atgccaagtg ctctttatac aaaatatttt taatagtcaa 126540
aactaccaaa taaaaagtaa aatatgacct ccactttaca gataaagaaa gaaggcttaa 126600
aaatgttaag aaatttttgt gaatttaagt gctattcatg gggtttaaat ttatgtccaa 126660
gtgaactatg ttctaaagtc cagtctctta actaaatgat catattctcc cagcagacag 126720
tataatgcct ataaccctag tagatctcag gaagaggcaa agaagtttta caaaatcaaa 126780
tggggatatt ttaactttac aaaagcaata gttgatttag ggttcagatc acagtggtct 126840
ctgtttatgc aaataatttg aaatagtaat gtattctcaa attagaaaat aatttaacgt 126900
gtttattgat tttcattgaa ctaaatgtga acaaattcta tattgacaca acttgagcaa 126960
gagtccatgt tggccttcgc aattggtaca ttttccgtct tcactacatt ccctcagttg 127020
agttttacct tccttctact gtggaataat gggaaaagtg catggtgaag tcataaagac 127080
agaaattcaa actctagatc tgctatttat agattgtatg tttctttgtg caactacttt 127140
agtctctgtt agattcagat tcattatccc taaacagtca aaactaaaac taaactataa 127200
ggatagtttt gggatttaaa taagagcata tataaattgc ccagtagtgt gcttgacatg 127260
cactaagaaa tcaataagct cctggaaata tttaagtaac agcataaatg tttaactgtt 127320
aagaagatac cacaagacac aatctaataa agtttttaac tttacaaaaa ttaatgcagg 127380
ccagagaagc aagagaggtc atcaggaggg atgagaatag aaccaagcct caagtaagag 127440
atgtggcaaa aatctagaca tattatctta actgtcgatc tacgtacaga gcttattgtg 127500
tttcttctat ttttaaaatt agaagtataa attttcatcc aactggtgtt atagaacatc 127560
tcatatttaa aatatacttt tatatgcttt agaatctagt gaagtctaga aaaaattaat 127620
tagatattaa tgactatttg ctcattcatt ttaaaaaata ctaaatatat tacctacttt 127680
aaaatagaca gtcatacggg caatagcatg tgcaatagca taaaattaaa aaatcagaat 127740
ttataccata ggtttctttg tctgttttgt gctgctatag ctacagactg ggtaatttat 127800
aaagaataga agtgtatttg gctcacagtt ctggaggctg ggaagtctaa gggcatgggg 127860
cctgcttttg gtgagtgctt cctgtgtgtt atttcatggc agaagggcag aaggcatcac 127920
atggtgagca atcatgtgag acagagagag ggaatcaggc tgaactcatt cttttatcag 127980
aagctcactc cctcaataac taactcccac ttccgtgata atggcattaa tccactcata 128040
atgatggaac cctgatggtc taattcacct cttaaaggcc ctacttctca acattgttac 128100
aacactgtta caatgactaa tttcaaggaa catttaaatg atagcaagtc tttttgaatg 128160
gatcatttag tgaaactgga ctaaaggcca caccatttgc ctatcaacac attacgctta 128220
ataatacacc atggtcttgg catatacaaa acatccagat gaaaatttat gtttttttatc 128280 aatctcattt tatttttatt tgtgaatatt tataggaata aatatttgat tgaaccttga 128340
tccttgccat tataaaacta aaaaagttta tggcagcatg gcttacttta ttttcctatt 128400
aaattatttg attatttcta catccactga cagcaacaag gttccaaaaa taaaattaca 128460
caattctcaa atccagtttt ctacactttg taaaacgtta aggtattttg attattttgt 128520
gagtcctgaa ttttcaagtt ttaagaattc atgtataaaa cttgatattt atattttgat 128580
aaagagaata tatattatct actgtaaagg gcaataatta tacctaatag tcacttctgg 128640
cccaataact atagttaatg ctattttcac acatgcctga ttctgtcgtg tgatttgcca 128700
agcatattaa aaatctgagt gacacaaagt attttatcaa tactgaagcc atttctcaac 128760
caaaccactt ctctattctt tccctgtttt gctatcattt tataagactt ctaatagttt 128820
taaatataag gtcctcaaca gttgattatt tcactaaagt aggataaaaa atgctgaaat 128880
atttgtttta agctgtgagc ataataggag aatgaacata ctactggctg caatatagtt 128940
ttttcccctg cagtttatat tagatatatg ctgttgctat gtttatatag acacaaagca 129000
aactgtagaa acatgcagcc aactccaaca agggtatcta tttgttggta taaaagaaga 129060
aaacttttaa agatatctat ttccatgcta tctttcaact ttaaaaatta cggaccatag 129120

-continued

```
ccaatttctg aaccttcaag cttagctact tctttcctgg ctgatctttg ggacctcacc 129180
ttatacacaa aatcaggaat atatgcagac aactgtactc ttcagaaaga agagagaagc 129240
ttttctcagt ggaaactctt gcccgttaac ctatctggtt agcatcaaaa catccatgaa 129300
gatgtcatac ctctcctgac aagaaagcaa caaaaccata tgaggaatga caaagacaga 129360
attaatcact agaaaggtct ttgtataaat aatcagtcct tgagttgttc tgagaagcag 129420
atacatgtca aatacaggtt ttgtcttaaa agaatacaat tttcaactga tcttctctgg 129480
tttattatgg tatacagcag aaaaataatt tttagtttca tttaaaagat attcatttgt 129540
aatcctggct actaaccaca atattagagc aagtcccctg atttatgctt ttaggctcat 129600
ttatttaaag ccttaggggt ttgtttggtg gccttgcaca acttaagagt cctaaaaacc 129660
ttgtgaagac ttccttgaca tcactggaca tctcacgata aagactgtca atgtgatgtt 129720
cacagaaaat ttgaaatatt tattagctag actagttgta ttctttccaa cattgttgta 129780
tgatctttct tgtaacgttt tcttgcattt ctacctcagt tttttaatta tagtaaatag 129840
aagttacgat attaaaacta tatgacatat ccctatttct gctttctgct ttagttatag 129900
gatcatcggt ggaaactctc agttcacgat caacccatcg acaggacaaa tcatcaccag 129960
cgcattgtta gatagggaaa caaaagataa ttatactttg gtagtggtct gcagtgatgc 130020
gggatcccca gagcctcttt ccagttccac cagtgtgctt gtcactgtga ctgatgtcaa 130080
tgacaatcca ccaagatttc agcatcaccc atatgtcact cacatcccat ctcctactct 130140
tccaggtaat caaccaaatt ctgaggccac atggatataa acaaactatg tatcagacat 130200
ttctataaaa atatttatga tattttacat acatatttct gatatagcct aattttgcaa 130260
atcctctaaa attcaggttg ttttgtctga tggaaatgaa aaaatgcttg aaacttgaaa 130320
attaaccctt tcttgctaga ctaattgtgt ataatgtttt ataattgtta tgtattatta 130380
tttcttaata ttacttgaat attataaata attaacatat atattacatc atcgttaatg 130440
atgtttatgg cctgaggtat aactttgtgt aagtttgcta agaggagggg cattgtctct 130500
attttgcatg ccatatgcca ctacctgaaa catgatatgg gagataatag gcattcaact 130560
atgtttgtca gtggaaaatg aatatttgac ttcaattttt catagatatg ttttcaaaaa 130620
gtttaataaa tggataattc ttgttaatat ttattttatt ccaggtttta caaatgaaaa 130680
ctgttctgtt agcaagttta tggatccatt tatgaatcat tttcatattg acaatatgca 130740
tttatccttc tgtatctctt taaatttagt ttgacatttg ctaagaaagg catactctaa 130800
gaactgcaca aatctgccat tttaattttt aaaatgagtt ttcaaagagg aaaatataga 130860
aatatagctc attattgatt taatcttcct tgctcggaaa tatttttaat tattagaaga 130920
aaaacttaac agatagagtt aacagatcct cctttcagtg atctttgatc ttctattaat 130980
ctgagaatga taccaatcta aaatatagga ttcataaatt tatgtgccaa ctttctatca 131040
aaggaaatgt cagtatcaaa atgataaata cctgctaaag gtcttcagat gaaatgatgt 131100
tggcaggcat ggttctaatt acatccaatg tgtggtggtg caagataaaa tttcctatgt 131160
aaaatgaggt atgcttaagc atcttttcct cattggactt ataaccactg gccttttttaa 131220
aattaaagat attttacttt tgttaccgtt tcttctgtag ggtgagagt gcaggtttgg 131280
gaatggtttc tgaatgagta gattgaaaat atgtccttat ggcagctttt ctgcatattt 131340
ttacgacaat ctgtttcatt ggcactcagt ctaagcacta acttttggag tccaagttga 131400
gtccattatc cctcaattct tatttcttac tactttacaa ttattttaat tggcttatgt 131460
atatatctgt gtatgtatat acacacacat ataaacatac acatatgcac tttttttcc 131520
```

atctgataat agttcacgta taaaggaatt ttgtcataaa acagtgggga caaggaataa 131580
atggtaatga acatgatttt tgttgacaag attacatata aagtgattgg aagatatttt 131640
aagacacact agagcaacgg tatcattgca ttgggtagag gcatagcact ttgcagagct 131700
cgcatattat gtttcttgga atgttgtttt atgtgcagat tttctcccta gaaactatga 131760
tttttgaacg attagcaagt tcttttccct aggcttctct caaaggcata ctgaaaagta 131820
ttaaatccaa cagactgtat aaattttagt tagaaaatgg caggttagtc tctgaagaca 131880
atcatagagc agatttgact tgtgaacctc ggagaaaata taggagatac tgttctccct 131940
agtaatcatg agaaaataag gtcacatcaa gcagcaatag agtgtcttat atgcacttat 132000
ctgctaccaa atattttatt taaattccac gtgagtataa ctgcacactt tctcttttat 132060
aggttccttt gtctttgcgg ttacagtcac agatgctgat attggaccaa attctgaact 132120
gcattattct ctttcgggta gaaattctga aaaatttcac attgacccac tgaggggagc 132180
cattatggcc gccggaccac taaacggagc ttcagaagtg acattttctg tgcatgtaaa 132240
agatggtggc tcatttccaa agacagattc tacaacagtg actgttagat tcgtgaataa 132300
ggccgatttc cctaaagtga gagccaaaga acaaacgttc atgtttcctg aaaaccaacc 132360
agtcagctct cttgtcacca ccatcacagg atcctcttta agaggagaac ctatgtcata 132420
ttatatcgca agtgggaatc ttggcaatac tttccagatt gatcagttaa cagggcaggt 132480
gtctattagt caacctctgg attttgaaaa gatacaaaaa tatgttgtat ggatagaggc 132540
cagagacggt ggtttccctc ctttctcctc ttacgagaaa cttgatataa cagtattaga 132600
tgtcaatgat aatgccccaa tttttaagga agacccattt atatctgaaa tattggaaaa 132660
cctttcccct cgaaaaatac ttactgtttc ggcaatggac aaggacagtg gacccaatgg 132720
acagttagat tatgaaattg ttaatggcaa catggaaaat agtttcagta tcaatcatgc 132780
tactggtgaa attagaagcg ttagaccttt ggacagggaa aaagtatctc attatgtcct 132840
aaccataaaa tcatcagaca aagggtcccc gtctcagagt acttcagtaa aagtcatgat 132900
taacatttta gatgaaaatg ataatgcccc taggttttct cagatattta gtgcccatgt 132960
tcctgaaaat tccccccttag gatacacagt tacccgtgtc acaacttctg atgaagacat 133020
tgggatcaat gcaattagta gatattctat aatggatgca agtcttccat ttacaattaa 133080
tcccagcaca ggggatattg tcataagcag acctttaaat agggaagata cagaccgtta 133140
cagaattcga gtttccgcac atgattctgg gtggactgta agtacagatg tcacaatatt 133200
tgtgacagac atcaatgaca atgctccaag atttagcaga acttcctatt atttagattg 133260
ccctgaactt actgagattg gctccaaagt aactcaggta tttgcaacag atcctgatga 133320
gggatcaaat ggacaagtgt tttatttcat aaaatcccaa tcagaatatt tcaggattaa 133380
tgccaccact ggagagattt tcaataaaca gatcttaaaa taccaaaatg tcactggctt 133440
cagtaatgtg aatatcaaca ggcatagttt tatagtgaca tcttcagatc gaggtaaacc 133500
ttccttaatt agtgagacaa cagttaccat caatatagtg gacagtaatg acaatgcacc 133560
tcaatttctt aaaagtaaat atttcactcc agtcaccaaa aatgttaagg ttggtacgaa 133620
gttaatcaga gttacagcaa tagatgacaa agattttgga ctgaattcag aagtggagta 133680
tttcatttct aatgataacc atttaggaaa atttaagttg gacaatgata cggggtggat 133740
ttcagtagca tcctccctga tttctgactt gaaccaaaac ttttttatca cagtcactgc 133800
aaaggataag ggaaaccctc cactttcttc ccaagcaact gttcacataa ctgtcactga 133860
ggaaaactac catacacctg aattctctca aagccacatg agtgcaacca tccctgagag 133920
ccatagcatt gggtccattg tcagaactgt ttctgcaaga gatagagatg cagcgatgaa 133980
tggcttgatt aagtacagca tttcttcagg aaatgaagaa ggcatttttg caatcaattc 134040
ttctacaggt atattaacac tagccaaagc tcttgattat gagctatgcc agaaacacga 134100
aatgacgatt agtgctatag atggaggatg ggttgcaaga actggttact gcagtgtgac 134160
cgtaaatgtg attgatgtga atgataattc tccagtattc ctctctgatg actatttccc 134220
tactgttttg gaaaatgccc caagtggaac aacagttatc cacctaaatg caacagatgc 134280
tgactctgga acaaatgctg tgattgcgta tactgtacag tcatctgaca gtgacctctt 134340
tgtcattgac cctaacacag gagtcataac cactcaaggc ttcttggatt ttgaaaccaa 134400
gcagagctac catcttactg tgaaagcctt caatgtcccc gatgaggaaa ggtgtagctt 134460
tgccactgtt aatatacaat taaaagggac aaatgaatat gtgccccgtt ttgtttccaa 134520
actttactat tttgaaatct cagaagcagc tcctaaaggt actattgttg gagaagtgtt 134580
tgctagcgac cgtgatttgg gcactgatgg ggaggtacac tatttgattt ttggtaatag 134640
tcgaaagaag ggtttccaga tcaataagaa gactggacag atttatgttt ctggaattct 134700
tgatcgagaa aaagaagaaa gggtgtcttt gaaggtattg gccaagaact ttggcagcat 134760
tagaggtgca gatatagatg aggtcactgt aaatgtcacc gtgcttgatg caaatgaccc 134820
acccattttt actctaaaca tctacagtgt gcagatcagt gaaggggtcc caataggaac 134880
tcatgtgacc tttgtcagtg cctttgactc agactccatc cccagctgga gcaggttttc 134940
ttacttcatc ggatcaggga atgaaaatgg tgccttttct attaatccgc agacaggaca 135000
gatcaccgtt actgcagaat tagatcgaga aacccttccc atctataatc tctcagtttt 135060
ggctgttgat tcagggaccc cctcagctac aggtagtgcc tctttattag tcaccctgga 135120
agatataaat gataacgggc ccatgctgac tgtcagtgaa ggagaagtca tggaaaacaa 135180
acggccaggc actttggtga tgacccttca gtccactgac cctgatctcc ctccaaatca 135240
aggtcccttt acttattact tgctgagcac aggtcctgcc accagttatt tcagtctgag 135300
cactgctgga gttctgagca caaccagaga gattgacaga gagcagattg cagacttcta 135360
tctgtctgtg gttaccaagg attctggtgt tcctcaaatg tcttccacag gaactgtgca 135420
tatcacagtt atagaccaaa atgacaatcc ttcacagtct cggacggtgg agatatttgt 135480
taattattat ggtaacttgt ttcccggtgg gattttaggc tctgtgaagc cacaggatcc 135540
agatgtgtta gacagcttcc actgctccct tacttcagga gttaccagcc tcttcagtat 135600
tccaggggggt acttgtgatc tgaattccca gccaaggtcc acagatggca cgtttgatct 135660
gactgtcctt agcaatgatg gagttcacag cacagtcacg agcaacatcc gagttttctt 135720
tgctggattt tccaatgcca cagtggataa cagcatctta cttcgtctcg gcgtaccaac 135780
agtaaaggac ttcttgacca accactatct tcattttttta cgcattgcca gctcacagct 135840
gacaggctta gggactgctg tgcaactgta cagtgcatat gaagagaaca atagaacgtt 135900
tcttttggca gctgtgaagc gaaatcataa tcagtatgtg aatcccagtg gcgtagccac 135960
cttctttgaa agcatcaaag agatccttct ccggcagagt ggagtaaagg tggaatctgt 136020
ggatcatgac tcctgtgtgc atggcccatg tcagaatgga gggagctgtc tacgaagatt 136080
ggctgtgagc tccgtattaa aaagccgtga gagtcttcca gtcatcatcg tggcaaatga 136140
acctctgcag cctttcttat gcaagtgtct gccaggatat gcgggtagct ggtgtgaaat 136200
agatatagat gaatgtcttc catcaccttg ccacagtggt ggaacctgtc acaatttagt 136260

-continued gggaggattt tcatgcagct gcccagatgg cttcactggt agggcgtgtg agagagatat 136320
caatgagtgc ctgcagagtc cttgcaagaa tggtgccatc tgccagaatt ttccaggaag 136380
cttcaactgt gtttgcaaaa ctggatacac aggtatgaca acgtttgtac ttttctcact 136440
aagactttag ccatgtcaag tatattgaaa cgaaataatt ttatcatttt ccaatgattt 136500
tcatataaat gagcataata gtaacaaatg tttttaaaca tttactgttg gtcaaatact 136560
gttctaagca ctttttatgt atttgttttg tttacttctt acaagaaaac ttatgaggta 136620
ggaatatttt ccagtttcta taggcaagga agttgaagta gagagtaagt aattaggttt 136680
tctcaggtga ttcagttact ttgctgtaat gtcactattc aagtctacac agttaaatcc 136740
agaacttaag tgcttaatct cgtagcgtct cttacaagag caaaaaagag aataatatct 136800
acttaaaaga gtattctaga tattaaagga taaaatatat acaaaacata agatttggac 136860
cattttgtgt gttaaataat tgttaacaat gattgttgtt gattctttat catcatcgtt 136920
tttgtgacct tttaaaatca tagtcgtcat tattatcgaa atgtgatcca catcgtgaga 136980
agagcgagaa tcatgttttc agatttagat taaaatgatg tgttattggg ccaggcaagg 137040
tggctcatgc ctgtaatccc agcactttgg aaggccaagg cgggcagatc acgaggctga 137100
gagatcgaga ccatcctggc caacatgtga aaacccatct ctactaaaaa tgcaaaaatt 137160
aactgggcgc ggtgttgtgc gcctgtagtc ccagctactc gggaggctga ggcagaagaa 137220
tcacttaaat tcgggaggca gaggttgcag tgagccgaga tcgcgtcact gcactccagc 137280
ctggcaacag agcaagactc tgtcttaaaa aaaaaaaaaa aatggtgtgt tattcctaat 137340
ggttgggtag aaagcacaat aggcttattt ctcaagaaag ctagaacaca actgagccac 137400
agcttatctt gacagactag aaagcagcat taaacatagc agtaaaaatt ttgaactagt 137460
ctttggcacc ctagtgggat atgatgtcca tatatacata gatctctacc tatttctact 137520
ccatgtctat atcattatta tctatcaacc tatctattag ttaatcagtg gttgatgttc 137580
cttcaaatgt gaataaatgt tatgctattg ataagttcga ggagagcaaa attctatctt 137640
ataacttgca cattatacat ttgtaaagca tgcatattac attgagttac tctgcagtat 137700
ttataaacat aatttacagt actagtagta taggtagaat caagatagat tgctttaact 137760
tttgtagatg tattacagaa taatatttta agcaaatgca tttctatgtt atattttcaa 137820
aagtgtccat tatgtgtata ctgatggttt tatatttgga gaattgaatc acttgaggaa 137880
aatatagagc aagtttgaaa atgttgaaac agaacatgca gtctttgcct tctaatgaaa 137940
taactttgaa atgtaaatga agaaaaagtg gcagaaaaca tgtgtaatag aaaaagtgat 138000
agatttcaca gaatctgatt tagctatagc ttttgggaag tcacctaacc ttagctgatt 138060
cttcatttct ctgtccacaa aatgggaata atcataagta ctttcagggt ttttgtaatg 138120
agtaaatata atgtttgtaa aacacctagt acaggccagg tgcagtggct cacgcctgta 138180
atcccaggac tttgggaggc tgaggcaggt ggatcacctg aggtcaggag ttcaagacca 138240
gcctgtccaa catggtgaaa cccatctcta ctaaaaatac aaaaattagc tgggcgtggt 138300
ggcaggtgcc tgtaatctca gctactcagg agactgaggc agaggaattg ctggaacccg 138360
ggagatggag gttgcagtga gctgaggtcg cgccattgca ctccagccca ggccgacaac 138420
agtaagactc catttcaaaa caaacaaaca aaacccacgt ggtacactgt gcagtattca 138480
gtaattgcag tctaattagt agtagtaata atggtattag tatagtggta gtaatagagg 138540
agtaccacag aatttttaaa aagacatgaa acctgtgtag cggaagttaa ctgtgagtct 138600

-continued

```
tatgagagtt atttatatgc taagatcatg aataatagag ctatatacat gctgaggtca 138660
ggatttctag aacacttccc tcactctttc ttacccatcc ccaaaattac tttatcggct 138720
gggaattcaa caataagagt ttttatattc tacattagtc taatgcattt attcacactt 138780
aggtttagat tgagtttaca tttagtccta gaatgaagaa agtgcaaatg tattaggtat 138840
ggataagaaa catggaaagt actactggtg tgaacaaagg caccatttgc tgattttagc 138900
ataaatgatg agtaagttac ttctgtctgg cttgtttatt tctttgtttc atttcattta 138960
aatatacatt gcatactttt ctaaacgtga tagttgaaac tcttaaaaat gcctttcctt 139020
acatcataaa atattaataa catttatcaa gcagttatgt aaagcacttt ttaaatctcc 139080
ttgcattata gacattatta catttagttc ttacaactct gtaagatgga tattatgatt 139140
attgttccaa ttttgaagac caaaaaaatta agtcttcgag tcattaaaag agattagaca 139200
acttgcctcc agccatggca cagaaagtgt tctaactagt tttttactag aaacttggct 139260
ctggtgcctc tgctatttat atacatgtcg cactcatcac actttgattt gcacttgcta 139320
tggagtgtta tggtgagttc tatggtgata ttatttaaga atgttttgtc catcattcta 139380
ttaatactta atcctcacag aaagcctata agacagtgta ttgtctgaga ctgatcagaa 139440
atcggaacta ctctcagact ttgaggcagg aaagtatttg ctacaaggaa acagcttaca 139500
aaatcttcaa actggctaag aatacaggtc aggaacattc accaatgggc gcagcaataa 139560
agacatggca ggcattgcaa gacaccgctg ctgatcctct tgcccacctg cagtgctgca 139620
ccaagtgatc tgaggagaat ggttcctgct ttgcttttac cattcagata tcatcacagt 139680
ctttttgct ggcagaatat aaacttgaac cccgctggaa gggagtctgg aaaaggtagt 139740
tttcagactt ccagcccttg caatatggaa aggtaggaac gatgctgaat gtcagcagat 139800
gatatgtggc tcaggaagat gttattattc ttcctgtttt acactgtagg aaattgagcc 139860
tacagtctgg tgactccagg gccagagctg ccaaagtcta tatcataaac tctttctagg 139920
gaaggttgtt tgaagttata cattaacgtt acatacttct cctcagagtt cacttcagtc 139980
ttcatttgca tagtaggaga taatccaact gatcaggaat gatataaaca aacataaaat 140040
tgaatgatta agatgaatct tacatttttt aaatcaagtt tcaaattctg tatgaaaaaa 140100
accatccagt aaaactggca gataattaat gtctgacagt tttatttcct ttttgtattt 140160
tgtaggaaac aatatgaaaa aagcatagtg agtggcaaat gttaatccat actttaaatt 140220
agaaatgtat tgcttaaatt tctatagttt gttaattttt tttgtagagg taatctctga 140280
aggatcattc tgagttattc tttttaccta gtctctgcca gatagcctgg ctcaggaaga 140340
cagagctaat ataccaaaac atcttaacat ctaacctagt cagagctaat aaaccataag 140400
acaaaattta cacataactg tatgtgtgcc tcatagaatg attttttaaa aaattactca 140460
taatagctag attttacttc agttaacatg aattaaattg tagtgcctta gtaaagcttc 140520
acttcttcaa ggtctgtata taatttttgg ccatcagaat tattttaaat tactgtattt 140580
ttcatactct acttttgtgg gcttccacct gcattttatc aataggtttc aaagtctgtg 140640
aaattacaaa ttggagctgc acaattttct gaactttctg cttaaaataa tcctcagcca 140700
ctacccatac ccagtttctc tcatacacac acacacacac acacacacac acacacacca 140760
ctgagtattt tatgtggatt tagaaattgt gttaaggatt agaagagtaa gtggcttatg 140820
agttgatgca aactaagaga ctttatcccc agaatcccct agggtgtgat taaatgttag 140880
ctgaatggag attttatgta gagaacaact tataaggacg caagtatgaa aatgataatc 140940
atggaacaaa aaataggaag ggatatagtt attatcatac tgtcacaagt ttatttctga 141000
```

aatattctta aagtttattt tcaagtctgt aaccatgcac ataagtataa aacaactata 141060
tttttaatg aatgagtgat ttagagggaa tgaatttgta taacatgtat ttcttatctc 141120
ttttccttag ttactggaaa aagaaccaaa agaaaattga aaaaaagtaa catattcagt 141180
tataatcact tcatatgttt cattattaag aaaattttct tataattttt atattaatat 141240
caccatatga agctttgatt aactgtaaca taaattatta gaaaagatgg ataaagttta 141300
ttatagtata ggccatgtga aaaattaatt tctaaatttt cacaaaatgt aatgacacca 141360
aaaattaaca tcagttgtca gtatgcctca gtgaataaaa actattattc ctgccacata 141420
agtctagggg ttcctagagg aaaactttag cctaataacg acacatgtag tatttatttt 141480
catatacaaa tgaaaatgtc ttgcacttaa tagaacacta attagaaagt acagtaatag 141540
taaccacatc aacatttgtc tactgctgcc aggttttcgc tgtttgcatc acattcctgg 141600
cattaaatcc ttcatgggaa tggatggtgt tataaaatgc agcattttga tagagcttat 141660
ttataaatct ggctatctta taacataatt agttcatagt ctctttaacc ttttccattc 141720
actttcacac atctggatgc atttcaggtg tagtatttgg aataatgccg gggggtttatt 141780
accttatgga gaagttttcc tatgttctca attaagtccc gatatttcag gaaagatgag 141840
gtttgttcat tcatcacttt tatgtcattt gacagtataa acagtaaaat tttttcagac 141900
ataccaactt atatacagaa tatgcatagt aattttactg agaaacttgc cagatatttg 141960
ctttcataaa gatggaaaga gttactaaga gtgattcttt taaaattact acggtcatgt 142020
attggtgttg ttgatgatca tgtgaccgga aaaccatata atataaaaga aatttagtaa 142080
atatatatga aattaaattt tgtttgagat aaagaagagt ggctcatgta agagacaata 142140
aagagtgcaa ttatttttat ttaatttgat tcctgaaagc agaattaggc agtttacatt 142200
aggtaataca ttaacttata aaagcattaa taacgtatgt ttctaagaag tagcttaaat 142260
gcttatttct gtagaaaata agcatatatt tataagctta tgaacattat gtgtgtaatc 142320
atatgtaatc atttgtagtc tcattgaggt tgtgtttgtg cttgttttac aagacaaagg 142380
taaaaacttt ttttggttgt tgcttttgtt actggcagcc cttattaaaa catggtattt 142440
ttgcttttgt ttcaatgcaa aaaagccata aggctattga acaggatact tagactatct 142500
tcatagctcc ttaacaataa tgggaaacat ttgcatactg tgcaaaagac agctactttt 142560
tgctaaaata atttggaaaa tatataagat aaatgcctag aatgaatagc atatatttat 142620
tatagaattt ctttattaat aacataatca atttagacct aaaatggatt tttagagttg 142680
cacatattct cccatctcct ctgtgtagaa atacaggaga tttaaaaata atatttatgg 142740
tagtctaata tgtatatata atctaagatc ttaaattgaa ggctacatgt atcatagggt 142800
atcaaaaatt atcgtatctt catggagtgg tccaatttag cagttgagaa taaatttagc 142860
tctatttcac ataatccaac attaaaatgt gcttggacaa gtgaaacttg aatatacatt 142920
cttgttgaaa agaccatagg tgattacaat agattcagtt tatgttcaac acgtcatcac 142980
atcttctgcc cccaaacatg aaaatagaca caaaatttct cctgtaagtt taggaaagtc 143040
tgcggatacc atggattcct attatgcatt tattttcacc ttaagctatt cccactttcc 143100
atgtgctaag aatttacact tcttcaagca catctccttc tagttatgat aaatagtgta 143160
tggcaacaca attaattgat ggatgtcaaa gcaatgagat caatttattc ttctaaacag 143220
ctgctatggc agtaaacata tcttaatgga aggaggcctc ttgagttcaa gaggaataaa 143280
tgcctgtctt tgtgcaagtc ctatcagcat acttccaagc ctgaaggcgt ttggcaagta 143340
ttgttaattg acttgtagca ttaattaagt taatgatcca agattttgtt tcacagtgct 143400
tcaacacatc agattattgt accaagagca tgttagagta attcaaacta ctgcattctc 143460
tgatactcat tatgctatta acactacaat ttaagtagat agacttgcac aaaacaattc 143520
agaattttgt taatttctaa ttgggtaaaa aagcataaac tttccaaacc tgagaaatat 143580
gcatttagaa gctttctttt gattctaagt aaaattatgg aatccttttc tcacacaaaa 143640
gacacaggtg ttttaaataa taatttaaat ttaaatctgt tttcctacta tgtctttgaa 143700
ttcaagtatc tgctatggca acctctgagt tcatgaattg taaaaaattt ttactcttta 143760
aatggagaac tcaattttta aatagtaaat aatttacata ctctaccacc aacagataag 143820
actatttttt ccaaactcaa caacaaattc ctttatttaa ccccaaacaa agccatttta 143880
tctatttttt taacttatat tttaggttct gggtacatgt gaaggtttgg tacataggta 143940
aactcatgtc acagggttcg ttatacagat tatttcatca actaggaatt aagcccaata 144000
ccaaatagtg atctttcctg ctcccctccc tcctcccacc ctccaccctc cagtagaccc 144060
cagtgtctgt tgtttccttc tctgtgtcca tgtgttctca tcatttagct cccacttata 144120
agtgagaaca ggtggtattt ggttttctgt tcctatgtta gtttgctgag gataatagcc 144180
tccagctcca tccatgttcc cacaaaagac ataatcttgt tctttttat gactgcatag 144240
tattccatga tgtgtatgta ccacattttc tttatccaat ctgtcattta tcagcattta 144300
ggttaattcc atgtctttgc tattgtgaat agtgctgcat tgcacattca tttgtatgtg 144360
tctgtatggt aaaatgattt atattcctct gggtatatac ccagtaatgg gattgttggg 144420
tcaaacagta gttctgcttt tagctcttga ggaatagcca ttattaatta tttgtaatta 144480
tccactaaga caaagtaaaa aggaacaacc ttatttttaa actgaaatac tgaatgcaag 144540
gttgaatttg tttttcttta acaatttcta tttctatttg tgtatacttg aagaatcaga 144600
ttctattgag aatttaagtt ttataggaaa ttcgttctca aaattagtat tttattggtt 144660
tgtaacatct tctgccactt tgtaatcact gtatgtttta ataaatgaat aagtcttatt 144720
tgtgttagga tatatttcca ctcctcactc tggagtaact gcaatagcct gtattttata 144780
tttaaattaa actcagatgt ctatgttaaa atattttata cagggttaaa taagaattga 144840
ttcatataat tatacacaaa aagaacaaca cgtaaatttc atttgttgct atttaactca 144900
agatttataa aggtagtatt tgtaaatgaa attcaaaaaa catatagtag ctttatagga 144960
acaatgactt gggatttata ctcatatatt tttgtcagag agcacatatg tccaattatt 145020
tgagtaagta tacatagcag taccctctac atttgttact tcttatttgt tcctcatttc 145080
cagtcgttaa gaagtgaagg tggcaatttt gtaacccact aacatgtttt catgataaca 145140
aggctatatt gaacacactt ataaatacat atataagtct atgtatttta tacatgttac 145200
ttttaacaca actctaaaat aattttttgg ataaagaaag gaatgaaaga aagtaaaact 145260
gtacctagtc aaaaagcaca agtgaaaatt atgtgtgctt ttacagtgaa aaccaaatgg 145320
aaagagtaga atattacttt attgatgaca actaatcaaa aatatggcca gtagacctta 145380
tgtatttgca actgggaaat actgtgctgt aagaaaaaaa aatctacatc actaaaatgg 145440
ccttcacata atcagttgaa aaacaaaaca ggaaagagtt ctgtgaaacc gcaactctct 145500
ggtgagaaat caagcactat ttgaagtttt cctgcctatt tctccaatgt agtacactgc 145560
tacaatactt aaaacctgat ttctgtgccc ataaatttgt aacttgttta ttttcatgcc 145620
cttgccttaa caatacaaag gtattctgaa attgttagct caatgttttg ccttataagg 145680
aggttcccaa tttatttata agggaaaaaa tgttgtgttt atgattctgt gatgtacaga 145740

-continued aatgggctta gttagcatca tgagatctga ctcacactta taatttcaga ccagaataag 145800
tgtggctccg taatcaagcc acaaaaacag aaccaattta aacaaaattt tgactgtgtt 145860
ttaagcaaag ttagtatgat gaaatgaagt atctatgctc agcagtaggt ctcgttgtgc 145920
atatagaatg catatcattt cctgagctat ctaataaatg cattagtgaa attgggctgg 145980
gaagtagaaa gtaacttcca gaaacaaatg atgtagtatt tacaatccta ctctcaatga 146040
aaagaaatta actaagaatt ctgtaacatc tcactgcatt atgaaatttg aaaattagat 146100
cctaacgaat gtatcaaatg attgcaatac tttaaagtta tagaacagtg gtattagaac 146160
atgtttaagt ttaggtaaaa ataagtaaca acaacaaaaa caagtgggac ttatactcca 146220
agttttatac accacgtgat caactaccat agttttgtga aacctggata tgggagcaga 146280
agccctaaat tggtctgtgt catagtttta cagtttcaca gacaatatat tagcctccaa 146340
gaggctttta ttcttcactt ttgaaatgta aatatttcct ttgtatggat taatactccc 146400
tactgaaatg gaaacacagt ctgaagacac ttgtttgctt tcttcactgc catatccccc 146460
tccattatca tgtctggccc ataataagca ctcactcaat attagttgat tcaatttaac 146520
aagatcatgt atgagaaaag tctttataaa ctgaaaaata tgctgtttag gtattatcgc 146580
ttcagacaaa agacaaagta tacataatct gtagtcaaga ataaattttc ataagcattt 146640
gaaaatatga tgtgttttct tatttcttat tctgctttac aacagatatg tgtaattcaa 146700
gtgatatttc ttagtagtag aaagagtgta gtttgataaa taagataagt tattatcttt 146760
gaaataccta agtcaagaaa atctctgcag tgaaaagaat actgtaagtt tcaactttct 146820
atctataaaa tataaaagat gaagggacat tgacacagaa aataaattca gtgaaagcat 146880
ttaaatatgt ttatcatgtc atttctctgc aaacagtatt ttcttccaag atgattatgt 146940
aaattatttc ctaagtatta taatgcacat tttacaatag gacaactaaa caagatttta 147000
aattctaaga tattattcta atttccttat gtcaagtaaa acgtttttat atttcttttc 147060
tccgtgatat gccttaggaa agatttttac gtatggtaat ggtgtaacgg tgttaatata 147120
tttatgtatg agatttaaaa aaaactgaat ttgatatatt ttagggaaaa tgtgtgaatc 147180
ttcagtcaat tactgtgaat gcaacccctg ctttaatggt ggttcctgcc aaagtggtgt 147240
ggattcttat tattgtcatt gtccatttgg tgagtaaaac ttatttgttg atataaaata 147300
taagtttatt tttgcacaca gtttagcaat tttgttttat tatgagtatg aaagaccaaa 147360
aaattattgt tttacatgga aggttttatt aaaataaaat cttaaatgtt taacatttgt 147420
aaaagttatg gaaatcccat tgaatacatt gcattggtca ttactagaaa aagagtcaac 147480
tcaagataat tgaattaata ttgtttccat aggatatttc cccccaaaga tttatggata 147540
tcttcttttc agctgagaag ttatgaaata aaaaaattct gtaagcactc tttcacgtca 147600
ctctctattt caaatcttta agagtagtca aagtaaggtt ttttgtttgt ttcacttttg 147660
tgaattttgc tttattttt atttttgttt tttacattag tttttaattt tgttttttat 147720
gttaattcag ccacttttat tagaaggact tagtaactat acctgacgtt ttcataatag 147780
gctttttgta gctgatacta cctgactaat aaaatttcag actaatctgt cttttggata 147840
agaaaaattg ttaaaaagaa cttttttgta tacatacata tttattcacc ctagtggaat 147900
gaactaaaag attccttcca ggtcttatcc agctgttacc cattactgtg ccagccaaaa 147960
accatgagat tcagaggaag catttgtatt agcttggctt gtttcataag tttgtgatta 148020
ttccattctt tttaaaggct gctttacacc acagcataga atccatctcc aaatgactct 148080

-continued gtctcttttc tttttttttt tgtccccttt gtatatctat ttatttattt ttttattata 148140
ctttaagttc tagggtaatg tgcacaacgt gcaggtttgt tacatatgta tacatgtgcc 148200
atgttggttt gctgcaccca tcaactcgtc atttacatta ggtatttctc ctaatgctat 148260
ccctcccccc ttccccaccc catgacaggt cacggtgtgt gaagatcccc ttcctgtgtc 148320
caagtgttct cattgttcaa ttcccaccta tgagtgagaa catgcggtgt ttggtttttt 148380
gtccttgcga tagtttgctg agaatgatgg tttccagctt catctatgtc tcttttctta 148440
agcaagaaag agcaaggata tttttctagt cttcctttgg gcatataact gtgctatatg 148500
gacctgaaca gtaaagctca atctatagta gataatagaa tttaaaagac atacgcagtt 148560
cctaataacc tgtataattt actaggtatt tttaatttcc aaacaacttc atgactatct 148620
gtttttatta agcacatcca tagaatgata aagacaaaca aaatagaaaa atatctaatt 148680
ttgaggaatg tattttacca atggttttga ggcccagaaa ttggctgatt tgcccaaagt 148740
caaaaaatga agttgaggca aaactacccc aagacgatgt agcaactaga acacaatttt 148800
ttattttcag tccagtatga cattcacaga accccttttt atacaatttc tttgaaattc 148860
taacaatgcc tgtgaagtaa tgaaaggtat atcaaggtca aaataaccac aacttgagat 148920
gtccaaaaac tttttcttc tttcaatggt gtctcatcat tttaagtggt gctgctttct 148980
acagataacc acagtcaaat ttcatggttt aacttaacat tttgagataa aagataaggg 149040
gattagagtg taaactagaa atgattttca agtgactgaa cagagatgtt catattttta 149100
gggatccctt tgcaaatttt aaggatttaa gttttgagga ttttgagttg caaatttggg 149160
gatttaagaa aattgataca caataaaaac aagttgctgc tgcagtgtag tggtacaact 149220
gtcgttgcct attaagtgga actacttgag gggccaaatg taccttcttg tcactctgta 149280
gacatcgcca ggggaagagg aatagcacaa tgtaaattaa aatagacaca aatcacacat 149340
agccggcagt gcaaatttct ccccctattc cttccagggg caaagacaaa aaacattatc 149400
taaacttaga tattgtcagt tgacaacata agcacttaca aaagaaaaca aaaatcactg 149460
aaacactgct atgtaatttg aaactaaaga gatagaagca gaaacaaaaa tgatttttgt 149520
tctcaaatgg aatgtggatg aaaggtacaa ataaccatgt cagatggcat gcctcaaata 149580
aatagccaga ggtaggtagt tacacttgca tcctttaaaa caaaacttta tcattttgaa 149640
gttagaaaaa agtttttgc actgtttagc ttctcatcaa taaaagattg gctatttgga 149700
tttcaaaaaa ttttttcgat acttagattt tttaatttaa attacatctt aggaaaaaca 149760
tagtgcttca gacattataa aggcgacatg tataattata acttcttaga attaagatgc 149820
gacctttctg tgaaaacagt accaaaacct tttaagaata aatattttaa attccataaa 149880
gaaatatttt catgtttgaa aatacagtat caatttgaat taaaatgtaa gtatctatat 149940
actttctcca tatatttaca ctcaaatatt cagcacattg ttatagattt attgaagttt 150000
attcagaaga gacctaagtg aacacataat acaaattttt tcagtagtat ttttatttca 150060
tttatatgct ttatttttcc ttttacttta acttcactta ctctttctgc atagatagca 150120
tatttatata caaattatta atacatacaa attataaata ttaaatatag atgccacaga 150180
aatgtataaa atacaaatac aaattctaca ggatagatat aagtatataa tgtataagat 150240
tatactatgt ataaaatatt atctctatat atcatatata tgacataaca tatatatcaa 150300
taaatatcat ttctataatt cctttgcctt ttcttcaact ttggttaaag attaaaaatt 150360
aaaaattatg tataatttct tttttttttt ttttgagacg gagtctcgct ctgtcgccca 150420
ggctggagtg cagtggcatg ttctaggctc actgcaagct cagcctccca ggttcacgcc 150480

-continued attctcctgc ctcagcctcc cgagtagctg tgactgcagg tgcctgccac catgcccggc 150540
taattttttt ttgtattttt agtagaaacg gggtttcacc gtgttagcca ggatggtctt 150600
gatctcctga cctcgtgatc cgcccacctc ggcctcccaa agtgctggga ttacaggcgt 150660
gagccaccat gcctggccaa aatgatgttt aatttctact catttataat aaatattatt 150720
tcagtctgga cagaaaagga aaagataaat aacacaaact tttatagcaa cttctaggct 150780
gttttaattt taaaaatgtt ctgatataac atgtggtagt caaaatagct agacaatcag 150840
tagatctggc ctcaaatttt ggctgtttct cttggttctg tgaccttagg caagttttaa 150900
atactctata aaataatggc attggttcct tctagctgaa caattctctc actctaaatt 150960
ttatgcattt atgggacata taaagccaaa attaagaaat gaaacttttg caagttaata 151020
agaatcatga ggtattggca tgggttaatt ttccaatcat ttgccacagt ctactaatat 151080
ttgtgggaaa agaattttgg cataacattg taacatcaat aaaactcatt tttcaagttt 151140
gaaaaagaac cagcacaaac aaatgggaat gctgactttc agaaaaacag acagctattt 151200
taaagtagcc tgctataaat catacccaca gagggtataa aacaagaaag agataaaaac 151260
ttaaaagaca gttatttcct ttcctaaacc aatgattcca cttgtcagat tttgtggccc 151320
ttgaaaataa catgaatata ggtactgatt ttaaaaaaat caaaacaaat gcatttgcca 151380
tcttcaattg agttgaaata gtttttaaga actatatatt atgaaggaag tatgttggct 151440
gaaaattgta gcataataca acttttaaaa gatcaacaaa tttgggccgc ttgcggtagc 151500
tcatgcctgt aatcccaaca ctttgggagg ctgaggcagg cggatcacct gaggtcagga 151560
gttcaagacc agcctgacca acaaggtgaa atctcgtctc tattaaaaat acaaaattag 151620
ccaggcatgg ttcccggcac ctataatccc agcttctcgg gaagctgaga caagagaatc 151680
gcttgaaccc agtaggcaga ggttgcagtg agcaggcact ctagtctagg caacaagagc 151740
aaaactctgt cccaaaataa aaaaaataaa aaaaaaatca atgaattttg aaacgtttct 151800
gggaaagaaa tctcttcaga catactccat tccactaagc ctttcatttt gagaaacaaa 151860
acatacttag atatgttccc taattagaca atgaaaaata attacatcag ttaatcattt 151920
ctgccatgtt ttaaagatca ttcattcata aagatcatta actattttaa ttttagttta 151980
gatgaaattt tttggaaagt aaaaaaagtt gttaaaagat atctcatttt ataattcaaa 152040
aatattttaa tcaaaatata taataaaatt ttcatgaaat tttatgccag tttgtcaatt 152100
ttccctccaa caggtgtctt tggaaaacac tgcgagttga acagttatgg atttgaggag 152160
ttatcataca tggaatttcc aagcttggac cccaataaca actatattta tgtcaaattt 152220
gccacgatta aaagtcatgc cttattgctt tacaactatg acaaccagac aggcgaccgg 152280
gctgagtttt tggcccttga aattgccgaa gaaagactaa gattctctta taatttaggc 152340
agtggtacat ataagctcac caccatgaag aaggtgtcag atggacattt tcacactgtg 152400
attgccagga gagcaggaat ggtaagatat ttcattttat tgttgttgta tatccaactg 152460
gatcttcaaa taaagtatga attggggtgc aaatcatgtt aaattaggtt tattcattaa 152520
atgaacactt tagttatgaa aaacttagac ataatatttt tcttttgctc atgacaactc 152580
tgttcaaaaa caataaaaag gagaacaatt gagaatatag cctagtgcgt gaaataattt 152640
cattgatatt ttttgtatgt ttttaaggcc atgtcaggac tatacttaaa ataactacct 152700
ttctttccta agtatttctg ccttgactaa gtatttctgc cttgactgaa gaaacaattt 152760
aggaacagag gagacttttc tacaaaatct acataaaata acttaatcaa aaacacttta 152820
ttgttaaaaa atggtaacaa tagtcttagc tagtcatagt ctttttgctg gtggagggtc 152880
ttgccttgat attggtggct cctgactgag ccaggtagta gtggctgaag attcgtggtg 152940
ggggctatgg aaatgtctta aaataaaaca acaggaaacg ttgtcacatt gattaactcc 153000
tttttcatga aagatttctc tgtagcattt gaggctattt gattgatacc attttaccca 153060
cagatgaaat tgtttcaaac ttgaagtcaa gcctctctca aaccttgatg ctaatttatt 153120
aattaagcct atggaatatt ctaaatcctc tgttgtcatt tcaacaatgt tcacagcatc 153180
ttcacctgga gtaagttgta tcttaataaa ccgcttcctt tgtttatccc taagaagcag 153240
cttctcatcc tttcatgttt gttttgcaag attgtagcag ctcaatcaca tcttcgggct 153300
tcacttcaaa ttctagttct cccactgtgt ctaccacatt ggcaattact tcctccattg 153360
aagtctggaa gccctcaagc tcatccatga gagtcaaaaa tcaacttcct ccgaactcct 153420
tttaatattt gatattttga cctccttcca ttaatcatga atgttcttca tggcatctag 153480
aatggtgact cctttccaga aggtttttaa tttactttgc ccagacctat cagaggaatc 153540
atcatctgtg gcagctatag ccttatgaaa tgtatttttt aaataatagg acttgaaagt 153600
ccaagtgact ctttgatcca taggctgtag tctggatgct gtgttagcaa gcatgaaaac 153660
aacactaatc tccttataca tcattgtcag agcttttggg tgaccaggtg cattgtcagt 153720
gagcagtaat attttgaaag gaatcttttt ttccgagtag tagatcttaa cagtaggcta 153780
aaaaatattc aataaaccat gctgtaaaca gatgcactgt catccaggca tttctgttta 153840
ctgatagagc acagatgcag tagatttagc ataattctta aagaccctag gatttttaat 153900
atggaaaagg agcactggtt tcaatttcaa gacaccagct atattcaccc ctgatgagag 153960
agtcagccta tcctttgaag cttttaaccc aggcattcac ttcttttctc tagctatgaa 154020
aatcctagat gacatcttct aataaaaggc tgttttttta cattgaaagt ctgttcttta 154080
gtgtaaccac cttcatcaat gaccttagct agatcttctg gataacttgc tgcagcttct 154140
atatcaccat tcactgcttt gctttgtcct actaccttac agagatgact tctttcctta 154200
aacctcatga gccaacctct gctacattcc aacttttctt ctgtactttc ctcacctctc 154260
tcagccttca tgcaatggaa gagagttagt gccttttttct agattagatg ttggcttaag 154320
ggaatgttgt aacaggtttg atcttctatc cagactgcta aaactttctc catatcagca 154380
ataaggctgt cttgctttct tatcatttgt atattcactg gagtagcacc tttaatttcc 154440
ttcaagaact tttactttgc atttacagct cggctaacta tttggcacaa gaagcctatt 154500
tggcctatct tgactttcga aatgccttcg tcactaagct tattcatttt tacattttca 154560
tataaagtga gagaaatgca actcttcctt tcacttgagc acttagaggc cattgtaggg 154620
ttattcgttg gcataatttc agtagtgttt tatctcaagg tacaaggaag cctgaggata 154680
ggtagagaga ccagagacag ataattgctg gaacagccag aacataaata acatttatca 154740
attaagcttg ccatcgtata tggcacggtt catgttgcca caaaataatt ataatagtaa 154800
catccaagga cacttcactc atcacagatc accataccac ataaaataat aatgaaatat 154860
ttgaaatatt gtgagaatta ttcaaatgtg actcacagtc acaaagtaag cacatgctgt 154920
tggaaaaatg gtgctgatag acttgctgga tgcaggatta ccagaaacct tcaattggta 154980
aaaaataaaa tatctgcaaa gtgcaataaa gtgaagagca ataaaatgag gcatgcatgt 155040
atttatagat tatattgatt ttattatgtg gctttcatgt tacaagaatg acatatctat 155100
ttaggacttg tgtttattaa ataaatactt ttctttataa aggaaaatgc atcacatctt 155160
ttctttatta atgtttgaaa atatttgaca tagtataata gaatggaatg gcttatttat 155220
tttttattct ttatttatct tcacaactat ctctccatat ttcccccatc tctaacagct 155280
atcaaggatt tttaataaga aaatgctaac aaatctgtct taaagtattt ttgcacttta 155340
actttgagcc tttaaaagtg tagttactgg tggccaggcg gggtggctca cgcctgtaat 155400
cccagcactt tgggaggccg aggcgggcgg atcacgaggt caggagatcg agaccatcct 155460
ggctaacaca gtgaaaccct gtctctacta aaaatacaaa aaaaaaaaaa aaaaaaaaaa 155520
aaaaaaaaat tagcccggca tagcggtgtg cgcctgtagt cccagctgct ggggataggc 155580
aggagaatgg cgtgaacctg ggaggcggag cttgcagtga gccgagatct cgccactgca 155640
cgccagcctg ggtgacagag caagactctg tctcaaaaaa aaaaaaaaaa agggtagtta 155700
ctggtaagat ttataattca ccctagataa aggaattgtg taaaatgtta aattgtctgt 155760
taaaaagaaa gcctagccaa aacaacaaaa taagtgccct taaatcattt taaatgaaaa 155820
aacttggtat gtaaatgatt ataattgtat ttctgacttc atggcaatct ttaaaatata 155880
tgacaactta tatagtcctt agactgatca tatgaatcat acatttgtgt gactatagag 155940
aaatttttgc cactaaatgt atggaatatg ttatattgct gaatgcatat cagcaatatt 156000
cagaagtaat atttaaaatg tttttaacca agcttttgct agtttttttc cctatgacac 156060
gtagttaatt ttaaaggcta aaatttatgc aatctataat taccaatttc ataagggcat 156120
aagacagaaa ctaccttata atattaatta tttttgacca gtacacataa cagacaatct 156180
attatgaaag aacaaaattt gtcatttgat ctcaggaata ttttataaat ccatgtttat 156240
tttgaattgg catcagatac aatgacattt ctctcctcca ctctaattta ctacaacatt 156300
aaaggaaatt taagcaagtt ttaaaataca gaactatttt taattatgag gggaaaaaag 156360
aataatgatt agctttaaat ataaccaatt gattgtgtca acatggtcaa gggtagctgc 156420
tcagacatgt cattcacgga tatcgccaca tccatcaaac tgcattcagg gtcctaccag 156480
gttattaaat gtatgttact tgaaatattg gtgagaaaac aacagaagta ttgtatggtt 156540
tttatcaatc attttagtta tagatggttt tccatttcct tttgaactta gtgttaatat 156600
tttccagctg gaacattttt ctaatatatt taatttatat agtgtttact taataaaatt 156660
acccccaaca ttccaaaaat gttgtcaaga cataatgtta tattttatat tttaattcta 156720
atatgcccac atttccatat tattgtaaag gttaatatta atcataatta aaattttatt 156780
tctgtgaatt aggtgcttaa acaggtgttg gtcaccctga attatcacca acacaaccca 156840
catataacct tttgaagtaa aataatggaa tattttactt gatcttggtc tcaatgaagt 156900
ttacattatg agtagtgcct aaaaatccac ctgactttaa tgaacattag tagaggtata 156960
acaaacaaat cttggataaa atatattttc tgattagtat aggttactgc actgattttt 157020
gcttgagatt ttaaaaatcc agcattctct ggaagaatat agatttaatc aattctagta 157080
ttcctgatga ttgatgtaac cagaaatatt gggccttaaa gaattagaaa aacatttaga 157140
gattgatata tatagattgg gctcacatta gccataataa tatcctaaaa ctgatgagta 157200
atagtagaca tcacctcacc cccattctcc acacatatgt aagataacca tatttctgat 157260
atgttgtcaa gtatactata atgtaaaata aacgatttta cctgatgacc tccaaggtct 157320
ctttaaactt catgagcatt tgattctatc agacaaggac atgggatcaa gaggtgagtg 157380
gagaaggatg cagtttcatt tgtattattg tgaccatagt catcaatttt taataatacc 157440
aaatgtgaaa aaaactctgt cattattact tgagtcatag gaaaaatgtc ttcctgtttc 157500
agaaaacatc caaaataagg cccctactgg attctgaatt tgtcattttc tacatttcaa 157560

-continued aataattttg gttggaaact ggcaaaatca ttaacctcta agctttaagt cattgcatag 157620
ttgggataaa acattttaat ttatggtggt aaagctataa aaattcaaca gtaaaagaga 157680
atttaactct gaagattaaa ttgcataagc ttactattaa aataaaacat ctcctccatt 157740
attctttctt tgagttgtat cagcaagctt ttagatgtat acgaaatatt aacaatgact 157800
aaaatataat tatgttatcc aaggttattt ttctaattga ggcatttata aatatccatg 157860
tggtactttc tagtttatga tacttttagg gatctctaca aggatacttg cataatatat 157920
gtggagagat gtgttcaatc aagtagtcac ctaagcagca gaagttgaat tataaaaacc 157980
taatactgct tttgagattg gatgtcaccg cattttacag ataactgaaa ataatcataa 158040
ctatcaaaag agtaaactaa atggggcatg aatgacttgc cagagaattg gaagtataaa 158100
tttttcctac aaatgttagt atttattata atttacttga aaaaaatggc aaaaaaaatt 158160
ccatgtggct cacaagagtt tactgtatag agcttataat aattaactta gaaacattta 158220
agaatatgtt agccagtaat atttgataaa caattaataa atggattata cattcacctc 158280
agtctttgtt tttaaaatgt gagatacttc agataaattt ttacaagtct cccatttaaa 158340
tatatgtttt atggatactg cctaaaaatc ataagcaata ttgataaaag taggatatta 158400
aggaaattaa tcattttcat tcctaatgaa agtggcctga tttttaata cagaaaattt 158460 gatatccaaa actttgcatt taagtttggc atgttattag tcaacttgct taacttcctg 158520
cactgttttc tacatttgct ttgctcttat taaactgaaa tgataagcat cctgataaat 158580
gaatagttgc attgtattta tatttctctg ctacatatgt aacaaatttg gattaaccct 158640
gtctgtggca ttcgtaaatt tagaataacg ctttattgtc tgcattggga gaaacctttc 158700
aacctcttgt ccatttggat aatgaattat tgctattcct gtgatatact ggcactacac 158760
tccatccttc ttacaatttc agcaagtaaa gtgtgcaaag tttgtcattt gtcaaatttt 158820
aatgaagttt ggggaacaaa ggaggtgtat cacaatagca ttggagatta cacaataata 158880
tagatataca actttggtct tagactgcac tgcagccatc ctcacttgct ggtactcatt 158940
atacaggact ctgacttgta tggttatcat gttctgaggc cttttaacca taaatttatg 159000
actttgttta tcaatcaaaa ggagtattca tatgttctac taaacagaag gcttttgtct 159060
caagggaata cgcatccctt agaatgcaaa aatactactt agtcattatt taaatactat 159120
tggggatttt ttactgtaaa gtgatctaca gtaatacatc ctgattatac agaaatatgc 159180
tgtaatgtta tttataaata attattctta acaaaaatga gaggagcact tacttgattt 159240
aacaaatttc aaattttaat ccaaatattt aaattttcat agattgctat atagtattta 159300
tattgtattt tcctaatctt tttgtaaatg tggctgaaat catattagaa taagactttt 159360
gaaaatcaaa aattaagtgt cttttgttaa catagcttga cagtacaata aacacgtttc 159420
ttaagattgt aatctacagg aagatgtttc agacctattg tgtattattc taaaaaagat 159480
taacggcatt tttatctttt ttcacctata aaacagggga gcaggagagg atttttaaag 159540 gtacccttttt acctctcata ggtatagata gtcataattt tagtttgaga tatcaaagaa 159600
acatgtgccc atgattcaat attataatta tgtgatttat acattaaatc aagatgttat 159660
catagtttct aagtcatgtt cacatagaag caagtcatgg gtagtgttgg ctggaaaggc 159720
taatagggac ggtagaactc aaagttgaat gtttctttct cttgcttcgt aggcagcctc 159780
cttaactgtg gactcctgtt ctgagaacca agagccagga tattgtactg tcagtaatgt 159840
ggcagtttca gatgactggt aaggaatagg attagtttaa tttttattat tacttaaaat 159900
tttttaaaat aaactttata cctaaaaata attataggat gctaagtagt acataaagct 159960

-continued taagatattt tatttccctc tccaaatttt cataatataa aatagtcaat aattactgtg 160020
caaaatgtgt taaaatgtgt gaaatgaagt ggtagaaata aggataaaat tggagaaaag 160080
gaaattaaat atagccagta gtctttggaa agattcatga aataattgca tatgaccttc 160140
attctgaaaa acatgtagga taaagacctc agttctttca aatgcgtttc taaaagttta 160200
cgtgaaaatt attaacagat atttttccat agcacttaaa gctgagcaca gcagtaatct 160260
accagaaaat aagtgatttt aataggaaaa atgataaaca gagaaaaata agtagtcacg 160320
catcatgatg catcattcat tgcctcaatc aacttattgg catcccttgc attgatcaac 160380
ttactgatat tctttatcat ctcttcaggg aaggagcagt gtaatctaac gtaaatatta 160440
gagttgtcac taattctaca gcattttatt ttccctctga gagtatgctc cttcttgttg 160500
actcagtatt gtgataatat acatctaact tgactaattg aaaacataat ttccataaat 160560
attattattt ttcataattc ggaagtctaa caactctgtg tgtgtattgg acactcttct 160620
acatattttc cattgaaatt tatcacacta taataaatgt caaaaaaaag ctatattcac 160680
tctttttcga actaaacatt atactaaaaa tgtaatcttt tgacactaat atttatatct 160740
tccattattt atttaggact cttgatgttc agccaaatag agttacagtt ggaggtatca 160800
gatctctaga accaatcctt cagagaagag gacacgtgga aagccatgat tttgttgggt 160860
gtataatgga gtttgcagtc aatggaaggc ctctggaacc cagccaagct ttggcagcac 160920
aaggcatcct agatcagtat ggcgatttta tttcttactg ttttaaagaa aaaaaatgca 160980
aaaaagtatg cttcagtgag catcaaaaga tgaaattatt atgctcaaat ctctaaaaat 161040
accaaatgat ttacattgtt ttgaatttta aatactatac ctttgaaatt ttggcataaa 161100
gtatgatatt taattagaaa attaatatgt ttctagattc ttatacatat atatatatat 161160
atatatgcat gtgggcatgt atatgtttta tcctcttaca gagagttgtg aagattaaat 161220
tagttaagtt ggtaaattat ataaaaaagg gttccagcac agagagatat gtagatgtta 161280
gccatcatgg acacatagaa ctttatttca cattaaatag ttttacttat agacatacat 161340
attcctaaaa acttgataca gctttaaaaa caggcaataa cttgattaat tatgaactgt 161400
aaggcttttt tatttgatta ttaattaggt ttctagcaat aacttaggga tgttagaaat 161460
tacatatttt attttaaaat tccttttgtt cattatcgaa gtttgaaaaa ttctgaaaaa 161520
atacaaggaa gaaaacaaaa ttaacctata atctaaccac ccagagacaa ctactcttag 161580
gttattgtca tgttttgact gcttagtatc ccaagatgtg aatgtgctat attttaactg 161640
ttgctataca ctttagttat ttccaatttt attaatatac caattaccct gtgatgaaca 161700
cattttcaca aaaatctttg ctcacattat tttttggatg agattaccag aaataaaact 161760
attaaaggca aagctaggaa tactttctaa tgtttgtaac ttaagtattt taataacatt 161820
ttctatttgc ctttcttttc ctacatgttg ttactgtttt gttacaaagt cacactagtt 161880
cgttattatt attaatcaaa cagtacagaa aaacaaagga ttgggattgc caccattgtt 161940
aatacttcgg tgtgcatcct tttatatctc cgtgttcaca caagtacttt tttaaatatc 162000
aatttttttt ttcatttaga gatattttgt gaacatcttt ttaggtcaaa acctactgaa 162060
acaaaacttt tagacttacc tttaactcct ctgtttctgt tagaccttat gtccagaatg 162120
atgtttctgt ttgtttgttt gtttgctttt tgagacagag tcttgttctg tcgcccaggc 162180
tggagtgcaa tggcgggatc tcggccccct gcaacctcca cctcctgggt tcaagcaatt 162240
atctgcctca gcctccggag tagctgggat tacaggtgcc tgccaccacg cacagctaat 162300
ttttgtattt ttagtagaga cggggtttca ccatgttgac caggctggtc ttgaactcct 162360
gacctcatga tccaccacct cagcctccca aagtgctggg attatagagg agagccactg 162420
cacccagcct agaatggttt ttaaaacata agtcagttaa cttttcactt cttggctcaa 162480
agtgcttcaa tagcttccca tctcacccag cttcaaagcc aaaatcctga ccctgaatga 162540
aaacattttt atgatctgcc atctcccttc acttcctgaa catatctaac tattcttctt 162600
cttgtgccct gagctccaac catgttgggc ctcggtgttt ctcaaacatg gcagtacgct 162660
ttcacttcaa ggctttctca ctggctgttt cctctagctg aaaagatatt ctaccagata 162720
tacttcattc ccttatttta tttaggtctt aacaaagatt aagattaatt cactgcctaa 162780
tctaaagatt cagcaaaccc gcaaactcac tataccettt ctcaccttga ttttctctat 162840
agctattttt ttctttattt tctgcctctt ccacaagaaa aaataagtac ttcctcagta 162900
cacggttatt ttttcattac tttacttcca tgcttagaac agtgcttagc atatggtagg 162960
cattcaataa acattagttg catgagtatc ctgatagaca tgtgtcaaaa aatatgtggt 163020
ccctggatca tatgtattaa ccaaagtgtt tatttgacca aggtatttta ttcaagtaag 163080
aattaattta aagaagaaat tgtcacagct ttctcattat tatataagac ataatttttt 163140
ttgaatcttc tttagtgtga ggcagactat gttttctagg aaaacttctg gtttgattag 163200
tttctccaaa tgtagttgta acttgagctt caaataatgg agtgcttgaa attaaacaag 163260
ctaataaaag tgtatattga gttttagcaa acttctcctc atcttttatg tgcgttattg 163320
ttctcattat gatttatttt agatgcccta ggctggaagg cgcttgtact cgcagcccat 163380
gccaacatgg tggcacatgt atggattact ggtcatggca gcagtgtcat tgcaaagagg 163440
gactcactgg gaaatactgt gaaaaatgta tgtaaggtct tccgtcttcc cctggaaatt 163500
ttaataacta tgaaaagtaa aatatatgca cccaagtatg taatcaaatt aaaaattatg 163560
ctttcattct aaatattaaa atattaaatg gacaataatt ggtaaaatac agtgacattt 163620
taaaaattat ttttgtaacc tgaagaagaa tgatatcctt ttaaaaaatc gtttactaac 163680
taaatctcta gcttccactt taaaggtatt ttattcactt atttttgttt gttttatttc 163740
ttagaattct aggcaatcta aaagatcaaa ggttatagtt aggctttttt tcatattatc 163800
tgcctttggg ggatattttt ctggtgaatt tttgtgcata aaaaggtata cacactaaat 163860
cactcaacac tgagatcaaa acatcataca gagccatcat aatatgttaa aattaatgtt 163920
gatactttca ttttaatgta caagtagtag aattaatttt gaatattact ttttaaaatc 163980
ctttcatcat tgtcttctaa gcctaatgtt attatttaga cattaatgat gttcatatca 164040
tcattagaaa atggtgctct ctaatttcga gctgcacatc tcactaacta accctaatgg 164100
ttcctctttt gtaaaaattc ttcattttca aacaagtggt tactacttaa ctccattgca 164160
ggtatctgac tacatttaag gagtcatttg attaaattat attatgaaaa caaatagaaa 164220
tgcataataa aattgaggat ataatataat ctaaaaggtc ttagcagaaa gtgtaattgt 164280
gtgtaataat attagatata atgaaaacat agaaaatata tactgtcatg tgattttcaa 164340
tgtaataaat atttattaag gagcctaatt atatctgaaa tatgagtcat tggctagata 164400
aataccagag acactttttc ttaaatcatg atataactca catactataa aatgtattct 164460
tttaaagtgt atctttcagg gctgaaatcc atttgagctc attttcttaa tattctttct 164520
ttagctatat tatttgtttc tataacttaa gcttcaatat ttctggaatg tggatttttt 164580
tcagattaca ataaactata atatacatac tgattataca tgatgataaa ttatatgtga 164640
tgattactga aaataaagtt agttaccgat gtaaatactt gattgaacac ttctttgtcc 164700
taatttatag catactagag actaaagatt acaaatcatt ttaaccatgc aaacgtatat 164760
tttggaaaca cagtgaaaat gattacaaac aaatttttca agtacatatt accaacaagt 164820
gcctgtcttt agatattcat aatttacgta atgtggcaaa tagtttagta aaatatttcc 164880
caaatggtta atgactgtca tagagtattt taagttcatg gttctgaaat gcatttaaac 164940
atgtgaaatc aacttatata atgattcata aatggaaatt attttttaag agtagagttg 165000
ggggacatta attcccaaaa cgacattttc attgtccttt ttatattttt gtcactatag 165060
aaaacactcc aagaaatgcc aaatgaatgc attcattttc ccttttttcc tttgacttcc 165120
agctgttact cctgacactg ccttatcatt agaaggcaaa gggcgcttgg actaccacat 165180
gagtcagaat gagaagcggg aatatttgtt aaggcaaagc ttacgaggtg ccatgttgga 165240
gccttttggt gtgaacagtc tggaagtaaa atttaggacc agaagcgaga atggcgtttt 165300
aatccatatc caagaaagca gcaattacac tactgtgaag gtgagataaa agctaatggt 165360
gacttcattt gattagaccg cctgccgtgt agtggtttaa atcacttccc ccataatttc 165420
tgtccttttc tttacaaccc attagagttc cgactaatgc tgggcactat tccaatgtca 165480
tctatcttaa ctattcccca ggcattggcc agagtaacaa agatctgaat ggtttggttt 165540
ctacacactt ttgtgttgct ttagagtaga gaaccctgcc aggtaggcca gcacacaaag 165600
aattagttgc aatctatttt tctggtaaga atttatatca cttcttttct tacttttaga 165660
caaagcaaac caaaaatata atgtttgttt gaaatacaaa aatatttttc tccaacaatt 165720
atttcaaata ttgatatgta tatgtcaatt gacaggatta gaataaggaa aaacattttg 165780
aaataagcaa aaacattttg aaattatatg atttctggag catatattca attctctata 165840
taaactctgt ggagtaaagt atatttggaa ttcattataa ttttacttaa cctttccaaa 165900
taatttttaa ataatcttaa aaattatgct tcatgagaac aatggattta tcattaggct 165960
tttacataat ttgtttttc ttatctgtaa ataagatact agacttatat acagatgaat 166020
aatttcatta gatatccatt tttgcatcgg ccccttagctt tctgaagttt taaacctatg 166080
ttctgctttc tttcccacaa ataagtcatc tcctagacca acagtttctt tagtttagtt 166140
atatttactg ccttccatta atattacttt gtatcattct actgataatt ttttatataa 166200
attttagtaa attcttaaga taacaaatcc agatttcctg aattattttc atctattagt 166260
caatatttaa taactactcc agggatagtt cacagagaaa aagagcaatt tgttcagaaa 166320
aattatttgg tttaattcac atataatact aaaaataaaa atagatgttc acttctaaac 166380
ttcagcctct ttcatcctca aaattttct ctgtgcaagc caaccatgat tatgttgcat 166440
ataaatatat ttaataagta gtacaaaaac caatatttct taccttctca aatgataatt 166500
cctctagtcc agtcatttcc aactaggata gattttaccc ccatgggaca tttggcaata 166560
tctggagaca ttttcaattg tcacggttag gagttgggag agtacttctg gcgtctagcg 166620
gtagaggtca agaatgctgc taaacagtag cacttcacaa caaagagtta tctggcccca 166680
aatatcatta gtgccaaatg gcagacactc taccctttc ccttacaaga gaacatcttc 166740
aggttttaac tttacctcta ttgaagcaaa ggacccagtt ccagagttaa taaaacaact 166800
gtaaaagaga acacataagc cattgtatta cattattatc tggtacttat aattttcatt 166860
gaaaatggta ttagaagtaa acaaagtaaa gaagcaaaaa aagaaataga tcctcatctt 166920
ctataagaaa catattttat atggtttgag aggctttgac attgaggtct gtgtgttatc 166980
tgttaagttg cttccaagtc ttcgtgccat ttaaatgaca tatgaaatat ttctgtacta 167040
acgtacactt aaagccaagg aattcagtca aaatacaatg tggttgaaaa aaatcagaga 167100
cacatttttt tcttcactaa ggaaaaagct gaatgtcagg atccattttt gtcaccataa 167160
attcttctac ttccaacagg acagcgcata caactccaga ttttgttagc ttggtagcaa 167220
taacttaatt tttttcctga aaggaaagta agtgcaaatt aataaaaaaa tgaataatac 167280
agaccaaaat gcatagtttt atatgaaaat tttgaaaaga agcttttcaa aggggcttgg 167340
caggtaaaga gaataggtaa gaaaaaataa caacagtgaa ttaagaataa ctaagtaaac 167400
caaaagaaag tggctgttgt aagcaggcaa attatttgga tgataggagt atcaagtgct 167460
tatacagact aggaagctag ttaggatgga cttttactta tcaattagct tattggtcac 167520
caagacccca gggttccgtt tttttttttt ttttttttgg ctccttttct gatcctttct 167580
ttaactcttt cttatggttt gcattctctc tctctcattc tcttttctat cattctttct 167640
ctctctctct acagacacac atacacacac acacacacac acacacacac acacacacgc 167700
agacagaaga tgaggacatt ttgtgaaaaa tgaggaaggg tgttgggtaa atgggattcc 167760
atgtggctag aagagagaga gggtgtcagt gtcaggtgtg ggcagcaata gtgatgagag 167820
gagagagaag aatatgtaga atcaattggg tctattcaga aaaagaaaaa attaagaaaa 167880
gaaagtttca gagagaaagg caaaaggaaa gcataattgt gtaaaacttt gtaggccaat 167940
atttaactca tttcacaaat ctctcttcat tcatggcatg ccctatagct ccatatttga 168000
tgttctgtaa taatagtaat gtgatggact ttatttctac tctaaatcag ttcttttgtg 168060
tttgtctggt ttttttaagt gggcaacata ggtgatacag aataattgga ataaggaatt 168120
caaagctcta tagattcaaa ttaaataaat gaacaaataa atgcagtcat gagttgcata 168180
atgacaggaa tgcatttcga taaatgcatt gttaggtgat ttcattcttg tgcaaacatc 168240
atagagtgaa cttgctcaaa cctagatggt acaacctact atacacctag gctatatgga 168300
atagtctatt gctcctgtgc tataaacctg tatggcatgt ttactgtact aaatactgta 168360
ggcaattgtg acacagtgga aagtatttgt gtatataatc atatccaaaa ataaaaaagg 168420
tacagtaaaa aggctgcatt gaagattttt ggggggatgg gggacagcct gggcaacagg 168480
gtcttgctct gttgcccagg ctggagtgca gtggcatgat ctcggctcac tgcagcctct 168540
gcctcctggg ctcaatgtat cctcccacct cagcctccca agtagatggg actacaggtg 168600
tgcgtaacca tgccgggcta acttttgtat ttttttgtag ggatgaggtt tcacatgttg 168660
cctaaattgc acttactgtg actgaagctt gtaggactga aagttgctct gagtcagaga 168720
gtcattaagc aagtggtggg tcaatgtgaa ggcctaagac attattatac acttctgcag 168780
actttataaa cactgtatgc ttaggttaca ttaaatttat caaaaatatt tttcttcaat 168840
aataaattaa ctttagctta ctgtaactct tttagtttat aaacttaaaa tttttaactt 168900
ttttctcttt tgtaataaca attaaaacac aaatacattg tacagctgta caaaaatatt 168960
ttctttcctt atacccttat tccataagct ttttttctat tttaaaagtt ttttatttca 169020
ttttattttt acttttaaac ttttgcatta gtaactaaga aacaaaaaaa cacattagcc 169080
tcagcctaca cagggtcagt atcatcaaat ccctgtcttc cacctccaca tcttgtccca 169140
gtggaaggtc ttcagggaca ataacacaga tggaactgtc atctcctatg ataacaatgc 169200
cttcttctgg aatcccacct aaaggacctg gatgaggctg gtttacagct atttttttata 169260 tcattagaag cagtaccctc taaaataatg attaaaaaaa cggtgtagta aatgcataaa 169320
ccactaatat agtcatttat tatcaaattg catgtgatat acttttatac aactggcagc 169380
tcagtaggct tgcttacacc tgtatccccg caatgagtaa ttcgttgtgc tatgacatta 169440
caatggctac taggtcacta ggcaataata atttttcagc tcctatggtt catcattgac 169500
tgtttattaa taaataaaac caagcaaaaa ttagcatgat gttttaaaag tgaagaatta 169560
tataagtgtt aagtacagta ctgccaggga gaaggaaaac attaagaatg ttataatggg 169620
aacttatatt cttatccacc ccaatttgtg gtatattcca agtgctcttt catcaaaaat 169680
ttattgaata aaaggatgac atgatgaaat caattaggag gaaagagctg ggagaaggct 169740 tttcctttt tttttttca aaaaggactc cagctataac caaagaaagt tgctgttttt 169800
actgtgtgtc atgagatgtt gcccatttga tgaaatgtta ttgtcattta gctagaattt 169860
tctgtttttt ttttttagtt tggtactgaa atatattatt atctggaaaa attggcttta 169920
ataaaatatt gctatatgaa taacatatgt aaatgtgtta gacatctttt cggtaaagta 169980
caaatgaact gatttttagt tttaccagat gtgtttgtta catgtagaaa tagcatttga 170040
tctgagtgac aaaataaact gatccatctt ttcattcccg ttatttgagg aacagtgcca 170100
ctgcatcccc ctgccaacac accagctctg tctggcagtg gtaacaggat tatgctccct 170160
gaaccaaatg ttcatcttgc ctcataaatt atctcatttt ctaaaatggt ctactcagga 170220
tactggaaac tcggtagctg gaaactggag tgggagcacc ctgttaccca atgttctcct 170280
ggacaaaata aaataaacca aatatccttt agataaattg taaaagacag ccaaagtgaa 170340
ggcttgccca gacacctcat taagaattca ctctttgttc atcatagttt ttgatctcaa 170400
taaatgatat aaacaatagg catcattttt tcctaaaatt tgtgtgtaaa agatgagagg 170460
taaaacaatt attttcatct ttatttttaa actatgcttc ccttttagct gagcattctt 170520
tttctttttg caagtggttt tcacaatttt ttagtactat gggcctttta ctaaacgaac 170580
cagcataaca cactccaatg gcaggttgtc attggaatac aaataattta aaaaggtata 170640
atttaattat cttaaatgga cattcgcccc tttattattt caattgtgtt ctggaaaata 170700
attcatcaag ttttgagaaa ttaggtatac atataagaat acgttgaaaa ccattgaaac 170760
ttaaatgtaa aagtacatgt tgcctaaaat tagagacaaa gtgtgtaagt atattctaat 170820
acaaccagat tcttcagcta ttctatctgc tgtggactgg tcaaaaattt aagtttagtt 170880
ttgttaatga tttttattta agcataccat attttaattg catactattt ttaatatgtt 170940
ttacagatta agaatggcaa agtatatttt acatccgatg caggaattgc tgggaaagtg 171000
gagagaaata ttcctgaagt atatgttgca gacggccact ggcacacttt tctaattggg 171060
aaaaatggaa cagcaacagt attgtctgtt gacagaatat ataacagaga tattatccac 171120
cctactcagg acttcggtgg ccttgatgtg cttactatat cacttggagg aattccaccc 171180
aatcaagcac atcgagatgc ccaaacaggt aaatgccttt attaagtaga gtcacaaggg 171240
aagtaaaatt gttcttcaaa aagtaattgc tttttcttgt ggcaagacta cacatttaac 171300
atgaatctca tatacagaac aatttcattc aataaaattt atgtttaaaa aagtagtttg 171360
atgtctgata atatcaatta taaatatcct aagaatgtca taactatctt cagaaagttt 171420
gtaataaact attagccacc actttctcga gagcttgcat ctttcttacc aaggttgtaa 171480
ttcagtccat agtgttttga tgctttgctt gtccaccaag catttcatat acatttgttc 171540
atttatttat tcattcacag ccactctctt catagaccat taatggagac aaacattaat 171600
caaattctta cacaagtaac tgcattattc taatgtgtga taaataatac aaatgaagaa 171660
tgtagaattc taaaatatag tgaaaaaaga gaaaggaagg ggaattttgc tgtggaattg 171720
acatgtatac ataaatctga atgatgagga ggatgaaagt gtacgaaagg ttaatttatg 171780

-continued

```
ttgataggaa tttttttaaa gaaatcgttt aagccaaagt tatagaagac aacacattgg 171840
aggctaacat cataggcaaa tgatgaagtt ggagaatgaa gcaacttcct gaccatgttg 171900
cagttttggt cttatttaca gagcaatggg aagtaattga aaactttaat cacagtagga 171960
tcaagttaga tatgcagtaa tattacagat cattcaggct acagcatgga gaatgaattg 172020
gaggaggaca cgagtggatc tacagaaatg agttgggatc tgggcaagat gtcttctgag 172080
ctcctactag tgtggtggct gaggagttag aaagaaatgg ataggcaaga aatattctgg 172140
gaactaaaat caaccaaact gttagtgatt atggtaaaat tcaaggaggt ttctacttct 172200
caactcaaag aagggtaggt cagcaagaga ggaaactgca gaaccctcca aaagcagcat 172260
atgtctgaga aatattagat ttggtttggg acattttgga tttgaagcat ctttgagaaa 172320
atcctttgga tggatgggct ggaaatcaga aatagacttt agctggaaat atatatttaa 172380
gagtggtcag tgtcaagcag gtaactgaag tactggacat ggatgtgatc acctaacatg 172440
agggcgtaga gtgaaaagaa agcctgggac gtcatcttga ttaaccgtaa gagttaatgg 172500
ttatgtagag gagaataagt cggaaaaagaa gactaagtaa taggaagaaa atcaggagta 172560
taggaacaaa aagaaaagat gtcacaaaag ctcatggaaa aaatatatca agaatgagaa 172620
tgtcactatg gtagaatgat gcattaaata agaggaaaaa aatgcatgtg agactaatag 172680
atttaaggca taaaagttaa agtccaggtc ataagtcctt tttatatggt tattatagaa 172740
tgttgtgaga aaacaaacca atggaaatta cgctttttgt agtgtcaaaa tagattgttg 172800
ggccctgaga taggaatatc agcactgtta acacactcaa gtgtaatgaa gtgtttctta 172860
actttgcatt ttatctttat cattccccta aggagacact taatatagtc taaactttgc 172920
catccccaag tcataaaatg ttaacaccag aggtatgttt ttatctgcct tttagaggcc 172980
cacaaaccat tgtaatagct aagatttttt tgttttgctc cccaagaacc tatgttccac 173040
acctttggtg tattatcacc ttcaatggga atgcatgatt tagtagttga agccattggc 173100
ctatttcatg ttctttacaa atttaaaaaa tatatatttt atttgtatgt atgcaatttt 173160
tggtatatgg gatgtaaaaa ggaaggaaat tgataaataa atgagtaaga aaaagaaaat 173220
tcagcctgcc caagtcattc ataaatcttc agaatgagtg ggattcaagc aatctgaccc 173280
atgtttggtc atggtaatct taacgcacct tgctaagtta taagatgcac agcttaatta 173340
tctttcagct ggatgatggt tctgagactg aggtttctgt attcatgtat tcatatgagg 173400
tgattgtgga gcttctcttt acaagaaccc agcagtgtag tataagctct tttttttttt 173460
tttttttttt gtaaaaagcc ttactccttc ttcttctccc agcaggtttt gatggctgca 173520
ttgcttctat gtggtatggt ggagaaagtc ttcctttcag cgggaagcat agcttggcct 173580
ccatctcaaa aacagatccc tcagtgaaga ttggctgccg tggcccgaac atttgtgcca 173640
gcaacccctg ctggggtgat ttgctgtgca ttaatcagtg gtatgcctac aggtgtgtcc 173700
ctcctgggga ctgtgcctcc cacccgtgcc agaatggtgg cagctgtgag ccaggcctgc 173760
actccggctt cacctgtagc tgcccagact cgcacacggg aaggacctgt gagatggtgg 173820
tggcctgtct tggcgtcctc tgtcctcagg ggaaggtgtg caaagctgga agtcctgcgg 173880
ggcatgtctg tgttctgagt cagggccctg aagagatctc tctgcctttg tgggctgtgc 173940
ctgccatcgt gggcagctgc gcaaccgtct tggccctcct ggtccttagc ctgatcctgt 174000
gtaaccagtg caggggggaag aaggccaaaa atcccaaaga ggagaagaaa ccgaaggaga 174060
agaagaaaaa gggaagtgag aacgttgctt ttgatgaccc tgacaatatc cctccctatg 174120
gggatgacat gactgtgagg aagcagcctg aagggaaccc aaaaccagat atcattgaaa 174180
```

gggaaaaccc ctaccttatc tatgatgaaa ctgatattcc tcacaactca gaaaccatcc 174240
ccagcgcccc tttggcatct ccagagcagg agatagagca ctatgacatt gacaacgcca 174300
gcagcatcgc cccttcggat gcagacatca ttcaacacta caagcagttc cgcagccaca 174360
caccaaaatt ttcaatccag aggcacagtc ccctaggctt tgcaaggcaa tcccccatgc 174420
ccttaggagc aagcagtttg acttaccagc cttcatatgg tcaaggtttg agaaccagct 174480
ccctaagcca ctcagcatgc ccaactccca accctctgtc tcgacacagt ccagcccctt 174540
tctccaaatc ttctacgttc tatagaaaca gcccagcaag ggaattgcat cttcctataa 174600
gggatggtaa tactttggaa atgcatggtg acacctgcca acctggcatt ttcaactatg 174660
ccacaaggct gggaaggaga agcaagagtc ctcaggccat ggcatcacat ggttctagac 174720
cagggagtcg cctaaagcag ccgattgggc agattccact ggaatcttct cctccagtcg 174780
gactttctat tgaagaagtg gagaggctca acacacctcg ccctagaaac ccaagtatct 174840
gcagtgcaga ccatgggagg tcttcttcag aggaggactg cagaaggcca ctgtctagaa 174900
caaggaatcc agcggatggc attccagctc cagaatcctc ttctgatagt gactcccatg 174960
aatctttcac ttgctcagaa atggaatatg acagggagaa gccaatggta tatacttcca 175020
gaatgcccaa attatctcaa gtcaatgaat ctgatgcaga tgatgaagat aattatggag 175080
ccagactgaa gcctcgaagg taccacggtc gcagggccga gggaggacct gtgggcaccc 175140
aggcagcagc accaggcact gctgacaaca cactgcccat gaagctaggg cagcaagcag 175200
ggactttcaa ctgggacaac cttttgaact ggggccctgg ctttggccat tatgtagatg 175260
tttttaaaga tttggcatct cttccagaaa aagcagcagc aaatgaagaa ggcaaagctg 175320
ggacaactaa accagtcccc aaagatgggg aagcagaaca gtatgtgtga agtttatgta 175380
ctggcactat aaaatataaa aacaagaaat aatactcaaa ccattgtaaa gttgctgact 175440
aggttgggtc acatttgaaa aacaggccag tatggactag tggtggaggg aaaactttaa 175500
aaataataac cacaatgctg ctgaaacaga ctcacaacaa ctcttaattt aaacatgtgt 175560
ggttgaattt atttccctgc atgcattgtg ttttgtaact agttatgtgg catgcagcat 175620
ttggaaaatt tttcttattt accagtgttt gatttgtgat ttttaaaaat tgataccttt 175680
accattgcag aaaagaactt gtgctttccc agtggcgtat gtgtattgtt tcaactgtat 175740
tattataatt atattttgca ttgcaagatt cttgatgtta aaccaatcct tgtaaagtgt 175800
aaaaaggaac cctcctatcg tggaatgaaa gattaagtat attaacactt ttcagaatga 175860
tagtttctgt atttgatgtt gctcagaaat gtctcagtat ttgagtaagt tttacatgac 175920
agtgggtact gaaattaagt cattttgttc agcactttaa cgctttctta tagaattgtc 175980
ttaaaacttc tggatccttg agcaaatgat tatagtctcc tgactttcat gaggcttcca 176040
ttaggaacag aatgattgca tgttgtcccc agaacactgc caccttgcta tgcgaatgat 176100
gttctcagca gcacttctaa gaaacactct taaaagttat ttattgaaaa tttttcgtat 176160
gcttttaata ttttaaagaa ttgacctaag gaaagcttat gattggactt attttccaac 176220
cagataacat ttactctaag tacccagttt ttataattta tatgaaatca gatttcaaca 176280
cttactttgt cattttgtag atcatttttt taaaatactg tgtaaaaact ttttttacac 176340
ctaagctgtg tttttgatac tgatattttc ctatgctgaa tagttttctt actttcaggg 176400
aaggtaagaa aatacttttt ttatatttgt tacttatgta acattcatat ttttctcatt 176460
ttgatatttg taacatactg tatgctttct acttgtaaat gtcaacaata gaattaaaat 176520
atttatttaa aata 176534

<210> SEQ ID NO 5
<211> LENGTH: 16123
<212> TYPE: DNA
<213> ORGANISM: Homo sapiens

<400> SEQUENCE: 5
gggagccagg accatggact tagcaccaga cagggctact ggccgcccgt ggctcccgtt 60
gcacactcta tcagtatctc agctccttcg agtgttttgg ctactgtcat tgcttccggg 120
gcaggcctgg gtccacgggg ccgagccgcg ccaggtgttc caagtgctgg aagagcaacc 180
tccaggcact ctggtaggca ccatccagac gcgccccggc ttcacctaca ggctcagcga 240
aagccacgcc ctgtttgcca taaacagtag caccggagcc ctgtacacca cctccaccat 300
cgaccgcgag agcctgccca gcgacgtgat caacctggtg gtcctttcca gcgcgcccac 360
ctaccccacc gaagtgcgag tgctggtgcg ggacctcaat gacaacgccc ccgttttccc 420
ggacccctct atcgtggtca ctttcaagga agacagtagc agcggacgcc aagtcatctt 480
agacaccgcc accgactcgg acatcggctc aaacggtgtg gaccaccgct cctaccgcat 540
catccgcggc aatgaggcgg ggcgcttccg tctggacatc accctgaacc cgagcggcga 600
gggagcgttc ctgcatctgg tgtccaaggg cggactggac cgtgaggtca ctccgcagta 660
ccagctcctg gttgaggtgg aggacaaggg tgagcctaag cggcggggct accttcaggt 720
aaacgtgact gtgcaagaca ttaatgacaa cccccccggtt tttggcagtt ctcactacca 780
ggcgggggtg cctgaggacg cggttgtggg ttccagcgtc ctccaggtgg cggcggcgga 840
cgcggacgag ggcaccaacg cggacatccg ctatcgcctg caggacgagg ggaccccctt 900
ccaaatggac cctgagacgg gacttatcac ggtgcgggag cccctggact tcgaagctcg 960
gcgccaatac tcgcttacgg tgcaggcgat ggacagaggc gtgccttccc tcactgggcg 1020
cgccgaggcg ctgattcagc tgctggacgt gaatgacaat gacccggtag tgaagttccg 1080
ctacttcccg gccacctcgc gctacgcctc ggtagatgag aatgctcaag tgggcaccgt 1140
ggtggctctg ctcaccgtga cggacgcaga ttctcccgcg gccaacggga acatctccgt 1200
gcaaattctc gggggcaatg agcagcgcca ctttgaagtg caaagcagca aagtgccgaa 1260
cctgagccta atcaaggtgg ccagcgcctt ggaccgcgag cgcatccctt cctacaacct 1320
cacagtttcc gtctctgata actacggggc gccccctggc gcagcagtcc aggcgcgctc 1380
ttctgtggca agcctggtga tttttgttaa tgacatcaat gaccatcctc ctgtcttttc 1440
acagcaagtg tacagagtga acctgagcga ggaggcgcct ccgggaagct atgtgagtgg 1500
gatatctgcc actgatggcg actctggtct caatgctaat ctgcgttaca gcattgtctc 1560
tggcaatgga ctgggatggt tccatatcag tgaacatagc ggcctcgtga ccactgggtc 1620
ctctgggggc ctggaccgtg aacttgcttc ccagattgtt ctgaatataa gtgcccggga 1680
ccagggagtt caccccaagg tgtcctatgc ccagcttgta gtaactctcc tagatgtgaa 1740
tgatgaaaag ccagtattta gccagccaga agggtatgat gtgtctgtgg ttgagaatgc 1800
cccaacaggg acagaactgt tgatgctcag ggcaactgac ggggacctgg gtgacaacgg 1860
aacagtgcgc ttctccttac aagaggcaga gactgaccgg aggtccttcc gtctggatcc 1920
tgtgtctggg aggttgagta ctatttcctc cttggacaga gaagagcaag ccttctactc 1980
cctgttggtt ctggccacag atctgggctc ccctccccag tcatcaatgg ctcgcataaa 2040
tgtgagtctt ctggatataa atgataacag ccctgtcttc tacccggtcc aatactttgc 2100

```
tcacattaag gagaatgagc ctggaggtag ctacatcacc actgtgtctg ccactgaccc   2160
agacttgggt accaatggta ctgtcaaata tagcatatct gctggggaca ggtctcggtt   2220
tcaggtcaat gctcagagtg gggttatttc tacaagaatg gccctagaca gagaagaaaa   2280
aacagcttat cagttgcaaa tagtagctac tgatggtggc aatttacaat ctcccaacca   2340
ggcaatagta accatcactg tattggacac tcaagacaac ccacctgtat tcagtcaggt   2400
tgcctacagc tttgtggttt ttgagaacgt ggcgctggga tatcatgtgg gtagtgtgtc   2460
tgcatccacc atggatctca attccaacat cagttatctc attactactg ggatcagaa    2520
aggtatgttt gctatcaacc aggtcactgg gcagcttacc acagcaaatg tgattgatag   2580
agaagagcaa tccttttatc agctgaaggt agtggccagt gggggcacag tgactggaga   2640
cactatggtt aacataacag ttaaggattt gaatgacaac tctccccatt tccttcaggc   2700
aatagagagt gtaaatgtgg tggagaattg gcaggcaggt cacagcattt tccaggccaa   2760
agctgtggac cctgatgaag gtgtcaatgg catggtactc tatagtctga agcaaaaccc   2820
caagaacctg tttgctatca atgaaaagaa tggcactatt agtctgcttg ggcccctgga   2880
tgttcatgct ggctcctacc aaatagagat cttggcatct gacatgggtg tcccacagct   2940
ctcctctagt gtcatcttaa cagtttatgt ccatgatgta aatgacaatt caccagtgtt   3000
tgaccaactc tcttatgaag tcaccctttc tgagtcagaa cctgtgaatt ctcgattctt   3060
taaagtacaa gcttctgata aggattcagg agcaaatggt gaaattgcat acaccattgc   3120
tgaaggaaat acaggggatg cttttggcat attcccagat ggtcaattgt atataaaaag   3180
tgaactggac cgtgaacttc aagacagata tgttttaatg gttgttgctt ctgacagagc   3240
agtggaaccc cttagtgcta ctgtgaatgt tactgtaatt ttagaagatg taaatgataa   3300
cagacctctt tttaacagta ccaattacac attttacttc gaagaagagc agagggctgg   3360
gtcgtttgtg ggcaaagtaa gtgctgtaga taaagacttt gggccaaatg gagaagtaag   3420
gtattctttt gaaatggtgc agccagattt tgagttgcat gccatcagtg gggaaattac   3480
aaatactcat cagtttgaca gggagtctct tatgaggcgg agagggactg ctgtgtttag   3540
ctttacagtc atagcaacag atcaggggat ccctcagcct ctcaaggatc aggccactgt   3600
acatgtttac atgaaggata taaatgataa tgctcccaaa tttttaaaag acttttacca   3660
agctacaata tcagaatcag cagccaatct gacacaagtg ttaagagtat ctgcctcaga   3720
tgttgatgaa ggtaataatg gacttattca ctattctata ataaaaggaa atgaagaaag   3780
acagtttgct atagacagta cctctggtca ggtaacacta attggcaaat tagactatga   3840
agcaacacct gcctattccc ttgtaattca agcagtggat tcagggacaa tcccccctcaa   3900
ttcaacgtgt actttaaata ttgatatttt agatgaaaat gacaataccc cttctttccc   3960
taaatcaaca ctctttgttg atgttttgga aaacatgaga attggtgaac tcgtgtcctc   4020
tgttactgca actgattccg attcaggtga caatgctgat ttatattaca gtattactgg   4080
gactaacaac cacggaactt ttagcattag cccaaacact gggagtattt ttcttgccaa   4140
aaaactggac tttgaaacac agtctttgta taaattaaat ataacagcaa aagaccaagg   4200
aagacctcct cgttcatcta caatgtcagt ggttattcac gtgagggact ttaatgacaa   4260
tcctcctagc tttcctcctg gagatatttt caagtctatt gttgagaaca ttcccatcgg   4320
tacatctgtc atttcagtga ctgcacatga ccctgatgca gacattaatg gtcaactatc   4380
ctacacaatc attcaacaga tgccaagagg caaccacttt accatagatg aagtcaaagg   4440
```

```
gactatatat actaatgctg aaatagatcg ggaatttgct aatctctttg agttgactgt   4500
aaaagccaat gatcaagctg tgccaataga aactagacgg tatgctttga agaacgtgac   4560
cattttggtt acagacctca atgacaatgt cccaatgttt atatcacaaa acgcccttgc   4620
tgcagaccca tcagctgtga ttggttccgt tctgacaaca attatggctg ctgacccaga   4680
tgaaggtgct aatggagaaa tagagtatga gatcatcaat ggggacacag acaccttcat   4740
tgttgatcgt tatagtggag acctgagagt ggcttcagcg ttggtgcctt cacagttgat   4800
ctacaatctc atagtttcag caacagacct tgggcctgaa aggaggaaat cgaccactga   4860
attgaccatc attcttcagg gccttgatgg acctgttttt actcaaccca aatatataac   4920
tattttgaag gaaggagaac ccattggcac aaacgtgata tcaatagaag cagctagccc   4980
cagaggatct gaggccccag tggagtatta tattgtttca gttcgttgtg aagaaaaaac   5040
tgttggacgc ctctttacta ttggacgaca tactggtata attcagaccg cagccattct   5100
ggaccgggag caaggagcat gtctttacct ggtggatgtt tatgccatag aaaaatcaac   5160
tgcttttccc agaacacaga gagcagaggt agaaataaca cttcaggata tcaatgacaa   5220
tccaccagta tttccaacgg acatgctgga tctcacggta gaggagaaca ttggagatgg   5280
ctctaagatt atgcagctga cagccatgga tgctgatgag ggtgcaaatg ctctcgtcac   5340
atacactatc attagtggag ctgatgatag ttttcgcatc gacccagaat ccggagatct   5400
gatagcaacc aggcggttgg acagggaacg ccgctccaaa tattcactgc tagttcgtgc   5460
tgatgatggt cttcagtcct cggatatgag aattaatatc actgtcagtg atgtgaatga   5520
ccatacaccc aaattttcca gacccgtgta ctcttttgac attcctgagg acacaatccc   5580
tggttctttg gtagcagcca ttttagccac ggatgatgac tctggtgtga atggagaaat   5640
tacatatatt gtgaatgaag atgatgaaga tggcatcttt ttcctgaatc ctattactgg   5700
ggtctttaat ttgactcgat tattagatta tgaagtacag caatattata tcctcactgt   5760
tcgagcagaa gatggtgggg gacaatttac taccatcaga gtttatttca atattctaga   5820
tgtaaatgat aatccaccta ttttcagctt gaattcatac agcacatctt taatggagaa   5880
tctacctgtg ggatctactg ttcttgtgtt taatgttact gatgcagatg atggcatcaa   5940
ctctcaattg acttatagca ttgcttcagg tgatagcctt gggcagttta ctgttgacaa   6000
gaatggtgta ctcaaagtcc taaaagcttt ggatcgggaa agtcagtcct tctacaactt   6060
ggttgttcaa gtgcatgacc tgccacagat tccagcctcc agattcacaa gcactgctca   6120
agtctccatt attttgttgg atgtaaatga taacccaccg acatttcttt cccctaaatt   6180
gacatacatt ccagaaaata cacctattga tactgttgtt ttcaaagctc aagcaactga   6240
cccagatagt ggcccaaaca gctatattga gtacactctg ctgaaccctt tgggaaacaa   6300
gttcagtatt gggaccattg atggtgaagt gaggctcact ggagaactgg acagagaaga   6360
agtttctaat tatactctaa cagtggtggc tacagacaaa ggtcaaccat ctctctcttc   6420
atctacagag gttgtagtta tggtacttga catcaatgat aacaacccca tctttgcaca   6480
agctttgtat aaagtggaga ttaatgaaaa cacacttact ggaacagata taatacaagt   6540
gttcgcagca gatggagatg aaggcacaaa tggacaggtt cgctatggca ttgttaatgg   6600
taataccaat caggaatttc ggatagactc tgtcacaggt gccatcactg tcgctaaacc   6660
tttggataga gaaaagaccc ctacctacca tttaactgtt caggcaacag atcgaggcag   6720
cacacccaga actgatacct ccacggtcag cattgttcta ctggatatta atgactttgt   6780
tcctgtattt gagctatctc catattctgt aaatgtccct gagaatttag ggacactacc   6840
```

-continued

```
cagaacaatt cttcaggtgg tggcaagaga tgatgatcga ggatctaaca gcaaactctc   6900
atatgttctg tttggtggta atgaagacaa tgcttttact ctctcagcca gtggagaact   6960
tggagtaaca cagagtctgg atcgggaaac aaaagagcgc tttgtcttaa tgattacagc   7020
tacagattca ggatcccctg ccttgactgg aactggaaca atcaacgtca tagtagatga   7080
tgtcaatgac aatgtcccca catttgccag taaagcgtat ttcacaacaa ttcctgagga   7140
tgcaccaact ggaacagatg ttttattggt aaatgcctca gatgctgatg cttcaaagaa   7200
tgcagttata aggatcatcg gtggaaactc tcagttcacg atcaacccat cgacaggaca   7260
aatcatcacc agcgcattgt tagataggga aacaaaagat aattatactt tggtagtggt   7320
ctgcagtgat gcgggatccc cagagcctct ttccagttcc accagtgtgc ttgtcactgt   7380
gactgatgtc aatgacaatc caccaagatt tcagcatcac ccatatgtca ctcacatccc   7440
atctcctact cttccaggtt cctttgtctt tgcggttaca gtcacagatg ctgatattgg   7500
accaaattct gaactgcatt attctctttc gggtagaaat tctgaaaaat ttcacattga   7560
cccactgagg ggagccatta tggccgccgg accactaaac ggagcttcag aagtgacatt   7620
ttctgtgcat gtaaaagatg gtggctcatt tccaaagaca gattctacaa cagtgactgt   7680
tagattcgtg aataaggccg atttccctaa agtgagagcc aaagaacaaa cgttcatgtt   7740
tcctgaaaac caaccagtca gctctcttgt caccaccatc acaggatcct ctttaagagg   7800
agaacctatg tcatattata tcgcaagtgg gaatcttggc aatactttcc agattgatca   7860
gttaacaggg caggtgtcta ttagtcaacc tctggatttt gaaaagatac aaaaatatgt   7920
tgtatggata gaggccagag acggtggttt ccctcctttc tcctcttacg agaaacttga   7980
tataacagta ttagatgtca atgataatgc cccaattttt aaggaagacc catttatatc   8040
tgaaatattg gaaaaccttt cccctcgaaa aatacttact gtttcggcaa tggacaagga   8100
cagtggaccc aatggacagt tagattatga aattgttaat ggcaacatgg aaaatagttt   8160
cagtatcaat catgctactg gtgaaattag aagcgttaga cctttggaca gggaaaaagt   8220
atctcattat gtcctaacca taaaatcatc agacaaaggg tccccgtctc agagtacttc   8280
agtaaaagtc atgattaaca ttttagatga aaatgataat gcccctaggt tttctcagat   8340
atttagtgcc catgttcctg aaaattcccc cttaggatac acagttaccc gtgtcacaac   8400
ttctgatgaa gacattggga tcaatgcaat tagtagatat tctataatgg atgcaagtct   8460
tccatttaca attaatccca gcacagggga tattgtcata agcagacctt taaataggga   8520
agatacagac cgttacagaa ttcgagtttc cgcacatgat tctgggtgga ctgtaagtac   8580
agatgtcaca atatttgtga cagacatcaa tgacaatgct ccaagattta gcagaacttc   8640
ctattattta gattgccctg aacttactga gattggctcc aaagtaactc aggtatttgc   8700
aacagatcct gatgagggat caaatggaca agtgttttat ttcataaaat cccaatcaga   8760
atatttcagg attaatgcca ccactggaga gatttttcaat aaacagatct taaaatacca   8820
aaatgtcact ggcttcagta atgtgaatat caacaggcat agttttatag tgacatcttc   8880
agatcgaggt aaaccttcct taattagtga gacaacagtt accatcaata tagtggacag   8940
taatgacaat gcacctcaat ttcttaaaag taaatatttc actccagtca ccaaaaatgt   9000
taaggttggt acgaagttaa tcagagttac agcaatagat gacaaagatt ttggactgaa   9060
ttcagaagtg gagtatttca tttctaatga taaccattta ggaaaattta agttggacaa   9120
tgatacgggg tggatttcag tagcatcctc cctgatttct gacttgaacc aaaacttttt   9180
```

-continued

```
tatcacagtc actgcaaagg ataagggaaa ccctccactt tcttcccaag caactgttca   9240
cataactgtc actgaggaaa actaccatac acctgaattc tctcaaagcc acatgagtgc   9300
aaccatccct gagagccata gcattgggtc cattgtcaga actgtttctg caagagatag   9360
agatgcagcg atgaatggct tgattaagta cagcatttct tcaggaaatg aagaaggcat   9420
ttttgcaatc aattcttcta caggtatatt aacactagcc aaagctcttg attatgagct   9480
atgccagaaa cacgaaatga cgattagtgc tatagatgga ggatgggttg caagaactgg   9540
ttactgcagt gtgaccgtaa atgtgattga tgtgaatgat aattctccag tattcctctc   9600
tgatgactat ttccctactg ttttggaaaa tgccccaagt ggaacaacag ttatccacct   9660
aaatgcaaca gatgctgact ctggaacaaa tgctgtgatt gcgtatactg tacagtcatc   9720
tgacagtgac ctctttgtca ttgaccctaa cacaggagtc ataaccactc aaggcttctt   9780
ggattttgaa accaagcaga gctaccatct tactgtgaaa gccttcaatg tccccgatga   9840
ggaaaggtgt agctttgcca ctgttaatat acaattaaaa gggacaaatg aatatgtgcc   9900
ccgttttgtt tccaaacttt actattttga aatctcagaa gcagctccta aaggtactat   9960
tgttggagaa gtgtttgcta gcgaccgtga tttgggcact gatggggagg tacactattt  10020
gatttttggt aatagtcgaa agaagggttt ccagatcaat aagaagactg gacagattta  10080
tgtttctgga attcttgatc gagaaaaaga agaaagggtg tctttgaagg tattggccaa  10140
gaactttggc agcattagag gtgcagatat agatgaggtc actgtaaatg tcaccgtgct  10200
tgatgcaaat gacccaccca tttttactct aaacatctac agtgtgcaga tcagtgaagg  10260
ggtcccaata ggaactcatg tgacctttgt cagtgccttt gactcagact ccatccccag  10320
ctggagcagg ttttcttact tcatcggatc agggaatgaa aatggtgcct tttctattaa  10380
tccgcagaca ggacagatca ccgttactgc agaattagat cgagaaaccc ttcccatcta  10440
taatctctca gttttggctg ttgattcagg gaccccctca gctacaggta gtgcctcttt  10500
attagtcacc ctggaagata taaatgataa cgggcccatg ctgactgtca gtgaaggaga  10560
agtcatggaa aacaaacggc caggcacttt ggtgatgacc cttcagtcca ctgaccctga  10620
tctccctcca aatcaaggtc cctttactta ttacttgctg agcacaggtc ctgccaccag  10680
ttatttcagt ctgagcactg ctggagttct gagcacaacc agagagattg acagagagca  10740
gattgcagac ttctatctgt ctgtggttac caaggattct ggtgttcctc aaatgtcttc  10800
cacaggaact gtgcatatca cagttataga ccaaaatgac aatccttcac agtctcggac  10860
ggtggagata tttgttaatt attatggtaa cttgtttccc ggtgggattt taggctctgt  10920
gaagccacag gatccagatg tgttagacag cttccactgc tcccttactt caggagttac  10980
cagcctcttc agtattccag gggtacttg tgatctgaat tcccagccaa ggtccacaga  11040
tggcacgttt gatctgactg tccttagcaa tgatggagtt cacagcacag tcacgagcaa  11100
catccgagtt ttctttgctg gattttccaa tgccacagtg gataacagca tcttacttcg  11160
tctcggcgta ccaacagtaa aggacttctt gaccaaccac tatcttcatt ttttacgcat  11220
tgccagctca cagctgacag gcttagggac tgctgtgcaa ctgtacagtg catatgaaga  11280
gaacaataga acgtttcttt tggcagctgt gaagcgaaat cataatcagt atgtgaatcc  11340
cagtggcgta gccaccttct ttgaaagcat caaagagatc cttctccggc agagtggagt  11400
aaaggtggaa tctgtggatc atgactcctg tgtgcatggc ccatgtcaga atggagggag  11460
ctgtctacga agattggctg tgagctccgt attaaaaagc cgtgagagtc ttccagtcat  11520
catcgtggca aatgaacctc tgcagccttt cttatgcaag tgtctgccag gatatgcggg  11580
```

-continued

```
tagctggtgt gaaatagata tagatgaatg tcttccatca ccttgccaca gtggtggaac  11640
ctgtcacaat ttagtgggag gattttcatg cagctgccca gatggcttca ctggtagggc  11700
gtgtgagaga gatatcaatg agtgcctgca gagtccttgc aagaatggtg ccatctgcca  11760
gaattttcca ggaagcttca actgtgtttg caaaactgga tacacaggga aaatgtgtga  11820
atcttcagtc aattactgtg aatgcaaccc ctgctttaat ggtggttcct gccaaagtgg  11880
tgtggattct tattattgtc attgtccatt tggtgtcttt ggaaaacact gcgagttgaa  11940
cagttatgga tttgaggagt tatcatacat ggaatttcca agcttggacc ccaataacaa  12000
ctatatttat gtcaaatttg ccacgattaa aagtcatgcc ttattgcttt acaactatga  12060
caaccagaca ggcgaccggg ctgagttttt ggcccttgaa attgccgaag aaagactaag  12120
attctcttat aatttaggca gtggtacata taagctcacc accatgaaga aggtgtcaga  12180
tggacatttt cacactgtga ttgccaggag agcaggaatg gcagcctcct taactgtgga  12240
ctcctgttct gagaaccaag agccaggata ttgtactgtc agtaatgtgg cagtttcaga  12300
tgactggact cttgatgttc agccaaatag agttacagtt ggaggtatca gatctctaga  12360
accaatcctt cagagaagag gacacgtgga aagccatgat tttgttgggt gtataatgga  12420
gtttgcagtc aatggaaggc ctctggaacc cagccaagct ttggcagcac aaggcatcct  12480
agatcaatgc cctaggctgg aaggcgcttg tactcgcagc ccatgccaac atggtggcac  12540
atgtatggat tactggtcat ggcagcagtg tcattgcaaa gagggactca ctgggaaata  12600
ctgtgaaaaa tctgttactc ctgacactgc cttatcatta gaaggcaaag ggcgcttgga  12660
ctaccacatg agtcagaatg agaagcggga atatttgtta aggcaaagct tacgaggtgc  12720
catgttggag ccttttggtg tgaacagtct ggaagtaaaa tttaggacca gaagcgagaa  12780
tggcgtttta atccatatcc aagaaagcag caattacact actgtgaaga ttaagaatgg  12840
caaagtatat tttacatccg atgcaggaat tgctgggaaa gtggagagaa atattcctga  12900
agtatatgtt gcagacggcc actggcacac ttttctaatt gggaaaaatg gaacagcaac  12960
agtattgtct gttgacagaa tatataacag agatattatc caccctactc aggacttcgg  13020
tggccttgat gtgcttacta tatcacttgg aggaattcca cccaatcaag cacatcgaga  13080
tgcccaaaca gcaggttttg atggctgcat tgcttctatg tggtatggtg gagaaagtct  13140
tcctttcagc gggaagcata gcttggcctc catctcaaaa acagatccct cagtgaagat  13200
tggctgccgt ggcccgaaca tttgtgccag caacccctgc tggggtgatt tgctgtgcat  13260
taatcagtgg tatgcctaca ggtgtgtccc tcctggggac tgtgcctccc acccgtgcca  13320
gaatggtggc agctgtgagc caggcctgca ctccggcttc acctgtagct gcccagactc  13380
gcacacggga aggacctgtg agatggtggt ggcctgtctt ggcgtcctct gtcctcaggg  13440
gaaggtgtgc aaagctggaa gtcctgcggg gcatgtctgt gttctgagtc agggccctga  13500
agagatctct ctgcctttgt gggctgtgcc tgccatcgtg ggcagctgcg caaccgtctt  13560
ggccctcctg gtccttagcc tgatcctgtg taaccagtgc agggggaaga aggccaaaaa  13620
tcccaaagag gagaagaaac cgaaggagaa gaagaaaaag ggaagtgaga acgttgcttt  13680
tgatgaccct gacaatatcc ctccctatgg ggatgacatg actgtgagga agcagcctga  13740
agggaaccca aaaccagata tcattgaaag ggaaaacccc taccttatct atgatgaaac  13800
tgatattcct cacaactcag aaaccatccc cagcgcccct ttggcatctc cagagcagga  13860
gatagagcac tatgacattg acaacgccag cagcatcgcc ccttcggatg cagacatcat  13920
```

-continued tcaacactac aagcagttcc gcagccacac accaaaattt tcaatccaga ggcacagtcc 13980
cctaggcttt gcaaggcaat cccccatgcc cttaggagca agcagtttga cttaccagcc 14040
ttcatatggt caaggtttga gaaccagctc cctaagccac tcagcatgcc caactcccaa 14100
ccctctgtct cgacacagtc cagccccttt ctccaaatct tctacgttct atagaaacag 14160
cccagcaagg gaattgcatc ttcctataag ggatggtaat actttggaaa tgcatggtga 14220
cacctgccaa cctggcattt tcaactatgc cacaaggctg ggaaggagaa gcaagagtcc 14280
tcaggccatg gcatcacatg gttctagacc agggagtcgc ctaaagcagc cgattgggca 14340
gattccactg gaatcttctc ctccagtcgg actttctatt gaagaagtgg agaggctcaa 14400
cacacctcgc cctagaaacc caagtatctg cagtgcagac catgggaggt cttcttcaga 14460
ggaggactgc agaaggccac tgtctagaac aaggaatcca gcggatggca ttccagctcc 14520
agaatcctct tctgatagtg actcccatga atctttcact tgctcagaaa tggaatatga 14580
cagggagaag ccaatggtat atacttccag aatgcccaaa ttatctcaag tcaatgaatc 14640
tgatgcagat gatgaagata attatggagc cagactgaag cctcgaaggt accacggtcg 14700
cagggccgag ggaggacctg tgggcaccca ggcagcagca ccaggcactg ctgacaacac 14760
actgcccatg aagctagggc agcaagcagg gactttcaac tgggacaacc ttttgaactg 14820
gggccctggc tttggccatt atgtagatgt ttttaaagat ttggcatctc ttccagaaaa 14880
agcagcagca aatgaagaag gcaaagctgg gacaactaaa ccagtcccca aagatgggga 14940
agcagaacag tatgtgtgaa gtttatgtac tggcactata aaatataaaa acaagaaata 15000
atactcaaac cattgtaaag ttgctgacta ggttgggtca catttgaaaa acaggccagt 15060
atggactagt ggtggaggga aaactttaaa aataataacc acaatgctgc tgaaacagac 15120
tcacaacaac tcttaattta aacatgtgtg gttgaattta tttccctgca tgcattgtgt 15180
tttgtaacta gttatgtggc atgcagcatt tggaaaattt ttcttattta ccagtgtttg 15240
atttgtgatt tttaaaaatt gataccttta ccattgcaga aaagaacttg tgctttccca 15300
gtggcgtatg tgtattgttt caactgtatt attataatta tattttgcat tgcaagattc 15360
ttgatgttaa accaatcctt gtaaagtgta aaaaggaacc ctcctatcgt ggaatgaaag 15420
attaagtata ttaacacttt tcagaatgat agtttctgta tttgatgttg ctcagaaatg 15480
tctcagtatt tgagtaagtt ttacatgaca gtgggtactg aaattaagtc attttgttca 15540
gcactttaac gctttcttat agaattgtct taaaacttct ggatccttga gcaaatgatt 15600
atagtctcct gactttcatg aggcttccat taggaacaga atgattgcat gttgtcccca 15660
gaacactgcc accttgctat gcgaatgatg ttctcagcag cacttctaag aaacactctt 15720
aaaagttatt tattgaaaat ttttcgtatg cttttaatat tttaaagaat tgacctaagg 15780
aaagcttatg attggactta ttttccaacc agataacatt tactctaagt acccagtttt 15840
tataatttat atgaaatcag atttcaacac ttactttgtc attttgtaga tcattttttt 15900
aaaatactgt gtaaaaactt tttttacacc taagctgtgt ttttgatact gatattttcc 15960
tatgctgaat agttttctta ctttcaggga aggtaagaaa atactttttt tatatttgtt 16020
acttatgtaa cattcatatt tttctcattt tgatatttgt aacatactgt atgctttcta 16080
cttgtaaatg tcaacaatag aattaaaata tttatttaaa ata 16123

<210> SEQ ID NO 6
<211> LENGTH: 9669
<212> TYPE: DNA
<213> ORGANISM: Homo sapiens

<400> SEQUENCE: 6

```
atggtaacaa cggtagtggc agtgggtgat accttagctc aaccattagc tgcagctgaa      60
gtgtttattg tagaaataac acttcaggat atcaatgaca atccaccagt atttccaacg     120
gacatgctgg atctcacggt agaggagaac attggagatg gctctaagat tatgcagctg     180
acagccatgg atgctgatga gggtgcaaat gctctcgtca catacactat cattagtgga     240
gctgatgata gttttcgcat cgacccagaa tccggagatc tgatagcaac caggcggttg     300
gacagggaac gccgctccaa atattcactg ctagttcgtg ctgatgatgg tcttcagtcc     360
tcggatatga gaattaatat cactgtcagt gatgtgaatg accatacacc caaattttcc     420
agacccgtgt actcttttga cattcctgag gacacaatcc ctggttcttt ggtagcagcc     480
attttagcca cggatgatga ctctggtgtg aatggagaaa ttacatatat tgtgaatgaa     540
gatgatgaag atggcatctt tttcctgaat cctattactg ggtctttaa tttgactcga      600
ttattagatt atgaagtaca gcaatattat atcctcactg ttcgagcaga agatggtggg     660
ggacaattta ctaccatcag agtttatttc aatattctag atgtaaatga taatccacct     720
attttcagct tgaattcata cagcacatct ttaatggaga atctacctgt gggatctact     780
gttcttgtgt ttaatgttac tgatgcagat gatggcatca actctcaatt gacttatagc     840
attgcttcag gtgatagcct tgggcagttt actgttgaca agaatggtgt actcaaagtc     900
ctaaaagctt tggatcggga aagtcagtcc ttctacaact tggttgttca agtgcatgac     960
ctgccacaga ttccagcctc cagattcaca agcactgctc aagtctccat tattttgttg    1020
gatgtaaatg ataacccacc gacatttctt tcccctaaat tgacatacat tccagaaaat    1080
acacctattg atactgttgt tttcaaagct caagcaactg acccagatag tggcccaaac    1140
agctatattg agtacactct gctgaaccct ttgggaaaca agttcagtat tgggaccatt    1200
gatggtgaag tgaggctcac tggagaactg gacagagaag aagtttctaa ttatactcta    1260
acagtggtgg ctacagacaa aggtcaacca tctctctctt catctacaga ggttgtagtt    1320
atggtacttg acatcaatga taacaacccc atctttgcac aagctttgta taaagtggag    1380
attaatgaaa acacacttac tggaacagat ataatacaag tgttcgcagc agatggagat    1440
gaaggcacaa atggacaggt tcgctatggc attgttaatg gtaataccaa tcaggaattt    1500
cggatagact ctgtcacagg tgccatcact gtcgctaaac ctttggatag agaaaagacc    1560
cctacctacc atttaactgt tcaggcaaca gatcgaggca gcacacccag aactgatacc    1620
tccacggtca gcattgttct actggatatt aatgactttg ttcctgtatt tgagctatct    1680
ccatattctg taaatgtccc tgagaattta gggacactac ccagaacaat tcttcaggtg    1740
gtggcaagag atgatgatcg aggatctaac agcaaactct catatgttct gtttggtggt    1800
aatgaagaca atgcttttac tctctcagcc agtggagaac ttggagtaac acagagtctg    1860
gatcgggaaa caaaagagcg ctttgtctta atgattacag ctacagattc aggatcccct    1920
gccttgactg gaactggaac aatcaacgtc atagtagatg atgtcaatga caatgtcccc    1980
acatttgcca gtaaagcgta tttcacaaca attcctgagg atgcaccaac tggaacagat    2040
gttttattgg taaatgcctc agatgctgat gcttcaaaga atgcagttat aaggatcatc    2100
ggtggaaact ctcagttcac gatcaaccca tcgacaggac aaatcatcac cagcgcattg    2160
ttagataggg aaacaaaaga taattatact ttggtagtgg tctgcagtga tgcgggatcc    2220
ccagagcctc tttccagttc caccagtgtg cttgtcactg tgactgatgt caatgacaat    2280
```

-continued

```
ccaccaagat ttcagcatca cccatatgtc actcacatcc catctcctac tcttccaggt   2340
tcctttgtct ttgcggttac agtcacagat gctgatattg gaccaaattc tgaactgcat   2400
tattctcttt cgggtagaaa ttctgaaaaa tttcacattg acccactgag gggagccatt   2460
atggccgccg gaccactaaa cggagcttca gaagtgacat ttctgtgca tgtaaaagat    2520
ggtggctcat ttccaaagac agattctaca acagtgactg ttagattcgt gaataaggcc   2580
gatttcccta aagtgagagc caaagaacaa acgttcatgt ttcctgaaaa ccaaccagtc   2640
agctctcttg tcaccaccat cacaggatcc tctttaagag gagaacctat gtcatattat   2700
atcgcaagtg ggaatcttgg caatactttc cagattgatc agttaacagg gcaggtgtct   2760
attagtcaac ctctggattt tgaaaagata caaaaatatg ttgtatggat agaggccaga   2820
gacggtggtt tccctccttt ctcctcttac gagaaacttg atataacagt attagatgtc   2880
aatgataatg ccccaatttt taaggaagac ccatttatat ctgaaatatt ggaaaacctt   2940
tcccctcgaa aaatacttac tgtttcggca atggacaagg acagtggacc caatggacag   3000
ttagattatg aaattgttaa tggcaacatg gaaaatagtt tcagtatcaa tcatgctact   3060
ggtgaaatta gaagcgttag acctttggac agggaaaaag tatctcatta tgtcctaacc   3120
ataaaatcat cagacaaagg gtccccgtct cagagtactt cagtaaaagt catgattaac   3180
attttagatg aaaatgataa tgcccctagg ttttctcaga tatttagtgc ccatgttcct   3240
gaaaattccc ccttaggata cacagttacc cgtgtcacaa cttctgatga agacattggg   3300
atcaatgcaa ttagtagata ttctataatg gatgcaagtc ttccatttac aattaatccc   3360
agcacagggg atattgtcat aagcagacct ttaaataggg aagatacaga ccgttacaga   3420
attcgagttt ccgcacatga ttctgggtgg actgtaagta cagatgtcac aatatttgtg   3480
acagacatca atgacaatgc tccaagattt agcagaactt cctattattt agattgccct   3540
gaacttactg agattggctc caaagtaact caggtatttg caacagatcc tgatgaggga   3600
tcaaatggac aagtgtttta tttcataaaa tcccaatcag aatatttcag gattaatgcc   3660
accactggag agattttcaa taaacagatc ttaaaatacc aaaatgtcac tggcttcagt   3720
aatgtgaata tcaacaggca tagttttata gtgacatctt cagatcgagg taaaccttcc   3780
ttaattagtg agacaacagt taccatcaat atagtggaca gtaatgacaa tgcacctcaa   3840
tttcttaaaa gtaaatattt cactccagtc accaaaaatg ttaaggttgg tacgaagtta   3900
atcagagtta cagcaataga tgacaaagat tttggactga attcagaagt ggagtatttc   3960
atttctaatg ataaccattt aggaaaattt aagttggaca atgatacggg gtggatttca   4020
gtagcatcct ccctgatttc tgacttgaac caaaactttt ttatcacagt cactgcaaag   4080
gataagggaa accctccact ttcttcccaa gcaactgttc acataactgt cactgaggaa   4140
aactaccata cacctgaatt ctctcaaagc cacatgagtg caaccatccc tgagagccat   4200
agcattgggt ccattgtcag aactgtttct gcaagagata gagatgcagc gatgaatggc   4260
ttgattaagt acagcatttc ttcaggaaat gaagaaggca tttttgcaat caattcttct   4320
acaggtatat taacactagc caaagctctt gattatgagc tatgccagaa acacgaaatg   4380
acgattagtg ctatagatgg aggatgggtt gcaagaactg gttactgcag tgtgaccgta   4440
aatgtgattg atgtgaatga taattctcca gtattcctct ctgatgacta tttccctact   4500
gttttggaaa atgccccaag tggaacaaca gttatccacc taaatgcaac agatgctgac   4560
tctggaacaa atgctgtgat tgcgtatact gtacagtcat ctgacagtga cctctttgtc   4620
attgacccta acacaggagt cataaccact caaggcttct tggattttga aaccaagcag   4680
```

agctaccatc ttactgtgaa agccttcaat gtccccgatg aggaaaggtg tagctttgcc 4740
actgttaata tacaattaaa agggacaaat gaatatgtgc cccgttttgt ttccaaactt 4800
tactattttg aaatctcaga agcagctcct aaaggtacta ttgttggaga agtgtttgct 4860
agcgaccgtg atttgggcac tgatggggag gtacactatt tgatttttgg taatagtcga 4920
aagaagggtt tccagatcaa taagaagact ggacagattt atgtttctgg aattcttgat 4980
cgagaaaaag aagaaagggt gtctttgaag gtattggcca agaactttgg cagcattaga 5040
ggtgcagata tagatgaggt cactgtaaat gtcaccgtgc ttgatgcaaa tgacccaccc 5100
atttttactc taaacatcta cagtgtgcag atcagtgaag gggtcccaat aggaactcat 5160
gtgacctttg tcagtgcctt tgactcagac tccatcccca gctggagcag gttttcttac 5220
ttcatcggat cagggaatga aaatggtgcc ttttctatta atccgcagac aggacagatc 5280
accgttactg cagaattaga tcgagaaacc cttcccatct ataatctctc agttttggct 5340
gttgattcag ggaccccctc agctacaggt agtgcctctt tattagtcac cctggaagat 5400
ataaatgata acgggcccat gctgactgtc agtgaaggag aagtcatgga aaacaaacgg 5460
ccaggcactt tggtgatgac ccttcagtcc actgaccctg atctccctcc aaatcaaggt 5520
ccctttactt attacttgct gagcacaggt cctgccacca gttatttcag tctgagcact 5580
gctggagttc tgagcacaac cagagagatt gacagagagc agattgcaga cttctatctg 5640
tctgtggtta ccaaggattc tggtgttcct caaatgtctt ccacaggaac tgtgcatatc 5700
acagttatag accaaaatga caatccttca cagtctcgga cggtggagat atttgttaat 5760
tattatggta acttgtttcc cggtgggatt ttaggctctg tgaagccaca ggatccagat 5820
gtgttagaca gcttccactg ctcccttact tcaggagtta ccagcctctt cagtattcca 5880
gggggtactt gtgatctgaa ttcccagcca aggtccacag atggcacgtt tgatctgact 5940
gtccttagca atgatggagt tcacagcaca gtcacgagca acatccgagt tttctttgct 6000
ggattttcca atgccacagt ggataacagc atcttacttc gtctcggcgt accaacagta 6060
aaggacttct tgaccaacca ctatcttcat tttttacgca ttgccagctc acagctgaca 6120
ggcttaggga ctgctgtgca actgtacagt gcatatgaag agaacaatag aacgtttctt 6180
ttggcagctg tgaagcgaaa tcataatcag tatgtgaatc ccagtggcgt agccaccttc 6240
tttgaaagca tcaaagagat ccttctccgg cagagtggag taaaggtgga atctgtggat 6300
catgactcct gtgtgcatgg cccatgtcag aatggaggga gctgtctacg aagattggct 6360
gtgagctccg tattaaaaag ccgtgagagt cttccagtca tcatcgtggc aaatgaacct 6420
ctgcagcctt tcttatgcaa gtgtctgcca ggatatgcgg gtagctggtg tgaaatagat 6480
atagatgaat gtcttccatc accttgccac agtggtggaa cctgtcacaa tttagtggga 6540
ggattttcat gcagctgccc agatggcttc actggtaggg cgtgtgagag agatatcaat 6600
gagtgcctgc agagtccttg caagaatggt gccatctgcc agaattttcc aggaagcttc 6660
aactgtgttt gcaaaactgg atacacaggt gtctttggaa aacactgcga gttgaacagt 6720
tatggatttg aggagttatc atacatggaa tttccaagct tggaccccaa taacaactat 6780
atttatgtca aatttgccac gattaaaagt catgccttat tgctttacaa ctatgacaac 6840
cagacaggcg accgggctga gtttttggcc cttgaaattg ccgaagaaag actaagattc 6900
tcttataatt taggcagtgg tacatataag ctcaccacca tgaagaaggt gtcagatgga 6960
cattttcaca ctgtgattgc caggagagca ggaatggcag cctccttaac tgtggactcc 7020

-continued

```
tgttctgaga accaagagcc aggatattgt actgtcagta atgtggcagt ttcagatgac   7080
tggactcttg atgttcagcc aaatagagtt acagttggag gtatcagatc tctagaacca   7140
atccttcaga gaagaggaca cgtggaaagc catgattttg ttgggtgtat aatggagttt   7200
gcagtcaatg gaaggcctct ggaacccagc caagctttgg cagcacaagg catcctagat   7260
cagtatggcg attttatttc ttactgtttt aaagaaaaaa aatgcaaaaa agtatgcttc   7320
actgttactc ctgacactgc cttatcatta gaaggcaaag ggcgcttgga ctaccacatg   7380
agtcagaatg agaagcggga atatttgtta aggcaaagct tacgaggtgc catgttggag   7440
ccttttggtg tgaacagtct ggaagtaaaa tttaggacca gaagcgagaa tggcgtttta   7500
atccatatcc aagaaagcag caattacact actgtgaaga ttaagaatgg caaagtatat   7560
tttacatccg atgcaggaat tgctgggaaa gtggagagaa atattcctga agtatatgtt   7620
gcagacggcc actggcacac ttttctaatt gggaaaaatg gaacagcaac agtattgtct   7680
gttgacagaa tatataacag agatattatc caccctactc aggacttcgg tggccttgat   7740
gtgcttacta tatcacttgg aggaattcca cccaatcaag cacatcgaga tgcccaaaca   7800
gcaggttttg atggctgcat tgcttctatg tggtatggtg gagaaagtct tcctttcagc   7860
gggaagcata gcttggcctc catctcaaaa acagatccct cagtgaagat tggctgccgt   7920
ggcccgaaca tttgtgccag caacccctgc tggggtgatt tgctgtgcat taatcagtgg   7980
tatgcctaca ggtgtgtccc tcctggggac tgtgcctccc acccgtgcca gaatggtggc   8040
agctgtgagc caggcctgca ctccggcttc acctgtagct gcccagactc gcacacggga   8100
aggacctgtg agatggtggt ggcctgtctt ggcgtcctct gtcctcaggg gaaggtgtgc   8160
aaagctggaa gtcctgcggg gcatgtctgt gttctgagtc agggccctga agagatctct   8220
ctgcctttgt gggctgtgcc tgccatcgtg ggcagctgcg caaccgtctt ggccctcctg   8280
gtccttagcc tgatcctgtg taaccagtgc aggggggaaga aggccaaaaa tcccaaagag   8340
gagaagaaac cgaaggagaa gaagaaaaag ggaagtgaga acgttgcttt tgatgaccct   8400
gacaatatcc ctccctatgg ggatgacatg actgtgagga agcagcctga agggaaccca   8460
aaaccagata tcattgaaag ggaaaacccc taccttatct atgatgaaac tgatattcct   8520
cacaactcag aaaccatccc cagcgcccct ttggcatctc cagagcagga gatagagcac   8580
tatgacattg acaacgccag cagcatcgcc ccttcggatg cagacatcat tcaacactac   8640
aagcagttcc gcagccacac accaaaattt tcaatccaga ggcacagtcc cctaggcttt   8700
gcaaggcaat cccccatgcc cttaggagca agcagtttga cttaccagcc ttcatatggt   8760
caaggtttga gaaccagctc cctaagccac tcagcatgcc caactcccaa ccctctgtct   8820
cgacacagtc cagccccttt ctccaaatct tctacgttct atagaaacag cccagcaagg   8880
gaattgcatc ttcctataag ggatggtaat actttggaaa tgcatggtga cacctgccaa   8940
cctggcattt tcaactatgc cacaaggctg ggaaggagaa gcaagagtcc tcaggccatg   9000
gcatcacatg gttctagacc agggagtcgc ctaaagcagc cgattgggca gattccactg   9060
gaatcttctc ctccagtcgg actttctatt gaagaagtgg agaggctcaa cacacctcgc   9120
cctagaaacc caagtatctg cagtgcagac catgggaggt cttcttcaga ggaggactgc   9180
agaaggccac tgtctagaac aaggaatcca gcggatggca ttccagctcc agaatcctct   9240
tctgatagtg actcccatga atctttcact tgctcagaaa tggaatatga cagggagaag   9300
ccaatggtat atacttccag aatgcccaaa ttatctcaag tcaatgaatc tgatgcagat   9360
gatgaagata attatggagc cagactgaag cctcgaaggt accacggtcg cagggccgag   9420
```

```
ggaggacctg tgggcaccca ggcagcagca ccaggcactg ctgacaacac actgcccatg   9480

aagctagggc agcaagcagg gactttcaac tgggacaacc ttttgaactg gggccctggc   9540

tttggccatt atgtagatgt ttttaaagat ttggcatctc ttccagaaaa agcagcagca   9600

aatgaagaag gcaaagctgg gacaactaaa ccagtcccca aagatgggga agcagaacag   9660

tatgtgtga                                                           9669
```

<210> SEQ ID NO 7
<211> LENGTH: 551
<212> TYPE: DNA
<213> ORGANISM: Homo sapiens

<400> SEQUENCE: 7

```
gtgatgttca cagaaaattt gaaatattta ttagctagac tagttgtatt ctttccaaca     60

ttgttgtatg atctttcttg taacgttttc ttgcatttct acctcagttt tttaattata    120

gtaaatagaa gttacgatat taaaactata tgacatatcc ctatttctgc tttctgcttt    180

agttatagga tcatcggtgg aaactctcag ttcacgatca acccatcgac aggacaaatc    240

atcaccagcg cattgttaga tagggaaaca aaagataatt atactttggt agtggtctgc    300

agtgatgcgg gatccccaga gcctctttcc agttccacca gtgtgcttgt cactgtgact    360

gatgtcaatg acaatccacc aagatttcag catcacccat atgtcactca catcccatct    420

cctactcttc caggttcctt tgtctttgcg gttacagtca cagatgctga tattggacca    480

aattctgaac tgcattattc tctttcgggt agaaattctg aaaaatttca cattgaccca    540

ctgaggggag c                                                         551
```

<210> SEQ ID NO 8
<211> LENGTH: 4981
<212> TYPE: PRT
<213> ORGANISM: Homo sapiens

<400> SEQUENCE: 8

```
Met Asp Leu Ala Pro Asp Arg Ala Thr Gly Arg Pro Trp Leu Pro Leu
1               5                   10                  15

His Thr Leu Ser Val Ser Gln Leu Leu Arg Val Phe Trp Leu Leu Ser
            20                  25                  30

Leu Leu Pro Gly Gln Ala Trp Val His Gly Ala Glu Pro Arg Gln Val
        35                  40                  45

Phe Gln Val Leu Glu Glu Gln Pro Pro Gly Thr Leu Val Gly Thr Ile
    50                  55                  60

Gln Thr Arg Pro Gly Phe Thr Tyr Arg Leu Ser Glu Ser His Ala Leu
65                  70                  75                  80

Phe Ala Ile Asn Ser Ser Thr Gly Ala Leu Tyr Thr Thr Ser Thr Ile
                85                  90                  95

Asp Arg Glu Ser Leu Pro Ser Asp Val Ile Asn Leu Val Val Leu Ser
            100                 105                 110

Ser Ala Pro Thr Tyr Pro Thr Glu Val Arg Val Leu Val Arg Asp Leu
        115                 120                 125

Asn Asp Asn Ala Pro Val Phe Pro Asp Pro Ser Ile Val Val Thr Phe
    130                 135                 140

Lys Glu Asp Ser Ser Ser Gly Arg Gln Val Ile Leu Asp Thr Ala Thr
145                 150                 155                 160

Asp Ser Asp Ile Gly Ser Asn Gly Val Asp His Arg Ser Tyr Arg Ile
                165                 170                 175
```

```
Ile Arg Gly Asn Glu Ala Gly Arg Phe Arg Leu Asp Ile Thr Leu Asn
            180                 185                 190

Pro Ser Gly Glu Gly Ala Phe Leu His Leu Val Ser Lys Gly Gly Leu
        195                 200                 205

Asp Arg Glu Val Thr Pro Gln Tyr Gln Leu Leu Val Glu Val Glu Asp
    210                 215                 220

Lys Gly Glu Pro Lys Arg Arg Gly Tyr Leu Gln Val Asn Val Thr Val
225                 230                 235                 240

Gln Asp Ile Asn Asp Asn Pro Pro Val Phe Gly Ser Ser His Tyr Gln
                245                 250                 255

Ala Gly Val Pro Glu Asp Ala Val Val Gly Ser Ser Val Leu Gln Val
            260                 265                 270

Ala Ala Ala Asp Ala Asp Glu Gly Thr Asn Ala Asp Ile Arg Tyr Arg
        275                 280                 285

Leu Gln Asp Glu Gly Thr Pro Phe Gln Met Asp Pro Glu Thr Gly Leu
    290                 295                 300

Ile Thr Val Arg Glu Pro Leu Asp Phe Glu Ala Arg Arg Gln Tyr Ser
305                 310                 315                 320

Leu Thr Val Gln Ala Met Asp Arg Gly Val Pro Ser Leu Thr Gly Arg
                325                 330                 335

Ala Glu Ala Leu Ile Gln Leu Leu Asp Val Asn Asp Asn Asp Pro Val
            340                 345                 350

Val Lys Phe Arg Tyr Phe Pro Ala Thr Ser Arg Tyr Ala Ser Val Asp
        355                 360                 365

Glu Asn Ala Gln Val Gly Thr Val Val Ala Leu Leu Thr Val Thr Asp
    370                 375                 380

Ala Asp Ser Pro Ala Ala Asn Gly Asn Ile Ser Val Gln Ile Leu Gly
385                 390                 395                 400

Gly Asn Glu Gln Arg His Phe Glu Val Gln Ser Ser Lys Val Pro Asn
                405                 410                 415

Leu Ser Leu Ile Lys Val Ala Ser Ala Leu Asp Arg Glu Arg Ile Pro
            420                 425                 430

Ser Tyr Asn Leu Thr Val Ser Val Ser Asp Asn Tyr Gly Ala Pro Pro
        435                 440                 445

Gly Ala Ala Val Gln Ala Arg Ser Ser Val Ala Ser Leu Val Ile Phe
    450                 455                 460

Val Asn Asp Ile Asn Asp His Pro Pro Val Phe Ser Gln Gln Val Tyr
465                 470                 475                 480

Arg Val Asn Leu Ser Glu Glu Ala Pro Pro Gly Ser Tyr Val Ser Gly
                485                 490                 495

Ile Ser Ala Thr Asp Gly Asp Ser Gly Leu Asn Ala Asn Leu Arg Tyr
            500                 505                 510

Ser Ile Val Ser Gly Asn Gly Leu Gly Trp Phe His Ile Ser Glu His
        515                 520                 525

Ser Gly Leu Val Thr Thr Gly Ser Ser Gly Gly Leu Asp Arg Glu Leu
    530                 535                 540

Ala Ser Gln Ile Val Leu Asn Ile Ser Ala Arg Asp Gln Gly Val His
545                 550                 555                 560

Pro Lys Val Ser Tyr Ala Gln Leu Val Val Thr Leu Leu Asp Val Asn
                565                 570                 575

Asp Glu Lys Pro Val Phe Ser Gln Pro Glu Gly Tyr Asp Val Ser Val
            580                 585                 590
```

-continued

```
Val Glu Asn Ala Pro Thr Gly Thr Glu Leu Leu Met Leu Arg Ala Thr
        595                 600                 605

Asp Gly Asp Leu Gly Asp Asn Gly Thr Val Arg Phe Ser Leu Gln Glu
    610                 615                 620

Ala Glu Thr Asp Arg Arg Ser Phe Arg Leu Asp Pro Val Ser Gly Arg
625                 630                 635                 640

Leu Ser Thr Ile Ser Ser Leu Asp Arg Glu Glu Gln Ala Phe Tyr Ser
                645                 650                 655

Leu Leu Val Leu Ala Thr Asp Leu Gly Ser Pro Pro Gln Ser Ser Met
            660                 665                 670

Ala Arg Ile Asn Val Ser Leu Leu Asp Ile Asn Asp Asn Ser Pro Val
        675                 680                 685

Phe Tyr Pro Val Gln Tyr Phe Ala His Ile Lys Glu Asn Glu Pro Gly
    690                 695                 700

Gly Ser Tyr Ile Thr Thr Val Ser Ala Thr Asp Pro Asp Leu Gly Thr
705                 710                 715                 720

Asn Gly Thr Val Lys Tyr Ser Ile Ser Ala Gly Asp Arg Ser Arg Phe
                725                 730                 735

Gln Val Asn Ala Gln Ser Gly Val Ile Ser Thr Arg Met Ala Leu Asp
            740                 745                 750

Arg Glu Glu Lys Thr Ala Tyr Gln Leu Gln Ile Val Ala Thr Asp Gly
        755                 760                 765

Gly Asn Leu Gln Ser Pro Asn Gln Ala Ile Val Thr Ile Thr Val Leu
    770                 775                 780

Asp Thr Gln Asp Asn Pro Pro Val Phe Ser Gln Val Ala Tyr Ser Phe
785                 790                 795                 800

Val Val Phe Glu Asn Val Ala Leu Gly Tyr His Val Gly Ser Val Ser
                805                 810                 815

Ala Ser Thr Met Asp Leu Asn Ser Asn Ile Ser Tyr Leu Ile Thr Thr
            820                 825                 830

Gly Asp Gln Lys Gly Met Phe Ala Ile Asn Gln Val Thr Gly Gln Leu
        835                 840                 845

Thr Thr Ala Asn Val Ile Asp Arg Glu Glu Gln Ser Phe Tyr Gln Leu
    850                 855                 860

Lys Val Val Ala Ser Gly Gly Thr Val Thr Gly Asp Thr Met Val Asn
865                 870                 875                 880

Ile Thr Val Lys Asp Leu Asn Asp Asn Ser Pro His Phe Leu Gln Ala
                885                 890                 895

Ile Glu Ser Val Asn Val Val Glu Asn Trp Gln Ala Gly His Ser Ile
            900                 905                 910

Phe Gln Ala Lys Ala Val Asp Pro Asp Glu Gly Val Asn Gly Met Val
        915                 920                 925

Leu Tyr Ser Leu Lys Gln Asn Pro Lys Asn Leu Phe Ala Ile Asn Glu
    930                 935                 940

Lys Asn Gly Thr Ile Ser Leu Leu Gly Pro Leu Asp Val His Ala Gly
945                 950                 955                 960

Ser Tyr Gln Ile Glu Ile Leu Ala Ser Asp Met Gly Val Pro Gln Leu
                965                 970                 975

Ser Ser Ser Val Ile Leu Thr Val Tyr Val His Asp Val Asn Asp Asn
            980                 985                 990

Ser Pro Val Phe Asp Gln Leu Ser  Tyr Glu Val Thr Leu  Ser Glu Ser
        995                 1000                1005

Glu Pro  Val Asn Ser Arg Phe  Phe Lys Val Gln Ala  Ser Asp Lys
```

```
    1010                1015                1020

Asp Ser  Gly Ala Asn Gly Glu  Ile Ala Tyr Thr Ile  Ala Glu Gly
    1025                1030                1035

Asn Thr  Gly Asp Ala Phe Gly  Ile Phe Pro Asp Gly  Gln Leu Tyr
    1040                1045                1050

Ile Lys  Ser Glu Leu Asp Arg  Glu Leu Gln Asp Arg  Tyr Val Leu
    1055                1060                1065

Met Val  Val Ala Ser Asp Arg  Ala Val Glu Pro Leu  Ser Ala Thr
    1070                1075                1080

Val Asn  Val Thr Val Ile Leu  Glu Asp Val Asn Asp  Asn Arg Pro
    1085                1090                1095

Leu Phe  Asn Ser Thr Asn Tyr  Thr Phe Tyr Phe Glu  Glu Glu Gln
    1100                1105                1110

Arg Ala  Gly Ser Phe Val Gly  Lys Val Ser Ala Val  Asp Lys Asp
    1115                1120                1125

Phe Gly  Pro Asn Gly Glu Val  Arg Tyr Ser Phe Glu  Met Val Gln
    1130                1135                1140

Pro Asp  Phe Glu Leu His Ala  Ile Ser Gly Glu Ile  Thr Asn Thr
    1145                1150                1155

His Gln  Phe Asp Arg Glu Ser  Leu Met Arg Arg Arg  Gly Thr Ala
    1160                1165                1170

Val Phe  Ser Phe Thr Val Ile  Ala Thr Asp Gln Gly  Ile Pro Gln
    1175                1180                1185

Pro Leu  Lys Asp Gln Ala Thr  Val His Val Tyr Met  Lys Asp Ile
    1190                1195                1200

Asn Asp  Asn Ala Pro Lys Phe  Leu Lys Asp Phe Tyr  Gln Ala Thr
    1205                1210                1215

Ile Ser  Glu Ser Ala Ala Asn  Leu Thr Gln Val Leu  Arg Val Ser
    1220                1225                1230

Ala Ser  Asp Val Asp Glu Gly  Asn Asn Gly Leu Ile  His Tyr Ser
    1235                1240                1245

Ile Ile  Lys Gly Asn Glu Glu  Arg Gln Phe Ala Ile  Asp Ser Thr
    1250                1255                1260

Ser Gly  Gln Val Thr Leu Ile  Gly Lys Leu Asp Tyr  Glu Ala Thr
    1265                1270                1275

Pro Ala  Tyr Ser Leu Val Ile  Gln Ala Val Asp Ser  Gly Thr Ile
    1280                1285                1290

Pro Leu  Asn Ser Thr Cys Thr  Leu Asn Ile Asp Ile  Leu Asp Glu
    1295                1300                1305

Asn Asp  Asn Thr Pro Ser Phe  Pro Lys Ser Thr Leu  Phe Val Asp
    1310                1315                1320

Val Leu  Glu Asn Met Arg Ile  Gly Glu Leu Val Ser  Ser Val Thr
    1325                1330                1335

Ala Thr  Asp Ser Asp Ser Gly  Asp Asn Ala Asp Leu  Tyr Tyr Ser
    1340                1345                1350

Ile Thr  Gly Thr Asn Asn His  Gly Thr Phe Ser Ile  Ser Pro Asn
    1355                1360                1365

Thr Gly  Ser Ile Phe Leu Ala  Lys Lys Leu Asp Phe  Glu Thr Gln
    1370                1375                1380

Ser Leu  Tyr Lys Leu Asn Ile  Thr Ala Lys Asp Gln  Gly Arg Pro
    1385                1390                1395

Pro Arg  Ser Ser Thr Met Ser  Val Val Ile His Val  Arg Asp Phe
    1400                1405                1410
```

-continued

Asn Asp Asn Pro Pro Ser Phe Pro Pro Gly Asp Ile Phe Lys Ser
1415 1420 1425

Ile Val Glu Asn Ile Pro Ile Gly Thr Ser Val Ile Ser Val Thr
1430 1435 1440

Ala His Asp Pro Asp Ala Asp Ile Asn Gly Gln Leu Ser Tyr Thr
1445 1450 1455

Ile Ile Gln Gln Met Pro Arg Gly Asn His Phe Thr Ile Asp Glu
1460 1465 1470

Val Lys Gly Thr Ile Tyr Thr Asn Ala Glu Ile Asp Arg Glu Phe
1475 1480 1485

Ala Asn Leu Phe Glu Leu Thr Val Lys Ala Asn Asp Gln Ala Val
1490 1495 1500

Pro Ile Glu Thr Arg Arg Tyr Ala Leu Lys Asn Val Thr Ile Leu
1505 1510 1515

Val Thr Asp Leu Asn Asp Asn Val Pro Met Phe Ile Ser Gln Asn
1520 1525 1530

Ala Leu Ala Ala Asp Pro Ser Ala Val Ile Gly Ser Val Leu Thr
1535 1540 1545

Thr Ile Met Ala Ala Asp Pro Asp Glu Gly Ala Asn Gly Glu Ile
1550 1555 1560

Glu Tyr Glu Ile Ile Asn Gly Asp Thr Asp Thr Phe Ile Val Asp
1565 1570 1575

Arg Tyr Ser Gly Asp Leu Arg Val Ala Ser Ala Leu Val Pro Ser
1580 1585 1590

Gln Leu Ile Tyr Asn Leu Ile Val Ser Ala Thr Asp Leu Gly Pro
1595 1600 1605

Glu Arg Arg Lys Ser Thr Thr Glu Leu Thr Ile Ile Leu Gln Gly
1610 1615 1620

Leu Asp Gly Pro Val Phe Thr Gln Pro Lys Tyr Ile Thr Ile Leu
1625 1630 1635

Lys Glu Gly Glu Pro Ile Gly Thr Asn Val Ile Ser Ile Glu Ala
1640 1645 1650

Ala Ser Pro Arg Gly Ser Glu Ala Pro Val Glu Tyr Tyr Ile Val
1655 1660 1665

Ser Val Arg Cys Glu Glu Lys Thr Val Gly Arg Leu Phe Thr Ile
1670 1675 1680

Gly Arg His Thr Gly Ile Ile Gln Thr Ala Ala Ile Leu Asp Arg
1685 1690 1695

Glu Gln Gly Ala Cys Leu Tyr Leu Val Asp Val Tyr Ala Ile Glu
1700 1705 1710

Lys Ser Thr Ala Phe Pro Arg Thr Gln Arg Ala Glu Val Glu Ile
1715 1720 1725

Thr Leu Gln Asp Ile Asn Asp Asn Pro Pro Val Phe Pro Thr Asp
1730 1735 1740

Met Leu Asp Leu Thr Val Glu Glu Asn Ile Gly Asp Gly Ser Lys
1745 1750 1755

Ile Met Gln Leu Thr Ala Met Asp Ala Asp Glu Gly Ala Asn Ala
1760 1765 1770

Leu Val Thr Tyr Thr Ile Ile Ser Gly Ala Asp Asp Ser Phe Arg
1775 1780 1785

Ile Asp Pro Glu Ser Gly Asp Leu Ile Ala Thr Arg Arg Leu Asp
1790 1795 1800

Arg Glu Arg Arg Ser Lys Tyr Ser Leu Leu Val Arg Ala Asp Asp
1805 1810 1815

Gly Leu Gln Ser Ser Asp Met Arg Ile Asn Ile Thr Val Ser Asp
1820 1825 1830

Val Asn Asp His Thr Pro Lys Phe Ser Arg Pro Val Tyr Ser Phe
1835 1840 1845

Asp Ile Pro Glu Asp Thr Ile Pro Gly Ser Leu Val Ala Ala Ile
1850 1855 1860

Leu Ala Thr Asp Asp Asp Ser Gly Val Asn Gly Glu Ile Thr Tyr
1865 1870 1875

Ile Val Asn Glu Asp Asp Glu Asp Gly Ile Phe Phe Leu Asn Pro
1880 1885 1890

Ile Thr Gly Val Phe Asn Leu Thr Arg Leu Leu Asp Tyr Glu Val
1895 1900 1905

Gln Gln Tyr Tyr Ile Leu Thr Val Arg Ala Glu Asp Gly Gly Gly
1910 1915 1920

Gln Phe Thr Thr Ile Arg Val Tyr Phe Asn Ile Leu Asp Val Asn
1925 1930 1935

Asp Asn Pro Pro Ile Phe Ser Leu Asn Ser Tyr Ser Thr Ser Leu
1940 1945 1950

Met Glu Asn Leu Pro Val Gly Ser Thr Val Leu Val Phe Asn Val
1955 1960 1965

Thr Asp Ala Asp Asp Gly Ile Asn Ser Gln Leu Thr Tyr Ser Ile
1970 1975 1980

Ala Ser Gly Asp Ser Leu Gly Gln Phe Thr Val Asp Lys Asn Gly
1985 1990 1995

Val Leu Lys Val Leu Lys Ala Leu Asp Arg Glu Ser Gln Ser Phe
2000 2005 2010

Tyr Asn Leu Val Val Gln Val His Asp Leu Pro Gln Ile Pro Ala
2015 2020 2025

Ser Arg Phe Thr Ser Thr Ala Gln Val Ser Ile Ile Leu Leu Asp
2030 2035 2040

Val Asn Asp Asn Pro Pro Thr Phe Leu Ser Pro Lys Leu Thr Tyr
2045 2050 2055

Ile Pro Glu Asn Thr Pro Ile Asp Thr Val Val Phe Lys Ala Gln
2060 2065 2070

Ala Thr Asp Pro Asp Ser Gly Pro Asn Ser Tyr Ile Glu Tyr Thr
2075 2080 2085

Leu Leu Asn Pro Leu Gly Asn Lys Phe Ser Ile Gly Thr Ile Asp
2090 2095 2100

Gly Glu Val Arg Leu Thr Gly Glu Leu Asp Arg Glu Glu Val Ser
2105 2110 2115

Asn Tyr Thr Leu Thr Val Val Ala Thr Asp Lys Gly Gln Pro Ser
2120 2125 2130

Leu Ser Ser Ser Thr Glu Val Val Val Met Val Leu Asp Ile Asn
2135 2140 2145

Asp Asn Asn Pro Ile Phe Ala Gln Ala Leu Tyr Lys Val Glu Ile
2150 2155 2160

Asn Glu Asn Thr Leu Thr Gly Thr Asp Ile Ile Gln Val Phe Ala
2165 2170 2175

Ala Asp Gly Asp Glu Gly Thr Asn Gly Gln Val Arg Tyr Gly Ile
2180 2185 2190

Val Asn Gly Asn Thr Asn Gln Glu Phe Arg Ile Asp Ser Val Thr

-continued

```
    2195                2200                2205

Gly Ala  Ile Thr Val Ala Lys  Pro Leu Asp Arg Glu  Lys Thr Pro
    2210                2215                2220

Thr Tyr  His Leu Thr Val Gln  Ala Thr Asp Arg Gly  Ser Thr Pro
    2225                2230                2235

Arg Thr  Asp Thr Ser Thr Val  Ser Ile Val Leu Leu  Asp Ile Asn
    2240                2245                2250

Asp Phe  Val Pro Val Phe Glu  Leu Ser Pro Tyr Ser  Val Asn Val
    2255                2260                2265

Pro Glu  Asn Leu Gly Thr Leu  Pro Arg Thr Ile Leu  Gln Val Val
    2270                2275                2280

Ala Arg  Asp Asp Asp Arg Gly  Ser Asn Ser Lys Leu  Ser Tyr Val
    2285                2290                2295

Leu Phe  Gly Gly Asn Glu Asp  Asn Ala Phe Thr Leu  Ser Ala Ser
    2300                2305                2310

Gly Glu  Leu Gly Val Thr Gln  Ser Leu Asp Arg Glu  Thr Lys Glu
    2315                2320                2325

Arg Phe  Val Leu Met Ile Thr  Ala Thr Asp Ser Gly  Ser Pro Ala
    2330                2335                2340

Leu Thr  Gly Thr Gly Thr Ile  Asn Val Ile Val Asp  Asp Val Asn
    2345                2350                2355

Asp Asn  Val Pro Thr Phe Ala  Ser Lys Ala Tyr Phe  Thr Thr Ile
    2360                2365                2370

Pro Glu  Asp Ala Pro Thr Gly  Thr Asp Val Leu Leu  Val Asn Ala
    2375                2380                2385

Ser Asp  Ala Asp Ala Ser Lys  Asn Ala Val Ile Arg  Ile Ile Gly
    2390                2395                2400

Gly Asn  Ser Gln Phe Thr Ile  Asn Pro Ser Thr Gly  Gln Ile Ile
    2405                2410                2415

Thr Ser  Ala Leu Leu Asp Arg  Glu Thr Lys Asp Asn  Tyr Thr Leu
    2420                2425                2430

Val Val  Val Cys Ser Asp Ala  Gly Ser Pro Glu Pro  Leu Ser Ser
    2435                2440                2445

Ser Thr  Ser Val Leu Val Thr  Val Thr Asp Val Asn  Asp Asn Pro
    2450                2455                2460

Pro Arg  Phe Gln His His Pro  Tyr Val Thr His Ile  Pro Ser Pro
    2465                2470                2475

Thr Leu  Pro Gly Ser Phe Val  Phe Ala Val Thr Val  Thr Asp Ala
    2480                2485                2490

Asp Ile  Gly Pro Asn Ser Glu  Leu His Tyr Ser Leu  Ser Gly Arg
    2495                2500                2505

Asn Ser  Glu Lys Phe His Ile  Asp Pro Leu Arg Gly  Ala Ile Met
    2510                2515                2520

Ala Ala  Gly Pro Leu Asn Gly  Ala Ser Glu Val Thr  Phe Ser Val
    2525                2530                2535

His Val  Lys Asp Gly Gly Ser  Phe Pro Lys Thr Asp  Ser Thr Thr
    2540                2545                2550

Val Thr  Val Arg Phe Val Asn  Lys Ala Asp Phe Pro  Lys Val Arg
    2555                2560                2565

Ala Lys  Glu Gln Thr Phe Met  Phe Pro Glu Asn Gln  Pro Val Ser
    2570                2575                2580

Ser Leu  Val Thr Thr Ile Thr  Gly Ser Ser Leu Arg  Gly Glu Pro
    2585                2590                2595
```

Met Ser Tyr Tyr Ile Ala Ser Gly Asn Leu Gly Asn Thr Phe Gln
2600 2605 2610

Ile Asp Gln Leu Thr Gly Gln Val Ser Ile Ser Gln Pro Leu Asp
2615 2620 2625

Phe Glu Lys Ile Gln Lys Tyr Val Val Trp Ile Glu Ala Arg Asp
2630 2635 2640

Gly Gly Phe Pro Pro Phe Ser Ser Tyr Glu Lys Leu Asp Ile Thr
2645 2650 2655

Val Leu Asp Val Asn Asp Asn Ala Pro Ile Phe Lys Glu Asp Pro
2660 2665 2670

Phe Ile Ser Glu Ile Leu Glu Asn Leu Ser Pro Arg Lys Ile Leu
2675 2680 2685

Thr Val Ser Ala Met Asp Lys Asp Ser Gly Pro Asn Gly Gln Leu
2690 2695 2700

Asp Tyr Glu Ile Val Asn Gly Asn Met Glu Asn Ser Phe Ser Ile
2705 2710 2715

Asn His Ala Thr Gly Glu Ile Arg Ser Val Arg Pro Leu Asp Arg
2720 2725 2730

Glu Lys Val Ser His Tyr Val Leu Thr Ile Lys Ser Ser Asp Lys
2735 2740 2745

Gly Ser Pro Ser Gln Ser Thr Ser Val Lys Val Met Ile Asn Ile
2750 2755 2760

Leu Asp Glu Asn Asp Asn Ala Pro Arg Phe Ser Gln Ile Phe Ser
2765 2770 2775

Ala His Val Pro Glu Asn Ser Pro Leu Gly Tyr Thr Val Thr Arg
2780 2785 2790

Val Thr Thr Ser Asp Glu Asp Ile Gly Ile Asn Ala Ile Ser Arg
2795 2800 2805

Tyr Ser Ile Met Asp Ala Ser Leu Pro Phe Thr Ile Asn Pro Ser
2810 2815 2820

Thr Gly Asp Ile Val Ile Ser Arg Pro Leu Asn Arg Glu Asp Thr
2825 2830 2835

Asp Arg Tyr Arg Ile Arg Val Ser Ala His Asp Ser Gly Trp Thr
2840 2845 2850

Val Ser Thr Asp Val Thr Ile Phe Val Thr Asp Ile Asn Asp Asn
2855 2860 2865

Ala Pro Arg Phe Ser Arg Thr Ser Tyr Tyr Leu Asp Cys Pro Glu
2870 2875 2880

Leu Thr Glu Ile Gly Ser Lys Val Thr Gln Val Phe Ala Thr Asp
2885 2890 2895

Pro Asp Glu Gly Ser Asn Gly Gln Val Phe Tyr Phe Ile Lys Ser
2900 2905 2910

Gln Ser Glu Tyr Phe Arg Ile Asn Ala Thr Thr Gly Glu Ile Phe
2915 2920 2925

Asn Lys Gln Ile Leu Lys Tyr Gln Asn Val Thr Gly Phe Ser Asn
2930 2935 2940

Val Asn Ile Asn Arg His Ser Phe Ile Val Thr Ser Ser Asp Arg
2945 2950 2955

Gly Lys Pro Ser Leu Ile Ser Glu Thr Thr Val Thr Ile Asn Ile
2960 2965 2970

Val Asp Ser Asn Asp Asn Ala Pro Gln Phe Leu Lys Ser Lys Tyr
2975 2980 2985

```
Phe Thr  Pro Val Thr Lys Asn  Val Lys Val Gly Thr  Lys Leu Ile
    2990                 2995                 3000

Arg Val  Thr Ala Ile Asp Asp  Lys Asp Phe Gly Leu  Asn Ser Glu
    3005                 3010                 3015

Val Glu  Tyr Phe Ile Ser Asn  Asp Asn His Leu Gly  Lys Phe Lys
    3020                 3025                 3030

Leu Asp  Asn Asp Thr Gly Trp  Ile Ser Val Ala Ser  Ser Leu Ile
    3035                 3040                 3045

Ser Asp  Leu Asn Gln Asn Phe  Phe Ile Thr Val Thr  Ala Lys Asp
    3050                 3055                 3060

Lys Gly  Asn Pro Pro Leu Ser  Ser Gln Ala Thr Val  His Ile Thr
    3065                 3070                 3075

Val Thr  Glu Glu Asn Tyr His  Thr Pro Glu Phe Ser  Gln Ser His
    3080                 3085                 3090

Met Ser  Ala Thr Ile Pro Glu  Ser His Ser Ile Gly  Ser Ile Val
    3095                 3100                 3105

Arg Thr  Val Ser Ala Arg Asp  Arg Asp Ala Ala Met  Asn Gly Leu
    3110                 3115                 3120

Ile Lys  Tyr Ser Ile Ser Ser  Gly Asn Glu Glu Gly  Ile Phe Ala
    3125                 3130                 3135

Ile Asn  Ser Ser Thr Gly Ile  Leu Thr Leu Ala Lys  Ala Leu Asp
    3140                 3145                 3150

Tyr Glu  Leu Cys Gln Lys His  Glu Met Thr Ile Ser  Ala Ile Asp
    3155                 3160                 3165

Gly Gly  Trp Val Ala Arg Thr  Gly Tyr Cys Ser Val  Thr Val Asn
    3170                 3175                 3180

Val Ile  Asp Val Asn Asp Asn  Ser Pro Val Phe Leu  Ser Asp Asp
    3185                 3190                 3195

Tyr Phe  Pro Thr Val Leu Glu  Asn Ala Pro Ser Gly  Thr Thr Val
    3200                 3205                 3210

Ile His  Leu Asn Ala Thr Asp  Ala Asp Ser Gly Thr  Asn Ala Val
    3215                 3220                 3225

Ile Ala  Tyr Thr Val Gln Ser  Ser Asp Ser Asp Leu  Phe Val Ile
    3230                 3235                 3240

Asp Pro  Asn Thr Gly Val Ile  Thr Thr Gln Gly Phe  Leu Asp Phe
    3245                 3250                 3255

Glu Thr  Lys Gln Ser Tyr His  Leu Thr Val Lys Ala  Phe Asn Val
    3260                 3265                 3270

Pro Asp  Glu Glu Arg Cys Ser  Phe Ala Thr Val Asn  Ile Gln Leu
    3275                 3280                 3285

Lys Gly  Thr Asn Glu Tyr Val  Pro Arg Phe Val Ser  Lys Leu Tyr
    3290                 3295                 3300

Tyr Phe  Glu Ile Ser Glu Ala  Ala Pro Lys Gly Thr  Ile Val Gly
    3305                 3310                 3315

Glu Val  Phe Ala Ser Asp Arg  Asp Leu Gly Thr Asp  Gly Glu Val
    3320                 3325                 3330

His Tyr  Leu Ile Phe Gly Asn  Ser Arg Lys Lys Gly  Phe Gln Ile
    3335                 3340                 3345

Asn Lys  Lys Thr Gly Gln Ile  Tyr Val Ser Gly Ile  Leu Asp Arg
    3350                 3355                 3360

Glu Lys  Glu Glu Arg Val Ser  Leu Lys Val Leu Ala  Lys Asn Phe
    3365                 3370                 3375

Gly Ser  Ile Arg Gly Ala Asp  Ile Asp Glu Val Thr  Val Asn Val
```

-continued

```
    3380                3385                3390

Thr Val  Leu Asp Ala Asn Asp  Pro Pro Ile Phe Thr  Leu Asn Ile
    3395                3400                3405

Tyr Ser  Val Gln Ile Ser Glu  Gly Val Pro Ile Gly  Thr His Val
    3410                3415                3420

Thr Phe  Val Ser Ala Phe Asp  Ser Asp Ser Ile Pro  Ser Trp Ser
    3425                3430                3435

Arg Phe  Ser Tyr Phe Ile Gly  Ser Gly Asn Glu Asn  Gly Ala Phe
    3440                3445                3450

Ser Ile  Asn Pro Gln Thr Gly  Gln Ile Thr Val Thr  Ala Glu Leu
    3455                3460                3465

Asp Arg  Glu Thr Leu Pro Ile  Tyr Asn Leu Ser Val  Leu Ala Val
    3470                3475                3480

Asp Ser  Gly Thr Pro Ser Ala  Thr Gly Ser Ala Ser  Leu Leu Val
    3485                3490                3495

Thr Leu  Glu Asp Ile Asn Asp  Asn Gly Pro Met Leu  Thr Val Ser
    3500                3505                3510

Glu Gly  Glu Val Met Glu Asn  Lys Arg Pro Gly Thr  Leu Val Met
    3515                3520                3525

Thr Leu  Gln Ser Thr Asp Pro  Asp Leu Pro Pro Asn  Gln Gly Pro
    3530                3535                3540

Phe Thr  Tyr Tyr Leu Leu Ser  Thr Gly Pro Ala Thr  Ser Tyr Phe
    3545                3550                3555

Ser Leu  Ser Thr Ala Gly Val  Leu Ser Thr Thr Arg  Glu Ile Asp
    3560                3565                3570

Arg Glu  Gln Ile Ala Asp Phe  Tyr Leu Ser Val Val  Thr Lys Asp
    3575                3580                3585

Ser Gly  Val Pro Gln Met Ser  Ser Thr Gly Thr Val  His Ile Thr
    3590                3595                3600

Val Ile  Asp Gln Asn Asp Asn  Pro Ser Gln Ser Arg  Thr Val Glu
    3605                3610                3615

Ile Phe  Val Asn Tyr Tyr Gly  Asn Leu Phe Pro Gly  Gly Ile Leu
    3620                3625                3630

Gly Ser  Val Lys Pro Gln Asp  Pro Asp Val Leu Asp  Ser Phe His
    3635                3640                3645

Cys Ser  Leu Thr Ser Gly Val  Thr Ser Leu Phe Ser  Ile Pro Gly
    3650                3655                3660

Gly Thr  Cys Asp Leu Asn Ser  Gln Pro Arg Ser Thr  Asp Gly Thr
    3665                3670                3675

Phe Asp  Leu Thr Val Leu Ser  Asn Asp Gly Val His  Ser Thr Val
    3680                3685                3690

Thr Ser  Asn Ile Arg Val Phe  Phe Ala Gly Phe Ser  Asn Ala Thr
    3695                3700                3705

Val Asp  Asn Ser Ile Leu Leu  Arg Leu Gly Val Pro  Thr Val Lys
    3710                3715                3720

Asp Phe  Leu Thr Asn His Tyr  Leu His Phe Leu Arg  Ile Ala Ser
    3725                3730                3735

Ser Gln  Leu Thr Gly Leu Gly  Thr Ala Val Gln Leu  Tyr Ser Ala
    3740                3745                3750

Tyr Glu  Glu Asn Asn Arg Thr  Phe Leu Leu Ala Ala  Val Lys Arg
    3755                3760                3765

Asn His  Asn Gln Tyr Val Asn  Pro Ser Gly Val Ala  Thr Phe Phe
    3770                3775                3780
```

-continued

Glu Ser Ile Lys Glu Ile Leu Leu Arg Gln Ser Gly Val Lys Val
3785 3790 3795

Glu Ser Val Asp His Asp Ser Cys Val His Gly Pro Cys Gln Asn
3800 3805 3810

Gly Gly Ser Cys Leu Arg Arg Leu Ala Val Ser Ser Val Leu Lys
3815 3820 3825

Ser Arg Glu Ser Leu Pro Val Ile Ile Val Ala Asn Glu Pro Leu
3830 3835 3840

Gln Pro Phe Leu Cys Lys Cys Leu Pro Gly Tyr Ala Gly Ser Trp
3845 3850 3855

Cys Glu Ile Asp Ile Asp Glu Cys Leu Pro Ser Pro Cys His Ser
3860 3865 3870

Gly Gly Thr Cys His Asn Leu Val Gly Gly Phe Ser Cys Ser Cys
3875 3880 3885

Pro Asp Gly Phe Thr Gly Arg Ala Cys Glu Arg Asp Ile Asn Glu
3890 3895 3900

Cys Leu Gln Ser Pro Cys Lys Asn Gly Ala Ile Cys Gln Asn Phe
3905 3910 3915

Pro Gly Ser Phe Asn Cys Val Cys Lys Thr Gly Tyr Thr Gly Lys
3920 3925 3930

Met Cys Glu Ser Ser Val Asn Tyr Cys Glu Cys Asn Pro Cys Phe
3935 3940 3945

Asn Gly Gly Ser Cys Gln Ser Gly Val Asp Ser Tyr Tyr Cys His
3950 3955 3960

Cys Pro Phe Gly Val Phe Gly Lys His Cys Glu Leu Asn Ser Tyr
3965 3970 3975

Gly Phe Glu Glu Leu Ser Tyr Met Glu Phe Pro Ser Leu Asp Pro
3980 3985 3990

Asn Asn Asn Tyr Ile Tyr Val Lys Phe Ala Thr Ile Lys Ser His
3995 4000 4005

Ala Leu Leu Leu Tyr Asn Tyr Asp Asn Gln Thr Gly Asp Arg Ala
4010 4015 4020

Glu Phe Leu Ala Leu Glu Ile Ala Glu Glu Arg Leu Arg Phe Ser
4025 4030 4035

Tyr Asn Leu Gly Ser Gly Thr Tyr Lys Leu Thr Thr Met Lys Lys
4040 4045 4050

Val Ser Asp Gly His Phe His Thr Val Ile Ala Arg Arg Ala Gly
4055 4060 4065

Met Ala Ala Ser Leu Thr Val Asp Ser Cys Ser Glu Asn Gln Glu
4070 4075 4080

Pro Gly Tyr Cys Thr Val Ser Asn Val Ala Val Ser Asp Asp Trp
4085 4090 4095

Thr Leu Asp Val Gln Pro Asn Arg Val Thr Val Gly Gly Ile Arg
4100 4105 4110

Ser Leu Glu Pro Ile Leu Gln Arg Arg Gly His Val Glu Ser His
4115 4120 4125

Asp Phe Val Gly Cys Ile Met Glu Phe Ala Val Asn Gly Arg Pro
4130 4135 4140

Leu Glu Pro Ser Gln Ala Leu Ala Ala Gln Gly Ile Leu Asp Gln
4145 4150 4155

Cys Pro Arg Leu Glu Gly Ala Cys Thr Arg Ser Pro Cys Gln His
4160 4165 4170

Gly Gly Thr Cys Met Asp Tyr Trp Ser Trp Gln Gln Cys His Cys
4175 4180 4185

Lys Glu Gly Leu Thr Gly Lys Tyr Cys Glu Lys Ser Val Thr Pro
4190 4195 4200

Asp Thr Ala Leu Ser Leu Glu Gly Lys Gly Arg Leu Asp Tyr His
4205 4210 4215

Met Ser Gln Asn Glu Lys Arg Glu Tyr Leu Leu Arg Gln Ser Leu
4220 4225 4230

Arg Gly Ala Met Leu Glu Pro Phe Gly Val Asn Ser Leu Glu Val
4235 4240 4245

Lys Phe Arg Thr Arg Ser Glu Asn Gly Val Leu Ile His Ile Gln
4250 4255 4260

Glu Ser Ser Asn Tyr Thr Thr Val Lys Ile Lys Asn Gly Lys Val
4265 4270 4275

Tyr Phe Thr Ser Asp Ala Gly Ile Ala Gly Lys Val Glu Arg Asn
4280 4285 4290

Ile Pro Glu Val Tyr Val Ala Asp Gly His Trp His Thr Phe Leu
4295 4300 4305

Ile Gly Lys Asn Gly Thr Ala Thr Val Leu Ser Val Asp Arg Ile
4310 4315 4320

Tyr Asn Arg Asp Ile Ile His Pro Thr Gln Asp Phe Gly Gly Leu
4325 4330 4335

Asp Val Leu Thr Ile Ser Leu Gly Gly Ile Pro Pro Asn Gln Ala
4340 4345 4350

His Arg Asp Ala Gln Thr Ala Gly Phe Asp Gly Cys Ile Ala Ser
4355 4360 4365

Met Trp Tyr Gly Gly Glu Ser Leu Pro Phe Ser Gly Lys His Ser
4370 4375 4380

Leu Ala Ser Ile Ser Lys Thr Asp Pro Ser Val Lys Ile Gly Cys
4385 4390 4395

Arg Gly Pro Asn Ile Cys Ala Ser Asn Pro Cys Trp Gly Asp Leu
4400 4405 4410

Leu Cys Ile Asn Gln Trp Tyr Ala Tyr Arg Cys Val Pro Pro Gly
4415 4420 4425

Asp Cys Ala Ser His Pro Cys Gln Asn Gly Gly Ser Cys Glu Pro
4430 4435 4440

Gly Leu His Ser Gly Phe Thr Cys Ser Cys Pro Asp Ser His Thr
4445 4450 4455

Gly Arg Thr Cys Glu Met Val Val Ala Cys Leu Gly Val Leu Cys
4460 4465 4470

Pro Gln Gly Lys Val Cys Lys Ala Gly Ser Pro Ala Gly His Val
4475 4480 4485

Cys Val Leu Ser Gln Gly Pro Glu Glu Ile Ser Leu Pro Leu Trp
4490 4495 4500

Ala Val Pro Ala Ile Val Gly Ser Cys Ala Thr Val Leu Ala Leu
4505 4510 4515

Leu Val Leu Ser Leu Ile Leu Cys Asn Gln Cys Arg Gly Lys Lys
4520 4525 4530

Ala Lys Asn Pro Lys Glu Glu Lys Lys Pro Lys Glu Lys Lys Lys
4535 4540 4545

Lys Gly Ser Glu Asn Val Ala Phe Asp Asp Pro Asp Asn Ile Pro
4550 4555 4560

Pro Tyr Gly Asp Asp Met Thr Val Arg Lys Gln Pro Glu Gly Asn 4565 4570 4575

Pro Lys Pro Asp Ile Ile Glu Arg Glu Asn Pro Tyr Leu Ile Tyr
4580 4585 4590

Asp Glu Thr Asp Ile Pro His Asn Ser Glu Thr Ile Pro Ser Ala
4595 4600 4605

Pro Leu Ala Ser Pro Glu Gln Glu Ile Glu His Tyr Asp Ile Asp
4610 4615 4620

Asn Ala Ser Ser Ile Ala Pro Ser Asp Ala Asp Ile Ile Gln His
4625 4630 4635

Tyr Lys Gln Phe Arg Ser His Thr Pro Lys Phe Ser Ile Gln Arg
4640 4645 4650

His Ser Pro Leu Gly Phe Ala Arg Gln Ser Pro Met Pro Leu Gly
4655 4660 4665

Ala Ser Ser Leu Thr Tyr Gln Pro Ser Tyr Gly Gln Gly Leu Arg
4670 4675 4680

Thr Ser Ser Leu Ser His Ser Ala Cys Pro Thr Pro Asn Pro Leu
4685 4690 4695

Ser Arg His Ser Pro Ala Pro Phe Ser Lys Ser Ser Thr Phe Tyr
4700 4705 4710

Arg Asn Ser Pro Ala Arg Glu Leu His Leu Pro Ile Arg Asp Gly
4715 4720 4725

Asn Thr Leu Glu Met His Gly Asp Thr Cys Gln Pro Gly Ile Phe
4730 4735 4740

Asn Tyr Ala Thr Arg Leu Gly Arg Arg Ser Lys Ser Pro Gln Ala
4745 4750 4755

Met Ala Ser His Gly Ser Arg Pro Gly Ser Arg Leu Lys Gln Pro
4760 4765 4770

Ile Gly Gln Ile Pro Leu Glu Ser Ser Pro Pro Val Gly Leu Ser
4775 4780 4785

Ile Glu Glu Val Glu Arg Leu Asn Thr Pro Arg Pro Arg Asn Pro
4790 4795 4800

Ser Ile Cys Ser Ala Asp His Gly Arg Ser Ser Ser Glu Glu Asp
4805 4810 4815

Cys Arg Arg Pro Leu Ser Arg Thr Arg Asn Pro Ala Asp Gly Ile
4820 4825 4830

Pro Ala Pro Glu Ser Ser Ser Asp Ser Asp Ser His Glu Ser Phe
4835 4840 4845

Thr Cys Ser Glu Met Glu Tyr Asp Arg Glu Lys Pro Met Val Tyr
4850 4855 4860

Thr Ser Arg Met Pro Lys Leu Ser Gln Val Asn Glu Ser Asp Ala
4865 4870 4875

Asp Asp Glu Asp Asn Tyr Gly Ala Arg Leu Lys Pro Arg Arg Tyr
4880 4885 4890

His Gly Arg Arg Ala Glu Gly Gly Pro Val Gly Thr Gln Ala Ala
4895 4900 4905

Ala Pro Gly Thr Ala Asp Asn Thr Leu Pro Met Lys Leu Gly Gln
4910 4915 4920

Gln Ala Gly Thr Phe Asn Trp Asp Asn Leu Leu Asn Trp Gly Pro
4925 4930 4935

Gly Phe Gly His Tyr Val Asp Val Phe Lys Asp Leu Ala Ser Leu
4940 4945 4950

Pro Glu Lys Ala Ala Ala Asn Glu Glu Gly Lys Ala Gly Thr Thr
4955 4960 4965

```
Lys Pro  Val Pro Lys Asp Gly  Glu Ala Glu Gln Tyr  Val
    4970                 4975                 4980


<210> SEQ ID NO 9
<211> LENGTH: 3222
<212> TYPE: PRT
<213> ORGANISM: Homo sapiens

<400> SEQUENCE: 9

Met Val Thr Thr Val Val Ala Val Gly Asp Thr Leu Ala Gln Pro Leu
1               5                   10                  15

Ala Ala Ala Glu Val Phe Ile Val Glu Ile Thr Leu Gln Asp Ile Asn
            20                  25                  30

Asp Asn Pro Pro Val Phe Pro Thr Asp Met Leu Asp Leu Thr Val Glu
        35                  40                  45

Glu Asn Ile Gly Asp Gly Ser Lys Ile Met Gln Leu Thr Ala Met Asp
    50                  55                  60

Ala Asp Glu Gly Ala Asn Ala Leu Val Thr Tyr Thr Ile Ile Ser Gly
65                  70                  75                  80

Ala Asp Asp Ser Phe Arg Ile Asp Pro Glu Ser Gly Asp Leu Ile Ala
                85                  90                  95

Thr Arg Arg Leu Asp Arg Glu Arg Arg Ser Lys Tyr Ser Leu Leu Val
            100                 105                 110

Arg Ala Asp Asp Gly Leu Gln Ser Ser Asp Met Arg Ile Asn Ile Thr
        115                 120                 125

Val Ser Asp Val Asn Asp His Thr Pro Lys Phe Ser Arg Pro Val Tyr
    130                 135                 140

Ser Phe Asp Ile Pro Glu Asp Thr Ile Pro Gly Ser Leu Val Ala Ala
145                 150                 155                 160

Ile Leu Ala Thr Asp Asp Asp Ser Gly Val Asn Gly Glu Ile Thr Tyr
                165                 170                 175

Ile Val Asn Glu Asp Asp Glu Asp Gly Ile Phe Phe Leu Asn Pro Ile
            180                 185                 190

Thr Gly Val Phe Asn Leu Thr Arg Leu Leu Asp Tyr Glu Val Gln Gln
        195                 200                 205

Tyr Tyr Ile Leu Thr Val Arg Ala Glu Asp Gly Gly Gly Gln Phe Thr
    210                 215                 220

Thr Ile Arg Val Tyr Phe Asn Ile Leu Asp Val Asn Asp Asn Pro Pro
225                 230                 235                 240

Ile Phe Ser Leu Asn Ser Tyr Ser Thr Ser Leu Met Glu Asn Leu Pro
                245                 250                 255

Val Gly Ser Thr Val Leu Val Phe Asn Val Thr Asp Ala Asp Asp Gly
            260                 265                 270

Ile Asn Ser Gln Leu Thr Tyr Ser Ile Ala Ser Gly Asp Ser Leu Gly
        275                 280                 285

Gln Phe Thr Val Asp Lys Asn Gly Val Leu Lys Val Leu Lys Ala Leu
    290                 295                 300

Asp Arg Glu Ser Gln Ser Phe Tyr Asn Leu Val Val Gln Val His Asp
305                 310                 315                 320

Leu Pro Gln Ile Pro Ala Ser Arg Phe Thr Ser Thr Ala Gln Val Ser
                325                 330                 335

Ile Ile Leu Leu Asp Val Asn Asp Asn Pro Pro Thr Phe Leu Ser Pro
            340                 345                 350

Lys Leu Thr Tyr Ile Pro Glu Asn Thr Pro Ile Asp Thr Val Val Phe
```

```
        355                 360                 365

Lys Ala Gln Ala Thr Asp Pro Asp Ser Gly Pro Asn Ser Tyr Ile Glu
    370                 375                 380

Tyr Thr Leu Leu Asn Pro Leu Gly Asn Lys Phe Ser Ile Gly Thr Ile
385                 390                 395                 400

Asp Gly Glu Val Arg Leu Thr Gly Glu Leu Asp Arg Glu Glu Val Ser
                405                 410                 415

Asn Tyr Thr Leu Thr Val Val Ala Thr Asp Lys Gly Gln Pro Ser Leu
            420                 425                 430

Ser Ser Ser Thr Glu Val Val Val Met Val Leu Asp Ile Asn Asp Asn
        435                 440                 445

Asn Pro Ile Phe Ala Gln Ala Leu Tyr Lys Val Glu Ile Asn Glu Asn
    450                 455                 460

Thr Leu Thr Gly Thr Asp Ile Ile Gln Val Phe Ala Ala Asp Gly Asp
465                 470                 475                 480

Glu Gly Thr Asn Gly Gln Val Arg Tyr Gly Ile Val Asn Gly Asn Thr
                485                 490                 495

Asn Gln Glu Phe Arg Ile Asp Ser Val Thr Gly Ala Ile Thr Val Ala
            500                 505                 510

Lys Pro Leu Asp Arg Glu Lys Thr Pro Thr Tyr His Leu Thr Val Gln
        515                 520                 525

Ala Thr Asp Arg Gly Ser Thr Pro Arg Thr Asp Thr Ser Thr Val Ser
    530                 535                 540

Ile Val Leu Leu Asp Ile Asn Asp Phe Val Pro Val Phe Glu Leu Ser
545                 550                 555                 560

Pro Tyr Ser Val Asn Val Pro Glu Asn Leu Gly Thr Leu Pro Arg Thr
                565                 570                 575

Ile Leu Gln Val Val Ala Arg Asp Asp Asp Arg Gly Ser Asn Ser Lys
            580                 585                 590

Leu Ser Tyr Val Leu Phe Gly Gly Asn Glu Asp Asn Ala Phe Thr Leu
        595                 600                 605

Ser Ala Ser Gly Glu Leu Gly Val Thr Gln Ser Leu Asp Arg Glu Thr
    610                 615                 620

Lys Glu Arg Phe Val Leu Met Ile Thr Ala Thr Asp Ser Gly Ser Pro
625                 630                 635                 640

Ala Leu Thr Gly Thr Gly Thr Ile Asn Val Ile Val Asp Asp Val Asn
                645                 650                 655

Asp Asn Val Pro Thr Phe Ala Ser Lys Ala Tyr Phe Thr Thr Ile Pro
            660                 665                 670

Glu Asp Ala Pro Thr Gly Thr Asp Val Leu Leu Val Asn Ala Ser Asp
        675                 680                 685

Ala Asp Ala Ser Lys Asn Ala Val Ile Arg Ile Ile Gly Gly Asn Ser
    690                 695                 700

Gln Phe Thr Ile Asn Pro Ser Thr Gly Gln Ile Ile Thr Ser Ala Leu
705                 710                 715                 720

Leu Asp Arg Glu Thr Lys Asp Asn Tyr Thr Leu Val Val Val Cys Ser
                725                 730                 735

Asp Ala Gly Ser Pro Glu Pro Leu Ser Ser Ser Thr Ser Val Leu Val
            740                 745                 750

Thr Val Thr Asp Val Asn Asp Asn Pro Pro Arg Phe Gln His His Pro
        755                 760                 765

Tyr Val Thr His Ile Pro Ser Pro Thr Leu Pro Gly Ser Phe Val Phe
    770                 775                 780
```

-continued

Ala Val Thr Val Thr Asp Ala Asp Ile Gly Pro Asn Ser Glu Leu His
785 790 795 800

Tyr Ser Leu Ser Gly Arg Asn Ser Glu Lys Phe His Ile Asp Pro Leu
805 810 815

Arg Gly Ala Ile Met Ala Ala Gly Pro Leu Asn Gly Ala Ser Glu Val
820 825 830

Thr Phe Ser Val His Val Lys Asp Gly Gly Ser Phe Pro Lys Thr Asp
835 840 845

Ser Thr Thr Val Thr Val Arg Phe Val Asn Lys Ala Asp Phe Pro Lys
850 855 860

Val Arg Ala Lys Glu Gln Thr Phe Met Phe Pro Glu Asn Gln Pro Val
865 870 875 880

Ser Ser Leu Val Thr Thr Ile Thr Gly Ser Ser Leu Arg Gly Glu Pro
885 890 895

Met Ser Tyr Tyr Ile Ala Ser Gly Asn Leu Gly Asn Thr Phe Gln Ile
900 905 910

Asp Gln Leu Thr Gly Gln Val Ser Ile Ser Gln Pro Leu Asp Phe Glu
915 920 925

Lys Ile Gln Lys Tyr Val Val Trp Ile Glu Ala Arg Asp Gly Gly Phe
930 935 940

Pro Pro Phe Ser Ser Tyr Glu Lys Leu Asp Ile Thr Val Leu Asp Val
945 950 955 960

Asn Asp Asn Ala Pro Ile Phe Lys Glu Asp Pro Phe Ile Ser Glu Ile
965 970 975

Leu Glu Asn Leu Ser Pro Arg Lys Ile Leu Thr Val Ser Ala Met Asp
980 985 990

Lys Asp Ser Gly Pro Asn Gly Gln Leu Asp Tyr Glu Ile Val Asn Gly
995 1000 1005

Asn Met Glu Asn Ser Phe Ser Ile Asn His Ala Thr Gly Glu Ile
1010 1015 1020

Arg Ser Val Arg Pro Leu Asp Arg Glu Lys Val Ser His Tyr Val
1025 1030 1035

Leu Thr Ile Lys Ser Ser Asp Lys Gly Ser Pro Ser Gln Ser Thr
1040 1045 1050

Ser Val Lys Val Met Ile Asn Ile Leu Asp Glu Asn Asp Asn Ala
1055 1060 1065

Pro Arg Phe Ser Gln Ile Phe Ser Ala His Val Pro Glu Asn Ser
1070 1075 1080

Pro Leu Gly Tyr Thr Val Thr Arg Val Thr Thr Ser Asp Glu Asp
1085 1090 1095

Ile Gly Ile Asn Ala Ile Ser Arg Tyr Ser Ile Met Asp Ala Ser
1100 1105 1110

Leu Pro Phe Thr Ile Asn Pro Ser Thr Gly Asp Ile Val Ile Ser
1115 1120 1125

Arg Pro Leu Asn Arg Glu Asp Thr Asp Arg Tyr Arg Ile Arg Val
1130 1135 1140

Ser Ala His Asp Ser Gly Trp Thr Val Ser Thr Asp Val Thr Ile
1145 1150 1155

Phe Val Thr Asp Ile Asn Asp Asn Ala Pro Arg Phe Ser Arg Thr
1160 1165 1170

Ser Tyr Tyr Leu Asp Cys Pro Glu Leu Thr Glu Ile Gly Ser Lys
1175 1180 1185

-continued

```
Val Thr  Gln Val Phe Ala Thr  Asp Pro Asp Glu Gly  Ser Asn Gly
    1190                 1195                 1200

Gln Val  Phe Tyr Phe Ile Lys  Ser Gln Ser Glu Tyr  Phe Arg Ile
    1205                 1210                 1215

Asn Ala  Thr Thr Gly Glu Ile  Phe Asn Lys Gln Ile  Leu Lys Tyr
    1220                 1225                 1230

Gln Asn  Val Thr Gly Phe Ser  Asn Val Asn Ile Asn  Arg His Ser
    1235                 1240                 1245

Phe Ile  Val Thr Ser Ser Asp  Arg Gly Lys Pro Ser  Leu Ile Ser
    1250                 1255                 1260

Glu Thr  Thr Val Thr Ile Asn  Ile Val Asp Ser Asn  Asp Asn Ala
    1265                 1270                 1275

Pro Gln  Phe Leu Lys Ser Lys  Tyr Phe Thr Pro Val  Thr Lys Asn
    1280                 1285                 1290

Val Lys  Val Gly Thr Lys Leu  Ile Arg Val Thr Ala  Ile Asp Asp
    1295                 1300                 1305

Lys Asp  Phe Gly Leu Asn Ser  Glu Val Glu Tyr Phe  Ile Ser Asn
    1310                 1315                 1320

Asp Asn  His Leu Gly Lys Phe  Lys Leu Asp Asn Asp  Thr Gly Trp
    1325                 1330                 1335

Ile Ser  Val Ala Ser Ser Leu  Ile Ser Asp Leu Asn  Gln Asn Phe
    1340                 1345                 1350

Phe Ile  Thr Val Thr Ala Lys  Asp Lys Gly Asn Pro  Pro Leu Ser
    1355                 1360                 1365

Ser Gln  Ala Thr Val His Ile  Thr Val Thr Glu Glu  Asn Tyr His
    1370                 1375                 1380

Thr Pro  Glu Phe Ser Gln Ser  His Met Ser Ala Thr  Ile Pro Glu
    1385                 1390                 1395

Ser His  Ser Ile Gly Ser Ile  Val Arg Thr Val Ser  Ala Arg Asp
    1400                 1405                 1410

Arg Asp  Ala Ala Met Asn Gly  Leu Ile Lys Tyr Ser  Ile Ser Ser
    1415                 1420                 1425

Gly Asn  Glu Glu Gly Ile Phe  Ala Ile Asn Ser Ser  Thr Gly Ile
    1430                 1435                 1440

Leu Thr  Leu Ala Lys Ala Leu  Asp Tyr Glu Leu Cys  Gln Lys His
    1445                 1450                 1455

Glu Met  Thr Ile Ser Ala Ile  Asp Gly Gly Trp Val  Ala Arg Thr
    1460                 1465                 1470

Gly Tyr  Cys Ser Val Thr Val  Asn Val Ile Asp Val  Asn Asp Asn
    1475                 1480                 1485

Ser Pro  Val Phe Leu Ser Asp  Asp Tyr Phe Pro Thr  Val Leu Glu
    1490                 1495                 1500

Asn Ala  Pro Ser Gly Thr Thr  Val Ile His Leu Asn  Ala Thr Asp
    1505                 1510                 1515

Ala Asp  Ser Gly Thr Asn Ala  Val Ile Ala Tyr Thr  Val Gln Ser
    1520                 1525                 1530

Ser Asp  Ser Asp Leu Phe Val  Ile Asp Pro Asn Thr  Gly Val Ile
    1535                 1540                 1545

Thr Thr  Gln Gly Phe Leu Asp  Phe Glu Thr Lys Gln  Ser Tyr His
    1550                 1555                 1560

Leu Thr  Val Lys Ala Phe Asn  Val Pro Asp Glu Glu  Arg Cys Ser
    1565                 1570                 1575

Phe Ala  Thr Val Asn Ile Gln  Leu Lys Gly Thr Asn  Glu Tyr Val
```

-continued

```
    1580                1585                1590

Pro Arg  Phe Val Ser Lys Leu  Tyr Tyr Phe Glu Ile  Ser Glu Ala
    1595                1600                1605

Ala Pro  Lys Gly Thr Ile Val  Gly Glu Val Phe Ala  Ser Asp Arg
    1610                1615                1620

Asp Leu  Gly Thr Asp Gly Glu  Val His Tyr Leu Ile  Phe Gly Asn
    1625                1630                1635

Ser Arg  Lys Lys Gly Phe Gln  Ile Asn Lys Lys Thr  Gly Gln Ile
    1640                1645                1650

Tyr Val  Ser Gly Ile Leu Asp  Arg Glu Lys Glu Glu  Arg Val Ser
    1655                1660                1665

Leu Lys  Val Leu Ala Lys Asn  Phe Gly Ser Ile Arg  Gly Ala Asp
    1670                1675                1680

Ile Asp  Glu Val Thr Val Asn  Val Thr Val Leu Asp  Ala Asn Asp
    1685                1690                1695

Pro Pro  Ile Phe Thr Leu Asn  Ile Tyr Ser Val Gln  Ile Ser Glu
    1700                1705                1710

Gly Val  Pro Ile Gly Thr His  Val Thr Phe Val Ser  Ala Phe Asp
    1715                1720                1725

Ser Asp  Ser Ile Pro Ser Trp  Ser Arg Phe Ser Tyr  Phe Ile Gly
    1730                1735                1740

Ser Gly  Asn Glu Asn Gly Ala  Phe Ser Ile Asn Pro  Gln Thr Gly
    1745                1750                1755

Gln Ile  Thr Val Thr Ala Glu  Leu Asp Arg Glu Thr  Leu Pro Ile
    1760                1765                1770

Tyr Asn  Leu Ser Val Leu Ala  Val Asp Ser Gly Thr  Pro Ser Ala
    1775                1780                1785

Thr Gly  Ser Ala Ser Leu Leu  Val Thr Leu Glu Asp  Ile Asn Asp
    1790                1795                1800

Asn Gly  Pro Met Leu Thr Val  Ser Glu Gly Glu Val  Met Glu Asn
    1805                1810                1815

Lys Arg  Pro Gly Thr Leu Val  Met Thr Leu Gln Ser  Thr Asp Pro
    1820                1825                1830

Asp Leu  Pro Pro Asn Gln Gly  Pro Phe Thr Tyr Tyr  Leu Leu Ser
    1835                1840                1845

Thr Gly  Pro Ala Thr Ser Tyr  Phe Ser Leu Ser Thr  Ala Gly Val
    1850                1855                1860

Leu Ser  Thr Thr Arg Glu Ile  Asp Arg Glu Gln Ile  Ala Asp Phe
    1865                1870                1875

Tyr Leu  Ser Val Val Thr Lys  Asp Ser Gly Val Pro  Gln Met Ser
    1880                1885                1890

Ser Thr  Gly Thr Val His Ile  Thr Val Ile Asp Gln  Asn Asp Asn
    1895                1900                1905

Pro Ser  Gln Ser Arg Thr Val  Glu Ile Phe Val Asn  Tyr Tyr Gly
    1910                1915                1920

Asn Leu  Phe Pro Gly Gly Ile  Leu Gly Ser Val Lys  Pro Gln Asp
    1925                1930                1935

Pro Asp  Val Leu Asp Ser Phe  His Cys Ser Leu Thr  Ser Gly Val
    1940                1945                1950

Thr Ser  Leu Phe Ser Ile Pro  Gly Gly Thr Cys Asp  Leu Asn Ser
    1955                1960                1965

Gln Pro  Arg Ser Thr Asp Gly  Thr Phe Asp Leu Thr  Val Leu Ser
    1970                1975                1980
```

Asn Asp Gly Val His Ser Thr Val Thr Ser Asn Ile Arg Val Phe
1985 1990 1995

Phe Ala Gly Phe Ser Asn Ala Thr Val Asp Asn Ser Ile Leu Leu
2000 2005 2010

Arg Leu Gly Val Pro Thr Val Lys Asp Phe Leu Thr Asn His Tyr
2015 2020 2025

Leu His Phe Leu Arg Ile Ala Ser Ser Gln Leu Thr Gly Leu Gly
2030 2035 2040

Thr Ala Val Gln Leu Tyr Ser Ala Tyr Glu Glu Asn Asn Arg Thr
2045 2050 2055

Phe Leu Leu Ala Ala Val Lys Arg Asn His Asn Gln Tyr Val Asn
2060 2065 2070

Pro Ser Gly Val Ala Thr Phe Phe Glu Ser Ile Lys Glu Ile Leu
2075 2080 2085

Leu Arg Gln Ser Gly Val Lys Val Glu Ser Val Asp His Asp Ser
2090 2095 2100

Cys Val His Gly Pro Cys Gln Asn Gly Gly Ser Cys Leu Arg Arg
2105 2110 2115

Leu Ala Val Ser Ser Val Leu Lys Ser Arg Glu Ser Leu Pro Val
2120 2125 2130

Ile Ile Val Ala Asn Glu Pro Leu Gln Pro Phe Leu Cys Lys Cys
2135 2140 2145

Leu Pro Gly Tyr Ala Gly Ser Trp Cys Glu Ile Asp Ile Asp Glu
2150 2155 2160

Cys Leu Pro Ser Pro Cys His Ser Gly Gly Thr Cys His Asn Leu
2165 2170 2175

Val Gly Gly Phe Ser Cys Ser Cys Pro Asp Gly Phe Thr Gly Arg
2180 2185 2190

Ala Cys Glu Arg Asp Ile Asn Glu Cys Leu Gln Ser Pro Cys Lys
2195 2200 2205

Asn Gly Ala Ile Cys Gln Asn Phe Pro Gly Ser Phe Asn Cys Val
2210 2215 2220

Cys Lys Thr Gly Tyr Thr Gly Val Phe Gly Lys His Cys Glu Leu
2225 2230 2235

Asn Ser Tyr Gly Phe Glu Glu Leu Ser Tyr Met Glu Phe Pro Ser
2240 2245 2250

Leu Asp Pro Asn Asn Asn Tyr Ile Tyr Val Lys Phe Ala Thr Ile
2255 2260 2265

Lys Ser His Ala Leu Leu Leu Tyr Asn Tyr Asp Asn Gln Thr Gly
2270 2275 2280

Asp Arg Ala Glu Phe Leu Ala Leu Glu Ile Ala Glu Glu Arg Leu
2285 2290 2295

Arg Phe Ser Tyr Asn Leu Gly Ser Gly Thr Tyr Lys Leu Thr Thr
2300 2305 2310

Met Lys Lys Val Ser Asp Gly His Phe His Thr Val Ile Ala Arg
2315 2320 2325

Arg Ala Gly Met Ala Ala Ser Leu Thr Val Asp Ser Cys Ser Glu
2330 2335 2340

Asn Gln Glu Pro Gly Tyr Cys Thr Val Ser Asn Val Ala Val Ser
2345 2350 2355

Asp Asp Trp Thr Leu Asp Val Gln Pro Asn Arg Val Thr Val Gly
2360 2365 2370

-continued

```
Gly Ile  Arg Ser Leu Glu Pro  Ile Leu Gln Arg Arg  Gly His Val
    2375                 2380                 2385

Glu Ser  His Asp Phe Val Gly  Cys Ile Met Glu Phe  Ala Val Asn
    2390                 2395                 2400

Gly Arg  Pro Leu Glu Pro Ser  Gln Ala Leu Ala Ala  Gln Gly Ile
    2405                 2410                 2415

Leu Asp  Gln Tyr Gly Asp Phe  Ile Ser Tyr Cys Phe  Lys Glu Lys
    2420                 2425                 2430

Lys Cys  Lys Lys Val Cys Phe  Thr Val Thr Pro Asp  Thr Ala Leu
    2435                 2440                 2445

Ser Leu  Glu Gly Lys Gly Arg  Leu Asp Tyr His Met  Ser Gln Asn
    2450                 2455                 2460

Glu Lys  Arg Glu Tyr Leu Leu  Arg Gln Ser Leu Arg  Gly Ala Met
    2465                 2470                 2475

Leu Glu  Pro Phe Gly Val Asn  Ser Leu Glu Val Lys  Phe Arg Thr
    2480                 2485                 2490

Arg Ser  Glu Asn Gly Val Leu  Ile His Ile Gln Glu  Ser Ser Asn
    2495                 2500                 2505

Tyr Thr  Thr Val Lys Ile Lys  Asn Gly Lys Val Tyr  Phe Thr Ser
    2510                 2515                 2520

Asp Ala  Gly Ile Ala Gly Lys  Val Glu Arg Asn Ile  Pro Glu Val
    2525                 2530                 2535

Tyr Val  Ala Asp Gly His Trp  His Thr Phe Leu Ile  Gly Lys Asn
    2540                 2545                 2550

Gly Thr  Ala Thr Val Leu Ser  Val Asp Arg Ile Tyr  Asn Arg Asp
    2555                 2560                 2565

Ile Ile  His Pro Thr Gln Asp  Phe Gly Gly Leu Asp  Val Leu Thr
    2570                 2575                 2580

Ile Ser  Leu Gly Gly Ile Pro  Pro Asn Gln Ala His  Arg Asp Ala
    2585                 2590                 2595

Gln Thr  Ala Gly Phe Asp Gly  Cys Ile Ala Ser Met  Trp Tyr Gly
    2600                 2605                 2610

Gly Glu  Ser Leu Pro Phe Ser  Gly Lys His Ser Leu  Ala Ser Ile
    2615                 2620                 2625

Ser Lys  Thr Asp Pro Ser Val  Lys Ile Gly Cys Arg  Gly Pro Asn
    2630                 2635                 2640

Ile Cys  Ala Ser Asn Pro Cys  Trp Gly Asp Leu Leu  Cys Ile Asn
    2645                 2650                 2655

Gln Trp  Tyr Ala Tyr Arg Cys  Val Pro Pro Gly Asp  Cys Ala Ser
    2660                 2665                 2670

His Pro  Cys Gln Asn Gly Gly  Ser Cys Glu Pro Gly  Leu His Ser
    2675                 2680                 2685

Gly Phe  Thr Cys Ser Cys Pro  Asp Ser His Thr Gly  Arg Thr Cys
    2690                 2695                 2700

Glu Met  Val Val Ala Cys Leu  Gly Val Leu Cys Pro  Gln Gly Lys
    2705                 2710                 2715

Val Cys  Lys Ala Gly Ser Pro  Ala Gly His Val Cys  Val Leu Ser
    2720                 2725                 2730

Gln Gly  Pro Glu Glu Ile Ser  Leu Pro Leu Trp Ala  Val Pro Ala
    2735                 2740                 2745

Ile Val  Gly Ser Cys Ala Thr  Val Leu Ala Leu Leu  Val Leu Ser
    2750                 2755                 2760

Leu Ile  Leu Cys Asn Gln Cys  Arg Gly Lys Lys Ala  Lys Asn Pro
```

2765 2770 2775

Lys Glu Glu Lys Lys Pro Lys Glu Lys Lys Lys Lys Gly Ser Glu
2780 2785 2790

Asn Val Ala Phe Asp Asp Pro Asp Asn Ile Pro Pro Tyr Gly Asp
2795 2800 2805

Asp Met Thr Val Arg Lys Gln Pro Glu Gly Asn Pro Lys Pro Asp
2810 2815 2820

Ile Ile Glu Arg Glu Asn Pro Tyr Leu Ile Tyr Asp Glu Thr Asp
2825 2830 2835

Ile Pro His Asn Ser Glu Thr Ile Pro Ser Ala Pro Leu Ala Ser
2840 2845 2850

Pro Glu Gln Glu Ile Glu His Tyr Asp Ile Asp Asn Ala Ser Ser
2855 2860 2865

Ile Ala Pro Ser Asp Ala Asp Ile Ile Gln His Tyr Lys Gln Phe
2870 2875 2880

Arg Ser His Thr Pro Lys Phe Ser Ile Gln Arg His Ser Pro Leu
2885 2890 2895

Gly Phe Ala Arg Gln Ser Pro Met Pro Leu Gly Ala Ser Ser Leu
2900 2905 2910

Thr Tyr Gln Pro Ser Tyr Gly Gln Gly Leu Arg Thr Ser Ser Leu
2915 2920 2925

Ser His Ser Ala Cys Pro Thr Pro Asn Pro Leu Ser Arg His Ser
2930 2935 2940

Pro Ala Pro Phe Ser Lys Ser Ser Thr Phe Tyr Arg Asn Ser Pro
2945 2950 2955

Ala Arg Glu Leu His Leu Pro Ile Arg Asp Gly Asn Thr Leu Glu
2960 2965 2970

Met His Gly Asp Thr Cys Gln Pro Gly Ile Phe Asn Tyr Ala Thr
2975 2980 2985

Arg Leu Gly Arg Arg Ser Lys Ser Pro Gln Ala Met Ala Ser His
2990 2995 3000

Gly Ser Arg Pro Gly Ser Arg Leu Lys Gln Pro Ile Gly Gln Ile
3005 3010 3015

Pro Leu Glu Ser Ser Pro Pro Val Gly Leu Ser Ile Glu Glu Val
3020 3025 3030

Glu Arg Leu Asn Thr Pro Arg Pro Arg Asn Pro Ser Ile Cys Ser
3035 3040 3045

Ala Asp His Gly Arg Ser Ser Ser Glu Glu Asp Cys Arg Arg Pro
3050 3055 3060

Leu Ser Arg Thr Arg Asn Pro Ala Asp Gly Ile Pro Ala Pro Glu
3065 3070 3075

Ser Ser Ser Asp Ser Asp Ser His Glu Ser Phe Thr Cys Ser Glu
3080 3085 3090

Met Glu Tyr Asp Arg Glu Lys Pro Met Val Tyr Thr Ser Arg Met
3095 3100 3105

Pro Lys Leu Ser Gln Val Asn Glu Ser Asp Ala Asp Asp Glu Asp
3110 3115 3120

Asn Tyr Gly Ala Arg Leu Lys Pro Arg Arg Tyr His Gly Arg Arg
3125 3130 3135

Ala Glu Gly Gly Pro Val Gly Thr Gln Ala Ala Ala Pro Gly Thr
3140 3145 3150

Ala Asp Asn Thr Leu Pro Met Lys Leu Gly Gln Gln Ala Gly Thr
3155 3160 3165

```
Phe Asn  Trp Asp Asn Leu Leu  Asn Trp Gly Pro Gly  Phe Gly His
    3170                 3175                 3180

Tyr Val  Asp Val Phe Lys Asp  Leu Ala Ser Leu Pro  Glu Lys Ala
    3185                 3190                 3195

Ala Ala  Asn Glu Glu Gly Lys  Ala Gly Thr Thr Lys  Pro Val Pro
    3200                 3205                 3210

Lys Asp  Gly Glu Ala Glu Gln  Tyr Val
    3215                 3220


<210> SEQ ID NO 10
<211> LENGTH: 201
<212> TYPE: DNA
<213> ORGANISM: Homo sapiens

<400> SEQUENCE: 10

atattccaga aagatcacat tttgtcaata ttatttgtgg gaatgtatga tagaaaagtt     60

tgccttgtct gttatgatca acatttttaa taatgaaaat ygcttgaaaa cttttaaggc    120

cccaataatt ctataaatca aatcatgcta gagttgcctt caattaccag acatgaaatg    180

catttgactt aattttattt t                                              201


<210> SEQ ID NO 11
<211> LENGTH: 201
<212> TYPE: DNA
<213> ORGANISM: Homo sapiens

<400> SEQUENCE: 11

acattaagag tagaaccttg ggaattaagt tgtgtggaat tgaatcctga ctctactatt     60

actattgcat tagtatgggc aaattaacat ttctggaccc rgttttcagt ggattaagca    120

gagtaataat gaaactaact ttaaagagag taagtaaaat aatttaagtg agctggttag    180

aatagcacca ggaacaaaaa a                                              201


<210> SEQ ID NO 12
<211> LENGTH: 201
<212> TYPE: DNA
<213> ORGANISM: Homo sapiens

<400> SEQUENCE: 12

gaattacagc acaatgtgta tatcagaaat attcagatct ttcttgaaat ctcactgtaa     60

gtcttaaaat accacattta aaaatgtcca atttactatg ycttccataa agctgtgaat    120

ttttagagag ctaaatgtct catgtatttt taccacaagt gaatcattga gatgaattat    180

tattcaaaat attttcctga a                                              201


<210> SEQ ID NO 13
<211> LENGTH: 201
<212> TYPE: DNA
<213> ORGANISM: Homo sapiens

<400> SEQUENCE: 13

gcagtacctt ccagcttctt gtcagtggta aagactccag ggctgcttta catgggtcac     60

atctcagtga cattcctcac taggtctgtg gccttgaaaa rgctacttaa actttctaaa    120

cttgagctta ctcatatacc aaatggagat gacagcagtg ctgatttatg gggattagat    180

aagacagttt atgtaaactt c                                              201


<210> SEQ ID NO 14
```

<211> LENGTH: 201
<212> TYPE: DNA
<213> ORGANISM: Homo sapiens

<400> SEQUENCE: 14
ataaatgaaa cattcaactg ctatttttct ttccccaaat aaataaatgt ttgaaaacat 60
ttttaaatga agccaaatta agtggaatca gtaatttcaa wattggtatt ttgaaaataa 120
gcttaaattt agacattgtt taaatttaat tgttaaataa agaagatata aagaatttgt 180
taggctttat gcctagaaga t 201

<210> SEQ ID NO 15
<211> LENGTH: 201
<212> TYPE: DNA
<213> ORGANISM: Homo sapiens

<400> SEQUENCE: 15
caggagttcg agactagcct gaccgacaag gtgaaacccc gtctctacta aaaacacaaa 60
aattagccaa gtatggtgac acatgcctgt aatcccagct rcttggaagg ttgagccagg 120
agaatcgctt gaacccggga ggcggaggtt gcagtgagcc gagatcacac cgctgctctt 180
cagcctgggc aacaagagcg a 201

<210> SEQ ID NO 16
<211> LENGTH: 201
<212> TYPE: DNA
<213> ORGANISM: Homo sapiens

<400> SEQUENCE: 16
ggacgtgaga tcaaatgaaa gagagaaatc agaatcatct aagttttcca ctcaaacacc 60
taggcagatc atgatatgat atcatttact gaaatgggta rcattgaagg aggaacagtt 120
ttgtgagaag tcagaagtat tctatttgaa tacagtttca aatgactgtt actcattcat 180
ttagagatac cagttaggaa g 201

<210> SEQ ID NO 17
<211> LENGTH: 201
<212> TYPE: DNA
<213> ORGANISM: Homo sapiens

<400> SEQUENCE: 17
gcagatgctg tttcttagac agtatataga atattaccaa tcagatatag ggaaattctc 60
ttgtatgaga tgtataaatt cctgaatatg aagttgaatg yttacaaact tgatcctgtc 120
ttccattgag tcattcattt atttctataa taaagtaaat gctgtgatga cctgctgttt 180
ttttctagtg catgttaaag a 201

<210> SEQ ID NO 18
<211> LENGTH: 201
<212> TYPE: DNA
<213> ORGANISM: Homo sapiens

<400> SEQUENCE: 18
agaaatttaa aatctatgcc aagattattg tgctcaaatg tcccacaaac ttaagctggc 60
cagtagtgaa ggtccctccc tgttgggcct cttcacctcc ygcctggtgc tcttctaggc 120
tcagcgacag agctgcttgt ccagaccccc aaagcagcgc aggaagcagc actgttcccc 180
ctactggcag taccttccag c 201

<210> SEQ ID NO 19
<211> LENGTH: 201
<212> TYPE: DNA
<213> ORGANISM: Homo sapiens

<400> SEQUENCE: 19
atggttctat aagggcttca ccccacttca ctctgcacat ctcatttttc tctctcctgc 60
tgccttgtga ataaggacat gtttgcttct gattctgcca ygattataag tttcctgagg 120
cctccccagc tctgggttaa ttgtgagtca attaaacctc tttcctttat aaattgccca 180
gtcccaggta tggccttata g 201

<210> SEQ ID NO 20
<211> LENGTH: 201
<212> TYPE: DNA
<213> ORGANISM: Homo sapiens

<400> SEQUENCE: 20
agttgaatgt ttacaaactt gatcctgtct tccattgagt cattcattta tttctataat 60
aaagtaaatg ctgtgatgac ctgctgtttt tttctagtgc rtgttaaaga ttcattgcaa 120
aatgctatcc tatgcttgtg aattatgctt gtaaatttgg tctagaaaaa ttgtattcat 180
actctcaaac tgttttacaa a 201

<210> SEQ ID NO 21
<211> LENGTH: 201
<212> TYPE: DNA
<213> ORGANISM: Homo sapiens

<400> SEQUENCE: 21
tattcttctc atatcatctt ttttactcct aatatattct ttcttttaca atatctggta 60
cataacagtg gttgtcactt aaataaatgc attgaatgaa ygattttaat attctctgga 120
atggctgctt ttactcattc tatttttact acaacattct tgaaagcttc acaacctgtt 180
ttctctgacc atttattcct g 201

<210> SEQ ID NO 22
<211> LENGTH: 201
<212> TYPE: DNA
<213> ORGANISM: Homo sapiens

<400> SEQUENCE: 22
tttatttgcc tcccatggcc taggaaagtc attttagtgc ctcaaaggct tagtttctgc 60
atcaataaaa atgaacataa aaatttatac tttacagttt rtgagacaaa catttactaa 120
ccacctacta tgtatcaaac agtatgtatg gaatcagtta atatccataa atgtctctgg 180
cataattatt aggacataga a 201

<210> SEQ ID NO 23
<211> LENGTH: 201
<212> TYPE: DNA
<213> ORGANISM: Homo sapiens

<400> SEQUENCE: 23
gatacgagtg gaaatagaaa gaaaagatgt atttttcttc ccattaaagg ttgagcgtgg 60
actttaaagg gggaaattct gagtgattct taaaacaaca kgtgaacttt tttatttccc 120
ccagacatta gttgccaata tgtaaacatt tcagcaagaa attttatacc acctcctctg 180
tttgtcaggc agcatttaat g 201

<210> SEQ ID NO 24
<211> LENGTH: 201
<212> TYPE: DNA
<213> ORGANISM: Homo sapiens

<400> SEQUENCE: 24
tgagcttagt atttttcagt atacttcaaa tattccggga gaaatttgag ttttgctatg 60
tctgcatgta ttttttagat gtagtgtatg tggccaaagt yactttttag acttgtcaga 120
aatgaaaagt tattttcttt acagtaaagt aaatgcagat ggattccatg acctgtaatt 180
gcagcaatta attttcagtt c 201

<210> SEQ ID NO 25
<211> LENGTH: 201
<212> TYPE: DNA
<213> ORGANISM: Homo sapiens

<400> SEQUENCE: 25
agtagggcac tgctgtaaaa ataccaaagt gactttggaa ctgggtaact ggcagagact 60
ggaacagttt ggagggttca gaataagaga gaaaaatgtt sgaaagtttg gaacttccta 120
cagacttttt gaatggcttt gaccaaaatg ctgaggtgtt atggaaaatg aagtccaggc 180
tgaggtggtc acagatggag a 201

<210> SEQ ID NO 26
<211> LENGTH: 201
<212> TYPE: DNA
<213> ORGANISM: Homo sapiens

<400> SEQUENCE: 26
atatagtgtt tttgatagat tcctatgcaa aaataatgaa aaaaatatta agtgtgtata 60
tatctaattt atataagcat atatgtagaa ctaattagca rcaatacatt attttataaa 120
acagaatttt taaaatacag aagtgttgtt aatatttaaa ttgttacata ccttttgttt 180
tatgtatttt ttgtattcaa a 201

<210> SEQ ID NO 27
<211> LENGTH: 201
<212> TYPE: DNA
<213> ORGANISM: Homo sapiens

<400> SEQUENCE: 27
actaggccac gagtaattac aatctaagaa catagaagaa tgattgaata gtggtaaagg 60
aaataccagc aaatcacttg actattagaa aataaatatgg kaaggttgtg aatctcaata 120
ccattctgtg ataatgaggg cactccataa acattttaca aataaatgaa tgagtggctt 180
tatttacaga atattgaatg g 201

<210> SEQ ID NO 28
<211> LENGTH: 201
<212> TYPE: DNA
<213> ORGANISM: Homo sapiens

<400> SEQUENCE: 28
agcaaagctg gagtcagtga attaaagggc aatggcagaa gtatgcatca acatgagcat 60
ctcttggctc tgctttaaca attatacttc cttcctcaaa rtctttcaat tccagtttgc 120
ctatggtata accccccagtc ttcaaattct agtcacccca taaatggccc cagctaattc 180
tgcaaaactc tgcaacatat g 201

<210> SEQ ID NO 29
<211> LENGTH: 201
<212> TYPE: DNA
<213> ORGANISM: Homo sapiens

<400> SEQUENCE: 29
aaagatattt tacttttgtt accgtttctt ctgtaggggt gagagtgcag gtttgggaat 60
ggtttctgaa tgagtagatt gaaaatatgt ccttatggca rcttttctgc atatttttac 120
gacaatctgt ttcattggca ctcagtctaa gcactaactt ttggagtcca agttgagtcc 180
attatccctc aattcttatt t 201

<210> SEQ ID NO 30
<211> LENGTH: 201
<212> TYPE: DNA
<213> ORGANISM: Homo sapiens

<400> SEQUENCE: 30
gttcacctcc ttcttaattt gcgtgtgtgt gtaacaataa aatgtactag tgcaatgaac 60
aaactggttt ttacatcatt gaataaatgt acattaaatg ycttctgtac cctaggcgtt 120
atattgaaac tgatctaaat gtttcactgt ttgaaactta gaaaagaagc aggctttctg 180
agttttgttt tgttttgttt t 201

<210> SEQ ID NO 31
<211> LENGTH: 201
<212> TYPE: DNA
<213> ORGANISM: Homo sapiens

<400> SEQUENCE: 31
tgactgtcat gaaagatttc tctgtagcat tcaatactgt ttgagagcat tttacacata 60
gtagaatgtc attcaaaact ggagtcaatc ctctcaaacc ytgccactct tttatcagct 120
aagttgattt attattctaa atattttgtt gtcatttcaa cggtatttac agcatcttca 180
ccaggaatag gttccatctc a 201

<210> SEQ ID NO 32
<211> LENGTH: 201
<212> TYPE: DNA
<213> ORGANISM: Homo sapiens

<400> SEQUENCE: 32
atttgatacg cttttatttt tattttattg tgataagaac attaatgtga gatctgccct 60
tttaaaagat ttctaaatgt acaatacagt attgttaact mtaggcacga tgttgtacag 120
tagatctaga aattattcct cttgcataag tgaagatgta tacccatggc ttataagctc 180
ctgatttctc cctactgtct g 201

<210> SEQ ID NO 33
<211> LENGTH: 201
<212> TYPE: DNA
<213> ORGANISM: Homo sapiens

<400> SEQUENCE: 33
tatctaagga actgtggagt agagaaaagg gaatgggcaa ttaaggaaaa atatctagat 60
tttcaagaaa tggaatatga agttattcac ttttcttttt hattcttttt tgagacagag 120
tctcactctg tcgctgaggc tggagtgcag tgatgccatc ttggctcact gcaacctctg 180
catcctgggt tcaagcgatt c 201

<210> SEQ ID NO 34
<211> LENGTH: 201
<212> TYPE: DNA
<213> ORGANISM: Homo sapiens

<400> SEQUENCE: 34
ttaaaaacag aattattcca attcccatat tgtatgttac ttcatcaaat attaccatta 60
tatcatgttt cttgtactaa agtgtttcct gtgaaataac rtaataaaat ggcctttagt 120
atgcatgata atatttaaat acgcattttc tagtaaaata taatgcttat tcattttttt 180
cttctagttc taaagaaaaa a 201

<210> SEQ ID NO 35
<211> LENGTH: 201
<212> TYPE: DNA
<213> ORGANISM: Homo sapiens

<400> SEQUENCE: 35
aacctagatc cttcgcatgc accattcaca atagggtcca cccttctttg agaatctaat 60
gccgcagctg atctgacagg aggcagagct caggcagtaa ygctcacttg cccgcccctc 120
acctgctgct atgggccggg ttcctaacag gccacaaacc agtaccggtc tgtgcccagg 180
ggttggagac ccctgttata g 201

<210> SEQ ID NO 36
<211> LENGTH: 201
<212> TYPE: DNA
<213> ORGANISM: Homo sapiens

<400> SEQUENCE: 36
aaagaaaaaa atagtaagtc attattatga gtagttactg aattatcata aaatatcatt 60
tcataacata aaaattatat atgatagcat gttcccacac maaaactagg aaatcaatag 120
gtttgaattg ctttaaaata tcattgtaat agtggataac tttgattaat acatctttat 180
atgccagtag aatgcctatg t 201

<210> SEQ ID NO 37
<211> LENGTH: 201
<212> TYPE: DNA
<213> ORGANISM: Homo sapiens

<400> SEQUENCE: 37
ttaataaaaa tgtaaaaatg acctggattt gcttaaaaac agaaatattt ctagaggaga 60
atttacatgc tagacatgga taagttgtca gaatgagcag racacattat tgctcttgga 120
atctcagaat atagaagtct ctaatttaag taatataaat gatcttcagt atcctgaaga 180
tatttgcaat tacctatgtt g 201

<210> SEQ ID NO 38
<211> LENGTH: 201
<212> TYPE: DNA
<213> ORGANISM: Homo sapiens

<400> SEQUENCE: 38
caccatgtcc agctaatttt tgtattttta gtggagacat ggtttcacca tgttggccag 60
gctggtattg aactcgtgac ctcaggtaat ccacccacct yggcctccca aagtgcttgg 120
attacaggta tgagccaccg cgcttggcca gacattgata tttaactctt tcttaatcaa 180
attttgaact tatttcatac c 201

<210> SEQ ID NO 39
<211> LENGTH: 201
<212> TYPE: DNA
<213> ORGANISM: Homo sapiens

<400> SEQUENCE: 39
aggagaaata cctaatgtaa atgacgagtt aatgggtgca gtaaaccaac atggcatatg 60
tatacatatg taacaaacct gcacgttgtg cacgtgaacc stagatctta agtataatta 120
aaaataaata aataaatagg cctggcgcgg tggctcatgc ctgtaatccc agtactttgg 180
gaggctgaga taggcggatc a 201

<210> SEQ ID NO 40
<211> LENGTH: 201
<212> TYPE: DNA
<213> ORGANISM: Homo sapiens

<400> SEQUENCE: 40
tcaatagggc tacggcattc atgccttcct ttaaaaatta attgagggca agaaaccatt 60
gtttaatatg taatttcaaa catctagatg aagaaaatat mtgtattaga aaataataag 120
gactatgtat atatgatttc agacgatttc ctatttaaat aaattaggat aaatgacata 180
tttgttatag ggtgaaatgt t 201

<210> SEQ ID NO 41
<211> LENGTH: 201
<212> TYPE: DNA
<213> ORGANISM: Homo sapiens

<400> SEQUENCE: 41
agagtttcaa atgagtttgt gaatggatat catacccttc cacaaatgac agagatggac 60
tattaaatca gagttggtag tttttgcttt tgtttactgt rtttctcatt caccctaaat 120
ggtcctatct ataacaagct ttggaaaagc accatgcacc tgaaattctt gcattctgat 180
gttcatacct agagagattt a 201

<210> SEQ ID NO 42
<211> LENGTH: 201
<212> TYPE: DNA
<213> ORGANISM: Homo sapiens

<400> SEQUENCE: 42
gctgatttcc ttgaaagtac tccctcctca ttctctacag taagccattg aatgttacta 60
gggatggaca ctaagcagaa agatttctga gtatctattc rtcttcccca atcagacagt 120
cctttaaatt taaagaagaa tgcctgaccc ttaagacagg gaggttcatc atatttccca 180
ttctgacagt ttggaatgaa a 201

<210> SEQ ID NO 43
<211> LENGTH: 201
<212> TYPE: DNA
<213> ORGANISM: Homo sapiens

<400> SEQUENCE: 43
catttgtttt gaattttcca gtatattaaa acaatggcta acaattatag ttgagagaaa 60
tatatttagg aaaagtaatg cattattcag cattctatta wctatactat attaacacat 120

-continued

```
gtgttatggg ctgaaattac accagtatca catgagggta aatgggttga aagtgtaagt    180

ttaaaagagt ttcaaatgag t                                              201


<210> SEQ ID NO 44
<211> LENGTH: 201
<212> TYPE: DNA
<213> ORGANISM: Homo sapiens

<400> SEQUENCE: 44

ctactcagaa ggctgaggca ggagaatcgc ttgaaaccag gaggcggagg ttgcagtgag     60

ccgagatcac accactgttc tccagcctgg gcaacaagaa ygaaactcgt ctcaaaataa    120

acaaataaat taaataataa taatttcttc ataatatgag tatgaagtat tttctgtttg    180

ccattaaatg aaatatttgt t                                              201


<210> SEQ ID NO 45
<211> LENGTH: 201
<212> TYPE: DNA
<213> ORGANISM: Homo sapiens

<400> SEQUENCE: 45

agaggtgatc tgacaagtgt tcattcaaac tctgcaacct tgattgagac tgtgctagat     60

gatataaaaa tacatatgcc ctaacaggga ggataggcaa mcaaacaatt aattttaaaa    120

ttgtgaattt acaaactgtg ggttattata tgctacagaa gccacacaga gaaagagtta    180

tttgctctgt ttcagaaaat a                                              201


<210> SEQ ID NO 46
<211> LENGTH: 201
<212> TYPE: DNA
<213> ORGANISM: Homo sapiens

<400> SEQUENCE: 46

tccagcctgg atctctggga gggagaagta gttccaaaga ttacagtgct taatcttaac     60

tctgaaaaca ctacttattg actctccact ggattccact ygcccaaatt ccctagatgg    120

attttccctc aggatgaaac aacctaaatt caagtgtcct aaactgtctt cctctccctc    180

ctgccattgc ctttccttgt t                                              201


<210> SEQ ID NO 47
<211> LENGTH: 201
<212> TYPE: DNA
<213> ORGANISM: Homo sapiens

<400> SEQUENCE: 47

tactgaacaa taatacatat gcacttaatt gtagtcatcc ccctgactat actcacaaaa     60

cttaacatgt ctttagggga ggaggatgga ttgcagatat rctattagag gcatagccat    120

ctttacttca ttaaaagttt agtttactaa aatttgcaaa tgtttaaaat atggtcttgc    180

ttaatttcac aaattctggg a                                              201


<210> SEQ ID NO 48
<211> LENGTH: 201
<212> TYPE: DNA
<213> ORGANISM: Homo sapiens

<400> SEQUENCE: 48

tagtcaggtg gagataattc accccacgtc ttaaggccaa atggaaaaaa tcttcttact     60

ctggaattag gtggttaagt atcttgattt taatggatgt ygttgttttc ctaataattg    120
```

agttatttgt attaaaatgc taaactggca atatatgccg atggccaatt tacctccaaa 180
tatattgagt tcatacatat t 201

<210> SEQ ID NO 49
<211> LENGTH: 201
<212> TYPE: DNA
<213> ORGANISM: Homo sapiens

<400> SEQUENCE: 49
acactgctgg catgtgcttt gtgaatatgt ttgaatcaag ggcctttaca aagggctcag 60
accttcctcc tagggggttg tcatttaccg tggatgctct ygtttgttgt ggtaaacagc 120
ctcagaaaac gtcttgacat tgtcaattcc aacagattaa tgaagtaact gggccataca 180
tcccttcccc tttacatatg a 201

<210> SEQ ID NO 50
<211> LENGTH: 201
<212> TYPE: DNA
<213> ORGANISM: Homo sapiens

<400> SEQUENCE: 50
gggcggggga actccagtgt gattataagt gagtatatag gaaaaaaaga aatgaaatta 60 acctttttt ctttagaaat cttgtgttta attttatgtt ycagtgtttt aaataactga 120
aaccttatta tggacaaatt tacctgttat gttaggagaa atgagtttca tttaccatct 180
tcatcagcga tccccaacct t 201

<210> SEQ ID NO 51
<211> LENGTH: 201
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n is c or t

<400> SEQUENCE: 51
gctaaactgg caatatatgc cgatggccaa tttacctcca aatatattga gttcatacat 60
attcattaag tgggatattt tggagaatat actgcttata ygttcaaatg caaataattt 120
aattcgctgt gatttataat actgttactc agtaaatgga ctaaaggcag ggtaagattt 180
atcagtctta aaaatgtaac t 201

<210> SEQ ID NO 52
<211> LENGTH: 201
<212> TYPE: DNA
<213> ORGANISM: Homo sapiens

<400> SEQUENCE: 52
tggggacccc ttatctacat ccacgttttc tatgtttgtg aagatttgat gtggggttat 60
gggtttgagg agctaaaaat tatagttagt agaaggaaag rcagctagaa gtggaaagta 120
aaatcactta cattgtactt ttactaggac ctatattgta ggtattataa atcatacaaa 180
caagtttgtt atacaaaaca t 201

<210> SEQ ID NO 53
<211> LENGTH: 201
<212> TYPE: DNA
<213> ORGANISM: Homo sapiens

<400> SEQUENCE: 53
ctgtggccca ggggttgggg accccttatc tacatccacg ttttctatgt ttgtgaagat 60
ttgatgtggg gttatgggtt tgaggagcta aaaattatag ytagtagaag gaaagacagc 120
tagaagtgga aagtaaaatc acttacattg tacttttact aggacctata ttgtaggtat 180
tataaatcat acaaacaagt t 201

<210> SEQ ID NO 54
<211> LENGTH: 201
<212> TYPE: DNA
<213> ORGANISM: Homo sapiens

<400> SEQUENCE: 54
gttttttttc tgtcggcagt gtatcacaag tattttcctc agtggcctaa acagaccctg 60
agtggaaggc tggtaaaagc aacctcgtct gcatgcatca ytttgaatga tttcaaagag 120
gaaagaagca gctgtgacaa tgttcacatg aaccactcag agtggcctta tctttgtagt 180
ctaacaataa tagtacaccc t 201

<210> SEQ ID NO 55
<211> LENGTH: 201
<212> TYPE: DNA
<213> ORGANISM: Homo sapiens

<400> SEQUENCE: 55
gtgaagtttg agaatttgca aagccataat gatagaatca acccaaaggt cccagaaatt 60
ttcaataatc tatcatcctt atttaaaatt attatacaat waaaaattgt gttttaatcg 120
catgagtaga cagatgttta tgctgttatt cagcgaatct tgcaaaagtg agtgtaattc 180
atagaataaa acaatgttgg a 201

<210> SEQ ID NO 56
<211> LENGTH: 201
<212> TYPE: DNA
<213> ORGANISM: Homo sapiens

<400> SEQUENCE: 56
aatatgtttt acagattaag aatggcaaag tatattttac atccgatgca ggaattgctg 60
ggaaagtgga gagaaatatt cctgaagtat atgttgcaga yggccactgg cacacttttc 120
taattgggaa aaatggaaca gcaacagtat tgtctgttga cagaatatat aacagagata 180
ttatccaccc tactcaggac t 201

<210> SEQ ID NO 57
<211> LENGTH: 201
<212> TYPE: DNA
<213> ORGANISM: Homo sapiens

<400> SEQUENCE: 57
atagaagcag cagcataaat atctatatag aattagccag gttctagtct ggcacatcat 60
cacatagtag cacatttaat gcccccaatt attctatgat rtagatacta ctagtttccc 120
cattttccta atgagaaaag tgagtcatag tcaggtggag ataattcacc ccacgtctta 180
aggccaaatg gaaaaaatct t 201

<210> SEQ ID NO 58
<211> LENGTH: 201
<212> TYPE: DNA
<213> ORGANISM: Homo sapiens

<400> SEQUENCE: 58
atttaaattt aaatcaaaca gttctcactg aaataattag gggtaaaatg gacctctgtt 60
gatgctattt gaaaaaacta tttgaacaat gagaacactt rgacacaggg tgggaaacat 120
cacacaccgg ggcctgtcgt gaccggggcc tgtcgtgggg tgaggggagg ggagaggaat 180
agcattagga gaaataccta a 201

<210> SEQ ID NO 59
<211> LENGTH: 201
<212> TYPE: DNA
<213> ORGANISM: Homo sapiens

<400> SEQUENCE: 59
atttcaaagc ttattatttt tccattacta cctaacactt gtgtatctct tcttcagctt 60
tcaaagagtt ttcaggtgag ttatctaatt tgaacattac rttacatctg tgaggttgat 120
tacagaaaag taattaacac attttagaga aaggaaaaca taaatgaaaa gagacttact 180
caaagtcaca aagtaacggt g 201

<210> SEQ ID NO 60
<211> LENGTH: 201
<212> TYPE: DNA
<213> ORGANISM: Homo sapiens

<400> SEQUENCE: 60
aaataactca tacaattcac tttaagctgt ttctttgata tgcaattctt agccattact 60
ctttgagcct gtcgtactac tgtcattatt atcattattt ktgaccctgc cttttgcatt 120
ccgcatcatt acacattctt tagttcaaag tggagaacta atgtcttcct gcttcaagcg 180
aggctgtctt gtcagctctt t 201

<210> SEQ ID NO 61
<211> LENGTH: 201
<212> TYPE: DNA
<213> ORGANISM: Homo sapiens

<400> SEQUENCE: 61
aacaaaagat tgtttttctt ctttatttga gaaccatttt atgtagattg caggaaggtt 60
gtgaattaaa atatgtttag attttttcat tccgttcatt ragaaacatt tgatttaagc 120
tgcagagagg atatgcattt aagaatatgt ttagaattgt ggttgaggtg gcaaccacca 180
tgcaattatc agtttattaa c 201

<210> SEQ ID NO 62
<211> LENGTH: 201
<212> TYPE: DNA
<213> ORGANISM: Homo sapiens

<400> SEQUENCE: 62
tgccagttga acctgtatgt gggactggaa ttctgatttt taaaaatacc ttttctcaaa 60
gcctttctct ggctctaaga agcttccaga tctgtcctaa yagcttgaaa accaagatct 120
tgacttttta tagaatactt cactctgtgc cagaaactgt gttaagcatt ttctttacct 180
atatcatcag gatttagtct t 201

<210> SEQ ID NO 63
<211> LENGTH: 201
<212> TYPE: DNA

<213> ORGANISM: Homo sapiens

<400> SEQUENCE: 63
tctgctataa gtgctataag taataatata gaaatagttg acctcacagt taatttatta 60
agcaaatagt ggagaagatg ctagtaattt ctagaccttg yctcaggggc tgtgaatata 120
ggaggggata agataaaaag tggctctttc attggagtat caattgtggg gagagattga 180
atatcctcaa taatatctta a 201

<210> SEQ ID NO 64
<211> LENGTH: 201
<212> TYPE: DNA
<213> ORGANISM: Homo sapiens

<400> SEQUENCE: 64
gctttggaaa agcaccatgc acctgaaatt cttgcattct gatgttcata cctagagaga 60
tttatggtga cataagcagc caaatagcac aagtgaaatt ktatatgaag tatatgacat 120
gcatgattca atatatatgc ccacttttaa atataccaat agtatatttg gactataata 180
atgaattcat ttcaaatatt g 201

<210> SEQ ID NO 65
<211> LENGTH: 201
<212> TYPE: DNA
<213> ORGANISM: Homo sapiens

<400> SEQUENCE: 65
aataaattag ttcaggacct tgttaaatgt gaggtcactc tgagatacca gtggaaatat 60
ccagcaggca gatggatatg tgaactggag cacaacagag wagtctagat taaaatttgc 120
atttggagtg tagtatccat gaaagtagcc acgagcttgg atatgttgtc caaaagaatg 180
tggactctct tctcatcatt c 201

<210> SEQ ID NO 66
<211> LENGTH: 201
<212> TYPE: DNA
<213> ORGANISM: Homo sapiens

<400> SEQUENCE: 66
ttgatgacga attgaatgta gatgtggaag atgatggaag aaccaaggaa gatggcttag 60
tttctgcctt gagcaactaa gtggatgatg agttagggaa yaccggatga ggagtcataa 120
caagaagaca ataaattagt tcaggacctt gttaaatgtg aggtcactct gagataccag 180
tggaaatatc cagcaggcag a 201

<210> SEQ ID NO 67
<211> LENGTH: 201
<212> TYPE: DNA
<213> ORGANISM: Homo sapiens

<400> SEQUENCE: 67
ctccagctcc atccatgttc ctgcaaagga catgatcttg ttcttttaat ggctgcgtag 60
tattccatgg tgtgtatgta ctatatatat atttttaatc yggtctacca ttgatgggta 120
tttgggttga ttccacgtct ttgccattgt gaatagtgtt gcaatgaaca taacatgtgc 180
atctttacaa tagaatgatg c 201

<210> SEQ ID NO 68
<211> LENGTH: 201

<212> TYPE: DNA
<213> ORGANISM: Homo sapiens

<400> SEQUENCE: 68
acacatagaa aaaaatgtag gcttgttagc atcaagtaag ttgccaaata tgatattgcc 60
ccttatataa cttgaataac tttaggtgtt acttaaattc rtaggcacat attggcatct 120
tcagagcaag atgaattaac actctggagt ttttatttta tttatttaaa aatagattat 180
cacttgagaa aagacagcat c 201

<210> SEQ ID NO 69
<211> LENGTH: 201
<212> TYPE: DNA
<213> ORGANISM: Homo sapiens

<400> SEQUENCE: 69
attggaagat attttaagac acactagagc aacggtatca ttgcattggg tagaggcata 60
gcactttgca gagctcgcat attatgtttc ttggaatgtt kttttatgtg cagatttttc 120
tcctagaaac tatgattttt gaacgattag caagttcttt tccctaggct tctctcaaag 180
gcatactgaa aagtattaaa t 201

<210> SEQ ID NO 70
<211> LENGTH: 201
<212> TYPE: DNA
<213> ORGANISM: Homo sapiens

<400> SEQUENCE: 70
ggagaaagtt cttggcttga aaacagactc atatagatgt agaatcacct atggggctga 60
tcgtggctta aggatcatct gccagtcttg agaatcattt rctaatctca aggatcaaca 120
aatgatcctc aagccagaat tgtctgttgt cacctgagtg ctttgaaaat catctggaaa 180
aataagttga tattctttgg t 201

<210> SEQ ID NO 71
<211> LENGTH: 201
<212> TYPE: DNA
<213> ORGANISM: Homo sapiens

<400> SEQUENCE: 71
gttttcaaaa agtttaataa atggataatt cttgttaata tttattttat tccaggtttt 60
acaaatgaaa actgttctgt tagcaagttt atggatccat wtatgaatca ttttcatatt 120
gacaatatgc atttatcctt ctgtatctct ttaaatttag tttgacattt gctaagaaag 180
gcatactcta agaactgcac a 201

<210> SEQ ID NO 72
<211> LENGTH: 201
<212> TYPE: DNA
<213> ORGANISM: Homo sapiens

<400> SEQUENCE: 72
tttttatgtt gtttttatct taattactct aacagagaca aatttcatct aaagaggtga 60
tatctaaagg aaatgtagag atcagaatat aggacagatt kttttaaaaa gtttgatatt 120
tattattagg tgcctaataa atgctccttc tagtttatga agctttattt ctaaaactat 180
aatctatgtt tatgtgtgtt t 201

<210> SEQ ID NO 73

<211> LENGTH: 201
<212> TYPE: DNA
<213> ORGANISM: Homo sapiens

<400> SEQUENCE: 73
tcctccaatc ggcaagctcc aggccaccac tgttctgctt tctgttccca tgaagttgac 60
tacttttgct aactgatata aatggaatca tacatatttg yttttctgtg tctggcttat 120
tttacttagc ataatgtcct ccaggtagat ccaagttgta gtaaatgtca gaatttcctt 180 ttttttaaa gaccgaatag t 201

<210> SEQ ID NO 74
<211> LENGTH: 201
<212> TYPE: DNA
<213> ORGANISM: Homo sapiens

<400> SEQUENCE: 74
gaacatatta ctggtgaatg gggaagctgg cttaaaaaaa agggagggtc ttctcagaca 60
gttctctttt tacatacgtg gcacaatgat tcatgatttg ytatattgtg aatgttgaat 120
gtggaatatt tataggaatg caaatcacat ttcctttaca caatagtatt aaactgattt 180
caaagtgttt tgatatatgc t 201

<210> SEQ ID NO 75
<211> LENGTH: 201
<212> TYPE: DNA
<213> ORGANISM: Homo sapiens

<400> SEQUENCE: 75
aattatcaaa tcatttttca caacaataaa aattgtatac aaggcaaact atgtacatat 60
atgtgggtgt ccttaggaat aaatgcataa tttcaaagac rtggaatttg taagtgttag 120
tcatgttctc acctgtaata aagcaatgtg ttaatgaaat tgggtgctta tatatattta 180
tatataattt cttagtttga g 201

<210> SEQ ID NO 76
<211> LENGTH: 201
<212> TYPE: DNA
<213> ORGANISM: Homo sapiens

<400> SEQUENCE: 76
tctttgctga tggaatattg aacacgctct cactctgatg tacagttata gtgtatacta 60
ggtaagaaaa gagagtccca ggccaattta aacaatgata rggtttgctt ttctgaattc 120
tgagaagcta gttcagggga agaaatgaaa ccacagtgta gagggtcgaa tggtgaaggt 180
gaaaaattag tatcaagcct c 201

<210> SEQ ID NO 77
<211> LENGTH: 201
<212> TYPE: DNA
<213> ORGANISM: Homo sapiens

<400> SEQUENCE: 77
gtgacaagac taatataagt agaatatagt tgagttacag aatatgttgt aatagtcttt 60
acaatgcaca tccaatgaac atcatataga cagatattaa yatcaatata tctacacata 120
attgatatat agtatatatt ataataaata taagatatga taatataaca gataatataa 180
tagaaatcat agatatctgt a 201

<210> SEQ ID NO 78
<211> LENGTH: 201
<212> TYPE: DNA
<213> ORGANISM: Homo sapiens

<400> SEQUENCE: 78
cagtctctcg attgataata aaatttgtca ttttctcagt taaattgata cagattcttg 60
tagagcaaaa agacctaaag ataagatttg ggatagattt wtaccttaac ccaggtaata 120
aatagattat tcgggtactt taatagtaac aaaggaatca aatggaattt taattgaaat 180
gattttacta atatggtcat t 201

<210> SEQ ID NO 79
<211> LENGTH: 201
<212> TYPE: DNA
<213> ORGANISM: Homo sapiens

<400> SEQUENCE: 79
tattatcttc taattatcct tttaaatcaa aaacatactt tcatgttggt atgagtatca 60
taaccaaaag agaagagaaa cttcaaagag aaaactgaat yagtggagag taacttaatt 120
tcagaagaaa atcgtacttt catataaatt catagtgaaa ggtaactatg tgataccagc 180
attcagggaa caaatgccct t 201

<210> SEQ ID NO 80
<211> LENGTH: 201
<212> TYPE: DNA
<213> ORGANISM: Homo sapiens

<400> SEQUENCE: 80
ctttgattga gtctgactgt catgaaagat ttctctgtag cattcaatac tgtttgagag 60
cattttacac atagtagaat gtcattcaaa actggagtca rtcctctcaa accctgccac 120
tcttttatca gctaagttga tttattattc taaatatttt gttgtcattt caacggtatt 180
tacagcatct tcaccaggaa t 201

<210> SEQ ID NO 81
<211> LENGTH: 201
<212> TYPE: DNA
<213> ORGANISM: Homo sapiens

<400> SEQUENCE: 81
ccacccttct ttgagaatct aatgccgcag ctgatctgac aggaggcaga gctcaggcag 60
taacgctcac ttgcccgccc ctcacctgct gctatgggcc rggttcctaa caggccacaa 120
accagtaccg gtctgtgccc aggggttgga gacccctgtt atagactaat aaccaactga 180
aatagaatag catagctatg a 201

<210> SEQ ID NO 82
<211> LENGTH: 201
<212> TYPE: DNA
<213> ORGANISM: Homo sapiens

<400> SEQUENCE: 82
catcaagatg agacagtaaa ctattattag agttaccaca agtttgaaca aagttgatta 60
tacatcgcaa acaaataaat acttaaaacc ttgttcatag rgatcaggcc ttgcatacct 120
acatagtcca aacattacat tcctgacatt tagaacattt aaatgcaaac tgttctttgt 180
tagggctttc tcataactga a 201

<210> SEQ ID NO 83
<211> LENGTH: 201
<212> TYPE: DNA
<213> ORGANISM: Homo sapiens

<400> SEQUENCE: 83
gttgttgttt ttagttgctt ataataaata ttaatgcttt tagataaacc tttgttttat 60
tttctacttt attctcagct ccttacctct tagccaaatt wtggggaaaa tattttaaaa 120
attttctctc ttttcaaatc ctggctctgt tttctttctt catctagttt gagtaagact 180
cgagattatg taggtcatca g 201

<210> SEQ ID NO 84
<211> LENGTH: 201
<212> TYPE: DNA
<213> ORGANISM: Homo sapiens

<400> SEQUENCE: 84
tttttgaatt ttgttccaca aggataatat ctgcacatag taaaaaacta aaatgatgga 60
aatgtttgaa acttcgttat aaatattgtt ctactctttt scttcatata tttaactacc 120
taggtgaaac tgctcttaaa aatttttatg aagccttcca aaaatgctgt gcattagctt 180
tacacatatt tttacacaaa t 201

<210> SEQ ID NO 85
<211> LENGTH: 201
<212> TYPE: DNA
<213> ORGANISM: Homo sapiens

<400> SEQUENCE: 85
caagtagcag gaaattatca gggaaactag aagagtatac tttaaaaaat gaattcagat 60
aattaattta gaaatggaag tatatcatgt agttaaatac rtagacttta tagttaaacc 120
ccagttcaca tcctacctct gacattccca gctatatgac cttcaacaac tttactattc 180
cttcatgttt gtatctatga t 201

<210> SEQ ID NO 86
<211> LENGTH: 201
<212> TYPE: DNA
<213> ORGANISM: Homo sapiens

<400> SEQUENCE: 86
tgggtcaatt aaacctcttt cctttataaa ttacccagtc ttgggtatgt ctttattagc 60
tgcatgacag cagactaata caggttactg atatcagaga ragtagggca ctgctgtaaa 120
aataccaaag tgactttgga actgggtaac tggcagagac tggaacagtt tggagggttc 180
agaataagag agaaaaatgt t 201

<210> SEQ ID NO 87
<211> LENGTH: 201
<212> TYPE: DNA
<213> ORGANISM: Homo sapiens

<400> SEQUENCE: 87
agaagtattc tatttgaata cagtttcaaa tgactgttac tcattcattt agagatacca 60
gttaggaagc tggagatatg agtgtggagc ttagggttgg rgttagggct ggatatacac 120
atttgagagt catcagtgtt tagaggacat ttaaaaccaa taaactgaat gagaacacgt 180
ttgcggagtg tattagtctg t 201

<210> SEQ ID NO 88
<211> LENGTH: 201
<212> TYPE: DNA
<213> ORGANISM: Homo sapiens

<400> SEQUENCE: 88
ttaaaatgaa aattgaagct atttttgtct tgtgaataaa aaacattcaa ttcacttgca 60
aattaacagg gcaaacaatt attgcagctt aaatagaaaa yattttcaca gacaaagtaa 120
atagttatta taacctcaac tttatttact ctggtttgat aaaatcttaa tggaatataa 180
tgtattttat ggttggtgtt a 201

<210> SEQ ID NO 89
<211> LENGTH: 201
<212> TYPE: DNA
<213> ORGANISM: Homo sapiens

<400> SEQUENCE: 89
gtttatgcaa ataatttgaa atagtaatgt attctcaaat tagaaaataa tttaacgtgt 60
ttattgattt tcattgaact aaatgtgaac aaattctata ytgacacaac ttgagcaaga 120
gtccatgttg gccttcgcaa ttggtacatt ttccgtcttc actacattcc ctcagttgag 180
ttttaccttc cttctactgt g 201

<210> SEQ ID NO 90
<211> LENGTH: 201
<212> TYPE: DNA
<213> ORGANISM: Homo sapiens

<400> SEQUENCE: 90
ataaatggta atgaacatga tttttgttga caagattaca tataaagtga ttggaagata 60
ttttaagaca cactagagca acggtatcat tgcattgggt rgaggcatag cactttgcag 120
agctcgcata ttatgtttct tggaatgttg ttttatgtgc agatttttct cctagaaact 180
atgatttttg aacgattagc a 201

<210> SEQ ID NO 91
<211> LENGTH: 201
<212> TYPE: DNA
<213> ORGANISM: Homo sapiens

<400> SEQUENCE: 91
tgtgaacctc ggagaaaata taggagatac tgttctccct agtaatcatg agaaaataag 60
gtcacatcaa gcagcaatag agtgtcttat atgcacttat ytgctaccaa atattttatt 120
taaattccac gtgagtataa ctgcacactt tctcttttat aggttccttt gtctttgcgg 180
ttacagtcac agatgctgat a 201

<210> SEQ ID NO 92
<211> LENGTH: 201
<212> TYPE: DNA
<213> ORGANISM: Homo sapiens

<400> SEQUENCE: 92
taaaaaagca taaactttcc aaacctgaga aatatgcatt tagaagcttt cttttgattc 60
taagtaaaat tatggaatcc ttttctcaca caaaagacac mggtgtttta aataataatt 120
taaatttaaa tctgttttcc tactatgtct ttgaattcaa gtatctgcta tggcaacctc 180
tgagttcatg aattgtaaaa a 201

<210> SEQ ID NO 93
<211> LENGTH: 201
<212> TYPE: DNA
<213> ORGANISM: Homo sapiens

<400> SEQUENCE: 93
ctccctcctc ccaccctcca ccctccagta gaccccagtg tctgttgttt ccttctctgt 60
gtccatgtgt tctcatcatt tagctcccac ttataagtga raacaggtgg tatttggttt 120
tctgttccta tgttagtttg ctgaggataa tagcctccag ctccatccat gttcccacaa 180
aagacataat cttgttcttt t 201

<210> SEQ ID NO 94
<211> LENGTH: 201
<212> TYPE: DNA
<213> ORGANISM: Homo sapiens

<400> SEQUENCE: 94
gagattacca gaaataaaac tattaaaggc aaagctagga atactttcta atgtttgtaa 60
cttaagtatt ttaataacat tttctatttg cctttctttt yctacatgtt gttactgttt 120
tgttacaaag tcacactagt tcgttattat tattaatcaa acagtacaga aaaacaaagg 180
attgggattg ccaccattgt t 201

<210> SEQ ID NO 95
<211> LENGTH: 201
<212> TYPE: DNA
<213> ORGANISM: Homo sapiens

<400> SEQUENCE: 95
atactgatta tacatgatga taaattatat gtgatgatta ctgaaaataa agttagttac 60
cgatgtaaat acttgattga acacttcttt gtcctaattt rtagcatact agagactaaa 120
gattacaaat cattttaacc atgcaaacgt atattttgga aacacagtga aaatgattac 180
aaacaaattt ttcaagtaca t 201

<210> SEQ ID NO 96
<211> LENGTH: 201
<212> TYPE: DNA
<213> ORGANISM: Homo sapiens

<400> SEQUENCE: 96
tgctccccaa gaacctatgt tccacacctt tggtgtatta tcaccttcaa tgggaatgca 60
tgatttagta gttgaagcca ttggcctatt tcatgttctt yacaaattta aaaaatatat 120
attttatttg tatgtatgca atttttggta tatgggatgt aaaaaggaag gaaattgata 180
aataaatgag taagaaaaag a 201

<210> SEQ ID NO 97
<211> LENGTH: 201
<212> TYPE: DNA
<213> ORGANISM: Homo sapiens

<400> SEQUENCE: 97
attatgacct gagaatttta atccatcccc tgtcaagttt tattggattt cctggaatac 60
agttactcta ctctgtagag ggcagagcaa ctccatcttg katgctcatc ttccatgtct 120
acttctgatt aaccccagtt ctgggaatgc ctctaatatt tccagtatat ctatagttcc 180

-continued

```
ttatgtaaga gcttgtacta a                                              201


<210> SEQ ID NO 98
<211> LENGTH: 201
<212> TYPE: DNA
<213> ORGANISM: Homo sapiens

<400> SEQUENCE: 98

taagttagcc tgtaagtctt gctattgcat ccacttttta aatttgttca acaccagagc     60

tactgtgtgc caagcaccat atttagataa gtgagagatg rctcttgcct tcaagaggtt    120

tgcagttttt ggtgactaga ctttcccttt tccaaagtag tttaagattt gcatagctct    180

gtttgcagag aattatttaa a                                              201


<210> SEQ ID NO 99
<211> LENGTH: 201
<212> TYPE: DNA
<213> ORGANISM: Homo sapiens

<400> SEQUENCE: 99

ctctataata ttaatttcat attacatctt aagactttca tttaagcaaa ttacataact     60

cctaaaaggt gctgcattga ggccaggcac ggtggctcat rcctgtaatc ccagcacttt    120

gggaggccga gacaggtgga tcacctgagg tcaggagttt cagaccagcc tggctaacat    180

ggtgaaaccc catttgtact a                                              201


<210> SEQ ID NO 100
<211> LENGTH: 201
<212> TYPE: DNA
<213> ORGANISM: Homo sapiens

<400> SEQUENCE: 100

caataaattt gttaccttta tattcagaaa cctaattgaa tcggagtaga cgaggactaa     60

aagcataagg aataataatc actaatcttc actatttttc yttgtttgtg ttgcaaatat    120

tgtgtgttgg ctggtgttag gcatggtgaa atatatgaaa atgatattaa tataaaacaa    180

tgtccaagtc ctagaggcaa c                                              201


<210> SEQ ID NO 101
<211> LENGTH: 201
<212> TYPE: DNA
<213> ORGANISM: Homo sapiens

<400> SEQUENCE: 101

tcttgggtat gtctttatta gctgcatgac agcagactaa tacaggttac tgatatcaga     60

gagagtaggg cactgctgta aaaataccaa agtgactttg raactgggta actggcagag    120

actggaacag tttggagggt tcagaataag agagaaaaat gttggaaagt ttggaacttc    180

ctacagactt tttgaatggc t                                              201
```

BIOMARKERS FOR PREDICTING WEIGHT LOSS AND WEIGHT MAINTENANCE

CROSS-REFERENCE TO RELATED APPLICATIONS

The present application is the National Stage of International Application No. PCT/EP2015/076010, filed on Nov. 9, 2015 which claims benefit to European Application No. 14194223.5, filed Nov. 21, 2014. The entire contents of the above applications are incorporated by reference as if recited in full herein.

FIELD OF INVENTION

The present invention provides biomarkers and biomarker combinations that can be used to predict the degree of weight loss attainable by applying one or more dietary interventions to a subject and/or the predisposition of a subject to maintenance of weight loss following one or more dietary interventions.

BACKGROUND

Obesity is a chronic metabolic disorder that has reached epidemic proportions in many areas of the world and is the major risk factor for serious co-morbidities such as type 2 diabetes mellitus, cardiovascular disease, dyslipidaemia and certain types of cancer (World Health Organ Tech Rep Ser. 2000; 894:i-xii, 1-253).

It has long been recognized that low calorie dietary interventions can be very efficient in reducing weight and that this weight loss is generally accompanied by an improvement for the risk of obesity related co-morbidities, in particular type 2 diabetes mellitus. Empirical data suggests that a weight loss of at least 10% of the initial weight results in a considerable decrease in risk for obesity related co-morbidities (World Health Organ Tech Rep Ser. 2000; 894:i-xii, 1-253). However, the capacity to lose weight shows large inter-subject variability.

It has been shown that a percentage of the population do not successfully lose weight on a low calorie diet (Ghosh, S. et al., Obesity (Silver Spring), (2011) 19(2):457-463). This leads to an unrealistic expectation of weight loss, which in turn causes non-compliance, drop-outs and generally unsuccessful dietary intervention.

Some studies also demonstrate that there are methods in the art for monitoring weight loss which include monitoring levels of particular biomarkers in plasma (e.g. Lijnen et al., Thromb Res. 2012 January, 129(1): 74-9; Cugno et al., Intern Emerg Med. 2012 June, 7(3): 237-42; and Bladbjerg et al., Br J Nutr. 2010 December, 104(12): 1824-30). However, these methods do not provide a prediction or indication of the degree of weight loss attainable by a particular subject. There is no predictive value in looking at the correlation of biomarker levels with weight loss.

Keeping weight lost stable also presents a major challenge to the patient. It is known that only one year after a weight loss intervention, about one-third of the lost weight is regained (Hensrud, Obes. Res. 9 Suppl 4, 348S-353S, 2001). Moreover, diet-induced weight loss induces several physiological changes that facilitate weight regain (Sumithran and Proietto, Clin. Sci. Lond. Engl. 1979 124, 231-241 (2013)). These changes include alterations in energy expenditure, substrate metabolism and hormone pathways involved in appetite regulation. Our understanding of these physiological and molecular changes remains so far limited.

The solution for successful planning and design of dietary interventions, for example low calorie diets, lies in the availability of a method which predicts a weight loss trajectory. In addition, successful planning and design of weight management interventions would be aided by the availability of a test to predict the success (or failure) of a patient at keeping his/her weight loss stable during a weight maintenance program.

United States Patent Application US 2011/0124121 discloses a method for predicting weight loss success. The methods disclosed comprises selecting a patient who is undergoing or considering undergoing a weight loss therapy such as gastric banding, measuring one or more hormone responses of the patient to caloric intake and predicting success of a weight loss therapy based on the hormone response. The hormones measured are gastrointestinal hormones such as a pancreatic hormone.

European Patent Application EP 2 420 843 discloses a method for determining the probability that a person will maintain weight loss after an intentional weight loss by determining the level of angiotensin I converting enzyme (ACE) before and after the dietary period.

There is, however, still a need for a method of accurately predicting the degree of weight loss and weight maintenance in a subject. Consequently, it was the objective of the present invention to provide biomarkers that can be detected easily and that can facilitate the prediction of weight loss and weight maintenance in a subject. Such biomarkers may be used to predict weight trajectories during weight loss and during weight maintenance and may help for stratification of patients into adapted treatment groups according to their biological weight loss and weight maintenance capacities.

Protocadherin Fat 4, also known as cadherin family member 14 (CDHF14) or FAT tumor suppressor homolog 4 (FAT4), is a protein that in humans is encoded by the FAT4 gene. FAT4 is associated with the Hippo signaling pathway. The Hippo pathway has emerged as a conserved signaling pathway that is essential for the proper regulation of organ growth in *Drosophila* and vertebrates (Halder, 2011, Development, January; 138(1):9-22).

It has recently been shown that *Drosophila* Fat (Ft) cadherin has a direct role in regulating mitochondrial morphology and metabolism (Sing et al., 2014, Cell, 158, 1293-1308). It was shown that proteolytic cleavage of Ft releases a soluble fragment ($Ft^{mito}$) that is imported into the mitochondria and that such cleavage functions as a switch mechanism to coordinate cell cycle and metabolism. It was suggested that altering the levels of $Ft^{mito}$ may allow an organism to directly adjust metabolic rates in accordance with changing energy requirements.

SUMMARY OF THE INVENTION

The present invention identifies biomarkers useful in predicting the predisposition of a subject to change in weight-related phenotypes by applying one or more dietary interventions to a subject. The present invention also identifies biomarkers useful in predicting the predisposition of a subject to maintenance of weight-related phenotypes following one or more dietary interventions.

In particular, the invention discloses specific polymorphisms/alleles of the FAT4 gene that are related to change in weight-related phenotypes as well as diagnostic tools and kits based on these susceptibility alterations. Thus, the invention can be used in predicting the outcome to a weight management program (including weight loss program or weight maintenance program).

Accordingly the present invention provides in one aspect a method for assessing the predisposition of a subject to weight loss attainable by applying one or more dietary interventions to a subject and/or the predisposition of a subject to maintenance of weight loss following one or more dietary interventions which method comprises determining the presence of one or more polymorphic markers in the FAT4 gene or a regulatory element thereof.

The present invention provides in one aspect a method for assessing the predisposition of a subject to weight loss attainable by applying one or more dietary interventions to a subject and/or the predisposition of a subject to maintenance of weight loss following one or more dietary interventions which method comprises determining the nucleotide of the subject at one or more polymorphic positions selected from:

(i) position 101 of SEQ ID NO:1 (rs953211)

(ii) position 101 of SEQ ID NO:2 (rs1509290)

(iii) position 101 of SEQ ID NO:3 (rs1509289)

and/or detecting one or more biomarkers genetically linked to said polymorphic positions.

In one embodiment, the one or more biomarkers (e.g., SNPs) are within the FAT4 gene or a regulatory element thereof. In one embodiment, the biomarker is less than 20, 15, 10, 5, 4, 3, 2, 1 kilobases (kb) from said polymorphic positions defined above.

Preferably the method comprises determining the nucleotide of the subject at both position 101 of SEQ ID NO:1 and position 101 of SEQ ID NO:2. In one embodiment, the method comprises determining the nucleotide of the subject at position 101 of SEQ ID NO:1, position 101 of SEQ ID NO:2 and position 101 of SEQ ID NO:3.

In one embodiment the method comprises determining the presence of A or G at position 101 of SEQ ID NO:1, and/or A or G at position 101 of SEQ ID NO:2, and/or A or G at position 101 of SEQ ID NO:3.

In one embodiment the method for assessing the predisposition of a subject to maintenance of weight loss by applying one or more dietary interventions comprises determining the presence of A or G at position 101 of SEQ ID NO:1 wherein the weight loss is represented by a change in body mass index (BMI), fat mass, hip circumference or waist circumference.

In another embodiment the method for assessing the predisposition of a subject to maintenance of weight loss by applying one or more dietary interventions comprises determining the presence of A or G at position 101 of SEQ ID NO:2 wherein the weight loss is represented by a change in BMI, fat free mass, hip circumference or waist circumference.

In another embodiment the method for assessing the predisposition of a subject to maintenance of weight loss by applying one or more dietary interventions comprises determining the presence of A or G at position 101 of SEQ ID NO:3 wherein the weight loss is represented by a change in BMI, fat mass, fat free mass, hip circumference or waist circumference.

In another embodiment the method for assessing the predisposition of a subject to maintenance of weight loss by applying one or more dietary interventions comprises determining the presence of A or G at position 101 of SEQ ID NO:1 and the presence of A or G at position 101 of SEQ ID NO:2 wherein the weight loss is represented by BMI, fat mass, fat free mass, hip circumference or waist circumference.

In a particularly preferred embodiment subjects having a genotype comprising a G at position 101 of SEQ ID NO:1 and an A at position 101 of SEQ ID NO:2 are identified as having a predisposition maintain weight loss following a dietary intervention.

By "G at position 101" referred to above it is meant that the subject has at least one copy of G at said site, i.e., the subject may have the genotype G/G (homozygous) or G/A (heterozygous).

By "A at position 101" referred to above it is meant that the subject has at least one copy of A at said site, i.e., the subject may have the genotype A/A (homozygous) or G/A (heterozygous).

Preferably the method for assessing the predisposition of a subject to maintenance of weight loss comprises determining the presence of a genotype selected from:

(i) G/G (homozygous) at position 101 of SEQ ID NO:1 and A/A (homozygous) at position 101 of SEQ ID NO:2;

(ii) G/G (homozygous) at position 101 of SEQ ID NO:1 and G/A (heterozygous) at position 101 of SEQ ID NO:2;

(iii) G/A (heterozygous) at position 101 of SEQ ID NO:1 and G/A (heterozygous) at position 101 of SEQ ID NO:2; and (iv) G/A (heterozygous) at position 101 of SEQ ID NO:1 and A/A (homozygous) at position 101 of SEQ ID NO:2;

and wherein the presence of said genotype indicates that a subject has a predisposition to maintain weight loss following a dietary intervention.

Preferably the method for assessing the predisposition of a subject to maintenance of weight loss comprises determining the presence of a genotype selected from:

(i) A/A (homozygous) at position 101 of SEQ ID NO:1 and A/A (homozygous) at position 101 of SEQ ID NO:2;

(ii) A/A (homozygous) at position 101 of SEQ ID NO:1 and A/G (heterozygous) at position 101 of SEQ ID NO:2;

(iii) A/A (homozygous) at position 101 of SEQ ID NO:1 and G/G (homozygous) at position 101 of SEQ ID NO:2;

(iv) A/G (heterozygous) at position 101 of SEQ ID NO:1 and G/G (homozygous) at position 101 of SEQ ID NO:2; and (v) G/G (homozygous) at position 101 of SEQ ID NO:1 and G/G (homozygous) at position 101 of SEQ ID NO:2;

and wherein the presence of said genotype indicates that a subject has a predisposition not to maintain weight loss following a dietary intervention.

Preferably the maintenance of weight loss is assessed by measuring a change in BMI.

In another embodiment the method for assessing the predisposition of a subject to weight loss attainable by applying on or more dietary interventions comprises determining the presence of A or G at position 101 of SEQ ID NO:1 and wherein the weight loss is represented by a change in hip circumference.

In another embodiment the method for assessing the predisposition of a subject to weight loss attainable by applying on or more dietary interventions comprises determining the presence of A or G at position 101 of SEQ ID NO:2 and wherein the weight loss is represented by a change in BMI or hip circumference.

In another embodiment the method for assessing the predisposition of a subject to weight loss attainable by applying on or more dietary interventions comprises determining the presence of A or G at position 101 of SEQ ID NO:3 and wherein the weight loss is represented by a change in BMI or hip circumference.

In another embodiment the method for assessing the predisposition of a subject to weight loss attainable by applying on or more dietary interventions comprises detecting the presence of A or G at position 101 of SEQ ID NO:1 and the presence of A or G at position 101 of SEQ ID NO:2 and wherein the weight loss is represented by a change in BMI or a change in hip circumference.

In a particularly preferred embodiment subjects having a genotype comprising a G at position 101 of SEQ ID NO:1 and an A at position 101 of SEQ ID NO:2 are identified as having a predisposition to lose weight.

By "G at position 101" referred to above it is meant that the subject has at least one copy of G at said site, i.e., the subject may have the genotype G/G (homozygous) or G/A (heterozygous).

By "A at position 101" referred to above it is meant that the subject has at least one copy of A at said site, i.e., the subject may have the genotype A/A (homozygous) or G/A (heterozygous).

Preferably the method for assessing the predisposition of a subject to weight loss attainable by applying on or more dietary interventions comprises determining the presence of a genotype selected from:

(i) G/G (homozygous) at position 101 of SEQ ID NO:1 and A/A (homozygous) at position 101 of SEQ ID NO:2;

(ii) G/G (homozygous) at position 101 of SEQ ID NO:1 and G/A (heterozygous) at position 101 of SEQ ID NO:2;

(iii) G/A (heterozygous) at position 101 of SEQ ID NO:1 and G/A (heterozygous) at position 101 of SEQ ID NO:2; and (iv) G/A (heterozygous) at position 101 of SEQ ID NO:1 and A/A (homozygous) at position 101 of SEQ ID NO:2;

and wherein the presence of said genotype indicates that a subject has a predisposition to lose weight following a dietary intervention.

Preferably the method for assessing the predisposition of a subject to weight loss attainable by applying on or more dietary interventions comprises determining the presence of a genotype selected from:

(i) A/A (homozygous) at position 101 of SEQ ID NO:1 and A/A (homozygous) at position 101 of SEQ ID NO:2;

(ii) A/A (homozygous) at position 101 of SEQ ID NO:1 and A/G (heterozygous) at position 101 of SEQ ID NO:2;

(iii) A/A (homozygous) at position 101 of SEQ ID NO:1 and G/G (homozygous) at position 101 of SEQ ID NO:2;

(iv) A/G (heterozygous) at position 101 of SEQ ID NO:1 and G/G (homozygous) at position 101 of SEQ ID NO:2; and (v) G/G (homozygous) at position 101 of SEQ ID NO:1 and G/G (homozygous) at position 101 of SEQ ID NO:2;

and wherein the presence of said genotype indicates that a subject has a predisposition not to lose weight following a dietary intervention.

In another aspect of the present invention there is provided a method for assessing the predisposition of a subject to weight loss attainable by applying one or more dietary interventions to a subject and/or the predisposition of a subject to maintenance of weight loss following one or more dietary interventions which method comprises determining the nucleotide of the subject at one or more polymorphic positions shown in FIG. 7 (SEQ ID NOs 10 to 101).

The present invention provides in another aspect a method for assessing the predisposition of a subject to weight loss attainable by applying one or more dietary interventions and/or the predisposition of a subject to maintenance of weight loss following one or more dietary interventions which method comprises determining the sequence of FAT4 gene or a regulatory element thereof.

The dietary intervention referred to herein is preferably a low calorie diet.

The dietary intervention may comprise administering at least one diet product to the subject.

A low calorie diet may comprise a decreased consumption of fat and/or an increase in consumption of low fat foods. By way of example only, low fat foods may include wholemeal flour and bread, porridge oats, high-fibre breakfast cereals, wholegrain rice and pasta, vegetables and fruit, dried beans and lentils, baked potatoes, dried fruit, walnuts, white fish, herring, mackerel, sardines, kippers, pilchards, salmon and lean white meat.

In one embodiment the low calorie diet may comprises a calorie intake of about 600 to about 1200 kcal/day and/or may comprise administration of at least one diet product.

The low calorie diet may also comprise administration of up to, for example, about 400 g vegetables/day.

Preferably the diet product is Optifast® or Modifast®.

Thus, the diet may comprise a product such as Optifast® or Modifast®. This may be supplemented with three portions of non-starchy vegetables such that the total energy intake is about 2.5 MJ (600 kcal/day). This may be further supplemented with at least 2 L of water or other energy free beverages per day.

In another embodiment, the diet may comprise, for example, a composition which is 46.4% carbohydrate, 32.5% protein and 20.1% with fat, vitamins, minerals and trace elements; 2.1 MJ per day (510 kcal/day); This may be supplemented with three portions of non-starchy vegetables such that the total energy intake is about 2.5 MJ (600 kcal/day). This may be further supplemented with at least 2 L of water or other energy free beverages per day.

In one embodiment, the low calorie diet has a duration of up to 12 weeks, e.g. 6 to 12 weeks.

The methods referred to herein may further comprise determining one or more anthropometric measures and/or lifestyle characteristics of the subject.

The anthropometric measure may be selected from, for example, the group consisting of gender, weight, height, age and body mass index, and the lifestyle characteristic may be, for example, whether the subject is a smoker or a non-smoker.

According to another aspect of the present invention there is provided a method for optimizing one or more dietary interventions for a subject comprising:

assessing the predisposition of a subject to weight loss attainable by one or more dietary interventions and/or the predisposition of a subject to maintenance of weight loss following one or more dietary interventions according to the method defined herein; and applying one or more dietary interventions to the subject.

According to another aspect of the present invention there is provided a method for selecting a modification of lifestyle of a subject, the method comprising:

(a) performing a method of assessing the predisposition of a subject to weight loss attainable by one or more dietary interventions and/or the predisposition of a subject to maintenance of weight loss following one or more dietary interventions according to the method defined herein; and (b) selecting a suitable modification in lifestyle based upon the predicted weight loss attainable and/or predicted maintenance of weight loss from (a).

In one embodiment, the modification of lifestyle comprises a dietary intervention, preferably a dietary intervention defined herein.

According to another aspect of the present invention there is provided a low calorie diet for weight loss, wherein the diet product is administered to a subject that is predicted to attain weight loss by the method defined herein.

According to another aspect of the present invention there is provided a diet product for use as part of a low calorie diet for weight loss, wherein the diet product is administered to a subject that is predicted to attain weight loss or maintenance by the method defend herein.

According to another aspect of the present invention there is provided a diet product for use as part of a low calorie diet for weight loss, wherein the diet product is administered to a subject that is predicted to attain both weight maintenance and weight loss by the method defined herein.

According to another aspect of the present invention there is provided a diet product for use in treating obesity or an obesity-related disorder, wherein the diet product is administered to a subject that is predicted to attain weight maintenance and/or weight loss by the method defined herein.

In one embodiment, the diet product may comprise a product such as Optifast® or Modifast®.

In another embodiment, the diet product may comprise, for example, a composition which is 46.4% carbohydrate, 32.5% protein and 20.1% with fat, vitamins, minerals and trace elements; 2.1 MJ per day (510 kcal/day); This may be supplemented with three portions of non-starchy vegetables such that the total energy intake is about 2.5 MJ (600 kcal/day). This may be further supplemented with at least 2 L of water or other energy free beverages per day.

According to another aspect of the present invention there is provided an allele-specific oligonucleotide probe capable of detecting a polymorphic position within the FAT4 gene or a regulatory element thereof.

According to another aspect of the present invention there is provided an allele-specific oligonucleotide primer capable of detecting a polymorphic position within the FAT4 gene or a regulatory element thereof.

According to another aspect of the present invention there is provided an allele-specific oligonucleotide probe capable of detecting a polymorphic position selected from:

(i) position 101 of SEQ ID NO:1;
(ii) position 101 of SEQ ID NO:2; or
(iii) position 101 of SEQ ID NO:3.

According to another aspect of the present invention there is provided an allele-specific oligonucleotide primer capable of detecting a polymorphic position selected from:

(i) position 101 of SEQ ID NO:1;
(ii) position 101 of SEQ ID NO:2; or
(iii) position 101 of SEQ ID NO:3.

According to another aspect of the present invention there is provided a diagnostic kit comprising an allele-specific oligonucleotide primer and/or an allele-specific oligonucleotide probe as defined in.

According to another aspect of the present invention there is provided a diagnostic kit comprising (i) an allele-specific oligonucleotide primer and/or an allele-specific oligonucleotide probe capable of detecting the presence of G at position 101 of SEQ ID NO:1 and (ii) an allele-specific oligonucleotide primer and/or an allele-specific oligonucleotide probe capable of detecting the presence of A at position 101 of SEQ ID NO:2.

In one embodiment the diagnostic kit further comprises an allele-specific oligonucleotide primer and/or an allele-specific oligonucleotide probe capable of detecting the presence of A at position 101 of SEQ ID NO:3.

In a further aspect of the present invention, there is provided a computer program product comprising computer implementable instructions for causing a programmable computer to predict the degree of weight loss attainable by a subject according to the methods described herein.

DESCRIPTION OF THE FIGURES

FIG. 3: Sequence of rs953211 (SEQ ID NO:1), rs1509290 (SEQ ID NO:2) and rs1509289 (SEQ ID NO: 3). The polymorphic position is shown in square brackets, i.e., [A/G].

FIG. 4: Genomic sequence of FAT4 gene (SEQ ID NO: 4). The polymorphic positions rs953211, rs1509290 and rs1509289 are identified as bold bases within the underlined sequences.

FIGS. 5A, 5B and 5C: Sequences of three FAT4 transcripts (SEQ ID NOs 5, 6 and 7)

FIGS. 6 A and 6B: Sequences of two FAT4 protein sequences (SEQ ID NOs: 8 and 9.

FIG. 7: SNPs located nearby the FAT4 gene (+/−10 Kb). Shown are ninety-two SNPs have a p-value smaller than 5%.

DETAILED DESCRIPTION OF THE INVENTION

Predicting Weight Loss and Weight Maintenance

Figure 1:
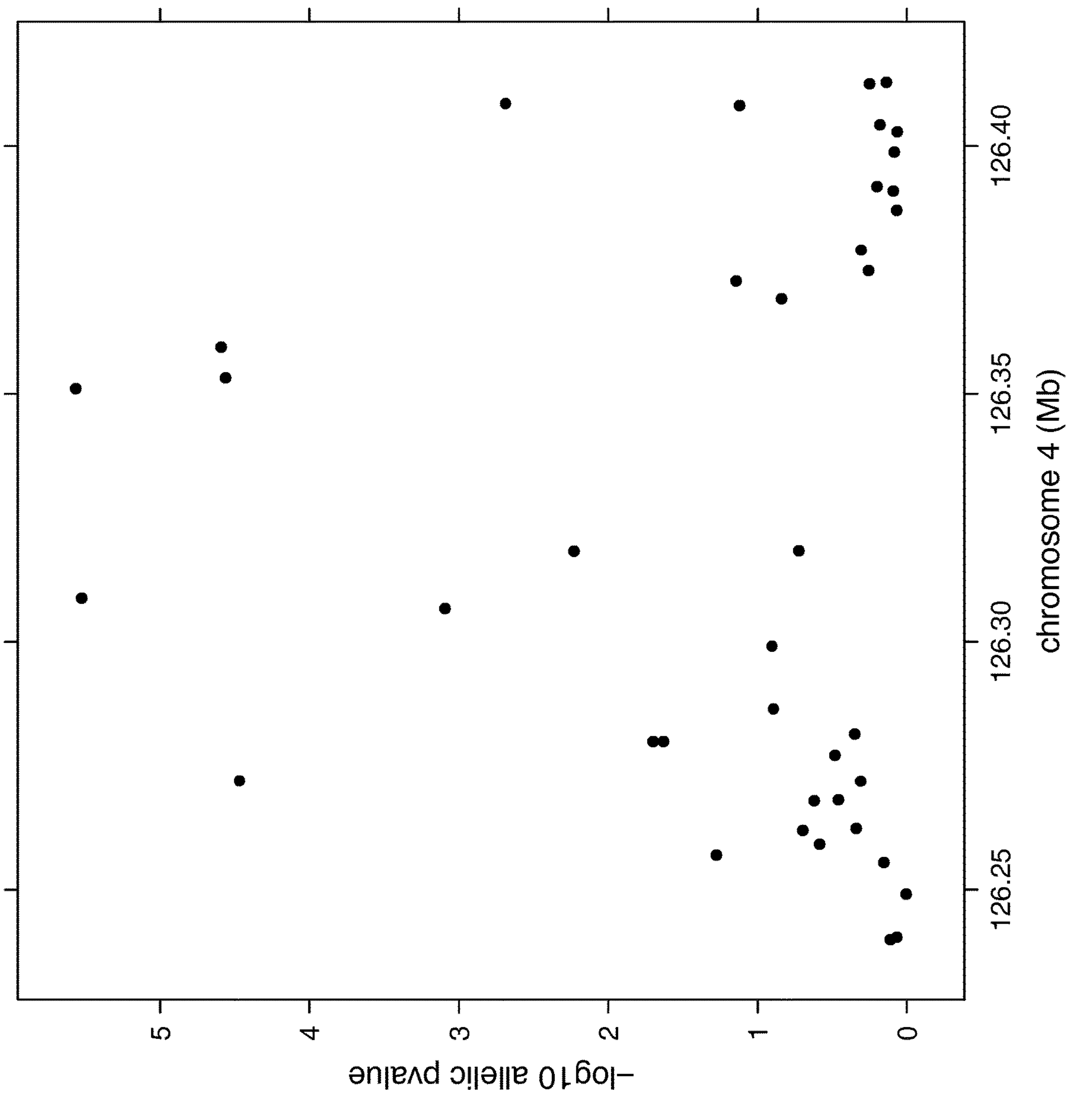
FIG. 1: Association between SNPs located nearby the FAT4 gene and change in BMI during weight maintenance. The X axis shows the SNP's coordinate on chromosome 4 and the Y axis shows the −log 10 p-value from an allelic test. This figure displays results from SNPs assayed on the genotyping array.

The present invention provides a method for assessing the predisposition of a subject to weight loss attainable by applying one or more dietary interventions to a subject and/or the predisposition of a subject to maintenance of weight loss following one or more dietary interventions. The invention allows accurate prediction of weight trajectory of a patient, prior to a weight loss intervention and/or prior to a weight maintenance intervention.

The method may be used to make an informed prediction of the subject's capacity to lose weight and/or maintain weight loss, and select or adjust one or more dietary intervention accordingly.

For example, the present invention can be used for predicting the outcome of a weight management program, for adapting the weight management program and for stratifying patients following such a program into groups of successful or less successful profiles. For example, the method can be used to identify subjects with either a "high" or "low" likelihood of achieving weight loss by applying a dietary intervention. Similarly, the method can be used to identify subjects with either a "high" or "low" likelihood of maintaining weight loss following a dietary intervention.

Where the dietary intervention is a low calorie diet, the method could be used to aid in the appropriate diet for the subject or to adjust the daily calorie intake or duration of a particular diet and aid in setting realistic expectations for the subject.

In particular, the method provides a skilled person with a useful tool for assessing which subjects will most likely benefit from a particular dietary intervention, e.g. a low calorie diet. The present method therefore enables dietary interventions such as a low calorie diet and modifications in lifestyle to be optimised.

Weight loss as defined herein may refer to a reduction in parameters such as weight (e.g. in kilograms), body mass index ($kgm^{-2}$), waist-hip ratio (e.g. in centimetres), fat mass (e.g. in kilograms), hip circumference (e.g. in centimetres) or waist circumference (e.g. in centimetres).

Weight loss may be calculated by subtracting the value of one or more of the aforementioned parameters at the end of the dietary intervention from the value of said parameter at the onset of the dietary intervention.

The degree of weight loss may be expressed as a percentage change of one of the aforementioned weight phenotype parameters (e.g., a percentage change in a subject's body weight (e.g. in kilograms) or body mass index ($kgm^2$)). For example, a subject predisposed to lose weight following a dietary intervention may be likely to lose at least 10% of their initial body weight, at least 8% of their initial body weight, or at least 5% of their initial body weight. By way of example only, a subject may be likely to lose between 5 and 10% of their initial body weight.

In one embodiment, a degree of weight loss of at least 10% of initial body weight results in a considerable decrease in risk for obesity related co-morbidities.

Weight maintenance as defined herein may refer to the maintenance in parameters such as weight (e.g. in kilograms), body mass index ($kgm^{-2}$), waist-hip ratio (e.g. in centimetres) fat mass (e.g. in kilograms), hip circumference (e.g. in centimetres) or waist circumference (e.g. in centimetres) following a dietary intervention The degree of weight maintenance may be calculated by determining the change in one or more of the aforementioned parameters during a period of time following the end of the dietary intervention. The period of time may be for example at least 4, 8, 12, 16, 20, 24, 28, 32, 36, 40, 44, 48 or 52 weeks following the end of the dietary intervention.

The degree of weight maintenance may be expressed as the percentage of weight change during a period following the end of the dietary intervention. For example, a subject predisposed to weight maintenance may be likely to regain less than 50, 40, 30, 20, 10, 5% or 1% of the weight lost during the dietary intervention.

Biomarkers

The term "polymorphism" refers to two or more alternate forms (alleles) in a population of a genetic locus that differ in nucleotide sequence or have variable numbers of repeated nucleotide units. Polymorphisms occur in coding regions (exons), non-coding regions of genes or outside of genes (intergenic regions).

An "allele" is a particular form of a gene, genetic marker or other genetic locus, that is distinguishable from other forms of the gene, genetic marker or other genetic locus. The term allele includes, for example and without limitation, one form of a single nucleotide polymorphism (SNP). An individual can be homozygous for a certain allele in diploid cells; i.e. the allele on both paired chromosomes is identical; or heterozygous for said allele; i.e. the alleles on both paired chromosomes are not identical.

The term "gene" refers to a unit of DNA which performs one function. Usually, this is equated with the production of one RNA or one protein. A gene may contain coding regions, introns, untranslated regions and control regions.

As used herein, the phrase "genetic marker" refers to a feature of an individual's genome (e.g., a nucleotide or a polynucleotide sequence that is present in an individual's genome) that is associated with one or more loci of interest. Typically, a genetic marker is polymorphic and the variant forms of genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), Microsatellites or Simple sequence repeat (SSRs) among many other examples.

A "single nucleotide polymorphism (SNP)" is a DNA sequence variation occurring when a single nucleotide—A (for Adenine), T (for Thymine), C (for Cytosine), or G (for Guanine)—in the genome (or other sequence shared between individuals of a species) differs between individuals of a species (or between paired chromosomes in an individual).

A "genotype" as used herein refers to the combination of both alleles of a genetic marker, e.g. without limitation of a SNP, on a single genetic locus on paired (homologous) chromosomes in an individual.

The term "haplotype" refers to variants or alleles from distinct markers (e.g. SNPs) that are co-located on the same chromosome.

"linkage disequilibrium" (also called "allelic association") refers to a phenomenon wherein particular alleles at two or more loci tend to remain together in linkage groups when segregating from parents to offspring with a greater frequency than expected from their individual frequencies in a given population.

In one aspect the present invention provides a method for assessing the predisposition of a subject to weight loss attainable by applying one or more dietary interventions to a subject and/or the predisposition of a subject to maintenance of weight loss following one or more dietary interventions which method comprises determining the nucleotide of the subject at one or more polymorphic positions selected from:

(i) position 101 of SEQ ID NO:1 (rs953211)

(ii) position 101 of SEQ ID NO:2 (rs1509290)

(iii) position 101 of SEQ ID NO:3 (rs1509289)

and/or detecting one or more biomarkers genetically linked to said polymorphic positions.

Preferably the method comprises determining the presence of A or G at position 101 of SEQ ID NO:1, and/or A or G at position 101 of SEQ ID NO:2, and/or A or G at position 101 of SEQ ID NO:3.

It should be noted that in this application, SNPs are referred to by, for example, reference to a position in SEQ ID NO:1 (e.g. position 101), SEQ ID NO:2 (e.g. position 101) or SEQ ID NO:3 (e.g. position 101). However, when such references are made, it will be understood that the invention is not to be limited to the exact sequence as set out in the SEQ ID NO but includes variants and derivatives thereof. Instead, identification of SNP locations in similar sequences are contemplated (i.e. SNPs at positions which the skilled person would consider correspond to the positions identified in the SEQ ID numbers). The person skilled in the art can readily align similar sequences and locate the same SNP locations.

It should further be noted that detection of the nucleotide in the complement strand to SEQ ID NO:1, 2 or 3 that base-pairs with the nucleotide at position 101 of SEQ ID NO:1, 2 or 3 is of course within the scope of the claimed invention.

In the context of the present invention, detecting the presence of a biomarker in a FAT4 gene or regulatory element thereof comprises determining the identity of one or more nucleotides at a polymorphic site in a FAT4 encoding gene or regulatory element thereof of the individual. Similarly, detecting the presence of a biomarker genetically linked to the polymorphic positions 101 of SEQ ID NO:1, position 101 of SEQ ID NO:2 and position 101 of SEQ ID NO:3 comprises determining the identity of one or more nucleotides at a polymorphic site genetically linked to said positions.

The polymorphic site will be one which has an association with weight loss attainable by applying one or more dietary interventions and/or maintenance of weight loss following one or more dietary interventions in a subject population. By this is meant that a particular nucleotide or nucleotide sequence at the polymorphic site is correlated with said weight loss and/or maintenance.

It will be apparent to the person skilled in the art that there are a large number of analytical procedures which may be used to detect the presence or absence of variant nucleotides at one or more polymorphic positions of the invention. In general, the detection of allelic variation requires a mutation discrimination technique, optionally an amplification reaction and optionally a signal generation system.

Detection of Alleles

The nucleic acids obtained from the sample can be genotyped to identify the particular allele present for a marker locus. A sample of sufficient quantity to permit direct detection of marker alleles from the sample may be obtained.

Alternatively, a smaller sample is obtained from the subject and the nucleic acids are amplified prior to detection. Optionally, the nucleic acid sample is purified (or partially purified) prior to detection of the marker alleles.

Examples of allele detection methods are given below:

Allele Specific PCR

Allele-specific PCR differentiates between target regions differing in the presence of absence of a variation or polymorphism. PCR amplification primers are chosen based upon their complementarity to the target sequence, such as a sequence disclosed herein. The primers bind only to certain alleles of the target sequence.

Allele Specific Oligonucleotide Screening Methods

Further screening methods employ the allele-specific oligonucleotide (ASO) screening methods (e.g. see Saiki et al., Nature 324:163-166, 1986).

Oligonucleotides with one or more base pair mismatches are generated for any particular allele. ASO screening methods detect mismatches between one allele in the target genomic or PCR amplified DNA and the other allele, showing decreased binding of the oligonucleotide relative to the second allele (i.e. the other allele) oligonucleotide. Oligonucleotide probes can be designed that under low stringency will bind to both polymorphic forms of the allele, but which at high stringency, bind to the allele to which they correspond. Alternatively, stringency conditions can be devised in which an essentially binary response is obtained, i.e., an ASO corresponding to a variant form of the target gene will hybridize to that allele, and not to the wildtype allele.

Ligase Mediated Allele Detection Method

Ligase can also be used to detect point mutations, such as the SNPs in a ligation amplification reaction (e.g. as described in Wu et al., Genomics 4:560-569, 1989). The ligation amplification reaction (LAR) utilizes amplification of specific DNA sequence using sequential rounds of template dependent ligation (e.g. as described in Wu, supra, and Barany, Proc. Nat. Acad. Sci. 88:189-193, 1990).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation.

Each melting domain melts cooperatively at a distinct, base-specific melting temperature (Tm). Melting domains are at least 20 base pairs in length, and can be up to several hundred base pairs in length.

Differentiation between alleles based on sequence specific melting domain differences can be assessed using polyacrylamide gel electrophoresis, as described in Chapter 7 of Erlich, ed., PCR Technology, Principles and Applications for DNA Amplification, W. H. Freeman and Co., New York (1992).

Generally, a target region to be analyzed by denaturing gradient gel electrophoresis is amplified using PCR primers flanking the target region. The amplified PCR product is applied to a polyacrylamide gel with a linear denaturing gradient as described in Myers et al., Meth. Enzymol. 155:501-527, 1986, and Myers et al., in Genomic Analysis, A Practical Approach, K. Davies Ed. IRL Press Limited, Oxford, pp. 95 139, 1988. The electrophoresis system is maintained at a temperature slightly below the Tm of the melting domains of the target sequences.

In an alternative method of denaturing gradient gel electrophoresis, the target sequences can be initially attached to a stretch of GC nucleotides, termed a GC clamp, as described in Chapter 7 of Erlich, supra. In one example, at least 80% of the nucleotides in the GC clamp are either guanine or cytosine. In another example, the GC clamp is at least 30 bases long. This method is particularly suited to target sequences with high Tm's.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which can be visualized by ethidium bromide staining.

Temperature Gradient Gel Electrophoresis

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-Strand Conformation Polymorphism Analysis

Target sequences or alleles can be differentiated using single-strand conformation polymorphism analysis, which identifies base differences by alteration in electrophoretic migration of single stranded PCR products, for example as described in Orita et al., Proc. Nat. Acad. Sci. 85:2766-2770, 1989. Amplified PCR products can be generated as described above, and heated or otherwise denatured, to form single stranded amplification products. Single-stranded nucleic acids can refold or form secondary structures which are partially dependent on the base sequence. Thus, electrophoretic mobility of single-stranded amplification products can detect base-sequence difference between alleles or target sequences.

Chemical or Enzymatic Cleavage of Mismatches

Differences between target sequences can also be detected by differential chemical cleavage of mismatched base pairs, for example as described in Grompe et al., Am. J. Hum. Genet. 48:212-222, 1991. In another method, differences between target sequences can be detected by enzymatic cleavage of mismatched base pairs, as described in Nelson et al., Nature Genetics 4:11-18, 1993. Briefly, genetic material from an animal and an affected family member can be used to generate mismatch free heterohybrid DNA duplexes. As used herein, 'heterohybrid' means a DNA duplex strand comprising one strand of DNA from one animal, and a second DNA strand from another animal, usually an animal differing in the phenotype for the trait of interest.

Non-Gel Systems

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e. there is a mismatch of some form, the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

Many current methods for the detection of allelic variation are reviewed by Nollau et ah, Clin. Chem. 43, 1114-1120, 1997; and in standard textbooks, for example "Laboratory Protocols for Mutation Detection", Ed. by U. Landegren, Oxford University Press, 1996 and "PCR", 2nd Edition by Newton & Graham, BIOS Scientific Publishers Limited, 1997.

Sample

The test sample of nucleic acid is conveniently a sample of blood, mouth swab, biopsy, or other body fluid or tissue obtained from an individual. It will be appreciated that the test sample may equally be a nucleic acid sequence corresponding to the sequence in the test sample, that is to say that all or a part of the region in the sample nucleic acid may firstly be amplified using any convenient technique e.g. PCR, before analysis of allelic variation. The invention includes the detection of the polymorphism determined from a nucleic acid sample (which may be as defined above) that has already been removed from the individual.

Primers/Probes

According to one aspect of the present invention there is provided an allele-specific oligonucleotide primer or an allele-specific oligonucleotide probe capable of detecting a polymorphism (e.g., a SNP) in a FAT4 gene (or its complimentary strand) or a regulatory region thereof.

According to another aspect of the present invention there is provided an allele-specific oligonucleotide primer or an allele-specific oligonucleotide probe capable of detecting a polymorphic position selected from:

(i) position 101 of SEQ ID NO:1;

(ii) position 101 of SEQ ID NO:2; or (iii) position 101 of SEQ ID NO:3.

It should be noted that reference to an allele-specific oligonucleotide primer or an allele-specific oligonucleotide probe which is capable of detecting a polymorphic position selected from position 101 of SEQ ID NO:1, position 101 of SEQ ID NO:2 or position 101 of SEQ ID NO:3 includes an allele-specific oligonucleotide primer or an allele-specific oligonucleotide probe which is capable of detecting the compliment of a polymorphism at position 101 of SEQ ID NO:1, position 101 of SEQ ID NO:2 or position 101 of SEQ ID NO:3, respectively.

The allele-specific primers of the present invention are used, generally together with a constant primer, in an amplification reaction such as a PCR reaction, which provides the discrimination between alleles through selective amplification of one allele at a particular sequence position e.g. as used for ARMS™ assays. The allele-specific primers of the present invention are preferably 15-50 nucleotides, more preferably about 15-35 nucleotides, still more preferably about 17-30 nucleotides.

An allele-specific primer capable of detecting a polymorphism at position 101 of SEQ ID NO:1 may discriminate, in an amplification reaction such as a PCR reaction, between a sequence comprising base A at position 101 of SEQ ID NO:1 (or a sequence complementary to such a gene or fragment), and a sequence comprising base G at position 101 of SEQ ID NO:1 (or a sequence or fragment complementary to such a gene or fragment).

An allele-specific primer capable of detecting a polymorphism at position 101 of SEQ ID NO:2 may discriminate, in an amplification reaction such as a PCR reaction, between a sequence comprising base A at position 101 of SEQ ID NO:2 (or a sequence complementary to such a gene or fragment), and a sequence comprising base G at position 101 of SEQ ID NO:2 (or a sequence or fragment complementary to such a gene or fragment).

Similarly, an allele-specific primer capable of detecting a polymorphism at position 101 of SEQ ID NO:3 may discriminate, in an amplification reaction such as a PCR reaction, between a sequence comprising base A at position 101 of SEQ ID NO:3 (or a sequence complementary to such a gene or fragment), and a sequence comprising base G at position 101 of SEQ ID NO:3 (or a sequence or fragment complementary to such a gene or fragment).

Primers may be manufactured using any convenient method of synthesis. Examples of such methods may be found in standard textbooks, for example "Protocols for Oligonucleotides and Analogues; Synthesis and Properties," Methods in Molecular Biology Series; Volume 20; Ed. Sudhir Agrawal, Humana ISBN: 0-89603-247-7; 1993; 1st Edition. If required the primer(s) may be labelled to facilitate detection.

The design of probes will be apparent to the molecular biologist of ordinary skill. Such probes are of any convenient length such as, for example, up to 100 bases, up to 50 bases, up to 40 bases and up to 30 bases in length. For example, the probes may be 10 to 30 bases, preferably 18-30 bases in length. The probes may comprise base sequences entirely complementary to the target sequence. However, if required one or more mismatches may be introduced, provided that the discriminatory power of the oligonucleotide probe is not unduly affected. The probes of the invention may carry one or more labels to facilitate detection.

An allele-specific probe capable of detecting a polymorphism at position 101 of SEQ ID NO:1 may discriminate, in a hybridisation reaction, between a sequence comprising base A at position 101 of SEQ ID NO:1 (or a sequence complementary to such a gene or fragment), and sequence comprising base G at position 101 of SEQ ID NO:1 (or a sequence or fragment complementary to such a gene or fragment).

An allele-specific probe capable of detecting a polymorphism at position 101 of SEQ ID NO:2 may discriminate, in a hybridisation reaction, between a sequence comprising base A at position 101 of SEQ ID NO:2 (or a sequence complementary to such a gene or fragment), and sequence comprising base G at position 101 of SEQ ID NO:2 (or a sequence or fragment complementary to such a gene or fragment).

An allele-specific probe capable of detecting a polymorphism at position 101 of SEQ ID NO:3 may discriminate, in a hybridisation reaction, between a sequence comprising base A at position 101 of SEQ ID NO:3 (or a sequence complementary to such a gene or fragment), and sequence comprising base G at position 101 of SEQ ID NO:3 (or a sequence or fragment complementary to such a gene or fragment).

The primers and/or probes of the present invention will typically be in the form of nucleic acids (e.g. DNA or cDNA). Alternatively, the primers and/or probes may be in the form of nucleic acid analogues, for example PNA (Peptide Nucleic Acids), LNA (Locked Nucleic Acids) or BNA (Bridged Nucleic Acids). The primers or probes may be nucleic acids which have been substituted in part by LNA or PNA.

Primer Design Strategy

Increased use of polymerase chain reaction (PCR) methods has stimulated the development of many programs to aid in the design or selection of oligonucleotides used as primers for PCR. Four examples of such programs that are freely available via the Internet are: PRIMER by Mark Daly and Steve Lincoln of the Whitehead Institute (UNIX, VMS, DOS, and Macintosh), Oligonucleotide Selection Program (OSP) by Phil Green and LaDeana Hiller of Washington University in St. Louis (UNIX, VMS, DOS, and Macintosh), PGEN by Yoshi (DOS only), and Amplify by Bill Engels of the University of Wisconsin (Macintosh only).

Generally these programs help in the design of PCR primers by searching for bits of known repeated-sequence elements and then optimizing the Tm by analyzing the length and GC content of a putative primer. Commercial software is also available 35 and primer selection procedures are rapidly being included in most general sequence analysis packages.

Designing oligonucleotides for use primers requires selection of an appropriate sequence that specifically recognizes the target, and then testing the sequence to eliminate the possibility that the oligonucleotide will have a stable secondary structure. Inverted repeats in the sequence can be identified using a repeat-identification or RNA-folding programs.

If a possible stem structure is observed, the sequence of the primer can be shifted a few nucleotides in either direction to minimize the predicted secondary structure.

For PCR primers used to amplify genomic DNA, the primer sequence should be compared to the sequences in the GenBank database to determine if any significant matches occur. If the oligonucleotide sequence is present in any known DNA sequence or, more importantly, in any known repetitive elements, the primer sequence should be changed.

Kits

According to another aspect of the present invention there is provided a diagnostic kit comprising an allele-specific oligonucleotide probe of the invention and/or an allele-specific primer of the invention.

In one embodiment the diagnostic kit comprises (i) an allele-specific oligonucleotide primer and/or an allele-specific oligonucleotide probe capable of detecting the presence of G at position 101 of SEQ ID NO:1 and (ii) an allele-specific oligonucleotide primer and/or an allele-specific oligonucleotide probe capable of detecting the presence of A at position 101 of SEQ ID NO:2.

In one embodiment the diagnostic kit comprises (i) an allele-specific oligonucleotide primer capable of detecting the presence of G at position 101 of SEQ ID NO:1 and (ii) an allele-specific oligonucleotide primer capable of detecting the presence of A at position 101 of SEQ ID NO:2.

In one embodiment the diagnostic kit comprises (i) an allele-specific oligonucleotide probe capable of detecting the presence of G at position 101 of SEQ ID NO:1 and (ii) an allele-specific oligonucleotide probe capable of detecting the presence of A at position 101 of SEQ ID NO:2.

The diagnostic kits may comprise appropriate packaging and instructions for use in the methods of the invention. Such kits may further comprise appropriate buffer(s) and polymerase(s) such as thermostable polymerases, for example taq polymerase.

FAT4 Gene

Protocadherin Fat 4, also known as cadherin family member 14 (CDHF14) or FAT tumor suppressor homolog 4 (FAT4), is a protein that in humans is encoded by the FAT4 gene. FAT4 is associated with the Hippo signaling pathway. The Hippo pathway has emerged as a conserved signaling pathway that is essential for the proper regulation of organ growth in *Drosophila* and vertebrates (Halder, 2011, Development, January; 138(1):9-22).

The FAT4 gene referred to herein may contain coding regions, introns, untranslated regions and control regions.

FIG. 4 shows the genomic sequence of FAT4 gene (SEQ ID NO: 4).

FIGS. 5A, 5B and 5C show examples of three FAT4 transcripts (SEQ ID NOs 5, 6 and 7)

FIGS. 6 A and 6B show examples of two protein sequences (SEQ ID NOs: 8 and 9) translated from the FAT4 gene.

It has recently been shown that *Drosophila* Fat (Ft) cadherin has a direct role in regulating mitochondrial morphology and metabolism (Sing et al., 2014, Cell, 158, 1293-1308). It was shown that proteolytic cleavage of Ft releases a soluble fragment) ($Ft^{mito}$) that is imported into the mitochondria and that such cleavage functions as a switch mechanism to coordinate cell cycle and metabolism. It was suggested that altering the levels of $Ft^{mito}$ may allow an organism to directly adjust metabolic rates in accordance with changing energy requirements.

It will be understood that reference to FAT4 is not limited to the exact sequences disclosed above but includes variants and derivatives thereof. Identification of polymorphisms e.g., SNPs in similar sequences are contemplated (i.e. SNPs at positions which the skilled person would consider correspond to the positions identified herein.

Subject

Preferably the subject is a mammal, preferably a human. The subject may alternatively be a non-human mammal, including for example, a horse, cow, sheep or pig. In one embodiment, the subject is a companion animal such as a dog or a cat.

Dietary Intervention

By the term "dietary intervention" is meant an external factor applied to a subject which causes a change in the subject's diet. In one embodiment, the dietary intervention is a low calorie diet.

The low calorie diet is one which is adjusted to the starting body weight of the animal.

Preferably the low calorie diet comprises a calorie intake of about 600 to about 1500 kcal/day, more preferably about 600 to about 1200 kcal/day, most preferably about 800 kcal/day. In one embodiment, the low calorie diet may comprise a predetermined amount (in grams) of vegetables per day. Preferably up to about 400 g vegetables/day, e.g. about 200 g vegetables/day.

The low calorie diet may comprise administration of at least one diet product. The diet product may be a meal replacement product or a supplement product which may e.g. suppress the subject's appetite. The diet product can include food products, drinks, pet food products, food supplements, nutraceuticals, food additives or nutritional formulas.

In one embodiment, the diet may comprise a product such as Optifast® or Modifast®. This may be supplemented with three portions of non-starchy vegetables such that the total energy intake is about 2.5 MJ (600 kcal/day). This may be further supplemented with at least 2 L of water or other energy free beverages per day.

In another embodiment, the diet may comprise, for example, a composition which is 46.4% carbohydrate, 32.5% protein and 20.1% with fat, vitamins, minerals and trace elements; 2.1 MJ per day (510 kcal/day); This may be supplemented with three portions of non-starchy vegetables such that the total energy intake is about 2.5 MJ (600 kcal/day). This may be further supplemented with at least 2 L of water or other energy free beverages per day.

In one embodiment, the low calorie diet has a duration of up to 12 weeks. Preferably the low calorie diet has a duration of between 6 and 12 weeks, preferably between 8 and 10 weeks, e.g. 8 weeks.

Combining the Genotyping with Anthropometric Measures and/or Lifestyle Characteristics In one embodiment, the present method further comprises combining the determination of the genotype as referred to herein (e.g., determining the presence of a polymorphic marker e.g., SNP/determining the sequence of the FAT4 gene or a regulatory element thereof) with one or more anthropometric measures and/or lifestyle characteristics of the subject.

As is known in the art, an anthropometric measure is a measurement of a subject. In one embodiment, the anthropometric measure is selected from the group consisting of gender, age (in years), weight (in kilograms), height (in centimetres), and body mass index (in $kg/m^{-2}$). Other anthropometric measures will also be known to the skilled person in the art.

By the term "lifestyle characteristic" is meant any lifestyle choice made by a subject, this includes all dietary intake data, activity measures or data from questionnaires of lifestyle, motivation or preferences. In one embodiment, the lifestyle characteristic is whether the subject is a smoker or a non-smoker. This is also referred to herein as the smoking status of the subject.

Subject Stratification

The predisposition to weight loss and/or weight maintenance predicted by the method of the present invention may be used to stratify subjects into categories.

Subjects may be stratified into categories which are indicative of the degree of predicted weight loss/maintenance. Such stratification is useful to determine which subjects would benefit most from certain interventions. In this way, dietary intervention and modification of lifestyle can be optimised, and realistic expectations of the weight loss to be achieved by the subject can be set.

In one embodiment, the categories include weight loss resistant subjects and weight loss sensitive subjects.

By the term "weight loss resistant" is meant a predicted degree of weight loss which is less than a predetermined value. In one embodiment, "weight loss resistant" is defined as a subject having a weight loss percentage inferior to a predetermined value e.g. a subject predicted to lose less weight than the $10^{th}$, $15^{th}$, $20^{th}$ or $30^{th}$ percentile of the expected weight loss.

By the term "weight loss sensitive" is meant a predicted degree of weight loss of more than a predetermined value. In one embodiment, "weight loss sensitive" is defined as a subject having a weight loss percentage superior to a predetermined threshold value.

For example a subject predicted to lose more weight than the $85^{th}$, $80^{th}$ or $75^{th}$ percentile of the expected weight loss.

The "expected weight loss" can be obtained from data of a population of subjects that have undergone the same dietary intervention as the one being tested.

In another embodiment, the categories include weight maintenance resistant subjects and weight maintenance sensitive subjects.

By the term "weight maintenance resistant" is meant a predicted degree of weight maintenance which is less than a predetermined value. In one embodiment, "weight maintenance resistant" is defined as a subject having a degree of weight maintenance inferior to a predetermined threshold value e.g. a subject predicted to maintain a lesser degree of the weight loss following a dietary intervention than the $10^{th}$, $15^{th}$, $20^{th}$ or $30^{th}$ percentile of the subject population.

By the term "weight maintenance sensitive" is meant a predicted degree of weight maintenance which is more than a predetermined value. In one embodiment, "weight maintenance sensitive" is defined as a subject having a degree of weight maintenance superior to a predetermined threshold value. e.g. a subject predicted to maintain a greater degree of the weight loss following a dietary intervention than the $10^{th}$, $15^{th}$, $20^{th}$ or $30^{th}$ percentile of the subject population.

The subject population can be obtained from data of a population of subjects that have undergone the same dietary intervention as the one being tested.

Method for Selecting a Modification of Lifestyle of a Subject

In a further aspect, the present invention provides a method for modifying the lifestyle of a subject. The modification in lifestyle in the subject may be any change as described herein, e.g. a change in diet, more exercise, a different working and/or living environment etc.

Preferably the modification is a dietary intervention as described herein. More preferably the dietary intervention includes the administration of at least one diet product. The diet product preferably has not previously been consumed or was consumed in different amounts by the subject. The diet product may be as described herein. Modifying a lifestyle of the subject also includes indicating a need for the subject to change his/her lifestyle, e.g. prescribing more exercise or stopping smoking.

For example, if a subject is not predicted to lose weight on a low calorie diet, a modification may include more exercise in the subject's lifestyle.

Use of Diet Products

In one aspect, the present invention provides a diet product for use as part of a low calorie diet for weight loss. The diet product being administered to a subject that is predicted to achieve a weight loss by the methods described herein.

In another aspect, the present invention provides a diet product for use in treating obesity or an obesity-related disorder, wherein the diet product is administered to a subject that is predicted to attain weight loss by the methods described herein.

The obesity-related disorder may be selected from the group consisting of diabetes (e.g. type 2 diabetes), stroke, high cholesterol, cardiovascular disease, insulin resistance, coronary heart disease, metabolic syndrome, hypertension and fatty liver. In a further aspect, the present invention provides the use of a diet product in a low calorie diet for weight loss where the diet product is administered to a subject that is predicted to attain weight loss by the methods described herein.

Computer Program Product

The methods described herein may be implemented as a computer program running on general purpose hardware, such as one or more computer processors. In some embodiments, the functionality described herein may be implemented by a device such as a smartphone, a tablet terminal or a personal computer.

In one aspect, the present invention provides a computer program product comprising computer implementable instructions for causing a programmable computer to predict the degree of weight loss/maintenance based on the genotyping of the present invention and optionally anthropometric measures and/or lifestyle characteristics from the user. As described herein, anthropometric measures include age, weight, height, gender and body mass index and lifestyle characteristics include smoking status.

In a particularly preferred embodiment, the user inputs into the device the results of the genotyping of the present invention, optionally along with age, body mass index, gender and smoking status. The device then processes this information and provides a prediction on the degree of weight loss/maintenance attainable by the user from a dietary intervention.

The device may generally be a server on a network. However, any device may be used as long as it can process biomarker data and/or anthropometric and lifestyle data using a processor, a central processing unit (CPU) or the like. The device may, for example, be a smartphone, a tablet terminal or a personal computer and output information indicating the degree of weight loss attainable by the user.

Those skilled in the art will understand that they can freely combine all features of the present invention described herein, without departing from the scope of the invention as disclosed.

Various preferred features and embodiments of the present invention will now be described by way of non-limiting examples.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; and E. M. Shevach and W. Strober, 1992 and periodic supplements, *Current Protocols in Immunology*, John Wiley & Sons, New York, N.Y. Each of these general texts is herein incorporated by reference.

EXAMPLES

Background Information

Diogenes (Diet Genes and Obesity) is an intervention study in overweight/obese patients (with BMI between 27 and 45 kg/m$^2$) (Larsen, T. M. et al. *N. Engl. J. Med.* 363, 2102-2113 (2010)). To our knowledge, Diogenes is the largest and most comprehensive study on weight management.

Patients followed a low-caloric diet (about 800 kcal/d) for 8 weeks. Then participants that had lost at least 8% of their initial body weight, were randomly assigned, in a two-by-two factorial design, to one of five ad libitum diets to prevent weight regain over a 26-week period: a low-protein and low-glycemic-index diet, a low-protein and high-glycemic-index diet, a high-protein and low-glycemic-index diet, a high-protein and high-glycemic-index diet, or a control diet.

The aim of our analyses was to analyze whether genetic markers (SNPs) would be classifiers of weight loss and weight maintenance.

Example 1—Material and Methods

Study Design

Diogenes (ClinicalTrials.gov identifier: NCT00390637) is composed of two main periods:

Weight loss period with a low-caloric diet (800 kcal/d) for 8 weeks

Weight maintenance diet for 26 weeks

A number of clinical measurements and biological samples were taken at different time points. Four time points are of notable interest for the present invention:

1. Screening visit
2. Clinical Intervention Day 1 (CID1): start of the weight loss period 3. CID2: end of the weight loss period, randomization into one weight maintenance diet and start of the weight maintenance period
4. CID3: end of the weight maintenance period Genotype Data The Illumina 660-quad Bead chips were used to perform the Whole Genome Scan (Hypothesis-free approach). The Illumina technology is based on a DNA chip allowing the genotyping of approximately 660'000 single nucleotide polymorphisms (SNPs) per subject. SNPs are distributed over all the chromosomes and are used as tagging markers of the corresponding genomic area. The details of the process and experimental protocol followed the manufacturer recommendations (www.illumina.com).

Quality Control of the Genotype Data

SNPs were excluded from the analysis, if they fulfilled at least one of the following:

Low call rate (<95%)

Violating Hardy-Weinberg equilibrium (FDR<20%)

Minor allele frequency <0.28%

Subjects were excluded from the analysis, if they fulfilled at least one of the following:

Low call rate (<95%)

Abnormal autosomal heterozygosity (FDR<1%)

For pairs of subjects with Identity-By-State >0.95, the subject with the lowest call rate was excluded.

Individuals that were outliers in terms of genetic structure: 6 standard deviation distant from the Diogenes cluster's centroid, based on a principal component analysis (2 first components) performed on genotypes from Diogenes and the Hapmap project (with CEU, YRI and CHB+JPT panels)

Individuals having gender discrepancies between records from the clinical database and inferred gender from genotype data The final genotype dataset, after QC, included 516'636 SNPs and 869 subjects.

About Genomic Coordinates

All genomic coordinates (SNPs, genes) used in this document correspond to the Human genome assembly hg19.

Genome-Wide Association Tests

Genome-wide scan was performed using the following linear model:

$$BMI3 \sim BMI2+SNP+center+gender+age+\varepsilon$$

In this model, BMI2 and BMI3 refer to Body Mass Index (BMI) measured respectively before and after the weight maintenance period (i.e. CID2 and CID3). Center refers to one the Diogenes center. Age refers to the subject's age measured at the screening visit. ε corresponds to the model's residuals term.

Association was tested independently for each SNP using the GenABEL qtscore function (Aulchenko et al., *Genetics* 177, 577-585 (2007)). The method first regresses on the trait of interest for co-variables then test association between the obtained residuals and a SNP using least-square methods. This function implements both allelic and genotypic tests. Since allelic tests are more powerful than genotypic tests, only allelic tests were considered for data interpretation.

The initial number of subjects (n=869) becomes much smaller when removing subjects with missing values either for BMI or any covariate of the regression tests (including the SNP being modelled). The average number of subjects, without any missing values, that was used for each of the 516'636 models was n=461.

TagSNP Identification

We used the LD select methodology proposed by Carlson (Carlson et al., *Am. J. Hum. Genet.* 74, 106-120 (2004)). Tag SNP analysis was performed with the following settings: MAF threshold 10% and R-square threshold 50%.

Haplotype Phasing

Genotype data were phased using the MACH software (Li, et al., *Genet. Epidemiol.* 34, 816-834 (2010)) with the following parameters: —rounds 50—states 200—phase.

Haplotype Association Tests

Subsequently to the phasing with MACH, association between change in BMI during weight maintenance and all haplotype blocks was tested using the following model:

$$BMI3 \sim BMI2+center+gender+age+AAC+AAT+AGC+GAC+GAT+GGC+\varepsilon$$

Center refers to one the Diogenes center. Age refers to the subject's age measured at the screening visit. ε corresponds to the model's residuals term.

Both additive (number of haplotypes: 0, 1 or 2) and dominant (absence/presence) genetic models were tested. Backward selection was then performed on the fitted model (stepAIC function in R (R Development Core Team (2013). R: A language and environment for statistical computing. R Foundation for Statistical Computing, Vienna, Austria. ISBN 3-900051-07-0, URL http://www.R-project.org.)).

Additional Linear Models

Change in a given trait over a period of interest (weight maintenance or weight loss period) was tested using linear models.

These models were used to test either single-SNP or epistatic effect (interaction between two SNPs) with several weight-related phenotypes.

Those models can be written in the Wilkinson-Roger notation as follows:

$$Trait\_at\_time(i) \sim Trait\_at\_time(i-1)+genetic\ effect+center+gender+age+\varepsilon$$

The trait can be any quantitative trait like BMI; waist or hip circumferences; fat-free mass or fat mass weight. The time points (i−1) and (i) refer to before and after a given period (e.g. weight maintenance or weight loss period). Such modeling allows predicting the trait at time (i) while adjusting for baseline values at time (i−1).

Center refers to one the Diogenes center. Age refers to the subject's age measured at the screening visit. ε corresponds to the model's residuals term.

The genetic effect can be either a single SNP or the interaction between two SNPs (SNP1 and SNP2). For single-SNP effect, genotypic models were used. When testing SNP interaction, SNP1 and SNP2, were each coded for presence/absence of a given allele. The c term corresponds to residuals of the model.

Significance of each term in the model was tested using a type III ANOVA (Fox & Weisberg, *An R Companion to Applied Regression*. (Sage, 2011). at http://socserv.socsci.mcmaster.ca/jfox/Books/Companion).

Dichotomizing Changes in BMI Over Time

A recurrent challenge in weight maintenance studies is to define a threshold that allows classifying patients into groups of good and bad weight maintainers. Frequently such classification is made with the two most extreme groups of patients (for e.g. patients that have a response below the $10^{th}$ percentile or above the $90^{th}$ percentiles). Yet the decision on which percentile to use is an entirely arbitrary one. One cannot exclude the risk (prior doing the analyses) that different conclusions might be reached depending on the chosen cutoff. Instead of making such an arbitrary decision, we decided to use several cutoffs as explained below.

First, we expressed change in BMI during weight maintenance as:

$$\Delta = 100 * \frac{BMI_2 - BMI_3}{BMI_2}$$

where BMI2 and BMI3 stands for BMI before and after the weight maintenance period (i.e. CID2 and CID3). This difference (Δ) corresponds to the percentage of BMI change during weight maintenance relative to the baseline BMI (BMI before weight maintenance).

Interpretation of Δ is as follows:

- Δ<0 implies that BMI2<BMI3, therefore the patient regained weight (i.e. bad weight maintenance profile)
- Δ>0 implies that BMI2>BMI3, therefore the patient continued to lose weight (i.e. good weight maintenance profile)

Next, we computed dichotomized Δ into groups of "good" and "bad" weight maintainer profiles. Such dichotomization was made by selecting the patients with the most extreme Δ values. This is achieved by selecting Δ above or below a given percentile. For example, using the $10^{th}$ and $90^{th}$ percentiles, we defined the following groups:

- "Bad weight maintainers" as patients with a Δ below the $10^{th}$ percentile
- "Good weight maintainers" as patients with a Δ above the $90^{th}$ percentile In this example, subjects with A between the $10^{th}$ and $90^{th}$ percentiles are not included in the analysis. These subjects can be referred to as those with "an intermediate profile" and for which one cannot decide whether they should be classified to one group or another.

To avoid bias due to the choice of an arbitrary percentile threshold, we analyzed data from several classification schemes:

- Patients with Δ below the $10^{th}$ percentile or above the $90^{th}$ percentile
- Patients with Δ below the $25^{th}$ percentile or above the $75^{th}$ percentile
- Patients with Δ below the $33^{rd}$ percentile or above the $66^{th}$ percentile
- Patients with Δ below the $50^{th}$ percentile or above the $50^{th}$ percentile It can be noted that the first three schemes discard patients with intermediate profiles (e.g. Δ between the $10^{th}$ and $90^{th}$ percentiles) and thus only use a subset of the data, while the last scheme classifies all patients into two distinct groups. Therefore classification using the first three schemes can be challenged by the fact only a limited subset of the data is used. In contrast, the fourth scheme uses all available data but the two groups would each have high heterogeneity and since patients with "intermediate profiles" are not discarded, the distinction between those two groups might not be clear. Therefore this last classification scheme is expected to be the most complex case.

Similar dichotomization was applied on BMI during the weight loss period, using the following formula:

$$\Delta = 100 * \frac{BMI_1 - BMI_2}{BMI_1}$$

In this formula, $BMI_1$ and $BMI_2$ correspond respectively to before and after the weight loss period (i.e. CID1 and CID2).

Classification Analysis

Following dichotomization of the BMI into groups of "bad" and "good" weight maintainers, we assessed the classification performance with simple contingency tables like:

| | Bad weight maintainers | Poor weight maintainers |
|---|---|---|
| Protective genotypes | a | b |
| Non-protective genotypes | c | d |

Where a, b, c and d correspond to the number of patients from a given category.

From such table, one can compute the accuracy of classification:

$$ACC = 100 * \frac{a+d}{a+b+c+d}$$

Ninety-five confidence intervals (95% CI) for the classification accuracy are then derived with a binomial test (binom.test function in R (R Development Core Team (2013). R: A language and environment for statistical computing. R Foundation for Statistical Computing, Vienna, Austria. ISBN 3-900051-07-0, URL http://www.R-project.org.)). A one-sided binomial test is also performed to test whether the classification accuracy is better than the "no information rate," which is taken to be the largest class percentage in the data (see the confusionMatrix function in the caret package (Kuhn *J. Stat. Softw.* 28, 1-26 (2008)).

By non-protective genotypes, we aim at identifying subjects with a low Δ (patients regaining weight). Conversely, with protective genotypes, we aim at identifying subjects with high Δ (patients regaining less weight, or even still losing weight).

Protective and non-protective genotypes were defined as follows:

| SNP(s) | Protective genotype | Non-protective genotype |
|---|---|---|
| rs1509289 | A carriers | G/G |
| rs1509290 | A carriers | G/G |
| rs953211 | G carriers | A/A |
| rs953211 and rs1509290 | rs953211 G carriers; rs1509290 A carriers | Any other genotypes |

The same methodology was applied on BMI changes during a weight loss period.

Analysis of Imputed SNPs

Genotype from additional SNPs located nearby FAT4 were obtained using imputation. Imputation was performed using the MACH software (Li et al., *Genet. Epidemiol.* 34, 816-834 (2010)) and using subjects of European ancestry from the 1000 Genome Project (Consortium, T. 1000 G. P. *Nature* 491, 56-65 (2012)) (phase II) as a reference data. Imputation was performed following recommended steps from the MACH software. Analysis of allele dosage value was performed using ProbABEL (Aulchenko, et al., *BMC Bioinformatics* 11, 134 (2010)) and using the following model:

$$BMI3 \sim BMI2 + center + gender + age + SNP + \varepsilon$$

BMI3 and BMI2 refer to BMI measured respectively at CID3 and CID2. Center refers to one the Diogenes center.

Age refers to the subject's age measured at the screening visit. ε corresponds to the model's residuals term. The SNP term corresponds to the imputed allele dosage values.

Example 2—Detailed Results

GWA Scan for Weight Maintenance

From the genome-wide analysis, SNPs located on chromosome 4 were found significantly associated with BMI trajectories during the weight maintenance period. In particular, the two following SNPs: rs953211 and rs1509289 (Table 1), both intronic variants in the FAT4 gene, emerged within the genome-wide list as top ranking SNPs. Since these two SNPs are only in moderate linkage disequilibrium (LD) (R-square=50.61%) and given that there were other nearby SNPs with association pvalues less than 5% (FIG. 1), we searched whether the observed association could be due to a haplotype.

Haplotype Tests for Weight Maintenance

To restrict the list of SNPs to be used for haplotype phasing, a tagSNP search was performed. This search identified the following three SNPs: rs953211, rs1509290 and rs13136889 as best tag SNPs for other SNPs found marginally associated with BMI during weight maintenance (pvalues <5%, see FIG. 1). Six distinct haplotypes can be defined using these three SNPs: AAT, GAC, GGC, AAC, GAT and AGC (The order of SNPs in each haplotype is rs953211, rs1509290 and rs13136889).

Next, these haplotypes were tested for association with change in BMI during the weight maintenance. Both dominant and additive genetic models were considered. Results are shown in Table 2-5. These analyses identified presence of the GAC and GAT haplotypes as significantly associated with a more favourable BMI after the weight maintenance intervention. In particular, patients carrying at least one copy of either haplotypes are less prone to regain weight compared to patients no carrying any of these haplotypes. These results were reproduced using univariate approaches (rank-sum tests) and with the Plink software (Purcell, S. et al. PLINK: a tool set for whole-genome association and population-based linkage analyses. *Am. J. Hum. Genet.* 81, 559-575 (2007)).

Since favourable weight maintenance is observed with both the GAC and GAT haplotypes, the third SNP does not seem to contribute much and therefore the protective haplotype can be simplified as rs953211-G and rs1509290-A. Conversely, this result also implies the rs953211-A and rs1509290-G haplotype as a deleterious haplotype.

Epistasy Tests for Weight Maintenance

In the light of the haplotype results, we defined the following genotype groups:

rs953211-G carriers and rs1509290-A carriers
rs953211-G carriers and rs1509290-G/G
rs953211-A/A and rs1509290-A carriers
rs953211-A/A and rs1509290-G/G The interaction between rs953211 and rs1509290, as defined with the above groups, was found significantly associated with change in BMI during weight maintenance (p=7.96E-05, for details about the methodology see Additional linear models). Full results from the linear model and from the subsequent ANOVA are shown respectively in Table 6 and Table 7. These results show that rs953211-G carriers and rs1509290-A carriers have significantly better BMI profiles than the three remaining genotype groups.

To facilitate genetic diagnostic, the four genotype groups can be simplified as "rs953211-G carriers and rs1509290-A carriers" and subjects from the three remaining group pooled together. Such genetic dichotomization is also significantly associated with the BMI trajectories during the weight maintenance period. Results from the linear model are shown in Table 8. This table also includes the 95% confidence intervals (CI) on the regression coefficient for each term of the model. These 95% CI were obtained by performing bootstrap (Davison. & Hinkley *Bootstrap Methods and Their Applications*. (Cambridge University Press, 1997). at http://statwww.epfl.ch/davison/BMA) of the linear model (with n=1'000 resampling and using the boot package (Canty, A. & Ripley, B. D. *boot: Bootstrap R* (*S-Plus*) *Functions*. (2014)) in R). Interpretation of these coefficients is as follows: when adjusting for covariates such as age, gender, participating center and BMI before weight maintenance; the effect of being "rs953211-G carriers and rs1509290-A carriers" is −0.76 $kg/m^2$ on the BMI after weight maintenance. In other words, the effect on BMI after a weight maintenance period is −0.76 $kg/m^2$ (with 95% CI=[−1.1, −0.43]) for subjects that are "rs953211-G carriers and rs1509290-A carriers" compared to subjects from any other genotype combination.

An even simpler way to look at these results is to only consider the change in BMI, before and after weight maintenance and without adjusting for covariates (age, gender, etc. . . . ). Without any genetic stratification (i.e. not knowing the genotype of a subject), the median change in BMI is +0.38 $kg/m^2$ (Table 9). This means that subjects tend regain weight. When the genotype is available for rs953211 and rs1509290; subjects from these three genotype groups: "rs953211 A/A; rs1509290 A carriers"; "rs953211 A/A; rs1509290 G/G" and "rs953211 G carriers; rs1509290 G/G" all regain weight (median BMI changes are respectively +0.57, +0.63 and +0.68 $kg/m^2$). By contrast, subjects that are "rs953211 G carriers; rs1509290 A carriers", do not tend to regain weight (median BMI change=0).

Therefore this combination of these two genetic markers:

Identifies a group of patients ("rs953211 G carriers; rs1509290 A carriers") that has better weight maintenance than the three others groups Demonstrates that knowing the genotype of these two markers brings additional information compared to not knowing the genotype. The BMI change for each of the four genotype groups is different from the average BMI change of the global population.

Epistasy Tests for Weight Loss

The same combination of SNPs was found associated with BMI changes during the weight loss period (p=0.0243, for details about the methodology see Additional linear models). Results from the linear model and its subsequent ANOVA are shown respectively in Table 10 and Table 11.

As done for the weight maintenance analyses, the combination of these two SNPs was dichotomized into "rs953211-G carriers and rs1509290-A carriers" and all remaining subjects pooled together. Results from a linear model modeling BMI changes during the weight loss period are shown in Table 12. This table shows that subjects "rs953211 G carriers; rs1509290 A carriers" have a stronger weight loss (BMI change=−0.20 kg/m2 with 95% CI [−0.34, −0.06]) compared to subjects with other genotype combinations.

Computing the median change in BMI before and after the weight loss period, one can observe that "rs953211 G carriers; rs1509290 A carriers" lose more weight (median BMI change=−3.69 $kg/m^2$) than the other genetic groups (see Table 13).

Epistasy Tests for Baseline BMI

No difference in BMI at baseline (CID1) was found between the different genotype groups, as defined by rs953211 and rs1509290 (ranksum p=0.93). This indicates that this combination of markers is predictive of weight upon an intervention (e.g. weight loss or weight maintenance) but is not prognostic.

Association Between FAT4 SNPs and Weight-Related Phenotypes

Since FAT4 SNPs were associated with change in BMI, we tested whether the same SNPs would also be associated with additional weight-related phenotypes such as change in fat mass, fat-free mass, hip circumference and waist circumference (for details about the methodology see Additional linear models). And indeed, those SNPs: rs1509289, rs1509290, rs953211; alone or in combination, are significantly associated with change in weight-related phenotypes during weight maintenance (Table 14).

During the weight loss period, several SNPs (rs1509289, rs1509290 and the interaction between rs953211 and rs1509290) were found significantly associated with change in BMI and hip circumference (Table 15).

These analyses demonstrate that FAT4 SNPs are associated with both BMI and several additional weight-related phenotypes both for the weight maintenance and weight loss periods.

Using FAT4 SNPs as Classifiers of Dichotomized BMI Changes

In order to estimate the performance at predicting the outcome of a weight loss or weight maintenance intervention, we computed the percentage of change in BMI and dichotomized this value into groups of “good” and “bad” profile (For methodological details, see section Dichotomizing changes in BMI over time). We also dichotomized the genotypes of our genetic markers into combinations that are expected to identify subjects with either a “good” or “bad” profile (see Classification analysis).

Although analyzing dichotomized values results in significant loss of statistical power, such simple scheme gives very conservative estimates about the prediction performance.

We performed such analyses for BMI during both weight maintenance and weight loss periods. Also to avoid introducing biases due to the choice of the cutoff to dichotomize the BMI, we repeated the analysis with several cutoffs.

The predictive performance for the different genetic markers is shown in Table 16 and Table 17. These tables present results respectively for BMI outcome after weight maintenance or weight loss intervention.

These tables include odds ratios with their 95% confidence intervals, and p-value from a Fisher’s exact test performed on the contingency table (derived from the classification). These values assess the association between the classifiers (genotypes) and the true outcome (dichotomized percentage of BMI change). A p-value below 5% indicates a significant association between the classifier and outcome.

These tables also include performance metrics such as the classification accuracy (i.e. fraction of correctly classified subjects) and the 95% confidence interval for the accuracy. A random classifier (e.g. tossing a coin to predict the outcome) would have 50% of accuracy. When the lowest confidence interval is above 50%, it means that the classifier is doing significantly better than the random classifier. Another metric to evaluate whether the accuracy is significantly better than a random classifier is referred as the accuracy’s p-value. This one-sided p-value, obtained with a binomial test, assesses whether the observed accuracy is better than the no information rate (Kuhn, *J. Stat. Softw.* 28, 1-26 (2008)).

These analyses shows that FAT4 genetic markers (rs1509289, rs150929 and rs953211), used independently or in combination have a significantly higher accuracy than a random classifier at predicting the BMI outcome, after a weight maintenance period (all accuracy pvalues are <5%, see Table 16).

Regarding the BMI outcome after weight loss period, the classification accuracy for rs953211 is not better than a random classifier (accuracy pvalues >5%, see Table 17). This was expected because rs953211 was not found significantly associated with BMI change during weight loss.

For the two other SNPs (rs1509289 and rs150929) and for the combination of rs953211 and rs1509290, the classification accuracies are significantly better than the random classifier for the majority of the dichotomization schemes (Table 17).

Therefore, FAT4 markers used alone or in combination, can be used as classifier of weight outcome following weight loss or weight maintenance period.

Finding Additional SNPs as Potentially Better Classifiers

Providing that some candidate regions have been identified, it is straight-forward to refine association signals. Extensive reviews have been written to describe the process of refining association signals (McCarthy & Hirschhorn *Hum. Mol. Genet.* 17, R156-R165 (2008); Ioannidis et al., *Nat. Rev. Genet.* 10, 318-329 (2009); and McCarthy et al. *Nat. Rev. Genet.* 9, 356-369 (2008)). A few strategies are summarized below.

Gene Re-Sequencing and Additional Genotyping

With the advent of next-generation sequencing (NGS), it is now possible to sequence either exome or full genome of large cohorts. Following experimental protocols from vendors and using recent analytical pipelines from the community (McKenna et al. *Genome Res.* 20, 1297-1303 (2010)), additional SNPs, not assayed with classical SNP arrays, can be identified. Genotyping additional markers is possible with a wide range of technologies. This includes and is not limited to sequencing (exome-sequencing, full-genome sequencing, targeted sequencing, RNA-sequencing, pyrosequencing); genotyping assays (either high-density SNP arrays, custom SNP-arrays, targeted genotyping with Taqman, Fluidigm), PCR-based assays, mass-spectrometry genotyping techniques, etc.

Once additional markers have been genotyped, it is straight-forward to test each of those for association with a trait (e.g. change in BMI) and identify the causal marker(s). Notably by genotyping additional markers located nearby our identified SNPs (for e.g. +/−100 Kb) and repeating the same analyses described above, one may identify further markers or combination of markers useful at predicting change in weight-related phenotypes during a weight loss or weight maintenance period.

Using Imputed SNPs

Obtaining additional markers can also be achieved using imputation techniques (Marchini & Howie, *Nat. Rev. Genet.* 11, 499-511 (2010)). With the availability of public reference datasets (Consortium, T. I. H. 3., *Nature* 467, 52-58 (2010); Consortium, T. 1000 G. P. *Nature* 491, 56-65 (2012); Gibbs et al., *Nature* 426, 789-796 (2003); The International HapMap Consortium. A haplotype map of the human genome. *Nature* 437, 1299-1320 (2005)) and well-established imputation tools (Li et al., *Genet. Epidemiol.* 34, 816-834 (2010); Marchini & Howie, *Nat. Rev. Genet.* 11, 499-511 (2010)), this strategy is commonly used in genome-wide association studies, to increase the number of markers to be tested.

Figure 2:
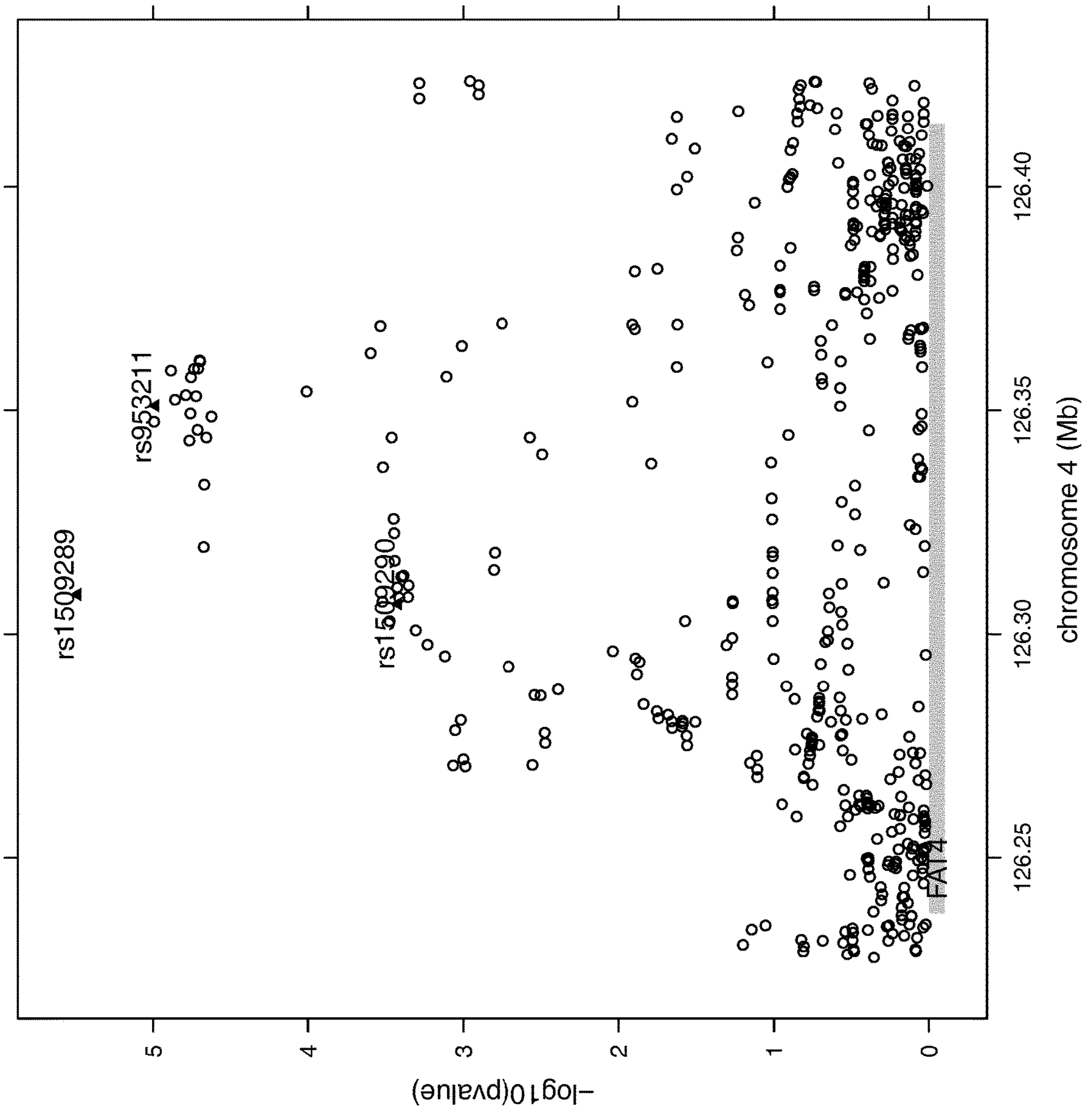
FIG. 2: Association between SNPs located nearby the FAT4 gene and change in BMI during weight maintenance. The X axis shows the SNP's coordinate on chromosome 4 and the Y axis shows the −log 10 p-value from an allele dosage test. This figure displays results from SNPs either assayed on the genotyping array or whose genotype was obtained from imputation.

Such a strategy was applied to our data, leading to the availability of genotype data for 475 SNPs located nearby the FAT4 gene (+/−10 Kb) (see section Analysis of imputed SNPs). Subsequently, these SNPs were tested for association with BMI change during weight maintenance. The results are displayed in FIG. 2. Ninety-two SNPs have a p-value smaller than 5%, indicating that other genetic variants, located nearby FAT4, are associated with weight management (see list in FIG. 7). Yet none of these SNPs have a stronger association (lower p-value) than the already detected SNPs (FIG. 2). This suggests that although those imputed SNPs could act as proxy SNPs for rs953211, rs1509290 or rs1509289; they are unlikely to have a significantly better predictive value.

Meta-Analyses

Meta-analyses aim at combining results from multiple studies so that consistent patterns can be found across those studies. Specifically meta-analysis of GWA studies aim at identifying SNPs associated with a trait of interest that could be missed when analyzing a single study. Statistical methodologies to perform genetic meta-analysis are well established (Ioannidis et al., *Nat. Rev. Genet.* 10, 318-329 (2009); Evangelou & Ioannidis *Nat. Rev. Genet.* 14, 379-389 (2013)) and are frequently used in large consortia (Yang et al. *Nat. Genet.* 44, 369-375, S1-3 (2012); DIAbetes Genetics Replication And Meta-analysis (DIAGRAM) Consortium et al. *Nat. Genet.* 46, 234-244 (2014)) to identify additional markers.

By combining, results from several studies and focusing on SNPs located within and nearby the FAT4 gene (for e.g. +/−100 Kb), additional SNPs may be found.

Multi-Dimensional Reduction Analyses

Another approach, once a region of interest has been detected is to screen all possible 2-SNPs or even higher order SNP interactions (e.g. 3-SNPs interaction) using a multi-dimensional reduction approach (Moore *Adv. Genet.* 72, 101-116 (2010); Pan et al., *Methods Mol. Biol.* Clifton N.J. 1019, 465-477 (2013)). Multi-dimensional reduction approach (MDR) can be used to test SNP-SNP interactions in case-control studies. MDR is non-parametric, model-free method that aims at identifying the combination of SNPs with the best accuracy at predicting a binary class. When using MDR, cross-validation are recommended to evaluate the accuracies on a training dataset and on a validation dataset. These accuracies are referred to as classification accuracy and prediction accuracy respectively for the training and validation datasets (for additional details see this review by Motsinger and Ritchie (*Hum. Genomics* 2, 318-328 (2006)). Cross-validation consistency can also be evaluated. That is when doing several random split of the data into training and validation set, how many times the same best classifier (combination of SNPs) would be identified.

We applied such technique onto SNPs located within the FAT4 gene (+/−10 kb), and aimed at identifying the best SNP or best combination of two SNPs to predict dichotomized change in BMI during weight maintenance or weight loss (see section: Dichotomizing changes in BMI over time). Results are shown in Table 18 and Table 19 respectively for BMI changes during weight maintenance or during weight loss. These analyses essentially found the rs1509289, rs953211, rs1509290 SNPs as being the best classifiers for BMI changes. This is consistent with our previous analyses and shows that these are the preferred markers for predicting weight loss/maintenance.

Example 3—Summary of Preferred Embodiment

FAT4 SNPs and Change in BMI During Weight Maintenance Our various analyses demonstrated that SNPs located nearby FAT4 were associated with change in BMI during a weight maintenance period. These results can be summarized as follows:

- Patients tend to regain weight during the weight maintenance phase. This observation can be made irrespectively of the genotype of any SNPs
- When a skilled person knows the genotype at FAT4 SNPs, in our preferred embodiment at the rs953211 and rs1509290 SNPs, the following predictions can be made:
  - Patients that are “rs953211 G carriers; rs1509290 A carriers” tend to have neutral change in BMI (median change in BMI close to 0)
  - Patients from any other genotype groups tend to regain significantly more weight than “rs953211 G carriers; rs1509290 A carriers”; and also more weight than the average (or median) change in the population (i.e. all patients pooled together irrespectively of their genotypes)

Therefore knowing the genotype of FAT4 SNPs, the following predictions can be made:

| Group | Predicted outcome after weight maintenance |
|---|---|
| Overall population (not knowing the genotypes) | Regain weight (i.e. increase in BMI) |
| “rs953211 A/A; rs1509290 A carriers” | Regain weight |
| “rs953211 A/A; rs1509290 G/G” | Regain weight |
| “rs953211 G carriers; rs1509290 A carriers” | Neutral change in weight (i.e. median BMI change is 0) |
| “rs953211 G carriers; rs1509290 G/G” | Regain weight |

FAT4 SNPs and Change in BMI During Weight Loss

Our analyses also found that the same FAT4 SNPs that predict weight maintenance outcome could also be used to predict weight loss outcome. The results can be used as follow:

| Group | Predicted outcome after weight loss |
|---|---|
| Overall population (not knowing the genotypes) | Lose weight |
| “rs953211 A/A; rs1509290 A carriers” | Lose weight |
| “rs953211 A/A; rs1509290 G/G” | Lose weight |
| “rs953211 G carriers; rs1509290 A carriers” | Lose more weight than all other groups |
| “rs953211 G carriers; rs1509290 G/G” | Lose weight |

FAT4 SNPs and Change in Other Weight-Related Phenotypes During Weight Maintenance FAT4 SNPs were found associated with change during weight maintenance in additional weight-related phenotypes, such as hip and waist circumference, fat mass and fat-free mass. Median changes for those phenotypes stratified per genotype group are shown in Table 20. These results can be used as follows:

| Group | Fat mass | Fat free mass | Waist circumference | Hip circumference |
|---|---|---|---|---|
| Overall population (not knowing the genotypes) | Neutral change | Increase fat free mass | Increase waist circumference | Neutral change |
| "rs953211 A/A; rs1509290 A carriers" | Neutral change | Increase fat free mass | Increase waist circumference | Neutral change |
| "rs953211 A/A; rs1509290 G/G" | Neutral change | Increase fat free mass | Increase waist circumference | Increase hip circumference |
| "rs953211 G carriers; rs1509290 A carriers" | Lose fat mass | Increase fat free mass | Neutral change | Neutral change |
| "rs953211 G carriers; rs1509290 G/G" | Neutral change | Increase fat free mass | Increase waist circumference | Neutral change |

FAT4 SNPs and Change in Other Weight-Related Phenotypes During Weight Loss

FAT4 SNPs were found significantly associated with change in hip circumference during weight maintenance. Median changes for hip and other weight-related phenotypes stratified per genotype group are shown in Table 21. Results for hip circumference can be summarized as follows:

| Group | hip circumference |
|---|---|
| Overall population (not knowing the genotypes) | Reduce hip circumference |
| "rs953211 A/A; rs1509290 A carriers" | Reduce hip circumference |
| "rs953211 A/A; rs1509290 G/G" | Reduce hip circumference |
| "rs953211 G carriers; rs1509290 A carriers" | Reduce hip circumference (slightly bigger change than change occurring in the other groups) |
| "rs953211 G carriers; rs1509290 G/G" | Reduce hip circumference |

Tables

TABLE 1

Top SNPs on chromosome 4 identified with the genome-wide analysis

| SNP | chr | Position | allele A | allele B | beta coefficient (allele B) | Beta standard error | allelic test p-value | allelic test p-value adjusted for genomic control | SNP call rate | MAF | Overlapping gene |
|---|---|---|---|---|---|---|---|---|---|---|---|
| rs953211 | 4 | 126351049 | A | G | −0.59 | 0.13 | 2.74E−06 | 3.73E−06 | 100.00% | 36.66% | FAT4, intron |
| rs1509289 | 4 | 126308835 | G | A | −0.64 | 0.14 | 3.00E−06 | 4.06E−06 | 100.00% | 25.60% | FAT4, intron |

TABLE 2

FAT4 haplotype additive analysis (rs953211, rs1509290, rs13136889), results from the following linear regression: BMI3~BMI2 + center + gender + age + AAC + AAT + AGC + GAC + GAT + GGC + ε

| | Estimate | Std. Error | t value | Pr(>\|t\|) |
|---|---|---|---|---|
| Intercept | 2.997204 | 0.957387 | 3.131 | 0.001858 |
| BMI2 | 0.928099 | 0.018983 | 48.892 | <2e−16 |
| center | −0.122483 | 0.031351 | −3.907 | 0.000108 |
| gender | −0.256245 | 0.178685 | −1.434 | 0.152248 |
| age | 0.001246 | 0.013732 | 0.091 | 0.927753 |
| AAC | 0.201121 | 0.224391 | 0.896 | 0.370574 |
| AAT | 0.917214 | 0.820991 | 1.117 | 0.264502 |
| AGC | 0.358763 | 0.206106 | 1.741 | 0.082423 |
| GAC | −0.803172 | 0.293798 | −2.734 | 0.006508 |

TABLE 2-continued

FAT4 haplotype additive analysis (rs953211, rs1509290, rs13136889), results from the following linear regression: BMI3~BMI2 + center + gender + age + AAC + AAT + AGC + GAC + GAT + GGC + ε

| | Estimate | Std. Error | t value | Pr(>\|t\|) |
|---|---|---|---|---|
| GAT | −0.261936 | 0.233207 | −1.123 | 0.261953 |
| GGC* | NA | NA | NA | NA |

*Coefficients for the GGC haplotypes could not be estimated due to singularity in the data.

TABLE 3

FAT4 haplotype additive analysis (rs953211, rs1509290, rs13136889), results from backward selection on the following linear regression: BMI3~BMI2 + center + gender + age + AAC + AAT + AGC + GAC + GAT + GGC + ε

| | Estimate | Std. Error | t value | Pr(>\|t\|) |
|---|---|---|---|---|
| Intercept | 2.97142 | 0.6078 | 4.889 | 1.41E−06 |
| BMI2 | 0.92619 | 0.01891 | 48.974 | <2e−16 |
| center | −0.12471 | 0.03117 | −4 | 7.38E−05 |

TABLE 3-continued

FAT4 haplotype additive analysis (rs953211, rs1509290, rs13136889), results from backward selection on the following linear regression: BMI3~BMI2 + center + gender + age + AAC + AAT + AGC + GAC + GAT + GGC + ε

| | Estimate | Std. Error | t value | Pr(>\|t\|) |
|---|---|---|---|---|
| AGC | 0.21733 | 0.14177 | 1.533 | 0.125973 |
| GAC | −0.96774 | 0.25632 | −3.775 | 0.000181 |
| GAT | −0.39107 | 0.17892 | −2.186 | 0.02934 |

TABLE 4

FAT4 haplotype dominant analysis (rs953211, rs1509290, rs13136889), results from the following linear regression: BMI3~BMI2 + center + gender + age + AAC + AAT + AGC + GAC + GAT + GGC + ε

| | Estimate | Std. Error | t value | Pr (>\|t\|) |
|---|---|---|---|---|
| Intercept | 3.5225218 | 0.9816641 | 3.588 | 0.000369 |
| BMI2 | 0.9276853 | 0.0190143 | 48.789 | <2e−16 |
| center | −0.1244909 | 0.0314629 | −3.957 | 8.83E−05 |
| gender | −0.249386 | 0.1786981 | −1.396 | 0.163532 |
| age | 0.0009298 | 0.0137588 | 0.068 | 0.946152 |
| AACpresent | −0.0634121 | 0.2412081 | −0.263 | 0.792753 |
| AATpresent | 0.6913093 | 0.824904 | 0.838 | 0.402449 |
| AGCpresent | 0.1547387 | 0.2616326 | 0.591 | 0.554526 |
| GACpresent | −1.1271817 | 0.2835424 | −3.975 | 8.18E−05 |
| GATpresent | −0.5652319 | 0.225268 | −2.509 | 0.012452 |
| GGCpresent | −0.2576433 | 0.2480019 | −1.039 | 0.29942 |

TABLE 5

FAT4 haplotype dominant analysis (rs953211, rs1509290, rs13136889), results from backward selection on the following linear regression: BMI3~BMI2 + center + gender + age + AAC + AAT + AGC + GAC + GAT + GGC + ε

| | Estimate | Std. Error | t value | Pr(>\|t\|) |
|---|---|---|---|---|
| Intercept | 3.6015 | 0.64308 | 5.6 | 3.71E−08 |
| BMI2 | 0.92823 | 0.01892 | 49.065 | <2e−16 |
| center | −0.12568 | 0.03123 | −4.025 | 6.68E−05 |
| gender | −0.25106 | 0.1768 | −1.42 | 0.15628 |
| GACpresent | −1.11961 | 0.25072 | −4.466 | 1.01E−05 |
| GATpresent | −0.57589 | 0.17441 | −3.302 | 0.00104 |

TABLE 6

FAT4 epistasis analysis (rs953211, rs1509290), results from the following linear regression: BMI3~BMI2 + center + gender + age + genotype_group + ε

| | Estimate | Std. Error | t value | Pr(>\|t\|) |
|---|---|---|---|---|
| Intercept | 3.621 | 0.9464 | 3.826 | 0.0001485 |
| age | 0.0002888 | 0.01382 | 0.02089 | 0.9833 |
| BMI2 | 0.9271 | 0.01919 | 48.32 | 1.94E−180 |
| genotype_group (rs953211 A/A; rs1509290 G/G) | 0.247 | 0.2678 | 0.9223 | 0.3569 |
| genotype_group (rs953211 G carriers; rs1509290 A carriers) | −0.6924 | 0.2286 | −3.028 | 0.002599 |
| genotype_group (rs953211 G carriers; rs1509290 G/G) | −0.1202 | 0.3093 | −0.3886 | 0.6977 |
| gender | −0.2954 | 0.1797 | −1.644 | 0.1009 |
| center | −0.121 | 0.03158 | −3.833 | 0.0001446 |

In this model, the term "genotype_group" has the following levels: "rs953211 A/A; rs1509290 A carriers", "rs953211 A/A; rs1509290 G/G", "rs953211 G carriers; rs1509290 A carriers", "rs953211 G carriers; rs1509290 G/G"

TABLE 7

FAT4 epistasis analysis (rs953211, rs1509290), results from a type III Anova on the following linear regression: BMI3~BMI2 + center + gender + age + genotype_group + ε

| | F value | Pr(>F) |
|---|---|---|
| Intercept | 14.64 | 0.0001485 |
| age | 0.0004366 | 0.9833 |
| BMI2 | 2335 | 1.94E−180 |
| genotype_group | 7.362 | 7.96E−05 |
| gender | 2.702 | 0.1009 |
| center | 14.69 | 0.0001446 |

In this model, the term "genotype_group" has the following levels: "rs953211 A/A; rs1509290 A carriers", "rs953211 A/A; rs1509290 G/G", "rs953211 G carriers; rs1509290 A carriers", "rs953211 G carriers; rs1509290 G/G"

TABLE 8

FAT4 epistasis analysis (rs953211, rs1509290), results from the following linear regression: BMI3~BMI2 + center + gender + age + genotype_group + ε.

| PARAM | Estimate | Std. Error | t value | Pr(>\|t\|) | 95% bootstrap CI estimates |
|---|---|---|---|---|---|
| (Intercept) | 3.68 | 0.93 | 3.97 | 0.0001 | [1.64, 6.12] |
| genotype_group | −0.76 | 0.17 | −4.52 | 0.0000 | [−1.1, −0.43] |
| BMI2 | 0.93 | 0.02 | 48.39 | 0.0000 | [0.88, 0.97] |
| center | −0.12 | 0.03 | −3.85 | 0.0001 | [−0.18, −0.05] |
| gender | −0.30 | 0.18 | −1.65 | 0.1000 | [−0.62, 0.04] |
| age | 0.00 | 0.01 | 0.01 | 0.9942 | [−0.03, 0.03] |

Estimates of the different terms have been assessed with bootstrap (with n=1000 resampling). In this model, the term "genotype_group" has the following levels: "other", "rs953211-G carriers and rs1509290-A carriers".

TABLE 9

Median change and 95% bootstrap confidence interval (from n = 1000 replicates) on BMI difference between CID3 and CID2

| group | median change (BMI3-BMI2) | 95% bootstrap CI estimates |
|---|---|---|
| Any | 0.38 | [0.19, 0.53] |
| rs953211 A/A; rs1509290 A carriers | 0.57 | [0.22, 0.93] |
| rs953211 A/A; rs1509290 G/G | 0.63 | [0.3, 0.95] |
| rs953211 G carriers; rs1509290 A carriers | 0.00 | [−0.35, 0.32] |
| rs953211 G carriers; rs1509290 G/G | 0.68 | [0.32, 0.91] |

TABLE 10

FAT4 epistasis analysis (rs953211, rs1509290), results from the following linear regression: BMI2~BMI1 + center + gender + age + genotype_group + ε.

| PARAM | Estimate | Std. Error | t value | Pr(>\|t\|) |
|---|---|---|---|---|
| Intercept | −0.9409 | 0.4187 | −2.247 | 0.02495 |
| age | 0.009702 | 0.00606 | 1.601 | 0.1099 |
| BMI1 | 0.8855 | 0.00766 | 115.6 | 0 |
| genotype_group (rs953211 A/A; rs1509290 G/G) | 0.1496 | 0.1197 | 1.25 | 0.2119 |

TABLE 10-continued

FAT4 epistasis analysis (rs953211, rs1509290), results from the following linear regression: BMI2~BMI1 + center + gender + age + genotype_group + ε.

| PARAM | Estimate | Std. Error | t value | Pr(>\|t\|) |
|---|---|---|---|---|
| genotype_group (rs953211 G carriers; rs1509290 A carriers) | −0.09215 | 0.1019 | −0.9041 | 0.3663 |
| genotype group (rs953211 G carriers; rs1509290 G/G) | 0.1945 | 0.1386 | 1.403 | 0.161 |
| gender | 0.3858 | 0.07871 | 4.901 | 1.21E−06 |
| center | 0.01319 | 0.014 | 0.9422 | 0.3465 |

In this model, the term "genotype_group" has the following levels: "rs953211 A/A; rs1509290 A carriers", "rs953211 A/A; rs1509290 G/G", "rs953211 G carriers; rs1509290 A carriers", "rs953211 G carriers; rs1509290 G/G"

TABLE 11

FAT4 epistasis analysis (rs953211, rs1509290), results from a type III Anova on the following linear regression: BMI2~BMI1 + center + gender + age + genotype_group + ε

| PARAM | F value | Pr(>F) |
|---|---|---|
| Intercept | 5.051 | 0.02495 |
| age | 2.563 | 0.1099 |
| BMI1 | 1.34E+04 | 0 |
| genotype_group | 3.157 | 0.02434 |
| gender | 24.02 | 1.21E−06 |
| center | 0.8877 | 0.3465 |

In this model, the term "genotype_group" has the following levels: "rs953211 A/A; rs1509290 A carriers", "rs953211 A/A; rs1509290 G/G", "rs953211 G carriers; rs1509290 A carriers", "rs953211 G carriers; rs1509290 G/G"

TABLE 12

FAT4 epistasis analysis (rs953211, rs1509290), results from the following linear regression: BMI2~BMI1 + center + gender + age + genotype_group + ε. Estimates of the different terms have been assessed with bootstrap(with n = 1000 resampling).

| PARAM | Estimate | Std. Error | t value | Pr(>\|t\|) | 95% bootstrap CI estimates |
|---|---|---|---|---|---|
| Intercept | −0.83 | 0.41 | −2.01 | 0.0450 | [−1.6, −0.08] |
| genotype_group | −0.20 | 0.07 | −2.65 | 0.0082 | [−0.34, −0.06] |
| BMI1 | 0.89 | 0.01 | 115.62 | 0.0000 | [0.87, 0.9] |
| center | 0.01 | 0.01 | 0.93 | 0.3534 | [−0.01, 0.04] |
| gender | 0.38 | 0.08 | 4.86 | 0.0000 | [0.23, 0.56] |
| age | 0.01 | 0.01 | 1.61 | 0.1078 | [0, 0.02] |

In this model, the term "genotype_group" has the following levels: "other", "rs953211-G carriers and rs1509290-A carriers".

TABLE 13

Median change and 95% bootstrap confidence interval (from n = 1000 replicates) on BMI difference between CID2 and CID1

| group | median change (BMI2-BMI1) | 95% bootstrap CI estimates |
|---|---|---|
| Any | −3.59 | [−3.66, −3.5] |
| rs953211 A/A; rs1509290 A carriers | −3.47 | [−3.7, −3.31] |
| rs953211 A/A; rs1509290 G/G | −3.57 | [−3.72, −3.39] |
| rs953211 G carriers; rs1509290 A carriers | −3.69 | [−3.83, −3.58] |
| rs953211 G carriers; rs1509290 G/G | −3.48 | [−3.64, −3.17] |

TABLE 14

Anova p-values assessing significance of a genetic term from the following linear regression: trait_at_CID3~trait_at_CID2 + center + gender + age + genetic_component + ε.

| phenotype | rs953211 * rs1509290 | rs1509289 | rs1509290 | rs953211 |
|---|---|---|---|---|
| BMI (kg/m2) | **7.34E−05** | **0.000167** | **0.004939** | **0.0002769** |
| Fat free mass (kg) | **0.008892** | **0.006536** | **0.02874** | 0.1644 |
| Fat mass (kg) | **0.01184** | **0.04789** | 0.4854 | **0.00613** |
| Hip (cm) | **0.001831** | **0.002953** | **0.03591** | **0.002632** |
| Waist (cm) | **2.38E−05** | **0.006161** | **0.02719** | **0.007947** |

P values smaller than 5% (10%) are shown in bold (italic). Genotypic models were used in these analyses.

TABLE 15

Anova p-values assessing significance of a genetic term from the following linear regression: trait_at_CID2~trait_at_CID1 + center + gender + age + genetic_component + ε.

| phenotype | rs953211 * rs1509290 | rs1509289 | rs1509290 | rs953211 |
|---|---|---|---|---|
| BMI (kg/m2) | **0.02755** | **0.04307** | **0.04041** | 0.438 |
| Fat free mass (kg) | 0.7917 | 0.8083 | 0.5731 | 0.2791 |
| Fat mass (kg) | 0.3087 | 0.5614 | 0.6296 | 0.4783 |
| Hip (cm) | **0.008625** | **0.01202** | *0.09093* | *0.08627* |
| Waist (cm) | 0.4302 | 0.5895 | 0.2597 | 0.6784 |

P values smaller than 5% (10%) are shown in bold (italic). Genotypic models were used in these analyses.

TABLE 16

| Performance of genetic markers at predicting dichotomized percentage of BMI change during weight maintenance | | | | | | | |
|---|---|---|---|---|---|---|---|
| genetic marker | percentile for dichoto-mization | Odds ratio and 95% CI | Fisher's exact test p value | Accuracy and 95% CI | Accuracy P value | Sensi-tivity | Speci-ficity |
| rs953211 and rs1509290 | 0.1 | 3.36 [1.33; 8.85] | 0.0063 | 0.65 [0.54; 0.75] | 0.0042 | 0.67 | 0.63 |
| rs953211 and rs1509290 | 0.25 | 2.41 [1.37; 4.29] | 0.0014 | 0.61 [0.54; 0.67] | 0.0013 | 0.59 | 0.62 |
| rs953211 and rs1509290 | 0.33 | 2.41 [1.48; 3.95] | 0.0002 | 0.61 [0.55; 0.66] | 0.0002 | 0.59 | 0.62 |
| rs953211 and rs1509290 | 0.5 | 1.99 [1.35; 2.95] | 0.0003 | 0.58 [0.54; 0.63] | 0.0003 | 0.6 | 0.57 |
| rs1509289 | 0.1 | 0.27 [0.1; 0.69] | 0.0032 | 0.66 [0.55; 0.76] | 0.0022 | 0.69 | 0.63 |
| rs1509289 | 0.25 | 0.5 [0.28; 0.88] | 0.0117 | 0.59 [0.52; 0.65] | 0.0069 | 0.59 | 0.58 |
| rs1509289 | 0.33 | 0.46 [0.28; 0.75] | 0.0012 | 0.59 [0.54; 0.65] | 0.0007 | 0.61 | 0.58 |
| rs1509289 | 0.5 | 0.53 [0.36; 0.78] | 0.0009 | 0.58 [0.53; 0.62] | 0.0006 | 0.63 | 0.52 |
| rs1509290 | 0.1 | 0.37 [0.13; 1.02] | 0.0404 | 0.6 [0.5; 0.71] | 0.037 | 0.4 | 0.8 |
| rs1509290 | 0.25 | 0.43 [0.23; 0.82] | 0.0076 | 0.59 [0.52; 0.65] | 0.0097 | 0.37 | 0.8 |
| rs1509290 | 0.33 | 0.5 [0.29; 0.86] | 0.0104 | 0.57 [0.51; 0.63] | 0.0119 | 0.36 | 0.78 |
| rs1509290 | 0.5 | 0.59 [0.39; 0.9] | 0.0123 | 0.56 [0.51; 0.6] | 0.0106 | 0.39 | 0.73 |
| rs953211 | 0.1 | 2.87 [1.12; 7.61] | 0.0193 | 0.63 [0.52; 0.73] | 0.0135 | 0.53 | 0.72 |
| rs953211 | 0.25 | 2.44 [1.36; 4.44] | 0.0016 | 0.6 [0.54; 0.67] | 0.0014 | 0.48 | 0.73 |
| rs953211 | 0.33 | 2.31 [1.4; 3.85] | 0.0006 | 0.6 [0.54; 0.65] | 0.0005 | 0.48 | 0.72 |
| rs953211 | 0.5 | 1.66 [1.12; 2.47] | 0.0097 | 0.56 [0.51; 0.61] | 0.0064 | 0.46 | 0.66 |

Levels of the genetic markers are encoded as follows:

rs953211 and rs1509290: "other" vs "rs953211 G carriers; rs1509290 A carriers)"

rs1509289: "G/G" vs "A carriers"

rs1509290: "G/G" vs "A carriers"

rs953211: "A/A" vs "G carriers"

TABLE 17

| Performance of genetic markers at predicting dichotomized percentage of BMI change during weight loss | | | | | | | |
|---|---|---|---|---|---|---|---|
| genetic marker | percentile for dichoto-mization | Odds ratio and 95% CI | Fisher's exact test p value | Accuracy and 95% CI | Accuracy P value | Sensi-tivity | Speci-ficity |
| rs953211 and rs1509290 | 0.1 | 1.6 [0.75; 3.45] | 0.2149 | 0.56 [0.47; 0.65] | 0.1243 | 0.52 | 0.59 |
| rs953211 and rs1509290 | 0.25 | 1.61 [1.01; 2.58] | 0.0433 | 0.56 [0.5; 0.62] | 0.0189 | 0.55 | 0.57 |
| rs953211 and rs1509290 | 0.33 | 1.68 [1.12; 2.51] | 0.0111 | 0.56 [0.52; 0.61] | 0.0048 | 0.55 | 0.58 |
| rs953211 and rs1509290 | 0.5 | 1.47 [1.06; 2.04] | 0.0173 | 0.55 [0.5; 0.61] | 0.0096 | 0.56 | 0.54 |
| rs1509289 | 0.1 | 0.51 [0.24; 1.1] | 0.0764 | 0.58 [0.49; 0.67] | 0.0457 | 0.6 | 0.56 |
| rs1509289 | 0.25 | 0.64 [0.4; 1.02] | 0.0562 | 0.55 [0.5; 0.61] | 0.0322 | 0.6 | 0.51 |
| rs1509289 | 0.33 | 0.61 [0.41; 0.92] | 0.0146 | 0.56 [0.51; 0.61] | 0.0084 | 0.59 | 0.53 |
| rs1509289 | 0.5 | 0.7 [0.51; 0.98] | 0.0315 | 0.54 [0.5; 0.58] | 0.0178 | 0.59 | 0.49 |
| rs1509290 | 0.1 | 0.43 [0.18; 0.99] | 0.0353 | 0.59 [0.5; 0.68] | 0.0309 | 0.4 | 0.78 |
| rs1509290 | 0.25 | 0.55 [0.33; 0.92] | 0.0208 | 0.56 [0.51; 0.62] | 0.0143 | 0.37 | 0.75 |
| rs1509290 | 0.33 | 0.6 [0.38; 0.93] | 0.0203 | 0.55 [0.51; 0.6] | 0.014 | 0.37 | 0.74 |
| rs1509290 | 0.5 | 0.8 [0.57; 1.13] | 0.2048 | 0.52 [0.48; 0.56] | 0.1249 | 0.35 | 0.7 |
| rs953211 | 0.1 | 1.26 [0.57; 2.83] | 0.5769 | 0.53 [0.44; 0.62] | 0.3288 | 0.37 | 0.69 |
| rs953211 | 0.25 | 1.19 [0.73; 1.93] | 0.4862 | 0.52 [0.46; 0.58] | 0.269 | 0.38 | 0.66 |
| rs953211 | 0.33 | 1.34 [0.88; 2.05] | 0.1562 | 0.53 [0.49; 0.58] | 0.0941 | 0.4 | 0.67 |
| rs953211 | 0.5 | 1.31 [0.94; 1.82] | 0.105 | 0.53 [0.49; 0.57] | 0.0611 | 0.42 | 0.64 |

Levels of the genetic markers are encoded as follows:

rs953211 and rs1509290: "other" vs "rs953211 G carriers; rs1509290 A carriers)"

rs1509289: "G/G" vs "A carriers"

rs1509290: "G/G" vs "A carriers"

rs953211: "A/A" vs "G carriers"

TABLE 18

| Genetic markers identified with multi-dimensional reduction analyses for predicting dichotomized percentage of BMI change during weight maintenance | | | | |
|---|---|---|---|---|
| best combination of SNPs | percentile for dichotomization | classification accuracy | prediction accuracy | cross validation consistency (max = 5) |
| rs1509289 | 0.1 | 66.77 | 63.92 | 4 |
| rs953211 | 0.25 | 60.25 | 60.42 | 3 |
| rs1509289 | 0.33 | 60.59 | 55.05 | 2 |
| rs1509289 | 0.5 | 58.01 | 57.11 | 4 |

TABLE 19

| Genetic markers identified with multi-dimensional reduction analyses for predicting dichotomized percentage of BMI change during weight loss | | | | |
|---|---|---|---|---|
| best combination of SNPs | percentile for dichotomization | classification accuracy | prediction accuracy | cross validation consistency (max = 5) |
| rs1509290 | 0.1 | 64.67 | 62.69 | 4 |
| rs1509290 | 0.25 | 56.99 | 54.02 | 2 |
| rs2710559, rs1509290 | 0.33 | 58.84 | 54.51 | 3 |
| rs1509289 | 0.5 | 55.18 | 50.82 | 4 |

TABLE 20

| Median change during weight maintenance and 95% bootstrap confidence interval (from n = 1000 replicates) on various weight-related phenotypes stratified by FAT4 genotypes | | | | | |
|---|---|---|---|---|---|
| genotype | BMI (kg/m2) | fat mass (kg) | fat free mass (kg) | waist (cm) | hip (cm) |
| Overall population (not knowing the genotypes) | 0.38 [0.20, 0.51] | −0.30 [−0.61, 0.20] | 1.16 [0.84, 1.3] | 0.70 [0.15, 1.35] | 0.150 [−0.25, 0.75] |
| rs953211 A/A; rs1509290 A carriers | 0.57 [0.24, 0.90] | 0.45 [−1.10, 1.10] | 0.84 [0.20, 1.3] | 1.50 [0.00, 3.50] | 0.550 [−0.45, 1.50] |
| rs953211 A/A; rs1509290 G/G | 0.63 [0.25, 0.95] | 0.10 [−0.40, 1.40] | 1.31 [0.98, 1.8] | 1.38 [0.25, 2.25] | 1.425 [0.50, 2.33] |
| rs953211 G carriers; rs1509290 A carriers | 0.00 [−0.35, 0.32] | −0.66 [−1.60, −0.08] | 0.96 [0.52, 1.4] | −0.75 [−1.50, 0.98] | −0.450 [−1.50, 0.30] |
| rs953211 G carriers; rs1509290 G/G | 0.68 [0.32, 0.91] | 0.15 [−1.85, 1.72] | 1.45 [0.83, 2.0] | 1.80 [0.10, 4.90] | −0.087 [−1.00, 1.50] |

TABLE 21

| Median change during weight loss and 95% bootstrap confidence interval (from n = 1000 replicates) on various weight-related phenotypes stratified by FAT4 genotypes | | | | | |
|---|---|---|---|---|---|
| genotype | BMI (kg/m2) | fat mass (kg) | fat free mass (kg) | waist (cm) | hip (cm) |
| Overall population (not knowing the genotypes) | −3.6 [−3.7, −3.5] | −7.3 [−7.5, −7.0] | −3.0 [−3.3, −2.7] | −9.1 [−9.6, −8.8] | −6.9 [−7.0, −6.5] |
| rs953211 A/A; rs1509290 A carriers | −3.5 [−3.7, −3.3] | −7.0 [−7.7, −6.5] | −3.1 [−4.0, −2.3] | −9.3 [−11.5, −8.3] | −6.0 [−6.7, −5.3] |
| rs953211 A/A; rs1509290 G/G | −3.6 [−3.7, −3.4] | −7.2 [−7.7, −6.5] | −3.2 [−3.8, −2.6] | −9.1 [−9.9, −8.0] | −6.5 [−7.2, −6.1] |
| rs953211 G carriers; rs1509290 A carriers | −3.7 [−3.8, −3.6] | −7.3 [−7.9, −6.9] | −2.8 [−3.3, −2.5] | −9.2 [−10.0, −8.5] | −7.0 [−7.8, −6.9] |
| rs953211 G carriers; rs1509290 G/G | −3.5 [−3.6, −3.2] | −7.6 [−8.4, −6.7] | −2.9 [−3.7, −2.2] | −9.0 [−10.0, −8.0] | −6.8 [−7.8, −5.8] |

The invention claimed is:

1. A method to attain or maintain weight loss for a subject having an rs953211-G carrier at a polymorphic position that is position 101 of SEQ ID NO:1 (rs953211), the method comprising:

(1) obtaining a nucleic acid sample from the subject;

(2) identifying the rs953211-G carrier of the subject at the polymorphic position that is position 101 of SEQ ID NO:1 (rs953211) within the nucleic acid sample; and (3) administering one or more dietary interventions to the subject having the rs953211-G carrier at the polymorphic position that is position 101 of SEQ ID NO: 1 (rs953211), wherein the one or more dietary interventions comprise a low calorie diet.

2. The method according to claim 1 which method comprises determining the presence of G at position 101 of SEQ ID NO:1 and wherein the dietary intervention is effective to attain or maintain a change in body mass index (BMI), fat mass, hip circumference or waist circumference.

3. The method according to claim 1 which method comprises determining the presence of G at position 101 of SEQ ID NO:1 and wherein the dietary intervention is effective to attain or maintain a change in hip circumference.

4. The method according to claim 1, wherein the low calorie diet comprises a calorie intake of about 600 to about 1200 kcal/day.

5. The method according to claim 1, wherein the low calorie diet comprises administration of at least one diet product.

6. The method according to claim 1, wherein the low calorie diet has a duration of 6 to 12 weeks.

7. The method according to claim 1, wherein the method further comprises determining one or more anthropometric measures and/or lifestyle characteristics of the subject.

8. The method according to claim 7, wherein the anthropometric measure is selected from the group consisting of gender, weight, height, age and body mass index, and wherein the lifestyle characteristic is whether the subject is a smoker or a non-smoker.

9. The method according to claim 1, further comprising the step of selecting a modification of lifestyle of a subject based upon the determined nucleotide of the subject at one or more polymorphic positions.

* * * * *